US012648548B2

(12) United States Patent
Kokkinaki et al.

(10) Patent No.: US 12,648,548 B2
(45) Date of Patent: Jun. 9, 2026

(54) MULTITRANSGENIC PIGS COMPRISING TEN GENETIC MODIFICATIONS FOR XENOTRANSPLANTATION

(71) Applicant: Revivicor, Inc., Blacksburg, VA (US)

(72) Inventors: Maria Kokkinaki, Salem, VA (US); Kasinath V. Kuravi, Blacksburg, VA (US)

(73) Assignee: Revivicor, Inc., Blacksburg, VA (US)

( * ) Notice: Subject to any disclaimer, the term of this patent is extended or adjusted under 35 U.S.C. 154(b) by 418 days.

(21) Appl. No.: 17/948,105

(22) Filed: Sep. 19, 2022

(65) Prior Publication Data

US 2023/0255185 A1     Aug. 17, 2023

Related U.S. Application Data

(60) Provisional application No. 63/261,393, filed on Sep. 20, 2021.

(51) Int. Cl.
| | |
|---|---|
| *A01K 67/0275* | (2024.01) |
| *A01K 67/027* | (2024.01) |
| *A01K 67/0276* | (2024.01) |
| *A01K 67/0278* | (2024.01) |
| *C07K 14/525* | (2006.01) |
| *C07K 14/705* | (2006.01) |

(52) U.S. Cl.
CPC .... *A01K 67/0275* (2013.01); *A01K 2217/206* (2013.01); *A01K 2227/108* (2013.01)

(58) Field of Classification Search
None
See application file for complete search history.

(56) References Cited

U.S. PATENT DOCUMENTS

| | | | |
|---|---|---|---|
| 4,736,866 | A | 4/1988 | Leder et al. |
| 4,873,191 | A | 10/1989 | Wagner et al. |
| 4,994,384 | A | 2/1991 | Prather et al. |
| 5,057,420 | A | 10/1991 | Massey |
| 5,453,457 | A | 9/1995 | Meltzer et al. |
| 5,523,226 | A | 6/1996 | Wheeler |
| 5,789,156 | A | 8/1998 | Bujard et al. |
| 5,814,618 | A | 9/1998 | Bujard et al. |
| 5,945,577 | A | 8/1999 | Stice et al. |
| 6,066,725 | A | 5/2000 | Deboer et al. |
| 6,147,276 | A | 11/2000 | Campbell et al. |
| 6,215,041 | B1 | 4/2001 | Stice et al. |
| 6,235,969 | B1 | 5/2001 | Stice et al. |
| 6,252,133 | B1 | 6/2001 | Campbell et al. |
| 6,258,998 | B1 | 7/2001 | Damiani et al. |
| 6,525,243 | B1 | 2/2003 | Stockman Campbell et al. |
| 6,548,741 | B2 | 4/2003 | Desousa et al. |
| 6,639,122 | B1 | 10/2003 | Tu et al. |
| 6,872,868 | B1 | 3/2005 | Wagner et al. |
| 7,368,284 | B2 | 5/2008 | Koike |
| 7,378,569 | B2 | 5/2008 | Tu et al. |
| 2005/0155095 | A1 | 7/2005 | Koike |
| 2006/0068479 | A1 | 3/2006 | Koike |

FOREIGN PATENT DOCUMENTS

| | | |
|---|---|---|
| WO | WO-90/03432 A1 | 4/1990 |
| WO | WO-93/01294 | 1/1993 |
| WO | WO-94/24274 A1 | 10/1994 |
| WO | WO-94/26884 A1 | 11/1994 |
| WO | WO-97/07668 A1 | 3/1997 |
| WO | WO-97/07669 A1 | 3/1997 |
| WO | WO-98/07841 A1 | 2/1998 |
| WO | WO-98/30683 A2 | 7/1998 |
| WO | WO-99/07829 A1 | 2/1999 |
| WO | WO-99/53042 A2 | 10/1999 |
| WO | WO-99/57266 A2 | 11/1999 |
| WO | WO-00/22098 A1 | 4/2000 |
| WO | WO-00/51424 A2 | 9/2000 |
| WO | WO-01/30966 A2 | 5/2001 |
| WO | WO-03/005810 A2 | 1/2003 |
| WO | WO-03/055302 A1 | 7/2003 |
| WO | WO-03/059923 A2 | 7/2003 |
| WO | WO-2004/016742 A2 | 2/2004 |

(Continued)

OTHER PUBLICATIONS

Mohiuddin et al.(2016) Nature Comm.,vol. 7:11138.DOI:10.1038/ncomms11138, pp. 1-10 (Year: 2016).*
Kemter et al.,"Xeno-organ donor pigs with multiple genetic modifications-the more the better?", Current Opinion in Genetics & Development,Jun. 30, 2020,64:60-65. (Year: 2020).*
U.S. Appl. No. 61/721,283, filed Nov. 1, 2012, Zhang et al.
U.S. Appl. No. 61/736,465, filed Dec. 12, 2012, Zhang et al.
Beldi et al., "The role of purinergic signaling in the liver and in transplantation: effects of extracellular nucleotides on hepatic graft vascular injury, rejection and metabolism," Frontiers in Bioscience, Jan. 1, 2008, 13:2588-2603.
Bleck et al., "Production of Bovine alpha-Lactalbumin in the Milk of Transgetic Pigs," J. Anim. Sci., 1998, 76:3072-2078.
Brinster et al., "Factors affecting the efficiency of introducing foreing DNA into mice by microinjecting eggs," PNAS, Jul. 1984, 82:4438-4442.

(Continued)

*Primary Examiner* — Anna Skibinsky
*Assistant Examiner* — Catherine L Mccormick
(74) *Attorney, Agent, or Firm* — Foley & Lardner LLP

(57) ABSTRACT

The present invention provides transgenic animals (e.g., transgenic porcine animals), organs, tissues, and cells derived from the transgenic animals that are particularly useful for xenotransplantation therapies. In particular, the present invention provides transgenic porcine animals, as well as organs, tissues and cells derived from the transgenic porcine animals, which lack any expression of a functional alpha 1,3 galactosyltransferase (GTKO) gene and comprise at least six transgenes under the control of at least three promoters within a single multi-gene expression vector, and further comprise at least four additional genetic modifications. Also provided are methods of making the transgenic animals (e.g., transgenic porcine animals), and methods of using the transgenic animals, organs, tissues, and cells derived from the transgenic animals for xenotransplantation therapies and treating a disease or condition.

18 Claims, 22 Drawing Sheets

Specification includes a Sequence Listing.

(56)                    References Cited

FOREIGN PATENT DOCUMENTS

| WO | WO-2004/028243 A2 | 4/2004 | |
|---|---|---|---|
| WO | WO-2007/035213 A2 | 3/2007 | |
| WO | WO-2008132729 A2 * | 11/2008 | ................ A61P 9/10 |
| WO | WO-2017044864 A1 * | 3/2017 | ......... A01K 67/0275 |
| WO | WO-2019/185936 A2 | 10/2019 | |

OTHER PUBLICATIONS

Campbell et al., "Production of Live Lambs Following Nuclear Transfer of Cultured Embryonic Disc Cells," Theriogenology, 1995, 43:181.

Campbell et al., "Somatic cell nuclear transfer: Past, present and future perspectives," Theriogenology, 2007, 68S:S214-S231.

Chen et al., "Complete Inhibition of Acute Humoral Rejection Using Regulated Expression of Membrane-tethered Anticoagulants on Xenograft Endothelium," American Journal of Transplantation, 2004; 4(12):1958-1963.

Chen et al., "Hearts from transgenic pigs constructed with CD59/DAF genomic clones demonstrate improved survival in primates," Xenotransplantation, Aug. 1999, 6(3):194-200.

Collas et al., "Nuclear Transplantation by Microinjection of Inner Cell Mass and Granulosa Cell Nuclei," Mol. Reprod. Dev., 1994, 38:264-267.

Cooper et al., "Justification of specific genetic modifications in pigs for clinical organ xenotransplantation," Xenotransplantation, Apr. 15, 2019, 26(4):e12516, 1-12.

Costa et al., "Transgenic pigs designed to express human CD59 and H-transferase to avoid humoral xenograft rejection," Xenotransplantation, Jan. 2002, 9(1):45-57.

Cowan et al., "The coagulation barrier in xenotransplantation: incompatibilities and strategies to overcome them," Current Opinion in Organ Transplantation, Apr. 2008, 13(2):178-183.

Dai et al., "Targeted disruption of the alpha 1,3-galactosyltransferase gene in cloned pigs," Nature Biotechnology, Mar. 2002, 20:251-255.

De Veylder et al., "Herbicide Safener-Inducible Gene Expression in *Arabidopsis thaliana*," Plant Cell Physiol., 1997, 38(5):568-577.

Diamond et al., "A Human CD46 Transgenic Pig Model System for the Study of Discordant Xenotransplantation," Transplantation, Jan. 15, 2001, 71(1):132-142.

Dwyer et al., "The Transgenic Expression of Human CD39 on Murine Islets Inhibits Clotting of Human Blood," Transplantation, Aug. 15, 2006, 82(3):428-432.

Dwyer et al., "Thromboregulatory manifestations in human CD39 transgenic mice and the implications for thrombotic disease and transplantation," J. Clin. Invest., May 2004; 113(10): 1440-1446.

Estrada et al., "Evaluation of human and non-human primate antibody binding to pig cells lacking GGTA1/CMAH/beta4GalNT2 genes," Xenotransplantation, 2015, 22:194-202.

Gatz et al., "Regulation of a modified CaMN 35S promoter by the Tn10-encoded Tet repressor in transgenic tobacco," Mol. Gen. Genet., 1991, 227:229-237.

Giraldo et al., "Production of Transgenic and Knockout Pigs by Somatic Cell Nuclear Transfer," Xenotransplantation: Methods and Protocols, in Methods in Molecular Biology, Costa et al., Eds., 2012, 885:105-123.

Gordon, Jon W., "Transgenic Animals," in International Review of Cytology, Bourne et al., Eds., 1989, 115:171-229.

Griffith et al., "Genetically Modified Procine-to-Human Cardiac Xenotransplantation," N. Engl. J. Med., Jun. 22, 2022, 387(1):35-44.

Hinrichs et al., "Growth hormone receptor knockout to reduce the size of donor pigs for preclinical xenotransplantation studies," Xenotransplantation, Nov. 25, 2020, 28(2):e12664, 1-9.

Hinrichs et al., "Growth hormone receptor-deficient pigs resemble the pathophysiology of human Laron syndrome and reveal altered activation of signaling cascades into the liver," Molecular Metabolism, Mar. 15, 2018, 11:113-128.

Huang et al., "Protein expression of lymphocytes in HLA-DR transgenic pigs by a proteomic approach," Proteomics, Nov. 2006, 6(21):5815-5825.

Ide et al., "Role for CD47-SIPRalpha signaling in xenograft rejection by macrophages," PNAS USA. Mar. 20, 2007, 104(12):5062-5066.

Iino et al., "Thrombomodulin expression on Langerhans' islet: can endogenous 'anticoagulant on demans' overcome detrimental thrombotic complications in clinical islet transplantation?", Journal of Thrombosis and Haemostasis, May 2004; 2(5):833-843.

Keefer et al., "Bovine Inner Cell Mass Cells as Donor Nuclei in the Production of nuclear Transfer Embryos and Calves," Biology of Reproduction, 1994, 50:935-939.

Keown et al., "Methods for Introducing DNA into Mammalian Cells, "Methods in Enzymology, 1990, 185:527-537.

Kim et al., "Recombinant fragment assay for gene targeting based on the polymerase chain reaction," Nucleic Acids Research, 1988, 16(18):8887-8903.

Klose et al., "Expression of Biologically Active Human TRAIL in Transgenic Pigs," Transplantation, Jul. 28, 2005, 80(2):222-230.

Klymiuk et al., "Genetic Modification of Pigs as Organ Donors for Xenotranslplantation," Molecular Reproduction and Development, 2010, 77:209-221.

Lavitrano et al., "Sperm Cells as Vectors for Introducing Foreign DNA into Eggs: Genetic Transformation of Mice," Cell, Jun. 2, 1989, 57:717-723.

Li et al., "Efficient generation of genetically distinct pigs in a single pregnancy using multiplexed single-guide RNA and carbohydrate selection," Xenotransplantation, 2015, 22(1):20-31.

Li et al., "Overexpressing endothelial cell protein C receptor alters the hemostatic balance and protects mice from endotoxin," Journal of Thrombosis and Haemostasis, Jul. 2005, 3(7):1351-1359.

Lo, Cecilia W., "Transformation by Ionophoretic Microinjection of DNA" Multiple Integrations Without Tandem Insertions, Molecular and Cellural Biology, Oct. 1983, 3(10:1803-1814.

Mali et al., "RNA-Guided Human Genome Engineering via Cas9," Science, Feb. 15, 2013, 339(6121):823-826.

Mirenda et al., "Achieving Permanent Survival of Islet Xenografts by Independent Manipulation of Direct and Indirect T-Cell Responses," Diabetes, Apr. 2005, 54:1048-1055.

Ono et al., "Transient Assay System for the Analysis of PR-1a Gene Promoter in Tobacco BY-2 Cells," Biosci. Biotechnol. Biochem., 2004, 68(4):803-807.

Phelps et al., "Production of alpha1,3-Galactosyltransferase: Deficient Pigs," Science, Jan. 17, 2003, 299(5605):411-414.

Platt et. al., "The Future of Transplantation," N. Engl. J. Med., Jul. 7, 2022, 387(1):77-78.

Polejaeva et al., "Cloned pigs produced by nuclear transfer from adult somatic cells," Nature, Sep. 2000, 407:86-90.

Riesbeck et al., "Expression of Hirudin Fusion Proteins in Mammalian Cells: A Strategy for Prevention of Intravascular Thrombosis," Circulation, Dec. 15, 1998, 98(24):2744-2752.

Robson et al., "Ectonucleotidases of CD39 Family Modulate Vascular Inflammation and Thrombosis in Transplantation," Seminars in Thrombosis and Hemostasis, Apr. 2005, 31(2):217-233.

Sendai et al., "alpha1,3-Galactosyltransferase-Gene Knockout in Cattle using a Single Targeting Vector with loxP Sequences and Cre-Expressing Adenovirus," Transplantation, 2006, 81(5):760-766.

Shapiro et al., "International Trial of the Edmonton Protocol for Islet Transplantation," N. Engl. J. Med., 2006, 355:1318-1330.

Sims et al., "Production of calves by transfer of nuclei from cultured inner cell mass cells," PNAS USA, Jun. 1994,91:6143-6147.

Stone et al., "Porcine and Bovine Cartilage Transplants in Cynomolgus Monkey," Transplantation, 1997, 63(5):640-645.

Thompson et al., "Germ Line Transmission and Expression of a Corrected HPRT Gene Produced by Gene Targeting in Embryonic Stem Cells," Cell, Jan. 27, 1989, 56:313-321.

Vajta et al., "Somatic cell nuclear transfer in pigs: recent achievements and future possibilities," Reprod. Fertil. Dev., 2007, 19(2):403-423.

(56)     References Cited

OTHER PUBLICATIONS

Van de Wouwer et al., "Thrombomodulin-Protein C-EPCR System: Integrated to Regulat Coagulation and Inflammation," Arterioscler. Thromb. Vasc. Biol., Aug. 2004, 24(8):1374-1383.

Van der Putten et al., "Efficient insertion of genes into the mouse germ line via retriviral vectors," PNAS USA, 1985, 82:6148-6152.

Vaughan et al., "Porcine CTLA4-Ig Lacks a MYPPY Motif, Binds Inefficiently to Human B7 and Specifically Suppresses Human CD4+ T Cell Responses Costimulated by Pig but Not Human B7," The Journal of Immunology, 2000, 164:3175-3181.

Weiss et al., "HLA-E/Human beta2-Microglubulin Transgenic Pigs: Protection Against Xenogeneic Human Anti-Pig Natural Killer Cell Cytotoxicity," Transplantation, Jan. 15, 2009, 87(1):35-43.

Whitworth et al., "Use of the CRISPR/Cas9 System to Produce Genetically Engineered Pigs from In Vitro-Derived Oocytes and Embryos," Biology of Reproduction, Aug. 6, 2014, 91(3):78, 1-13.

Ye et al., "Evidence that Intravenously Administered alpha-Galactosyl Carbohydrates Reduce Baboon Serum Cytotoxicity to Pig Kidney Cells (PK15) and Transplanted Pig Hearts," Transplantation, Aug. 15, 1994, 58: 330-337.

Yue et al., "Extensive germline genome engineering in pigs," Nature Biomedical Engineering, Sep. 21, 2020, 5(2):134-143.

Yun et al., "The induction of major histocompatibility complex class II expression is sufficient for the direct activation of human CD4+ cells by porcine vascular endothelial cells," Transplantation, Mar. 15, 2000, 69(5):940-944.

Yun et al., "Suppression of MHC class II expression by human class II trans-activator constructs lacking the N-terminal domain," International Immunology, Oct. 1997, 9(10):1545-1553.

* cited by examiner

FIG. 6
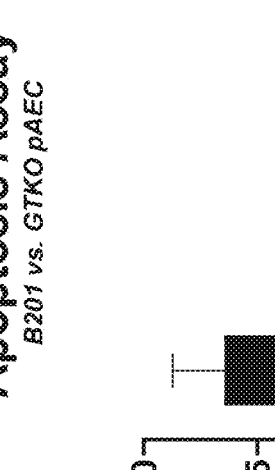
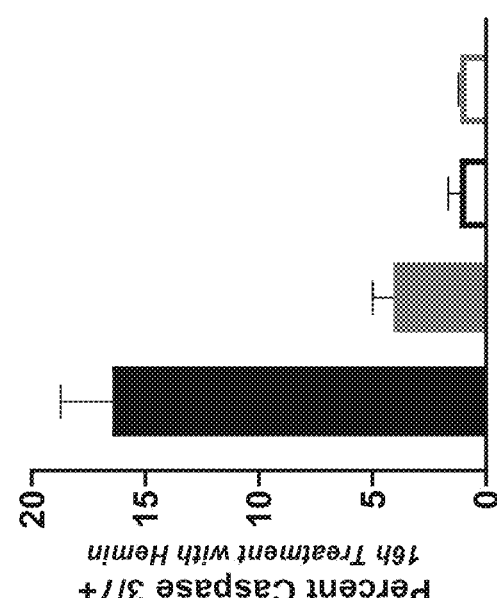

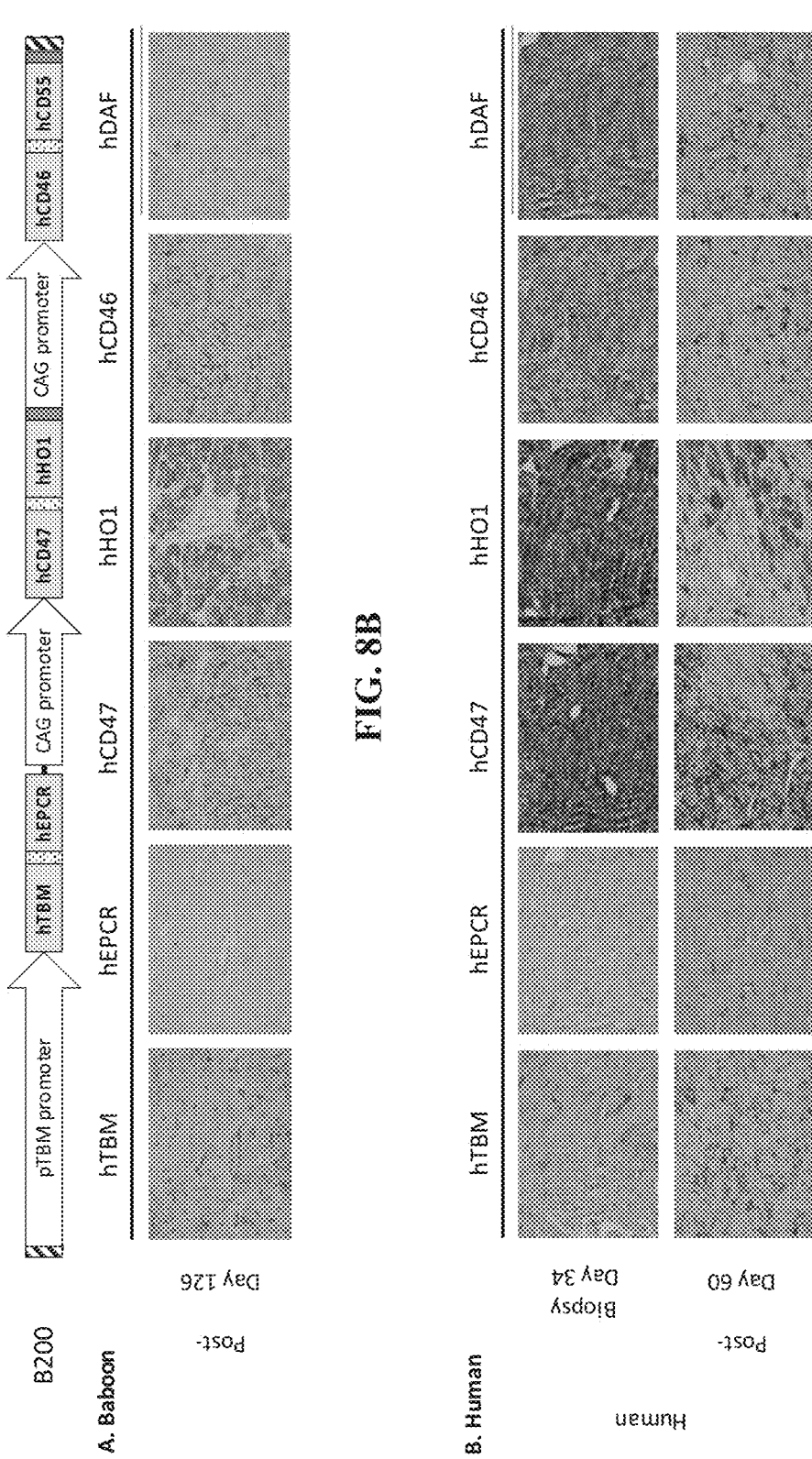

MULTITRANSGENIC PIGS COMPRISING TEN GENETIC MODIFICATIONS FOR XENOTRANSPLANTATION

CROSS-REFERENCE TO RELATED APPLICATIONS

This application claims the benefit of priority to U.S. Provisional Patent Application No. 63/261,393, filed Sep. 20, 2021, which is hereby incorporated by reference in its entirety for any and all purposes.

The instant application contains a Sequence Listing which has been submitted in XML format via Patent Center and is hereby incorporated by reference in its entirety. Said XML copy, created on Jan. 17, 2023, is named 080618-4482.xml and is 205,352 bytes.

TECHNICAL FIELD

The present disclosure relates generally to xenotransplantation therapies, and more particularly to multi-transgenic porcine animals comprising at least ten genetic modifications, which make these porcine animals suitable donors for xenotransplantation, as well as tissues and/or cells derived from the porcine animals.

BACKGROUND

The following description of the background of the present technology is provided simply as an aid in understanding the present technology and is not admitted to describe or constitute prior art to the present technology.

Xenotransplantation (transplant of organs, tissues and cells from a donor of a different species) could effectively address the shortage of human donor. While advantageous in many ways, xenotransplantation creates a more complex immunological scenario than allotransplantation. The most profound barrier to xenotransplantation is the rejection of the grafted organ by a cascade of immune mechanisms, divided into three phases: hyperacute rejection (HAR), acute humoral xenograft rejection (AHXR), and T-cell mediated cellular rejection. HAR is a very rapid event that results in irreversible graft damage and loss within minutes to hours following graft reperfusion.

Considerable effort has been directed at addressing the immune barrier posed by xenotransplantation through genetic modification of the donor animal. The most commonly used donor animals are pigs. Pigs have been the focus of most research in xenotransplantation because pigs share many anatomical and physiological characteristics with humans. Furthermore, pigs have relatively short gestation periods and can be bred in pathogen-free environments. Pigs also do not present the same ethical issues associated with most animal research (e.g., primates) because pigs are commonly used as a food source by humans.

Significant progress has been made to overcome the biologic barriers to the use of pig organs in preclinical models, with sustained organ function and recipient survival reaching months to years in some heart and kidney series. Genetically modified pigs lacking alpha-1,3-Gal epitopes (the major xenoantigens triggering HAR of pig-to-primate xenografts) are considered to be the basis for further genetic modifications that can address other rejection mechanisms and incompatibilities between the porcine and primate blood coagulation systems. While multiple genetic modifications are necessary for successful xenotransplantation, they present challenges, including production-related challenges.

Accordingly, there is a need for transgenic pigs that stably express multiple immune-modulating transgenes to overcoming xenograft rejection. The generation of multitransgenic pigs by traditional breeding that contain single transgenes has been utilized thus far with much success. However, breeding is time-consuming, expensive and consistent expression levels of the transgenes can be an issue over time.

The development of polycistronic expression systems for inserting multiple transgenes into a single locus, and into various cell types and animals, is a promising technology for the generation of multitransgenic pigs. While still in its infancy, polycistronic expression systems represent an alternative to the traditional approaches typically employed to generate multitransgenic pigs. This technology has certain drawbacks and is not yet efficient. For instance, a multicistronic system comprising three genes may only result in a transgenic pigs expressing two of the genes. Furthermore, the efficient expression of downstream genes from a multicistronic system depends on the expression of an upstream genes.

Accordingly, there is a need for a novel way of using polycistronic expression systems that result in stable integration and sufficient transgene expression in multitransgenic donor animals (i.e., pigs) for xenotransplantation therapies. The present disclosure addresses this need.

SUMMARY OF THE PRESENT TECHNOLOGY

An embodiment relates to transgenic animals (e.g., transgenic porcine animals), organs, tissues, and cells derived from the transgenic animals that are particularly useful for xenotransplantation therapies. In particular, an embodiment provides transgenic porcine animals, as well as organs, tissues and cells derived from the transgenic porcine animals, which lack any expression of a functional alpha 1,3 galactosyltransferase (GTKO) gene and comprise at least six transgenes under the control of at least three promoters within a single multi-gene expression vector, and further comprise at least four additional genetic modifications. Another embodiment is an improved method of generating transgenic animals (e.g., transgenic porcine animals), and methods of using the transgenic animals, organs, tissues, and cells derived from the transgenic animals for xenotransplantation therapies and treating a disease or condition. The methods provided herein facilitate efficient generation of multitransgenic founder animals (e.g. pigs), as well as breeding and production herd expansion. The novel, improved and efficient method of generating multitransgenic founder animals is based on the identification and insertion of six human transgenes in a single multi-gene expression vector, and the targeted insertion of the multi-gene expression vector (polycistronic or multicistronic vector (MCV)) to a known locus or landing pad for reliable and consistent transgene expression in the transgenic animal, and transplanted organs, tissues, and/or cells.

In one aspect, the present disclosure provides a transgenic porcine animal comprising genetic modifications that result in: (i) the lack of expression of functional alpha 1,3 galactosyltransferase; and (ii) incorporation and expression at a single genomic locus of (a) at least two complement inhibitor transgenes; (b) at least one immunosuppressant transgene; (c) at least one cytoprotective transgene; and (d) at least two anticoagulant transgenes. In some embodiments, the transgenes are human cDNA. In some embodiments, the transgenic animal comprises at least six, at least seven, or at least eight transgenes. In some embodiments, the transgenic animal comprises at least six transgenes. In some embodiments, the at least six transgenes are encoded by a polycistronic vector (multicistronic vector (MCV)). In some embodiments, the polycistronic vector comprises at least three bicistronic units. In some embodiments, each bicistronic unit comprises a promoter driving a first transgene linked via a cleavage peptide to a second transgene. In some embodiments, a first bicistronic unit comprises the at least two anticoagulant transgenes, a second bicistronic comprises at least two complement inhibitor transgenes; and a third bicistronic unit comprises the at least one cytoprotective transgene and the at least one immunosuppressant transgene. In some embodiments, the cleavage peptide is selected from the group consisting of T2A, P2A, F2A, and E2A.

In some embodiments, the transgenes are encoded by a polycistronic vector comprising: (i) at least two bicistronic unit, wherein each bicistronic unit comprises a promoter driving a first transgene linked via a cleavage peptide to a second transgene; and (ii) at least two non-polycistronic transgenes, wherein each non-polycistronic transgene is driven by its own promoter. In one embodiment, at least one bicistronic unit is driven by a tissue-specific promoter, at least one bicistronic unit is driven by an inducible promoter; and/or at least two bicistronic units are driven by a dedicated constitutive promoter. In one embodiments, the at least two bicistronic units are each driven by a constitutive promoter, and the at least two non-polycistronic transgenes are each driven by a tissue-specific promoter.

In some embodiments, the transgenes are under the control of at least three promoters within a polycistronic vector (MCV). In some embodiments, the promoter is a constitutive promoter or a tissue specific promoter. In some embodiments, the constitutive promoter is selected from the group consisting of CAG promoter, Tie-2 promoter, ICAM-2 promoter. In some embodiments, the tissue-specific promoter is an endothelial-cell specific promoter. In some embodiments, the inducible promoter is a Tetracycline/doxycycline regulatory promoter. In some embodiments, the tissue-specific promoter is selected from a porcine thrombomodulin promoter (pTBMpr), a human thrombomodulin promoter, a porcine EPCR promoter, a human EPCR promoter.

In some embodiments, the transgenic porcine animal comprises incorporation and expression at a single genomic locus of at least two complement inhibitors selected from the group consisting of CD46, DAF (CD55), CD59, CR1, and a combination thereof. In some embodiments, the at least two complement inhibitors are ubiquitously expressed and/or are expressed under the control of a constitutive promoter, or under the control of an inducible promoter.

In some embodiments, the transgenic porcine animal comprises incorporation and expression at a single genomic locus of at least one immunosuppressant transgene selected from the group consisting of Cytoxic T-Lymphocyte-Associated Protein 4 (CTLA4), cluster of differentiation 47 (CD47), and Class II transactivator-DN (CIITA-DN). In some embodiments, the at least one immunosuppressant transgene are under the control of a constitutive promoter.

In some embodiments, the transgenic porcine animal comprises incorporation and expression at a single genomic locus of at least one cytoprotective transgene selected from the group consisting of heme oxygenase 1 (HO-1), A20, FAT-1, soluble tumor necrosis factor-alpha (TNF-alpha), and a combination thereof. In some embodiments, at least one cytoprotective is under the control of a constitutive promoter, or is under the control of an endothelial-specific promoter.

In some embodiments, the transgenic porcine animal comprises incorporation and expression at a single genomic locus of at least two anticoagulant transgenes selected from the group consisting of endothelial protein C receptor (EPCR), thrombomodulin, CD39, hirudin, Tissue factor pathway inhibitor (TFPI), and a combination thereof. In some embodiments, the at least two anticoagulant transgenes are under the control of an endothelial-specific promoter.

In some embodiments, the at least six transgenes are encoded by a polycistronic vector and the polycistronic vector comprises a bicistronic unit selected from the group consisting of: (i) porcine TBM promoter driving a human TBM transgene linked via a 2A peptide to a human EPCR transgene (pTBMpr [hTBM-2A-hEPCR]); (ii) a CAG promoter driving a human CD47 transgene linked via 2A peptide to a human HO-1 transgene (CAGpr [hCD47-2A-hHO1]); (iii) a CAG promoter driving a human CD46 transgene linked via 2A peptide to a human DAF transgene (CAGpr [hCD46-2A-hDAF]); (iv) Poly-A signal fused to a porcine TBM promoter driving a human TBM transgene linked via a 2A peptide to a human EPCR transgene (PolyA/pTBMpr [hTBM-2A-hEPCR]); (v) a CAG promoter driving a human CD59 transgene linked via 2A peptide to a human HO-1 transgene (CAGpr [hCD59-2A-hHO1]); (vi) a porcine EPCR promoter driving a human TBM transgene linked via a 2A peptide to a human EPCR transgene (pEPCRpr [hTBM-2A-hEPCR]); (vii) a CAG promoter driving a human CD46 transgene linked via 2A peptide to a human CD47 transgene (CAGpr [hCD46-2A-hCD47]); (viii) a first U6 promoter driving a first GHR gRNA linked to a second U6 promoter driving a second GHR gRNA (U6p [GHR-gRNA-1]; U6p [GHRgRNA-2]), wherein the first and second gRNA are the same or different; (xix) a TRE3G promoter driving a Cas endonuclease, linked via an insulator to a CAG promoter driving a tTA (TRE3Gp[CAS9]; CAGpr [tTA]); and (x) a combination thereof.

In some embodiments, the polycistronic vector comprises: (i) pTBMpr [hTBM-2A-hEPCR]; CAGpr [hCD47-2A-hHO1]; and CAGpr [hCD46-2A-hDAF]; (ii) PolyA-pTBMpr [hTBM-2A-hEPCR]; CAGpr [hCD47-2A-hHO1]; and CAGpr [hCD46-2A-hDAF]; (iii) pTBMpr [hTBM-2A-hEPCR]; CAGpr [hCD59-P2A-hHO1]; and CAGpr [hCD46-P2A-hDAF]; (iv) PolyA-pTBMpr [hTBM]; CAG pr [hCD47-P2A-hHO1]; pEPCRpr [hEPCR]; and CAGpr [hCD46P-2A-hDAF]; (v) pTBMpr [hTBM-2A-hEPCR]; CAGpr [hCD59-P2A-hHO1]; CAGpr [hCD46-2A-hCD47]; (vi) pTBMpr [hTBM-2A-hEPCR]; CAGpr [hCD59-2A-hHO1]; CAGpr [hCD46-2A-hCD55]; (vii) U6p [GHR-gRNA-1]; U6p [GHRgRNA-2]; TRE3Gp[CAS9]; CAGpr [tTA]; CAGpr [hCD46-2A-hCD55]; (viii) SEQ ID NO: 7; (xix) SEQ ID NO: 8; (x) SEQ ID NO: 9; (xi) SEQ ID NO: 11; (xii) SEQ ID NO: 12; (xiii) SEQ ID NO: 13; or (xiv) SEQ ID NO: 14.

In some embodiments, the transgenic porcine animal comprising genetic modifications that result in: (i) the lack of expression of functional alpha 1,3 galactosyltransferase; (ii) incorporation and expression at a single genomic locus and the single genomic locus is a native locus or a modified native locus. In some embodiments, the modified native locus comprises: (i) a gene editing-mediated insertion, deletion or substitution; (ii) a transgenic DNA; (iii) a selectable gene maker; and/or (iv) a landing pad. In some embodiments, the single genomic locus is selected from the group consisting of AAVS1, GHR, ROSA26, CMAH, B4GalNT2, and GGTA1.

In some embodiments, the polycistronic vector encoding the transgenes further comprises nucleotide sequences for homology recombination and/or homology directed repair (HDR) at a locus selected from the group consisting of AAVS1, GHR, ROSA26, CMAH, B4GalNT2, and GGTA1.

In one aspect, the present disclosure provides a transgenic porcine animal comprising genetic modifications that result in: (i) the lack of expression of functional alpha 1,3 galactosyltransferase; (ii) incorporation and expression at a single genomic locus of (a) at least two complement inhibitor transgenes; (b) at least one immunosuppressant transgene; (c) at least one cytoprotective transgene; and (d) at least two anticoagulant transgenes; and (iii). further comprises at least one additional genetic modification selected from the group consisting of gene knock-outs; gene knock-ins; gene replacements; point mutations; deletions, insertions or substitutions of genes, gene fragments or nucleotides; large genomic insertions; or combinations thereof.

In some embodiments, the transgenic porcine animal further comprises a knockout of a gene selected from the group consisting of AAVS1, GHR, ROSA26, CMAH, B4GalNT2, GGTA1, and growth hormone receptor (GHR). In some embodiments, the gene knock-out comprises: (i) a gene editing-mediated insertion, deletion, or substitution; (ii) a CRISPR-Cas9-mediated gene editing; (iii) a homologous recombination-mediated insertion; and/or (iv) NeoR insertion-mediated gene knockout.

In some embodiments, the single genomic locus is CMAH, and the additional modification comprises the knockout of β4GalNT2, GGTA1, and GHR. In some embodiments, the single genomic locus is β4GalNT2 and the additional modification comprises the knockout of CMAH, GGTA1, and GHR. In some embodiments, the single genomic locus is GGTA1 and the additional modification comprises the knockout of β4GalNT2, CMAH, and GHR.

In one aspect, the present disclosure provides cells derived from the transgenic porcine animal of the present invention. In one aspect, the present disclosure provides an organ derived from the transgenic porcine animal of the present invention. In some embodiments, the organ is selected from the group consisting of heart, lung, liver, pancreas, and kidney. In one aspect, the present disclosure provides tissue derived from the transgenic porcine animal of the present invention. In some embodiments, the tissue is selected from the group consisting of vascular tissue, heart valve, retinal tissue, neural tissue, and corneal tissue. In some embodiments, the vascular tissue is a vascular graft.

In one aspect, the present disclosure provides a method for xenotransplantation comprising administering, to a subject in need thereof, organs, tissue or cells derived from the transgenic porcine animal of the present invention. In some embodiments, the subject is a non-human primate or a human. In some embodiments, the organ is selected from the group consisting of heart, lung, liver, pancreas, and kidney. In some embodiments, the tissue is selected from the group consisting of vascular tissue, retinal tissue, neural, and corneal tissue.

In one aspect, the present disclosure provides a method for xenotransplantation comprising administering, to a subject in need thereof, organs, tissue or cells derived from the transgenic porcine animal of the present invention and further comprises administering a clinically relevant immunosuppressant regimen to the subject following xenotransplantation of the organs, tissue, or cells.

In one aspect, the present disclosure provides a method of making the transgenic porcine animal of the present invention. In one aspect, the present disclosure provides a method of making a transgenic pig comprising at least six transgenes comprising the step of: (i) transfecting a porcine cell with a single polycistronic vector comprising: (a) at least two complement inhibitor transgenes; (b) at least one immunosuppressant transgene; (c) at least one cytoprotective transgene; and (d) at least two anticoagulant transgenes; (ii) producing a multitransgenic porcine cell comprising at least six transgenes by incorporating and expressing the polycistronic vector at a single genomic locus; (iii) generating a multitransgenic porcine zygote by injecting the nucleus of the multitransgenic porcine cell into a reconstructed somatic cell nuclear transfer (SCNT); and (iv) permitting the multitransgenic porcine zygote to mature into a multitransgenic pig (e.g. transgenic pig). In some embodiments, the porcine cell and the multitransgenic pig e.g. transgenic pig) lack expression of alpha 1,3 galactosyltransferase (GTKO).

In some embodiments, the porcine cell is a somatic cell. In some embodiments, the multitransgenic porcine cell comprises at least seven, at least eight, at least nine, or at least ten transgenes. In some embodiments, the at least six transgenes are encoded by a polycistronic vector, and optionally the polycistronic vector comprises at least three bicistronic units. In some embodiments, each bicistronic unit comprises a promoter driving a first transgene linked via a cleavage peptide to a second transgene. In some embodiments, a first bicistronic unit comprises the at least two anticoagulant transgenes, a second bicistronic comprises at least two complement inhibitor transgenes; and a third bicistronic unit comprises the at least one cytoprotective transgene and the at least one immunosuppressant transgene.

In some embodiments, the cleavage peptide is selected from the group consisting of T2A, P2A, F2A, and E2A. In some embodiments, the at least six transgenes are encoded by a polycistronic vector comprising: (i) at least two bicistronic unit, wherein each bicistronic unit comprises a promoter driving a first transgene linked via a cleavage peptide to a second transgene; and (ii) at least two non-polycistronic transgenes, wherein each non-polycistronic transgene is driven by its own promoter.

In some embodiments, at least one bicistronic unit is driven by a tissue-specific promoter, at least one bicistronic unit is driven by an inducible promoter, and/or at least two bicistronic units are driven by a dedicated constitutive promoter. In some embodiments, the at least two bicistronic units are each driven by a constitutive promoter, and the at least two non-polycistronic transgenes are each driven by a tissue-specific promoter. In some embodiments, the transgenes are under the control of at least three promoters within a polycistronic vector (e.g., MCV). In some embodiments, the promoter is a constitutive promoter or a tissue specific promoter. In some embodiments, the constitutive promoter is selected from the group consisting of CAG promoter, Tie-2 promoter, ICAM-2 promoter. In some embodiments, the inducible promoter is a Tetracycline/doxycycline regulatory promoter. In some embodiments, the tissue-specific promoter is an endothelial-cell specific promoter selected from a porcine thrombomodulin promoter (pTBMpr), a human thrombomodulin promoter, a porcine EPCR promoter, a human EPCR promoter.

In some embodiments, the method of making a transgenic pig comprising at least six transgenes comprises the step of transfecting a porcine cell with a single polycistronic vector comprising at least two complement inhibitors. In some embodiments, the at least two complement inhibitors are selected from the group consisting of CD46, DAF (CD55), CD59, CR1, and a combination thereof. In some embodiments, the at least two complement inhibitors are ubiquitously expressed; and/or are under the control of a constitutive promoter an inducible promoter.

In some embodiments, the method of making a transgenic pig comprising at least six transgenes comprises the step of transfecting a porcine cell with a single polycistronic vector comprising at least one immunosuppressant transgene. In some embodiment the at least one immunosuppressant transgene is selected from the group consisting of Cytotoxic T-Lymphocyte-Associated Protein 4 (CTLA4), cluster of differentiation 47 (CD47), and Class II transactivator-DN (CIITA-DN). In some embodiments, the at least one immunosuppressant transgene is under the control of a constitutive promoter.

In some embodiments, the method of making a transgenic pig comprising at least six transgenes comprises the step of transfecting a porcine cell with a single polycistronic vector comprising at least one cytoprotective transgene. In some embodiments, the at least one cytoprotective transgene is under the control of a constitutive promoter; or under the control of an endothelial-specific promoter. In some embodiments, the at least one cytoprotective transgene is selected from the group consisting of heme oxygenase 1 (HO-1), A20, FAT-1, soluble tumor necrosis factor-alpha (TNF-alpha), and a combination thereof.

In some embodiments, the method of making a transgenic pig comprising at least six transgenes comprises the step of transfecting a porcine cell with a single polycistronic vector comprising at least two anticoagulant transgenes. In some embodiments, the at least two anticoagulant transgenes are under the control of an endothelial-specific promoter. In some embodiments, the at least two anticoagulant transgenes are selected from the group consisting of endothelial protein C receptor (EPCR), thrombomodulin, CD39, hirudin, Tissue factor pathway inhibitor (TFPI), and a combination thereof.

In some embodiments, the method of making a transgenic pig comprising at least six transgenes comprises the step of transfecting a porcine cell with a single polycistronic vector. In some embodiments, the polycistronic vector comprises a bicistronic unit selected from the group consisting of (i) porcine TBM promoter driving a human TBM transgene linked via a 2A peptide to a human EPCR transgene (pTBMpr [hTBM-2A-hEPCR]); (ii) a CAG promoter driving a human CD47 transgene linked via 2A peptide to a human HO-1 transgene (CAGpr [hCD47-2A-hHO1]); (iii) a CAG promoter driving a human CD46 transgene linked via 2A peptide to a human DAF transgene (CAGpr [hCD46-2A-hDAF]); (iv) Poly-A signal fused to a porcine TBM promoter driving a human TBM transgene linked via a 2A peptide to a human EPCR transgene (PolyA/pTBMpr [hTBM-2A-hEPCR]); (v) a CAG promoter driving a human CD59 transgene linked via 2A peptide to a human HO-1 transgene (CAGpr [hCD59-2A-hHO1]); (vi) a porcine EPCR promoter driving a human TBM transgene linked via a 2A peptide to a human EPCR transgene (pEPCRpr [hTBM-2A-hEPCR]); (vii) a CAG promoter driving a human CD46 transgene linked via 2A peptide to a human CD47 transgene (CAGpr [hCD46-2A-hCD47]); (viii) a first U6 promoter driving a first GHR gRNA linked to a second U6 promoter driving a second GHR gRNA (U6p [GHR-gRNA-1]; U6p [GHRgRNA-2]), wherein the first and second gRNA are the same or different; (xix) a TRE3G promoter driving a Cas endonuclease, linked via an insulator to a CAG promoter driving a tTA (TRE3Gp[CAS9]; CAGpr [tTA]); and (x) a combination thereof.

In some embodiments, the polycistronic vector comprises: (i) pTBMpr [hTBM-2A-hEPCR]; CAGpr [hCD47-2A-hHO1]; and CAGpr [hCD46-2A-hDAF]; (ii) PolyA-pTBMpr [hTBM-2A-hEPCR]; CAGpr [hCD47-2A-hHO1]; and CAGpr [hCD46-2A-hDAF]; (iii) pTBMpr [hTBM-2A-hEPCR]; CAGpr [hCD59-P2A-hHO1]; and CAGpr [hCD46-P2A-hDAF]; (iv) PolyA-pTBMpr [hTBM]; CAG pr [hCD47-P2A-hHO1]; pEPCRpr [hEPCR]; and CAGpr [hCD46P-2A-hDAF]; (v) pTBMpr [hTBM-2A-hEPCR]; CAGpr [hCD59-P2A-hHO1]; CAGpr [hCD46-2A-hCD47]; (vi) pTBMpr [hTBM-2A-hEPCR]; CAGpr [hCD59-2A-hHO1]; CAGpr [hCD46-2A-hCD55]; (vii) U6p [GHR-gRNA-1]; U6p [GHRgRNA-2]; TRE3Gp[CAS9]; CAGpr [tTA]; CAGpr [hCD46-2A-hCD55]; (viii) SEQ ID NO: 7; (xix) SEQ ID NO: 8; (x) SEQ ID NO: 9; (xi) SEQ ID NO: 11; (xii) SEQ ID NO: 12; (xiii) SEQ ID NO: 13; or (xiv) SEQ ID NO: 14.

In some embodiments, the method of making a transgenic pig comprising at least six transgenes comprising the step of producing a multitransgenic porcine cell comprising at least six transgenes by incorporating and expressing the polycistronic vector at a single genomic locus. In some embodiments, the single genomic locus is a native locus or a modified native locus. In some embodiments, the modified native locus comprises: (i) a gene editing-mediated insertion, deletion or substitution; (ii) a transgenic DNA; (iii) a selectable gene maker; and/or (iv) a landing pad. In some embodiments, the single genomic locus is selected from the group consisting of AAVS1, ROSA26, CMAH, GHR, B4GalNT2, and GGTA1. In some embodiments, the polycistronic vector encoding the transgenes further comprises nucleotide sequences for homology recombination and/or homology directed repair (HDR) at a locus selected from the group consisting of AAVS1, GHR, ROSA26, CMAH, B4GalNT2, and GGTA1.

In one aspect, the present disclosure provides a method of making a transgenic pig comprising at least six transgenes comprising the step of: (i) transfecting a porcine cell with a single polycistronic vector comprising: (a) at least two complement inhibitor transgenes; (b) at least one immunosuppressant transgene; (c) at least one cytoprotective transgene; and (d) at least two anticoagulant transgenes; (ii) producing a multitransgenic porcine cell comprising at least six transgenes by incorporating and expressing the polycistronic vector at a single genomic locus and the multitransgenic porcine cell further comprises at least one additional genetic modification; (iii) generating a multitransgenic porcine zygote by injecting the nucleus of the multitransgenic porcine cell into a reconstructed somatic cell nuclear transfer (SCNT); and (iv) permitting the multitransgenic porcine zygote to mature into a multitransgenic pig. In some embodiments, the porcine cell and the multitransgenic pig lack expression of alpha 1,3 galactosyltransferase (GTKO), and the multitransgenic (e.g. transgenic) porcine animal further comprises at least one additional genetic modification. In some embodiments, the at least one additional genetic modification is selected from the group consisting of gene knock-outs; gene knock-ins; gene replacements; point mutations; deletions, insertions or substitutions of genes, gene fragments or nucleotides; large genomic insertions; or combinations thereof. In some embodiments, the transgenic porcine animal comprises a knockout of a gene selected from the group consisting of AAVS1, ROSA26, CMAH, B4GalNT2, GGTA1, and growth hormone receptor (GHR). In some embodiments, the gene knock-out comprises: (i) a gene editing-mediated insertion, deletion, or substitution; (ii) a CRISPR-Cas9-mediated gene editing; (iii) a homologous recombination-mediated insertion; and/or (iv) NeoR insertion-mediated gene knockout.

In some embodiments, the single genomic locus is CMAH, and the additional modification comprises the knockout of β4GalNT2, GGTA1, and GHR. In some embodiments, the single genomic locus is β4GalNT2 and the additional modification comprises the knockout of CMAH, GGTA1, and GHR. In some embodiments, the single genomic locus is GGTA1 and the additional modification comprises the knockout of β4GalNT2, CMAH, and GHR.

BRIEF DESCRIPTION OF THE DRAWINGS

FIG. 2A illustrates the insertion of the B200 vector (SEQ ID NO: 11) into the CMAH locus. FIG. 2B. illustrates the insertion of the B201 vector (SEQ ID NO: 12) into the GGTA1/Neo locus. FIG. 2C. illustrates the insertion of the B202 vector (SEQ ID NO: 13) into the GGTA1/Neo locus. FIG. 2D. illustrates the insertion of B209 vector (SEQ ID NO: 14) into the CMAH. FIG. 2E. illustrates the insertion of B212 (SEQ ID NO: 7) into the GGTA1/Neo locus. FIG. 2F illustrates the insertion of B214 (SEQ ID NO: 8) into the GGTA1/Neo locus. FIG. 2G illustrates the insertion of B217 (SEQ ID NO: 9) into the GGTA1/Neo locus. FIG. 2H shows as schematic representation of the B217 vector and a schematic representation of exemplary embodiments of the vectors described herein for the production of a multitransgenic animal comprising at least 10 modifications (e.i. 10GE pigs).

FIG. 6. shows a bar graph quantifying the results of an apoptosis assay performed on B201 and GTKO pAEC and demonstrating that while GTKO and B201 pAEC both exhibit apoptosis in response to hemin treatment, B201 cells had significantly less apoptosis than GTKO cells. FIG. 6 shows the protective function of the expressed HO-1 transgene in these cells. GTKO pAEC do not contain the HO-1 transgene and serve as a control.

Figure 7C:
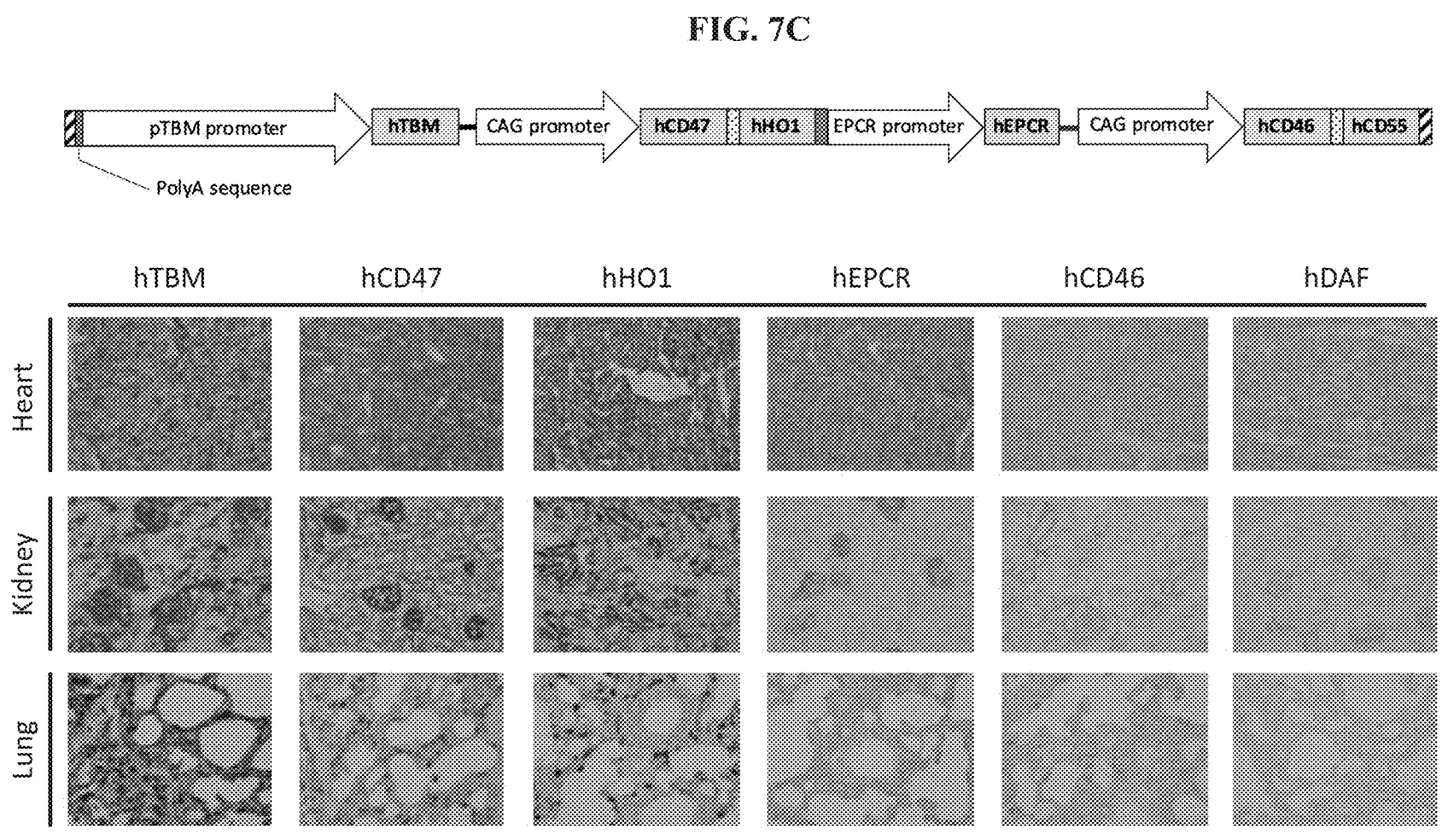
Figure 7E:
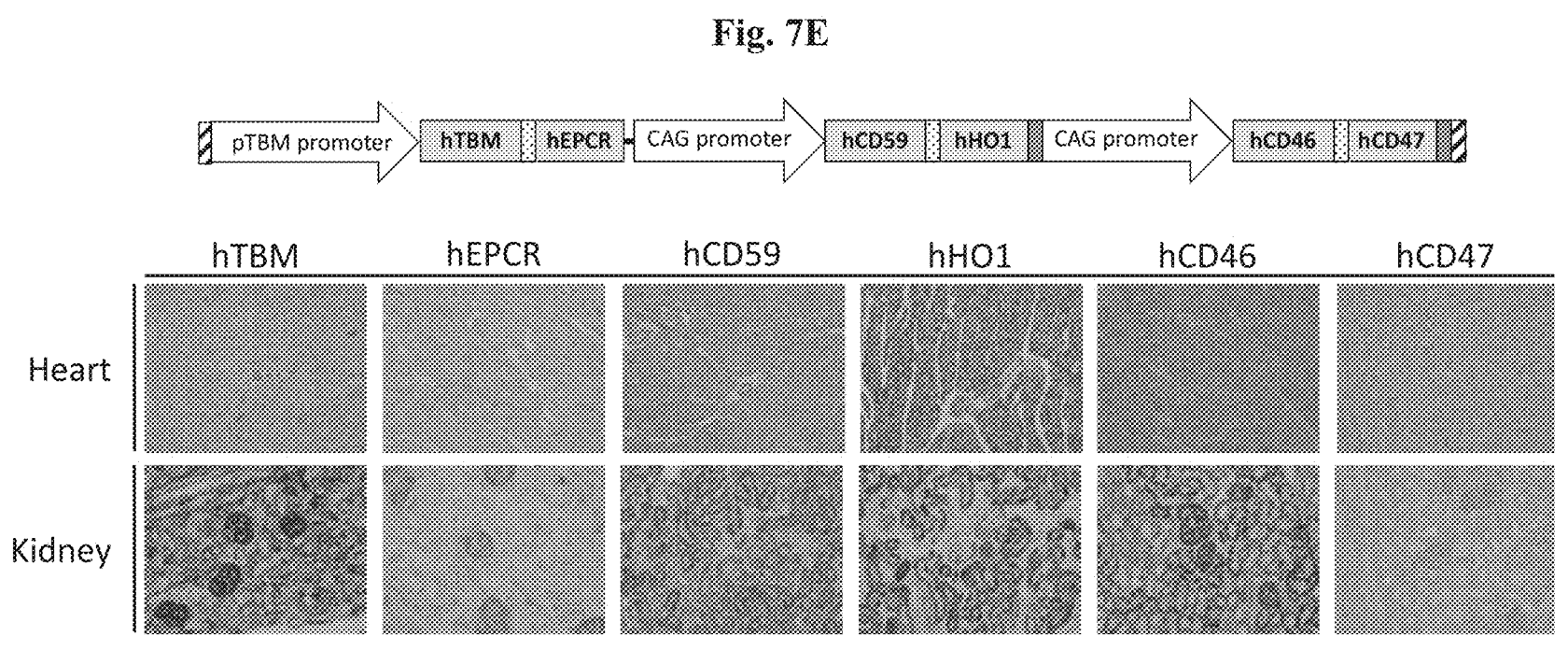

FIGS. 7A-E show representative images of immunohistochemical stainings of porcine lung, heart, and kidney tissues expressing human transgenes encoded by vectors B200 (FIG. 7A), B201 (FIG. 7B) and B202 (FIG. 7C), and of porcine heart and kidney tissues expressing human transgenes encoded by vectors B209 (FIG. 7D) and B212 (FIG. 7E).

FIGS. 8A-B show representative images of immunohistochemical stainings of porcine hearts expressing the B200 vector transgene in porcine hearts transplanted into a baboon and a human patient. FIG. 8A shows immunohistochemical stainings of porcine hearts obtained immediately post-mortem from a baboon recipient on Day 126 post-transplant, illustrating the expression of all six human transgenes encoded by the B200 vector. FIG. 8B shows immunohistochemical staining of a porcine hearts obtained from human transplant immediately post-mortem at Day 60 post-transplant, demonstrating the expression of all six human transgenes encoded by the B200 vector.

DETAILED DESCRIPTION

I. Overview

A. Multitransgenic Animals for Improving Xenotransplantation

Figure 1A:
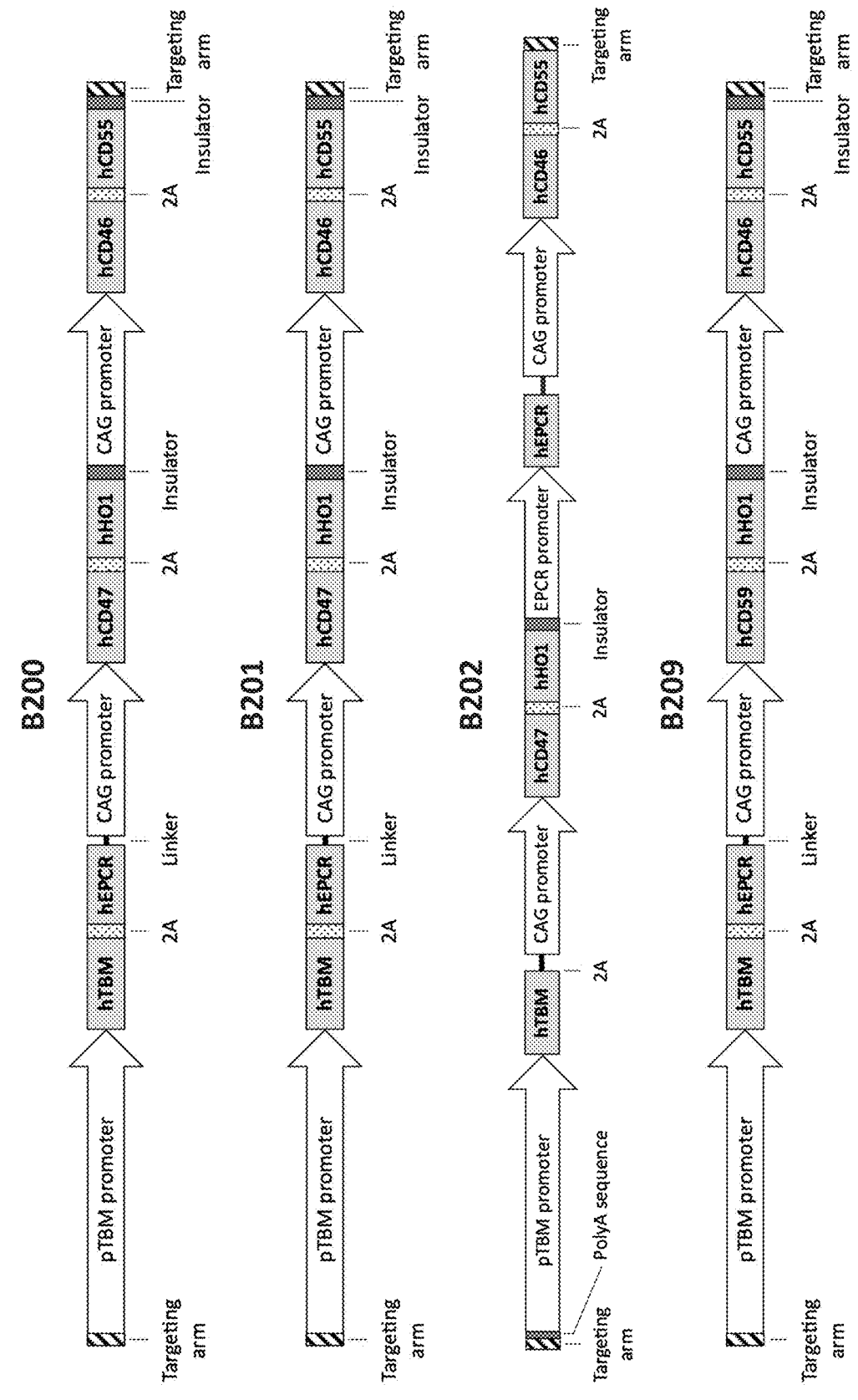
FIGS. 1A-B show a schematic illustrating of some embodiments of the multigene vectors of the present disclosure. In particular, the schematic representations of the B200 (SEQ ID NO: 11), B201 (SEQ ID NO: 12), B202 (SEQ ID NO: 13), B209 (SEQ ID NO: 14), B212 (SEQ ID NO: 7), B214 (SEQ ID NO: 8), and B217 (SEQ ID NO: 9) multicistronic vectors. B200 vector is a multicistronic vector (MCV) comprising three bi-cistron units (pTBMpr [hTBM-2A-hEPCR]/CAGpr [hCD47-2A-hHO1]/CAGpr [hCD46-2A-hDAF]) flanked by targeting arms for homology directed repair (HDR) at the CMAH gene locus. B201 vector is a MCV comprising three bi-cistron units (PolyA/pTBMpr [hTBM-2A-hEPCR]/CAGpr [hCD47-2A-hHO1]/CAGpr [hCD46-2A-hDAF]) flanked by targeting arms for HDR at GGTA1/Neo gene locus. B202 vector is a MCV comprising two mono-cistron units (PolyA/pTBMpr [hTBM]; pEPCRpr [hEPCR]) and two bi-cistron units, arranged in the following order: (PolyA/pTBMpr [hTBM]; CAGpr [hCD47-2A-hHO1]; pEPCRpr [hEPCR]/CAGpr [hCD46P-2A-hDAF] and flanked by targeting arms for HDR at GGTA1/Neo locus. B209 vector is a MCV comprising three bi-cistron units (pTBMpr [hTBM-2A-hEPCR]/CAGpr [hCD47-2A-hHO1]/CAGpr [hCD46-2A-hDAF], flanked by targeting arms for HDR at CMAH locus. B212 vector is a MCV comprising three bi-cistron units (pTBMpr [hTBM-2A-hEPCR]/CAGpr [hCD59-2A-hHO1]/CAGpr [hCD46-2A-hCD47]), flanked by targeting arms for HDR at GGTA1/Neo locus. B214 vector is a MCV comprising three bi-cistron units (pTBMpr [hTBM-2A-hEPCR]/CAGpr [hCD59-2A-hHO1]/CAGpr [hCD46-2A-hCD55]), flanked by targeting arms for HDR at GGTA1/Neo locus. B217 vector is a MCV comprising five expression units (U6promoter[GHRgRNA-1]/U6promoter[GHRgRNA-2]/, TRE3G[CAS9]/CAGpr [tTA]/CAGpr [hCD46-2A-hCD55]), flanked by targeting arms for HDR at GGTA1/Neo locus.

It is to be appreciated that certain aspects, modes, embodiments, variations, and features of the present methods are described below in various levels of detail in order to provide a substantial understanding of the present technology.

Xenotransplantation may alleviate the critical shortage of organs for human transplantation. Acceptance of porcine organs by human recipients requires numerous genetic modifications, including the silencing of major porcine xenoantigens and expression of key human proteins to modulate immune rejection, thrombosis, and inflammation. The present disclosure provides six human transgenes that, when expressed in porcine organs, are critical for long-term survival of porcine organs in non-human primates and by extension, human patients.

The present invention is directed to transgenic animals that are particularly useful as a source of organs, organ fragments, tissues or cells for xenotransplantation. In particular, the invention is directed to transgenic ungulates, and more particularly, transgenic porcine animals (pigs), useful as a source of organs, organ fragments, tissues, or cells for xenotransplantation. The invention also extends to the organs, organ fragments, tissues or cells derived from such donor animals, methods of producing such donor animals, as well as the use of organs, organ fragments, tissues or cells derived from such animal in the treatment of diseases and disorders.

Advantageously, the donor animals provide organs, organ fragments, tissues and cells that are functionally superior in a transplant (tx) context to organs, organ fragments, tissues and cells known in the art. Without wishing to be bound by any particular theory, it is believed that the organs, organ fragments, tissues and cells of the present invention have improved survival and/or functionality due to a noticeable reduction of consumptive coagulopathy (also known as disseminated intravascular coagulation (DIC)), and thrombotic microangiopathy currently observed following discordant xenotransplantation.

The organ or organ fragment may be any suitable organ, for example, a lung, heart, liver, kidney, or pancreas. The tissue may be any suitable tissue, for example, epithelial or connective tissue. The cell may be any suitable cell. The cell may be an islet cell, a pancreatic cell, a kidney cell, a cardiac cell, a hepatic cell, or a pulmonary cell.

In exemplary embodiments, the present invention provides a transgenic animal (e.g., ungulate, porcine animal) particularly useful as a source of organs (i.e., heart, kidney, liver, pancreas and lungs), organ fragments, tissues or cells for lung xenotransplantation, and extends to organs (i.e., heart, kidney, liver, pancreas and lungs), organ fragments, tissues and cells derived therefrom, as well as methods of producing the transgenic animal and methods of using the organs, tissues and cells derived therefrom for lung xenotransplantation.

B. Transgenic Animal Comprising at Least 10 Genetic Modifications

To facilitate efficient generation of transgenic founder pigs, as well as breeding and production herd expansion, inventors of the present disclosure included all six transgenes in a single multi-gene expression vector. Insertion of the vector into the porcine genome was targeted to specific loci known to be permissive for transgene expression to ensure reliable and consistent expression in transplanted organs. Targeting the multi-gene vector to a known locus or landing pad showed several advantages. First, it avoided off-target integration events by preventing potential deleterious random insertions. Second it facilitated genotypic characterization of the targeted gene vector and its genomic milieu to confirm the intended design. Third, consolidating all transgenes into a single, multi-gene vector, allowed the transgenes to be transmitted as a single locus. Transmission of the transgenes as a single locus was particularly important because it simplified and enhanced the breeding of pigs bearing all modifications (e.g. 4, 4 7, 9, 10, or 15 modifications) necessary for successful xenotransplantation. Fourth, a single multi-gene vector allowed for the addition of up to at least 10 modifications (e.g., 6 transgenes plus 4 gene knockouts) in a single step, rather than in multiple sequential steps. Accordingly, the process of the present disclosure saved weeks of time and valuable laboratory and animal resources for generating multitransgenic animals (e.g., pigs).

To generate a multitransgenic animal (e.g., pigs) comprising at least 10 modifications (e.g., 6 transgenes plus 4 gene knockouts), a single multi-gene vector that encoding at least 6 transgenes was generated. One of skill in the art understands that the aggregate size of a vector with 6 transgenes, each driven by its own promoter, would exceed the workable size for standard plasmid-based construction methods. Accordingly, the present inventors minimized the number of promoters by using viral-derived self-cleaving peptide (e.g. viral 2A sequences).

Linking the transgenes with a viral 2A sequence permitted the translation of the polypeptides/protein encoded by the transgenes from a single multitransgenic transcript, which was driven by a single promoter. This approach halved the number of promoters required, reducing the vector to a workable size.

Multi-cistronic vectors (MCVs) composed of three bicistronic units were then designed and generated. Each bicistron unit contained two human genes (e.g. the cDNA of two human genes) linked by a viral T2A or P2A peptide sequence, as defined herein, driven by an endothelial-specific promoter. In some embodiments, the endothelial-specific promoter was selected from the group consisting of a porcine thrombomodulin (TBM) promoter (pTBMpr); or porcine endothelial protein C receptor (EPCR) promoter (pEPCRpr). In some embodiments, each bicistron unit contained two human genes (cDNAs) linked by a viral T2A or P2A peptide sequence, as defined herein, driven by a constitutively active CAG promoter. In some embodiments, the constitutive promoter was selected from the group consisting of a CMV enhancer, chicken β-Actin promoter, and a rabbit β-Globulin intron. In some embodiments, the a bicistron unit was selected from the group consisting of hTBM-2A-hEPCR driven by the pTBM promoter; hCD47-

2A-hHO1 driven by the CAG promoter; hCD46-2A-hDAF driven by the CAG promoter, and hCD59-2A-hHO1 driven by the CAG promoter In some embodiments, the Multi-cistronic vectors (MCVs) contained different combinations of human genes (e.g. hTBM, hEPCR, hCD47, hHO1, hCD46, hDAF, hCD59) and each bi-cistrons was driven by a specific promoter. In some embodiments, a MCV comprised four bi-cistronic units. In some embodiments, the MCV comprises a hTBM-2A-hEPCR driven by the pTBM promoter; and hCD47-2A-hHO1, hCD46-2A-hDAF and hCD59-2A-hHO1, each driven by the CAG promoter. In some embodiments, a MCV comprising hTBM and hEPCR were driven separately by the pTBM and pEPCR promoters, respectively. A bicistronic unit comprised hTBM cDNA driven by a pTBM promoter (pTBMpr) linked via a 2A peptide to hEPCR cDNA driven by the pEPCR promoter (pEPCRpr) (pTBMpr-hTBM-2A-pEPCRpr-hTBM). A MCV comprising pTBMpr-hTBM-2A-pEPCRpr-hTBM and hCD47-2A-hHO1, hCD46-2A-hDAF and hCD59-2A-hHO1, each driven by the CAG promoter was generated.

Several bicistrons (bi-cistrons) were built to evaluate the effect of: 1) promoters, 2) transgene combination, and 3) order of transgenes within the bicistron, on transgene expression, biological function, and efficacy in supporting survival of transplanted organs. The bicistrons were used as basic units for constructiing larger, and more complex multicistronic vectors (MCVs). Selection of the bicistron combinations was based on their ability to express transgenes appropriately in a manner consistent with viability of the transgenic pigs and to enhance survival of the transplanted organ and its recipient. These unique, novel, and proven bicistron designs were an improvement over the art because they enhanced the ability to efficiently incorporate multiple transgenes into an MCV, which was and can be targeted for integration to permissive loci (e.g., CMAH, GGTA1, B4GalNT2) to ensure consistent, predictable, and appropriate expression of multiple transgenes from a single genomic locus.

To generate multitransgenic animal using the novel and unique combinations of bi-cistron, all vectors were introduced into porcine fetal fibroblasts in which the GGTA1 locus had previously been knocked out by insertional mutagenesis with NeoR. See, Dai, Y. et al., *Nat Biotechnol.* 20:251-5 (2002). For insertion into GGTA1 (B201, B202) vectors were equipped with homology arms targeted to NeoR.

C. Porcine Animal Lacking a Functional Alpha 1,3 Galactosyltransferase and at Least One Additional Genetic Modification Advantageously, organs, organ fragments, tissues or cells derived from the transgenic animal, following xenotransplanation, produce low to no levels of one or more of the following: hyperacute rejection (HAR), acute humoral rejection (AHXR/DXR) and/or acute cellular xenograft rejection (ACXR).

In one embodiment, organs, organ fragments, tissues or cells derived from the transgenic animal produce low to no levels of HAR and AHXR following xenotransplantation. In another embodiment, organs, organ fragments, tissues or cells derived from the transgenic animal produce low to no levels of HAR, AHXR and ACXR following xenotransplantation.

In exemplary embodiments, the transgenic animal is a porcine animal which lacks any expression of functional alpha 1,3 galactosyltransferase (alpha Gal) (as the result of genetic modification or otherwise) and incorporates at least several additional genetic modifications (e.g., gene knockouts, gene knock-ins, gene replacements, point mutations, deletions, insertions, or substitutions (i.e., of genes, gene fragments or nucleotides), large genomic insertions or combinations thereof). The genetic modifications may be mediated by any suitable technique, including for example homologous recombination or gene editing methods.

In exemplary embodiments, the transgenic animal is a porcine animal which lacks any expression of functional alpha 1,3 galactosyltransferase (alpha Gal) (as the result of genetic modification or otherwise) and incorporates and expresses at least six transgenes, under control of at least three promoters, at a single locus. In certain embodiments, one promoter controls expression of at least two transgenes. For example, expression of each of the at least six transgenes is controlled by a single (dedicated) promoter. In alternative embodiments, one promoter controls expression of more than one transgene, e.g., one promoter controls expression of two transgenes.

Advantageously, the six or more transgenes are co-integrated, co-expressed and co-segregate during breeding. The single locus may vary. In certain embodiments, the single locus is a native or modified native locus. The modified native locus may be modified by any suitable technique, including, but not limited to, CRISPR-induced insertion or deletion (indel), introduction of a selectable marker gene (e.g., neo) or introduction of a large genomic insert (e.g., a landing pad) intended to facilitate incorporation of one or more transgenes. In a particular embodiment, the single locus is a native or modified GGTA1 locus. The GGTA1 locus is inactivated by incorporation and expression of the at least six transgenes, for example by homologous recombination, application of gene editing or recombinase technology. The single locus may also be, for example, AAVS1, GHR, ROSA26, CMAH, or ß4GalNT2 Optionally, the transgenic animal may have one or more additional genetic modifications and/or the expression of one or more additional porcine genes may be modified by a mechanism other than genetic modification In exemplary embodiments, the transgenic animal is a porcine animal which lacks any expression of functional alpha 1,3 galactosyltransferase (alpha Gal) (as the result of genetic modification or otherwise) and incorporates and expresses at least three, at least four, at least five, at least six, at least seven, at least eight, at least nine, or at least ten transgenes or more at a single locus. In certain embodiments, expression of the at least three, at least four, at least five, at least six, at least seven, at least eight, at least nine, or at least ten transgenes or more is controlled by at least two, at least three, at least four, at least five, at least six, at least seven, at least eight, at least nine, or at least ten promoters or more. In certain embodiments, the promoter is dedicated to the transgene, i.e., one promoter controls expression of one transgene, while in alternative embodiments, one promoter controls expressions of more than one transgene, e.g., one promoter controls expression of two transgenes. Advantageously, the two or more additional transgenes are co-integrated, co-expressed and co-segregate during breeding. The single locus may vary. In certain embodiments, the single locus is a native or modified native locus. The modified native locus may be modified by any suitable technique, including, but not limited to, CRISPR-induced insertion or deletion (indel), introduction of a selectable marker gene (e.g., Neo) or introduction of a large genomic insert (e.g., a landing pad) intended to facilitate incorporation of one or more transgenes. In a particular embodiment, the single locus is a native or modified GGTA1 locus.

The GGTA1 locus is inactivated by incorporation and expression of the at least six transgenes, for example by homologous recombination, application of gene editing or recombinase technology. The single locus may also be, for example, AAVS1, GHR, ROSA26, CMAH, or ß4GalNT2. Optionally, the donor animal may have additional genetic modifications and/or the expression of one or more additional porcine genes may be modified by a mechanism other than genetic modification.

In exemplary embodiments, the transgenic animal is a porcine animal which lacks any expression of functional alpha 1,3 galactosyltransferase (alpha Gal) (as the result of genetic modification or otherwise) and incorporates and expresses at least six transgenes at a single locus (i.e., locus 1) also incorporates and expresses one or more additional transgenes at a second single locus (i.e., locus 2) and third single locus (i.e., locus 2). In certain embodiments, one promoter controls expression of one transgene, e.g., expression of each of the at least six transgenes at locus 1, locus 2, or locus 3 is controlled by a single (dedicated) promoter. In alternative embodiments, one promoter controls expression of more than one transgene, e.g., one promoter controls expression of two transgenes at locus 1. The particular loci may vary. In a particular embodiment, the first single locus is GGTA1 and the second and third single locus are, for example, CMAH, B4GalNT2, or Growth hormone receptor (GHR). In a particular embodiment, at least six transgenes are incorporated and expressed at each single locus, i.e., locus 1, locus 2, and locus 3, to produce an animal with twelve or more transgenes expressed at two distinct and independent loci.

In certain embodiments, the single locus is a native or modified native locus. The modified native locus may be modified by any suitable technique, including, but not limited to, CRISPR-induced insertion or deletion (indel), introduction of a selectable marker gene (e.g., neo) or introduction of a large genomic insert (e.g., a landing pad) intended to facilitate incorporation of one or more transgenes. Optionally, the donor animal may have additional genetic modifications and/or the expression of one or more additional porcine genes may be modified by a mechanism other than genetic modification. Advantageously, the two or more additional transgenes are co-integrated, co-expressed and co-segregate during breeding.

The at least three promoters may vary. The promoter may be exogenous or native. In exemplary embodiments, the promoters are constitutive or regulatable (e.g., tissue-specific, inducible promoter). In one embodiment all three promoters could be constitutively or ubiquitously expressed in the donor animal (e.g. from a CAG, Tie-2, ICAM-2, or similar promoter). In another embodiment with three promoters, one promoter would permit expression of transgenes in a tissue specific manner (e.g. endothelial specific expression, such as TBM, or EPCR promoter), while the second and third promoter would permit expression of one or more transgenes (at the same integration site) in a constitutive or ubiquitous manner (e.g. from a CAG or similar promoter).

In some embodiments, the promoter is a regulatable promoter. The regulatable promoter may be part of an inducible system. In some embodiments, the transgenes and/or CRISPR/Cas system is under the control of an inducible promoter. For example, the inducible system may include a tetracycline inducible promoter selected from a Tet-On or Tet-Off, small molecule two-hybrid transcription activations systems (FKBP, ABA, etc), or light inducible systems (Phytochrome, LOV domains, or cryptochrome). Examples of inducible DNA binding proteins and methods for their use are provided in U.S. 61/736,465 and U.S. 61/721,283 and WO 2014/018423 and U.S. Pat. Nos. 8,889, 418, 8,895,308, US20140186919, US20140242700, US20140273234, US20140335620, and WO2014093635 In some embodiment, the inducible system is a Light Inducible Transcriptional Effector (LITE) system that directs changes in transcriptional activity in a sequence-specific manner. The components of a light may include an enzyme or transgene, a light-responsive cytochrome heterodimer (e.g. from *Arabidopsis thaliana*), and a transcriptional activation/repression domain.

In some embodiments, the CRISPR/Cas9-mediated gene editing comprises: an inducible promoter or inducible system, a Tetracycline/Doxycycline regulatory system; a polycistronic vector comprising U6p [GHRgRNA-1]; U6p [GHRgRNA-2]; TRE3Gp[CAS9]; CAGpr [tTA]; CAGpr [hCD46-2A-hCD55]; or the nucleotide sequence of SEQ ID NO: 9. In some embodiments, the inducible promoter controls the expression of the growth hormone receptor gene.

In certain embodiments, the additional genetic modification (i.e. apart from the incorporation and expression of the multiple transgenes described above) may result in inactivation of a particular porcine gene, including, but not limited to, the porcine growth factor gene, or replacement of some or all of the porcine GHR gene with equivalent counterparts from the human GHR gene. In some embodiments, the growth hormone receptor gene expression is controlled by an inducible system comprising SEQ ID NO: 9. In some embodiments, the additional genetic modification in the GHR gene comprises a polycistronic vector comprising U6p [GHRgRNA-1]; U6p [GHRgRNA-2]; TRE3Gp[CAS9]; CAGpr [tTA]; CAGpr [hCD46-2A-hCD55]; or the nucleotide sequence of SEQ ID NO: 9. Other genes that may be inactivated in connection with the additional genetic modifications include, for example, CMP-NeuAc hydroxylase (CMAH), the isoGloboside 3 synthase, ß4Gal, NT2 Forrsman synthase, or combinations thereof. In certain embodiments, there the single locus for transgene incorporation is not GGTA1, the additional genetic modifications encompass inactivation of GGTA1.

In certain embodiments, the additional genetic modification is, for example, a gene editing-induced deletions/insertions or gene substitutions (INDELs). In certain embodiments, the additional genetic modification (i.e. apart from the incorporation and expression of the multiple transgenes described above) may result in incorporation and expression of one or more transgenes at a second locus.

In one embodiment, the present invention is a porcine animal which lacks any expression of functional alpha 1,3 galactosyltransferase (alpha Gal) (as the result of genetic modification or otherwise) and further comprises inactivation of the porcine Growth hormone receptor (GHR) gene, or replacement of some or all of the porcine GHR gene with equivalent counterparts from the human GHR gene. Optionally, the porcine animal comprises one or more additional genetic modifications. In certain embodiments, this animal may be bred with a second animal containing one or more genetic modifications.

The present invention also extends to methods of making and using such transgenic animals (or organs, tissues or cells derived therefrom). In exemplary embodiments, the present invention provides a method of making a transgenic pig expressing at least six transgenic genes but lacking expression of alpha 1,3 galactosyltransferase, comprising (i) incorporating at least six transgenes under the control of at least three promoters at a single locus within a pig genome to provide a polygene pig genome; (ii) permitting a cell comprising the polygene pig genome to mature into a transgenic pig. In certain embodiments, the pig genome is a somatic cell pig genome and the cell is a pig zygote. In certain embodiments, the pig genome is a selected from the group consisting of a gamete pig genome, zygote pig genome, an embryo pig genome or a blastocyst pig genome. In exemplary embodiments, incorporating comprises a method selected from the group consisting of biological transfection, chemical transfection, physical transfection, virus mediated transduction or transformation or combinations thereof. In certain embodiments, incorporating comprises cytoplasmic microinjection and pronuclear microinjection.

D. Multicistronic Vector System for Multitransgenic Pig Generation

The use of polycistronic expression systems was developed to insert multiple transgenes into various cell types and animals. Transgenic pigs expressing four fluorescent proteins using the 2A peptide bicistronic system and nuclear transfer via random integration of the transgenes was promising. Deng et al. Plos One, 6 (5): e19986) produced.

Moreover, the production of transgenic pigs expressing a complement regulatory factor CD59 and H-transferase genes using an IRES-mediated tricistronic vector system and nuclear transfer was generated. Attempts were made to express three genes using this tricistronic system, however, despite being present in the IRES vector, the expression of third gene in the tricistronic system was not detected in the transgenic pigs. Jeong et al., Plos One, 8 (5): e63241. Furthermore, others have reported that efficient expression of a downstream gene in a multicistronic system was impossible and could be achieved if the expression of the upstream gene was also efficient. Hurh et al, Plos One, 8:(7) e70486.

In exemplary embodiments, the methods involve use of bi- or multi-cistronic vectors that permit the transgenes to be co-integrated and co-expressed, with functional and/or production advantages, including multicistronic vectors utilizing 2A technology. In a preferred embodiment each bicistron, within a multicistronic vector containing at least six transgenes, is under control of its own promoter, and one or more promoters might result in constitutive expression of two or more genes, and the second promoter might result in tissue specific expression of two or more genes. These vectors are utilized in combination with genetic editing tools, including editing nucleases and/or site-specific integrases.

In certain embodiments, the methods involve the use of a single multi-cistronic vector that permits six or more transgenes to be co-integrated and co-expressed, to facilitate breeding where all transgenes cosegregate together, and passed as a single unit to progeny/offspring.

1. Generating a Transgenic Pig Comprising at Least Six Transgenes

The present invention provides a method of making a transgenic pig comprising at least six transgenes comprising the step of: (i) transfecting a porcine cell with a single polycistronic vector comprising (a) at least two complement inhibitor transgenes; (b) at least one immunosuppressant transgene; (c) at least one cytoprotective transgene; and (d) at least two anticoagulant transgenes; (ii) producing a multitransgenic porcine cell comprising at least six transgenes by incorporating and expressing the polycistronic vector at a single genomic locus; (iii) generating a multitransgenic porcine zygote by injecting the nucleus of the multitransgenic porcine cell into a reconstructed somatic cell nuclear transfer (SCNT); and (iv) permitting the multitransgenic porcine zygote to mature into a multitransgenic pig. In some embodiments, the porcine cell and the multitransgenic pig lack expression of alpha 1,3 galactosyltransferase. In some embodiments, the polycistronic vector comprises a bicistronic unit selected from the group consisting of: porcine TBM promoter driving a human TBM transgene linked via a 2A peptide to a human EPCR transgene (pTBMpr [hTBM-2A-hEPCR]); a CAG promoter driving a human CD47 transgene linked via 2A peptide to a human HO-1 transgene (CAGpr [hCD47-2A-hHO1]); a CAG promoter driving a human CD46 transgene linked via 2A peptide to a human DAF transgene (CAGpr [hCD46-2A-hDAF]); Poly-A signal fused to a porcine TBM promoter driving a human TBM transgene linked via a 2A peptide to a human EPCR transgene (PolyA/pTBMpr [hTBM-2A-hEPCR]); a CAG promoter driving a human CD59 transgene linked via 2A peptide to a human HO-1 transgene (CAGpr [hCD59-2A-hHO1]); a porcine EPCR promoter driving a human TBM transgene linked via a 2A peptide to a human EPCR transgene (pEPCRpr [hTBM-2A-hEPCR]); (vii) a CAG promoter driving a human CD46 transgene linked via 2A peptide to a human CD47 transgene (CAGpr [hCD46-2A-hCD47]); (viii) a first U6 promoter driving a first GHR gRNA linked to a second U6 promoter driving a second GHR gRNA (U6p [GHRgRNA-1]; U6p [GHRgRNA-2]), wherein the first and second gRNA are the same or different; (xix) a TRE3G promoter driving a Cas endonuclease, linked via an insulator to a CAG promoter driving a tTA (TRE3Gp [CAS9]; CAGpr [tTA]); and a combination thereof. In some embodiments, the polycistronic vector comprises: pTBMpr [hTBM-2A-hEPCR], CAGpr [hCD47-2A-hHO1], and CAGpr [hCD46-2A-hDAF]; PolyA-pTBMpr [hTBM-2A-hEPCR], CAGpr [hCD47-2A-hHO1], and CAGpr [hCD46-2A-hDAF]; pTBMpr [hTBM-2A-hEPCR], CAGpr [hCD59-P2A-hHO1], and CAGpr [hCD46-P2A-hDAF]; PolyA-pTBMpr [hTBM], CAG pr [hCD47-P2A-hHO1], pEPCRpr [hEPCR], and CAGpr [hCD46P-2A-hDAF]; pTBMpr [hTBM-2A-hEPCR], CAGpr [hCD59-P2A-hHO1], and CAGpr [hCD46-2A-hCD47]; pTBMpr [hTBM-2A-hEPCR], CAGpr [hCD59-2A-hHO1], and CAGpr [hCD46-2A-hCD55]; U6p [GHRgRNA-1], U6p [GHRgRNA-2], TRE3Gp[CAS9], CAGpr [tTA], and CAGpr [hCD46-2A-hCD55]; SEQ ID NO: 7; SEQ ID NO: 8; SEQ ID NO: 9; SEQ ID NO: 11; SEQ ID NO: 12; SEQ ID NO: 13; or SEQ ID NO: 14.

In some embodiments, the porcine cell is a somatic cell. In some embodiments, the multitransgenic porcine cell comprises at least seven, at least eight, at least nine, or at least ten transgenes. In some embodiments, at least six transgenes are encoded by a polycistronic vector, optionally wherein the polycistronic vector comprises at least three bicistronic units. In some embodiments, each bicistronic unit comprises a promoter driving a first transgene linked via a cleavage peptide to a second transgene. In some embodiments, a first bicistronic unit comprises the at least two anticoagulant transgenes, a second bicistronic comprises at least two complement inhibitor transgenes; and a third bicistronic unit comprises the at least one cytoprotective transgene and the at least one immunosuppressant transgene. In some embodiments, the cleavage peptide is selected from the group consisting of T2A, P2A, F2A, and E2A. In some embodiments, the at least six transgenes are encoded by a polycistronic vector comprising: (i) at least two bicistronic unit, wherein each bicistronic unit comprises a promoter driving a first transgene linked via a cleavage peptide to a second transgene; and at least two non-polycistronic transgenes, wherein each non-polycistronic transgene is driven by its own promoter. In some embodiments, at least one bicistronic unit is driven by a tissue-specific promoter, and at least two bicistronic units are driven by a dedicated constitutive promoter. In some embodiments, at least one bicistronic unit is driven by an inducible promoter. In some embodiments, the at least two bicistronic units are each driven by a constitutive promoter, and the at least two non-polycistronic transgenes are each driven by a tissue-specific promoter.

2. Making a Transgenic Pig Comprising at Least Six Transgenes

The present invention provides a transgenic porcine animal comprising genetic modifications that result in the lack of expression of functional alpha 1,3 galactosyltransferase gene; and incorporation and expression at a single genomic locus of: (a) at least two complement inhibitor transgenes; (b) at least one immunosuppressant transgene; (c) at least one cytoprotective transgene; and (d) at least two anticoagulant transgenes. In some embodiments, the transgenic porcine animal comprises at least six, at least seven, or at least eight, at least nine, at least ten, at least eleven, or at least twelve transgenes. The transgenic animal comprises at least six transgenes. In some embodiments, the at least six transgenes are encoded by a polycistronic vector, optionally the polycistronic vector comprises at least three bicistronic units. In some embodiments, each bicistronic unit comprises a promoter driving a first transgene linked via a cleavage peptide to a second transgene. In some embodiments, a first bicistronic unit comprises the at least two anticoagulant transgenes, a second bicistronic comprises at least two complement inhibitor transgenes; and a third bi-cistronic unit comprises the at least one cytoprotective transgene and the at least one immunosuppressant transgene. In some embodiments, the cleavage peptide is selected from the group consisting of T2A, P2A, F2A, and E2A.

As used herein, a "self-cleaving peptide" or "2A peptide" or "viral 2A sequence" refers to an oligopeptide that allow multiple proteins to be encoded as polyproteins, which dissociate into component proteins upon translation. Use of the term "self-cleaving" is not intended to imply a proteolytic cleavage reaction. Various "self-cleaving" or "2A peptides" or "viral 2A sequences" are known to those of skill in the art, including, without limitation, those found in members of the Picomaviridae virus family such as, foot-and-mouth disease virus (FMDV), equine rhinitis A virus (ERAVO, Thosea asigna virus (TaV), and porcine tescho virus-1 (PTV-1); and carioviruses, such as theilovirus and encephalomyocarditis viruses. Viral 2A sequences derived from FMDV, ERAV, PTV-1, and TaV are referred to herein as "F2A," "E2A," "P2A," and "T2A," respectively. Those of skill in the art would be able to select the appropriate self-cleaving peptide for use in the present invention.

In some embodiments, the transgenes are encoded by a polycistronic vector comprising (i) at least two bicistronic unit, wherein each bicistronic unit comprises a promoter driving a first transgene linked via a cleavage peptide to a second transgene; and (ii) at least two non-polycistronic transgenes. Each non-polycistronic transgene is driven by its own promoter. In some embodiments, the at least one bicistronic unit is driven by a tissue-specific promoter, and at least two bicistronic units are driven by a dedicated constitutive promoter. In some embodiments, the at least two bicistronic units are each driven by a constitutive promoter, and the at least two non-polycistronic transgenes are each driven by a tissue-specific promoter.

In some embodiments, the polycistronic vector comprises a bicistronic unit selected from the group consisting of: porcine TBM promoter driving a human TBM transgene linked via a 2A peptide to a human EPCR transgene (pTBMpr [hTBM-2A-hEPCR]); a CAG promoter driving a human CD47 transgene linked via 2A peptide to a human HO-1 transgene (CAGpr [hCD47-2A-hHO1]); a CAG promoter driving a human CD46 transgene linked via 2A peptide to a human DAF transgene (CAGpr [hCD46-2A-hDAF]); Poly-A signal fused to a porcine TBM promoter driving a human TBM transgene linked via a 2A peptide to a human EPCR transgene (PolyA/pTBMpr [hTBM-2A-hEPCR]); a CAG promoter driving a human CD59 transgene linked via 2A peptide to a human HO-1 transgene (CAGpr [hCD59-2A-hHO1]); a porcine EPCR promoter driving a human TBM transgene linked via a 2A peptide to a human EPCR transgene (pEPCRpr [hTBM-2A-hEPCR]); a CAG promoter driving a human CD46 transgene linked via 2A peptide to a human CD47 transgene (CAGpr [hCD46-2A-hCD47]); a first U6 promoter driving a first GHR gRNA linked to a second U6 promoter driving a second GHR gRNA (U6p [GHRgRNA-1]; U6p [GHR-gRNA-2]), wherein the first and second gRNA are the same or different; a TRE3G promoter driving a Cas endonuclease, linked via an insulator to a CAG promoter driving a tTA (TRE3Gp[CAS9]; CAGpr [tTA]); and a combination thereof. In some embodiments, the porcine promoter may be an endogenous promoter or an exogenous promoter.

In some embodiments, the polycistronic vector comprises pTBMpr [hTBM-2A-hEPCR]; CAGpr [hCD47-2A-hHO1]; and CAGpr [hCD46-2A-hDAF]; PolyA-pTBMpr [hTBM-2A-hEPCR]; CAGpr [hCD47-2A-hHO1]; and CAGpr [hCD46-2A-hDAF]; pTBMpr [hTBM-2A-hEPCR]; CAGpr [hCD59-P2A-hHO1]; and CAGpr [hCD46-P2A-hDAF]; PolyA-pTBMpr [hTBM]; CAG pr [hCD47-P2A-hHO1]; pEPCRpr [hEPCR]; and CAGpr [hCD46P-2A-hDAF]; pTBMpr [hTBM-2A-hEPCR], CAGpr [hCD59-P2A-hHO1], and CAGpr [hCD46-2A-hCD47]; pTBMpr [hTBM-2A-hEPCR], CAGpr [hCD59-2A-hHO1], and CAGpr [hCD46-2A-hCD55]; U6p [GHRgRNA-1], U6p [GHR-gRNA-2], TRE3Gp[CAS9], CAGpr [tTA], and CAGpr [hCD46-2A-hCD55]; SEQ ID NO: 7; SEQ ID NO: 8; SEQ ID NO: 9; SEQ ID NO: 11; SEQ ID NO: 12; SEQ ID NO: 13; or SEQ ID NO: 14.

E. Method of Treatment

The present invention also extends to method of treating a subject in need thereof with one or more organs, organ fragments, tissues or cells derived from a transgenic animal of the present invention. In exemplary embodiments, the organ is a liver, lung, heart, pancreas, or other solid organs. Examples of tissues contemplated by the present invention include, without limitation, epithelial and connective tissues. Transplants involving more than one organ or organ fragment are also contemplated by the invention. For example transplants involving a lung, a pancreas, a liver, a retina, a heart, a kidney, or a fragment thereof are contemplated by the present invention.

The present invention provides a method for xenotransplantation comprising administering to a subject in need thereof porcine organs, tissue, or cells derived from the transgenic porcine animal of the present invention. In some embodiments, the subject is a non-human primate or a human. In some embodiments, the organ is selected from the group consisting of heart, lung, liver, and kidney. In some embodiments, the tissue is selected from the group consisting of vascular tissue, retinal tissue, neural tissue, and corneal tissue. In some embodiments, the method of treatment further comprises administering a clinically relevant immunosuppressant regimen to the subject following xeno-transplantation of the organs, tissue or cells derived from the transgenic porcine animal of the present invention.

II. Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "adverse event" refers to any unfavorable or unintended sign (including an abnormal laboratory finding, for example), symptom, or disease temporarily associated with the use of a medicinal product (e.g., a xenotransplant), whether or not considered related to the medical product.

As used herein, the term "animal" refers to a mammal. In specific embodiments, the animals are at least six months old. In certain embodiments, the animals are postweaning age. In certain embodiments, the animal survives to reach breeding age. The animals of the invention are "genetically modified" or "transgenic," which means that they have a transgene, or other foreign DNA, added or incorporated, or an endogenous gene modified, including, targeted, recombined, interrupted, deleted, disrupted, replaced, suppressed, enhanced, or otherwise altered, to mediate a genotypic or phenotypic effect in at least one cell of the animal and typically into at least one germ line cell of the animal. In some embodiments, the animal may have the transgene integrated on one allele of its genome (heterozygous transgenic). In other embodiments, animal may have the transgene on two alleles (homozygous transgenic).

As used herein, the term "breeding" or "bred" or derivatives thereof refers to any means of reproduction, including both natural and artificial means.

As used herein, the term "breeding herd" or "production herd" refers to a group of transgenic animals generated by the methods of the present invention. In some embodiments, genetic modifications may be identified in animals that are then bred together to form a herd of animals with a desired set of genetic modifications (or a single genetic modification). See WO 2012/112586; PCT/US2012/025097. These offspring may be further bred to produce different or the same set of genetic modifications (or single genetic modification) in their progeny. This cycle of breeding for animals with desired genetic modification(s) may continue for as long as one desires. "Herd" in this context may comprise multiple generations of animals produced over time with the same or different genetic modification(s). "Herd" may also refer to a single generation of animals with the same or different genetic modification(s).

As used herein, the term "CRISPR" or "Clustered Regularly Interspaced Short Palindromic Repeats" or "SPIDRs" or "SPacer Interspersed Direct Repeats" refers to a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. CRISPR/Cas molecules are components of a prokaryotic adaptive immune system that is functionally analogous to eukaryotic RNA interference, using RNA base pairing to direct DNA or RNA cleavage. Directing DNA DSBs requires two components: the Cas9 protein, which functions as an endonuclease, and CRISPR RNA (crRNA) and tracer RNA (tracrRNA) sequences that aid in directing the Cas9/RNA complex to target DNA sequence (Makarova et al., Nat Rev Microbiol, 9(6):467-477, 2011). The modification of a single targeting RNA can be sufficient to alter the nucleotide target of a Cas protein. In some cases, crRNA and tracrRNA can be engineered as a single cr/tracrRNA hybrid to direct Cas9 cleavage activity (Jinek et al., Science, 337(6096):816-821, 2012). The CRISPR/Cas system can be used in bacteria, yeast, humans, and zebrafish, as described elsewhere (see, e.g., Jiang et al., Nat Biotechnol, 31(3):233-239, 2013; Dicarlo et al., Nucleic Acids Res, doi:10.1093/nar/gkt135, 2013; Cong et al., Science, 339(6121):819-823, 2013; Mali et al., Science, 339 (6121):823-826, 2013; Cho et al., Nat Biotechnol, 31(3): 230-232, 2013; and Hwang et al., Nat Biotechnol, 31(3): 227-229, 2013).

As used herein, the term "clinically relevant immunosuppressive regimen" refers to a clinically acceptable regimen of immunosuppressant drugs provided to a patient following organ, tissue or cell transplantation of a genetically modified pig as disclosed herein. Determining clinical relevance requires a judgment call generally by the FDA balancing acceptable risk versus potential benefit such that human safety is preserved while the efficacy of the drug or treatment is maintained.

As used herein, the term "constitutive" promoter refers to a nucleotide sequence which, when operably linked with a polynucleotide which encodes or specifies a gene product, causes the gene product to be produced in a cell under most or all physiological conditions of the cell.

As used herein, the term "donor" is meant to include any non-human animal that may serve as a source of donor organs, tissue, or cells for xenotransplantation. The donor may be in any stage of development, including, but not limited to fetal, neonatal, young and adult.

As used herein, the term "endogenous" as used herein in reference to nucleic acid sequences and an animal refers to any nucleic acid sequence that is naturally present in the genome of that animal. An endogenous nucleic acid sequence can comprise one or more gene sequences, intergenic sequences, portions of gene sequences or intergenic sequences, or combinations thereof.

As used herein, the terms "endothelial-specific", "specific transgene expression in endothelial tissue", "specifically expresses at least one transgene in endothelial tissue" and the like, it is understood that these terms refer to a transgene under control of an endothelial-specific regulatory element that allows for the restricted expression of a transgene in endothelial tissue and/or cells. The transgene function and expression are restricted to endothelial tissue and/or cells.

As used herein, the term "endothelium" is an epithelium of mesoblastic origin composed of a single layer of thin flattened cells that lines internal body cavities. For example, the serous cavities or the interior of the heart contain an endothelial cells lining and the "vascular endothelium" is the endothelium that lines blood vessel.

As used herein, the term "endothelial-specific regulatory element" and the like refer to a promoter, enhancer, or a combination thereof wherein the promoter, enhancer or a combination thereof drives restricted expression of a transgene in endothelial tissue and/or cells. The regulatory element provides transgene function and expression restricted to endothelial tissue and/or cells.

As used herein, the term "enhancer" refers to an element in a nucleic acid construct intended to facilitate increased expression of a transgene in a tissue-specific manner. Enhancers are outside elements that drastically alter the efficiency of gene transcription (Molecular Biology of the Gene, Fourth Edition, pp. 708-710, Benjamin Cummings Publishing Company, Menlo Park, CA © 1987). In certain embodiments, the animal expresses a transgene under the control of a promoter in combination with an enhancer element. In some embodiments, the promoter is used in combination with an enhancer element which is a non-coding or intronic region of DNA intrinsically associated or co-localized with the promoter.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The term "gene" is used herein broadly to refer to any segment of DNA associated with a biological function. Thus, genes include coding sequences and/or the regulatory sequences required for their expression. Genes can also include non-expressed DNA segments that, for example, form recognition sequences for other proteins. Genes can be obtained from a variety of sources, including cloning from a source of interest, or synthesizing from known or predicted sequence information, and may include sequences designed to have desired parameters.

As used herein, the term "gene editing" refers a type of genetic engineering in which DNA is inserted, replaced, or removed from a genome using gene editing tools. Examples of gene editing tools include, without limitation, zinc finger nucleases, TALEN and CRISPR.

As used herein, the term "gene-editing mediated" or similar terms refers to a modification of the gene (e.g., a deletion, substitution, re-arrangement) that involves the use of gene-editing/gene-editing tools.

As used herein, the term "gene knock-out" refers to a genetic modification resulting from the disruption of the genetic information encoded in a chromosomal locus.

As used herein, the term "gene knock-in" is a genetic modification resulting from the replacement of the genetic information encoded in a chromosomal locus with a different DNA sequence.

The term "genetic modification" as used herein refers to one or more alterations of a nucleic acid, e.g., the nucleic acid within an organism's genome. For example, genetic modification can refer to alterations, additions (e., gene knock-ins), and/or deletion of genes (e.g., gene knock-outs).

As used herein, the term "high" with reference to levels of expression refers to a level of expressed considered sufficient to provide a phenotype (detectable expression or therapeutic benefit). Typically a 'high' level of expression is sufficient to be capable of reducing graft rejection including hyperacute rejection (HAR), acute humoral xenograft rejection (AHXR), T cell-mediated cellular rejection and immediate blood-mediated inflammatory response (IBMIR).

As used herein, the term "homology driven recombination" or "homology direct repair" or "HDR" is used to refer to a homologous recombination event that is initiated by the presence of double strand breaks (DSBs) in DNA (Liang et al. 1998); and the specificity of HDR can be controlled when combined with any genome editing technique known to create highly efficient and targeted double strand breaks and allows for precise editing of the genome of the targeted cell; e.g. the CRISPR/Cas9 system (Findlay et al. 2014; Mali et al. February 2014; and Ran et al. 2013).

As used herein, the term "enhanced homology driven insertion or knock-in" is described as the insertion of a DNA construct, more specifically a large DNA fragment or construct flanked with homology arms or segments of DNA homologous to the double strand breaks, utilizing homology driven recombination combined with any genome editing technique known to create highly efficient and targeted double strand breaks and allows for precise editing of the genome of the targeted cell; e.g. the CRISPR/Cas9 system. (Mali et al. February 2013).

As used herein, the term "humanized" refers to nucleic acids or proteins whose structures (i.e., nucleotide or amino acid sequences) include portions that correspond substantially or identically with structures of a particular gene or protein found in nature in a non-human animal, and also include portions that differ from that found in the relevant particular non-human gene or protein and instead correspond more closely with comparable structures found in a corresponding human gene or protein. In some embodiments, a "humanized" gene is one that encodes a polypeptide having substantially the amino acid sequence as that of a human polypeptide (e.g., a human protein or portion thereof—e.g., characteristic portion thereof). The term "hyperacute rejection" refers to rejection of a transplanted material or tissue occurring or beginning within the first 24 hours after transplantation.

The term "implant" or "transplant" or "graft" as used herein shall be understood to refer to the act of inserting tissue or an organ into a subject under conditions that allow the tissue or organ to become vascularized; and shall also refer to the so-inserted (i.e. "implanted" or "transplanted" or "grafted") tissue or organ. Conditions favoring vascularization of a graft in a mammal comprise a localized tissue bed at the site of the graft having an extensive blood supply network.

As used herein, the term "immunomodulator" refers to a transgene with the ability to modulate the immune responses. In exemplary embodiments, an immunomodulator according to the present invention can be a complement inhibitor or an immunosuppressant. In specific embodiments, the immunomodulator is a complement inhibitor. The complement inhibitor can be CD46 (or MCP), CD55 CD59 and/or CRI. In a specific embodiment, at least two complement inhibitors can be expressed. In one embodiment, the complement inhibitors can be CD55 and CD59. In another embodiment, the immunomodulator can be a class II transactivator or mutants thereof. In certain embodiments, the immunomodulator can be a class II transactivator dominant negative mutant (CIITA-DN). In another specific embodiment, the immunomodulator is an immunosuppressant. The immunosuppressor can be CTLA4-Ig. Other immunomodulators can be selected from the group but not limited to CIITA-DN, PDL I, PDL2, or tumor necrosis factor-α related-inducing ligand (TRAIL), Fas ligand (FasL, CD95L) CD47, known as integrin-associated protein (CD47), HLA-E, HLA-DP, HLA-DQ, and/or HLA-DR.

As used herein, an "inducible" promoter is a promoter which is under environmental or developmental regulation. Examples of promoters that are inducible and that allow for spatiotemporal control of gene editing or gene expression may use a form of energy. The form of energy may include but is not limited to sound energy, electromagnetic radiation, chemical energy and/or thermal energy. Examples of inducible systems include tetracycline inducible promoters (Tet-On or Tet-Off), small molecule two-hybrid transcription activations systems (FKBP, ABA, etc), or light inducible systems (Phytochrome, LOV domains, or cryptochrome), such as a Light Inducible Transcriptional Effector (LIT E) that direct changes in transcriptional activity in a sequence-specific manner. The components of a light inducible system may include an enzyme or a transgene, a light-responsive cytochrome heterodimer (e.g. from *Arabidopsis thaliana*), and a transcriptional activation/repression domain. Further examples of inducible DNA binding proteins and methods for their use are provided in U.S. 61/736,465 and U.S. 61/721,283.

Transient or inducible expression can be achieved by using, for example, chemical-regulated promotors, where the application of an exogenous chemical may induce gene expression. The modulation of gene expression may also be obtained by a chemical-repressible promoter, where application of the chemical represses gene expression. Chemical-inducible promoters include, but are not limited to, the maize 1n2-2 promoter, activated by benzene sulfonamide herbicide safeners (De Veylder et al., (1997) Plant Cell Physiol 38:568-77), the maize GST promoter (GST-11-27, WO93/01294), activated by hydrophobic electrophilic compounds used as pre-emergent herbicides, and the tobacco PR-1 a promoter (Ono et al., (2004) Biosci Biotechnol Biochem 68:803-7) activated by salicylic acid. Promoters which are regulated by antibiotics, such as tetracycline-inducible and tetracycline-repressible promoters (Gatz et al., (1991) Mol Gen Genet 227:229-37; U.S. Pat. Nos. 5,814, 618 and 5,789,156) can also be used herein.

As used herein, the term "landing pad" or "engineered landing pad" refers to a nucleotide sequence containing at least one recognition sequence that is selectively bound and modified by a specific polynucleotide modification enzyme such as a site-specific recombinase and/or a targeting endonuclease. In general, the recognition sequence(s) in the landing pad sequence does not exist endogenously in the genome of the cell to be modified. The rate of targeted integration may be improved by selecting a recognition sequence for a high efficiency nucleotide modifying enzyme that does not exist endogenously within the genome of the targeted cell. Selection of a recognition sequence that does not exist endogenously also reduces potential off-target integration. In other aspects, use of a recognition sequence that is native in the cell to be modified may be desirable. For example, where multiple recognition sequences are employed in the landing pad sequence, one or more may be exogenous, and one or more may be native.

Multiple recognition sequences may be present in a single landing pad, allowing the landing pad to be targeted sequentially by two or more polynucleotide modification enzymes such that two or more unique sequences can be inserted. Alternatively, the presence of multiple recognition sequences in the landing pad, allows multiple copies of the same sequence to be inserted into the landing pad. A landing pad may comprise at least one recognition sequence. For example, an exogenous nucleic acid may comprise at least one, at least two, at least three, at least four, at least five, at least six, at least seven, at least eight, at least nine, or at least ten or more recognition sequences. In embodiments comprising more than one recognition sequence, the recognition sequences may be unique from one another (i.e. recognized by different polynucleotide modification enzymes), the same repeated sequence, or a combination of repeated and unique sequences. Optionally, the landing pad may include one or more sequences encoding selectable markers such as antibiotic resistance genes, metabolic selection markers, or fluorescence proteins. Other sequences, such as transcription regulatory and control elements (i.e., promoters, partial promoters, promoter traps, start codons, enhancers, introns, insulators and other expression elements) can also be present.

As used herein, the term "large targeting vector" or "LTVEC" includes large targeting vectors for eukaryotic cells that are derived from fragments of cloned genomic DNA larger than those typically used by other approaches intended to perform homologous gene targeting in eukaryotic cells. Examples of LTVEC, include, but are not limited to, bacterial artificial chromosome (BAC), a human artificial chromosome (HAC), and yeast artificial chromosome (YAC).

As used herein, the term "genomic locus" or "locus" (plural loci) is the specific location of a gene or DNA sequence on a chromosome, and can include both intron or exon sequences of a particular gene. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, introns, exons, promoter sequences, terminators, translational regulatory sequences such as ribosome binding sites and internal ribosome entry sites, enhancers, silencers, insulators, boundary elements, 5' or 3' regulatory sequences, replication origins, matrix attachment sites and locus control regions.

As used herein, the term "lung transplantation" refers to a surgical procedure in which a patient's diseased lungs are partially or totally replaced by lungs which come from a donor. Lung transplantation may be "single", in which just one of the two lungs is removed in the recipient and replaced with a single lung from the donor or "bilateral" which involves removing both lungs, one on each side and replacing both the lungs from the donor. In certain embodiments, the lung is transplanted together with a heart.

As used herein the term "lung preservation" refers to the process of maintaining and protecting a donor lung from the time of lung procurement up until implantation in the recipient has occurred.

As used herein, the term "heart transplantation" refers to a surgical procedure in which a patient's diseased heart is totally replaced by a heart from a donor. In certain embodiments, the heart is transplanted together with the lungs.

As used herein, the term "heart valve transplantation" refers to a surgical procedure in which a patient's diseased heart valve is replaced by a heart valve from a donor.

As used herein the term "heart preservation" refers to the process of maintaining and protecting a donor heart from the time of lung procurement up until implantation in the recipient has occurred.

As used herein, the term "kidney transplantation" refers to a surgical procedure in which a patient receives a donor kidney with or without their diseased kidney or kidneys being removed. In certain embodiments, the kidney is transplanted into the recipient's lower abdominal cavity.

As used herein, the phrase "loss of transplant function" refers to any physiological disruption or dysfunction of the normal processes the organ or tissue exhibits in the donor animal.

As used herein, the term "mammal" refers to any non-human mammal, including but not limited to pigs, sheep, goats, cattle (bovine), deer, mules, horses, monkeys, dogs, cats, rats, and mice. In certain embodiments, the animal is a porcine animal. The porcine animal may be of any size. For example, the porcine animal may weigh from about 10 pounds to about 500 pounds. In some embodiments, the porcine animal may weigh more than 500 pounds. The weight of the porcine animal may depend on the xenotransplant recipient's weight and size. In specific embodiments, the mammal is a porcine sow and has given birth at least one time. In certain embodiments, the mammal is a non-human primate, e.g., a monkey or baboon.

As used herein, a "marker" or a "selectable marker" is a selection marker that allows for the isolation of rare transfected cells expressing the marker from the majority of treated cells in the population. Such marker's gene's include, but are not limited to, neomycin phosphotransferase and hygromycin B phosphotransferase, or fluorescing proteins such as GFP.

As used herein, the term "nucleotide", "polynucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown.

The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein, the phrase "operably linked" comprises a relationship wherein the components operably linked function in their intended manner. In one instance, a nucleic acid sequence encoding a protein may be operably linked to regulatory sequences (e.g., promoter, enhancer, silencer sequence, etc.) so as to retain proper transcriptional regulation The term "organ" as used herein refers to is a collection of tissues joined in a structural unit to serve a common function. The organ may be a solid organ. Solid organs are internal organs that has a firm tissue consistency and is neither hollow (such as the organs of the gastrointestinal tract) nor liquid (such as blood). Examples of solid organs include the heart, kidney, liver, lungs, pancreas, spleen and adrenal glands.

As used herein, the term "primate" refers to of various mammals of the order Primates, which consists of the lemurs, lorises, tarsiers, New World monkeys, Old World monkeys, and apes including humans, and is characterized by nails on the hands and feet, a short snout, and a large brain. In certain embodiments, the primate is a non-human primate. In other embodiments, the primate is a human.

As used herein, the term "promoter" refers to a region of DNA, generally upstream (5') of a coding region, which controls at least in part the initiation and level of transcription. Reference herein to a "promoter" is to be taken in its broadest context and includes the transcriptional regulatory sequences of a classical genomic gene, including a TATA box or a non-TATA box promoter, as well as additional regulatory elements (i.e., activating sequences, enhancers and silencers) that alter gene expression in response to developmental and/or environmental stimuli, or in a tissue-specific or cell-type-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene, although they may also be many kb away. Promoters may contain additional specific regulatory elements, located more distal to the start site to further enhance expression in a cell, and/or to alter the timing or inducibility of expression of a structural gene to which it is operably connected.

As used herein, the terms "porcine", "porcine animal", "pig" and "swine" are generic terms referring to the same type of animal without regard to gender, size, or breed.

As used herein, the term "recognition site" or "recognition sequence" refers to a specific DNA sequence recognized by a nuclease or other enzyme to bind and direct site-specific cleavage of the DNA backbone.

As used herein, the term "recombination site" refers to a nucleotide sequence that is recognized by a site-specific recombinase and that can serve as a substrate for a recombination event.

As used herein, the terms "regulatory element" and "expression control element" are used interchangeably and refer to nucleic acid molecules that can influence the transcription and/or translation of an operably linked coding sequence in a particular environment. These terms are used broadly and cover all elements that promote or regulate transcription, including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include promoters, operator sequences and a ribosome binding sites. Regulatory elements that are used in eukaryotic cells may include, without limitation, promoters, enhancers, splicing signals, and polyadenylation signals.

As used herein, the term "regulatable promoter" refers to a promoter that can be used to regulate whether the peptide is expressed in the animal, tissue or organ. The regulatable promotor could be tissue specific and only expressed in a specific tissue, or temporally regulatable (turned on at a specific time (driven by developmental stage), or inducible such that is only turned on or off (expressed or not) as controlled by inducible elements. (can also be inducible promoters such as immune inducible promoter and cytokine response promoters. eg. induced by interferon gamma, TNF-alpha, IL-1, IL-6 or TGF-beta) For example, expression can be prevented while the organ or tissue is part of the pig, but expression induced once the pig has been transplanted to the human for a period of time to overcome the cellular immune response. In addition, the level of expression can be controlled by a regulatable promoter system to ensure that immunosuppression of the recipient's immune system does not occur.

As used herein, the terms "regulatory sequences," "regulatory elements," and "control elements" are interchangeable and refer to polynucleotide sequences that are upstream (5' non-coding sequences), within, or downstream (3' non-translated sequences) of a polynucleotide target to be expressed. Regulatory sequences influence, for example, the timing of transcription, amount or level of transcription, RNA processing or stability, and/or translation of the related structural nucleotide sequence. Regulatory sequences may include activator binding sequences, enhancers, introns, polyadenylation recognition sequences, promoters, repressor binding sequences, stem-loop structures, translational initiation sequences, translation leader sequences, transcription termination sequences, translation termination sequences, primer binding sites, and the like.

The term "safe harbor" locus as used herein refers to a site in the genome where transgenic DNA (e.g., a construct) can be added without harm and produce a consistent level expression. In certain embodiments, the present invention involves incorporation and expression of transgenic DNA includes transgenes within a safe harbor locus.

As used herein, the term "site-specific recombinase" refers to group of enzymes that can facilitate recombination between "recombination sites" where the two recombination sites are physically separated within a single nucleic acid molecule or on separate nucleic acid molecules. Examples of "site-specific recombinase" include, but are not limited to, phiC31, att, Bxb1, R4 (integrases) and or, Cre, Flp, and Dre recombinases.

As used herein, the term "subject" refers to any animal (e.g., a mammal), including, but not limited to, humans, non-human primates, rodents, and the like (e.g., that is to be the recipient of a particular treatment (e.g., transplant graft) or that is a donor of a graft. The terms "subject" and "patient" are used interchangeably in reference to a human subject, unless indicated otherwise herein (e.g., wherein a subject is a graft donor). In one embodiment, a subject may be a donor. In another embodiment, a subject may be a recipient.

As used herein, the term "targeting vector" refers to a recombinant DNA construct typically comprising tailored DNA arms homologous to genomic DNA that flanks critical elements of a target gene or target sequence. When introduced into a cell, the targeting vector integrates into the cell genome via homologous recombination. A "tissue-specific" promoter is a nucleotide sequence which, when operably linked with a polynucleotide which encodes or specifies a gene product, causes the gene product to be produced in a cell substantially only if the cell is a cell of the tissue type corresponding to the promoter.

As used herein, the term "tissue" refers to cellular organizational level intermediate between cells and a complete organ. A tissue is an ensemble of similar cells from the same origin that together carry out a specific function. Organs are then formed by the functional grouping together of multiple tissues. Examples of tissues contemplated by the present invention include, without limitation, connective tissue, muscle tissue, neural tissue, epithelial tissue and mineralized tissue. Blood, bone, tendon, ligament, adipose and areolar tissues are examples of connective tissues—which may also be classified as fibrous connective tissue, skeletal connective tissue, and fluid connective tissue. Muscle tissue is separated into three distinct categories: visceral or smooth muscle, found in the inner linings of organs; skeletal muscle, typically attached to bones and which generates gross movement; and cardiac muscle, found in the heart where it contracts to pump blood throughout an organism. Cells comprising the central nervous system and peripheral nervous system are classified as nervous (or neural) tissue. In the central nervous system, neural tissues form the brain and spinal cord. In the peripheral nervous system, neural tissues form the cranial nerves and spinal nerves, inclusive of the motor neurons.

The term transcription activator-like effector nucleases or "TALEN" as used herein refers to artificial restriction enzymes generated by fusing the TAL effector DNA binding domain to a DNA cleavage domain. These reagents enable efficient, programmable, and specific DNA cleavage and represent powerful tools for genome editing in situ. Transcription activator-like effectors (TALEs) can be quickly engineered to bind practically any DNA sequence. The term TALEN, as used herein, is broad and includes a monomeric TALEN that can cleave double stranded DNA without assistance from another TALEN. The term TALEN is also used to refer to one or both members of a pair of TALENs that are engineered to work together to cleave DNA at the same site. TALENs that work together may be referred to as a left-TALEN and a right-TALEN, which references the handedness of DNA. See U.S. Ser. No. 12/965,590; U.S. Ser. No. 13/426,991 (U.S. Pat. No. 8,450,471); U.S. Ser. No. 13/427,040 (U.S. Pat. No. 8,440,431); U.S. Ser. No. 13/427, 137 (U.S. Pat. No. 8,440,432); and U.S. Ser. No. 13/738, 381, all of which are incorporated by reference herein in their entirety.

As used herein, the term "transfected" or "transformed" or "transduced" refers to a process by which exogenous nucleic acid is transferred or introduced into the host cell. A "transfected" or "transformed" or "transduced" cell is one which has been transfected, transformed, or transduced with exogenous nucleic acid. The cell includes the primary subject cell and its progeny.

A "transgene" is a gene or genetic material that has been transferred from one organism to another. When a transgene is transferred into an organism, the organism can then be referred to as a transgenic organism. Typically, the term describes a segment of DNA containing a gene sequence that has been isolated from one organism and is introduced into a different organism. This non-native segment of DNA may retain the ability to produce RNA or protein in the transgenic organism, or it may alter the normal function of the transgenic organism's genetic code. In general, the DNA is incorporated into the organism's germ line. For example, in higher vertebrates this can be accomplished by injecting the foreign DNA into the nucleus of a fertilized ovum or via somatic cell nuclear transfer where a somatic cell, with the desired transgene(s) is incorporated into the host genome, is transferred to an enucleated oocyte and results in live offspring after transplantation into a surrogate mother. When inserted into a cell, a transgene can be either a cDNA (complementary DNA) segment, which is a copy of mRNA (messenger RNA), or the gene itself residing in its original region of genomic DNA. The transgene can be a genome sequence, in particular when introduced as large clones in BACs (bacterial artificial chromosomes) or cosmid, or could be a form of "minigene" often characterized by a combination of both genomic DNA (including intron regions, e.g. intron 1), 5' or 3' regulatory regions, along with cDNA regions.

Transgene "expression" in the context of the present specification, unless otherwise specified, means that a peptide sequence from a non-native nucleic acid is expressed in at least one cell in a host. The peptide can be expressed from a transgene that is incorporated in the host genome. A transgene can comprise a polynucleotide encoding a protein or a fragment (e.g., a functional fragment) thereof. A fragment (e.g., a functional fragment) of a protein can comprise at least or at least about 5%, 10%, 20%, 30%, 40%, 50%, 60%, 70%, 80%, 90%, 95%, or 99% of the amino acid sequence of the protein. A fragment of a protein can be a functional fragment of the protein. A functional fragment of a protein can retain part or all of the function of the protein.

As used herein the term "transplant tolerance" is defined as a state of donor-specific unresponsiveness without a need for ongoing pharmacologic immunosuppression. Transplantation tolerance could eliminate many of the adverse events associated with immunosuppressive agents. As such, induction of tolerance may result in improved receipt of a xenograft. In an embodiment, induction of tolerance may be identified by a decrease in clinical symptoms of xenograft rejection. In another embodiment, induction of tolerance may ameliorate or prevent the metabolic, inflammatory, and proliferative pathological conditions or diseases associated with xenograft transplantation. In still another embodiment, induction of tolerance may ameliorate or decrease or prevent the adverse clinical conditions or diseases associated with the administration of immunosuppressive therapy used to prevent xenograft rejection. In still yet another embodiment, induction of tolerance may promote xenograft survival. In a different embodiment, induction of tolerance may prevent relapses in patients exhibiting these diseases or conditions.

The term "ungulate" refers to hoofed mammals. Artiodactyls are even-toed (cloven-hooved) ungulates, including antelopes, camels, cows, deer, goats, pigs, and sheep. Perissodactyls are odd toes ungulates, which include horses, zebras, rhinoceroses, and tapirs. The term ungulate as used herein refers to an adult, embryonic or fetal ungulate animal.

The term "vector" as used herein refers to moiety which is capable of transferring a polynucleotide to a host cell. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses).

Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors can direct the expression of genes to which they are operatively-linked. Such vectors are referred to herein as "expression vectors." Common expression vectors of utility in recombinant DNA techniques are often in the form of plasmids. Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed.

Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, the contents of which are herein incorporated by reference in their entirety. Preferably the vector is a DNA vector and, more preferably, can express RNA encoding a protein according to the invention. Numerous suitable vectors are documented in the art; examples may be found in Molecular Cloning: a Laboratory Manual: 2nd edition, Sambrook et al., 1989, Cold Spring Harbor Laboratory Press or DNA cloning: a practical approach, Volume II: Expression systems, edited by D. M. Glover (IRL Press, 1995).

As used herein, the term "zinc finger nuclease" or "ZFN" refers to an artificial (engineered) DNA binding protein comprising a zinc finger DNA-binding domain and a DNA-cleavage domain. Zinc finger domains can be engineered to target specific desired DNA sequences, and this enables zinc-finger nucleases to target unique sequences within complex genomes. They facilitate targeted editing of the genome by creating double-strand breaks in DNA at user-specified locations. Each ZFN contains two functional domains: a.) A DNA-binding domain comprised of a chain of two-finger modules, each recognizing a unique hexamer (6 bp) sequence of DNA. Two-finger modules are stitched together to form a Zinc Finger Protein, each with specificity of ≥24 bp. b.) A DNA-cleaving domain comprised of the nuclease domain of Fok I. When the DNA-binding and DNA-cleaving domains are fused together, a highly-specific pair of 'genomic scissors' are created. ZFN are gene editing tools.

III. Transgenic Animals

The present invention provides a transgenic animal (e.g., a transgenic porcine animal) that serves as a source for organs, organ fragments, tissues or cells for use in xenotransplantation. The present invention extends to the organs, tissues and cells derived from the transgenic animal, as well as groups of such animals, e.g., production herds.

The animal may be any suitable animal. In exemplary embodiments, the animal is an ungulate and more particularly, a porcine animal or pig. The transgenic donor animal (e.g., ungulate, porcine animal or pig) is genetically modified and more particularly, comprises multiple transgenes, for example, multiple transgenes in a single locus. In certain embodiments, the transgenic donor animal is genetically modified to express multiple transgenes divided between a first locus (i.e., locus 1) and a second locus (i.e., locus 2). The loci may be a native or modified native locus. Various strategies for modifying a native locus to facilitate targeting are described herein.

In exemplary embodiments, the present invention provides a transgenic animal (e.g., a transgenic porcine animal) comprising incorporation and expression of at least six transgenes at a single locus under the control of at least three promoters (e.g., exogenous promoters, or a combination of exogenous and native promoters), and wherein the pig lacks expression of alpha 1,3 galactosyltransferase. Optionally, the transgenic animal comprises one or more additional genetic modifications, including, without limitation, additions and/or deletions of genes, including knock-outs and knock-ins, as well as gene substitutions and rearrangements.

In a particular embodiment, the present invention provides a transgenic porcine animal comprising at least six transgenes incorporated and expressed at a single locus, wherein expression of the at least six transgenes is controlled by dedicated promoters, i.e., a promoter drives the expression of each individual transgene. For example, where the transgenic animal incorporates and expresses six transgenes in a single locus, the expression of those transgenes is driven by four promoters, where each promoter is specific to a particular transgene. In an alternative embodiment, a given promoter controls expression of more than one transgene (e.g., two transgenes, three transgenes). For example, where the transgenic animal incorporates and expresses six transgenes, two of the six transgenes are expressed as a polycistron controlled by a first promoter, two of the six transgenes are expressed as a polycistron controlled by the second promoter, and two of the six transgenes are expressed as a polycistron controlled by the third promoter. In some embodiments, the first, second, and third promoters are the same. In some embodiments, the first, second, and third promoters are different. In some embodiments, at least one promoter is different.

In some embodiments, the at least six transgenes are selected from the group consisting of immunomodulators (e.g., immunosuppressants), anticoagulants, complement inhibitors and cryoprotective transgenes. In some embodiments, the single locus is a native locus. In other embodiments, the single locus is a modified native locus, such as a transgenic locus. The transgenic locus may be, for example, a locus containing a selectable marker gene or a locus containing a landing pad. In some embodiments, the at least six transgenes are provided in a multi-cistronic vector (MCV) and incorporated either by random integration, or by utilizing a gene editing tool.

Optionally, the transgenic animal may have one or more additional genetic modifications. The additional genetic modification may be, for example, a gene knock-out or gene knock-in. In particular embodiments, the additional genetic modification comprises a chimeric porcine-human vWF.

In another embodiment, the present invention provides a transgenic animal (e.g., a pig) that includes at least five genetic modifications, resulting in (i) lack of expression of alpha 1, galactosyltransferase (i.e., is alpha Gal null) and (ii) incorporation and expression of at least four, at least five, at least six, at least seven, at least eight, at least nine or at least ten transgenes in a single locus. The expression of the transgenes is driven by a promoter, either a dedicated promoter or a promoter which controls expression of two or more transgenes. The promoters may be exogenous or a combination of exogenous and native promoters.

In certain embodiments, if greater than six added transgenes might involve incorporation of transgenes at more than one locus in order to better modulate expression of the transgene combination (eg. integration of at least six transgenes under control of at least three promoters integrated at GGTA1, and a second multicistronic integration at a second locus (e.g. CMAH, B4GalNT2, AAVS1, GHR, or Rosa26). In certain embodiments where a second locus is genetically modified such second locus could be modified to inactivate expression of another porcine gene (eg. through application of gene editing and/or homologous recombination technology). In exemplary embodiments, the multiple transgenes incorporated and expressed as the second locus are selected from the group consisting of immunomodulators, complement inhibitors, anticoagulants and cryoprotective transgenes. In exemplary embodiments, the second locus is a native locus, a modified native locus or a transgenic locus (e.g., landing pad). In exemplary embodiments, the at least two transgenes at the second locus are provided in a MCV and incorporated utilizing a gene editing tool. Optionally, the transgenic animal may have one or more additional genetic modifications.

In one embodiment, the present invention provides a transgenic animal (e.g., a pig) that includes at least six genetic modifications, resulting in (i) reduced expression of alpha 1, galactosyltransferase and (ii) incorporation and expression of at least six transgenes in a single locus, where such six transgenes are expressed under control of at least three promoters (e.g., exogenous promoters or a combination of exogenous and native promoters). In exemplary embodiments, the transgene is selected from the group consisting of immunomodulators, anticoagulants, complement inhibitors and cryoprotective transgenes. In exemplary embodiments, the single locus is a native locus, a modified native locus or a transgenic locus (e.g., landing pad). In exemplary embodiments, the at least two transgenes are provided in a MCV and incorporated utilizing a gene editing tool (ie. CRISPR/cas9, TALEN, or ZFN) to enhance the efficiency of homologous recombination or homology dependent repair. Optionally, the transgenic animal may have one or more additional genetic modifications.

In some embodiments, the CRISPR/Cas9-mediated gene editing comprises: an inducible promoter or inducible system, a Tetracycline/Doxycycline regulatory system; a polycistronic vector comprising U6p [GHRgRNA-1]; U6p [GHRgRNA-2]; TRE3Gp[CAS9]; CAGpr [tTA]; CAGpr [hCD46-2A-hCD55]; or the nucleotide sequence of SEQ ID NO: 9. In some embodiments, the inducible promoter controls the expression of the growth hormone receptor gene.

In another embodiment, the present invention provides a transgenic animal (e.g., a pig) that includes at least five genetic modifications, resulting in (i) reduced expression of alpha 1, galactosyltransferase and (ii) incorporation and expression of at least four, at least five, at least six, at least seven, at least eight, at least nine or at least ten transgenes in a single locus, or divided between two loci. In exemplary embodiments, the transgene is selected from the group consisting of immunomodulators, complement inhibitors, anticoagulants and cryoprotective transgenes. In exemplary embodiments, the single locus is a native locus, a modified native locus, or a transgenic locus (e.g., landing pad). In exemplary embodiments, the at least two transgenes are provided in a MCV and incorporated utilizing a gene editing tool (ie. CRISPR/cas9, TALEN, or ZFN) to enhance the efficiency of homologous recombination or homology dependent repair. Optionally, the transgenic animal may have one or more additional genetic modifications.

In exemplary embodiments, the transgenic animal lacks expression of alpha 1, galactosyltransferase (i.e., is alpha Gal null) and comprises at least one, at least two, at least three, at least four, at least five, at least six or at least seven or more genetic modifications. Optionally, in addition to transgene integrations, additional knockouts include knockout of beta4GalNT2 gene or CMAH gene (both genes that have been implicated in cause of innate immunity and rejection of xenografts.

In exemplary embodiments, the transgenic animal has reduced expression of alpha 1, galactosyltransferase and comprises at least one, at least two, at least three, at least four, at least five, at least six or at least seven additional genetic modifications. In certain embodiment, expression of alpha 1, galactosyltransferase is reduced by about 10%, about 20%, about 30%, about 40%, about 50%, about 60%, about 70%, about 80%, about 90% or about 95%.

In exemplary embodiments, the transgenic animal comprises (i) a genetic modification that results in lack of expression of alpha 1,3 galactosyltransferase and (ii) at least ten additional genetic modifications, or more particularly six additional transgenes. These additional genetic modifications may be any suitable genetic modification, including but not limited to CRISPR-induced deletions/insertions or gene substitutions (INDELs) including knockout or knockin at other loci (e.g., B4GalNT2, CMAH, vWF, or GHR).

In exemplary embodiments, the transgenic animal comprises (i) a genetic modification that results in reduced expression of alpha 1,3 galactosyltransferase and (ii) at least six additional genetic modifications, or more particularly 10 additional genetic modifications. In exemplary embodiments, the transgenic animal comprises (i) a genetic modification that results in lack of expression of alpha 1,3 galactosyltransferase and (ii) at least five additional genetic modifications, or more particularly five additional genetic modifications. In exemplary embodiments, the transgenic animal comprises (i) a genetic modification that results in lack of expression of alpha 1,3 galactosyltransferase and (ii) at least six additional genetic modifications, or more particularly six additional genetic modifications.

In a particular embodiment, the donor animal (e.g., ungulate, porcine animal or pig) comprises genetic modifications that result in (i) lack of expression of alpha 1,3 galactosyltransferase and incorporation and expression of at least five, or at least six or more transgenes. In an exemplary embodiment, the donor animal (e.g., ungulate, porcine animal or pig) comprises genetic modifications that result in (i) reduced expression of alpha 1,3 galactosyltransferase and (ii) incorporation and expression of six additional transgenes. Optionally, the donor animal may contain or more additional genetic modifications.

In an exemplary embodiment, the donor animal (e.g., ungulate, porcine animal or pig) comprises genetic modifications that result in (i) reduced expression of alpha 1,3 galactosyltransferase and (ii) incorporation and expression of six additional transgenes. Optionally, the donor animal may contain one or more additional genetic modifications (knockouts, knockins, INDELs, modification of porcine vWF or GHR).

A. Transgene Expression

Expression of the transgene can be at any level, but in specific embodiments, the expression is at high levels. A variety of promoter/enhancer elements may be used depending on the level and tissue-specific expression desired. The promoter/enhancer may be constitutive or inducible, depending on the pattern of expression desired. The promoters may be exogenous or native, or a combination of exogenous and native promoters.

In certain embodiments, the transgene is expressed from a constitutive or ubiquitous promoter. In certain other embodiments, the transgene is expressed from a tissue-specific or cell type specific promoter, or inducible promoter, and may include additional regulatory elements such as enhancers, insulators, matrix attachment regions (MAR) and the like.

In exemplary embodiments, the six or more transgenes are co-expressed. In exemplary embodiments, the six or more transgenes are expressed in approximately molar equivalents. In some embodiments, the at least six transgenes are driven by a constitutive promoter, or a tissue-specific promoter. In some embodiments, the constitutive promoter is selected from the group consisting of CAG promoter, Tie-2 promoter, ICAM-2 promoter. In some embodiments, the inducible promoter is a Tetracycline/doxycycline regulatory promoter. In some embodiments, the tissue-specific promoter is an endothelial-cell specific promoter; and/or the tissue-specific promoter is selected from a porcine thrombomodulin promoter (pTBMpr), a human thrombomodulin promoter, a porcine EPCR promoter, a human EPCR promoter. In some embodiments, the porcine thrombomodulin promoter is an exogenous or endogenous promoter. In exemplary embodiments, the transgene is expressed by a promoter primarily active in endothelial cells. In certain embodiments, expression of the transgene is controlled by a porcine Icam-2 enhancer/promoter. In certain embodiments, expression of the transgene is controlled by a constitutive CAG promoter.

In certain embodiments, the transgenic animal is genetically modified to result in incorporation and expression of six or more transgenes, where at least one transgene is controlled by a constitutive promoter and at least one transgene is controlled by a tissue-specific promoter, or more particularly, a promoter primarily active in endothelial cells.

In exemplary embodiments, the transgenic animal is genetically modified to result in incorporation and expression of six or more transgenes in a single locus, where at least two transgenes are controlled by a constitutive promoter and at least two transgenes are controlled by a tissue-specific promoter, or more particularly, a promoter primarily active in endothelial cells.

The transgene can be any transgene suitable for use in modifying a donor animal (e.g., a porcine animal) for use in xenotransplantation. In exemplary embodiments, the transgene is selected from an immunomodulator (e.g., complement regulator, complement inhibitor, immunosuppressant), an anticoagulant, a cryoprotective gene or combinations thereof. In certain embodiments, the sequence of the transgene in human.

In certain embodiments, the transgene is an immunomodulator. In certain embodiments, the transgene is a complement regulator or more specifically, a complement inhibitor. The complement inhibitor may include, without limitation, CD46 (MCP), CD59 or CR1. The sequence of the complement inhibitor may be human. In certain embodiments, the transgene is a complement pathway inhibitor (i.e., a complement inhibitor) inhibitor. The complement inhibitor may include, without limitation, CD55 (DAF), CD59, CR1 and CD46 (MCP). The sequence of the complement inhibitor may be human. In some embodiments, the at least six transgenes comprise the at least two complement inhibitors selected from the group consisting of CD46, DAF (CD55), CD59, CR1, and a combination thereof. In some embodiments, the at least two complement inhibitors are ubiquitously expressed; and/or are under the control of a constitutive promoter or an inducible promoter.

In certain embodiments, at least one transgene is an immunosuppressant. In some embodiments, the at least one immunosuppressant transgene is selected from the group consisting of Cytotoxic T-Lymphocyte-Associated Protein 4 (CTLA4), cluster of differentiation 47 (CD47), and Class II transactivator-DN (CIITA-DN). In some embodiments, the at least one immunosuppressant transgene is under the control of a constitutive promoter.

In certain embodiments, the transgene is an immunosuppressor gene that has a T-cell modulating effect—such as CTLA4-Ig, or a dominant negative inhibitor of class II MHC (CIITA), or other genes that modulate the expression of B-cell or T cell mediated immune function. In further embodiments, such animals can be further modified to eliminate the expression of genes which affect immune function. In certain embodiments, the immunosuppressor is CD47. In certain embodiments, at least two transgenes are anticoagulants. In some embodiments, the at least two anticoagulant transgenes are under the control of an endothelial-specific promoter. In some embodiments, the at least two anticoagulant transgenes selected from the group consisting of endothelial protein C receptor (EPCR), thrombomodulin, CD39, hirudin, Tissue factor pathway inhibitor (TFPI), and a combination thereof. In some embodiments, the sequence of the anticoagulant may be human.

The transgenic animal may contain one or more additional genetic modification, as well. In one embodiment, the animal may be genetically modified to inhibit the expression of the CMP-Neu5Ac hydroxylase gene (CMAH) (see, for example, U.S. Patent Publication. 2005-0223418), the iGb3 synthase gene (see, for example, U.S. Patent Publication 2005-0155095), and/or the Forssman synthase gene (see, for example, U.S. Patent Publication 2006-0068479). In addition, the animals can be genetically modified to reduce expression of a pro-coagulant. In particular, in one embodiment, the animals are genetically modified to reduce or eliminate expression of a procoagulant gene such as the FGL2 (fibrinogen-like protein 2). In another embodiment, the animal may be genetically modified to inhibit the expression of beta-1,4 N-acetylgalactosaminyltransferase 2 (ß4GalNT2).

B. Specific Genetic Modifications

1. Alpha 1,3 Galactosyltransferase (Alpha.Gal)

In one embodiment, the present invention provides a transgenic animal suitable for use as a source of organs, tissues and cells for xenotransplantation, wherein the donor animal lacks expression of alpha Gal or expression has been reduced. The transgenic animal that lacks expression of alpha Gal (i.e., is alpha Gal null) has one or more additional genetic modifications, and in certain embodiments, at least four additional genetic modifications, at least five additional genetic modifications or at least six additional genetic modifications. These genetic modifications may be, for example, incorporation or expression of transgenes. In a particular embodiment, the transgenic animal has at least three genetic modifications, resulting in (i) lack of expression of alpha Gal; and (ii) incorporation and expression of at least two transgenes in a single locus. In certain embodiments, the single locus is modified alpha Gal.

A variety of strategies have been implemented to eliminate or modulate the anti-Gal humoral response caused by xenotransplantation, including enzymatic removal of the epitope with alpha-galactosidases (Stone et al., Transplantation 63: 640-645, 1997), specific anti-gal antibody removal (Ye et al., Transplantation 58: 330-337, 1994), capping of the epitope with other carbohydrate moieties, which failed to eliminate .alpha.GT expression and the introduction of complement inhibitory proteins reported that competitive inhibition of .alpha.GT in transgenic pigs results in only partial reduction in epitope numbers. Similarly, attempts to block expression of gal epitopes in N-acetylglucosaminyltransferase III transgenic pigs also resulted in only partial reduction of gal epitopes numbers and failed to significantly extend graft survival in primate recipients. Single allele knockouts of the alpha Gal locus in porcine cells and live animals are known in the art. A major breakthrough in the field of xenotransplantation was the production of the first live pigs lacking any functional expression of alpha Gal (Phelps et al. Science 299:411-414 (2003); see also PCT publication No. WO 04/028243 by Revivicor, Inc. and PCT Publication No. WO 04/016742 by Immerge Biotherapeutics, Inc.).

In one embodiment, animals (and organs, tissues and cells derived therefrom) are provided from a transgenic animal (e.g., a transgenic pig) comprising at least six transgenes, wherein the six transgenes are incorporated and expressed at a single locus under the control of at least three promoters, and wherein the pig lacks expression of alpha 1,3 galactosyltransferase. In an exemplary embodiments, the transgenes are incorporated and expressed at a modified alpha Gal locus. In certain embodiments, the at least three promoters are exogenous, native or a combination of exogenous and native.

In one embodiment, animals and organs, tissues and cells derived therefrom, are provided that (i) lack any expression of functional alpha Gal and (ii) incorporate and express at least four, at least five, at least six, at least seven, at least eight, at least nine or at least ten or more transgenes at a single locus. In some embodiments, the transgenes are incorporated and expressed at a modified alpha Gal locus. In certain embodiments, the animal may include one or more additional genetic modifications. These genetic modifications may result in incorporation and expression of one or more additional transgenes at the same locus or a different locus.

In another embodiment, animals, organs, tissue and cells are provided that have a reduced level of expression of functional alpha Gal and incorporate and express at least one, at least two, at least three, at least four, at least five, at least six, at least seven, at least eight, at least nine, at least ten, at least eleven, or at least twelve additional transgenes. The expression of functional alpha Gal may be reduced by, for example, by at least about 5%, about 10%, about 20%, about 30%, about 40%, about 50%, about 60%, about 70%, about 80%, about 90% or about 95%.

The lack or reduced level of expression of functional alpha.GT may be achieved by any suitable means known to those skilled in the art. In some embodiments, animals (e.g., ungulates, porcine animals) are provided in which one allele of the alpha Gal gene is inactivated via a genetic targeting event. In another embodiment, porcine animals are provided in which both alleles of the alpha Gal gene are inactivated via a genetic targeting event. In one embodiment, the gene can be targeted via homologous recombination. In other embodiments, the gene can be disrupted, i.e. a portion of the genetic code can be altered, thereby affecting transcription and/or translation of that segment of the gene. For example, disruption of a gene can occur through substitution, deletion ("knock-out") or insertion ("knock-in") techniques, including targeted insertion of a selectable marker gene (e.g., neo) that interrupts the coding region of the alpha Gal gene. Additional genes for a desired protein or regulatory sequence that modulate transcription of an existing sequence can be inserted.

In certain embodiments, the alleles of the alpha Gal gene are rendered inactive, such that the resultant alpha Gal enzyme can no longer generate Gal on the cell surface. In one embodiment, the alpha Gal gene can be transcribed into RNA, but not translated into protein. In another embodiment, the alpha Gal gene can be transcribed in a truncated form. Such a truncated RNA can either not be translated or can be translated into a nonfunctional protein. In an alternative embodiment, the alpha Gal gene can be inactivated in such a way that no transcription of the gene occurs. In a further embodiment, the alpha Gal gene can be transcribed and then translated into a nonfunctional protein.

In some embodiments, the expression of active alpha Gal gene can be reduced by use of alternative methods, such as those targeting transcription or translation of the gene. For example, the expression can be reduced by use of antisense RNA or siRNA targeting the native .alpha.GT gene or an mRNA thereof. In other embodiments, site specific recombinases are used to target a region of the genome for recombination. Examples of such systems are the CRE-lox system and the Flp-Frt systems.

Pigs that possess two inactive alleles of the alpha Gal gene are not naturally occurring. It was previously discovered that while attempting to knockout the second allele of the alpha Gal gene through a genetic targeting event, a point mutation was identified, which prevented the second allele from producing functional alpha Gal enzyme.

Thus, in another aspect of the present invention, the alpha Gal can be rendered inactive through at least one point mutation. In one embodiment, one allele of the alpha Gal gene can be rendered inactive through at least one point mutation. In another embodiment, both alleles of the alpha Gal gene can be rendered inactive through at least one point mutation. In one embodiment, this point mutation can occur via a genetic targeting event. In another embodiment, this point mutation can be naturally occurring. In a further embodiment, mutations can be induced in the alpha Gal gene via a mutagenic agent.

2. ß4GaINT2

In one embodiment, the present invention provides a transgenic animal suitable for use as a source of organs, tissues and cells for xenotransplantation, wherein the donor animal lacks expression of β1,4 N-acetyl-galactosaminyl transferase 2 (ß4GALNT2) or expression has been reduced. The transgenic animal that lacks expression of ß4GALNT2 (i.e., is ß4GALNT2 null) has one or more additional genetic modifications. These genetic modifications may be, for example, incorporation or expression of transgenes. In a particular embodiment, the transgenic animal which lacks expression of β1,4 N-acetyl-galactosaminyl transferase 2 (ß4GALNT2) or expression has been reduced is also characterized by (i) lack of expression of alpha Gal; and (ii) incorporation and expression of at least six transgenes in a single locus under the control of at least three promoters.

Glycans produced by ß4Gal-NT2 are xenoantigens for many humans. Estrada J L et al, Xenotransplantation 2015: 22: 194-202. In humans and mice, ß4GALNT2 catalyzes the addition of N-acetylgalactosamine to a sialic acid modified lactosamine to produce GalNAc b1-4(Neu5Ac a2-3) Gal b1-4GlcNAc b1-3Gal, the Sda blood group antigen. This gene is functional in transplantable organs (kidney, heart, liver, lung, and pancreas) and endothelial cells in the pig. Approximately 5% of humans possess inactive ß4GalNT2 and consequently develop antibodies against the SDa and CAD carbohydrates produced by this gene.

Any suitable method can be used to generate pigs whose genomes which lack or have reduced expression of endogenous ß4GALNT2. A disruption can be positioned at many sites in the endogenous porcine ß4GALNT2 nucleic acid sequence. Examples of disruptions include, but are not limited to, deletions in the native gene sequence and insertions of heterologous nucleic acid sequences into the native gene sequence. Examples of insertions can include, but are not limited to, artificial splice acceptors coupled to stop codons or splice donors coupled to fusion partners such as GFP. A knock-out construct can contain sequences that are homologous to the endogenous ß4GALNT2 nucleic acid sequence or to sequences that are adjacent to the endogenous ß4GALNT2 nucleic acid sequence. In some cases, a knock-out construct can contain a nucleic acid sequence encoding a selection marker (e.g., antibiotic resistance, a fluorescent reporter (e.g., GFP or YFP), or an enzyme (e.g., β-galacto-sidase)) operatively linked to a regulatory sequence (e.g., a promoter). A knock-out construct can include other nucleic acid sequences such as recombination sequences (e.g., loxP sequences, see Sendai, et al, Transplantation, 81(5):760-766 (2006)), splice acceptor sequences, splice donor sequences, transcription start sequences, and transcription stop sequences. Disruptions in the endogenous ß4GALNT2 nucleic acid sequence can result in reduced expression of the gene or non-functional truncations or fusions of the encoded polypeptide.

In one embodiment, the present invention provides a transgenic animal (e.g., a porcine animal) expressing reduced or no of ß4GALNT2. Optionally, the animal comprises one or more additional genetic modifications. In an exemplary embodiment, the present invention provides a transgenic animal (e.g., a porcine animal) incorporating and expression at least six transgenes under the control of at least three promoters, wherein the animal lacks or has reduced expression of ß4GALNT2. Optionally, the animal comprises one or more additional genetic modifications. In one embodiment, the present invention provides a transgenic animal (e.g., a porcine animal) expressing reduced or no Sda or SDa-like glycans produced by porcine ß4GALNT2. Optionally, the animal comprises one or more additional genetic modifications.

In an exemplary embodiment, the present invention provides a transgenic animal (e.g., a porcine animal) incorporating and expression at least six transgenes under the control of at least three promoters, wherein the animal lacks or has reduced expression of no Sda or SDa-like glycans produced from a porcine ß4GALNT2. Optionally, the animal comprises one or more additional genetic modifications.

3. CMAH

In one embodiment, the present invention provides a transgenic animal suitable for use as a source of organs, tissues and cells for xenotransplantation, wherein the donor animal lacks expression of cytidine monophosphate-N-acetylneuraminic acid hydroxylase (CMAH), or expression has been reduced. The transgenic animal that lacks expression of CMAH is CMAH null) has one or more additional genetic modifications. These genetic modifications may be, for example, incorporation or expression of transgenes. In a particular embodiment, the transgenic animal has at least four additional genetic modifications, resulting in (i) lack of expression of alpha Gal; and (ii) incorporation and expression of at least six transgenes in a single locus.

Porcine cells express cytidine monophosphate-N-acetyl-neuraminic acid hydroxylase (CMAH), which are not found in human cells. CMAH converts the sialic acid N-acetyl-neuraminic acid (Neu5Ac) to N-glycolylneuraminic acid (Neu5Gc). As such, when porcine tissue is transplanted into a human, these epitopes elicit an antibody-mediated rejection from the human patient immediately following implantation.

Any suitable method can be used to generate pigs whose genomes contain lack or have reduced expression of endogenous CMAH. A disruption can be positioned at many sites in the endogenous porcine CMAH nucleic acid sequence.

Examples of disruptions include, but are not limited to, deletions in the native gene sequence and insertions of heterologous nucleic acid sequences into the native gene sequence. Examples of insertions can include, but are not limited to, artificial splice acceptors coupled to stop codons or splice donors coupled to fusion partners such as GFP. A knock-out construct can contain sequences that are homologous to the endogenous CMAH nucleic acid sequence or to sequences that are adjacent to the endogenous CMAH nucleic acid sequence. In some cases, a knock-out construct can contain a nucleic acid sequence encoding a selection marker (e.g., antibiotic resistance, a fluorescent reporter (e.g., GFP or YFP), or an enzyme (e.g., β-galactosidase)) operatively linked to a regulatory sequence (e.g., a promoter). A knock-out construct can include other nucleic acid sequences such as recombination sequences (e.g., loxP sequences, see Sendai, et al, Transplantation, 81(5):760-766 (2006)), splice acceptor sequences, splice donor sequences, transcription start sequences, and transcription stop sequences. Disruptions in the endogenous CMAH nucleic acid sequence can result in reduced expression of the gene or non-functional truncations or fusions of the encoded polypeptide.

In one embodiment, the present invention provides a transgenic animal (e.g., a porcine animal) expressing reduced or no expression of CMAH glycosyltransferase. Optionally, the animal comprises one or more additional genetic modifications. In an exemplary embodiment, the present invention provides a transgenic animal (e.g., a porcine animal) incorporating and expression at least six transgenes under the control of at least three promoters, wherein the animal lacks or has reduced expression of CMAH. Optionally, the animal comprises one or more additional genetic modifications.

4. vWF

The von Willebrand factor (vWF) gene is large and complex gene, with multiple domains, and that encodes a multimeric glycoprotein. The main functions of the multimeric glycoprotein, von Willebrand factor (vWF), are platelet adhesion to connective tissues and sub-endothelium, as well as platelet aggregation as a function of the vWF binding to the platelet glycoprotein Ib (GPIb). However this phenomenon is less favorable during xenotransplantation when the aggregation of the recipient's platelets having a damaging effect on the survival of the donated organ. For example, the transplantation of the porcine lungs (and other organs) to humans or non-human primates result in spontaneous aggregation and sequestration of human platelets. This can be avoided by "humanization" of the porcine VWF gene in an effort to eliminate this spontaneous binding of porcine vWF to human platelets. In general, the humanization or modification to the porcine vWF gene requires the deletion of the gene sequence(s) associated with the spontaneous aggregation of human platelets and replacement with the human genetic counterpart that does not generate spontaneous aggregation. This could include deletion of all or part of the porcine vWF gene with replacement with all or part of the human vWF gene.

Modifications of porcine vWF aimed at elimination of the spontaneous platelet aggregation response could include regions within the D3 (partial), A1, A2, A3 (partial) domains that are known to be associated with folding and sequestration of the GP1b binding site in hvWF (D3 domain), as well as regions associated with the GP1b receptor (A1 domain) and the ADAMTS13 cleavage site (A2 domain). Exons 22-28 encompass these regions. Human platelets spontaneously aggregate in the presence of pig blood under normal stress forces. To avoid this potential threat to successful xenotransplantation, and since human vWF does NOT induce spontaneous platelet aggregation under conditions of normal shear stress in the blood, a region of the human vWF gene associated with folding of the vWF protein as well as regions associated with GPib binding, collagen binding (one of 2 regions), and ADAMTS13 cleavage could be utilized for replacement of the genomic homologs in the pig vWF gene (and resulting chimeric human/pig protein). In this way, alternate folding that could hide or mask the GP1b binding site on vWF, as well as a humanized receptor sites within the A domains could be provided with a single cDNA or genomic fragment from the human vWF gene. This could be achieved through homologous recombination or gene targeting, including where such mechanisms are enhanced utilizing gene editing methods (e.g.,) CRISPR-assisted homologous recombination can be used to integrate a human vWF fragment into the porcine vWF locus. This human fragment replaces regions that are implicated in the spontaneous platelet aggregation mentioned above, and could be in the form of a cDNA or genomic fragment from the human vWF gene).

In exemplary embodiments, the insertion of the relevant human vWF gene sequences can be done by any current method used for genome editing, for example, but not limited to, CRISPR/CAS9, TALEN nucleases. The modification of the porcine vWF can be done by replacing only the relevant regions of the porcine vWF gene or alternatively, by replacing the entire pvWF gene with hvWF.

In one embodiment, a region of the porcine vWF gene may be replaced with the human counterpart (E22-E28 region). Alternatively, the transgenic animal may have a complete knockout of the vWF gene and full replacement of the gene synthetic sequence of the human vWVF gene using a site-specific recombination system (i.e. the CRE-LOX recombination system and/or by specific nucleic acid base pair changes to replace nucleotides in the porcine vWF genomic sequence with human counterparts.

In one embodiment, the present invention is a transgenic animal (e.g. a porcine transgenic animal) that lacks expression of alpha Gal, as well as a genetic modification to the porcine vWF gene. The modification may be, for example, a knock-out of the porcine vWF gene and replacement with a humanized or chimeric vWF gene. The transgenic animal may contain one more additional genetic modifications. In one embodiment, the transgenic animal further comprises incorporation and expression of CD46.

The transgenic animal may be bread to a second transgenic animal containing one or more genetic modifications, as well. For example, an invention is a transgenic animal (e.g. a porcine transgenic animal) that lacks expression of alpha Gal, as well as a genetic modification to the porcine vWF gene may be bread to a second transgenic animal containing at least six transgenes at a single locus or at least six transgenes at a single locus and at least two transgenes at a second locus, thereby providing an animal containing multiple genetic modifications.

In one embodiment, the present invention is a transgenic animal (e.g. a porcine transgenic animal) that lacks expression of alpha Gal, as well as a genetic modification to the porcine vWF gene (e.g., a chimeric human-porcine vWF) and at least four genetic modifications at a single locus under the control of at least three promoters. The locus may vary. In exemplary embodiments, the locus is a native locus or a modified native locus. The locus may be, for example, AAVS1, GHR, ROSA26, CMAH, ß4GalNT2 and GGTA1.

The at least six transgenes may be incorporated by homologous recombination or a gene editing tools.

5. Growth Factor Receptor

The present invention provides a transgenic animal, such as a transgenic porcine animal, having a genetic alteration to confer one or more characteristics of Laron syndrome. Laron syndrome is characterized by a lack of IGF-1 production in response to growth hormone and is usually caused by a mutation in the growth hormone receptor. Patients with Laron syndrome have a small stature and may also have resistance to certain conditions, such as diabetes (type II) and certain cancers. The transgenic animal may have a genetic alteration resulting in decreased expression of growth human receptor (GHR), or an alteration causing a mutation in GHR that impairs the function of GHR. In some embodiments, the transgenic animal has a GHR knockout genetic alteration. Example of GHRKO alterations are described, for example, in Yu et al., Generation of GHR-modified pigs as Laron syndrome models via a dual-sgRNAs/Cas9 system and somatic cell nuclear transfer, J Transl Med 16:41 (2018). The transgenic animal may have 30%, 40%, 50%, 75%, or 90% or more decreased expression of GHR compared to animals without the genetic alteration. The transgenic animal may produce 30%, 40%, 50%, 75%, or 90% or less IGF-1 compared to animals without the genetic alteration. The genetic modifications may be made alone or in combination with other genetic modifications. For example, this genetic alteration may be included with the other genetic alterations described herein (FIGS. 2A-D).

The transgene introduced into the genome of the transgenic animal of the present invention may be any suitable transgene.

C. Complement Regulators

In one embodiment, the transgene is an immunomodulator. In exemplary embodiments, the donor animal has been genetically modified with the result that (i) expression of alpha Gal is lacking or reduced and (ii) at least six transgenes are incorporated and expressed at a single locus, wherein at least one of the at least two transgenes are an immunomodulator. The immunomodulator may be any suitable immunomodulator. In exemplary embodiments, the immunomodulator is a complement regulator (e.g., a complement inhibitor) or an immunosuppressant.

In one embodiment, the present invention provides a transgenic animal (e.g., porcine animal) suitable for use as a source of organs, tissues, and cells for xenotransplantation, wherein the donor animal has been genetically modified to incorporate and express at least one complement regulator, e.g., a complement inhibitor. In exemplary embodiments, the donor animal has been genetically modified with the result that (i) expression of alpha Gal is lacking or reduced and (ii) at least six transgenes are incorporated and expressed at a single locus, wherein at least one of the transgenes is a complement regulator or more specifically, a complement inhibitor.

Complement is the collective term for a series of blood proteins and is a major effector mechanism of the immune system. Complement activation and its deposition on target structures can lead to direct complement-mediated cell lysis or can lead indirectly to cell or tissue destruction due to the generation of powerful modulators of inflammation and the recruitment and activation of immune effector cells. Complement activation products that mediate tissue injury are generated at various points in the complement pathway. Inappropriate complement activation on host tissue plays an important role in the pathology of many autoimmune and inflammatory diseases, and is also responsible for many disease states associated with bioincompatibility, e.g. post-cardiopulmonary inflammation and transplant rejection. Complement deposition on host cell membranes is prevented by complement inhibitory proteins expressed at the cell surface.

The complement system comprises a collection of about 30 proteins and is one of the major effector mechanisms of the immune system. The complement cascade is activated principally via either the classical (usually antibody-dependent) or alternative (usually antibody-independent) pathways. Activation via either pathway leads to the generation of C3 convertase, which is the central enzymatic complex of the cascade. C3 convertase cleaves serum C3 into C3a and C3b, the latter of which binds covalently to the site of activation and leads to the further generation of C3 convertase (amplification loop). The activation product C3b (and also C4b generated only via the classical pathway) and its breakdown products are important opsonins and are involved in promoting cell-mediated lysis of target cells (by phagocytes and NK cells) as well as immune complex transport and solubilization. C3/C4 activation products and their receptors on various cells of the immune system are also important in modulating the cellular immune response. C3 convertases participate in the formation of C5 convertase, a complex that cleaves C5 to yield C5a and C5b. C5a has powerful proinflammatory and chemotactic properties and can recruit and activate immune effector cells. Formation of C5b initiates the terminal complement pathway resulting in the sequential assembly of complement proteins C6, C7, C8 and (C9)n to form the membrane attack complex (MAC or C5b-9). Formation of MAC in a target cell membrane can result in direct cell lysis, but can also cause cell activation and the expression/release of various inflammatory modulators.

There are two broad classes of membrane complement inhibitor: inhibitors of the complement activation pathway (inhibit C3 convertase formation), and inhibitors of the terminal complement pathway (inhibit MAC formation). Membrane inhibitors of complement activation include complement receptor 1 (CR1), decay-accelerating factor (DAF or CD55) and membrane cofactor protein (MCP or CD46). They all have a protein structure that consists of varying numbers of repeating units of about 60-70 amino acids termed short consensus repeats (SCR) that are a common feature of C3/C4 binding proteins. Rodent homologues of human complement activation inhibitors have been identified. The rodent protein Crl is a widely distributed inhibitor of complement activation that functions similar to both DAF and MCP. Rodents also express DAF and MCP, although Crl appears to be functionally the most important regulator of complement activation in rodents. Although there is no homolog of Crl found in humans, the study of Crl and its use in animal models is clinically relevant.

Control of the terminal complement pathway and MAC formation in host cell membranes occurs principally through the activity of CD59, a widely distributed 20 kD glycoprotein attached to plasma membranes by a glucosylphosphatidylinositol (GPI) anchor. CD59 binds to C8 and C9 in the assembling MAC and prevents membrane insertion.

Host cells are protected from their own complement by membrane-bound complement regulatory proteins like DAF, MCP and CD59. When an organ is transplanted into another species, natural antibodies in the recipient bind the endothelium of the donor organ and activate complement, thereby initiating rapid rejection. It has previously been suggested that, in contrast to human cells, those of the pig are very susceptible to human complement, and it was thought that this was because pig cell-surface complement regulatory proteins are ineffective against human complement. When an organ is transplanted into another species, natural antibodies in the recipient bind the endothelium of the donor organ and activate complement, thereby initiating rapid rejection. Several strategies have been shown to prevent or delay rejection, including removal of IgM natural antibodies and systemic de-complementation or inhibition of complement using sCRI, heparin or C1 inhibitor.

An alternative approach to the problem of rejection is to express human, membrane-bound, complement-regulatory molecules in transgenic pigs. Transgenic pigs expressing decay acceleration factor DAF (CD55), membrane co-factor protein MCP (CD46) and membrane inhibitor of reactive lysis, MIRL (CD59) have been generated. (see Klymium et al. Mol Reprod Dev (2010)77:209-221). These human inhibitors have been shown to be abundantly expressed on porcine vascular endothelium. Ex vivo perfusion of hearts from control animals with human blood caused complement-mediated destruction of the organ within minutes, whereas hearts obtained from transgenic animals were refractory to complement and survived for hours.

The rationale for expressing human complement regulatory proteins in pig organs to "humanize" them as outlined above is based on the assumption that endogenous pig regulatory proteins are inefficient at inhibiting human complement and thus will contribute little to organ survival in the context of xenotransplantation. In addition, soluble complement inhibitors can prevent complement-mediated lysis of islets in vitro.

Porcine analogues of several of the human complement regulatory proteins (CRP) have been isolated and characterized. Pig organs expressing human complement regulatory protein molecules were resistant to complement damage not because they expressed human CRP molecules, but because they expressed greatly increased amounts of functional CRP molecules. Increased expression of porcine CRP could be equally effective in protecting the donor organ from complement damage leading to hyperacute rejection as donor organs expressing human complement regulatory proteins.

CD46 has been characterized as a protein with regulatory properties able to protect the host cell against complement mediated attacks activated via both classical and alternative pathways may offer protection against complement lysis during inflammation and humoral rejection mediated by low levels of natural or induced anti-Gal or anti-nonGal antibodies. As a result, more islets are able to engraft and be subsequently better protected against rejection, thus reducing immunosuppression needs.

In one embodiment of the present invention, animals (and organs, tissues and cells derived therefrom) are provided that lack expression of functional alpha Gal (or have reduced expression of alpha Gal) and have been genetically modified to incorporate and express at least one, at least two, at least three, or at least four or more complement inhibitors. Expression of the complement inhibitor may be ubiquitous or under the control of a tissue-specific promoter.

In exemplary embodiments, the complement inhibitor is a membrane complement inhibitor. The membrane complement inhibitor may be either an inhibitor of the complement activation pathway (inhibit C3 convertase formation) or an inhibitor of the terminal complement pathway (inhibit MAC formation). Membrane inhibitors of complement activation include complement receptor 1 (CR1), decay-accelerating factor (DAF or CD55), membrane cofactor protein (MCP or CD46) and the like. Membrane inhibitors of the terminal complement pathway may include CD59 and the like.

In exemplary embodiments, the present invention provides a transgenic animal (e.g., ungulate, porcine animal) comprising genetic modifications that result in (i) lack of expression of alpha Gal and (ii) incorporation and expression of at least six transgenes at a single locus under the control of at least three promoters, wherein at least one of the at least two transgenes is a complement regulator and more specifically, a complement inhibitor and even more specifically, a membrane complement inhibitor. The single locus may be selected from a native locus, a modified native locus or a transgenic locus. In exemplary embodiments, the at least six transgenes are provided as a MCV and integration may be random integration or is facilitated by a genetic targeting tool. Optionally, the transgenic animal includes one or more additional genetic modifications, including but not limited to, modification of native porcine vWF, B4GalNT2, CMAH, or Forsmann genes.

In an exemplary embodiment, animals (and organs, tissues and cells derived therefrom) are provided comprising at least six transgenes, wherein the six transgenes are incorporated and expressed at a single locus under the control of at least three promoters, and wherein the pig lacks expression of alpha 1,3 galactosyltransferase, wherein the at least six transgenes include at leas two complement regulators, and more specifically, two complement inhibitors. The additional transgenes may be, for example, an immunosuppressant, cytoprotective gene or combinations thereof. The single locus may be selected from a native locus, a modified native locus or a transgenic locus. In exemplary embodiments, the at least six transgenes are provided as a MCV and integration is random or is facilitated by a genetic targeting tool. Optionally, the transgenic animal includes one or more additional genetic modifications.

In an exemplary embodiment, animals (and organs, tissues and cells derived therefrom) are provided that lack expression of functional alpha Gal (or expression is reduced) and have been genetically modified to incorporate and express at least four additional transgenes, wherein at least one of the at least two of the at least four additional transgenes are complement inhibitors, and more particularly, at least two membrane complement inhibitors.

In an exemplary embodiment, animals (and organs, tissues and cells derived therefrom) are provided that lack expression of functional alpha Gal (or expression is reduced) and have been genetically modified to (i) incorporate and express at least two complement inhibitors, and more particularly, at least two membrane complement inhibitors, and (ii) incorporate and express at least two additional transgenes selected from an anticoagulant, an immunosuppressant, cytoprotective gene or combinations thereof.

In one embodiment, animals (and organs, tissues and cells derived therefrom) are provided that lack expression of functional alpha Gal (or expression is reduced) and have been genetically modified to (i) incorporate and express CD46 and CD55 and (i) incorporate and express at least two additional transgenes. In a certain embodiment, the additional transgenes are selected from an anticoagulant, an immunosuppressant, cytoprotective gene or combination thereof.

In a particular embodiment, the animals (and organs, tissues and cells derived therefrom) are provided that lack expression of functional alpha Gal (or expression is reduced) and have been genetically modified to incorporate and express at least six transgenes under the control of at least three promoters, wherein at least one of the transgenes is CD46 and expression is controlled by a endogenous promoter.

In another embodiment, animals (and organs, tissues and cells derived therefrom are provided that lack expression of functional alpha Gal (or wherein expression is reduced) and have been genetically modified to (i) incorporate and express CD46 and CD55 and (i) incorporate and express at least three additional transgenes. In a certain embodiment, the additional transgenes are selected from an anticoagulant, an immunosuppressant cytoprotective gene or combination thereof. In an exemplary embodiment, the at least three additional transgenes include at least two anticoagulants. In an exemplary embodiment, the at least three additional transgenes include at least two anticoagulants and immunosuppressant.

In another embodiment, animals (and organs, tissues and cells derived therefrom) are provided that lack expression of functional alpha Gal (or expression is reduced) and have been genetically modified to (i) incorporate and express CD46 and CD55 and (i) incorporate and express at least four additional transgenes. In a certain embodiment, the additional transgenes are selected from an anticoagulant, an immunosuppressant, cytoprotective gene or combination thereof. In an exemplary embodiment, the at least four additional transgenes include at least two anticoagulants. In an exemplary embodiment, the at least four additional transgenes include at least two anticoagulants and an immunosuppressant. In an exemplary embodiment, the at least four additional transgenes include at least three anticoagulants.

In another embodiment, animals (and organs, tissues and cells derived therefrom) are provided that lack expression of functional alpha Gal (or expression is reduced) and have been genetically modified to (i) incorporate and express CD46 and CD55 and (i) incorporate and express at least five additional transgenes. In a certain embodiment, the additional transgenes are selected from an anticoagulant, an immunosuppressant, a cytoprotective gene or combination thereof. In an exemplary embodiment, the at least five additional transgenes include at least two anticoagulants and at least one immunosuppressant. In an exemplary embodiment, the at least five additional transgenes include at least three anticoagulants and at least one immunosuppressant. In an exemplary embodiment, the at least five additional transgenes include at least two anticoagulants and at least two immunosuppressants. In one embodiment, the animals can be modified to express a complement regulator peptide, a biologically active fragment or derivative thereof. In one embodiment, the complement regulator peptide is the full length complement regulator. In a further embodiment, the complement regulator peptide can contain less than the full length complement regulator protein.

Any human or porcine complement regulator sequences or biologically active portion or fragment thereof known to one skilled in the art can be according to the compositions and methods of the present invention. In additional embodiments, any consensus complement regulator peptide can be used according to the present invention. In another embodiment, nucleic acid and/or peptide sequences at least 80%, 85%, 90% or 95% homologous to the complement regulator peptides and nucleotide sequences described herein. In further embodiments, any fragment or homologous sequence that exhibits similar activity as complement regulator can be used. Optionally, the animal expressing at least one complement regulator (e.g., complement inhibitor) among the at least six transgenes and lacking expression of alpha 1,3 gal has at least one additional genetic modification.

D. Immunosuppressants

In one embodiment, the present invention provides a transgenic animal suitable for use as a source of organs, tissues and cells for xenotransplantation, wherein the donor animal has been genetically modified to incorporate and express at least one immunosuppressant. The transgenic animal typically has one or more additional genetic modifications, and more particularly, five or more additional genetic modifications and even more particularly, six or more additional genetic modifications.

An "immunosuppressant" transgene is capable of down-regulating an immune response. For any type of transplantation procedure, a balance between efficacy and toxicity is a key factor for its clinical acceptance. With respect to islet transplantation, a further concern is that many of the current immunosuppressive agents in particular glucocortecoids or a calcineurin inhibitor, such as Tarcolimus, damage beta cells or induce peripheral insulin resistance (Zeng et al. Surgery (1993) 113: 98-102). A steroid-free immunosuppressive protocol ("Edmonton protocol") that includes sirolimus, low dose Tarcolimus, and a monoclonal antibody (mAb) against IL-2 receptor has been used in a trial of islet transplantation alone for patients with type-1 diabetes (Shapiro, A. M. J. et al, (2000), N. Eng. J. Med., 343: 230-238). The recent success using the "Edmonton protocol" has renewed enthusiasm for the use of islet transplantation to treat diabetes. However, concerns regarding toxicity of the Tacrolimus may limit the application of this therapy in humans.

Biological agents that block key T cell costimulatory signals, in particular the CD28 pathway, are potential alternatives to protect islets. Examples of agents that block the CD28 pathway include but are not limited to soluble CTLA4 including mutant CTLA4 molecules.

T-cell activation is involved in the pathogenesis of transplant rejection. Activation of T-cells requires at least two sets of signaling events. The first is initiated by the specific recognition through the T-cell receptor of an antigenic peptide combined with major histocampatibility complex (MHC) molecules on antigen presenting cells (APC5). The second set of signals is antigen nonspecific and is delivered by T-cell costimulatory receptors interacting with their ligands on APCs. In the absence of costimulation, T-cell activation is impaired or aborted, which may result in an antigen specific unresponsive state of clonal anergy, or in deletion by apoptotic death. Hence, the blockade of T-cell costimulation may provide an approach for suppressing unwanted immune responses in an antigen specific manner while preserving normal immune functions. (Dumont, F. J. 2004 Therapy 1, 289-304).

1. CTLA4

Of several T cell costimulatory pathways identified to date, the most prominent is the CD28 pathway. CD28, a cell surface molecule expressed on T-cells, and its counter receptors, the B7.1 (CD80) and B7.2 (CD86) molecules, present on dendritic cells, macrophages, and B-cells, have been characterized and identified as attractive targets for interrupting T-cell costimulatory signals. A second T-cell surface molecule homologous to CD28 is known as cytoxic T-lymphocyte associated protein (CTLA4). CTLA4 is a cell surface signaling molecule, but contrary to the actions of CD28, CTLA4 negatively regulates T cell function. CTLA4 has 20-fold higher affinity for the B7 ligands than CD28.

The CD28/B7 pathway has become an attractive target for interrupting T cell costimulatory signals. The design of a CD28/B7 inhibitor has exploited the endogenous negative regulator of this system, CTLA4. A CTLA4-immunoglobulin (CTLA4-Ig) fusion protein has been studied extensively as a means to inhibit T cell costimulation. A difficult balance must be reached with any immunosuppressive therapy; one must provide enough suppression to overcome the disease or rejection, but excessive immunosuppression will inhibit the entire immune system. The immunosuppressive activity of CTLA4-Ig has been demonstrated in preclinical studies of animal models of organ transplantation and autoimmune disease. Soluble CTLA4 has recently been tested in human patients with kidney failure, psoriasis and rheumatoid arthritis and has been formulated as a drug developed by Bristol-Myers Squibb (Abatacept, soluble CTLA4-Ig) that has been approved for the treatment of rheumatoid arthritis. This drug is the first in the new class of selective T cell costimulation modulators. Bristol-Myers Squibb is also conducting Phase II clinical trials with Belatacept (LEA29Y) for allograft kidney transplants. LEA29Y is a mutated form of CTLA4, which has been engineered to have a higher affinity for the B7 receptors than wild-type CTLA4, fused to immunoglobulin. Repligen Corporation is also conducting clinical trials with its CTLA4-Ig for idiopathic thrombocytopenic purpura. U.S. Pat. No. 5,730,403 entitled "Methods for protecting allogeneic islet transplant using soluble CTLA4 mutant molecules", describes the use of soluble CTLA4-Ig and CTLA4 mutant molecules to protect allogeneic islet transplants.

Although CTLA-4 from one organism is able to bind to B7 from another organism, the highest avidity is found for allogeneic B7. Thus, while soluble CTLA-4 from the donor organism can thus bind to both recipient B7 (on normal cells) and donor B7 (on xenotransplanted cells), it preferentially binds B7 on the xenograft. Thus in the embodiments of the invention comprising porcine animals or cells for xenotransplantation, porcine CTLA4 is typical. PCT Publication No. WO 99/5 7266 by Imperial College describes a porcine CTLA4 sequence and the administration of soluble CTLA4-Ig for xenotransplantation therapy. Vaughn A. et al., J Immunol (2000) 3175-3181, describes binding and function of soluble porcine CTLA4-Ig. Porcine CTLA4-Ig binds porcine (but not human) B7, blocking CD28 on recipient T cells and rendering these local T cells anergic without causing global T cell immunosuppression (see Mirenda et. al., Diabetes 54:1048-1055, 2005).

Much of the research on CTLA4-Ig as an immunosuppressive agent has focused on administering soluble forms of CTLA4-Ig to the patient. Transgenic mice engineered to express CTLA4-Ig have been created and subject to several lines of experimentation. Ronchese et al. examined immune system function generally after expression of CTLA4 in mice (Ronchese et al. J Exp Med (1994) 179: 809; Lane et al. J Exp Med. (1994) March 1; 179(3):819). Sutherland et al. (Transplantation. 2000 69(9):1806-12) described the protective effect of CTLA4-Ig secreted by transgenic fetal pancreas allografts in mice to test the effects of transgenically expressed CTLA4-Ig on allogenic islet transplantation. Lui et al. (J Immunol Methods 2003 277: 171-183) reported the production of transgenic mice that expressed CTLA4-Ig under control of a mammary specific promoter to induce expression of soluble CTLA4-Ig in the milk of transgenic animals for use as a bioreactor.

PCT Publication No. WO 01/30966 by Alexion Pharmaceuticals Inc. describes chimeric DNA constructs containing the T cell inhibitor CTLA-4 attached to the complement protein CD59, as well as transgenic porcine cells, tissues, and organs containing the same. PCT Publication No.

WO2007035213 (Revivicor) describes transgenic porcine animals that have been genetically modified to express CTLA4-Ig.

Additional immunosuppressors can be expressed in the animals, tissues or cells. For example, genes which have been inactivated in mice to produce an immuno compromised phenotype, can be cloned and disrupted by gene targeting in pigs. Some genes which have been targeted in mice and may be targeted to produce immuno compromised pigs include beta 2-microglobulin. In one embodiment, the donor animals is modified to transgenically express a cytoxic T-lymphocyte associated protein 4-immunoglobin (CTLA4). The animals or cells can be modified to express CTLA4 peptide or a biologically active fragment (e.g., extracellular domain, truncated form of the peptide in which at least the transmembrane domain has been removed) or derivative thereof. The peptide may be, e.g., human or porcine. The CTLA4 peptide can be mutated.

Mutated peptides may have higher affinity than wildtype for porcine and/or human B7 molecules. In one specific embodiment, the mutated CTLA4 can be CTLA4 (Glu104, Tyr29). The CTLA4 peptide can be modified such that it is expressed intracellularly. Other modifications of the CTLA4 peptide include addition of a endoplasmic reticulum retention signal to the N or C terminus The endoplasmic reticulum retention signal may be, e.g., the sequence KDEL. The CTLA4 peptide can be fused to a peptide dimerization domain or an immunoglobulin (Ig) molecule. The CTLA4 fusion peptides can include a linker sequence that can join the two peptides. In another embodiment, animals lacking expression of functional immunoglobulin, produced according to the present invention, can be administered a CTLA4 peptide or a variant thereof (pCTLA4-Ig, or hCTLA4-Ig (Abatacept/Orencia, or Belatacept) as a drug to suppress their T-cell response. As used herein, CTLA4 is used to refer to any of these variants or those known in the art, e.g., CTLA4-Ig.

In one embodiment, the CTLA4 peptide is the full length CTLA4. In a further embodiment, the CTLA4 peptide can contain less than the full length CTLA4 protein. In one embodiment, the CTLA4 peptide can contain the extracellular domain of a CTLA-4 peptide. In a particular embodiment, the CTLA4 peptide is the extracellular domain of CTLA4. In still further embodiments, the present invention provides mutated forms of CTLA4. In one embodiment, the mutated form of CTLA4 can have higher affinity than wild type for porcine and/or human B7. In one specific embodiment, the mutated CTLA4 can be human CTLA4 (Glu104, Tyr29).

In one embodiment, the CTLA4 can be a truncated form of CTLA4, in which at least the transmembrane domain of the protein has been removed. In another embodiment, the CTLA4 peptide can be modified such that it is expressed intracellularly. In one embodiment, a Golgi retention signal can be added to the N or C terminus of the CTLA4 peptide. In one embodiment, the Golgi retention signal can be the sequence KDEL, which can be added to the C or N terminal of the CTLA4 peptide. In further embodiments, the CTLA4 peptide can be fused to a peptide dimerization domain. In one embodiment, the CTLA4 peptide can be fused to an immunoglobulin (Ig). In another embodiment, the CTLA4 fusion peptides can include a linker sequence that can join the two peptides.

Any human CTLA4 sequences or biologically active portion or fragment thereof known to one skilled in the art can be according to the compositions and methods of the present invention. Non-limiting examples include, but are not limited to the following Genbank accession numbers that describe human CTLA4 sequences: NM005214.2; BC074893.2; BC074842.2; AF414120.1; AF414120; AY402333; AY209009.1; BC070162.1; BC069566.1; L15006.1; AF486806.1; AC010138.6; AJ535718.1; AF225900.1; AF225900; AF411058.1; M37243.1; U90273.1; and/or AF316875.1. Further nucleotide sequences encoding CTLA4 peptides can be selected from those including, but not limited to the following Genbank accession numbers from the EST database: CD639535.1; A1733018.1; BM997840.1; BG536887.1; BG236211.1; BG058720.1; A1860i99.1; AW207094.1; AA210929.1; A1791416.1; BX113243.1; AW515943.1; BE837454.1; AA210902.1; BF329809.1; A1819438.1; BE837501.1; BE837537.1; and/or AA873138.1.

In additional embodiments, any consensus CTLA4 peptide can be used according to the present invention. In another embodiment, nucleic acid and/or peptide sequences at least 80%, 85%, 90% or 95% homologous to the native CTLA4 peptides and nucleotide sequences. In further embodiments, any fragment or homologous sequence that exhibits similar activity as CTLA4 can be used. In other embodiments, the amino acid sequence which exhibits T cell inhibitory activity can be amino acids 38 to 162 of the porcine CTLA4 sequence or amino acids 38 to 161 of the human CTLA4 sequence (see, for example, PCT Publication No. WO 01/30966). In one embodiment, the portion used should have at least about 25% and preferably at least about 50% of the activity of the parent molecule.

In other embodiments, the CTLA4 nucleic acids and peptides of the present invention can be fused to immunoglobulin genes and molecules or fragments or regions thereof. Reference to the CTLA4 sequences of the present invention include those sequences fused to immunoglobulins. In one embodiment, the Ig can be a human Ig. In another embodiment, the Ig can be IgG, in particular, IgG1. In another embodiment, the Ig can be the constant region of IgG. In a particular embodiment, the constant region can be the C.gamma.1 chain of IgG1. In one particular embodiment of the present invention, the extracelluar domain of porcine CTLA4 can be fused to human C.gamma.1 Ig. In another particular embodiment, the extracellular domain of human CTLA4 can be fused to IgG1 or IgG4. In a further particular embodiment, the extracellular domain of mutated CTLA4 (Glu 104, Tyr 29) can be fused to IgG1. In one embodiment, at least one of the transgenes is B7-H4, also known as B7x. B7-4H was identified in 2003, and belongs to the B7 family of immunoglobulins.

2. CIITA

In one embodiment, the donor animals is modified to transgenically express class II transactivators (CIITA) and mutants thereof PDL1, PDL2, tumor necrosis factor-.alpha.-related apoptosis-inducing ligand (TRAIL), Fas ligand (FasL, CD95L) integrin-associated protein (CD47), HLA-E, HLA-DP, HLA-DQ, or HLA-DR.

The class II transactivator (CIITA) is a bi- or multifunctional domain protein that acts as a transcriptional activator and plays a critical role in the expression of MHC class II genes. It has been previously demonstrated that a mutated form of the human CIITA gene, coding for a protein lacking the amino terminal 151 amino acids, acts as a potent dominant-negative suppressor of HLA class II expression (Yun et al., Int Immunol. 1997 October; 9(10):1545-53). Porcine MHC class II antigens are potent stimulators of direct T-cell recognition by human CD4+ T cells and are, therefore, likely to play an important role in the rejection responses to transgenic pig donors in clinical xenotransplantation. It was reported that one mutated human CIITA construct was effective in pig cells, markedly suppressing IFN[gamma]-induced as well as constitutive porcine MHC class II expression. Moreover, stably transfected porcine vascular endothelial cell lines carrying mutated human CIITA constructs failed to stimulate direct T-cell xenorecognition by purified human CD4+ T cells (Yun et al., Transplantation. 2000 Mar. 15; 69(5):940-4). Organs, tissues and cells from CIITA-DN transgenic animals could induce a much reduced T-cell rejection responses in human recipients. In combination with other transgenes, transgenic expression of a mutated CIITA might enable long-term xenograft survival with clinically acceptable levels of immunosuppression.

In one embodiment, the present invention provides a transgenic animal (e.g., a pig) comprising genetic modifications that result in (i) lack of expression of alpha Gal and (ii) incorporation and expression of at least two transgenes at a single locus, wherein the at least six transgenes include at least one immunosuppressant. The single locus may be selected from a native locus, a modified native locus or a transgenic locus. Optionally, the transgenic animal includes one or more additional genetic modifications.

In exemplary embodiments, the present invention provides a transgenic animal (e.g., ungulate, porcine animal) comprising genetic modifications that result in (i) lack of expression of alpha Gal and (ii) incorporation and expression of at least six transgenes at a single locus, wherein at least two of the at least two transgenes are immunosuppressants. The single locus may be selected from a native locus, a modified native locus or a transgenic locus. The at least six transgenes may be provided as an MCV and incorporated into the locus utilizing a gene editing tool. Optionally, the transgenic animal includes one or more additional genetic modifications In an exemplary embodiment, animals (and organs, tissues and cells derived therefrom) are provided that lack expression of functional alpha Gal (or expression is reduced) and have been genetically modified to (i) incorporate and express at least six transgenes at a single locus, wherein the at least six transgenes include at least one immunosuppressant. The immunosuppressant may be, for example, CIITA-DN or CLTA4-IG. The at least six transgenes may include additional transgenes selected from a complement inhibitor, an anticoagulant or combinations thereof. The single locus may be selected from a native locus, a modified native locus or a transgenic locus. The at least three transgenes may be provided as an MCV and incorporated into the locus utilizing a gene editing tool. Optionally, the transgenic animal includes one or more additional genetic modifications In an exemplary embodiment, animals (and organs, tissues and cells derived therefrom) are provided that lack expression of functional alpha Gal (or expression is reduced) and have been genetically modified to (i) incorporate and express at least six transgenes at a single locus, wherein the at least six transgenes include at least two immunosuppressants. The immunosuppressant may be, for example, CIITA-DN or CLTA4-IG. The at least six transgenes may also include at least one complement inhibitor, at least two anticoagulants, at least two complement inhibitors, or combinations thereof. The single locus may be selected from a native locus, a modified native locus or a transgenic locus. The at least six transgenes may be provided as an MCV and incorporated into the locus utilizing a gene editing tool. Optionally, the transgenic animal includes one or more additional genetic modifications.

E. Other Immunomodulators

1. PDL1, PDL2

Typical costimulatory molecules for T-cell activation are CD80/86 or CD40. In addition to these positive costimulatory pathways over the past several years, new costimulatory pathways that mediate negative signals and are important for the regulation of T-cell activation have been found. One of these newer pathways is the pathway consisting of Programmed death 1 (PD-1) receptor and its ligands, PD-L1 and PD-L2. The PD-1 receptor is not expressed in resting cells but is upregulated after T and B cell activation. PD-1 contains a cytoplasmic immunoreceptor tyrosine-based switch motif and binding of PD-L1 or PD-L2 to PD-1 leads to inhibitory signals in T cells. Recent data suggest that PD1/PDLigand pathways may play a role in the control of T-cell subsets exhibiting regulatory activity. In mice, PD-1 signals have been shown to be required for the suppressive activity of regulatory T cells (Treg) and the generation of adaptive Treg. These observations suggest that PD-1/PDLigand interactions do not only inhibit T-cell responses but may also provoke immunoregulation.

Several lines of evidence demonstrate that PD-1/PDLigand pathways can control engraftment and rejection of allografts implying that these molecules are interesting targets for immunomodulation after organ transplantation. Indeed, prolongation of allograft survival could be obtained by PDL1Ig gene transfer to donor hearts in a rat transplantation model. Moreover, enhancing PD-1 signaling by injection of PD-L1 Ig has also been reported to protect grafts from rejection in mice. Recent data also show that overexpression of PD-L1 IG on islet grafts in mice can partially prolong islet graft survival. Transgenic expression of human PD-LI or PD-L2 in pig cells and tissues should reduce early human anti-pig T-cell responses initiated via the direct route of sensitization (Plege et al., Transplantation. 2009 Apr. 15; 87(7):975-82). By the induction of Treg it might also be possible to control T cells sensitized to the xenograft through the indirect route that is required to achieve long-lasting tolerance.

In a particular embodiment, the transgenic animal lacking expression of alpha Gal and incorporating and expressing at least six transgenes under the control of at least three promoters comprises incorporation and expression of PDL1 or PDL2.

2. TRAIL/Fas L

Expression of apoptosis inducing ligands, such as Fas ligand (FasL, CD95L) or tumor necrosis factor-.alpha.-related apoptosis-inducing ligand (TRAIL, Apo-2L) may eliminate T cells attacking a xenograft. TRAIL is a type II membrane protein with an extracellular domain homologous to that of other tumor necrosis factor family members showing the highest amino acid identity to FasL (28%). TRAIL exerts its apoptosis-inducing action preferentially on tumor cells. In normal cells, binding of TRAIL receptors does not lead to cell death. Recent studies have shown that the cytotoxic effects of immune cells, including T cells, natural killer cells, macrophages, and dendritic cells, are mediated at least partly by TRAIL. Expression of human TRAIL in transgenic pigs may provide a reasonable strategy for protecting pig tissues against cell-mediated rejection after xenotransplantation to primates. Stable expression of human TRAIL has been achieved in transgenic pigs and TRAIL expressed has been shown to be biologically functional in vitro (Klose et al., Transplantation. 2005 Jul. 27; 80(2):222-30). In some embodiments, the transgenic animal lacking expression of alpha Gal and incorporating and expressing at least six transgenes under the control of at least three promoters comprises incorporation and expression of TRAIL or Fas L.

3. NK Cell Response-HLA-E/Beta 2 Microglobulin and HLA-DP, HLA-DQ, HLA-DR

Human natural killer (NK) cells represent a potential hurdle to successful pig-to-human xenotransplantation because they infiltrate pig organs perfused with human blood ex vivo and lyse porcine cells in vitro both directly and, in the presence of human serum, by antibody-dependent cell-mediated cytotoxicity. NK cell autoreactivity is prevented by the expression of major histocompatibility complex (MHC) class I ligands of inhibitory NK receptors on normal autologous cells. The inhibitory receptor CD94/NKG2A that is expressed on a majority of activated humanNK cells binds specifically to human leukocyte antigen (HLA)-E. The nonclassical human IHC molecule HLA-E is a potent inhibitory ligand for CD94/NKG2A-bearing NK cells and, unlike classical IHC molecules, does not induce allogeneic T-cell responses. HLA-E is assembled in the endoplasmic reticulum and transported to the cell surface as a stable trimeric complex consisting of the HLA-E heavy chain, .beta.2-microglobulin (.beta.2m), and a peptide derived from the leader sequence of some IHC class 1 molecules. The expression of HLA-E has been shown to provide partial protection against xenogeneic human NK cell cytotoxicity (Weiss et al., Transplantation. 2009 Jan. 15; 87(1):35-43). Transgenic expression of HLA-E on pig organs has the potential to substantially alleviate human NK cell-mediated rejection of porcine xenografts without the risk of allogeneic responses. In addition, transgenic pigs carrying other HLA genes have been successfully generated with the goal of "humanizing" porcine organs, tissues, and cells (Huang et al., Proteomics. 2006 November; 6(21): 5815-25, see also U.S. Pat. No. 6,639,122).

In a particular embodiment, the transgenic animal lacking expression of alpha Gal and incorporating and expressing at least six transgenes under the control of at least three promoters comprises incorporation and expression of HLA-3.

4. CD47

CD47 (Cluster of Differentiation 47) also known as integrin associated protein (IAP) is a transmembrane protein that in humans is encoded by the CD47 gene. CD47 is known to be both an immunosuppressant and immunomodulator and tolerogenic at of SIRP-alpha signaling. CD47 is a ubiquitously expressed 50-kDa cell surface glycoprotein that serves as a ligand for signal regulatory protein (SIRP)-alpha (also known as CD172a, SHPS-1, SIRP-alpha), an immune inhibitory receptor on macrophages. CD47 and SIRP-alpha constitute a cell-cell communication system (the CD47-SIRP-alpha system) that plays important roles in a variety of cellular processes including cell migration, adhesion of B cells, and T cell activation. In addition, the CD47-SIRP-alpha system is implicated in negative regulation of phagocytosis by macrophages. CD47 on the surface of several cell types (i.e., erythrocytes, platelets, or leukocytes) can protect against phagocytosis by macrophages by binding to the inhibitory macrophage receptor SIRP-alpha. The role of CD47-SIRP-alpha interactions in the recognition of self and inhibition of phagocytosis has been illustrated by the observation that primary, wild-type mouse macrophages rapidly phagocytose unopsonized RBCs obtained from CD47-deficient mice but not those from wild-type mice.

Through its SIRP-alpha receptors, CD47 inhibits both Fc gamma and complement receptor-mediated phagocytosis. Porcine CD47 does not induce SIRP-alpha.-tyrosine phosphorylation in human macrophage-like cell line, and soluble human CD47-Fc fusion protein inhibits the phagocytic activity of human macrophages toward porcine cells. As such, manipulating porcine cells for expression of human CD47 radically reduces the susceptibility of the cells to phagocytosis by human macrophages (Ide et al., Proc Natl Acad Sci USA. 2007 Mar. 20; 104(12):5062-6). Expression of human CD47 on porcine cells could provide inhibitory signaling to SIRP-alpha on human macrophages, providing an approach to preventing macrophage-mediated xenograft rejection.

In some embodiments, the transgenic animal lacking expression of alpha Gal and incorporating and expressing at least six transgenes under the control of at least three promoters comprises incorporation and expression of CD47. In an exemplary embodiment, animals (and organs, tissues and cells derived therefrom) are provided that lack expression of functional alpha Gal (or expression is reduced) and have been genetically modified to (i) incorporate and express at least six transgenes at a single locus, wherein one of the at least six transgenes is CD47. In some embodiments, the at least six transgenes may include additional transgenes selected from a complement inhibitor, an anticoagulant or combinations thereof. In some embodiments, the single locus may be selected from a native locus, a modified native locus or a transgenic locus. The at least three transgenes may be provided as an MCV and incorporated into the locus utilizing a gene editing tool. Optionally, the transgenic animal includes one or more additional genetic modifications F. Anticoagulants In one embodiment, the present invention provides a transgenic animal suitable for use as a source of organs, tissues, and cells for xenotransplantation, wherein the transgenic animal has been genetically modified to incorporate and express at least one anticoagulant. In some embodiments, the animal comprises additional genetic modifications. In some embodiments, the transgenic animal comprises at least ten genetic modifications, and even more particularly. In some embodiments, the ten genetic modifications comprise at least six transgenic insertion and at least four knockout genes. In exemplary embodiments, the present invention provides a transgenic animal which comprises at least ten genetic modifications that result in (i) lack of expression of alpha Gal and (ii) incorporation and expression of at least six transgenes at a single locus under the control of at least three promoters, wherein at least two transgenes are anticoagulants. In some embodiments, the at least two anticoagulant transgenes are under the control of an endothelial-specific promoter.

In some embodiments, the anticoagulant may be any suitable anticoagulant. Representative, non-limiting examples of suitable anticoagulant transgenes include tissue factor pathway inhibitor, hirudin, thrombomodulin, Endothelial cell protein C receptor (EPCR), CD39 and combinations thereof. In some embodiments, the anticoagulant is selected from the group consisting of endothelial protein C receptor (EPCR), thrombomodulin, CD39, hirudin, Tissue factor pathway inhibitor (TFPI), and a combination thereof. In some embodiments, expression of the anticoagulant may be ubiquitous or tissue specific. In some embodiment, expression of the anticoagulant is controlled by a promoter active primarily in endothelium.

1. TFPI

Tissue factor pathway inhibitor (TFPI) is a single-chain polypeptide which can reversibly inhibit Factor Xa (Xa) and Thrombin (Factor IIa) and thus inhibits TF dependent coagulation. For a review of TFPI, please see Crawley and Lane (Arterioscler Thromb Vasc Biol. 2008, 28(2):233-42). Dorling and colleagues generated transgenic mice expressing a fusion protein consisting of the three Kunitz domains of human TFPI linked to the transmembrane/cytoplasmic domains of human CD4, with a P-selectin tail for targeting to Weibel-Palade intracellular storage granules (Chen D, et al. Am J Transplant 2004; 4: 1958-1963.). The resulting activation-dependent display of TFPI on the endothelium was sufficient to completely inhibit thrombosis-mediated acute humoral rejection of mouse cardiac xenografts by cyclosporine-treated rats. There was also a suggestion that effective regulation of coagulation may prevent chronic rejection. Similar results were obtained with transgenic mouse hearts expressing a hirudin/CD4/P-selectin fusion protein, indicating that inhibition of thrombin generation or activity was the key to protection in this model.

2. Hirudin

Hirudin is a naturally occurring peptide in the salivary glands of medicinal leeches (such as *Hirudo medicinalis*) and is a potent inhibitor of thrombin. Dorling and coworkers (Chen et al., J Transplant. 2004 December; 4(12):1958-63) also generated transgenic mice expressing membrane-tethered hirudin fusion proteins, and transplanted their hearts into rats (mouse-rat Xeno-Tx). In contrast to control non-transgenic mouse hearts, which were all rejected within 3 days, 100% of the organs from both strains of transgenic mice were completely resistant to humoral rejection and survived for more than 100 days when T-cell-mediated rejection was inhibited by administration of ciclosporin A. Riesbeck et al., (Circulation. 1998 Dec. 15; 98(24):2744-52) also explored the expression of hirudin fusion proteins in mammalian cells as a strategy for prevention of intravascular thrombosis. Expression in cells reduced local thrombin levels and inhibited fibrin formation. Therefore, hirudin is another anticoagulant transgene of interest for preventing the thrombotic effects present in xenotransplantation.

3. Thrombomodulin

Thrombomodulin (TBM) functions as a cofactor in the thrombin-induced activation of protein C in the anticoagulant pathway by forming a 1:1 stoichiometric complex with thrombin. Endothelial cell protein C receptor (EPCR) is an N-glycosylated type I membrane protein that enhances the activation of protein C. The role of these proteins in the protein C anticoagulant system is reviewed by Van de Wouwer et al., Arterioscler Thromb Vasc Biol. 2004 August; 24(8):1374-83. Expression of these and other anticoagulant transgenes has been explored by various groups to potentially address the coagulation barriers to xenotransplantation (reviewed by Cowan and D'Apice, Cur Opin Organ Transplant. 2008 April; 13(2):178-83). Esmon and coworkers (Li et al., J Thromb Haemost. 2005 July; 3(7):1351-9 overexpressed EPCR on the endothelium of transgenic mice and showed that such expression protected the mice from thrombotic challenge. Iino et al., (J Thromb Haemost. 2004 May; 2(5):833-4), suggested ex-vivo over expression of TBM in donor islets via gene therapy as a means to prevent thrombotic complications in islet transplantation.

4. CD39

CD39 is a major vascular nucleoside triphosphate diphosphohydrolase (NTPDase), and converts ATP, and ADP to AMP and ultimately adenosine. Extracellular adenosine plays an important role in thrombosis and inflammation, and thus has been studied for its beneficial role in transplantation (reviewed by Robson et al. Semin Thromb Hemost. 2005 April; 31(2):217-33). Recent studies have shown that CD39 has a major effect in reducing the inflammatory response (Beldi et al., Front Biosci, 2008, 13:2588-2603). Transgenic mice expressing hCD39 exhibited impaired platelet aggregation, prolonged bleeding times, and resistance to systemic thromboembolism in a heart transplant model (Dwyer et al., J Clin Invest. 2004 May; 113(10): 1440-6). They were also shown to express CD39 on pancreatic islets and when incubated with human blood, these islets significantly delayed clotting time compared to wild type islets (Dwyer et al., Transplantation. 2006 Aug. 15; 82(3):428-32). Preliminary efforts at expressing hCD39 at high levels from a constitutive promoter system in transgenic pigs, showed high post-natal lethality (Revivicor, Inc., unpublished data). However, endothelial cell specific expression of CD39 has shown to be better tolerated by transgenic pigs. Thus there is a need to express certain anticoagulant transgenes in pigs in a manner that does not compromise the animal's wellbeing, yet still provides adequate levels of expression for utility in clinical xenotransplantation.

In exemplary embodiments, the present invention provides a transgenic animal (e.g., ungulate, porcine animal) that has genetic modifications that result in (i) lack of expression of alpha Gal (or expression is reduced) and (ii) incorporation and expression of at least six transgenes at a single locus under the control of three promoters, wherein at least one of two transgenes are anticoagulants.

In one embodiment, the anticoagulant is selected from tissue factor pathway inhibitor, hirudin, thrombomodulin, Endothelial cell protein C receptor (EPCR), CD39 and combinations thereof. In some embodiments, the single locus may be a native locus, modified native locus or transgenic locus. In some embodiments, the native locus could be GGTA1, B4GalNT2, GHR, CMAH, Rosa26, AAVS1, or other endogenous loci that might impart beneficial expression characteristics on the integrated transgenes.

In some embodiments, the at least six transgenes are under control of at least three promoters may be provided as an MCV and incorporation may involve a gene editing tool. Such editing may involve targeted insertion into a predetermined site (e.g. landing pad) that acts as either a "safe harbor" (so as not to interrupt any essential genes in the genome), and/or to provide desirable characteristics specific to the integration site. In the case of insertions at loci important to preventing xenograft rejection, insertion of the multi-transgenes also can have the outcome of inactivation of a porcine gene involved in inducing xeno reactions in primates (i.e. inactivation of alpha Gal, CMAH, or B4GalNT2 or others (iGB3, Forssman). Optionally, the animal may include one or more additional genetic modifications, and at more than one locus, wherein the at least six transgenes are inserted at one locus, and another set of two or more transgenes (under control of at least three promoters) could be co-integrated at a second site. An alternative embodiment provides for MCV insertion at one locus, and targeted inactivation at a different locus, where such inactivation might be facilitated by a gene editing tool.

In exemplary embodiments, the present invention provides a transgenic animal (e.g., ungulate, porcine animal) that has genetic modifications that result in (i) lack of expression of alpha Gal (or expression is reduced) and (ii) incorporation and expression of at least four, at least five, at least six, at least seven, or at least eight or more transgenes at a single locus, wherein at least one, at least two or at least three of the transgenes is an anticoagulant. In one embodiment, the anticoagulant is selected from tissue factor pathway inhibitor, hirudin, thrombomodulin, Endothelial cell protein C receptor, CD39 and combinations thereof. In some embodiments, at least six transgenes may be provided as an MCV and incorporation may involve a gene editing tool. In some embodiments, the single locus may be a native locus, modified native locus or transgenic locus. In some embodiments, the transgenic animal may include one or more additional genetic modifications.

The present invention provides a transgenic animal (e.g., ungulate, porcine animal) that lacks expression of alpha Gal (or expression is reduced) and has been genetically modified to incorporate and express at least three anticoagulants. In certain embodiments, the anticoagulant is selected from tissue factor pathway inhibitor (TFPI), hirudin, thrombomodulin, Endothelial cell protein C receptor, CD39 and combinations thereof. In certain embodiments, at least one of the at least three anticoagulants is controlled by expression of a promoter primarily active in endothelial cells. In certain embodiments, at least two of the at least three anticoagulants is controlled by expression of a promoter primarily active in endothelial cells.

In exemplary embodiments, the present invention provides a transgenic animal (e.g., ungulate, porcine animal) that lacks expression of alpha Gal (or expression is reduced) and has been genetically modified to incorporate and express at least three anticoagulants, wherein one of the at least three anticoagulant is EPCR.

In exemplary embodiments, the present invention provides a transgenic animal (e.g., ungulate, porcine animal) that lacks expression of alpha Gal (or expression is reduced) and has been genetically modified to incorporate and express at least three anticoagulants, wherein the at least three anticoagulants include EPCR and TBM.

In one embodiment, the present invention provides a transgenic animal (e.g., ungulate, porcine animal) that lacks expression of alpha Gal (or expression is reduced) and has been genetically modified to incorporate and express at least four additional transgenes, wherein the at least four additional transgenes include at least one anticoagulant. In certain embodiments, the at least one anticoagulant is selected from tissue factor pathway inhibitor, hirudin, thrombomodulin, Endothelial cell protein C receptor, CD39 and combinations thereof. In one embodiment, the at least one anticoagulant is EPCR.

In one embodiment, the present invention provides a transgenic animal (e.g., ungulate, porcine animal) that lacks expression of alpha Gal (or expression is reduced) and has been genetically modified to incorporate and express at least four additional transgenes, wherein the at least four additional transgenes include at least two anticoagulants. In certain embodiments, the at least two anticoagulants are selected from tissue factor pathway inhibitor, hirudin, thrombomodulin, Endothelial cell protein C receptor, CD39 and combinations thereof. In one embodiment, the at least two anticoagulants include EPCR and TBM. In another embodiment, the at least two anticoagulants include EPCR and TFPI.

In one embodiment, the present invention provides a transgenic animal (e.g., ungulate, porcine animal) that lacks expression of alpha Gal (or expression is reduced) and has been genetically modified to incorporate and express at least four additional transgenes, wherein the at least four additional transgenes include at least three anticoagulants. In certain embodiments, the at least three anticoagulants are selected from tissue factor pathway inhibitor, hirudin, thrombomodulin, Endothelial cell protein C receptor, CD39 and combinations thereof. In one embodiment, the at least three anticoagulants include EPCR, TBM and TFPI. In another embodiment, the at least three anticoagulants include EPCR, TBM and CD39.

In one embodiment, the present invention provides a transgenic animal (e.g., ungulate, porcine animal) that lacks expression of alpha Gal (or expression is reduced) and has been genetically modified to incorporate and express at least five additional transgenes, wherein the at least five additional transgenes include at least two anticoagulants. In certain embodiments, the at least two anticoagulants are selected from tissue factor pathway inhibitor, hirudin, thrombomodulin, Endothelial cell protein C receptor, CD39 and combinations thereof. In one embodiment, the at least two anticoagulants include EPCR and TBM. In another embodiment, the at least two anticoagulants include EPCR and TFPI.

In one embodiment, the present invention provides a transgenic animal (e.g., ungulate, porcine animal) that lacks expression of alpha Gal (or expression is reduced) and has been genetically modified to incorporate and express at least five additional transgenes, wherein the at least five additional transgenes include at least three anticoagulants. In certain embodiments, the at least three anticoagulants are selected from tissue factor pathway inhibitor, hirudin, thrombomodulin, Endothelial cell protein C receptor, CD39 and combinations thereof. In one embodiment, the at least three anticoagulants include EPCR, TBM and TFPI. In another embodiment, the at least three anticoagulants include EPCR, TBM and CD39.

In one embodiment, the present invention provides a transgenic animal (e.g., ungulate, porcine animal) that lacks expression of alpha Gal (or expression is reduced) and has been genetically modified to incorporate and express at least six additional transgenes, wherein the at least six additional transgenes include at least two anticoagulants. In certain embodiments, the at least two anticoagulants are selected from tissue factor pathway inhibitor, hirudin, thrombomodulin, Endothelial cell protein C receptor, CD39 and combinations thereof. In one embodiment, the at least two anticoagulants include EPCR and TBM. In another embodiment, the at least two anticoagulants include EPCR and TFPI. Optionally, the at least six additional transgenes also include at least one immunosuppressant.

In one embodiment, the present invention provides a transgenic animal (e.g., ungulate, porcine animal) that lacks expression of alpha Gal (or expression is reduced) and has been genetically modified to incorporate and express at least six additional transgenes, wherein the at least six additional transgenes include at least three anticoagulants. In certain embodiments, the at least three anticoagulants are selected from tissue factor pathway inhibitor, hirudin, thrombomodulin, Endothelial cell protein C receptor, CD39 and combinations thereof. In one embodiment, the at least three anticoagulants include EPCR, TBM and TFPI. In another embodiment, the at least three anticoagulants include EPCR, TBM and CD39.

G. Cytoprotective Transgenes

The present invention provides a transgenic animal suitable for use as a source of organs, tissues and cells for xenotransplantation, wherein the transgenic animal has been genetically modified to incorporate and express at least one cryoprotective transgene ("cytoprotectants'). In some embodiments, the at least one cytoprotective transgene is under the control of a constitutive promoter or an endothelial-specific promoter. In some embodiments, the at least one cytoprotective transgene is selected from the group consisting of heme oxygenase 1 (HO-1), A20, FAT-1, soluble tumor necrosis factor-alpha (TNF-alpha), and a combination thereof.

The present invention provides a transgenic animal (e.g., a pig) comprising genetic modifications that result in: (i) lack of expression of alpha Gal; and (ii) incorporation and expression of at least six transgenes at a single locus under the control of at least three promoters, wherein at least one of the at least six transgenes is a cytoprotective transgene.

Cytoprotective transgenes are considered to include anti-apoptotics, anti-oxidants and anti-inflammatories. Examples include A20, heme oxygenase 1 (HO-1), FAT-1, soluble tumor necrosis factor-alpha (TNF-alpha).

1. A20

A20 provides anti-inflammatory and anti-apoptotic activity. Vascularized transplanted organs may be protected against endothelial cell activation and cellular damage by anti-inflammatory, anticoagulant and/or anti-apoptotic molecules. Among genes with great potential for modulation of acute vascular rejection (AVR) is the human A20 gene (hA20) that was first identified as a tumor necrosis factor (TNF)-alpha inducible factor in human umbilical vein endothelial cells. Human A20 has a double cytoprotective function by protecting endothelial cells from TNF-mediated apoptosis and inflammation, via blockade of several caspases, and the transcription factor nuclear factor-kappa B, respectively. Viable A20 transgenic piglets have been produced and in these animals expression of hA20 was restricted to skeletal muscle, heart and PAECs which were protected against TNF mediated apoptosis by hA20 expression and at least partly against CD95(Fas)L-mediated cell death. In addition, cardiomyocytes from hA20-transgenic-cloned pigs were partially protected against cardiac insults (Oropeza et al., Xenotransplantation. 2009 November; 16(6):522-34).

2. HO-1

HO provides anti-inflammatory, anti-apoptotic, and anti-oxidant activity. Heme oxygenases (HOs), rate-limiting enzymes in heme catabolism, also named HSP32, belong to members of heat shock proteins, wherein the heme ring is cleaved into ferrous iron, carbon monoxide (CO) and biliverdin that is then converted to bilirubin by biliverdin reductase. Three isoforms of HOs, including HO-1, HO-2 and HO-3, have been cloned. The expression of HO-1 is highly inducible, whereas HO-2 and HO-3 are constitutively expressed (Maines M D et al., Annual Review of Pharmacology & Toxicology 1997; 37:517-554, and Choi A M et al., American Journal of Respiratory Cell & Molecular Biology 1996; 15:9-19). An analysis of HO-1$^{-/-}$ mice suggests that the gene encoding HO-1 regulates iron homeostasis and acts as a cytoprotective gene having potent antioxidant, anti-inflammatory and anti-apoptotic effects. Similar findings were recently described in a case report of HO-1 deficiency in humans.

The molecular mechanisms responsible for the cytoprotective effects of HO-1, including anti-inflammation, anti-oxidation and anti-apoptosis, are mediated by its' reaction products. HO-1 expression can be modulated in vitro and in vivo by protoporphyrins with different metals. Cobalt protoporphyrins (CoPP) and iron protoporphyrins (FePP) can upregulate the expression of HO-1. In contrast, tin protoporphyrins (SnPP) and zinc protoporphyrins (ZnPP) inhibit the activity of HO-1 at the protein level. Expression of HO-1 suppresses the rejection of mouse-to-rat cardiac transplants, protects islet cells from apoptosis, and improves the in vivo function of islet cells after transplantation. It has also been proved that administration of HO-1 by gene transfer provides protection against hyperoxia-induced lung injury, upregulation of HO-1 protects genetically fat Zucker rat livers from ischemia/reperfusion injury, and ablation or expression of HO-1 gene modulates cisplatin-induced renal tubular apoptosis. In transgenic animal models, it was shown that over-expression of HO-1 prevents the pulmonary inflammatory and vascular responses to hypoxia and protects heart against ischemia and reperfusion injury. Pigs carrying a HO-1 transgene have been produced however clinical effects related to their use in xenotransplantation were not reported (U.S. Pat. No. 7,378,569).

3. FAT-1

FAT-1 provides anti-inflammatory activity. Polyunsaturated fatty acids (PUFAs) play a role in inhibiting (n-3 class) inflammation. Mammalian cells are devoid of desaturase that converts n-6 to n-3 PUFAs. Consequently, essential n-3 fatty acids must be supplied with the diet. Unlike mammals, however, the free-living nematode *Caenorhabditis elegans* expresses a n-3 fatty acid desaturase that introduces a double bond into n-6-fatty acids at the n-3 position of the hydrocarbon chains to form n-3 PUFAs. Transgenic mice have been generated that express the elegans fat-1 gene and, consequently, are able to efficiently convert dietary PUFAs of the 6 series to PUFAs of 3-series, such as EPA (20:5 n-3) and DHA (22-6 n-3). Another group produced a transgenic mouse model wherein the codons of fat-1 cDNA were further optimized for efficient translation in mammalian systems; endogenous production of n-3 PUFAs was achieved through overexpressing a *C. elegans* n-3 fatty acid desaturase gene, mfat-1. This group showed that cellular increase of n-3 PUFAs and reduction of n-6 PUFAs through transgenic expression of mfat-1 enhanced glucose-, amino acid-, and GLP-1-stimulated insulin secretion in isolated pancreatic islets of the mice, and rendered the islets strongly resistant to cytokine-induced cell death (Wei et al., Diabetes. 2010 February; 59(2):471-8).

4. Soluble TNF-Alpha Receptor (sTNFR1)

Tumor necrosis factor (TNF, cachexin or cachectin and formally known as tumor necrosis factor-alpha) is a cytokine involved in systemic inflammation and is a member of a group of cytokines that stimulate the acute phase reaction. The primary role of TNF is in the regulation of immune cells. TNF is able to induce apoptotic cell death, to induce inflammation. Soluble TNF-alpha receptor 1 (sTNFR1) is an extracellular domain of TNFR1 and an antagonist to TNF-alpha (Su et al., 1998. Arthritis Rheum. 41, 139-149). Transgenic expression of sTNFR1 in xenografts may have beneficial anti-inflammatory effects.

Other cytoprotectives with relevant anti-oxidant properties include, without limitation, SOD and Catalyse. Oxygen is the essential molecule for all aerobic organisms, and plays predominant role in ATP generation, namely, oxidative phosphorylation. During this process, reactive oxygen species (ROS) including superoxide anion $(O(2)(-))$ and hydrogen peroxide $(H(2)O(2))$ are produced as by-products. In man, an antioxidant defense system balances the generation of ROS. Superoxide dismutase (SOD) and catalase are two enzymes with anti-oxidant properties. SOD catalyses the dismutation of superoxide radicals to hydrogen peroxide, the latter being converted to water by catalase and glutathione peroxidase. Cellular damage resulting from generation of ROS can occur in a transplant setting. Because of reduced antioxidant defenses, pancreatic beta-cells are especially vulnerable to free radical and inflammatory damage. Commonly used antirejection drugs are excellent at inhibiting the adaptive immune response; however, most are harmful to islets and do not protect well from reactive oxygen species and inflammation resulting from islet isolation and ischemia-reperfusion injury. Therefore there is an interest in treating islets ex-vivo with anti-oxidants, or expressing anti-oxidant genes via gene therapy or transgenic expression in donor tissues. Ex vivo gene transfer of EC-SOD and catalase were anti-inflammatory in a rat model of antigen induced arthritis (Dai et al., Gene Ther. 2003 April; 10(7): 550-8). In addition, delivery of EC-SOD and/or catalase genes through the portal vein markedly attenuated hepatic I/R injury in a mouse model (He et al., Liver Transpl. 2006 December; 12(12):1869-79). In a recent mouse study, pancreatic islets treated with catalytic antioxidant before syngeneic, suboptimal syngeneic, or xenogeneic transplant exhibited superior function compared with untreated controls. In this same study, diabetic murine recipients of catalytic antioxidant-treated allogeneic islets exhibited improved glycemic control post-transplant and demonstrated a delay in allograft rejection. Moreover, islet grafts overexpressing MnSOD functioned approximately 50% longer than control grafts. Moreover, certain anti-coagulants also provide anti-inflammatory activity including thrombomodulin, EPCR and CD39.

In exemplary embodiments, the present invention provides a transgenic animal (e.g., a pig) comprising genetic modifications that result in (i) lack of expression of alpha Gal; and (ii) incorporation and expression of at least six transgenes at a single locus (under control of at least three promoters), wherein at least one of the at least six transgenes is a cytoprotective transgene. The single locus may be a native locus, a modified native locus or a transgenic locus. The at least two transgenes may be provided as an MCV and incorporation may involve a gene editing tool. Optionally, the animal may have one or more additional genetic modifications.

In exemplary embodiments, the present invention provides a transgenic animal (e.g., a pig) comprising genetic modifications that result in (i) lack of expression of alpha Gal; and (ii) incorporation and expression of, at least five, at least six, at least seven, or at least eight transgenes at a single locus, or at least six transgenes at one locus and one or more transgenes at a second locus, wherein at least one of the transgenes is a cytoprotective transgene, and wherein the at least six transgenes are under control of at least three promoters, which could be different combinations of constitutive, ubiquitous, tissue-specific or inducible regulated promoter systems. The transgenes may be provided as an MCV and incorporation may involve a gene editing tool. The single locus may be a native locus, a modified native locus or a transgenic locus. Optionally, the animal may have one or more additional genetic modifications.

IV. Production of Transgenic Animals

The present invention provides a method of making a transgenic pig comprising at least six transgenes comprising the step of: (i) transfecting a porcine cell with a single polycistronic vector comprising (a) at least two complement inhibitor transgenes; (b) at least one immunosuppressant transgene; (c) at least one cytoprotective transgene; and (d) at least two anticoagulant transgenes; (ii) producing a multitransgenic porcine cell comprising at least six transgenes by incorporating and expressing the polycistronic vector at a single genomic locus; (iii) generating a multitransgenic porcine zygote by injecting the nucleus of the multitransgenic porcine cell into a reconstructed somatic cell nuclear transfer (SCNT); and (iv) permitting the multitransgenic porcine zygote to mature into a multitransgenic pig. In some embodiments, the porcine cell and the multitransgenic pig lack expression of alpha 1,3 galactosyltransferase.

Transgenic animals of the present invention can be produced by any method known to one of skill in the art including, but not limited to, selective breeding, nuclear transfer, introduction of DNA into oocytes, sperm, zygotes, or blastomeres, or via the use of embryonic stem cells. Genetic editing tools may also be utilized, as described further herein.

In some embodiments, genetic modifications may be identified in animals that are then bred together to form a herd of animals with a desired set of genetic modifications (or a single genetic modification). These offspring may be further bred to produce different or the same set of genetic modifications (or single genetic modification) in their progeny. This cycle of breeding for animals with desired genetic modification(s) may continue for as long as one desires. "Herd" in this context may comprise multiple generations of animals produced over time with the same or different genetic modification(s). "Herd" may also refer to a single generation of animals with the same or different genetic modification(s).

Cells useful for genetic modification (via, for example, but not limited to, homologous recombination, random insertion/integration, nuclease editing, zinc finger plus TALEN nucleases, CRISPR/Cas 9 nucleases) include, by way of example, epithelial cells, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells, etc. Moreover, the cells used for producing the genetically modified animal (via, for example, but not limited to, nuclear transfer) can be obtained from different organs, e.g., skin, lung, pancreas, liver, stomach, intestine, heart, reproductive organs, bladder, kidney, urethra and other urinary organs, etc. Cells can be obtained from any cell or organ of the body, including all somatic or germ cells.

Additionally, animal cells that can be genetically modified can be obtained from a variety of different organs and tissues such as, but not limited to, skin, mesenchyme, lung, pancreas, heart, intestine, stomach, bladder, blood vessels, kidney, urethra, reproductive organs, and a disaggregated preparation of a whole or part of an embryo, fetus, or adult animal. In one embodiment of the invention, cells can be selected from the group consisting of, but not limited to, epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, granulosa cells, cumulus cells, epidermal cells, endothelial cells, Islets of Langerhans cells, blood cells, blood precursor cells, bone cells, bone precursor cells, neuronal stem cells, primordial stem cells, adult stem cells, mesenchymal stem cells, hepatocytes, keratinocytes, umbilical vein endothelial cells, aortic endothelial cells, microvascular endothelial cells, fibroblasts, liver stellate cells, aortic smooth muscle cells, cardiac myocytes, neurons, Kupffer cells, smooth muscle cells, Schwann cells, and epithelial cells, erythrocytes, platelets, neutrophils, lymphocytes, monocytes, eosinophils, basophils, adipocytes, chondrocytes, pancreatic islet cells, thyroid cells, parathyroid cells, parotid cells, tumor cells, glial cells, astrocytes, red blood cells, white blood cells, macrophages, epithelial cells, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B-cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, squamous epithelial cells, osteocytes, osteoblasts, and osteoclasts. In one alternative embodiment, embryonic stem cells can be used. An embryonic stem cell line can be employed or embryonic stem cells can be obtained freshly from a host, such as a porcine animal. The cells can be grown on an appropriate fibroblast-feeder layer or grown in the presence of leukemia inhibiting factor (LIF).

Embryonic stem cells are a preferred germ cell type, an embryonic stem cell line can be employed, or embryonic stem cells can be obtained freshly from a host, such as a porcine animal. The cells can be grown on an appropriate fibroblast-feeder layer or grown in the presence of leukemia inhibiting factor (LIF).

Cells of particular interest include, among other lineages, stem cells, e.g. hematopoietic stem cells, embryonic stem cells, mesenchymal stem cells, etc., the islets of Langerhans, adrenal medulla cells which can secrete dopamine, osteoblasts, osteoclasts, epithelial cells, endothelial cells, leukocytes, e.g. B- and T-lymphocytes, myelomonocytic cells, etc., neurons, glial cells, ganglion cells, retinal cells, liver cells, e.g. hepatocytes, bone marrow cells, keratinocytes, hair follicle cells, and myoblast (muscle) cells.

In a particular embodiment, the cells can be fibroblasts or fibroblast-like cells having a morphology or a phenotype that is not distinguishable from fibroblasts, or a lifespan before senescence of at least 10 or at least 12 or at least 14 or at least 18 or at least 20 days, or a lifespan sufficient to allow homologous recombination and nuclear transfer of a non-senescent nucleus; in one specific embodiment, the cells can be fetal fibroblasts. Fibroblast cells are a suitable somatic cell type because they can be obtained from developing fetuses and adult animals in large quantities. These cells can be easily propagated in vitro with a rapid doubling time and can be clonally propagated for use in gene targeting procedures. The cells to be used can be from a fetal animal or can be neonatal or from an adult animal in origin. The cells can be mature or immature and either differentiated or non-differentiated.

A. Homologous Recombination

Homologous recombination permits site-specific modifications in endogenous genes and thus novel alterations can be engineered into the genome. A primary step in homologous recombination is DNA strand exchange, which involves a pairing of a DNA duplex with at least one DNA strand containing a complementary sequence to form an intermediate recombination structure containing heteroduplex DNA (see, for example Radding, C. M. (1982) Ann. Rev. Genet. 16: 405; U.S. Pat. No. 4,888,274). The heteroduplex DNA can take several forms, including a three DNA strand containing triplex form wherein a single complementary strand invades the DNA duplex (Hsieh et al. (1990) Genes and Development 4: 1951; Rao et al., (1991) PNAS 88:2984)) and, when two complementary DNA strands pair with a DNA duplex, a classical Holliday recombination joint or chi structure (Holliday, R. (1964) Genet. Res. 5: 282) can form, or a double-D loop ("Diagnostic Applications of Double-D Loop Formation" U.S. Ser. No. 07/755,462, filed Sep. 4, 1991). Once formed, a heteroduplex structure can be resolved by strand breakage and exchange, so that all or a portion of an invading DNA strand is spliced into a recipient DNA duplex, adding or replacing a segment of the recipient DNA duplex.

Alternatively, a heteroduplex structure can result in gene conversion, wherein a sequence of an invading strand is transferred to a recipient DNA duplex by repair of mismatched bases using the invading strand as a template (Genes, 3rd Ed. (1987) Lewin, B., John Wiley, New York, N.Y.; Lopez et al. (1987) Nucleic Acids Res. 15: 5643). Whether by the mechanism of breakage and rejoining or by the mechanism(s) of gene conversion, formation of heteroduplex DNA at homologously paired joints can serve to transfer genetic sequence information from one DNA molecule to another.

The ability of homologous recombination (gene conversion and classical strand breakage/rejoining) to transfer genetic sequence information between DNA molecules renders targeted homologous recombination a powerful method in genetic engineering and gene manipulation.

In homologous recombination, the incoming DNA interacts with and integrates into a site in the genome that contains a substantially homologous DNA sequence. In non-homologous ("random" or "illicit") integration, the incoming DNA is not found at a homologous sequence in the genome but integrates elsewhere, at one of a large number of potential locations. In general, studies with higher eukaryotic cells have revealed that the frequency of homologous recombination is far less than the frequency of random integration. The ratio of these frequencies has direct implications for "gene targeting" which depends on integration via homologous recombination (i.e. recombination between the exogenous "targeting DNA" and the corresponding "target DNA" in the genome). The present invention can use homologous recombination to inactivate a gene or insert and upregulate or activate a gene in cells, such as the cells described above. The DNA can comprise at least a portion of the gene(s) at the particular locus with introduction of an alteration into at least one, optionally both copies, of the native gene(s), so as to prevent expression of functional gene product. The alteration can be an insertion, deletion, replacement, mutation or combination thereof. When the alteration is introduced into only one copy of the gene being inactivated, the cells having a single unmutated copy of the target gene are amplified and can be subjected to a second targeting step, where the alteration can be the same or different from the first alteration, usually different, and where a deletion, or replacement is involved, can be overlapping at least a portion of the alteration originally introduced. In this second targeting step, a targeting vector with the same arms of homology, but containing a different mammalian selectable markers can be used. The resulting transformants are screened for the absence of a functional target antigen and the DNA of the cell can be further screened to ensure the absence of a wild-type target gene. Alternatively, homozygosity as to a phenotype can be achieved by breeding hosts heterozygous for the mutation.

A number of papers describe the use of homologous recombination in mammalian cells. Illustrative of these papers are Kucherlapati et al. (1984) Proc. Natl. Acad. Sci. USA 81:3153-3157; Kucherlapati et al. (1985) Mol. Cell. Bio. 5:714-720; Smithies et al. (1985) Nature 317:230-234; Wake et al. (1985) Mol. Cell. Bio. 8:2080-2089; Ayares et al. (1985) Genetics 111:375-388; Ayares et al. (1986) Mol. Cell. Bio. 7:1656-1662; Song et al. (1987) Proc. Natl. Acad. Sci. USA 84:6820-6824; Thomas et al. (1986) Cell 44:419-428; Thomas and Capecchi, (1987) Cell 51: 503-512; Nandi et al. (1988) Proc. Natl. Acad. Sci. USA 85:3845-3849; and Mansour et al. (1988) Nature 336:348-352; Evans and Kaufman, (1981) Nature 294:146-154; Doetschman et al.

(1987) Nature 330:576-578; Thoma and Capecchi, (1987) Cell 51:503-512; Thompson et al. (1989) Cell 56:316-321.

In one embodiment, the at least six transgenes incorporated and expressed in the transgenic animal of the present invention are introduced by homologous recombination. In another embodiment, at least one of the six transgenes incorporated and expressed in the transgenic animal of the present invention are introduced by homologous recombination.

B. Random Insertion

In one embodiment, the DNA encoding the transgene sequences can be randomly inserted into the chromosome of a cell. The random integration can result from any method of introducing DNA into the cell known to one of skill in the art. This may include, but is not limited to, electroporation, sonoporation, use of a gene gun, lipotransfection, calcium phosphate transfection, use of dendrimers, microinjection, the use of viral vectors including adenoviral, AAV, and retroviral vectors, and group II ribozymes. In one embodiment, the DNA encoding the can be designed to include a reporter gene so that the presence of the transgene or its expression product can be detected via the activation of the reporter gene. Any reporter gene known in the art can be used, such as those disclosed above. The reporter gene could also be one of the transgenes that is being added to the cell, such that cell surface expression of that transgene (e.g. DAF or CD46 or EPCR or CD47) could be used in conjunction with flow cytometry (and a florescent antibody specific for said transgene) as a means to enrich for gene transfer and subsequence expression of the transgene (and co-inserted transgene combinations). By selecting in cell culture those cells in which the reporter gene has been activated, cells can be selected that contain the transgene. In other embodiments, the DNA encoding the transgene can be introduced into a cell via electroporation. In other embodiments, the DNA can be introduced into a cell via lipofection, infection, or transformation. In one embodiment, the electroporation and/or lipofection can be used to transfect fibroblast cells. In a particular embodiment, the transfected fibroblast cells can be used as nuclear donors for nuclear transfer to generate transgenic animals as known in the art and described below.

Cells that have been stained for the presence of a reporter gene can then be sorted by FACS to enrich the cell population such that we have a higher percentage of cells that contain the DNA encoding the transgene of interest. In other embodiments, the FACS-sorted cells can then be cultured for a periods of time, such as 12, 24, 36, 48, 72, 96 or more hours or for such a time period to allow the DNA to integrate to yield a stable transfected cell population.

In one embodiment, the at least six transgenes incorporated and expressed in the transgenic animal of the present invention are introduced by random integration. In another embodiment, at least one of the six transgenes incorporated and expressed in the transgenic animal of the present invention are introduced by random integration. For example, a bi-cistronic vector comprising at least two transgenes is incorporated into the genome by random integration.

C. Targeted Genomic Editing

In exemplary embodiments, the transgenes are incorporated into the animal utilizing genomic editing tools. These tools include, but are not limited to, nucleases and site-specific recombinases. In exemplary embodiments, the method of insertion is facilitated by genome editing methods utilizing genetic editing tools such as, but not limited to, integrases (recombinases), CRISPR/CAS 9 nucleases, TALAN nucleases, Zinc Finger Nucleases.

The transgenes may be targeted to a single locus selected from a native locus, a modified native locus or a transgenic locus (e.g., landing pad). The native locus may be, for example, GGTA1, ß4GalNT2, CMAH, GHR, ROSA26, AAVS1. The native locus may be modified, i.e., a modified native locus, such as modified (GGTA1, ß4GalNT2, or CMAH)

In exemplary embodiments, the transgenes may be targeted to a landing pad and/or docking site or other stable expression site. In one embodiment, the landing pad or docking vector can be inserted into any locus of interest, e.g. GGTA1, CMAH, ß4Gal, ROSA26, GHR, AAVS1 or the transgenes may be targeted to any known "safe harbor" locus, or any predetermined locus that might provide a beneficial gene expression profile, or where the predetermined locus may also inactivate a preferred gene where simultaneous insertion and knockout is beneficial to the transplant outcome. In another embodiment gene editing can be utilized to create the double-strand break, that initiates the DNA repair machinery to create small insertions, deletions, or nucleic acid substitutions (INDELs) resulting in gene activation or knockout at the target site; in such cases an INDEL at one predetermined locus (e.g. GGTA1, CMAH, B4GalNT2) could be created in a cell or resulting cloned pig, simultaneously with gene-editing-enhanced knockin of a multicistronic vector at another locus.

In a particular embodiment, gene editing is used to simultaneously (using multiple Crispr-Cas9 guide RNAs, TALEN, or ZFN (or combinations thereof), to inactivate one, two or three endogenous loci in the porcine genome (eg. one or all of GGTA1, CMAH, B4GalNT2, GHR), and where one or more of these gene-editing-enhanced modifications also result in targeted insertion of a multicistronic vector with at least six transgenes under control of at least three promoters at one or more of such native or modified native loci.

In some embodiments, the CRISPR/Cas9-mediated gene editing comprises: an inducible promoter or inducible system, a Tetracycline/Doxycycline regulatory system; a polycistronic vector comprising U6p [GHRgRNA-1]; U6p [GHRgRNA-2]; TRE3Gp[CAS9]; CAGpr [tTA]; CAGpr [hCD46-2A-hCD55]; or the nucleotide sequence of SEQ ID NO: 9. In some embodiments, the inducible promoter controls the expression of the growth hormone receptor gene.

1. Zinc Finger Nucleases/TALENs

In one embodiment, the transgenes are incorporated utilizing zinc Finger Nucleases (ZFN). Zinc finger nucleases are fusions of a nonspecific DNA cleavage motif with a sequence-specific zinc finger protein. The nuclease activity is a derivative of the FokI bacterial restriction endonuclease, capable of creating a single strand break. ZFNs operate by dimerizing two DNA-binding domains with two FokI enzymes to produce double-strand breaks with 18 bp specificity. In another embodiment, the transgenes are incorporated using transcription activator-like effector nucleases (TALENs).

TALENs function like ZFNs to create double-stranded breaks by tethering the FokI endonuclease to DNA binding domains. In this process, the targeting efficiency of TALEN-directed mutagenesis has been reported with efficiencies reaching 73.1% with a 27.8% rate of biallelic knockout. TALENs may be distinguished from ZFNs by their ease of genes design, decreased cost, and marginally improved targeting frequencies. In one embodiment, the present invention utilizes the direct injection of ZFNs and TALENS into porcine zygotes that could introduce endogenous genes or small insertions or deletions or nucleotide substitutions, and produce piglets with the desired genetic modifications.

2. CRISPR/CAS9 Nuclease

In another embodiment, the transgenes are incorporated utilizing CRISPR/CAS 9 nucleases. CRISPR/Cas9 is derived from a bacterial defense mechanism that cleaves exogenous DNA by RNA-guided targeting. In bacteria, foreign DNA is digested and inserted into the CRISPR locus, from which CRISPR RNA (crRNA) is made. These short RNA sequences then associate with homologous—presumably foreign-sequences in the genome. When the homologous genomic sequence is followed by an appropriate 'protospacer-adjacent motif' (PAM) at the 3' end, the Cas9 endonuclease creates a double stranded break. The PAM spacer helps prevent the CRISPR-locus itself from being targeted. The CRISPR/Cas9 system has proven to be useful outside of bacteria and was first used to remove alpha Gal from the porcine genome in 2013. The most commonly used system originates from *Streptococcus pyogenes*, which has a 3' PAM sequence of NGG, where N represents any nucleotide. This system allows for the creation of a mutation event in any porcine genomic sequence consisting of $GN_{19}NGG$.

CRISPR/Cas9 system can also be used in conjunction with homology directed repair (HDR), a naturally occurring nucleic acid repair system that is initiated by the presence of double strand breaks (DSBs) in DNA (Liang et al. 1998). More specifically, the CRISPR/Cas9 system can be used to create targeted double strand breaks, it can be used to control the specificity of HDR genome engineering techniques (Findlay et al. 2014; Mali et al. February 2014; Ran et al. 2013) and useful to modify genomes in many organisms, including mammals and humans (Sander and Young, 2014).

Following the RNA-guided cleavage of a specific site of DNA to create a double stranded break, the DNA fragment or DNA construct of interest can be inserted. This donor template, fragment or construct has the desired insertion or modification, flanked by segments of DNA homologous to the blunt ends of the cleaved DNA. Thus, the natural DNA-repair mechanisms of the cell can be used to insert the desired genetic material, editing the genome of a target cell with high-precision, utilizing homology driven recombination combined with any genome editing technique known to create highly targeted double strand breaks. Genome modification carried out in this way can be used to insert novel genes, referred to as "enhanced homology driven insertion or knock-in" is described as the insertion of a DNA and to simultaneously knock out existing genes (Mali et al. February 2013).

The CRISPR/Cas system offers several advantages over previous site-specific nucleases. Foremost, the Cas9 endonuclease represents the first untethered method of DNA cleavage. It is free to associate with multiple guide RNAs and thereby allows for simultaneous targeting of several loci within a single transfection. This has allowed for the efficient combination of multiple genetic knockouts on a single cell. In 2013, the creation of a GGTA1, GGTA1/iGb3S, GGTA1/CMAH, and GGTA1/iGb3S/CMAH homozygous knockout cells was accomplished in a single reaction. The CRISPR/Cas9 system has been successfully used to generate transgenic animals in various vertebrates including zebrafish, monkeys, mice, rats, and pigs see Withworth et al., Biol. Reprod. 91(3):78, pp. 1-13 [2014] and Li et al.; Xenotransplantation 22(1), pp. 20-31 [2015].

Targeting efficiency, or the percentage of desired mutation achieved, is one of the most important parameters by which to assess a genome-editing tool. The targeting efficiency of Cas9 compares favorably with more established methods, such as TALENs or ZFNs. For example, in human cells, custom-designed ZFNs and TALENs could only achieve efficiencies ranging from 1% to 50%. In contrast, the Cas9 system has been reported to have efficiencies up to >70% in zebrafish and plants and ranging from 2-5% in induced pluripotent stem cells.

In one embodiment, the present invention may utilize a CRISPR/Cas9 system to generate transgenic pigs (e.g., ungulate, porcine animal) via micro-injection of CRISPRs designed specifically to target genes of interest into "in vitro" derived zygotes.

In another embodiment, the present invention may utilize a CRISPR/Cas9 system to generate transgenic pigs (e.g., ungulate, porcine animal) by modification of somatic donor cells with CRISPRs designed specifically to target genes of interest, followed by SCNT.

In another embodiment, the present invention may utilize a CRISPR/Cas9 system to generate transgenic pigs (e.g., ungulate, porcine animal) by target a specific region/sequence of an existing genetic modification. More specific embodiment, targeting a sequence of the neomycin gene sequence.

In another embodiment, the present invention may utilize genome editing system such as TALEN, Zinc Finger or CRISPR/Cas9 system to generate transgenic pigs (e.g., ungulate, porcine animal) by targeting a specific region/sequence of an existing genetic modification. More specific embodiment, targeting a single locus that can be a native locus, a modified native locus or a transgenic locus (e.g., landing pad).

In another embodiment the CRISPR/Cas9 system can be used to generate transgenic pigs (e.g., ungulate, porcine animal) by targeting a specific region/sequence of an existing genetic modification via the insertion of a large DNA fragment or construct flanked with arms or segments of DNA homologous to the double strand breaks, utilizing homology driven recombination.

In some embodiments, the CRISPR/Cas9-mediated gene editing comprises: an inducible promoter or inducible system, a Tetracycline/Doxycycline regulatory system; a poly-cistronic vector comprising U6p [GHRgRNA-1]; U6p [GHRgRNA-2]; TRE3Gp[CAS9]; CAGpr [tTA]; CAGpr [hCD46-2A-hCD55]; or the nucleotide sequence of SEQ ID NO: 9. In some embodiments, the inducible promoter controls the expression of the growth hormone receptor gene.

D. Site-Specific Recombinases

In exemplary embodiments, the transgenes are incorporated utilizing site-specific recombinases. Specific recombinase technology is widely used to carry out deletions, insertions, translocations and inversions at specific sites in the DNA of cells. It allows the DNA modification to be targeted to a specific cell type or be triggered by a specific external stimulus. It is implemented both in eukaryotic and prokaryotic systems. There are several recombination systems that work efficiently for genetic engineering strategies, The Flp-FRT and Cre-loxP recombinase systems are reversible and thus facilitate both site specific integration and excision. Integrases mediate the genome integration process that catalysis highly site specific recombination reaction that results in the precise integration, excision and/or inversion of DNA. Serine (ΦC31, Bxb1, R4) and tyrosine integrases (λ, P22, HP1) are the two major families of integrases currently applied to genome engineering. In broad, the process of site specific recombination involves the binding of recombinase to recombinase substrate(s) to bring them in close proximity via protein-protein interactions. During the process the substrates are cleaved and DNA ends reorganized in a strand exchange reaction so that the rejoining of the DNA backbone give rise to the recombinant products. In most cases serine integrase is catalyzing highly efficient irreversible recombination using simple att sites.

In order to make use of the high efficiency of site-specific recombinases, a docking site or landing pad comprises an attachment site for recombinase substrate binding sites, e.g. att sites; or the recombination systems, e.g. Flp-FRT and Cre-loxP can be introduced at the desired locus of cell line and/or anima line. This insertion of the docking vector into the target genome is either random or via homologous recombination. This allows for successive rounds of plasmid integration, where the plasmid or vector may contain different transgenes and/or additional DNA sequences. In return the recombination systems, such as Flp/FRT can be used to remove unwanted vector and marker sequences.

E. Vectors for Producing Transgenic Animals

Nucleic acid targeting vector constructs can be designed to accomplish homologous recombination in cells. In one embodiment, a targeting vector is designed using a promoter trap, wherein integration at the targeted locus allows the inserted open reading frame of the transgene to utilize the endogenous or native promoter to drive expression of the inserted gene (or inserted selectable marker; eg. Neo or Puro). In a particular embodiment a targeting vector is designed using a "poly(A) trap". Unlike a promoter trap, a poly(A) trap vector captures a broader spectrum of genes including those not expressed in the target cell (i.e. fibroblasts or ES cells). A polyA trap vector includes a constitutive promoter that drives expression of a selectable marker gene lacking a polyA signal. Replacing the polyA signal is a splice donor site designed to splice into downstream exons. In this strategy, the mRNA of the selectable marker gene can be stabilized upon trapping of a polyA signal of an endogenous gene regardless of its expression status in the target cells. In one embodiment, a targeting vector is constructed including a selectable marker that is deficient of signals for polyadenylation.

These targeting vectors can be introduced into mammalian cells by any suitable method including, but not limited, to transfection, transformation, virus-mediated transduction, or infection with a viral vector. In one embodiment, the targeting vectors can contain a 3' recombination arm and a 5' recombination arm (i.e. flanking sequence) that is homologous to the genomic sequence of interest. The 3' and 5' recombination arms can be designed such that they flank the 3' and 5' ends of at least one functional region of the genomic sequence. The targeting of a functional region can render it inactive, which results in the inability of the cell to produce functional protein. In another embodiment, the homologous DNA sequence can include one or more intron and/or exon sequences. In addition to the nucleic acid sequences, the expression vector can contain selectable marker sequences, such as, for example, enhanced Green Fluorescent Protein (eGFP) gene sequences, initiation and/or enhancer sequences, poly A-tail sequences, and/or nucleic acid sequences that provide for the expression of the construct in prokaryotic and/or eukaryotic host cells. The selectable marker can be located between the 5' and 3' recombination arm sequence.

Modification of a targeted locus of a cell can be produced by introducing DNA into the cells, where the DNA has homology to the target locus and includes a marker gene, allowing for selection of cells comprising the integrated construct. The homologous DNA in the target vector will recombine with the chromosomal DNA at the target locus. The marker gene can be flanked on both sides by homologous DNA sequences, a 3' recombination arm and a 5' recombination arm. Methods for the construction of targeting vectors have been described in the art, see, for example, Dai et al., Nature Biotechnology 20: 251-255, 2002; WO 00/51424. In such example, the selectable marker gene could be a promoterless neomycin phosphtransferase (Neo) gene that not only results in targeted insertion and expression of Neo (by trapping and utilizing the endogenous porcine alpha Gal gene promoter), but functional inactivation of the target locus (eg. GGTA1) from said targeted insertion and interruption of the GGTA1 catalytic domain.

A variety of enzymes can catalyze the insertion of foreign DNA into a host genome. Viral integrases, transposases and site-specific recombinases mediate the integration of virus genomes, transposons or bacteriophages into host genomes. An extensive collection of enzymes with these properties can be derived from a wide variety of sources. Retroviruses combine several useful features, including the relative simplicity of their genomes, ease of use and their ability to integrate into the host cell genome, permitting long-term transgene expression in the transduced cells or their progeny. They have, therefore, been used in a large number of gene-therapy protocols. Vectors based on Lentivirus vectors, have been attractive candidates for both gene therapy and transgenic applications as have adeno-associated virus, which is a small DNA virus (parvovirus) that is co-replicated in mammalian cells together with helper viruses such as adenovirus, herpes simplex virus or human cytomegalovirus. The viral genome essentially consists of only two ORFs (rep, a non-structural protein, and cap, a structural protein) from which (at least) seven different polypeptides are derived by alternative splicing and alternative promoter usage. In the presence of a helper-virus, the rep proteins mediate replication of the AAV genome. Integration, and thus a latent virus infection, occurs in the absence of helper virus.

Transposons are also of interest. These are segments of mobile DNA that can be found in a variety of organisms. Although active transposons are found in many prokaryotic systems and insects, no functional natural transposons exist in vertebrates. The *Drosophila* P element transposon has been used for many years as a genome engineering tool. The sleeping beauty transposon was established from non-functional transposon copies found in salmonid fish and is significantly more active in mammalian cells than prokaryotic or insect transposons.

Site-specific recombinases are enzymes that catalyze DNA strand exchange between DNA segments that possess only a limited degree of sequence homology. They bind to recognition sequences that are between 30 and 200 nucleotides in length, cleave the DNA backbone, exchange the two DNA double helices involved and religate the DNA. In some site-specific recombination systems, a single polypeptide is sufficient to perform all of these reactions, whereas other recombinases require a varying number of accessory proteins to fulfill these tasks. Site-specific recombinases can be clustered into two protein families with distinct biochemical properties, namely tyrosine recombinases (in which the DNA is covalently attached to a tyrosine residue) and serine recombinases (where covalent attachment occurs at a serine residue). The most popular enzymes used for genome modification approaches are Cre (a tyrosine recombinase derived from *E. coli* bacteriophage P1) and phiC31 integrase (a serine recombinase derived from the *Streptomyces* phage phiC31). Several other bacteriophage derived site-specific recombinases (including Flp, lambda integrase, bacteriophage HK022 recombinase, bacteriophage R4 integrase and phage TP901-1 integrase, and bxb1 integrase) have been used successfully to mediate stable gene insertions into mammalian genomes. Recently, a site-specific recombinase has been purified from the *Streptomyces* bacteriophage. The phiC31 recombinase is a member of the resolvase family and mediates phage integration. In this process the bacteriophage attP site recombines with the corresponding attB site in the bacterial genome. The crossover generates two sites, attL and attR, which are no longer a target for recombinase action, in the absence of accessory proteins. The reaction also takes place in mammalian cells and can therefore be used to mediate site-specific integration of therapeutic genes. The site-specificity of tyrosine-recombinases has been difficult to modify by direct protein engineering because the catalytic domain and the DNA recognition domain are closely interwoven. Therefore, changes in specificity are often accompanied by a loss in activity. Serine recombinases might be more amenable to engineering and a hyperactive derivative of Tn3 resolvase has been modified by exchange of the natural DBD for a zinc-finger domain of the human zinc-finger transcription factor Zif268. The DNA site-specificity of the resulting chimeric protein, termed Z-resolvase, had been switched to that of Zif268. Zinc-finger proteins can be modified by in vitro protein evolution to recognize any DNA sequence, therefore, this approach could enable development of chimeric recombinases that can integrate therapeutic genes into precise genomic locations. Methods for enhancing or mediating recombination include the combination of site-specific recombination and homologous recombination, AAV-vector mediated, and zinc-finger nuclease mediated recombination (ref: Geurts et. al., Science, 325: 433, 2009)

The term "vector," as used herein, refers to a nucleic acid molecule (preferably DNA) that provides a useful biological or biochemical property to an inserted nucleic acid. "Expression vectors" according to the invention include vectors that are capable of enhancing the expression of one or more molecules that have been inserted or cloned into the vector, upon transformation of the vector into a cell. Examples of such expression vectors include, phages, autonomously replicating sequences (ARS), centromeres, and other sequences which are able to replicate or be replicated in vitro or in a cell, or to convey a desired nucleic acid segment to a desired location within a cell of an animal. Expression vectors useful in the present invention include chromosomal-, episomal- and virus-derived vectors, e.g., vectors derived from bacterial plasmids or bacteriophages, and vectors derived from combinations thereof, such as cosmids and phagemids or virus-based vectors such as adenovirus, AAV, lentiviruses. A vector can have one or more restriction endonuclease recognition sites at which the sequences can be cut in a determinable fashion without loss of an essential biological function of the vector, and into which a nucleic acid fragment can be spliced in order to bring about its replication and cloning.

Vectors can further provide primer sites, e.g., for PCR, transcriptional and/or translational initiation and/or regulation sites, recombinational signals, replicons, selectable markers, etc. Clearly, methods of inserting a desired nucleic acid fragment which do not require the use of homologous recombination, transpositions or restriction enzymes (such as, but not limited to, UDG cloning of PCR fragments (U.S. Pat. No. 5,334,575), TA Cloning. RT-PCR, cloning (Invitrogen Corp., Carlsbad, Calif.)) can also be applied to clone a nucleic acid into a vector to be used according to the present invention.

Cells homozygous at a targeted locus can be produced by introducing DNA into the cells, where the DNA has homology to the target locus and includes a marker gene, allowing for selection of cells comprising the integrated construct. The homologous DNA in the target vector will recombine with the chromosomal DNA at the target locus. The marker gene can be flanked on both sides by homologous DNA sequences, a 3' recombination arm and a 5' recombination arm. Methods for the construction of targeting vectors have been described in the art, see, for example, Dai et al. (2002) Nature Biotechnology 20: 251-255; WO 00/51424, FIG. 6; and Gene Targeting: A Practical Approach. Joyner, A. Oxford University Press, USA; 2.sup.nd ed. Feb. 15, 2000.

Various constructs can be prepared for homologous recombination at a target locus. Usually, the construct can include at least 25 bp, 50 bp, 100 bp, 500 bp, 1 kbp, 2 kbp, 4 kbp, 5 kbp, 10 kbp, 15 kbp, 20 kbp, or 50 kbp of sequence homologous with the target locus.

Various considerations can be involved in determining the extent of homology of target DNA sequences, such as, for example, the size of the target locus, availability of sequences, relative efficiency of double cross-over events at the target locus and the similarity of the target sequence with other sequences. The targeting DNA can include a sequence in which DNA substantially isogenic flanks the desired sequence modifications with a corresponding target sequence in the genome to be modified. The substantially isogenic sequence can be at least about 95%, 97-98%, 99.0-99.5%, 99.6-99.9%, or 100% identical to the corresponding target sequence (except for the desired sequence modifications). The targeting DNA and the target DNA preferably can share stretches of DNA at least about 75, 150 or 500 base pairs that are 100% identical. Accordingly, targeting DNA can be derived from cells closely related to the cell line being targeted; or the targeting DNA can be derived from cells of the same cell line or animal as the cells being targeted.

Suitable selectable marker genes include, but are not limited to: genes conferring the ability to grow on certain media substrates, such as the tk gene (thymidine kinase) or the hprt gene (hypoxanthine phosphoribosyltransferase) which confer the ability to grow on HAT medium (hypoxanthine, aminopterin and thymidine); the bacterial gpt gene (guanine/xanthine phosphoribosyltransferase) which allows growth on MAX medium (mycophenolic acid, adenine, and xanthine). See Song et al. (1987) Proc. Nat'l Acad. Sci. U.S.A. 84:6820-6824. See also Sambrook et al. (1989) Molecular Cloning—A Laboratory Manual, Cold Spring Harbor Laboratory, Cold Spring Harbor, N.Y., see chapter 16. Other examples of selectable markers include: genes conferring resistance to compounds such as antibiotics, genes conferring the ability to grow on selected substrates, genes encoding proteins that produce detectable signals such as luminescence, such as green fluorescent protein, enhanced green fluorescent protein (eGFP). A wide variety of such markers are known and available, including, for example, antibiotic resistance genes such as the neomycin resistance gene (neo) (Southern, P., and P. Berg, (1982) J. Mol. Appl. Genet. 1:327-341); and the hygromycin resistance gene (hyg) (Nucleic Acids Research 11:6895-6911 (1983), and Te Riele et al. (1990) Nature 348:649-651).

Additional reporter genes useful in the methods of the present invention include acetohydroxyacid synthase (AHAS), alkaline phosphatase (AP), beta galactosidase (LacZ), beta glucoronidase (GUS), chloramphenicol acetyl-transferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, blasticidin, zeocin, methotrexate, phosphinothricin, puromycin, and tetracycline.

Methods to determine suppression of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

Combinations of selectable markers can also be used. To use a combination of markers, the HSV-tk gene can be cloned such that it is outside of the targeting DNA (another selectable marker could be placed on the opposite flank, if desired). After introducing the DNA construct into the cells to be targeted, the cells can be selected on the appropriate antibiotics. Selectable markers can also be used for negative selection. Negative selection markets generally kill the cells in which they are expressed either because the expression is per se toxic or produces a catalyst that leads to toxic metabolite, such as Herpes simplex virus Type I thymidine kinase (HSV-tk) or diphtheria toxin A. Generally, the negative selection marker is incorporated into the targeting vector so that it is lost following a precise recombination event. Similarly, conventional selectable markers such as GFP can be used for negative selection using, for example, FACS sorting the insertion of selected transgenes if expressed at significant levels on cell surface could serve as a "selectable marker" for gain or loss of function. Use of the inserted or targeted transgenes as the selection tool allows for positive selection without the use of added florescent markers (eg. GFP, RFP), or antibiotic selection genes. In certain cases, targeted insertion of the transgene may inactivate the target locus, such that loss of function could be monitored or selected for. E.g inactivation of the GGTA1 locus would eliminate or reduce binding of targeted cells to a lectin (1B4), or inactivation of B4GalNT2 would eliminate or reduce binding of targeted cells by DBA lectin, and in each case targeted integration could be sorted for, or enriched, in cells which lack such lectin binding.

Deletions can be at least about 50 bp, more usually at least about 100 bp, and generally not more than about 20 kbp, where the deletion can normally include at least a portion of the coding region including a portion of or one or more exons, a portion of or one or more introns, and can or cannot include a portion of the flanking non-coding regions, particularly the 5-non-coding region (transcriptional regulatory region). Thus, the homologous region can extend beyond the coding region into the 5'-non-coding region or alternatively into the 3-non-coding region. Insertions can generally not exceed 10 kbp, usually not exceed 5 kbp, generally being at least 50 bp, more usually at least 200 bp.

The region(s) of homology can include mutations, where mutations can further inactivate the target gene, in providing for a frame shift, or changing a key amino acid, or the mutation can correct a dysfunctional allele, etc. Usually, the mutation can be a subtle change, not exceeding about 5% of the homologous flanking sequences or even a single nucleotide change such as a point mutation in an active site of an exon. Where mutation of a gene is desired, the marker gene can be inserted into an intron, so as to be excised from the target gene upon transcription.

Various considerations can be involved in determining the extent of homology of target DNA sequences, such as, for example, the size of the target locus, availability of sequences, relative efficiency of double cross-over events at the target locus and the similarity of the target sequence with other sequences. The targeting DNA can include a sequence in which DNA substantially isogenic flanks the desired sequence modifications with a corresponding target sequence in the genome to be modified. The substantially isogenic sequence can be at least about 95%, or at least about 97% or at least about 98% or at least about 99% or between 95 and 100%, 97-98%, 99.0-99.5%, 99.6-99.9%, or 100% identical to the corresponding target sequence (except for the desired sequence modifications). In a particular embodiment, the targeting DNA and the target DNA can share stretches of DNA at least about 75, 150 or 500 base pairs that are 100% identical. Accordingly, targeting DNA can be derived from cells closely related to the cell line being targeted; or the targeting DNA can be derived from cells of the same cell line or animal as the cells being targeted.

The construct can be prepared in accordance with methods known in the art, various fragments can be brought together, introduced into appropriate vectors, cloned, analyzed and then manipulated further until the desired construct has been achieved. Various modifications can be made to the sequence, to allow for restriction analysis, excision, identification of probes, etc. Silent mutations can be introduced, as desired. At various stages, restriction analysis, sequencing, amplification with the polymerase chain reaction, primer repair, in vitro mutagenesis, etc. can be employed.

The construct can be prepared using a bacterial vector, including a prokaryotic replication system, e.g. an origin recognizable by *E. coli*, at each stage the construct can be cloned and analyzed. A marker, the same as or different from the marker to be used for insertion, can be employed, which can be removed prior to introduction into the target cell. Once the vector containing the construct has been completed, it can be further manipulated, such as by deletion of the bacterial sequences, linearization, introducing a short deletion in the homologous sequence. After final manipulation, the construct can be introduced into the cell.

Techniques which can be used to allow the DNA or RNA construct entry into the host cell include calcium phosphate/ DNA coprecipitation, microinjection of DNA into the nucleus, electroporation, bacterial protoplast fusion with intact cells, transfection, lipofection, infection, particle bombardment, or any other technique known by one skilled in the art. The DNA or RNA can be single or double stranded, linear or circular, relaxed or supercoiled DNA. For various techniques for transfecting mammalian cells, see, for example, Keown et al., Methods in Enzymology Vol. 185, pp. 527-537 (1990).

The following vectors are provided by way of example. Bacterial: pBs, pQE-9 (Qiagen), phagescript, PsiX174, pBluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWLneo, pSv2cat, pOG44, pXT1, pSG (Stratagene) pSVK3, pBPv, pMSG, pSVL (Pharmiacia). Also, any other plasmids and vectors can be used as long as they are replicable and viable in the host. Vectors known in the art and those commercially available (and variants or derivatives thereof) can in accordance with the invention be engineered to include one or more recombination sites for use in the methods of the invention. Such vectors can be obtained from, for example, Vector Laboratories Inc., Invitrogen, Promega, Novagen, NEB, Clontech, Boehringer Mannheim, Pharmacia, EpiCenter, OriGenes Technologies Inc., Stratagene, PerkinElmer, Pharmingen, and Research Genetics. Other vectors of interest include eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMC1neo, and pOG44 (Stratagene, Inc.), and pYES2, pAC360, pBlueBacHis A, B, and C, pVL1392, pBlueBacIII, pCDM8, pcDNA1, pZeoSV, pcDNA3 pREP4, pCEP4, and pEBVHis (Invitrogen, Corp.) and variants or derivatives thereof.

Other vectors include pUC18, pUC19, pBlueScript, pSPORT, cosmids, phagemids, YAC's (yeast artificial chromosomes), BAC's (bacterial artificial chromosomes), P1 (*Escherichia coli* phage), pQE70, pQE60, pQE9 (quagan), pBS vectors, PhageScript vectors, BlueScript vectors, pNH8A, pNH16A, pNH18A, pNH46A (Stratagene), pcDNA3 (Invitrogen), pGEX, pTrsfus, pTrc99A, pET-5, pET-9, pKK223-3, pKK233-3, pDR540, pRIT5 (Pharmacia), pSPORT1, pSPORT2, pCMVSPORT2.0 and pSY-SPORT1 (Invitrogen) and variants or derivatives thereof. Viral vectors can also be used, such as lentiviral vectors (see, for example, WO 03/059923; Tiscornia et al. PNAS 100: 1844-1848 (2003)).

Additional vectors of interest include pTrxFus, pThioHis, pLEX, pTrcHis, pTrcHis2, pRSET, pBlueBacHis2, pcDNA3.1/His, pcDNA3.1(–)/Myc-His, pSecTag, pEBVHis, pPIC9K, pPIC3.5K, pAO81S, pPICZ, pPICZA, pPICZB, pPICZC, pGAPZA, pGAPZB, pGAPZC, pBlueBac4.5, pBlueBacHis2, pMelBac, pSinRep5, pSinHis, pIND, pIND(SP1), pVgRXR, pcDNA2.1, pYES2, pZErO1.1, pZErO-2.1, pCR-Blunt, pSE280, pSE380, pSE420, pVL1392, pVL1393, pCDM8, pcDNA1.1, pcDNA1.1/Amp, pcDNA3.1, pcDNA3.1/Zeo, pSe, SV2, pRc/CMV2, pRc/RSV, pREP4, pREP7, pREP8, pREP9, pREP 10, pCEP4, pEBVHis, pCR3.1, pCR2.1, pCR3.1-Uni, and pCRBac from Invitrogen; .lamda. ExCell, .lamda. gt11, pTrc99A, pKK223-3, pGEX-1.lamda. T, pGEX-2T, pGEX-2TK, pGEX-4T-1, pGEX-4T-2, pGEX-4T-3, pGEX-3X, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE-4-abc(+), pOCUS-2, pTAg, pET-32L1C, pET-30LIC, pBAC-2 cp LIC, pBAC-gus-2 cp LIC, pT7Blue-2 LIC, pT7Blue-2, .lamda. SCREEN-1, .lamda. BlueSTAR, pET-3abcd, pET-7abc, pET9abcd, pET11 abcd, pETI2abc, pET-14b, pET-15b, pET-16b, pET-17b-pET-17xb, pET-19b, pET-20b(+), pET-21abcd(+), pET-22b(+), pET-23abcd(+), pET-24abcd(+), pET-25b(+), pET-26b(+), pET-27b(+), pET-28abc(+), pET-29abc(+), pET-30abc(+), pET-31b(+), pET-32abc(+), pET-33b(+), pBAC-1, pBACgus-1, pBAC4x-1, pBACgus4x-1, pBAC-3 cp, pBACgus-2 cp, pBACsurf-1, plg, Signal plg, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6xHis-GFP, pSEAP2-Basic, pSEAP2-Contral, pSEAP2-Promoter, pSEAP2-Enhancer, p.beta.gal-Basic, p.beta.gal-Control, p.beta.gal-Promoter, p.beta.gal-Enhancer, pCMV, pTet-Off, pTet-On, pTK-Hyg, pRetro-Off, pRetro-On, pIRESineo, pIRESihyg, pLXSN, pLNCX, pLAPSN, pMAMneo, pMAMneo-CAT, pMAMneo-LUC, pPUR, pSV2neo, pYEX4T-1/2/3, pYEX-Si, pBacPAK-His, pBacPAK8/9, pAcUW31, BacPAK6, pTri-plEx, 2.lamda.gt10, .lamda.gt11, pWE15, and .lamda. TriplEx from Clontech; Lambda ZAP II, pBK-CMV, pBK-RSV, pBluescript II KS+/–, pBluescript II SK+/–, pAD- GAL4, pBD-GAL4 Cam, pSurfscript, Lambda FIX II, Lambda DASH, Lambda EMBL3, Lambda EMBL4, Super-Cos, pCR-Scrigt Amp, pCR-Script Cam, pCR-Script Direct, pBS+/−, pBC KS+/−, pBC SK+/−, Phagescript, pCAL-n-EK, pCAL-n, pCAL-c, pCAL-kc, pET-3abcd, pET-11abcd, pSPUTK, pESP-1, pCMVLacI, pOPRSVI/MCS, pOPI3 CAT, pXT1, pSG5, pPbac, pMbac, pMClneo, pMClneo Poly A, pOG44, pOG45, pFRT.beta.GAL, pNEO.beta.GAL, pRS403, pRS404, pRS405, pRS406, pRS413, pRS414, pRS415, and pRS416 from Stratagene.

Additional vectors include, for example, pPC86, pDBLeu, pDBTrp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp and variants or derivatives thereof.

In an exemplary embodiment, the vector is a bicistronic vector. The bicistronic vector comprises a promoter and two transgenes. In a particular embodiment, the bicistronic vector comprises a promoter and two transgenes linked by a 2A sequence. This embodiment allows for the co-expression of multiple functional transgenes from a single transcript. More specifically, this embodiment utilizes a short (18-24aa) cleavage peptide, "2A", that allows for co-expression of linked open reading frames to express functional transgenes from a single transcript 2A vector system.

In an exemplary embodiment, the vector is a multi-cistronic vector (MCV). In one embodiment, MCV comprises a promoter and at least six transgenes. In a particular embodiment, the MCV comprises six transgenes linked by 2A peptide sequences, under control of at least three promoters. This embodiment allows for the co-expression of multiple functional transgenes from a single transcript. More specifically, this embodiment utilizes a short (18-24aa) cleavage peptide, "2A", that allows for co-expression of linked open reading frames to express functional transgenes from a single transcript 2A vector system.

In an exemplary embodiment, the vector is a 2A-peptide MCV vector comprising at least two bi-cistronic units, wherein each bi-cistronic unit contains 2 transgenes. In a particular embodiment one bicistronic unit is controlled by a constitutive or ubiquitous promoter (e.g. CAG), and the second bicistronic unit is controlled by an endothelial or other tissue specific or inducible promoter system. In a certain embodiment, only at least six transgenes are inserted at the single locus but where each is controlled by its own promoter or a total of at least three promoters per single locus insertion. In an exemplary embodiment, the vector is a 6-gene MCV comprising at least two anticoagulants and more particularly, at least three anticoagulants. In an exemplary embodiment, the vector is a 6-gene MCV vector comprising at least two anticoagulants and a complement inhibitor, and more particularly, three anticoagulants and a complement inhibitor. In an exemplary embodiment, the vector is a 6-gene MCV vector comprising two anticoagulants, a complement inhibitor and an immunosuppressant.

F. Regulatory Sequences

Vector constructs used to produce the animals of the invention can include regulatory sequences, including, but not limited to, a promoter-enhancer sequence, operably linked to the sequence, "2A" peptide technology and a docking vector. In some embodiments, the cleavage peptide is selected from the group consisting of T2A, P2A, F2A, and E2A. Large numbers of suitable vectors and promoters are known to those of skill in the art, and are commercially available.

In specific embodiments, the present invention provides animals, tissues and cells that express at least one transgene in endothelial cells (in combination with at least one transgene under control of a second same or different promoter), and more particularly, at least two, at least three or at least six transgenes in endothelial cells. To target expression to a particular tissue, the animal is developed using a vector that includes a promoter specific for endothelial cell expression. In a particular embodiment, expression is controlled by a promoter active primarily in endothelium.

1. Promoters

In one embodiment, the nucleic acid construct contains a regulatory sequence operably linked to the transgene sequence to be expressed. In one embodiment, the regulatory sequence can be a promoter sequence. In one embodiment, the promoter can be a regulatable promoter. In such systems, drugs, for example, can be used to regulate whether the peptide is expressed in the animal, tissue or organ. For example, expression can be prevented while the organ or tissue is part of the pig, but expression induced once the pig has been transplanted to the human for a period of time to overcome the cellular immune response. In addition, the level of expression can be controlled by a regulatable promoter system to ensure that immunosuppression of the recipient's immune system does not occur. Furthermore, gene knockout can be selectively achieved by inducible promoter system, such as tetracycline inducible CAS9 in CRISPR-CAS9 mediated gene edits (see Zhang et al., Comput Struct Biotechnol J., 2019, (17):1171-1177). The regulatable promoter system can be selected from, but not limited to, the following gene systems: a metallothionein promoter, inducible by metals such as copper (see Lichtlen and Schaffner, Swiss Med. Wkly., 2001, 131 (45-46):647-52); a tetracycline-regulated system (see Imhof et al., J Gene Med., 2000, 2(2):107-16); an ecdysone-regulated system (see Saez et al., Proc Natl Acad Sci USA., 2000, 97(26): 14512-7); a cytochrome P450 inducible promoter, such as the CYP1A1 promoter (see Fujii-Kuriyama et al., FASEB J., 1992, 6(2):706-10); a mifepristone inducible system (see Sirin and Park, Gene., 2003, 323:67-77); a coumarin-activated system (see Zhao et al., Hum Gene Ther., 2003, 14(17): 1619-29); a macrolide inducible system (responsive to macrolide antibiotics such as rapamycin, erythromycin, clarithromycin, and roxitiromycin) (see Weber et al., Nat Biotechnol., 2002, 20(9):901-7; Wang et al., Mol Ther., 2003, 7(6):790-800); an ethanol induced system (see Garoosi et al., J Exp Bot., 2005, 56(416):163542; Roberts et al., Plant Physiol., 2005, 138(3):1259-67); a streptogramin inducible system (see Fussenegger et al., Nat Biotechnol., 2000 18(11):1203-8) an electrophile inducible system (see Zhu and Fahl, Biochem Biophys Res Commun., 2001, 289(1):212-9); a nicotine inducible system (see Malphettes et al., Nucleic Acids Res., 2005, 33(12):e107), immune-inducible promoter, cytokine response promoters (e.g. promoters that are induced by IFN-gamma, TNF-alpha, IL-1, IL-6 or TGF-beta (or other secondary pathways), and thus can be turned on or upregulated in association with or in response to an immune or inflammatory response.

In particular embodiments, the animal includes an endothelial specific promoter, such as a porcine ICAM-2 or murine Tie-2 promoter, and further includes an enhancer element (e.g., murine Tie-2 enhancer or CMV enhancer). In other embodiments, the promoter can be a ubiquitous promoter element that further includes an enhancer element. In a particular element the ubiquitous promoter is CAG (CMV enhancer, chicken beta-Actin promoter, rabbit beta-globin intron) used in combination with a endothelium-specific Tie-2 enhancer element (Tie2-CAG). For Tie2-CAG, the transgene(s) would be expected to be expressed in both a constitutive and ubiquitous manner, but at an even higher level in endothelial cells versus other body cells. In some embodiments, the promoter is used in combination with an enhancer element which is a non-coding or intronic region of DNA intrinsically associated or co-localized with the promoter. In another specific embodiment, the enhancer element is ICAM-2 used in combination with the ICAM-2 promoter. Other ubiquitous promoters include, but are not limited to the following: viral promoters like CMV and SV40, also chicken beta actin and gamma-actin promoter, GAPDH promoters, H2K, CD46 promoter, GGTA1, ubiquitin and the ROSApromoter.

2. Multicistronic System

In a particular embodiment, the bicistronic vector includes two transgenes and a promoter that is active primarily in endothelial cells or a constitutive promoter that ubiquitously expresses transgenes in all organs, tissues and cells. In other embodiments the at least six transgenes in a multicistronic vector (MCV) are under control of at least three promoters. The promoters may be exogenous, native or a combination of both exogenous and native. In some embodiments, the at least six transgenes are encoded by a polycistronic vector, optionally wherein the polycistronic vector comprises at least three bicistronic units. In some embodiments, each bicistronic unit comprises a promoter driving a first transgene linked via a cleavage peptide to a second transgene. In some embodiments, a first bicistronic unit comprises the at least two anticoagulant transgenes, a second bicistronic comprises at least two complement inhibitor transgenes; and a third bi-cistronic unit comprises the at least one cytoprotective transgene and the at least one immunosuppressant transgene. In some embodiments, the cleavage peptide is selected from the group consisting of T2A, P2A, F2A, and E2A.

In a particular embodiment, the bi-cistronic vector includes two transgenes and a constitutive promoter that ubiquitously expresses transgenes in all organs, tissues and cells. In a particular embodiment, the bi-cistronic vector includes two transgenes and a tissue specific promoter controlling expression in organs, tissues, and cells. In an exemplary embodiment, the vector is a six-gene MCV comprising at least two anticoagulants under the control of an endothelial-specific promoter. In an exemplary embodiment, the vector is a six-gene MCV comprising at least one complement inhibitor transgene under the control of a constitutive promoter and at least one anticoagulant transgene under the control of an endothelial-cell specific promoter. In an exemplary embodiment, the vector is a six-gene MCV comprising at least one complement inhibitor transgene under the control of a constitutive promoter and at least one anticoagulant gene under the control of a second constitutive promoter.

In an exemplary embodiment, the vector is a six-gene MCV vector comprising an anticoagulant transgene and an immunosuppressant transgene under the control of an endothelial-cell promoter. In an exemplary embodiment the vector is a two-gene MCV vector comprising a total of two genes under control of at least two separate promoters; or in a selected embodiment a vector with multiple transgenes in a string, each with their own promoter, and all integrated into a single locus.

In some embodiments, the polycistronic (MCV) vector comprises a bicistronic unit selected from the group consisting of porcine TBM promoter driving a human TBM transgene linked via a 2A peptide to a human EPCR transgene (pTBMpr [hTBM-2A-hEPCR]); a CAG promoter driving a human CD47 transgene linked via 2A peptide to a human HO-1 transgene (CAGpr [hCD47-2A-hHO1]); a CAG promoter driving a human CD46 transgene linked via 2A peptide to a human DAF transgene (CAGpr [hCD46-2A-hDAF]); Poly-A signal fused to a porcine TBM promoter driving a human TBM transgene linked via a 2A peptide to a human EPCR transgene (PolyA/pTBMpr [hTBM-2A-hEPCR]); a CAG promoter driving a human CD59 transgene linked via 2A peptide to a human HO-1 transgene (CAGpr [hCD59-2A-hHO1]); a porcine EPCR promoter driving a human TBM transgene linked via a 2A peptide to a human EPCR transgene (pEPCRpr [hTBM-2A-hEPCR]); a CAG promoter driving a human CD46 transgene linked via 2A peptide to a human CD47 transgene (CAGpr [hCD46-2A-hCD47]); a first U6 promoter driving a first GHR gRNA linked to a second U6 promoter driving a second GHR gRNA (U6p [GHRgRNA-1]; U6p [GHR-gRNA-2]), wherein the first and second gRNA are the same or different; a TRE3G promoter driving a Cas endonuclease, linked via an insulator to a CAG promoter driving a tTA (TRE3Gp[CAS9]; CAGpr [tTA]); and a combination thereof.

In some embodiments, the polycistronic (MCV) vector comprises: pTBMpr [hTBM-2A-hEPCR]; CAGpr [hCD47-2A-hHO1]; and CAGpr [hCD46-2A-hDAF]; PolyA-pTBMpr [hTBM-2A-hEPCR]; CAGpr [hCD47-2A-hHO1]; and CAGpr [hCD46-2A-hDAF]; pTBMpr [hTBM-2A-hEPCR]; CAGpr [hCD59-P2A-hHO1]; and CAGpr [hCD46-P2A-hDAF]; or PolyA-pTBMpr [hTBM]; CAG pr [hCD47-P2A-hHO1]; pEPCRpr [hEPCR]; and CAGpr [hCD46P-2A-hDAF]; pTBMpr [hTBM-2A-hEPCR], CAGpr [hCD59-P2A-hHO1], and CAGpr [hCD46-2A-hCD47]; pTBMpr [hTBM-2A-hEPCR], CAGpr [hCD59-2A-hHO1], and CAGpr [hCD46-2A-hCD55]; U6p [GHR-gRNA-1], U6p [GHRgRNA-2], TRE3Gp[CAS9], CAGpr [tTA], and CAGpr [hCD46-2A-hCD55]. In some embodiments, the MCV comprises a nucleotide sequence selected from SEQ ID NO: 7; SEQ ID NO: 8; SEQ ID NO: 9; SEQ ID NO: 11, SEQ ID NO: 12, SEQ ID NO: 14 or SEQ ID NO; 14.

3. Enhancers

In other embodiments an enhancer element is used in the nucleic acid construct to facilitate increased expression of the transgene in a tissue-specific manner. Enhancers are outside elements that drastically alter the efficiency of gene transcription (Molecular Biology of the Gene, Fourth Edition, pp. 708-710, Benjamin Cummings Publishing Company, Menlo Park, Calif. COPYRGT. 1987). In a particular embodiment, the pdx-1 enhancer (also known as IPF-1, STF-1, and IDX1 (Gerrish K et al., Mol. Endocrinol., 2004, 18(3): 533; Ohlsson et al., EMBO J. 1993 November, 12(11):4251-9; Leonard et al., Mol. Endocrinol., 1993, 7(10):1275-83; Miller et al., EMBO J., 1994, 13(5):1145-56; Serup et al., Proc Natl Acad Sci USA., 1996, 93(17):9015-20; Melloul et al., Diabetes, 2002, 51 Suppl 3:S320-5; Glick et al., J Biol Chem., 2000, 275(3):2199-204; GenBank AF334615.)) is used in combination with the ins2 promoter, for pancreas specific expression of the transgene(s). In certain embodiments, the animal expresses a transgene under the control of a promoter in combination with an enhancer element.

G. Selection of Genetically Modified Cells

The present invention provides a method of making a transgenic pig comprising at least six transgenes comprising the step of: (i) transfecting a porcine cell with a single polycistronic vector comprising (a) at least two complement inhibitor transgenes; (b) at least one immunosuppressant transgene; (c) at least one cytoprotective transgene; and (d) at least two anticoagulant transgenes; (ii) producing a multitransgenic (i.e. a transgenic) porcine cell comprising at least six transgenes by incorporating and expressing the polycistronic vector at a single genomic locus; (iii) generating a multitransgenic porcine zygote by injecting the nucleus of the multitransgenic porcine cell into a reconstructed somatic cell nuclear transfer (SCNT); and (iv) permitting the multitransgenic porcine zygote to mature into a multitransgenic pig. In some embodiments, the porcine cell and the multitransgenic pig lack expression of alpha 1,3 galactosyltransferase.

In some embodiments, the multitransgenic cells have genetic modifications that are the result of targeted transgene insertion or integration (i.e. via homologous recombination) into the cellular genome. In some embodiments, the multitransgenic cells have genetic modification that are the result of non-targeted (random) integration into the cellular genome. In some embodiments, the multitransgenic cells can be grown in appropriately-selected medium to identify multitransgenic cells comprising the at least six transgenes at the appropriate integration site. Those multitransgenic cells which show the desired phenotype can then be further analyzed by restriction analysis, electrophoresis, Southern analysis, polymerase chain reaction, or another technique known in the art. By identifying fragments which show the appropriate insertion at the target gene site, (or, in non-targeted applications, where random integration techniques have produced the desired result) cells can be identified in which homologous recombination (or desired non-targeted integration events) has occurred to inactivate or otherwise modify the target gene.

The presence of the selectable marker gene or other positive selection agent or immunofluorescence establishes the integration of the target construct into the host genome. Those multitransgenic cells which show the desired phenotype can then be further analyzed by restriction digest analysis, electrophoresis, Southern analysis, polymerase chain reaction, etc. to analyze the DNA in order to establish whether homologous or non-homologous recombination occurred. This can be determined by employing probes for the insert and then sequencing the 5' and 3' regions flanking the insert for the presence of the gene extending beyond the flanking regions of the construct or identifying the presence of a deletion, when such deletion is introduced. Primers can also be used which are complementary to a sequence within the construct and complementary to a sequence outside the construct and at the target locus. In this way, one can only obtain DNA duplexes having both of the primers present in the complementary chains if homologous recombination has occurred. For example, by demonstrating the presence of the primer sequences or the expected size sequence, the occurrence of homologous recombination is supported.

The polymerase chain reaction used for screening homologous recombination events is known by those of skilled in the art, for example as described in Kim and Smithies, (1988) Nucleic Acids Res. 16:8887-8903; and Joyner et al. (1989) Nature 338:153-156. The cell lines obtained from the first round of targeting (or from non-targeted (random) integration into the genome) are likely to be heterozygous for the integrated allele. Homozygosity, in which both alleles are modified, can be achieved in a number of ways. One approach is to grow up a number of cells in which one copy has been modified and then to subject these cells to another round of targeting (or non-targeted (random) integration) using a different selectable marker. Alternatively, homozygotes can be obtained by breeding animals heterozygous for the modified allele.

In some situations, it can be desirable to have two different modified alleles. This can be achieved by successive rounds of gene targeting (or random integration) or by breeding heterozygotes, each of which carries one of the desired modified alleles. An event of genome editing with efficient targeted double-stranded breaks allows for frequent biallelic gene targeting event such that in a single transfection (or embryo or zygote targeting strategy), homozygousys knock out or knockin events can be achieved with high frequency. Such gene-editing-enhanced (e.g. Crispr-CAS9 nuclease) gene targeting or homology-dependent repair events, can include both monoallelic or heterozygous, and biallelic or homozygous knockout (via small nucleotide insertions, deletions, substitutions, otherwise described as INDELs), and also gene insertions, including both monallelic and biallelic insertion/knockin of a single transgene, multi-transgene string (strings of transgenes under their own promoters or bicistronic or multicistronic), or multicistronic vectors (including 6-transgene multicistonic vectors under control of at least 2 promoters where said promoters could be constitutive or tissue-specific, (e.g., CAG, Tie-2 and Icam-2). Alternatively, via use of multiple gene editing nucleases (e.g. Crispr/Cas9), one could expect to efficiently produce a cell (via transfection or infection) or zygote (simultaneously via microinjection) with a combination of base genotype (ie. GGTA1 knockout or GGTA1/CD46), where one genetic modification might include knockin (e.g., at GGTA1), or random insertion, of a 6-gene MCV (under control of at least three promoters), and simultaneously, either a nuclease-mediated INDEL at another locus (mono or biallelic, e.g., GGTA1, GHR, CMAH, B4GalNT2), or in a preferred embodiment, a targeted insertion of a multitransgene vector (bicistronic or 6-gene MCV) at two different loci (landing pads, safe harbor, or GGTA1, B4GalNT2, GHR, CMAH, ROSA26, AAVS1 or other predetermined locus, including native or modified native loci), for example targeted insertion of a 6-gene MCV at GGTA1 along with targeted, homologous recombination (or gene-editing-enhanced) insertion of a bicistronic or 6-gene MCV at a second locus (e.g., CMAH or B4GalNT2). In certain embodiments, a selection technique is used to obtain homologous knockout cells from heterozygous cells by exposure to very high levels of a selection agent. Such a selection can be, for example, by use of an antibiotic such as geneticin (G418).

Cells that have been transfected or otherwise received an appropriate vector can then be selected or identified via genotype or phenotype analysis. In one embodiment, cells are transfected, grown in appropriately-selected medium to identify cells containing the integrated vector. The presence of the selectable marker gene indicates the presence of the transgene construct in the transfected cells. Those cells which show the desired phenotype can then be further analyzed by restriction analysis, electrophoresis, Southern analysis, polymerase chain reaction, etc to analyze the DNA in order to verify integration of transgene(s) into the genome of the host cells. Primers can also be used which are complementary to transgene sequence(s). The polymerase chain reaction used for screening homologous recombination and random integration events is known in the art, see, for example, Kim and Smithies, Nucleic Acids Res. 16:8887-8903, 1988; and Joyner et al., Nature 338:153-156, 1989. The specific combination of a mutant polyoma enhancer and a thymidine kinase promoter to drive the neomycin gene has been shown to be active in both embryonic stem cells and EC cells by Thomas and Capecchi, supra, 1987; Nicholas and Berg (1983) in Teratocarcinoma Stem Cell, eds. Siver, Martin and Strikland (Cold Spring Harbor Lab., Cold Spring Harbor, N.Y. (pp. 469-497); and Linney and Donerly, Cell 35:693-699, 1983.

Cells that have undergone homologous recombination can be identified by a number of methods. In one embodiment, the selection method can detect the absence of an immune response against the cell, for example by a human anti-gal antibody. In a preferred embodiment, the selection method can utilize the inserted or targeted transgenes as the selection tool allows for positive selection without the use of added florescent markers (eg. GFP, RFP), or antibiotic selection genes. In certain cases, targeted insertion of the transgene may produce a cell surface protein, which with appropriate transgene specific florescence-marked cells can be sorted for positive expression of the desired transgene. Alternatively, one could inactivate the target locus, such that loss of function could be monitored or selected for example, inactivation of the GGTA1 locus would eliminate or reduce binding of targeted cells to a lectin (IB4), or inactivation of B4GalNT2 would eliminate or reduce binding of targeted cells by DBA lectin, and in each case targeted integration could be sorted for, or enriched, in cells which lack such lectin binding. In each case expression of the transgenes on the cell surface allows the selection of cells to be used for further analysis.

In other embodiments, the selection method can include assessing the level of clotting in human blood when exposed to a cell or tissue. Selection via antibiotic resistance has been used most commonly for screening. This method can detect the presence of the resistance gene on the targeting vector, but does not directly indicate whether integration was a targeted recombination event or a random integration. Alternatively, the marker can be a fluorescent marker gene such as GFP or RFP, or a gene that is detectable on the cell surface via cell sorting or FACs analysis. Certain technology, such as Poly A and promoter trap technology, increase the probability of targeted events, but again, do not give direct evidence that the desired phenotype has been achieved. In addition, negative forms of selection can be used to select for targeted integration; in these cases, the gene for a factor lethal to the cells (e.g. Tk or diptheria A toxin) is inserted in such a way that only targeted events allow the cell to avoid death. Cells selected by these methods can then be assayed for gene disruption, vector integration and, finally, gene depletion. In these cases, since the selection is based on detection of targeting vector integration and not at the altered phenotype, only targeted knockouts, not point mutations, gene rearrangements or truncations or other such modifications can be detected.

Characterization can be further accomplished by the following techniques, including, but not limited to: PCR analysis, Southern blot analysis, Northern blot analysis, specific lectin binding assays, and/or sequencing analysis. Phenotypic characterization can also be accomplished, including by binding of anti-mouse antibodies in various assays including immunofluorescence, immunocytochemistry, ELISA assays, flow cytometry, western blotting, testing for transcription of RNA in cells such as by RT-PCR. Genotype can be determined by Southern analysis and PCR. Gene expression is monitored by flow cytometry of PBMCs and endothelial cells, and in cells and organs by immunohistochemistry, Q-PCR (quantitative polymerase chain reaction) and Western blot analysis. Bioactivity assays specific to the transgenes will quantitate and characterize complement inhibition, platelet aggregation, activated protein C formation, ATPase activity, Factor Xa cleavage, mixed lymphocyte reaction (MLR) and apoptosis.

In other embodiments, GTKO animals or cells contain additional genetic modifications. Genetic modifications can include more than just homologous targeting, but can also include random integrations of exogenous genes, co-integration of a group or string of genes at a single locus, mutations, deletions and insertions of genes of any kind. The additional genetic modifications can be made by further genetically modifying cells obtained from the transgenic cells and animals described herein or by breeding the animals described herein with animals that have been further genetically modified. Such animals can be modified to eliminate the expression of at least one allele of .alpha.GT gene, the CMP-Neu5Ac hydroxylase gene (see, for example, U.S. Pat. No. 7,368,284), the iGb3 synthase gene (see, for example, U.S. Patent Publication No. 2005/0155095), and/or ß1,4 N-acetylgalactosaminyl transferase (ß4GalNT2; see for example Estrada J L et al., Xenotransplantation 22:194-202 [2015]) the Forssman synthase gene (see, for example, U.S. Patent Publication No. 2006/0068479).

In additional embodiments, the animals described herein can also contain genetic modifications to express transgenes of interest, more specifically human transgenes that are from the group consisting of immunomodulators, anticoagulants and cytoprotective transgenes. In a preferred embodiment, in addition to multitransgene integration (targeted or random, but exceeding at least 4 genes and where such at least 4 genes are controlled by at least three promoters), genetic modification of the porcine vWF locus can be achieved, including knockout (lack of function), INDELs, and simultaneous knockout of porcine vWF sequences in the genome, or including targeted knockin and replacement of some or all of defined porcine vWF exons (e.g. exons 22-28), with their human exon 22-28 counterparts from the human vWF gene sequence.

To achieve these additional genetic modifications, in one embodiment, cells can be modified to contain multiple genetic modifications. In other embodiments, animals can be bred together to achieve multiple genetic modifications. In one specific embodiment, animals, such as pigs, produced according to the process, sequences and/or constructs described herein, can be bred with animals, such as pigs, lacking expression of alpha Gal (for example, as described in WO 04/028243).

In another embodiment, the expression of additional genes responsible for xenograft rejection can be eliminated or reduced. Such genes include, but are not limited to the CMP-NEUAc Hydroxylase Gene (CMAH), Beta-4GalNT2, the isoGloboside 3 (iGb3) Synthase gene, and the Forssman synthase gene.

In addition, genes or cDNA encoding complement related proteins, which are responsible for the suppression of complement mediated lysis can also be expressed in the animals and tissues of the present invention. Such genes include, but are not limited to CD59, DAF (CD55), and CD46 (see, for example, WO 99/53042; Chen et al. Xenotransplantation, Volume 6 Issue 3 Page 194—August 1999, which describes pigs that express CD59/DAF transgenes; Costa C et al, Xenotransplantation. 2002 January; 9(1):45-57, which describes transgenic pigs that express human CD59 and H-transferase; Zhao L et al.; Diamond L E et al. Transplantation. 2001 Jan. 15; 71(1):132-42, which describes a human CD46 transgenic pigs.)

Additional modifications can include expression of compounds, such as antibodies, which down-regulate the expression of a cell adhesion molecule by the cells, such as described in WO 00/31126, entitled "Suppression of xeno-graft rejection by down regulation of a cell adhesion mol-ecules" and compounds in which co-stimulation by signal 2 is prevented, such as by administration to the organ recipient of a soluble form of CTLA-4 from the xenogeneic donor organism, for example as described in WO 99/57266, entitled "Immunosuppression by blocking T cell co-stimu-lation signal 2 (B7/CD28 interaction)".

H. Nuclear Transfer

In some embodiments, the method of making a transgenic pig comprising at least six transgenes comprises generating a multitransgenic porcine zygote by injecting the nucleus of the multitransgenic porcine cell of the present invention into a reconstructed somatic cell nuclear transfer (SCNT) cell. Genetically modified or transgenic animals such as ungu-lates or pigs described herein may be produced using any suitable techniques known in the art. These techniques include, but are not limited to, microinjection (e.g., of pronuclei and/or cytoplasmic), electroporation of ova or zygotes, and/or somatic cell nuclear transfer (SCNT). Any additional technique known in the art may be used to introduce the transgene, or multi-transgene or MCV vector(s) into animals. Such techniques include, but are not limited to pronuclear microinjection (see, for example, Hoppe, P. C. and Wagner, T. E., 1989, U.S. Pat. No. 4,873,191); cytoplasmic microinjection (see for example Whitworth et al., 2014): retrovirus mediated gene transfer into germ lines (see, for example, Van der Putten et al., 1985, Proc. Natl. Acad. Sci., USA 82:6148-6152); gene targeting in embryonic stem cells (see, for example, Thompson et al., 1989, Cell 56:313-321; Wheeler, M. B., 1994, WO 94/26884); electroporation of embryos (see, for example, Lo, 1983, Mol Cell. Biol. 3:1803-1814); transfection; trans-duction; retroviral infection; adenoviral infection; adenovi-ral-associated infection; liposome-mediated gene transfer; naked DNA transfer; and sperm-mediated gene transfer (see, for example, Lavitrano et al., 1989, Cell 57:717-723); etc. For a review of such techniques, see, for example, Gordon, 1989, Transgenic Anithals, Intl. Rev. Cytol. 115:171-229. In particular embodiments, the expression of CTLA4 and/or CTLA4-Ig fusion genes in ungulates can be accomplished via these techniques.

1 Electroporation of ova or zygotes

In one embodiment, microinjection of the constructs encoding the transgenes can be used to produce the trans-genic animals. In one embodiment, the nucleic acid con-struct or vector of the present invention is microinjected into the pronuclei of a zygote. In some embodiments, the con-struct or vector can be injected into the male pronuclei of a zygote. In another embodiment, the construct or vector can be injected into the female pronuclei of a zygote. In a further embodiment, the construct or vector, CRISPR(s), Messenger RNA (mRNA) coding for Cas9 and gRNA (single guided RNA), can be injected into the cytoplasm of fertilized oocytes either to achieve gene knockout or gene inactivation (insertions, deletions, substitutions) resulting from repair errors following treatment with such gene editing nucleases, or can be used to achieve targeted knockin of a transgene(s) or multigene vector in such zygotes, resulting in stable transmission of the genetic modification (reference, Whit-worth 2014?). In another embodiment, nuclear transfer can be initiated with an existing transgenic somatic cell, and following embryo reconstruction and fusion, the gene edit-ing nuclease (eg. Crispr/Cas9) can be injected into the cytoplasm of the reconstructed nuclear-transfer embryo, with or without a transgene vector, or multigene vector or MCV, such that the gene editing event occurs in the diploid embryo, and in the subsequent transgenic pig following embryo transfer.

Microinjection of the transgene construct or vector can include the following steps: superovulation of a donor female; surgical removal of the egg, fertilization of the egg; injection of the transgene transcription unit into the was injected into the cytoplasm of fertilized oocytes at postfer-tilization (e.g. presumptive zygotes at approximately 14 hours post-fertilization), and introduction of the transgenic embryo into the reproductive tract of a pseudopregnant host mother, usually of the same species. See for example U.S. Pat. No. 4,873,191, Brinster, et al. 1985. PNAS 82:4438; Hogan, et al., in "Manipulating the Mouse Embryo: A Laboratory Manual". Cold Spring Harbor Laboratory, Cold Spring Harbor, N.Y., 1986. Robertson, 1987, in Robertson, ed. "Teratocarcinomas and Embryonic Stem Cells a Practi-cal Approach" IRL Press, Evnsham. Oxford, England. Ped-ersen, et al., 1990. "Transgenic Techniques in Mice—A Video Guide", Cold Spring Harbor Laboratory, Cold Spring Harbor, N.Y. Transgenic pigs are routinely produced by the microinjection of a transgene construct or vector into pig embryos, see Withworth et al., Biol. Reprod. 91(3):78, 1-13 [2014].

In one embodiment, the presence of the transgene can be detected by isolating genomic DNA from tissue from the tail of each piglet and subjecting about 5 micrograms of this genomic DNA to nucleic acid hybridization analysis with a transgene specific probe. In a particular embodiment, trans-genic animals can be produced according to any method known to one skilled in the art, for example, as disclosed in Bleck et al., J. Anim. Sci., 76:3072 [1998]; also described in U.S. Pat. Nos. 6,872,868; 6,066,725; 5,523,226; 5,453,457; 4,873,191; 4,736,866; and/or PCT Publication No. WO/9907829.

In one embodiment, the pronuclear microinjection method can include linking at least approximately 50, 100, 200, 300, 400 or 500 copies of the transgene-containing construct or vector of the present invention to a promoter of choice, for example, as disclosed herein, and then the foreign DNA can be injected through a fine glass needle into fertilized eggs. In one embodiment, the DNA can be injected into the male pronucleus of the zygote. Pig zygotes are opaque and visualization of nuclear structures can be diffi-cult. In one embodiment, the pronuclei or nuclei of pig zygotes can be visualized after centrifugation, for example, at 15000 g for 3 mm. The injection of the pronucleus can be carried out under magnification and use of standard micro-injection apparatus. The zygote can be held by a blunt holding pipette and the zona pellucida, plasma membrane and pronuclear envelope can be penetrated by an injection pipette. The blunt holding pipette can have a small diameter, for example, approximately 50 um. The injection pipette can have a smaller diameter than the holding pipette, for example, approximately 15 um. DNA integration occurs during replication as a repair function of the host DNA. These eggs, containing the foreign DNA, can then be implanted into surrogate mothers for gestation of the embryo according to any technique known to one skilled in the art.

In some embodiments, pronuclear microinjection can be performed on the zygote 12 hours post fertilization. Uptake of such genes can be delayed for several cell cycles. The consequence of this is that depending on the cell cycle of uptake, only some cell lineages may carry the transgene, resulting in mosaic offspring. If desired, mosaic animals can be bred to form true germline transgenic animals.

In an exemplary embodiment, the cytoplasmic microinjection method can inject CRISPRs targeting at least one or more targeted native gene, or modified native locus, m RNA coding for Cas9 and gRNA through a fine glass needle into fertilized eggs. In a particular embodiment, CRISPRs targeting at least one or more targeted gene (e.g. GGTA1, B4GalNT2, CMAH, and including multiple guide RNAs, along with mRNA coding for Cas9 and gRNA can be injected into the cytoplasm of the zygote.

2. Somatic Cell Nuclear Transfer

The present invention provides a method for cloning an ungulate such as a pig containing certain transgenes via SCNT. In general, the pig can be produced by a nuclear transfer process comprising the following steps: obtaining desired differentiated pig cells to be used as a source of donor nuclei; obtaining oocytes from a pig; enucleating said oocytes; transferring the desired differentiated cell or cell nucleus into the enucleated oocyte, e.g., by fusion or injection, to form SCNT units; activating the resultant SCNT unit; and transferring said cultured SCNT unit to a host pig such that the SCNT unit develops into a fetus.

Nuclear transfer techniques or nuclear transplantation techniques are known in the art (see, for example, Dai et al. Nature Biotechnology 20:251-255; Polejaeva et al Nature 407:86-90 (2000); Campbell, et al., Theriogenology 68 Suppl 1:S214-3 1 (2007); Vajta, et al., Reprod Fertil Dev 19(2): 403-23 (2007); Campbell et al. (1995) Theriogenology, 43:181; Collas et al. (1994) Mol. Report Dev., 38:264-267; Keefer et al. (1994) Biol. Reprod., 50:935-939; Sims et al. (1993) Proc. Natl. Acad. Sci., USA, 90:6143-6147; WO 94/26884; WO 94/24274, and WO 90/03432, U.S. Pat. Nos. 4,944,384, 5,057,420, WO 97/07669, WO 97/07668, WO 98/30683, WO 00/22098, WO 004217, WO 00/51424, WO 03/055302, WO 03/005810, U.S. Pat. Nos. 6,147,276, 6,215,041, 6,235,969, 6,252,133, 6,258,998, 5,945,577, 6,525,243, 6,548,741, and Phelps et al. (Science 299:411-414 (2003)).

In some embodiments, ungulate cells such as porcine cells containing transgenes of the present invention can be used as donor cells to provide the nucleus for nuclear transfer into enucleated oocytes to produce cloned, transgenic animals. In one embodiment, the ungulate cell need not express the transgene protein in order to be useful as a donor cell for nuclear transfer. In one embodiment, the porcine cell can be engineered to express a transgene from a nucleic acid construct or vector that contains a promoter. Alternatively, the porcine cells can be engineered to express transgene under control of an endogenous promoter through homologous recombination. In one embodiment, the transgene nucleic acid sequence can be inserted into the genome under the control of a tissue specific promoter, tissue specific enhancer or both. In another embodiment, the transgene nucleic acid sequence can be inserted into the genome under the control of a constitutive promoter.

In certain embodiments, targeting vectors are provided, which are designed to allow targeted homologous recombination in somatic cells. These targeting vectors can be transformed into mammalian cells to target the endogenous genes of interest via homologous recombination. In one embodiment, the targeting construct inserts both the transgene nucleotide sequence and a selectable maker gene into the endogenous gene so as to be in reading frame with the upstream sequence and produce an active fusion protein. Cells can be transformed with the constructs using the methods of the invention and are selected by means of the selectable marker and then screened for the presence of recombinants.

A donor cell nucleus, which has been modified to contain a transgene of the present invention, is transferred to a recipient porcine oocyte. The use of this method is not restricted to a particular donor cell type. The donor cell can be as described in Wilmut et al. (1997) Nature 385:810; Campbell et al. (1996) Nature 380:64-66; or Cibelli et al. (1998) Science 280:1256-1258. All cells of normal karyotype, including embryonic, fetal and adult somatic cells which can be used successfully in nuclear transfer can in principle be employed. Fetal fibroblasts are a particularly useful class of donor cells. Generally suitable methods of nuclear transfer are described in Campbell et al. (1995) Theriogenology 43:181, Collas et al. (1994) Mol. Reprod. Dev. 38:264-267, Keefer et al. (1994) Biol. Reprod. 50:935-939, Sims et al. (1993) Proc. Nat'l. Acad. Sci. USA 90:6143-6147, WO-A-9426884, WO-A-9424274, WO-A-9807841, WO-A-9003432, U.S. Pat. Nos. 4,994,384 and 5,057,420, Campbell et al., (2007) Theriogenology 68 Suppl 1, S214-231, Vatja et al., (2007) Reprod Fertil Dev 19, 403-423).

Differentiated or at least partially differentiated donor cells can also be used. Donor cells can also be, but do not have to be, in culture and can be quiescent. Nuclear donor cells which are quiescent are cells which can be induced to enter quiescence or exist in a quiescent state in vivo. Prior art methods have also used embryonic cell types in cloning procedures (see, for example, Campbell et al. (1996) Nature, 380:64-68) and Stice et al. (1996) Biol. Reprod., 20 54:100-110). In a particular embodiment, fibroblast cells, such as porcine fibroblast cells can be genetically modified to contain the transgene of interest.

Methods for isolation of oocytes are well known in the art. Essentially, this can comprise isolating oocytes from the ovaries or reproductive tract of a pig. A readily available source of pig oocytes is slaughterhouse materials. For the combination of techniques such as porcine IVF (in vitro fertilization), SCNT, oocytes must generally be matured in vitro before these cells can be used as recipient cells for nuclear transfer, and before they can be fertilized by the sperm cell to develop into an embryo. This process generally requires collecting immature (prophase I) oocytes from mammalian ovaries, e.g., bovine ovaries obtained at a slaughterhouse, and maturing the oocytes in a maturation medium prior to fertilization or enucleation until the oocyte attains the metaphase II stage, which in the case of bovine oocytes generally occurs about 18-24 hours post-aspiration and in the case of porcine generally occurs at about 35-55 hours. This period of time is known as the maturation period.

A metaphase II stage oocyte can be the recipient oocyte, at this stage it is believed that the oocyte can be or is sufficiently "activated" to treat the introduced nucleus as it does a fertilizing sperm. Metaphase II stage oocytes, which have been matured in vivo have been successfully used in nuclear transfer techniques. Essentially, mature metaphase II oocytes can be collected surgically from either non-superovulated or superovulated porcine 35 to 48, or 39-41, hours past the onset of estrus or past the injection of human chorionic gonadotropin (hCG) or similar hormone.

After a fixed time maturation period, the oocytes can be enucleated. Prior to enucleation the oocytes can be removed and placed in appropriate medium, such as HECM or TCM199 containing 1 milligram per milliliter of hyaluronidase prior to removal of cumulus cells. The stripped oocytes can then be screened for polar bodies, and the selected metaphase II oocytes, as determined by the presence of polar bodies, are then used for nuclear transfer. Enucleation follows.

Enucleation can be performed by known methods, such as described in U.S. Pat. No. 4,994,384. For example, metaphase II oocytes can be placed in either HECM or TCM199, optionally containing 7-10 micrograms per milliliter cytochalasin B, for immediate enucleation, or can be placed in a suitable medium, for example an embryo culture medium such as PZM or Crlaa, plus 10% estrus cow serum, and then enucleated later, for example not more than 24 hours later or 16-18 hours later.

Enucleation can be accomplished micro-surgically using a micropipette to remove the polar body and the adjacent cytoplasm. The oocytes can then be screened to identify those of which have been successfully enucleated. One way to screen the oocytes is to stain the oocytes with 3-10 microgram per milliliter 33342 Hoechst dye in suitable holding medium, and then view the oocytes under ultraviolet irradiation for less than 10 seconds. The oocytes that have been successfully enucleated can then be placed in a suitable holding medium, for example, HECM or TCM 199.

A single mammalian cell of the same species as the enucleated oocyte can then be transferred into the perivitelline space of the enucleated oocyte used to produce the NT unit. The mammalian cell and the enucleated oocyte can be used to produce NT units according to methods known in the art. For example, the cells can be fused by electrofusion. Electrofusion is accomplished by providing a pulse of electricity that is sufficient to cause a transient breakdown of the plasma membrane. This breakdown of the plasma membrane is very short because the membrane reforms rapidly. Thus, if two adjacent membranes are induced to breakdown and upon reformation the lipid bilayers intermingle, small channels can open between the two cells. Due to the thermodynamic instability of such a small opening, it enlarges until the two cells become one. See, for example, U.S. Pat. No. 4,997,384 by Prather et al. A variety of electrofusion media can be used including, for example, sucrose, mannitol, sorbitol and phosphate buffered solution. For example, the fusion media can comprise a 280 milli molar (mM) solution of mannitol, containing 0.05 mM MgCl.sub.2 and 0.001 mM CaCl.sub.2 (Walker et al., Cloning and Stem Cells. 2002; 4(2):105-12). Fusion can also be accomplished using Sendai virus as a fusogenic agent (Graham, Wister Inot. Symp. Monogr., 9, 19, 1969). Also, the nucleus can be injected directly into the oocyte rather than using electroporation fusion. See, for example, Collas and Barnes, (1994) Mol. Reprod. Dev., 38:264-267. After fusion, the resultant fused NT units are then placed in a suitable medium until activation, for example, HECM or TCM199, until activation, 1-4 hours later. Typically activation can be effected shortly thereafter, for example less than 24 hours later, or about 4-9 hours later for bovine NT and 1-4 hours later for porcine NT.

The NT unit can be activated by known methods. Such methods include, for example, culturing the NT unit at sub-physiological temperature, in essence by applying a cold, or actually cool temperature shock to the NT unit. This can be most conveniently done by culturing the NT unit at room temperature, which is cold relative to the physiological temperature conditions to which embryos are normally exposed. Alternatively, activation can be achieved by application of known activation agents. For example, penetration of oocytes by sperm during fertilization has been shown to activate prelusion oocytes to yield greater numbers of viable pregnancies and multiple genetically identical calves after nuclear transfer. Also, treatments such as electrical and chemical shock can be used to activate NT embryos after fusion. See, for example, U.S. Pat. No. 5,496,720 to Susko- Parrish et al. Additionally, activation can be affected by simultaneously or sequentially by increasing levels of divalent cations in the oocyte, and reducing phosphorylation of cellular proteins in the oocyte. This can generally be affected by introducing divalent cations into the oocyte cytoplasm, e.g., magnesium, strontium, barium or calcium, e.g., in the form of an ionophore. Other methods of increasing divalent cation levels include the use of electric shock, treatment with ethanol and treatment with caged chelators. Phosphorylation can be reduced by known methods, for example, by the addition of kinase inhibitors, e.g., serine-threonine kinase inhibitors, such as 6-dimethyl-aminopurine, staurosporine, 2-aminopurine, and sphingosine.

Alternatively, phosphorylation of cellular proteins can be inhibited by introduction of a phosphatase into the oocyte, e.g., phosphatase 2A and phosphatase 2B. The activated NT units can then be cultured until they reach a suitable size for transferring to a recipient female, or alternately, they may be immediately transferred to a recipient female.

Culture media suitable for culturing and maturation of embryos are well known in the art. Examples of known media, which can be used for embryo culture and maintenance, include Ham's F-10+10% fetal calf serum (FCS), Tissue Culture Medium-199 (TCM-199)+10% fetal calf serum, Tyrodes-Albumin-Lactate-Pyruvate (TALP), Dulbecco's Phosphate Buffered Saline (PBS), Eagle's Whitten's media, PZM, NCSU23 and NCSU37. See Yoshioka K, Suzuki C, Tanaka A, Anas I M, Iwamura S. Biol Reprod. (2002) January; 66(1):112-9 and Petters R M, Wells K D. J Reprod Fertil Suppl. 1993; 48:61-73.

Afterward, the cultured NT unit or units can be washed and then placed in a suitable media contained in well plates which can optionally contain a suitable confluent feeder layer. Suitable feeder layers include, by way of example, fibroblasts and epithelial cells. The NT units are cultured on the feeder layer until the NT units reach a size suitable for transferring to a recipient female, or for obtaining cells which can be used to produce cell colonies. NT units can be cultured until at least about 2 to 400 cells, about 4 to 128 cells, or at least about 50 cells. Alternatively, NT units may be immediately transferred to a recipient female.

The methods for embryo transfer and recipient animal management in the present invention are standard procedures used in the embryo transfer industry. Synchronous transfers are important for success of the present invention, i.e., the stage of the NT embryo is in synchrony with the estrus cycle of the recipient female. See, for example, Siedel, G. E., Jr. (1981) "Critical review of embryo transfer procedures with cattle in Fertilization and Embryonic Development in Vitro, L. Mastroianni, Jr. and J. D. Biggers, ed., Plenum Press, New York, N.Y., page 323. Porcine embryo transfer can be conducted according to methods known in the art. For reference, see Youngs et al. "Factors Influencing the Success of Embryo Transfer in the Pig," Theriogenology (2002) 56: 1311-1320.

J. Multi-Transgenic Animal Breeding Herd

Animals (or fetuses) of the present invention can be reproduced according to the following means, including, but not limited to the group selected from: SCNT, natural breeding, rederivation via SCNT using cells from an existing cell line, fetus, or animal as nuclear donors—optionally adding additional transgenes to these cells prior to NT, sequential nuclear transfer, artificial reproductive technologies (ART) or any combination of these methods or other methods known in the art. In general, "breeding" or "bred" refers to any means of reproduction, including both natural and artificial means. Further, the present invention provides for all progeny of animals produced by the methods disclosed herein. It is understood that in certain embodiments such progeny can become homozygous for the genes described herein.

In one embodiment, the genetically modified animal produced by multicistronic vector design can be bred to an animal produced by a different multicistronic vector. In particular, each multicistronic vector would be comprised of four different transgenes and a two different promoter/enhancer system.

In another embodiment transgenic animals with different multicistronic vectors, thus having different transgenes, can be bred together and have a gene repertoire that equals eight different transgenes where expression of these genes are under control of their different promoter/enhancer systems.
K. Genetically Modified Organs, Organ Fragments, Tissues, or Cells In one embodiment, the present invention is an organ, organ tissue or cell derived from the transgenic animal (e.g., porcine animal) disclosed herein. In certain embodies, the organ is a lung. In certain embodiments, the tissue is lung tissue. In selected embodiments, the organ is a kidney, heart, lung, pancreas or liver. In other embodiments, the tissue is derived from liver (including isolated hepatocytes, or liver derived stem cells), from fat (including adipocytes or mesenchymal stem cells), from cardiac tissue including heart valves, pericardium, cardiac vessels or other derivatives (viable or non-viable), derived from skin, dermis or connective tissue, bone, bone derivatives or other orthopedic tissue, dura, blood vessels, or any other tissues, including from other organs, viable or non-viable.

The donor animal (e.g., porcine animal) of the present invention may be at any stage of development including, but not limited to, fetal, neonatal, young, and adult. In some embodiments, organs or tissue are isolated from adult porcine transgenic animals. In alternate embodiments, the organ or tissue is isolated from fetal or neonatal transgenic animals (see e.g. Mandel (1999) J. Mol. Med. 77:155-60; Cardona, et al. (2006) Nat. Med. 12:304-6).

In exemplary embodiments, the donor animal may be under the age of 10, 9, 8, 7, 6, 5, 4, 3, 2, or 1 year(s). In one embodiment, the organ or tissue or tissue isolated from transgenic animal under the age of 6 years. In another embodiment, the organ or tissue is isolated from transgenic animal under the age of 3 years. The donor animal may be any age between 0 to 2 years, 2 to 4 years, 4 to 6 years, 6 to 8 years, or 8 to 10 years. In another embodiment, the organ or tissue is isolated from the fetal or neonatal stage. In another embodiment, the organ or tissue is isolated from newborn to 6 months old transgenic pigs. In one embodiment, the organ or tissue is isolated from fetal to 2 year old transgenic animals. In a particular embodiment, the organ or tissue is isolated from 6 months old to 2 year old transgenic animals, and in a more particular embodiment, 7 months old to 1 year old transgenic animals. In one embodiment, the organs or tissues are isolated from 2-3 year old transgenic animal. In another embodiment, the organs or tissues are isolated from a transgenic animal that is matched in weight (not age) to provide organs or tissues of optimal size to the human transplant recipient, such that said pig organs or tissues are procured from donor animals customized for age, weight, and/or sex of the recipient/patient.

In certain embodiments, the donor transgenic heart, kidney, lung(s) or other tissues are surgically removed. Following surgical removal, the donor kidney, heart, lung, or tissue may be further processed or evaluated prior to transplantation.

L. "Xeno Organ Pre-Conditioning" or Immune Conditioning

The long term survival of transplanted lungs are inferior to other organs, including hearts, kidney, and liver. This inferior outcomes after organ transplant can be associated with a multitude of factors of which ischemia and reperfusion (IRI) injury, an inflammatory insult, initiated by ischemia mainly resulting from the donor being brain death after cardiac arrest, but include factors such as duration of organ retrieval during procurement, cold organ preservation, etc.

For example, ischemia and reperfusion (IRI) injury is exacerbated upon re-oxygenation of the xeno organ (e.g., lung tissue) when blood flow is restored. Further insult to injury is that in comparison to other transplanted organs, the newly transplanted xeno organ (e.g., lungs) can continue to be exposed to environmental antigens after surgery. This subsequent environmental antigen exposure can partially be blamed for the decrease in survival rates. The near continuous exposure of the transplanted xeno organ (e.g., lung) to environmental antigens has been proposed to create a unique situation where immune recognition pathways are activated, increased sensitivity to the consequences of inflammation, tissue damage, and IRI, which leads to rejection.

Accordingly, one aspect of the present disclosure provides a method of enhancing and/or increasing xeno organ survival rates.
1 Xeno Lung In some embodiments, the xeno organ is a lung. In that embodiment, lungs are perfused with a hyperoncotic, acellular serum that dehydrates edematous lungs by drawing fluid from extravascular compartments such that gas exchange can be improved and lungs initially judged to be unsuitable for transplant can be rendered usable.

In an exemplary embodiment strategy for lung transplant tolerance induction are taken in consideration, a non-limiting example of recondition lungs via ex vivo lung perfusion, more specifically perfusion of the lungs with a STEEN solution supplemented with AdhIL-10 as a gene therapy to enhance long term survival of transplanted lungs. In one further embodiment, the tolerance can be induced via "mixed chimerism", bone marrow collected from the sternum, thymus, with or without CD47.

Ex vivo lung perfusion (EVLP) may be used to evaluate and recondition lungs following removal from the donor, such that the function of marginal/injured lungs can be improved and significant, persistent dysfunction can be identified prior to recipient implantation.

Lungs placed in an ex vivo circuit (Toronto XVIVO™ System) and perfused normothermically with Steen Solution™ for 2 to 4 h for physiologic re-assessment. With respect to the decision for lung utilization, lungs with a delta pO2 (pO2 Pulmonary vein pO2 pulmonary artery pO2) during ex vivo perfusion assessment >400 mmHg, are considered transplantable. Lungs are excluded for transplantation: if pO2<400 mmHg or if they demonstrate >10% deterioration in any of the following functional parameters: pulmonary vascular resistance (PVR), dynamic compliance or airway pressures. Lungs are also excluded for transplantation if they are deemed unsuitable based on the clinical judgment of the lung transplant surgeon.

Additionally, anti-inflammatory cytokines may be infused into the lungs to promote injury repair, and vector-mediated transfer of interleukin (IL)-10 utilized to decrease proinflammatory cytokine production, promote recovery of intercellular alveolar epithelial tight junctions, improve oxygenation, and decrease vascular resistance. Antibiotics can also be infused to suppress/eliminate infection.

In one embodiment the ex vivo lung perfusion maybe utilized as a delivery mechanism to deliver IL-10, that is consistently expressed from an adeno-IL10 vector, to the xenolung. The embodiment facilitates the transplantation of the lung from the transgenic animal, by providing excellent control of early inflammation under lower exposure of conventional immunosuppression. In addition, anti-IL6r (antibiotic) can be given at lung transplant with conventional immunosuppression, and repeated after period of time (~4 months) with the tolerance conditioning regimen as a method to allow for the successful withdrawal of conventional immunosuppression.

Induction of mixed chimerism uses an intensive, non-myeloablative conditioning regimen during the 5-7 days prior to transplantation; attempts to shorten this to accommodate needs in the deceased donor setting were excessively toxic and poorly tolerated. Although not yet demonstrated clinically, "delayed" tolerance induction by depleting CD8$^+$ memory T cells, then timing the bone marrow transplant to minimize pro-inflammatory cytokines, has been used in non-human primate kidney transplant experiments.

2. Xeno Heart-Nonischemic Heart Preservation (NIHP)

In some embodiments, the xeno organ is a heart. IRI can have a deleterious effect on the survival rates after cardiac transplant. One strategy to overcome IRI for heart transplant is to utilize a nonischemic heart preservation (NIHP) system. NIHP is a portable device for ground and airborne transportation that may be used to prevent potential injuries, such as damage associated with cold, static xenogeneic, donor pig heart preservation and/or storage (e.g., the XVIVO Cardiac Preservation System). NIHP can be performed as known to one of skill in the art.

For example, after cardiectomy, the heart is continuously perfused with a cold (8° C.) oxygenated cardioplegic nutrition-hormone solution containing human erythrocytes in the XVIVO heart box. The pig donor heart can be safely preserved for 24 h. The endothelium contractile function can also be preserved for at least 8 h using the NIHP system. A reproducible survival of at least 200 days after orthotopic xenogeneic cardiac transplant using the XVIVO Cardiac Preservation System was observed by the present inventors using the methods and multitransgenic animal described herein. After induction of general anesthesia, the surgical site is aseptically prepared and sterilely draped. The anesthesia team will monitor and record blood pressure (peripheral cuff or via Arterial line accessed via the left or right femoral artery, body temperature, heart rate, and oxygen saturation end tidal CO2. Then, a midline incision is carried from the manubrium to the xiphoid process, and bleeding is controlled using electrocautery. The sternum is divided in its midline, again bleeding is controlled with electrocautery. Saline or Ringers Lactate is used to replace fluid losses, maintaining near normal blood pressure. The pericardial sac is incised, exposing the heart, and after systemic heparinization (100 IU/kg, iv), the aorta and pulmonary artery are controlled. Next, the heart is arrested using cold (8° C.) blood based XHS cardioplegia* (80 mL/kg) after occluding the ascending aorta. The heart is retracted caudally, and the cranial vena cava (CVC) and the aorta at the level of the innominate artery are divided. The heart is next retracted cranio-dorsally, and the IVC, hemiazygos vein, pulmonary artery (PA), and pulmonary veins are sequentially controlled, then divided at the level of pericardial reflection. The heart is then transferred to XVIVO heart box for static non ischemic cold (8° C.) perfusion.

The XHS solution (formulation described below) can be mixed with fresh porcine blood, then infused into the donor pig heart to arrest the heart immediately prior to donor cardiectomy. Under aseptic conditions, the excised donor heart can then be attached to the, XVIVO Heart Box System (XHBS; XVIVO Perfusion, Gothenburg, Sweden) for perfusion preservation lasting at last about 1-4 hours to simulate needed preservation expected for clinical applications. The temperature can be maintained at 8° C. and pressures are maintained at 20 mmHg. For perfusion preservation, the XHS solution can be combined with the subject's (e.g., baboon or human) blood (15% Hgb). The XHS/blood perfusate is administered each 15 minutes during the implant procedure at a volume of 60 cc over 60 secs into the occluded ascending aorta.

V. Method of Treatment

The present invention provides a method for xenotransplantation comprising administering, to a subject in need thereof, porcine organs, tissue or cells derived from the transgenic porcine animal of the present invention. The transgenic organs, cells, or tissues (e.g., heart, kidney, pancreas, liver, or lung) may be transplanted into the subject using any means known in the art.

In some embodiments, the subject is a non-human primate or a human. In some embodiments, the organ is selected from the group consisting of heart, lung, liver, and kidney. In some embodiments, the tissue is selected from the group consisting of vascular tissue, retinal tissue, neural tissue, and corneal tissue. In some embodiments, the method for xeno-transplantation further comprises administering a clinically relevant immunosuppressant regimen to the subject following xenotransplantation of the organs, tissue or cells.

The invention described herein encompasses methods of xenotransplantation of the organ, organ fragment, tissue or cell described herein. In an exemplary embodiment, the methods include, but are not limited to, administering an organ, organ fragment, tissue, or cell a donor animal described herein to a subject. The donor animal may be a porcine. The subject or host may be a primate, for example, a non-human primate (NHP) including, but not limited to, a baboon. The host may be a human and in particular, a human suffering from a disease or disorder that could be impacted therapeutically by the transplant.

In an exemplary embodiment, the methods include, but are not limited to, administering a tissue from a donor animal (e.g., modified transgenic described herein) to a host. The donor animal may be a porcine. The host may be a primate, for example, a non-human primate (NHP) including, but not limited to, a baboon. The host may be a human and in particular, a human suffering from a disease or disorder requiring xenotransplantation.

Advantageously, the transgenic organs, cells, or tissues (e.g., heart, kidney, pancreas, liver, or lung) tissues provided by the present disclosure have improved functionality relative to xenotransplants known in the art. In one embodiment, the transgenic organs, cells, or tissues have improved survival rate in an ex vivo model of pig-to-human xenotransplantation as compared to a wild-type organ, cell, or tissue, or a transgenic organ, cell, or tissue derived from a transgenic animal known to the art. In a particular embodiment, the transgenic organs, cells, or tissues survive at least about 90, at least about 120, or at least about 150, at least about 180, at least about 210, at least about 240, at least about 270, at least about 300, at least about 330, at least about 360 minutes or more as compared to a wild-type organ, cell, or tissue, or a transgenic organ, cell, or tissue derived from a transgenic animal known to the art. In a particular embodiment, the transgenic organs, cells, or tissues survive at least about 1, at least about 3, at least about 5, at least about 7, at least about 14, at least about 20, or at least about 30, at least about 50, at least about 60, at least about 70, at least about 80, at least about 90, or more as compared to a wild-type organ, cell, or tissue, or a transgenic organ, cell, or tissue derived from a transgenic animal known to the art. In another particular embodiment, the transgenic lungs survive at least about 2 times, at least about 4 times, at least about 8 times, at least about 10 times longer, at least about 20 times, at least about 30 times, at least about 40 times, at least about 50 times, at least about 60 times, at least about 70 times, at least about 80 times, at least about 90 times or at least about 100 times longer than as a wild-type organ, cell, or tissue, or a transgenic organ, cell, or tissue derived from a transgenic animal known to the art.

In another embodiment, the transgenic organs, cells, or tissues described herein have improved function and survivability in a life supporting in-vivo model. In a particular embodiment, the transgenic organs, cells, or tissues described herein support life (e.g., in a baboon in a life-supporting model) for at least about 10 hours, at least about 20 hours, at least about 30 hours, or about 30 hours or more. In another particular embodiment, the transgenic organs, cells, or tissues survive at least about 2 times, at least about 4 times, at least about 8 times, at least about 10 times longer, at least about 20 times, at least about 30 times, at least about 40 times, at least about 50 times, at least about 60 times, at least about 70 times, at least about 80 times, at least about 90 times or at least about 100 times longer than as a wild-type organ, cell, or tissue, or a transgenic organ, cell, or tissue derived from a transgenic animal known to the art.

Another method of the invention is a method of xeno-transplantation comprising the transgenic organs, cells, or tissues (e.g., heart, kidney, pancreas, liver, or lung) provided herein. In some embodiments, the transgenic organs, cells, or tissues (e.g., heart, kidney, pancreas, liver, or lung) are transplanted into a primate and, the transplanted transgenic organs, cells, or tissues survive at least about 1, at least about 2, at least about 3, at least about 4, at least about 5, at least about 6, at least about 7, at least about 8, at least about 9, at least about 10, at least about 11 or at least about 12 weeks or more.

In some embodiments, the transplanted transgenic organs, cells, or tissues survive at least about 1, at least about 2, at least about 3, at least about 4, at least about 5, at least about 6, at least about 7, at least about 8, at least about 9, at least about 10, at least about 11 or at least about 12 months or more.

In some embodiments, the subject transplanted with transgenic organs, cells, or tissues described herein and survives at least 30 days longer than a subject transplanted with organs, tissues or cells derived from a wild-type porcine animal. In some embodiments, the subject transplanted with transgenic organs, cells, or tissues described herein and survives at least 60 days longer than a subject transplanted with organs, tissues or cells derived from a wild-type porcine animal. In some embodiments, the subject can be the mammal. In one embodiment, the mammal is selected from a human, a non-human primate, a monkey or baboon.

In some embodiments, the transgenic organs, cells, or tissues can be a heart, a kidney, or a lung or a fragment thereof. In some embodiments, the transgenic organs, cells, or tissues can be transferred to an ex-vivo perfusion treatment system prior to transplantation.

An additional method of the invention is a method of xenotransplantation wherein the transgenic lung(s) or lung tissue provided herein is transplanted into a primate and, the transplanted lung or tissue survives for a period of time as described above. In one embodiment, a life-supporting model of lung xenotransplantation is used to assess lung function. In one embodiment, the life supporting model includes removing one lung from the primate and transplanting a single lung from the porcine donor of the present invention into the primate recipient. In another embodiment, life supporting model includes removing both lungs from the primate and transplanting both lungs from the porcine donor of the present invention into the primate recipient. In a further embodiment, both lungs and the heart can be removed from the primate and replaced with the porcine lungs and heart of the present invention. In embodiments of the present invention, duration of life-supporting lung function can be assessed in the primate. In some embodiments, the primate is human or a non-human primate.

To assess duration of life-supporting lung function, genetically modified porcine lungs of the present invention can be harvested from the pig. The heart-lung block can be excised, and either one lung, two lungs or two lungs and the heart can be prepared for transplant into the primate.

Primate recipients can be sedated and maintained under general anesthesia. The lung, lungs or heart and lungs can then be removed from primate using methods known in the art (see, for example, Nguyen et al The Journal of Thoracic and Cardiovascular Surgery May 2007; 133: 1354-63 and Kubicki et al International Journal of Surgery 2015: 1-8), transplanted into the primate and then the primate can be reperfused. Before and after graft reperfusion, blood and tissue biopsy specimens can be collected serially at predetermined time points for in vitro analysis. Vascular flow probes (Transonic Systems Inc, Ithaca, NY) on the aorta and left pulmonary artery can continuously measure cardiac output and flow to the transplanted organs, respectively. In models in which only one lung is transplanted and the second lung remains a native primate lung, blood flow to the native lung can be progressively occluded to assess the capacity of the transplanted lung to support life. Graft survival can be defined as duration of life-supporting lung function. For long-term survival experiments, flow probes placed on the aorta and one pulmonary artery allow monitoring of blood flow through the pulmonary transplant. The International Society for Heart and Lung Transplantation has recommended consistent achievement of three months of life-supporting function in a model such as this in order to consider a human trial (Kubicki et al International Journal of Surgery 2015: 1-8).

In some embodiments, the transgenic lung or lung tissue derived from the transgenic animal of the present invention are transplanted into a primate. In some embodiments, after the transplant, the primate (i.e. the subject in need of transplantation) requires reduced or no immunosuppressive therapy. Reduced or no immunosuppressive therapy includes, but is not limited to, a reduction (or complete elimination of) in dose of the immunosuppressive drug(s)/agent(s) compared to that required by other methods; a reduction (or complete elimination of) in the number of types of immunosuppressive drug(s)/agent(s) compared to that required by other methods; a reduction (or complete elimination of) in the duration of immunosuppression treatment compared to that required by other methods; and/or a reduction (or complete elimination of) in maintenance immunosuppression compared to that required by other methods.

The present invention provides methods of treating or preventing lung disease wherein the transgenic lung(s) or lung tissue provided herein is transplanted into a subject in need thereof (i.e. a primate) and, after the transplant, the primate has improved lung function. The transplanted primate may have improved lung function when compared to the level prior to transplant or when compared to the level achieved using other methods.

In some embodiments, the recipient (host) may be partially or fully immunosuppressed or not at all at the time of transplant. In some embodiments, the method further comprises administering a clinically relevant immunosuppressant regimen to the subject following xenotransplantation of the organs, tissue or cells derived from the transgenic animal of the present invention. In some embodiments, the immunosuppressive agents and/or drugs that may be used before, during and/or after the time of transplant are any known to one of skill in the art and include, but are not limited to, KPL-404 (Kiniksa Pharmaceuticals), TNX-1500 (Tonix Pharmaceuticals Holding Corp.), MMF (mycophenolate mofetil (Cellcept)), ATG (anti-thymocyte globulin), anti-CD154 (CD40L), anti-CD20 antibody, anti-CD40 (2C10R4 antibody therapy). See Mohiuddin M M. et al., April 5; 7:11138. [2016], alemtuzumab (Campath), CTLA4-Ig (Abatacept/Orencia), belatacept (LEA29Y), sirolimus (Rapimune), tacrolimus (Prograf), daclizumab (Zenapax), basiliximab (Simulect), infliximab (Remicade), cyclosporin, deoxyspergualin, soluble complement receptor 1, cobra venom, methylprednisolone, FTY720, everolimus, anti-CD154-Ab, leflunomide, anti-IL-2R-Ab, rapamycin, and human anti-CD154 monoclonal antibody. One or more than one immunosuppressive agents/drugs may be used together or sequentially. One or more than one immunosuppressive agents/drugs may be used for induction therapy or for maintenance therapy. The same or different drugs may be used during the induction and maintenance stages. In one embodiment, daclizumab (Zenapax) is used for induction therapy and tacrolimus (Prograf) and sirolimus (Rapimune) is used for maintenance therapy. In another embodiment, daclizumab (Zenapax) is used for induction therapy and low dose tacrolimus (Prograf) and low dose sirolimus (Rapimune) is used for maintenance therapy. In one embodiment, alemtuzumab (Campath) is used for induction therapy. See Teuteberg et al., Am J Transplantation, 10(2):382-388. 2010; van der Windt et al., 2009, Am. J. Transplantation 9(12): 2716-2726. 2009; Shapiro, The Scientist, 20(5):43. 2006; Shapiro et al., N Engl J. Med. 355:1318-1330. 2006 Immunosuppression may also be achieved using non-drug regimens including, but not limited to, whole body irradiation, thymic irradiation, and full and/or partial splenectomy, "mixed chimerism", bone marrow collected from the sternum, thymus (Sachs, 2014). These techniques may also be used in combination with one or more immunosuppressive drug/agent.

A. Single Lung Transplant

If the recipient is having a single lung transplant, he/she will have a thoracotomy incision either on their right or their left side, depending on which lung is being replaced. After the donor lung arrives in the operating room, the surgeon will remove the diseased lung. The recipient will be ventilated using the other lung. If the remaining lung is not able to exchange enough oxygen, the surgeon may place the recipient on cardiopulmonary bypass. Their blood will be filtered through a machine outside the body which will put oxygen into their blood and remove carbon dioxide.

Three connections will be used to attach the new lung. These connections are called anastomoses. First, the main bronchus from the donor lung is attached to the recipient's bronchus. Then the blood vessels are attached—first the pulmonary artery, and then the pulmonary veins. Finally, the incision is closed and the recipient will be taken to the intensive care unit, where he/she will be asleep for approximately 12 to 24 hours.

B. Bi-Lateral or Double Lung Transplant

If both lungs are transplanted (a bilateral transplant), the surgeon will make an incision below each breast, called an anterior thoracotomy, or an incision that goes from the right side to the left side at the base of the breasts. This is called a transverse sternotomy incision. In a bilateral lung transplant, each lung is replaced separately. The surgeon begins by removing the lung with the poorest function. The recipient will be ventilated using their remaining lung unless partial cardiopulmonary bypass is needed. Once the first lung is removed, a donor lung will be attached using three connections. The donor bronchus is attached to the recipient's main bronchus, then the blood vessels are attached-first the pulmonary artery, then the pulmonary veins. The recipient's second diseased lung is removed and the other new lung is attached in the same way. Once the second lung is completely connected, blood flow is restored.

Sufficient time may be allowed for engraftment, for example, 1 week, 3 weeks, and the like.

C. Assessing Successful Engraftment

Successful engraftment may be determined using any technique known to one skilled in the art. These techniques may include, but are not limited to, assessment of donor C-peptide levels, histological studies, intravenous glucose tolerance testing, exogenous insulin requirement testing, arginine stimulation testing, glucagon stimulation testing, testing of IEQ/kg (pancreatic islet equivalents/kg) requirements, testing for persistence of normoglycemia in recipient, testing of immunosuppression requirements, and testing for functionality of transplanted islets (See Rood et al., Cell Transplantation, 15:89-104. 2006; Rood et al., Transplantation, 83:202-210. 2007; Dufrane and Gianello, Transplantation, 86:753-760. 2008; van der Windt et al., 2009, Am. J. Transplantation, 9(12):2716-2726. 2009). One or more techniques may be used to determine if engraftment is successful. Successful engraftment may refer to relative to no treatment, or in some embodiments, relative to other approaches for transplantation (i.e., engraftment is more successful than when using other methods/tissues for transplantation). In some cases, successful engraftment is determined by assessment of donor C-peptide levels including life supporting function with added immunosuppression.

D. End Stage Organ Failure: Lung, Heart, and Kidney diseases

The present invention provides a method of treating a disease or disorder in a subject in need thereof comprising implanting a organ, cell, or tissue (e.g., heart, kidney, pancreas, liver, or lung) derived from a transgenic pig of the present invention into the subject. In some embodiments, the disease or disorder is selected from lung disease, heart disease, or kidney disease In some embodiments, the disease or disorder is a lung disease. The lung disease may be an advanced lung disease. In one embodiment, the advanced lung disease may be associated with primary pulmonary hypertension (PAH), chronic obstructive pulmonary disease (COPD), interstitial lung disease (ILD), sarcoidosis, bronchiectasis, idiopathic pulmonary fibrosis (IPD), cystic fibrosis (CF), alpha1-antitrypsin deficiency disease.

As would be understood by one of skill in the art, primary pulmonary hypertension (PAH) refers to high blood pressure in the arteries of the lung. As would be understood by one of skill in the art, cystic fibrosis refers to is a genetic disease that is recessively inherited, meaning both parents need to have the defective gene. Approximately 30,000 Americans have CF, and about 12 million carry the gene but are not affected by it. CF patients often have respiratory problems including bronchitis, bronchiectasis, pneumonia, sinusitis (inflammation of the sinuses), nasal polyps (growths inside the nose), or pneumothorax (collapsed lung). Symptoms of CF include frequent wheezing or pneumonia, chronic cough with thick mucus, persistent diarrhea, salty-tasting skin, and poor growth.

As would be understood by one of skill in the art, chronic obstructive pulmonary disease (COPD) refers to can be caused by asthma, chronic bronchitis, or emphysema. Over time, individuals with COPD slowly lose their ability to breathe. Symptoms of COPD range from chronic cough and sputum production to severe, disabling shortness of breath As would be understood by one of skill in the art, alpha1-antitrypsin disease/alpha-1 antitrypsin deficiency is a hereditary condition in which a lack of alpha-1 antitrypsin—a protein that protects the lungs-results in early-onset lung disease. Smoking greatly increases this risk. The first symptoms of alpha-1 related emphysema often appear between ages 20 and 40 and include shortness of breath following activity, decreased exercise capacity, and wheezing.

As would be understood by one of skill in the art, interstitial lung disease (ILD), is a general term that includes a variety of chronic lung disorders such as idiopathic pulmonary fibrosis, sarcoidosis, eosinophilic granuloma, Goodpasture's syndrome, idiopathic pulmonary hemosiderosis and Wegener's granulomatosis. When a person has ILD, the lung is affected in four ways: 1) The lung tissue becomes damaged, 2) the walls of the air sacs in the lung become inflamed, 3) scarring begins in the interstitium (tissue between the air sacs), and 4) the lung becomes stiff.

As would be understood by one of skill in the art, sarcoidosis refers to a disease involving abnormal collections of inflammatory cells (granulomas) that can form as nodules in multiple organs. The granulomas are most often located in the lungs or its associated lymph nodes. As would be understood by one of skill in the art, bronchiectasis refers to the irreversible widening of the airways. As airways widen, they become less rigid and more prone to collapse. It also becomes more difficult to clear away secretions. Bronchiectasis can be present at birth, or it can develop later as a result of injury or other diseases (most often cystic fibrosis). It can occur at any age but most often begins in childhood. Symptoms of bronchiectasis include coughing, fever, weakness, weight loss, and fatigue In some embodiments, the disease or disorder is a heart disease or disorder. heart disease or disorder that may eventually require a heart transplant are selected from the group consisting of coronary heart disease, heart failure, dilated cardiomyopathy, coronary artery disease, restrictive myopathy, hypertrophic cardiomyopathy, valvular heart disease, congenital heart disease.

As used herein, a coronary heart disease refers to a build-up of fatty substances in the arteries supplying the heart, which block or interrupt blood flow to the heart. As used herein, a heart failure refers to a serious health condition that occurs when the heart cannot pump enough blood to the rest of the body. Heart failure is the primary reason patients receive a heart transplant. As used herein, dilated cardiomyopathy refers to a condition where the left ventricle of the heart becomes enlarged and weakened so that it cannot pump blood correctly. As used herein, a coronary artery disease refers to a common form of heart disease where fatty deposits have narrowed the arteries that supply blood to the heart. In time, coronary artery disease can weaken the heart muscle. This weakening can cause myocardial infarction (heart attack). As used herein, a restrictive myopathy refers to rare form of cardiomyopathy where the lower chambers of the heart (the ventricles) are unusually rigid and cannot flex normally to fill with blood as the heart pumps. As used herein, a hypertrophic cardiomyopathy refers to a genetic disease where the heart muscle becomes too thick and affects the way the heart pumps. As used herein, a valvular heart disease refers to a condition where the valves are formed abnormally or stop functioning properly. As used herein, a congenital heart disease refers to a condition where a person's heart never functions normally from birth. Many people with congenital heart disease now survive well into adulthood.

In some embodiments, the transplant may involve a single lung or both lungs (bilateral). In some embodiments, the transplant can also involve cardiopulmonary transplantation or heart-lung transplantation that is the simultaneous surgical replacement of the heart and lungs in patients with end-stage cardiac and pulmonary disease. This procedure remains a viable therapeutic alternative for patients in specific disease states. Causes of end-stage cardiopulmonary failure that necessitate cardiopulmonary transplantation range from congenital cardiac disease to idiopathic causes and include the following: irreparable congenital cardiac anomalies with pulmonary hypertension (Eisenmenger complex), primary pulmonary hypertension with irreversible right-heart failure; sarcoidosis involving only the heart and lungs.

In some embodiments, the disease or disorder is a kidney disease. The kidney disease or disorder that that may eventually require a heart transplant may be end stage kidney disease. which End stage kidney disease occurs when the kidneys have lost around 90% of their filtering ability. t the kidneys can lose their filtering abilities when the nephrons become damaged. This means high and life-threatening levels of waste products and chemicals in the body. When the kidneys have lost around 90% of their filtering ability, A person is said to have end stage kidney disease because high and life-threatening levels of waste products and chemicals accumulate in the body.

Known and common causes of end stage kidney disease may include diabetes, high blood pressure, hypertension, renal artery stenosis, polycystic kidney disease, congenital disorders, and/or an immune disorder. In some cases, patients with Diabetes (e.g., diabetic kidney disease) have a continuously high blood sugar. This high blood sugar can damage the filters in the kidneys, leading to long-term kidney damage and finally kidney failure. This is called diabetic nephropathy. High blood pressure in the tiny blood vessels of the kidney can damage and prevent the filtering process. Renal artery stenosis refers to a the narrowing of one or more arteries that carry blood to the kidneys, resulting in arterial occlusion. Polycystic kidney disease is an inherited condition caused by a defects ion channels in the kidney (e.g., TRP channels). As result, several large cysts or hollow spaces formed within the kidney, causing the kidneys to enlarge and lose function over time. Some congenital kidney defects manifests when over 90% of the kidney function is compromised. Systemic lupus erythematosus (SLE) SLE is an autoimmune disease in which the immune system attacks its own tissues, causing widespread inflammation and tissue damage in the affected organs. It can affect the joints, skin, brain, lungs, kidneys, and blood vessels.

In some embodiments, the method further comprises administering to the subject one or more therapeutic agents. In some embodiments, the one or more therapeutic agents are selected from anti-rejection agents, anti-inflammatory agents, immunosuppressive agents, immunomodulatory agents, anti-microbial agents, anti-viral agents and combinations thereof.

VI. Additional Embodiments

In a first aspect, the present invention provides a transgenic pig comprising at least six transgenes, wherein the at least six transgenes are incorporated and expressed at a single locus under the control of at least three promoters, and wherein the pig lacks expression of alpha 1,3 galactosyltransferase.

The single locus may be any suitable locus. In one embodiment, the single locus is a native locus, unmodified. In an alternate embodiment, the single locus is a modified native locus. The locus may be modified by any suitable means including but not limited to insertions, deletions, or substitutions mediated by gene-editing tools. In certain embodiments, the modified native locus includes transgenic DNA. The transgenic DNA may be, for example, a selectable marker gene. In order embodiments, the transgenic DNA is a landing pad—as described further herein. In particular embodiments, the single locus is AAVS1, ROSA26, CMAH, ß4GalNT2, GHR, or GGTA1. According to this embodiment, this locus may be native or modified.

In an exemplary embodiment, the single locus is native GGTA1 or modified native GGTA1. In certain embodiments, the modified native GGTA1 locus includes a selectable marker gene, for example neo. In other embodiments, the modified native GGTA1 locus includes insertions, deletions or substitutions mediated by gene-editing tools. In yet other embodiments, the modified native GGTA1 locus includes a landing pad to facilitate gene targeting.

The promoters may vary. In exemplary embodiments, the promoters are endogenous, exogenous or a combination thereof. In exemplary embodiments, the promoters are constitutive or regulatable or a combination thereof. In certain embodiments, at least one of the promoters is regulatable (e.g., a tissue-specific or inducible promoter).

In an exemplary embodiment, the transgenic pig comprises six transgenes, wherein the six transgenes are expressed as a first, second, and third polycistron, and wherein a first promoter controls expression of the first polycistron, a second promoter controls expression of the second polycistron, and a third promoter controls expression of the third polycistron. In an exemplary embodiment, the transgenic pig comprises six transgenes, wherein each of the at least six transgenes is controlled by a dedicated promoter.

In a particular embodiment, the transgenic pig comprises at least six transgenes, wherein the at least six transgenes are incorporated and expressed at a single locus under the control of at least three promoters, wherein at least one of the promoters is constitutive (e.g., CAG) and at least one of the promoters is tissue-specific (e.g., an endothelial-specific promoter, such as ICAM-2), and wherein the pig lacks expression of alpha 1,3 galactosyltransferase.

In another particular embodiment, the transgenic pig comprises at least six transgenes, wherein the at least six transgenes are incorporated and expressed at a single locus under the control of at least three promoters, wherein at least two of the promoters are constitutive and wherein the pig lacks expression of alpha 1,3 galactosyltransferase.

The transgenes may vary. In exemplary embodiments, the transgenes are anti-coagulants, compliment inhibitors, immunomodulators, cytoprotective transgenes or combinations thereof.

In certain embodiments, at least one of the transgenes is an anti-coagulant. In one embodiment, the anti-coagulant is TBM, TFPI, EPCR, or CD39. In a particular embodiment, at least two of the transgenes are anti-coagulants. In certain embodiment, at least one of the transgenes is a compliment regulator, such as a complement inhibitor. In one embodiment, the compliment inhibitor is CD46, CD55 or CD59.

In certain embodiments, at least one of the transgenes is an immunomodulator. The immunomodulator may be, for example, an immunosuppressant. In one embodiment, the immunosuppressant is porcine CLTA4-IG or CIITA-DN. In a particular embodiment, at least one of the transgenes is CD47.

In exemplary embodiment, the transgenic animal comprises at least one additional genetic modification, i.e., in addition to expression of multiple transgenes and lack of expression of alpha Gal. The additional genetic modification may vary. In exemplary embodiments, the at least one genetic modification is a gene knock-out, gene knock-in, gene replacement, point mutations, deletions, insertions or substitutions of genes, gene fragments or nucleotides, large genomic insertions, or combinations thereof. In certain embodiments, the single locus is not GGTA1 and the at least one additional genetic modification comprises knock-out of the alpha 1,3 galactosyltransferase gene.

In other embodiments, the additional genetic modification involves incorporation and expression of at least one additional transgene. In one embodiment, the additional transgenes is a human CD46 gene, human HLA-3 and/or a humanized vWF or chimeric porcine-human vWF gene. In certain embodiments, the at least one additional genetic modification is a modification of the porcine vWF locus to reduce or eliminate spontaneous aggregation of human platelets.

In certain embodiments, the at least one additional genetic modification is a knock-out of a porcine gene. The porcine gene may be, in certain embodiments, ß4GalNT2, CMAH, isoGloboside 3 synthase, Forrsman synthase or vWF. In certain embodiments, the at least one additional genetic modification involves incorporation and expression of at least two or more additional transgenes. In one embodiment, the two or more additional transgenes are incorporated and expressed a single, second locus.

In an exemplary embodiment, the transgenic pig comprising at least six transgenes, wherein the at least six transgenes are incorporated and expressed at a first single locus (e.g., GGTA1) under the control of at least three promoters and (ii) at least two transgenes are incorporated and expressed under the control of at least one promoter at a second single locus (e.g., ß4GalNT2 or CMAH), and wherein the pig lacks expression of alpha 1,3 galactosyltransferase.

In a second aspect, the present invention is an organ or organ fragment derived from the transgenic pig of the first aspect of the invention. In exemplary embodiments, the organ is a lung, liver, heart or pancreas. In exemplary embodiments, the organ fragment is a lung fragment, liver fragment, heart fragment or pancreas fragment. In a third aspect, the present invention is a tissue derived from the transgenic pig of the first aspect of the invention. In exemplary embodiments, the tissue is an epithelial tissue or a connective tissue. In a fourth aspect, the present invention is a cell derived from the transgenic pig disclosed herein. In exemplary embodiments, the cell is an islet cell.

In a fifth aspect, the present invention is a method of making a transgenic pig expressing at least six transgenic genes but lacking expression of alpha 1,3 galactosyltransferase, comprising (i) incorporating at least six transgenes under the control of at least three promoters at a single locus within a pig genome to provide a polygene pig genome; (ii) permitting a cell comprising the polygene pig genome to mature into a transgenic pig.

In an exemplary embodiment, the pig genome is a somatic cell pig genome and the cell is a pig zygote, and wherein the pig zygote is provided by somatic cell nuclear transfer (SCNT) and transferring the polygene pig genome by micro-injection into a reconstructed SCNT zygote.

Optionally, the somatic cell genome and/or the polygene pig genome may include one or more additional genetic modifications. In one embodiment, the at least one genetic modification is selected from a is a gene knock-out, gene knock-in, gene replacement, point mutations, deletions, insertions or substitutions of genes, gene fragments or nucleotides, large genomic insertions, or combinations thereof.

In an exemplary embodiment, the pig genome is a selected from the group consisting of a gamete pig genome, zygote pig genome, an embryo pig genome or a blastocyst pig genome. Optionally, the pig genome or the polygene pig genome comprises at least one additional genetic modifica-tion. In one embodiment, the at least one genetic modifica-tion is selected from a is a gene knock-out, gene knock-in, gene replacement, point mutations, deletions, insertions or substitutions of genes, gene fragments or nucleotides, large genomic insertions, or combinations thereof.

The method of incorporation may vary. In exemplary embodiment, incorporation involves biological transfection, chemical transfection, physical transfection, virus mediated transduction or transformation or combinations thereof. In a particular embodiment, incorporation involves cytoplasmic microinjection. In another particular embodiment, incorpo-ration involves pronuclear microinjection. The single locus may vary, consistent with the first aspect of the invention.

In exemplary embodiments, the single locus includes transgenic DNA. In a particular embodiment, the transgenic DNA is a landing pad that includes one or more recognition sites for at least one polynucleotide modification enzyme. The polynucleotide modification enzyme may vary. In cer-tain embodiments, the polynucleotide modification enzyme is an engineered endonuclease, site specific recombinase, integrase or combinations thereof.

In one embodiment, the engineered endonuclease is a zinc finger nuclease, transcription activator-like effector nucle-ases or a clustered regularly interspaced short palindromic repeats/Cas9 nucleases.

In one embodiment, the site-specific recombinase is a lambda integrase, Cre recombinase, FLP recombinase, gamma-delta resolvase, Tn3 resolvase, (DC31 integrase, Bxb1-integrase, R4 integrase or combinations thereof. In one embodiment, the single locus is a native or modified locus selected from GGTA1, CMAH, ß4GalNT2, GHR, AAVS1 locus and ROSA26.

In embodiments, where the single locus is not a GGTA1 locus and the additional genetic modification comprises knocking-out the alpha 1,3 galactosyltransferase gene. Other knock-outs contemplated by the present invention as addi-tional genetic modifications include knock-outs of the porcine ß4GalNT2 gene, CMAH gene, 34GalNT2 gene, vWF or combinations thereof. In exemplary embodiments, the at least one additional genetic modification involves incorpo-ration and expression of at least one additional transgene. In certain embodiments, the transgene is human CD46, human HLA-E, a humanized vWF, a chimeric porcine-human vWF, or a fully human vWF. In a sixth aspect, the present invention is a transgenic pig or production herd produced by the method of the fifth aspect of the invention.

In a seventh aspect, the present invention is a method of breeding the transgenic pig of the present invention to a second transgenic pig, wherein the second transgenic pig is characterized by one or more genetic modifications. In exemplary embodiments, the second transgenic pig is char-acterized by one or more genetic modifications such as gene knock-out, gene knock-in, gene replacement, point muta-tions, deletions, insertions or substitutions of genes, gene fragments or nucleotides, large genomic insertions, or com-binations thereof.

In an eighth aspect, the present invention is a transgenic pig or production herd produced by the method of the seventh aspect of the invention.

In a ninth aspect, the present invention provides a method for treating a subject in need thereof, by implanting into the subject at least one organ, organ fragment, tissue or cell derived from the transgenic pig of the present invention. In exemplary embodiments, the organ or organ fragment is a lung or lung fragment, a kidney or kidney fragment, a liver or liver fragment, a pancreas or pancreas fragment or combination thereof.

In a particular embodiment, the organ is a lung. In another particular embodiment, the organ fragment is a lung frag-ment. In an exemplary embodiment, the lung or lung frag-ment is implanted in a subject having advanced lung disease. In an exemplary embodiment, the lung or lung fragment is implanted in a subject having advanced lung disease asso-ciated with chronic obstructive pulmonary disease (COPD), idiopathic pulmonary fibrosis (IPD), cystic fibrosis (CF), alpha1-antitrypsin disease, or primary pulmonary hyperten-sion. In certain embodiments, the method involves admin-istering one or more additional therapeutic agents to the subject. The one or more therapeutic agents may vary. In one embodiment, the therapeutic agent is an anti-rejection agent, an anti-inflammatory agent, an immunosuppressive agent, an immunomodulatory agent, an anti-microbial agent, and anti-viral agent and combinations thereof.

In a tenth aspect, the present invention provides a trans-genic pig having a genetic modification of the porcine vWF locus, and lacking expression of alpha 1,3 galactosyltrans-ferase. The transgenic pig may comprise one or more additional genetic modifications. In an exemplary embodi-ment, the transgenic pig has a genetic modification of the porcine vWF locus and incorporates and expresses at least six transgenes, as well as lacks expression of alpha 1,3 galactosyltransferase.

EXAMPLES

The present technology is further illustrated by the fol-lowing Examples, which should not be construed as limiting in any way. The examples herein are provided to illustrate advantages of the present technology and to further assist a person of ordinary skill in the art with preparing or using the compositions and systems of the present technology. The examples should in no way be construed as limiting the scope of the present technology, as defined by the appended claims. The examples can include or incorporate any of the variations, aspects, or embodiments of the present technol-ogy described above. The variations, aspects, or embodiments described above may also further each include or incorporate the variations of any or all other variations, aspects or embodiments of the present technology.

Example 1: Generation of 6 Gene Vectors

Vector constructions. Multiple bi-cistronic units were synthesized consisting of two (2) transgenes linked by 2A peptide sequences that share a single promoter. Two forms of 2A sequences, P2A (66 bp) and T2A (55 bp) were utilized to linked large number of two-transgene units to allow co-expression of both genes from one promoter. Promoters were either the constitutive CAG promoter (CMV enhancer, chicken actin promoter, rabbit b-globin intron1), the endothelial-specific porcine TBM promoter (pTBMpr), the endothelial-specific porcine ICAM-2 promoter or a combination of the Tie2 endothelial-specific enhancer with the CAG promoter. Pairs of human transgenes were constructed (connected by the 2A sequence) including thrombomodulin (TBM), EPCR, CD59, CD47, HO1, CD46 and CD55 (DAF). Exemplary embodiments of the vectors of the present invention are shown in FIGS. 1A-B and 2A-2H. Each vector was flanked with "targeting arms" (hatched) composed of unique DNA sequences homologous to genomic sequences at the site of desired vector insertion (also hatched). CRISPR/Cas9 RNPs were used to cut genomic DNA at the target site to facilitate homology-directed repair (HDR). As used herein, hCD55 in the vector diagram is synonymous with hDAF.

Figure 1B:
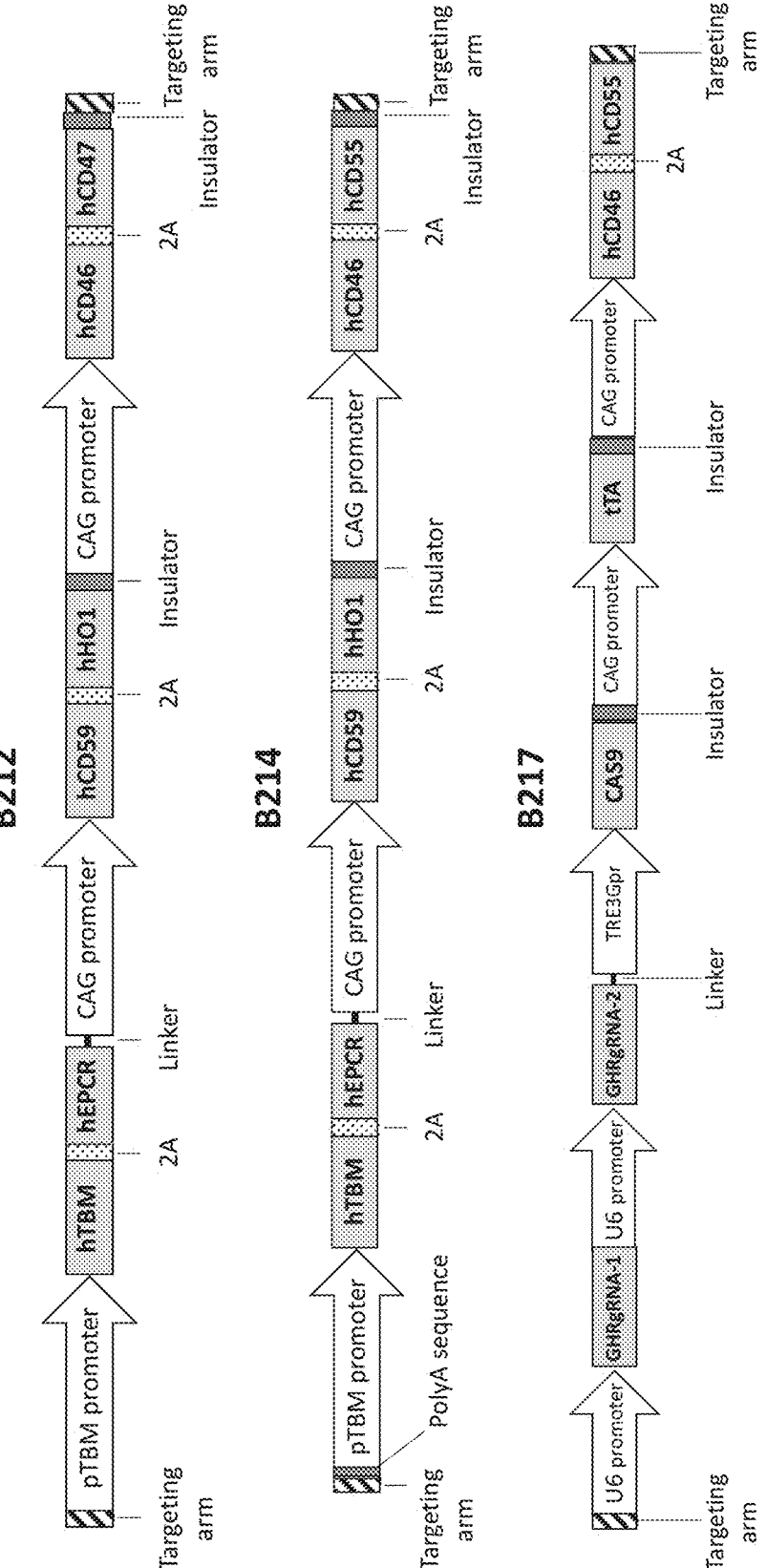
Figure 2A:
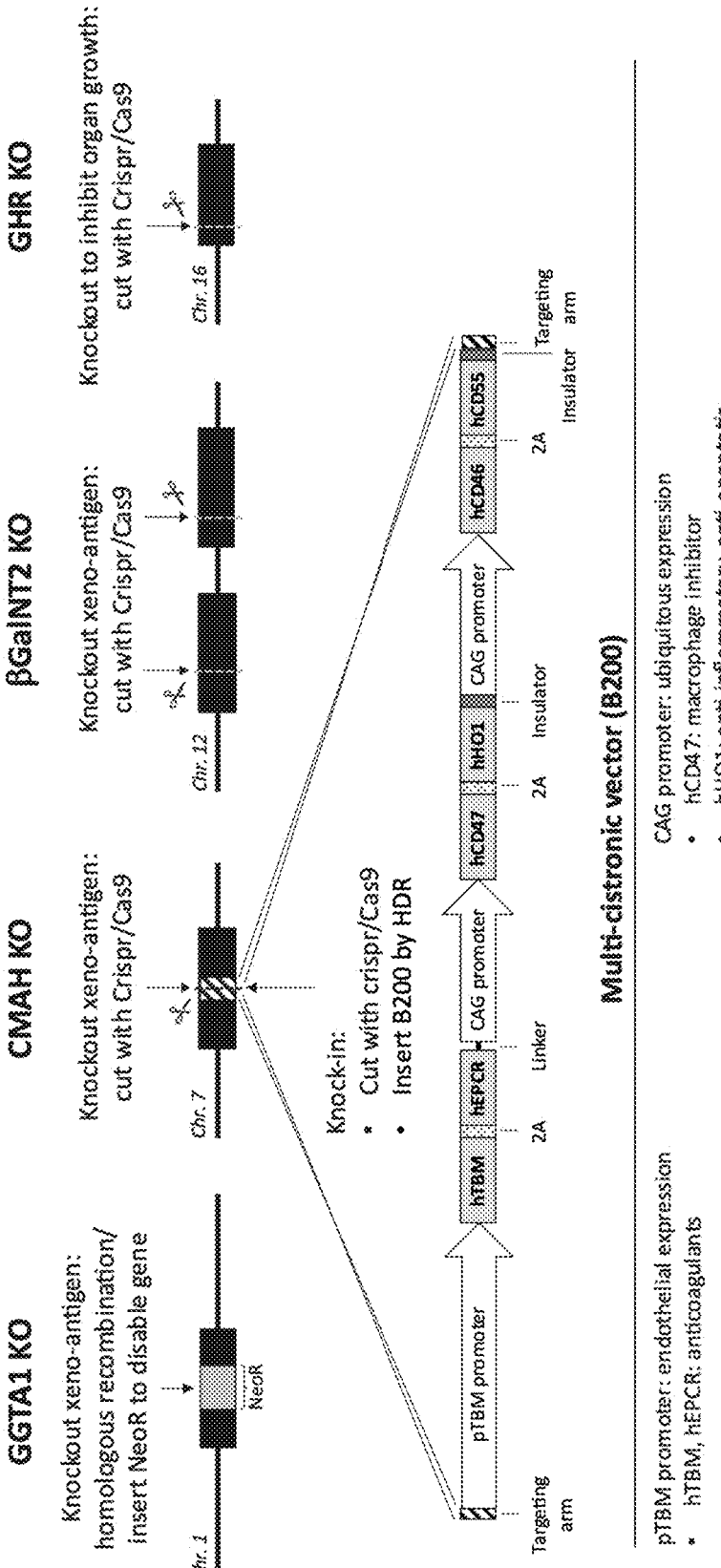
FIGS. 2A-H show a schematic representation of exemplary embodiments of the vectors of described herein for the production of a multitransgenic animal comprising at least 10 modifications (e.i. 10GE pigs), which may comprise a functional knockout of 4 pig genes (GGTA1, CMAH, B4GalNT2, and growth hormone receptor (GHR)) and targeted integration of a multicistronic vector comprising six human transgenes (6-gene vectors).

The B200 vector (SEQ ID NO: 11) is a multicistronic vector (MCV) comprising of three bi-cistron units and named pTBMpr [hTBM-2A-hEPCR]/CAGpr [hCD47-2A-hHO1]/CAGpr [hCD46-2A-hDAF] flanked by targeting arms for HDR at CMAH (FIGS. 1A-B; FIG. 2A). A first bi-cistron unit ((pTBMpr)[hTBM-2A-hEPCR]) contains a human Thrombomodulin (TBM) cDNA linked via a 2A peptide to a human endothelial protein C receptor (EPCR) cDNA and both transgenes are driven by a porcine thrombomodulin promoter (pTBMpr). A second bi-cistron unit (CAGpr [hCD47-2A-hHO1]) contained a human Cluster of Differentiation 47 (CD47) cDNA linked via a 2A peptide to a human Heme Oxygene 1 (HO-1) cDNA and both transgenes are driven by a CAG promoter (CAGpr). A third bi-cistron unit (CAGpr [hCD46-2A-hDAF]) contained a human Cluster of Differentiation 46 (CD46) cDNA linked via a 2A peptide to a human Cluster of Differentiation 55 (CD55 or DAF) cDNA and both transgenes are driven by a CAG promoter (CAGpr). The B200 vector was flanked by targeting arms for homology driven recombination (HDR) at the CMAH gene locus.

To generate the B200 vector (SEQ ID NO: 11), a porcine TBM promoter was cloned in two steps FIGS. 1A-B; FIG. 2A). First (Step 1), a 4266 bp genomic fragment of the porcine TBM promoter region was amplified from the porcine genome using primers TBM pr 4774F-CCCTCCTTCCCACAAAGCTT (SEQ ID NO: 1), TBMpr 9157R-ACTGGCATTGAGGAAGGTCG (SEQ ID NO: 2) and cloned as PshAI/FseI restriction fragment in the vector containing hTBM-2A-hEPCR; CAGpr [hCD47-2A-hHO1], flanked with HDR targeting arms for the CMAH locus. In Step 2, a 3267 bp genomic fragment of pTBM promoter (upstream of the fragment cloned in Step 1; was amplified from the pig genome using the primers TBMpr 738F-CCCACACACAACCAGAGACA (SEQ ID NO: 5), TBMpr 4311 R-GTGCAGGTATGTGGCCTCTT (SEQ ID NO: 6) and cloned as PshAI fragment into the construct generated at Step 1. The final vector, containing 6 genes, was generated by inserting the CAGpr [hCD46-2A-hDAF] fragment at the SwaI site of the vector from Step 2. This design allowed us to simultaneously inactivate CMAH gene and express the transgenes from permissive locus.

Figure 2B:
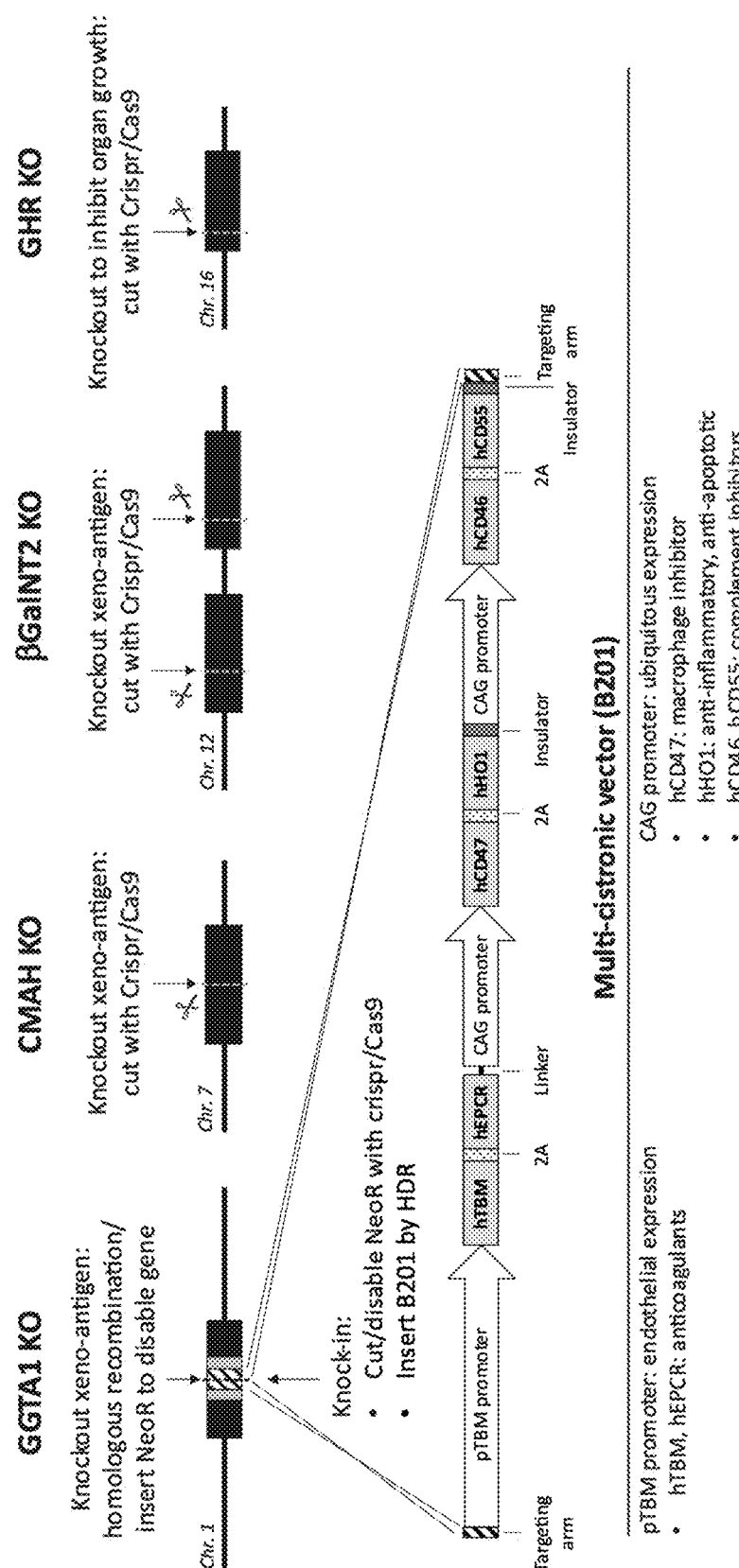

The B201 vector (SEQ ID NO: 12) is a MCV comprising three bi-cistron units and named PolyA/pTBMpr [hTBM-2A-hEPCR]/CAGpr [hCD47-2A-hHO1]/CAGpr [hCD46-2A-hDAF], flanked by targeting arms for HDR at GGTA1/Neo locus FIGS. 1A-B; FIG. 2B). Promiscuous expression of transgenes driven by the endothelial-specific porcine TBM promoter have been observed under some circumstances. This was likely a consequence of vector insertion into actively transcribed loci, like CMAH. To remedy this issue, a Poly A sequence was added upstream of the promoter sequence of the pTBM promoter. Poly A sequences in the genome act as terminators for transcription of active genes. Therefore, to avoid locus-specific influence on expression of the human transgenes driven by the pTBM promoter, the B200 vector was further modified in multiple steps by adding the bovine growth hormone (GH) poly A sequence in front (5') of the porcine TBM promoter. In addition, the CMAH HDR of the B200 vector were replaced with GGTA1/Neo HDR arms to generate the B201 vector. These modifications facilitated more regulatable, endothelial-specific expression of the hTBM and hEPCR transgenes.

Figure 2C:
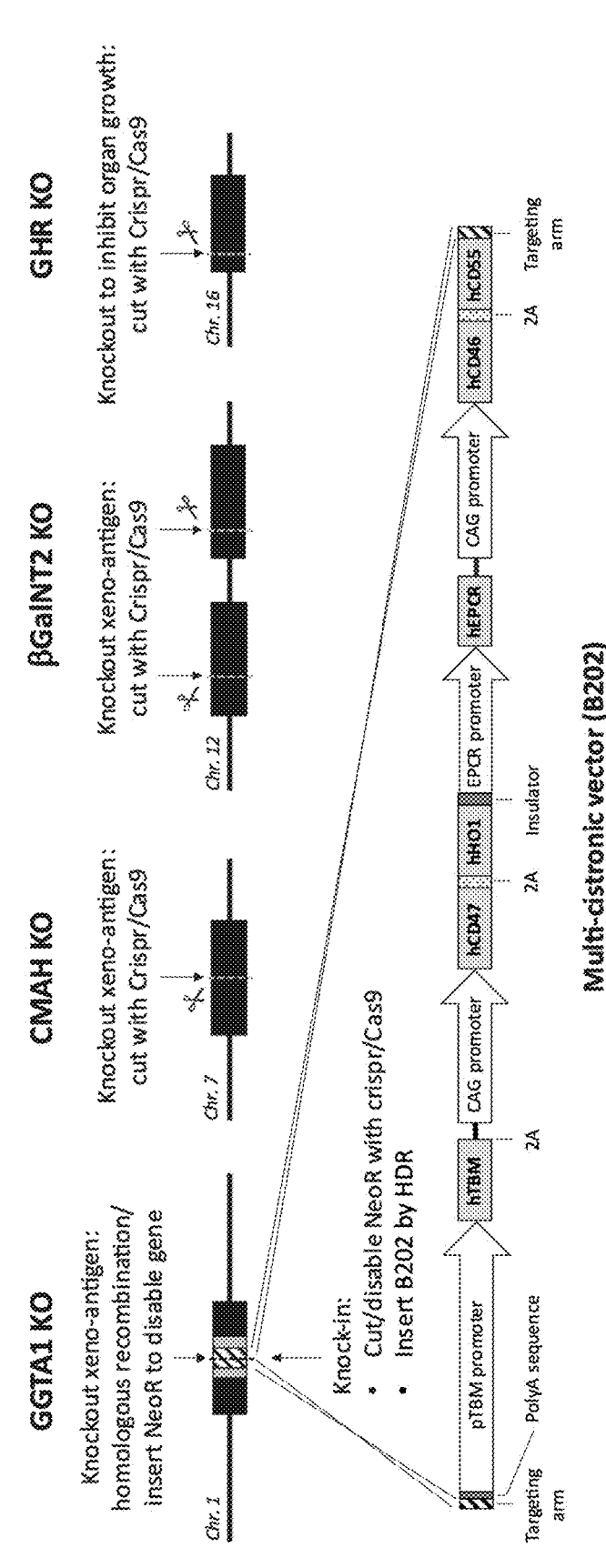

B202 vector (SEQ ID NO: 13) is a MCV comprised of two bi-cistron units (CAGpr [hCD47-2A-hHO1] and CAGpr [hCD46-2A-hDAF], and two mono-cistronic units named 1) PolyA/pTBMpr [hTBM] and 2) pEPCRpr [hEPCR]. The vector is flanked by targeting arms for HDR at GGTA1/Neo (FIG. 1A; FIG. 2C). In this next iteration of the B200 vector, a porcine EPCR promoter was cloned into a vector that contains the hEPCR/CAGpr [hCD46-P2A-hDAF] construct. As used herein, DAF means CD55. Subsequently, the fragment containing porcine EPCRpr [hEPCR]; CAGpr [hCD46-2A-hDAF] was inserted into the SwaI restriction site of a vector containing PolyA/pTBM-pr.hTBM and CAGpr [hCD47-2A-hHO1] with GGTA1/Neo HDR targeting arms. As used herein, pTBMpr means porcine/pig Thrombomodulin promoter. The B202 vector (SEQ ID NO: 13) therefore contains two human transgenes (hTBM and hEPCR) regulated by their corresponding porcine promoter sequences, which allowed for their independent expression in response to specific stimuli. This unique design permitted the use of two different endothelial specific promoters in one fragment and the expression of human transgenes driven by their corresponding porcine promoters.

Figure 2D:
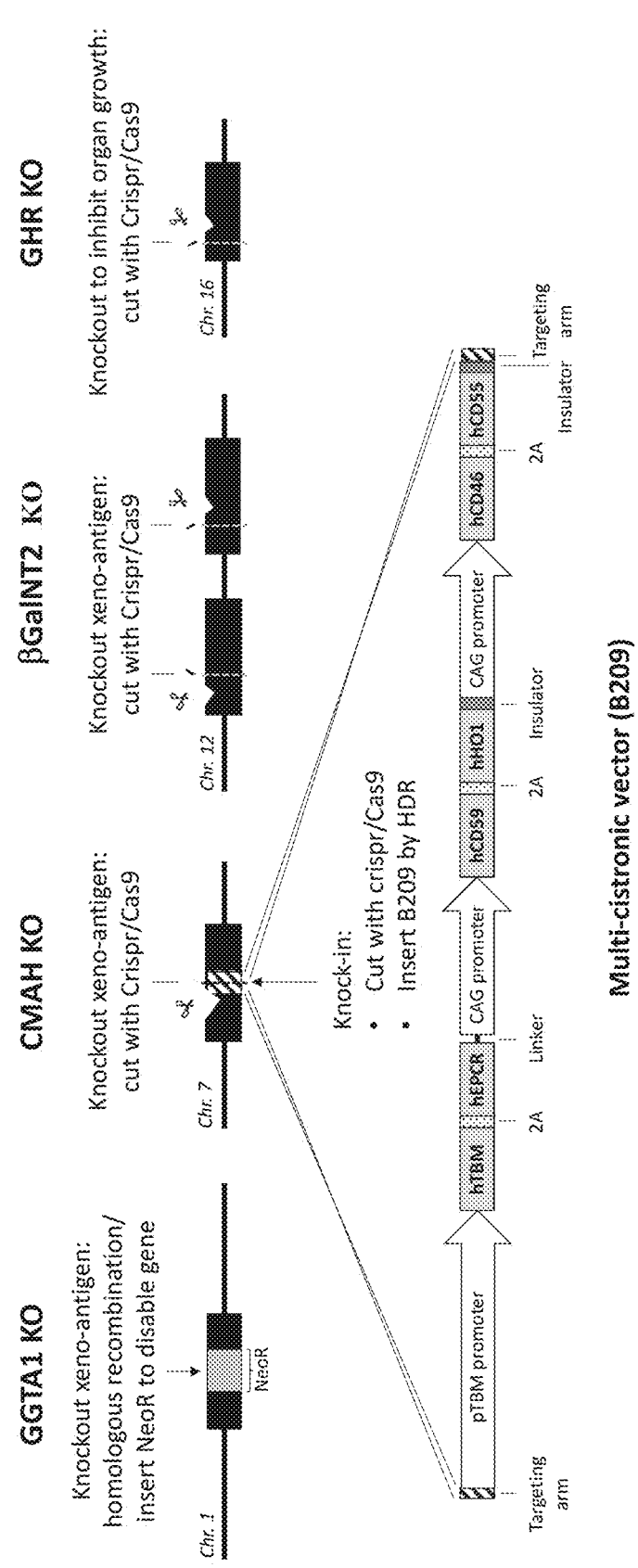

B209 vector (SEQ ID NO: 14) is a MCV comprising three bi-cistron units and named pTBMpr [hTBM-2A-hEPCR]; CAGpr [hCD59-2A-hHO1]; CAGpr [hCD46-2A-hDAF], flanked by targeting arms for HDR at CMAH (FIG. 1A; FIG. 2D). To accommodate an additional complement inhibitor in the multitransgenic vector, hCD47 was replaced with hCD59 in the B200 vector. This unique design allowed for the simultaneously inactivation of the CMAH gene locus and for the expression of the transgenes from permissive locus. B209 has three complement inhibitors whereas other vectors have only two. Additional sequences are shown in Table 2.

Figure 2E:
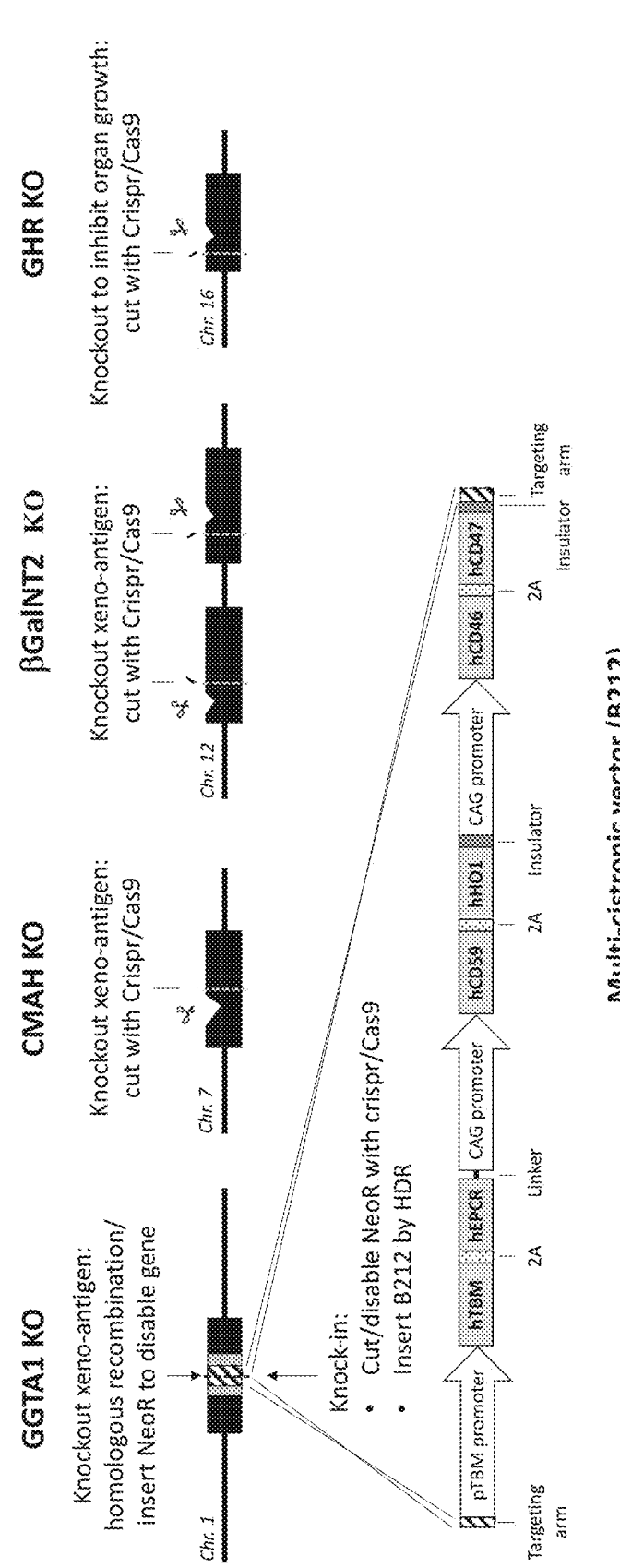

B212 vector (SEQ ID NO: 7) is a MCV comprising three bi-cistron units and named pTBM(short)pr [hTBM-2A-hEPCR]; CAGpr [hCD59-2A-hHO1]; CAGpr [hCD46-2A-hCD47], flanked by targeting arms for GGTA1/Neo (FIG. 1B; FIG. 2E). B212 contains two complement inhibitors (CD459 and CD46) and CD47 was placed in the third bi-cistron, in second position to CD46. Expression of the hTBM-2A-hEPCR bi-cistron is driven a short version of the pTBM promoter (4266 bp, cloned as described above for Step 1 of B200). As shown in FIG. 2E, The hTBM-2A-hEPCR bi-cistron is driven by a shorter (4157 bp) version of the pTBM promoter, rather than the longer version (7954 bp) used in the other vectors. Expression levels of hTBM and hEPCR expression have been shown to be similar between the short and long versions of the pTBM promoter. In addition, the short pTBM promoter driving hTBM-2A-hEPCR has been shown to support long term (>6 mo) xenograft survival in baboons. The hCD47 transgene was moved to second position in the third bi-cistron to moderate its expression.

Figure 2F:
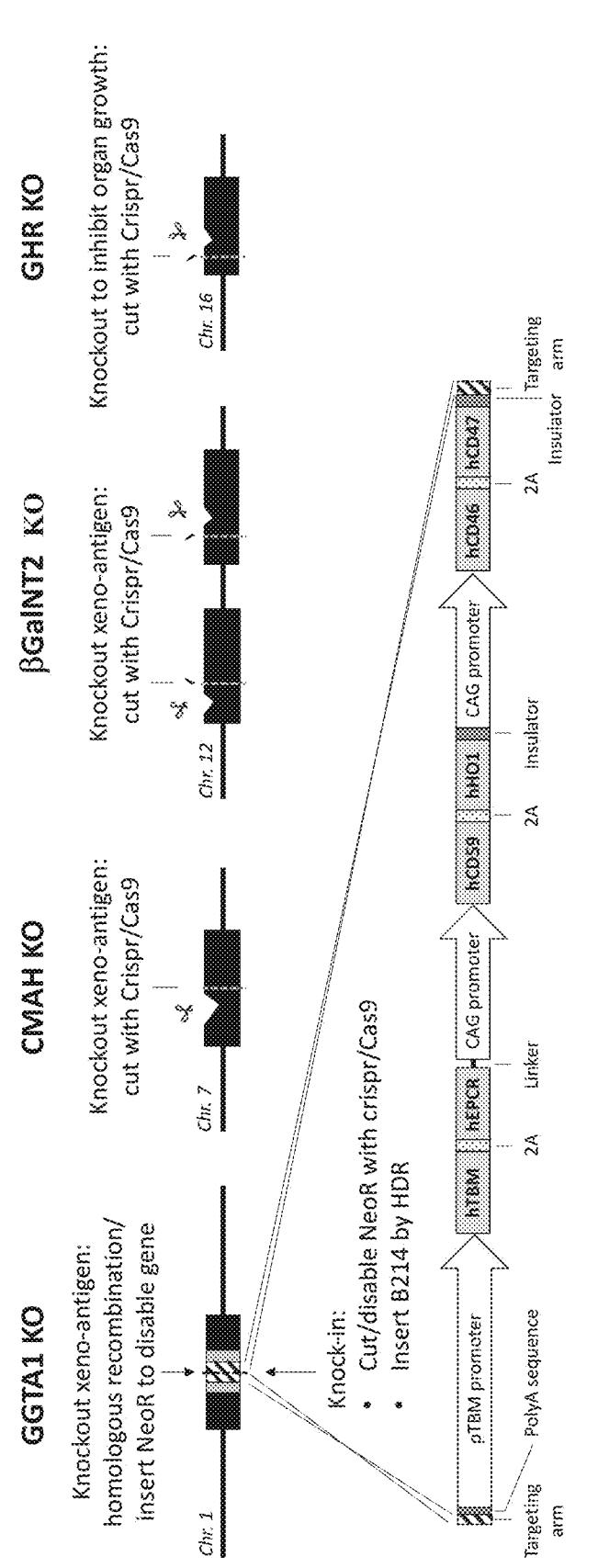

B214 vector (SEQ ID NO: 8) is a MCV comprising three bi-cistron units and named PolyA/pTBMpr [hTBM-2A-hEPCR]; CAGpr [hCD59-2A-hHO1]; CAGpr [hCD46-2A-hDAF], flanked by targeting arms for GGTA1/Neo (FIG. 1B; FIG. 2F). Unlike the other vectors described here, B212 lacks CD47. In addition, B214 has a PolyA sequence at the extreme 5' end, to block interference of the promoters in the vector from the upstream, endogenous GGTA1 promoter as described in more for B201. As shown in FIG. 2F, B214 is composed of the same three bi-cistrons as in B209 ([hTBM-2A-hEPCR]/CAGpr [hCD59-2A-hHO1]/CAGpr [hCD46-2A-hCD55] and flanked by targeting arms for HDR at the GGTA1/Neo locus instead of the CMAH locus. In addition, B214 has a the 5' Poly A sequence (as in B201) to minimize influence on expression from the upstream GGTA1 promoter.

Figure 2G:
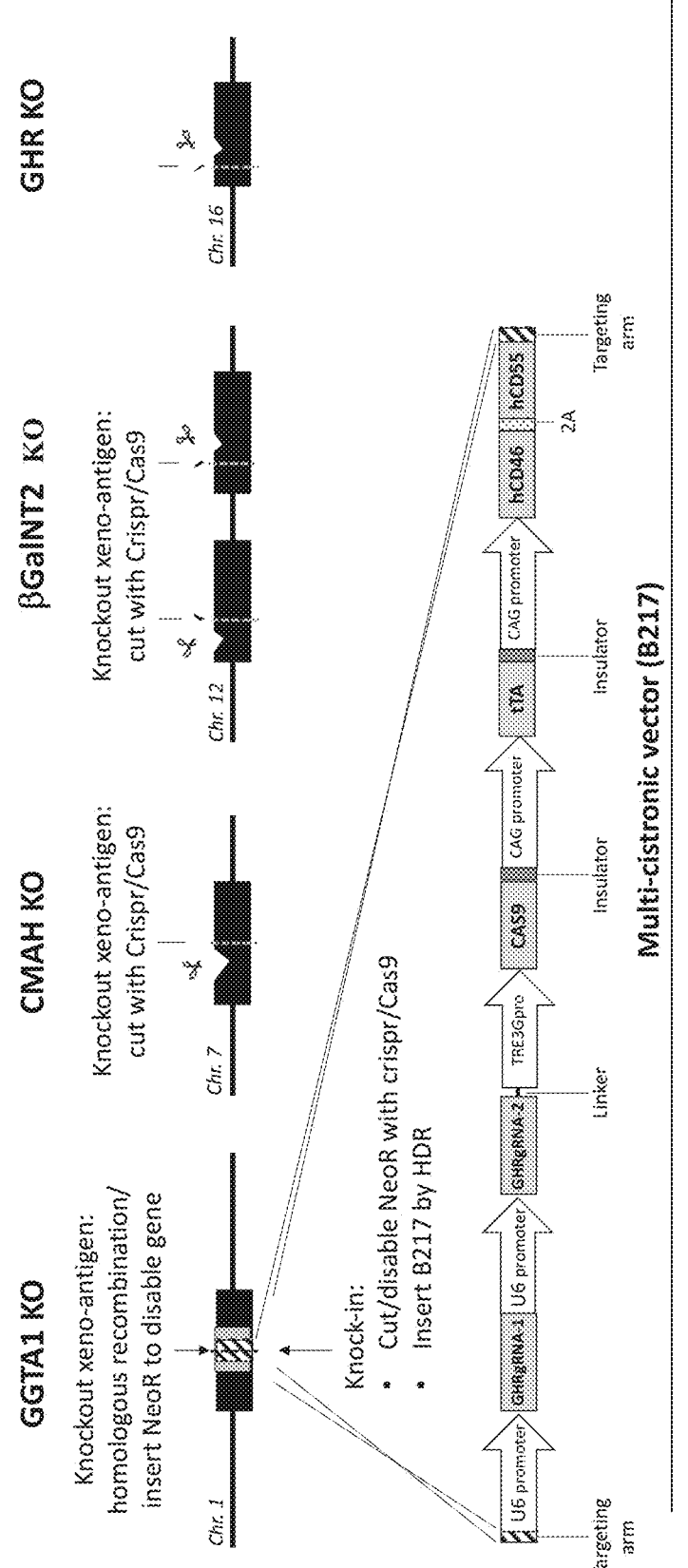
Figure 2H:
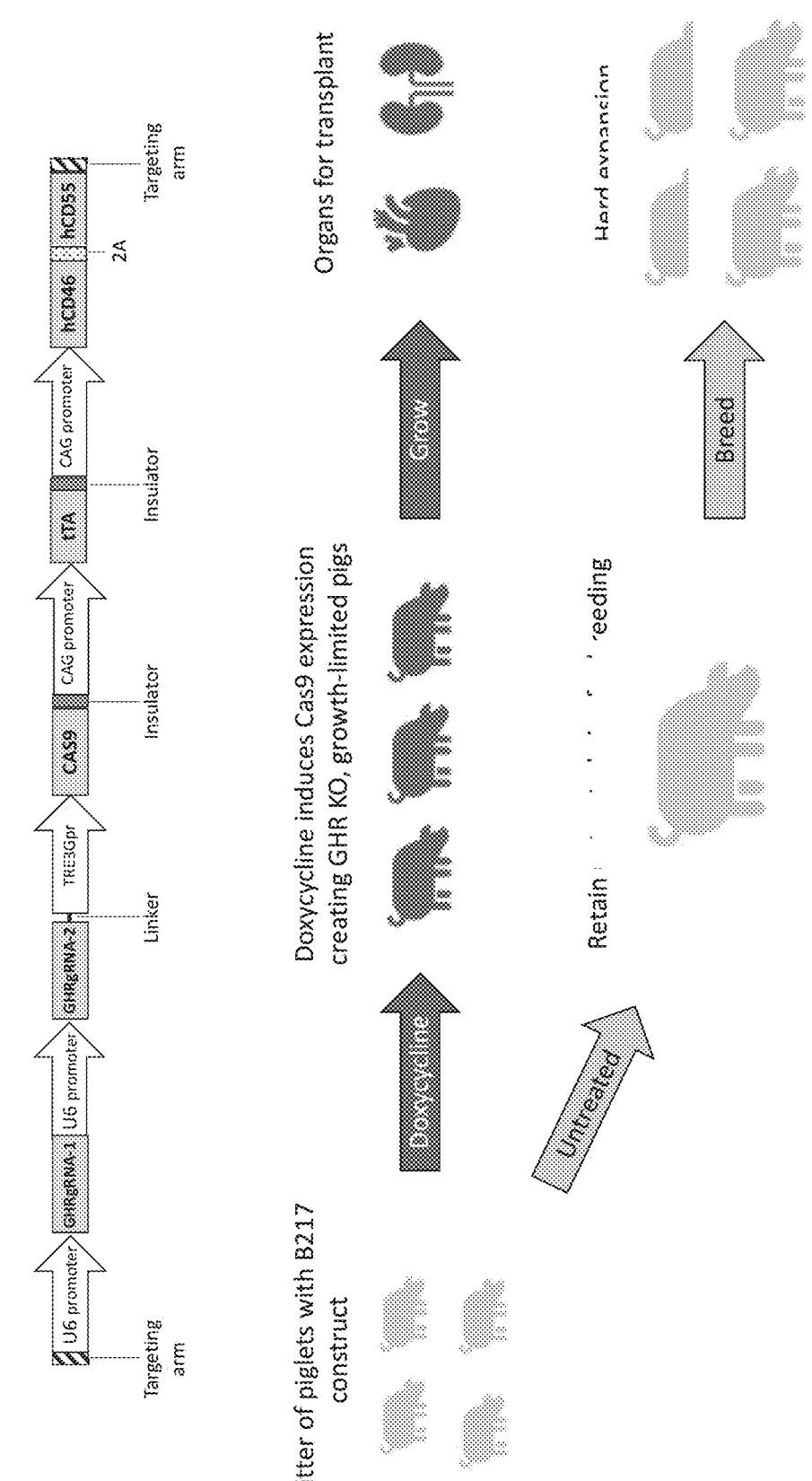

B217 vector (SEQ ID NO: 9) is a MCV comprising of five expression units (U6promoter[GHRgRNA-1]/U6promoter [GHRgRNA-2]/, TRE3G[CAS9]/CAGpr [tTA]/CAGpr [hCD46-2A-hCD55]), flanked by targeting arms for HDR at GGTA1/Neo locus. The B217 vector was designed to induce conditional knockout of the porcine GHR gene. GHRKO pigs grow and mature slowly. B217 was created to permit conditional GHRKO after pigs have grown to the desired size at the normal growth rate. To accomplish this, B217 contains two constitutively expressed sgRNAs targeted to the porcine GHR gene, a constitutively expressed tetracycline Transactivator (tTA) and a Tetracycline/Doxycycline inducible CAS9. B217 also has a CAG-hCD46-2A-hDAF bi-cistron to facilitate FACS of B217 transfected cells and for complement inhibition. Finally, B217 is flanked by targeting arms for HDR at GGTA1/Neo (FIG. 1B; FIG. 2G).

As shown in FIG. 2G, B217 is designed to generate a conditional knockout of the porcine GHR using an inducible Tet-On system. To accomplish this, two GHR-specific sgR-NAs, are constitutively expressed by U6 promoters. A CAG promoter is used to drive constitutive expression of the tetracycline controlled Transactivator (tTA). CAS9 expression is driven by a doxycycline-inducible tet-response element (3$^{rd}$ generation; TRE3G). In addition, B17 includes a CAG-driven hCD46-2A-hDAF bi-cistron (CAGpr [hCD46-2A-hCD55]) and is flanked by targeting arms for HDR at GGTA1/Neo locus. The B217 vector can be used to express complement inhibitors and inducible GHR knockout system from a single locus.

The B217 vector offers a novel approach to making GHRKO pigs and importantly, to overcoming some of the limitations of the GHRKO phenotype. GHRKO pigs are currently made by creating deletion mutants in fibroblasts prior to SCNT. The resulting pigs are born with GHRKO and as a result grow and mature very slowly, which increases the time required to reach a size appropriate for organ donation and sexual maturity for breeding. The B217 vector offers a novel way to overcome these limitations by allowing for the generation of pigs with wild type GHR at birth. The pigs can then be allowed to grow to organ donor size, then treated with tetracycline/doxycycline to activate CAS9 expression to induce GHRKO knockout.

Figure 10:
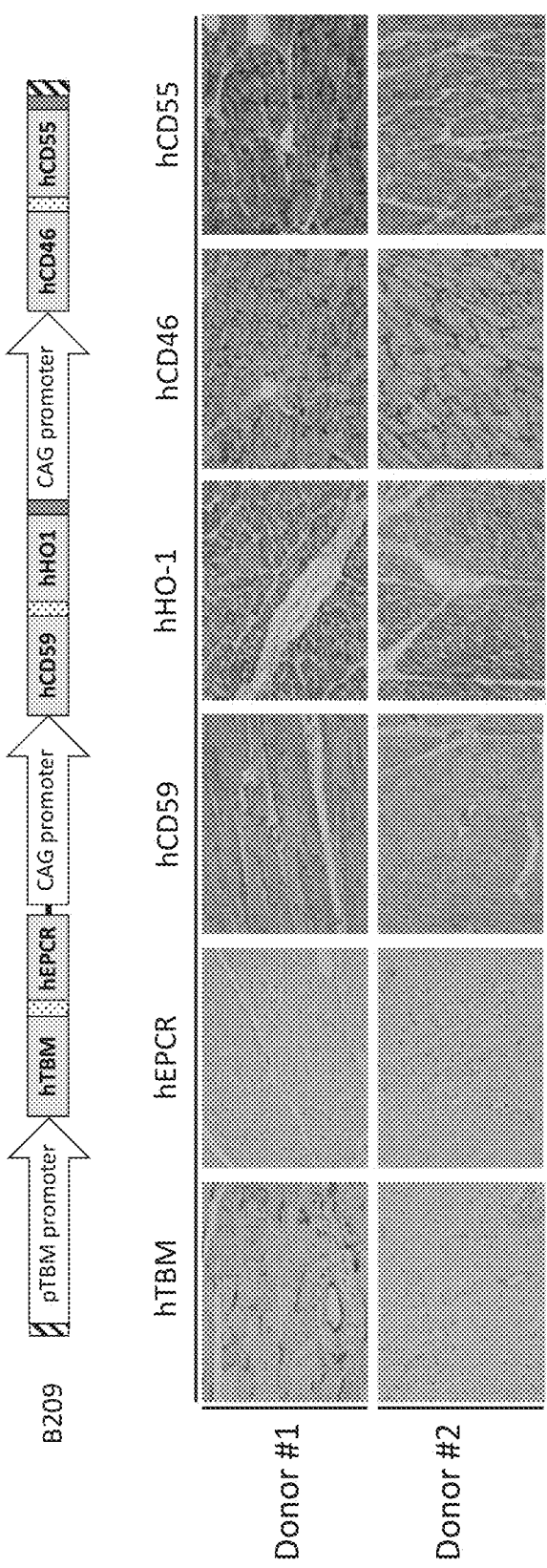
FIG. 10 shows representative images of immunohistochemical stainings of two porcine heart samples (Donors #1 and #2) expressing the B209 transgene in porcine hearts transplanted into brain dead human recipients and demonstrates the expression of all six human transgenes encoded by the B209 vector. The two porcine heart samples (Donors #1 and #2) were obtained and stained immediately postmortem.

As shown in FIG. 211, organs from transgenic pigs expressing the B217 vector will have the GHRKO which will achieve the aim of limiting organ growth after transplant. Breeding pigs will be left untreated by tetracycline/doxycycline to grow and mature as GHR wild type pigs and will transmit the B217 vector to their offspring, which can be used as GHRKO organ donors or GHR wild type breeding pigs. The B217 vector provides the opportunity to have transgenic pigs with intact GHR(+/+) for breeding and GHR(−/−) edited pigs for transplant. Slow growth and reproductive health related issues of transgenic pigs carrying GHR knockout have been characterized in the literature (Hinrichs et al., Mol Metab. 2018 (11) 113-128). The use of B217 will give rise to transgenic pigs with in which GHR can be knocked out on a conditional basis to accelerate the production of pigs for both herd expansion and organ donation (FIG. 10).

GHRKO will be induced by feeding Tetracycline/Doxycycline to upregulate TRE3G promoter to express CAS9 to complex with the GHR sgRNAs to create GHRKO. The sgRNAs are the same as we have used to successfully knockout GHR in porcine fibroblasts. B217 will be added to pigs with other vectors, such as those described above, to make pigs conditional GHRKO pigs for organ transplant. Alternatively, these pigs can be raised to maturity with GHR left as wild type and used for breeding and herd expansion.

Plasmid purification. The six-gene vectors of the present disclosure are very large plasmids (each having at least about 30 Kb). The size of the six-gene vector presented challenges for bacterial transformation, plasmid amplification and purification. Since the vector expressing the transgenes were standard vectors (i.e not BAC or YAC), this size of the plasmid necessitated several unique changes to the standard plasmid purification protocols to achieve high quality DNA (OD 260/OD280: 1.8-2.0) with a yield of 0.5-1 mg at a concentration of 1.0-2.0 mg/ml. It was impossible to prepare the DNA fragment for transfections without these changes. As such the present inventors devised new protocols that were not routine to culture and purified the six-gene vectors of the present disclosure. The new and improved for purification standard plasmids having at least 30 Kb comprised the following steps.

Step 1. Plasmid construction was performed in the electrocompetent Stbl4 E. coli (Thermofisher Scientific) to improve the transformation efficiency of large plasmids using standard procedure. From here on, a new non-standard protocol to achieve high concentrations of DNA for transfections was developed. Miniprep cultures composed of single colonies were grown overnight. Per the standard protocol, cultured colonies were inoculated in liquid cultures in larger scale (200-500 ml). However, this standard protocol consistently failed to amplify the large plasmids. Accordingly, a novel alternative approach was therefore developed. In this approach, plasmid DNA of a single miniprep colony was instead re-transformed into E. coli, from which 12 positive colonies were used to inoculate a 4 ml starter culture for 6 hours.

Step 2. Two ml of the starter culture were used to inoculate a 2-liter culture for 16 hrs. Carbenicillin, a more stable ampicillin analog, was used for selection in the overnight culture, to minimize the instability of large plasmids in liquid culture medium that frequently occurs under standard culture conditions.

Step 3. Bacteria were harvested and the weight of the bacterial pellet was determined. Prior experience indicated that a pellet weight of 8 grams was required for good plasmid yield in the subsequent steps.

Step 4. Alkaline lysis was performed as described in standard protocols (Qiagen Plasmid Purification Handbook February 2021, Mega Kit) with 50 ml P1, P2 and P3 solutions, with the modification: after lysis, separation of the debris by centrifugation and filtration, the lysate was precipitated with 0.7 volumes of isopropanol and the pellet resuspended in TE. The DNA solution was then passed through a QIAGEN-tip 500 column (Qiagen protocol for very low-copy plasmid purification). Quality control for each purified plasmid was performed by restriction enzyme digestion pattern analysis and next-generation sequencing.

Fragment isolation. To isolate the linear fragment containing the six human transgenes flanked by targeting arms, approximately 200 mg of purified plasmid DNA was digested with 900 units of each of the restriction endonucleases PacI and AsiSI (New England Biolabs) in a total volume of 1.9 ml for 5 hrs. After precipitation and resuspension in 300 ul TE, the digested plasmid was loaded in 8 wells of a 1% Low Melting Temperature agarose gel (gel dimensions: 11'W×14'L×0.8'H) and was separated by electrophoresis at 35 Volts for 18-20 hrs. The at least about 26 Kb linear fragment was subsequently excised from the gel and the DNA was purified from agarose using beta-Agarase (New England Biolabs). This method typically yielded 35-70 mg of linear fragment at a concentration of 0.5-1.0 mg/ul. The integrity of the purified fragment was confirmed by restriction pattern analysis, size determination in agarose electrophoresis, and next-generation sequencing. Fragments that passed all quality control standards were used for subsequent transfection experiments.

Example 2: Generation of Genetically Modified Fibroblasts

General methods. All modifications were introduced into GGTA1 KO porcine fetal fibroblasts, derived from a line of animals (e. g. pigs) in which GGTA1 was knocked out by insertional mutagenesis with NeoR. See Dai et al., *Nat Biotechnol.* 2002; 20:251-5 (2002). Transfections were performed by electroporation using the Lonza 2B or 4D system. DNA vector fragments were co-transfected with crispr/Cas9 ribonucleoprotein particles (RNP) designed to cut genomic DNA at the intended vector integration site to facilitate homology-directed repair (HDR). Other RNP designed to generate indels for knockout of genes encoding non-Gal xenoantigens (CMAH and B4GalNT2) were frequently co-transfected with the vector fragments as described below. In the case of CMAH, RNP were used to facilitate HDR on one allele and generate a knockout indel on the other allele. Crispr/Cas9 RNP were also used to knockout the Growth Hormone receptor gene (GHr). In some cases, to minimize cell stress and death due to large quantities of transfected DNA and RNP, reagents were introduced in two separate transfections spaced 3-4 days apart to permit cell recovery. After culturing for an additional 3-4 days to permit transgene expression from the vector, cells were enriched for fragment uptake by staining with antibodies against hCD46. Cells positive for hCD46 staining were collected using a BD FACSAria cell sorter, seeded into 10 cm plates at limiting dilution, and cultured for 10-14 days. Colonies composed of single cell clones (SCC) were then selected for expansion and DNA analysis. Colonies confirmed to be of the intended design were used to make pigs by somatic cell nuclear transfer (SCNT).

Transfection of the B200 vector. Fetal fibroblasts were transfected with GHr01 and B4Gal RNP, using the Lonza 2B system, to knockout GHR and β4GalNT2 genes. After three days, cells were transfected again, this time with the B200 vector fragment and CMAH RNP (FIG. 2A). After another three days, cells were stained with hCD46 antibodies and the positive cells collected by FACS, subjected to SCC, screened to confirm the intended modifications, and used for SCNT (Table 3). A total of 67 pigs were born, of which 17 were alive and had the correct, intended genotype (Table 4).

TABLE 3

| Generation of SCC with B200 | | | |
| --- | --- | --- | --- |
| | Colonies | | |
| Cell line | No. SCC | No. genotyped | No. used for NT |
| A5882-11 | 67 | 18 | 4 |
| A4991-13 | 56 | 4 | 1 |
| Total | 123 | 22 | 5 |

TABLE 4

| Generation of pigs with B200 | | | | | |
| --- | --- | --- | --- | --- | --- |
| | | # Recipients | | Born | |
| | # Embryos | ET | Farrowed | Total | Alive |
| Founder* | 5312 | 28 | 11 | 43 | 13 |
| Redone* | 2428 | 13 | 5 | 24 | 4 |
| Total | 7740 | 41 | 16 | 67 | 17 |

Founder* refers to first generation pigs cloned directly from B200 modified fibroblasts; and Reclone* refer to pigs cloned from first generation B200 pigs Transfection of the B201 vector to generate the 8 gene pigs. To generate pigs with eight modifications, including GGTA1KO, β4GalNT2KO and the six transgenes of B201, fetal fibroblasts were transfected with the B201 fragment and RNP to knockout the β4GalNT2 genes, using the Lonza 2B system. After three days, cells were stained with hCD46 antibodies, enriched by FACS, subjected to SCC, screened to confirm the intended modifications, and used for SCNT.

Transfection of the B201 vector to generate the 9 gene pigs. To generate pigs with nine modifications, including GGTA1KO, β4GalNT2KO GHRKO (but lacking CMAHKO), plus the six transgenes of B201, fetal fibroblasts were transfected with the B201 fragment and growth hormone (GHR) and β4GalNT2 RNP, using the Lonza 4d system, to knockout GHR and β4GalNT2 genes. After four days, cells were stained with hCD46 antibodies and enriched by FACS, subjected to SCC, screened to confirm the intended modifications, and used for SCNT.

Transfection of the B201 vector to generate the 10 gene pigs. Fetal fibroblasts were transfected with B201 fragment and GHR and β4GalNT2 RNP, using the Lonza 4d system, to knockout GHR and β4GalNT2 genes. After three-days, cells were transfected with CMAH RNP (FIG. 2B) using the Lonza 2b system. Three days later, cells were stained with hCD46 antibodies and enriched by FACS, subjected to SCC, screened to confirm the intended modifications, and used for SCNT.

Transfection results for 8-, 9- and 10 gene modifications with B201 are shown in Table 5. A total of 76 pigs were born with 8, 9, and 10 gene modifications, of which 15 were alive and had the correct, intended genotype (Table 6).

TABLE 5

Generation of SCC with B201. Data includes SCC with 8, 9, and 10 gene modifications.

| Cell line | Colonies | | |
|---|---|---|---|
| | No. SCC | No. genotyped | No. used for NT |
| A5882-11 | 48 | 16 | 5 |
| A4991-13 | 28 | 2 | 1 |
| A366-2 | 28 | 4 | 1 |
| Total | 104 | 22 | 7 |

TABLE 6

Generation of pigs with B201

| | | #Recipients | | Born | |
|---|---|---|---|---|---|
| | # Embryos | ET | Farrow | Total | Alive |
| Founder | 5951 | 32 | 14 | 76 | 15 |

Transfection of the B202 vector. Fetal fibroblasts were transfected with the B202 fragment as well as GHR, β4GalNT2, and CMAH RNP, using the Lonza 2B system, to knockout the genes for GHR, β4GalNT2, and CMAH (FIG. 2C). Four days after transfection, cells were stained with antibodies against CD46 and enriched by FACS, subjected to SCC, screened to confirm the intended modifications, and used for SCNT (Table 7). A total of 17 pigs were born, of which 1 was alive and had the correct, intended genotype (Table 8).

TABLE 7

Generation of SCC with B202

| Cell line | Colonies | | |
|---|---|---|---|
| | No. SCC | No. genotyped | No. used for NT |
| A5882-11 | 18 | 6 | 3 |
| A80-4:6 | 185 | 28 | 3 |
| E421:4 | 60 | 15 | 1 |
| Total | 263 | 49 | 7 |

TABLE 8

Generation of pigs with B202

| | | #Recipients | | Born | |
|---|---|---|---|---|---|
| | # Embryos | ET | Farrow | Total | Alive |
| Founder | 7343 | 41 | 8 | 17 | 1 |

Transfection of the B209 vector. Fetal fibroblasts were transfected with the B209 fragment as well as CMAH and β4GalNT2 RNP, using the Lonza 2B system, to facilitate HDR of B209 into CMAH, and to knockout the CMAH and β4GalNT2 genes. Three days later, cells were stained with hCD46 antibodies and enriched by FACS, subjected to SCC, screened to confirm the intended modifications. Colonies were screened and those with the intended design were transfected with GHR RNP, using the Lonza 2B system, to knockout GHR genes (FIG. 2D). Cells from this transfection were not screened for GHRKO but used directly for SCNT (Table 9). A total of 23 pigs were born, of which 10 were alive and had the correct, intended genotype (Table 10).

TABLE 9

Generation of SCC with B209

| Cell line | Colonies | | |
|---|---|---|---|
| | No. SCC | No. genotyped | No. used for NT |
| A5882-11 | 18 | 6 | 3 |
| A80-4:6 | 185 | 28 | 3 |
| E421:4 | 60 | 15 | 1 |
| Total | 263 | 49 | 7 |

TABLE 10

Generation of pigs with B209

| | | #Recipients | | Born | |
|---|---|---|---|---|---|
| | # Embryos | ET | Farrow | Total | Alive |
| Founder | 3510 | 19 | 5 | 23 | 10 |

Transfection of the B212 vector to generate the 9 gene pigs. B212 was targeted to the Neo sequence within the GGTA1 locus in Revivicor's GGTA1 knockout pigs. Triple knockout fibroblasts (TKO; GGTA1KO, CMAHKO, βGalNT2KO) were transfected with the B212 fragment using the Lonza 2B system. After three days, cells were stained with hCD46 antibodies and enriched by FACS, subjected to SCC, screened to confirm the intended modifications, and used for SCNT.

Transfection of the B212 vector to generate the 10 gene pigs. Quadruple knockout (QKO; GGTA1KO, CMAHKO, βGalNT2KO, GHRKO) fibroblasts were transfected with the B212 fragment using the Lonza 2B system. After three days, cells were stained with hCD46 antibodies and enriched by FACS, subjected to SCC, screened to confirm the intended modifications, and used for SCNT. Transfection results for 9 and 10 gene modifications with B212 are shown in Table 11. A total of 39 pigs were born with 9, and 10 gene modifications, of which 15 were alive and had the correct, intended genotype (Table 12). A total of 39 pigs were born, of which 16 were alive and had the correct, intended genotype.

TABLE 11

Generation of SCC with B212. Data includes SCC with 9 and 10 gene modifications.

| Cell line | Colonies | | |
|---|---|---|---|
| | No. SCC | No. genotyped | No. used for NT |
| A366-2 | 46 | 13 | 6 |
| 63D:5 | 21 | 8 | 4 |
| Total | 67 | 21 | 10 |

TABLE 12

| | | #Recipients | | Born | |
|---|---|---|---|---|---|
| | # Embryos | ET | Farrow | Total | Alive |
| Founder | 2650 | 14 | 7 | 39 | 16 |

Example 3: Screening Cell Colonies for Genotype

Characterization of single cell clonal colonies was accomplished by PCR for targeting and transgene analysis, digital drop PCR for estimating vector copy number and genomic sequencing analysis for indel analysis for gene knockouts. Single cell clonal colonies of about 2000 cells were expanded in 96 well plates. DNA for targeting, transgene and digital drop PCRs, as well as for NextGen (MiSeq) sequencing analysis, was obtained by adding 5 μl lysing solution to each well/sample. The plate is cycled at 65° C. for 10 minutes, and at 95° C. for 10 minutes. 1 μl of lysate was removed for each of the targeting PCRs, digital PCRs, and sequencing assays.

Targeting (5' and 3') PCRs amplify sequence that spans the HDR vector targeting sites at each specified or targeted locus. The targeting PCR assay design utilizes one PCR primer homologous to genomic sequence outside of the targeting vector, in the flanking genomic sequence, and the other PCR primer homologous to sequence in the targeting vector. Assays of this design identify targeted colonies when visualized on an agarose gel after electrophoresis. Correctly targeted colonies were then analyzed by digital drop PCR to estimate copy number of each individual transgene in the vector. Targeted colonies with intended transgene copy numbers were then subjected to MiSeq analysis as appropriate to identify indels and confirm the specified knockout (KO) edits.

Example 4: Generation of a Multitransgenic Animal Comprising at Least 6 Transgenes Somatic cell nuclear transfer. Live pigs were generated from genetically modified fibroblasts by SCNT, according to the methods described in detail by Giraldo et al. Methods Mol Biol. 885:105-23 (2012).

Screening piglets for genotype. Genotypic characterization of transgenic animals was performed by targeting and transgene PCR analysis, digital copy number PCR analysis, and genomic sequencing analysis as described for above for cell colonies, using DNA extracted from tail pig biopsies. In addition, Southern Blots were done to confirm targeting of the intact vector and the absence of random integrations. Collectively these methods identify and confirm that the targeting vector integrated at the targeted allele(s), that the vector is intact and that the construct has not otherwise integrated randomly into the genome.

Figures 3A, 3B, 3C:
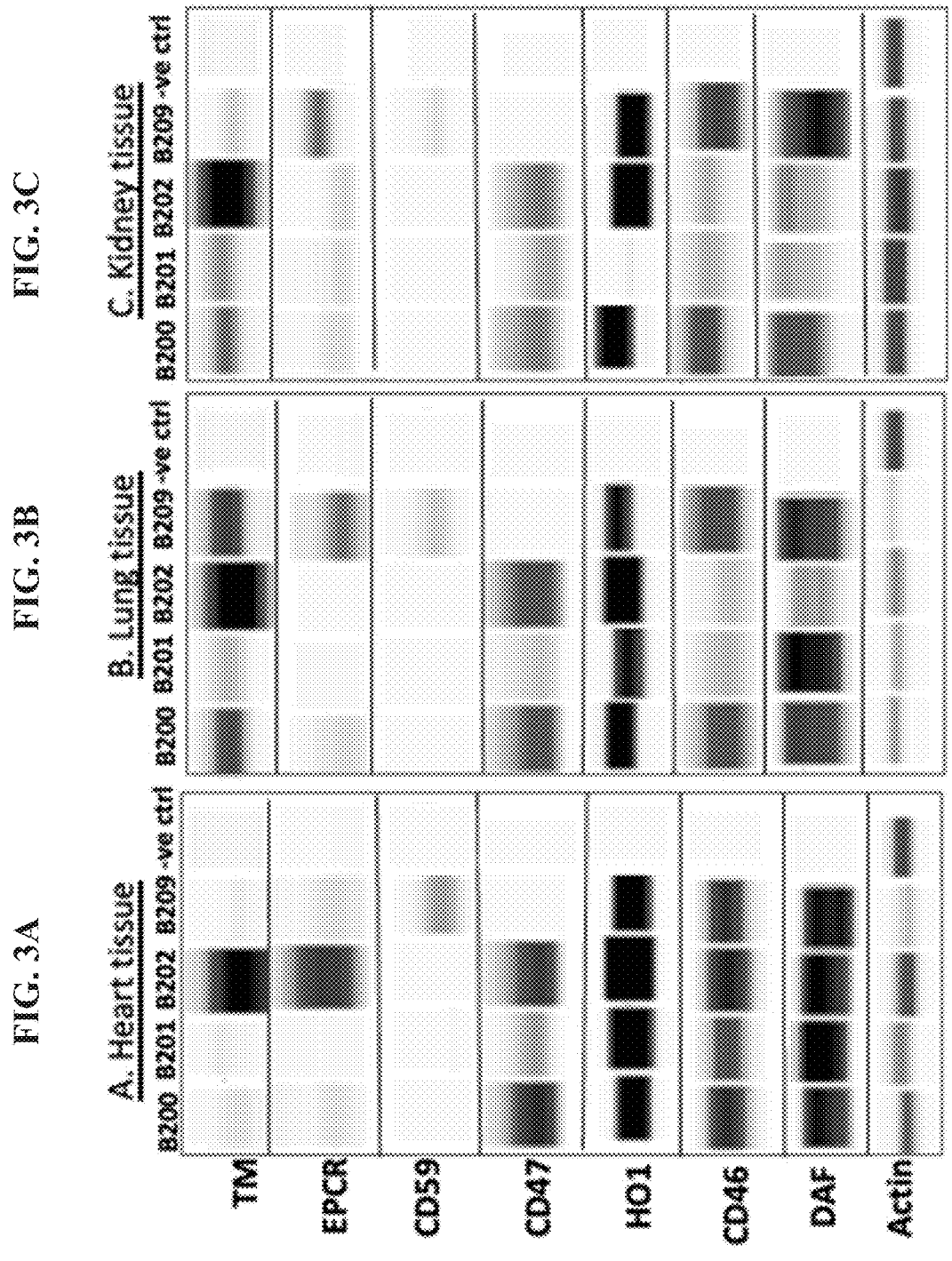
FIGS. 3A-C show a western blot analysis of tissue from a transgenic animal expressing a vector of the present invention demonstrating the protein expression of transgenes encoded by the B200, B201, B202, and B209 in heart (FIG. 3A), lung FIG. 3B) and kidney (FIG. 3C). Transgenic proteins from transgenic tissue samples had expected molecular weight by western blot.

Expression of human transgenes in porcine tissues. Expression of all human transgenes from each vector was confirmed in heart, lung, and kidney samples by western blot (FIGS. 3A-C), and immunohistochemical staining (FIGS. 7A-7E, 8A-8B, 9, and 10). Each of FIGS. 7A-7E, 8A-8B, 9, and 10 shows tissue sections stained for transgene expression by immunohistochemistry. Fresh tissue samples were fixed in paraformaldehyde, embedded in paraffin blocks, cut on a microtome, and affixed to glass slides. Sections were probed with primary antibodies human-specific to each protein expressed by the transgenes, then with appropriate second antibodies conjugated to horseradish peroxidase. Antibody-bound proteins were visualized with diaminobenzidine tetrahydrochloride (DAB) as indicated by the brown staining. Positive controls (tissues with previously verified transgene expression) and negative controls (processed without primary antibody) were included in each staining run, but these were not included in the figures.

Figure 4:
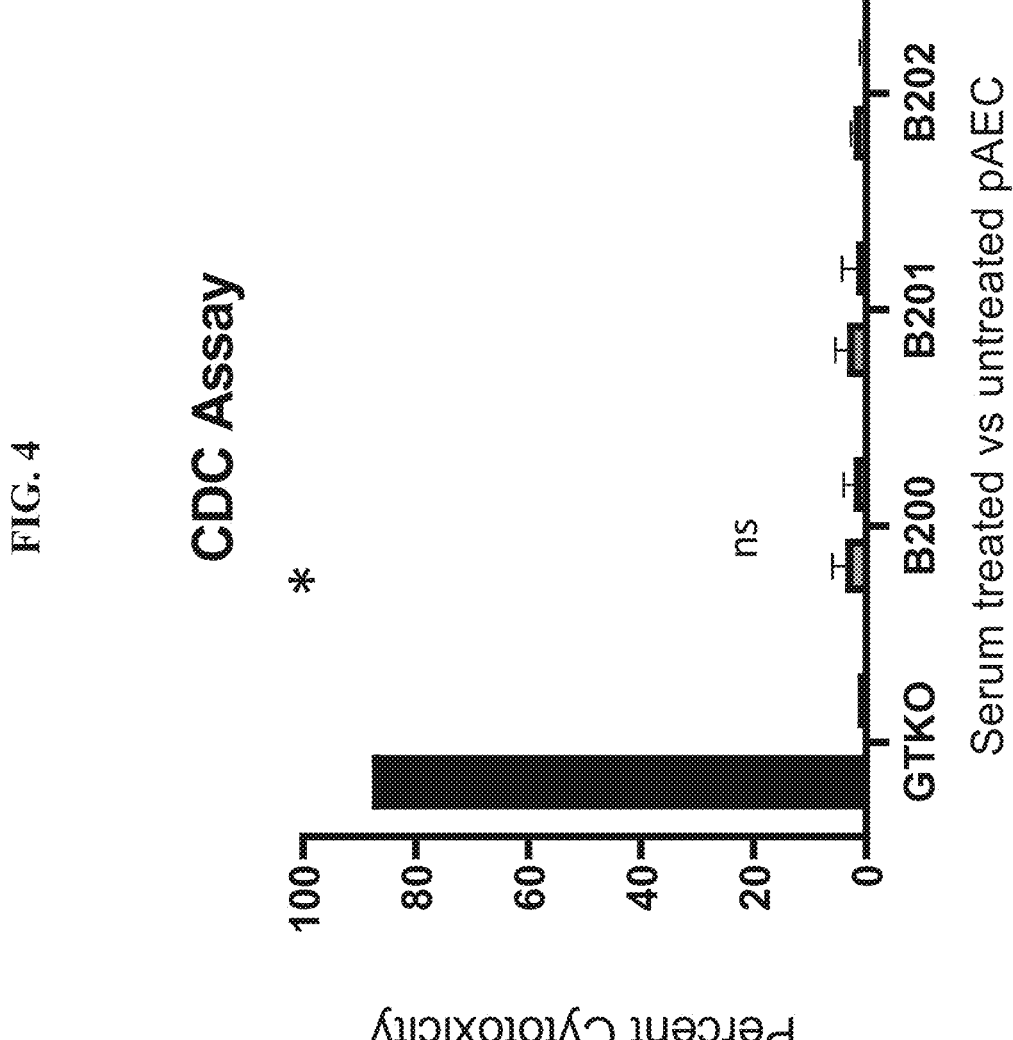
FIG. 4 shows a bar graph illustrating the results of a Complement-Dependent Cytotoxicity (CDC) assay performed on transgenic porcine aortic endothelial cells (pAEC) expressing the B200 vector (n=3), the B201 vector (n=4), and the B202 (n=4). Significantly more serum treated GTKO pAEC were lysed (87%) when compared to pAEC expressing the B200, the B201, and the B202 vector (3.7%, 3.4%, 2.2% respectively) (P<0.01), demonstrating the functionality of hCD46 and hDAF complement inhibitor transgenes. The quantification of the CDC assay is shown in Table 1. Bars indicate percent of lysed cells 60 minutes after the addition of a complement. Left bars are serum treated wells and right bars are untreated wells. GTKO pAEC (GGTA1 knockout (KO) only; lacking expression of human complement inhibitors; n=1) served as a control. Three replicate wells were run per treatment. Data were analyzed using GraphPad Prism software.

Example 5: Functional Analyses of Human Proteins Expressed in Porcine Tissues hCD46 hDAF function characterization using a Complement-Dependent Cytotoxicity (CDC) assay. Hyperacute rejection (HAR) occurs almost immediately after xenotransplantation of unprotected organs. HAR results from xeno-antibody binding to xenoantigens, followed by binding and activation of complement proteins and cell lysis. Expression of the complement inhibitors hCD46 and hDAF is a potent and effective means of blocking HAR in xenotransplanted organs. Accordingly, to assess the effectiveness of the multicistronic vector system of the present disclosure, a complement-dependent cytotoxicity (CDC) assay was conducted to assess the ability of transgenic hCD46 and hDAF to inhibit the human complement cascade in porcine aortic endothelial cells (pAEC). Human serum (pooled from three donors) was diluted in media and applied to cultured pAEC. After one hour, rabbit complement and Cytotox Red reagent, which emitted a red fluorescence upon entry into complement-lysed cells, was added to the cultures. Cells were imaged and counted using a BioTek Cytation™5 reader. Percent cytotoxicity was read as the number of red cells/total cells counted×100 (FIG. 4). As shown in FIG. 4 and Table 1, expression of transgenic hCD46 and hDAF nearly eliminated complement-induced cytotoxicity in this assay.

TABLE 1

Quantification of the CDC Assay of FIG. 4

| Cell Lines | Serum Treated | Untreated |
|---|---|---|
| GTKO (n = 1) | 87.74[a] | 1.52[b] |
| B200 (n = 3) | 3.73 ± 2.27[b] | 2.22 ± 1.87[b] |
| B201 (n = 4) | 3.44 ± 2.06[b] | 1.79 ± 2.57[b] |
| B202 (n = 4) | 2.24 ± 0.51[b] | .62 ± 0.57[b] | hTBM/hEPCR function characterization using Activated Protein C (APC) assay. Thrombomodulin and EPCR are membrane proteins on the luminal surface of vascular endothelial cells. Under hemostatic conditions, TBM binds circulating thrombin to form a TBM:thrombin complex, which activates Protein C to maintain an anticoagulant state. While porcine TBM can bind human thrombin, the pTBM: human thrombin complex is a poor activator of human protein C. Transgenic expression of hTBM in porcine organs overcomes this incompatibility and prevents post-transplant thrombosis of xenotransplanted organs. Expression of hEPCR further augments protein C activation to maintain an anti-thrombotic state.

Figure 5:
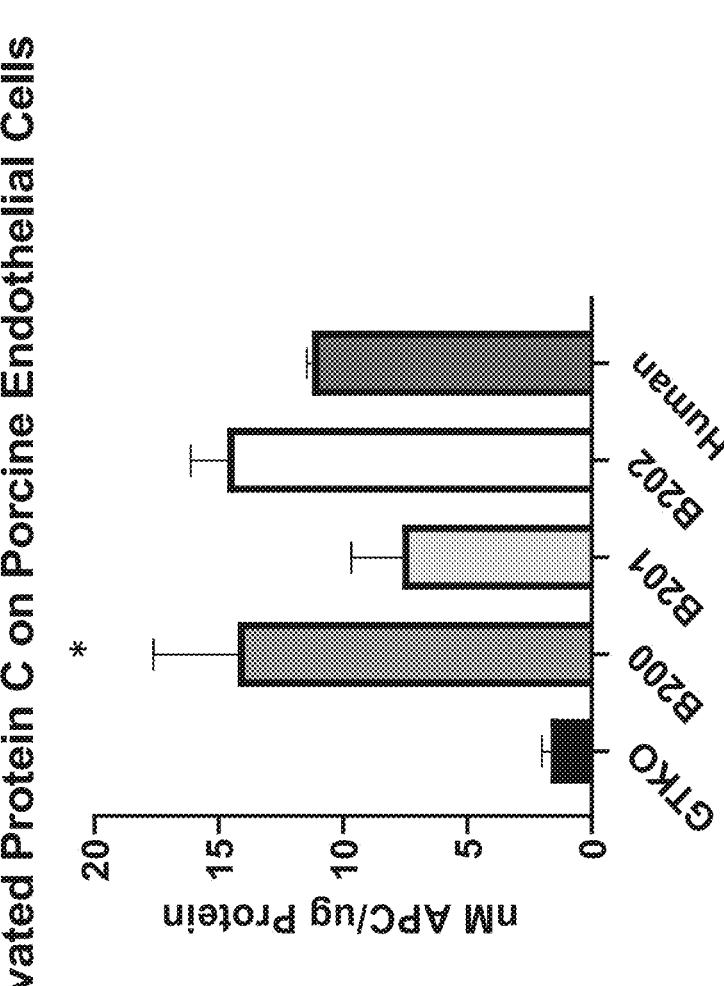
FIG. 5 shows a bar graph illustrating the quantification of an activated protein C (APC) Assay performed on pAEC expressing the B200 (n=3), B201 (n=4) and B202 (n=2) vector demonstrating that B200, B201 and B202 pAEC generated more APC than GTKO negative control (P<0.05), which demonstrated the anti-coagulant functionality of the hTBM and hEPCR transgenes.
Figure 7A:
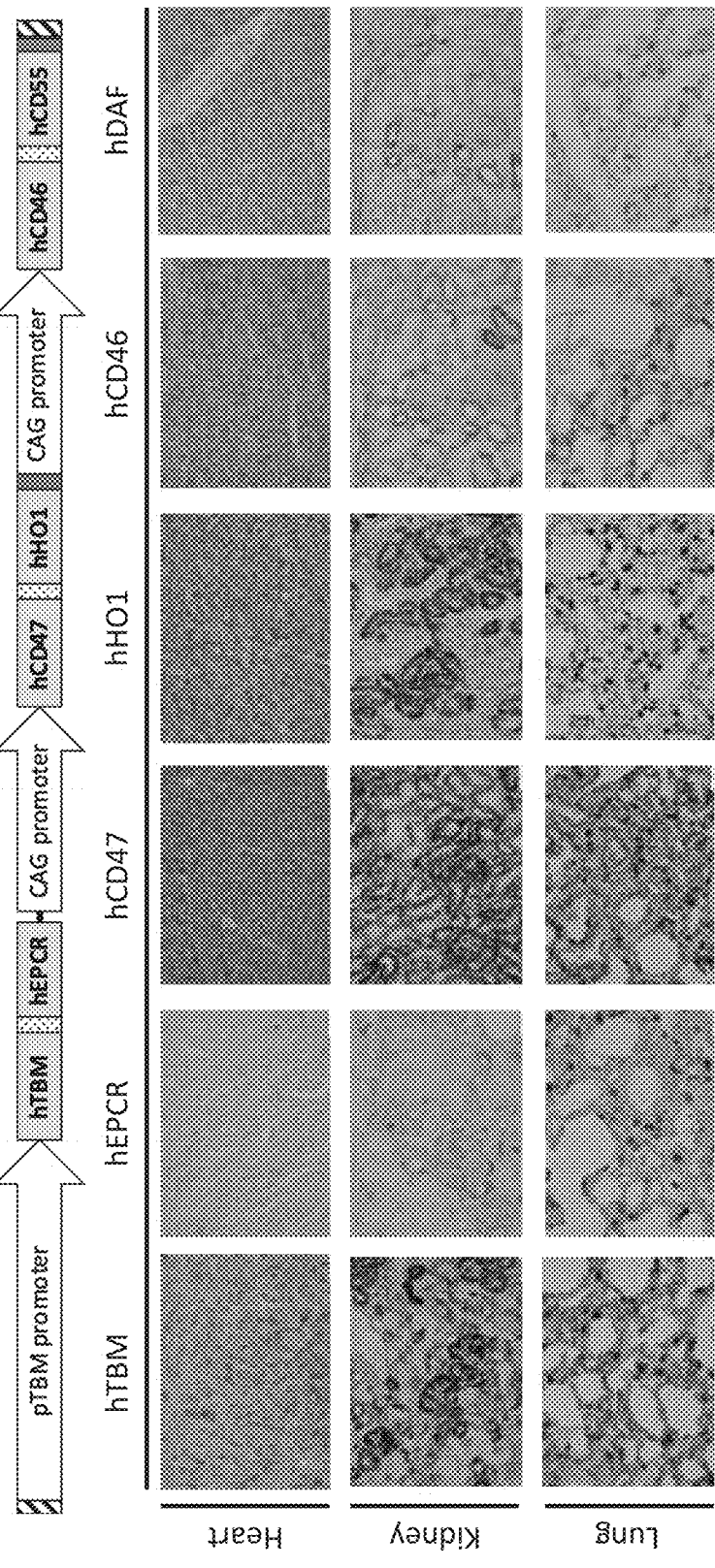
Figure 7B:
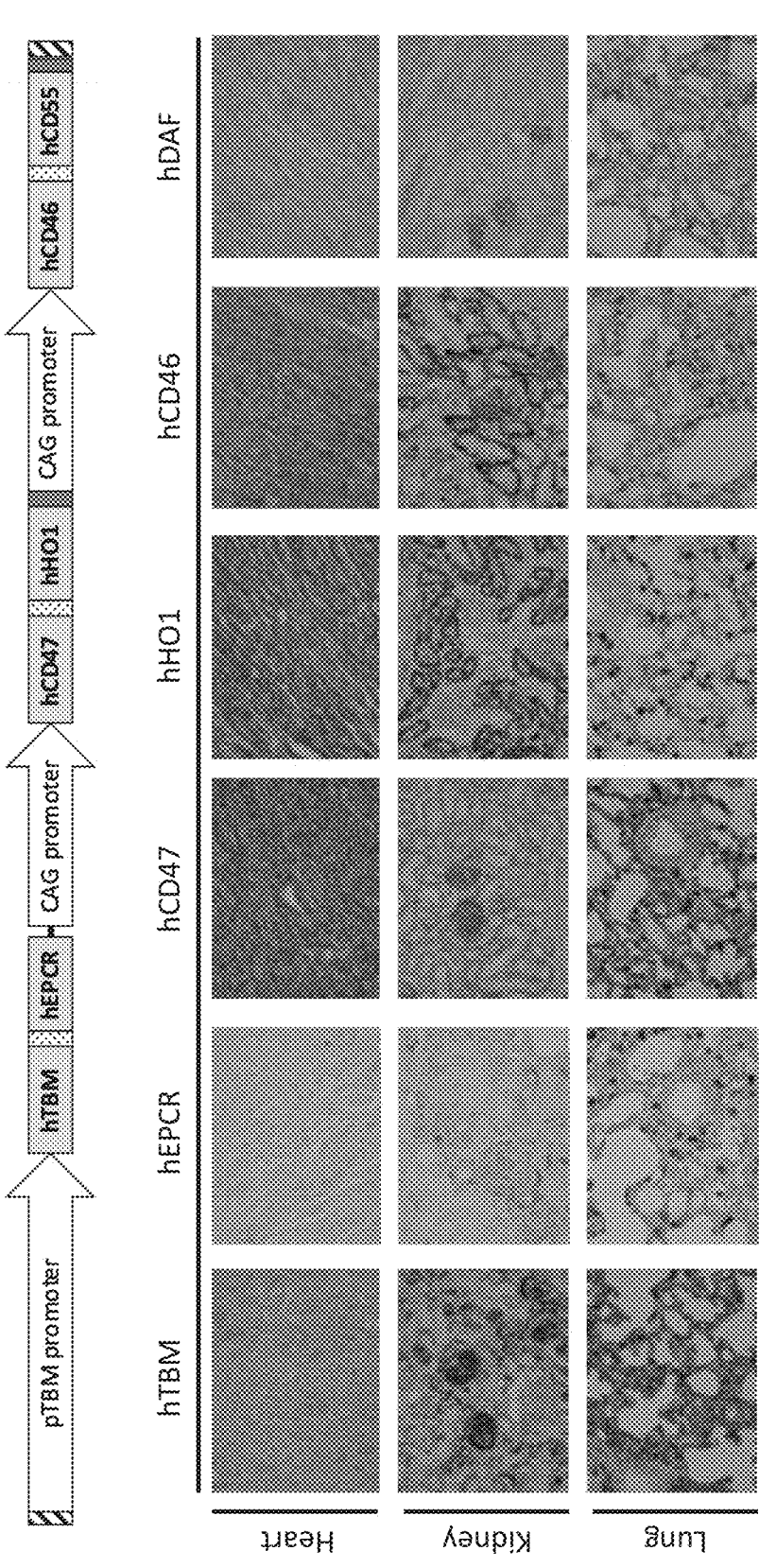
Figure 7D:
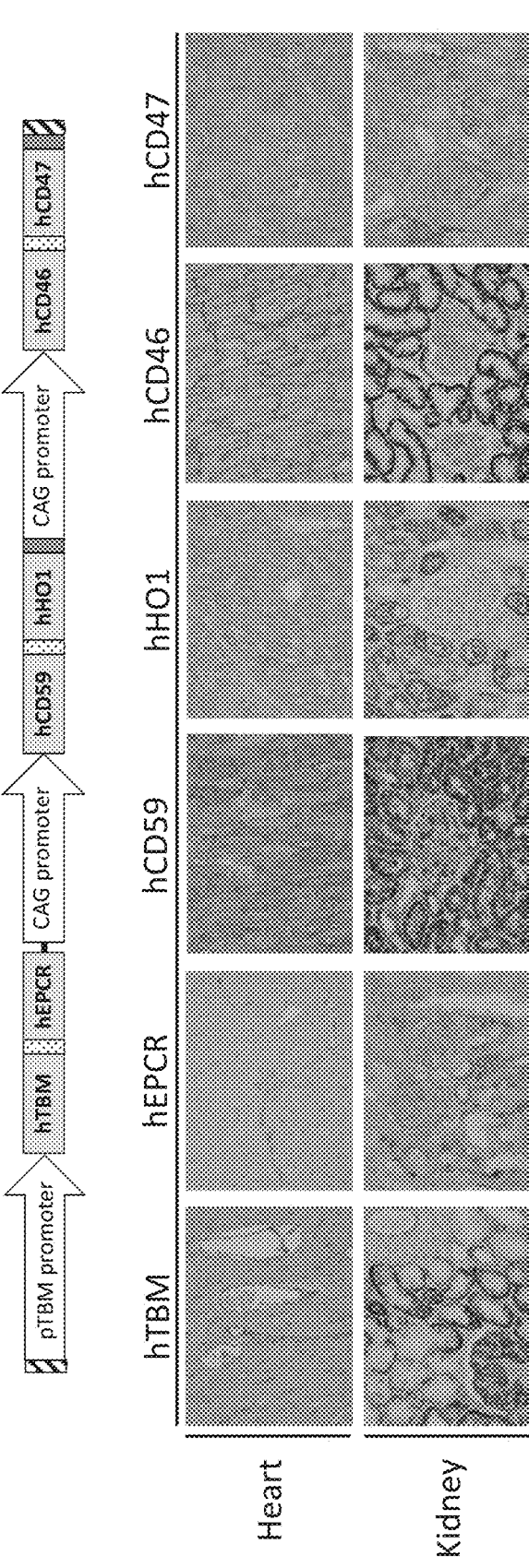

Accordingly, an activated protein C (APC) assay was conducted to assess the ability of transgenic hTBM and hEPCR to activate human Protein C. Primary porcine aortic endothelial cells (pAEC) were isolated from B200, B201 and B202 transgenic pigs and a GTKO (GGTA1 KO, control) pig. A human endothelial cell line served as a positive control. A standard curve using human activated protein C was prepared fresh on the day of assay. Thrombin and Protein C were added to each test well, incubated for 1 h and the reaction stopped with Hirudin. An aliquot was then transferred to the APC standard curve plate, Chromogenix S-2366 substrate was added to all wells which were read immediately at 405 nm. Assay results were normalized to nM APC/mg protein for final analysis (FIG. 5). As shown in FIG. 5, transgenic hTBM and hEPCR expressed in B200, B201 and B202 pAEC significantly elevated APC levels in this assay over GTKO control.

hHO1 function characterization with an Apoptosis assay. Heme proteins are released after ischemia-reperfusion during organ transplant, where they can induce apoptotic damage in the transplanted organ. Heme oxygenase-1 (HO-1) is expressed in response to heme proteins and protects cells against heme-induced apoptosis. An apoptosis assay was conducted to assess the anti-apoptotic function of transgenic hHO1 expressed by porcine cells. Primary pAEC from a B201 transgenic pig and a GTKO pig were used in a caspase 3/7 apoptosis assay. pAEC were grown to confluency overnight and 200 uM of hemin applied to each treated culture well, in addition to 4 uM of a Caspase-3/7 Green detection reagent. Cells were imaged and counted with a BioTek Cytation™5 reader. Percent caspase 3/7+ cells was calculated as the number of green fluorescing cells/total bright field cells counted×100. As shown in FIG. 6, transgenic hHO1 provided significant protection against hemin-induced apoptosis.

Additional methods used to the invention of the present disclosure can be found in WO 2017/044864 which is incorporated by reference in its entirety.

Example 6: B200 Supported Long-Term Survival of a Porcine Heart Transplanted into a Baboon A porcine heart expressing the 10 genetic modifications, including three xenoantigen gene knockouts (GGTA1; CMAH, β4GalNT2), GHR knockout to limit post-transplant heart growth, and six human transgenes expressed from vector B200, was transplanted into a baboon to evaluate the ability of this genotype for xenotransplantation in a primate model. The heart was procured from a four-month-old pig and transplanted into a baboon recipient by a human heart transplant team with significant experience in pig-to-baboon heart xenotransplants. With appropriate immunosuppression and post-operative care, the porcine heart sustained life in the baboon for 126 days (Table 13). The heart experienced ventricular fibrillation prior to failure, but no signs of organ rejection were observed. Immunohistochemistry (FIG. 8A) indicated that all transgenes were expressed in cardiac tissue obtained immediately post-mortem.

Transgenic pig heart expressing the B200 vector was also used for preclinical testing of pig to Baboon orthotopic xenoheart transplant. Baboon lived with pig heart for 120 days (Table 13). All transgenes were expressed in the explanted heart by IHC and westernblot (data not shown).

These observations indicated that the B200 vector functioned as intended in the heart for the entire post-transplant period.

Example 7: B200 Supported Long-Term Survival of a Porcine Heart Transplanted into a Human Patient A porcine heart from a B200 pig, with a genotype identical to the one in Example 6, was transplanted into a human patient. This transplant was the world's first pig-to-human organ xenotransplant and was performed by the same team in Example 6 under an FDA-approved Emergency Use Authorization protocol for compassionate use. The 57-year-old patient was suffering from end-stage heart failure but was deemed unsuitable for a human heart transplant. The porcine heart did not undergo HAR upon reperfusion, and myocardial biopsies taken on Day 34 (FIG. 8B) and Day 50 post-transplant, appeared normal and showed no signs of antibody or cell mediated rejection. A third biopsy on Day 56 indicated antibody (but not cell) mediated rejection, possibly due to anti-pig antibodies from intravenous immunoglobulin (IVIG) treatment. Though heart function weakened after this point, it sustained the patient's life for 60 days. Immunohistochemistry on the Day 34 biopsy (FIG. 8A) and Day 60 post-mortem sample (FIG. 8B) showed that all six transgenes were expressed at both timepoints.

Taken together, the results indicated that the genetic modifications functioned as intended. Knockout of the three xenoantigens, together with transgenic expression of hCD46 and hDAF, prevented HAR and delayed antibody-mediated rejection, save for that observed that observed on Day 56 which was possibly related to IVIG. Microvascular thrombosis was not observed, indicating that the two anticoagulant transgenes, hTBM and hEPCR, were effective in maintaining blood flow through capillaries and other small blood vessels. The expression of hCD47 and hHO-1 are consistent with the absence of cell-mediated rejection and inflammation, suggesting that these transgenes also contributed to success of the transplant. B200, along with the four knockouts, functioned as intended in sustaining the function of a porcine heart transplanted into a human patient. See e.g., Griffith et al., N. Engl, J. Med. 387(1):35-44 (2022) and Platt et. al., N. Engl. J. Med. 387(1); 77-78; and Table 13.

Figure 9:
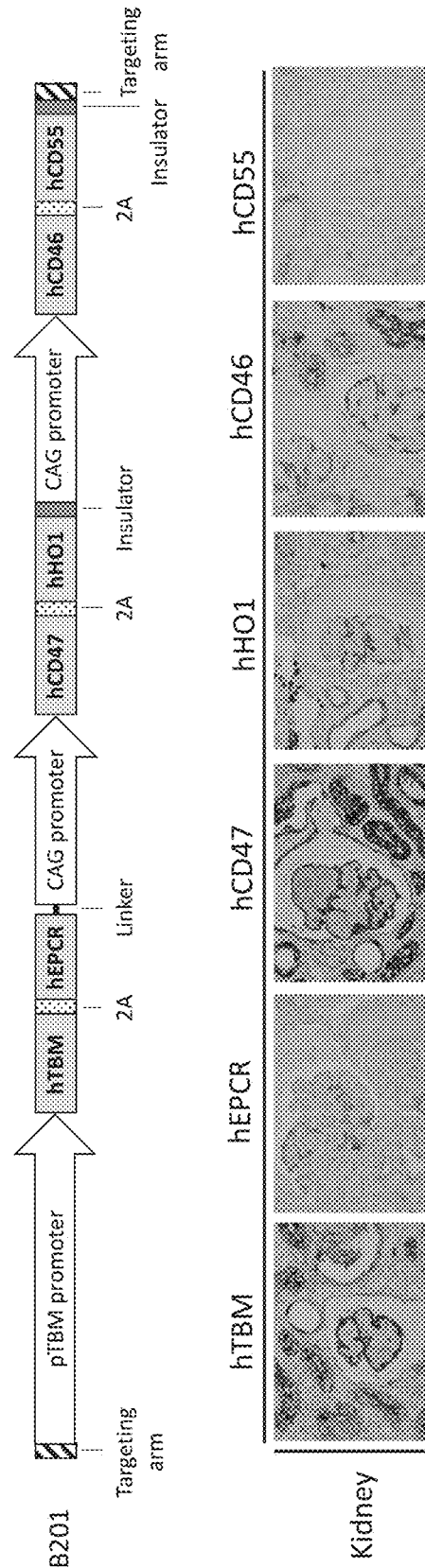
FIG. 9 shows representative images of immunohistochemical stainings of porcine kidneys expressing the B201 transgene in porcine kidney transplanted into a baboon; and demonstrates the expression of all human transgenes encoded by the B201 vector. Porcine kidneys were obtained and stained immediately post-mortem from a baboon on Day 120 post-transplant.

Example 7: B201 Supported Long-Term Kidney Survival after Transplantation into Baboons Porcine kidneys with B201, GHRKO and two xenoantigen knockouts (GGTA1, β4GalNT2) were transplanted into baboons and supported life for up to 120 days, and one transplanted kidney is ongoing and functioning well at 66 days. The kidneys in neither recipient underwent HAR, although signs of delayed rejection were noted at Day 120 in one recipient. Immunohistochemistry indicated that all six transgenes in B201 were expressed in post-mortem kidney tissue obtained at Day 120 post-transplant (FIG. 9).

Example 8: B201 Supported Long-Term Heart Survival after Transplantation into Baboons Two porcine hearts (10 and 9 modifications, the latter wild type at CMAH) were transplanted in a heterotopic position (abdominal) in baboon recipients. The endogenous hearts were left in place, so the transplanted hearts were not life-supporting. Nevertheless, the heterotopic model allows the heart to be assessed for rejection, inflammation, microvascular thrombosis, etc. The 10 gene heart survived for 118 days. Signs of rejection were noted at necropsy, likely due to the exposure and reaction to a neoantigen resulting from knockout of CMAH. The 9 gene heart, ongoing at 194 Days, is functioning well, and biopsies of this heart at Day 122 post-transplant showed no signs of rejection.

In additional experiments, transgenic pigs carrying single copy of B201 vector were used in numerous preclinical testing of pig to baboon xenoheart or xenokidney transplant (1 orthotopic heart, 5 heterotopic hearts, and 2 orthotopic kidneys). All transgenes were expressed in the explanted hearts or kidneys by IHC and western blot (data not shown).

Example 9: B209 Supported Planned, Short-Term Survival of a Porcine Hearts Transplanted into Human Brain-Dead Decedents Two porcine hearts from B209 pigs with 10 gene modifications were transplanted into brain dead human recipients. Both were designed as short-term transplants, authorized for up to 72 hours, primarily to assess whether the hearts would avoid HAR. Both hearts performed well for the full 72-hour period, and showed no signs of HAR, inflammation or microvascular thrombosis. This indicated that the transgenes expressed from B209, along with the xenoantigen knock-outs, could protect transplanted porcine hearts in human bodies from HAR. Immunohistochemical staining showed expression of all six transgenes in immediate post-mortem heart tissue (FIG. 10).

Two Transgenic pigs carrying a single copy B209 vector at CMAH locus were used in two different pre-clinical experiments of pig to human (Brain dead recipient) xeno-heart transplant. All transgenes were expressed in the explanted hearts by IHC and western blot. Representative IHC images are shown (FIG. 9).

TABLE 13

| Preclinical use of transgenic pig expressing B200 or B201 vector | | |
| --- | --- | --- |
| MCV | Transplant | Duration(Days) |
| B201 | Orthotopic Heart | 33 |
| B201 | Heterotopic heart | >169(on going) |
| B201 | Kidney | 131 |
| B201 | Heterotopic heart | <1 |
| B201 | Kidney | 4 |
| B201 | Heterotopic heart | 113 |
| B201 | Heterotopic heart | >8 |
| B201 | Heterotopic heart | 22 |
| B200 | Orthotopic Heart | 126 |
| B200 | Heart | 60 |
| B209 | Heart | 3 |
| B209 | Heart | 3 |

TABLE 2

| Sequences | | |
| --- | --- | --- |
| SEQ ID NO: | Description | Sequence |
| 1 | Primer TBM pr 4774F | ccctccttcccacaaagctt |
| 2 | Primer TBMpr 9157R | actggcattgaggaaggtcg |
| 5 | Primer TBMpr 738F- | cccacacacaaccagagaca |
| 6 | Primer TBMpr 4311 R | gtgcaggtatgtggcctctt |
| 11 | B200 vector | aaatacatcattgcaatgaaaataaatgttttttattaggcagaatccagatgc tcaaggcccttcataatatcccccagtttagtagttggacttagggaacaaa ggaacctttaatagaaattggacagcaagaaagctctagctttagaagaac tcatcaagaagtctgtagaaggcaattctctgggagtcaggggctgcaatg ccatagagcactaggaacctgtctgcccactctcccctagctcttctgcta tgtccctggttgctagggcaatgtcctggtacctgtcagccactcccagcct gccacagtctatgaagccagagaaccttccattttcaaccatgatgttggga aggcaggcatcccatgagtcaccactaggtcctcaccatctggcatgga tgccttgagcctggcaaatagttcagcaggggccaggccctggtgttcttc atccaagtcatcttggtccaccaggccagcctccatcctggttctggccctc tctatcctgtgcttggcctggtggtcaaaggggcaggtggctgggtcaag ggtgtggagtcttctcatggcatcagccatgattgacactttctcagctgga gctaggtgagaggaaaggaggtcctgcccaggcacctcacctagtagga gccagtcccttccagcttctgtgaccacatcaaggacagctgcacagggg accccagttgttgccaaccaggagagtctggcagcctcatcctggagctc attgagagccccactgaggtctgtctttacaaaaaggactggcctgccttg ggctgaaagtctgaaaactgctgcatcagagcaaccaatggtctgctgtgc ccagtcatagccaaacagtctctcaacccaggcagctggagaacctgcat gtaggccatcttgttcaatcatgatggctcctcctgtcaggagaggaaaga gaagaaggttagtacaattgctatagtgagttgtattatactatgcttatgatta attgttaaactagggctgcagggttcatagtgccacttttcctgcactgcccc atctcctgcccacccttcccaggcatagacagtcagtgacttaccaaactc acaggaggggagaaggcagaagcttttttgcaaaagcctaggctcatgaga caataaccctgataaatgcttcaataatattgaaaaaggaagagtatgagta ttcaacatttccgtgtcgcccttattcccttttttgcggcattttgccttcctgtttt tgctcacccagaaacgctggtgaaagtaaaagatgctgaagatcagttgg gtgcacgagtgggttacatcgaactggatctcaacagcggtaagatccttg agagttttcgccccgaagaacgttttccaatgatgagcacttttaaagttctg ctatgtggcgcggtattatcccgtattgacgccgggcaagagcaactcggt cgccgcatacactattctcagaatgacttggttgagtactcaccagtcacag aaaagcatcttacggatggcatgacagtaagagaattatgcagtgctgcca taaccatgagtgataacactgcggccaacttacttctgacaacgatcggag gaccgaaggagctaaccgcttttttgcacaacatgggggatcatgtaactc gccttgatcgttgggaaccggagctgaatgaagccataccaaacgacga gcgtgacaccacgatgcctgtagcaatggcaacaacgttgcgcaaactat taactggcgaactacttactctagcttcccggcaacaattaatagactggat ggaggcggataaagttgcaggaccacttctgcgctcggcccttccggctg gctggtttattgctgataaatctggagccggtgagcgtgggtctcgcggtat |

TABLE 2-continued

| Sequences | | |
|---|---|---|

| SEQ ID NO: Description | | Sequence |
|---|---|---|

```
cattgcagcactggggccagatggtaagccctcccgtatcgtagttatcta
cacgacggggagtcaggcaactatggatgaacgaaatagacagatcgct
gagataggtgcctcactgattaagcattggtaactgtcagaccaagtttact
catatatactttagattgatttaaaacttcatttttaatttaaaaggatctaggtg
aagatccttttttgataatctcatgaccaaaatcccttaacgtgagtttcgttcc
actgagcgtcagaccccgtagaaaagatcaaaggatcttcttgagatcctttt
ttttctgcgcgtaatctgctgcttgcaaacaaaaaaaccaccgctaccagcg
gtggtttgtttgccggatcaagagctaccaactctttttccgaaggtaactgg
cttcagcagagcgcagataccaaatactgttcttctagtgtagccgtagtta
ggccaccacttcaagaactctgtagcaccgcctacatacctcgctctgcta
atcctgttaccagtggctgctgccagtggcgataagtcgtgtcttaccgggt
tggactcaagacgatagttaccggataaggcgcagcggtcgggctgaac
gggggggttcgtgcacacagcccagcttggagcgaacgacctacaccga
actgagatacctacagcgtgagctatgagaaagcgccacgcttcccgaag
ggagaaaggcggacaggtatccggtaagcggcagggtcggaacagga
gagcgcacgagggagcttccaggggggaaacgcctggtatctttatagtcc
tgtcgggtttcgccacctctgacttgagcgtcgatttttgtgatgctcgtcag
gggggcggagcctatggaaaaacgccagcaacgcggcctttttacggtt
cctggccttttgctggccttttgctcacatggctcgacagatttaattaaacag
tgtgactagggaggcaaaacatacctactaaagggtggtagcataattcag
ttcttatgtgagtatgtgtatgtgtgtgagtatgtgcacatgcacatacatttta
aaaggtctgtaatatactaacatgttcatagtggttacacctagcttataggta
acattttttcccctgtatccttgtttgtgtttatcaaattttcataacagtaatggt
agaaggagtacctgacatggtaccatacatgctctgggccctgcctaatttc
tcaatttcctttattgcccatacccccattgcttgacaagcataagtccatact
ggcttgttttttcgttcctcagactcagtacaccatgtagctccatgccctggg
tctttgtatgtgctatttctactgcttagagtgctattgcccctgaccaccacgt
ggtcagcaacttctcttctgtgtctgtgtccatggtctatgattccagatgtcat
cttcactaactacccttctaatatgcccttccatcccacccgtcctcatcctta
ccccagccactctctatttggtggctctgtttttatttcttcctagctcatcactc
tttgaaatgaacttatttacttattcattatttgcttcttttcactagaatgaatgctc
catgagagcagggacctgctttatcttgctcgccactgtattctcagtgccta
gaactacgtctggcacatagtaggtgctcaataaatatcgatcaaatgaaa
gaatgagcaaacgaacaaatgaacaacacgtgaggtaggcatcatgattc
cattcaacagaggagaaaaacagacttaaagaattgaagtggtggagctg
cattttgatcttgactgactccaacatccatgctcttgaccactgtgcatctcc
agagtgtaatgaacatactttacttttatattccaccaaaataacaaagccat
gcccatgttagtagagagttaatcgacagtgcccttaaaatatgcatgcacc
cagggtacaactatgcatgctgccctgtgtttttcagttggatccaaatgaatt
gccgtaaacaaagagggggattcaatgtctttgactagtttgggatattttcct
agtaaccaactttgcaaaataaagccactaatgacaaggagctttgttctac
ttctgcatcactcaactgtcaattttttatctcttgcaagacttctaatctactaga
acttttgtttttctgtgatttctgaacagagaagactaatccaaaccctgtcatt
ccagaggaatggaaagcccaattcattaaaaccgtcggcgcgttcagcct
aaagctttttttctccgtatcccccccaggtgtctgcaggctcaaagagactcat
gtctcctatgtctcatctaaatggatgaggtttgagagttcccatcacggcat
ggtggaaacgaatccgactaggagccataagttcacggcttcgatccctg
gcctcgctcaggggttaaggatccggtgttgctgtgagctgtggtgtagg
tcacagatgcggttcggatctggcgttgctgcggctgtggtgtaggctggt
ggctgtagctccgatttgacccctagcctagggacctccatatgccgtggg
tatggccctaaaaagccaaataaaataaaataagtaaatggttgaggtttga
cacagaaagtttatttatttatgtatttacttatctttttttttttttttttttttttgtctttct
gctatttcttgggctgctcccgcggcatatggaggttcccaggctagggggt
cgaattggagctacagccaccagcctacaccacagccgcagcaatgcca
gatccgagccgcctctgtgacctacaccacagctcatggcaacgctggat
cgttaacccactgagcaagggctgggaccgaacccgcaacctcatggttc
ctagtcggattcgttaaccactgcgccatgacgggaactcctacttatctatt
tttttaaagcatatggaagttcccaggctagggggttgaatcggagctgcaa
ctgccggcttacaccacagccagagcaacgccggatctgagcagtgtct
gggacctacaccacagctcacagccacaccggatcctcaatccactgaat
gaggccaggaatcaaacctgtgtcctcatggatactagtcagattcatttcc
gctgagcaatgacaggaactcctgacacagaaattttagattaaaattgaa
gatgagcccttccttttgtacgacctttgtgtgcagattttcgaggataagtc
cttgagcttgaagtttagggtcatggatcctcataacagtttcctggcctgtg
aggcttggatctcagtataaacagaagtgctggcagcagtagacacagca
gcagctgttttcaggaacaaatactgggcacctgccttgtggacctgcctg
actccaccactctcttgggtatccacaaagtggacccagaggttcagagca
gccctgggatccaaatttttttaatttatttttttatctttttattttttgtcttttcgaaa
tttttagggctacacccatgagatatggaggttcccaggctcaagggtccaat
cggagctacaactgccggcctacaccacagctcatggcaatgctggatcc
ttaacccgctgagcgaggccagggatcaaacccacaacctcatgattcct
agttggattcgttaaccactgagccacgtgggaactccctgggatgcaaa
ttttgtcatctagccctaggatgtagctatcatcctgatttgagaagagaggc
agagtctcaggtggcttctctctcatgaatgcagagctcaagggtggccaca
```

TABLE 2-continued

Sequences

SEQ
ID
NO: Description                     Sequence cgtacttgagttcatccgatgcacacagcattgtgctaaaatattgaccattt
ggcccttttgctgacttttggtttgagggatatgaccttcatgagcatacaga
ggataaatatgtatgcatgtatgcatgtgtgtacacatgtgcgcatgcatgtat
atacctgcataattatgtatttgtttatgtatgcaggtgcatgtgtatgtatatat
ttattatttatttatttgggggccacacccatgacatttggaagttcctgggac
agagattgaatcccagccacagctttgacctacgccatggacacagcaac
actggattcttaacccctgtgccacagcgggaactcctagaagatagtatt
tcatgatgatatttgactaaaaatagggtcaggctttgaagtttaaataaatt
cgaccagataaatggccatccaggaagttatactttgccttgttcaaatttgg
accacggggaaggtggttggcgacatgtaacagaaatctgactccagtgc
aggtttcgctcccgtgacgggaagcccagaggtgggcagccctaaggct
ggggctctgatttcatgatgctcttagcatcttgagtcccttccctcttcttgct
tttatctcagcctcgggctgctgcaccttctgtctttgtggtgagtctacctatt
ccacttagctcggcttcagggtgtatttccacgacttcgttagagtaaggttg
gggccagctgtgctctgccggcaggaggtgtgcttgcaggggccatgga
tgtggccaggacctaatgtgacggtggggagcaggatggggatgaggat
gtgaccacagagccttgggaaccacgtcatccacgtcatacactgagagc
aggtggttctcatgcaggtgcatcagaatcccgaggacggcttgtccaaa
cccagatggctgggcccaagccctgagctcccgatttgggaggccttgg
ctgggccccgaaatctgccttcctgactagaccgagtgatgaatggtgttc
atagacaagacatacactaacactggtcttgggggctccttgccacaccct
gaaggggtccgtgaaactgacggggccagagaaggtgctggttcctcca
tggaaggtctcagtgaggccattctgctgcccggctgggtcacgctgggg
gagtgagggtgcatcccctcctgggatctggtcaaaggcagattctgattc
tggaagcacggggtagggccagagatgccaccttctaacaagcccccag
gtgaagatgttgacctgggaccttatggtgggggggtggcggagctcaag
gtggcagacaccctccctctctctcaacctgtgtcacagcagggccatccta
ctggctctcgctcggccagagatggcgatgccagaacacactgggggcag
ggtgtccacattttttgtcacttccactgagccctggggactgactcatttaaat
gacattctcaactctttggaaagaagctgggccagaaatggaaatggcag
caaacacttttttgggaaacaggaagccaatttttttttttcaatcatgattttccc
cagattcagagactgcttaactcccaatgaaatacttttagattacgagctaa
aataccgaaaagctgtcaagctcaagaccacaggaaaacagccgaaga
acaaacaccatgagaaaacagtcacagagtgcctctgcggcggatttcaa
gttccagacttccttgctgtcagctgtgtgtacttgtcccgcctgcagtagga
ccagctggggtttaagtctgtaccatggacactgctgccaggattctcctct
gcatctgctgacttccagctcttcagggccagctggccataggagcataaa
ctgacatccagttccaggaggcagcatctgtccccatggcctgcaggaca
ccagatcagtagaggcccccagggccacctttcctgtgggggcccttgaa
gggacccgggaaggctggatcttgctaaagcttccacaagtcccttccaa
aggagagtaaattctaaacagaagcttttgccagtgcttctctgggatctgg
cttcaggattattcctagtctgaaaagtcttcctggtggtttggacacgggca
aatgcttggtgggtgggctggctctggatgcaggtgagtggggtcggaa
gttctccctccttcccacaaagcttgacggagccaggggcacccgcggg
cctgtggatgggagaggggtttctggtgacggactcaagtcttggcagcc
cctgaccccagagcaggctccctccccacagctgctctccgtgagtccttc
acttgcccaagttcaagatgtacccagttctggagctgccaaaccatcctg
catcctgatgtcagccacccaagttctggggtagctggtctgccacccagg
tggatgaaaagaggccacatacctgcaccagcatctgcgaatctctgaag
aacatcaataataaaaagacaactaacccagttaaaacacaggtagagaa
tctgaacagacattcatcggaagaagaattacgactggccaaaaagctcat
aaaaagatggtcaaagtcattggtcagggaaatgtaaatcaaaccgcattg
agataccatctcactccctctcggatggctggaatgaaaaaaaacctcttct
ttcctcccttttcattgtcttggcacccttgtggaaattaattgactaaaattcat
gaaatacaaaaattttttaggagttcccgtcgtggctcagtggttaacaaatct
gactaggaaccatgaggtttcaggttcgattcctggcctcactcagtgggtt
agggatctggtgttgccatgagctgtggtgtaggtcacagacgcagctcg
gatcccgcattgctgtggctctggcgtaggccggcggctacagctctgatt
caacctctagcctgggaatagcccaagaaatggcaaaaagaccaaaaaa
aaaaaaaaaaaaaaactcgttttgagcatttttgcatgtgtacattgtccatt
tgtgtgccttccaagatttattttttggagtctcaactctgtcattgatttatgtctc
tccttaggccagaaccacactgtttttggtgaccatggctttgtagtaaaattt
gaaatctgaaagtgtgagccctcctgtttttgtttctcttctccatgattagtttg
gttattcagagtcccttgaatttccaggtgaattttaggattagcaggaaaatt
tctgcagagatggcagcagagattttaatagggattatgttgaatctggag
gttaatttcagttttgctaccttgactgtattaagtcttccagtctataagcataa
gatgtcttttatttacttaggtcttttaaaatttctttgggcactcccattgtggt
gcatcggaaatgaatccgactagtatccacaagaacacaggttcaatccct
ggcattgctcagtgggttaaggatcctgcattgccatgaagaactgtggtg
gaggccagcagctgcagctctgatttgacccctagcctgggaacttccata
tgccttgggtatggccctaaaaagcaaactaagtaagtaagtaaataaata
aatgaataaataaaatttctttcaacattgtaattttgtaatttttgtaattttcaga
gcgtacattttgcccttttcaatacattattcctacatattttattcttttttgatactat
tataaatgaaatttataattaattcatttatatgaatttcattttcaatttgcatattg TABLE 2-continued

| Sequences | | |
|---|---|---|

| SEQ ID NO: Description | | Sequence |
|---|---|---|

```
ctactacaatagaaatgcactttttaattattttttatggccatactatatatatatg
tgtgtgtgtgtgtgatgtgtgtcattttactgtacagcagaaattgacacaacat
tgtaaatcaactacacttaaaaaatgaagaaataaccacctgtgattatggct
actgtgttggacactttaggcatccccccaccccgtccccgccccacaccc
ctgagtgctagtgacggatgttcccacccaggggggcctggagcctttatca
ccagccatcgggaatcagaaccgtatctcacagtccccatgcctggagca
cctggaattgtgcccttggactcgtgggtgttctgcttctcagtgggagaag
cttaggttctaagtcagagcagggacagcccccatgtgctcaggacccag
tgtgaaggggtctgcctcaggggacctgggggttacaagggtaagagaa
ggtgttcatgttggaactagaagttcttttttcactgctctgaagaaaaaagct
gcctcccacccttggtacagctcttctgctaacagtgaatcaggcagaacg
tgttcaagaagtgacccagcctggtgggggcagacctgacccttgatgg
tccctcaaccctccgagggtcccgcccttcctttactgctttgttgtctgtcc
tgagaggtttggctaatgtcgaaccaagggtgtggctggtcctgtcccctttt
cctgtctcacgcacccacctctgaagtctctgtagctggttccagccgggat
ctggagccactcccccgccccaggcccagtggtacagactcttgcaga
gtcgggggcccctgactcagccccaccgccagcgggatgtcaggccag
cacccgccccactcccactgatctgggggggggtgtctttccttcctccttcc
aaaggagcctcagaccttcctgtgggggcacgggggcagtgggattcagg
aggctctgagtcagcaggccggcattgaggagtataaagggacccccagt
tcctccccctttcacttgtggcttatcgccgccccaccctgcccaaggtca
ctgcggtcagtacagtcctcagctgccagcaggtgcctgtctttacttgtga
ggccgccacgctctcctgtttctccaggtctgggctctgttggaagtgggg
gcccgacccccgggtaagatgggggatctgcgtgtcctgccctcagagg
cctcctcctccccgcacccctaaccctttcagcccaacaaggctggagatc
tcccacatctttggcttcgttaagagttcaacagcgccgccaccggcatgt
cgctgagcagaggatggcacagggtgttaaaaaaaaaaaaaggttgcca
cactccgttcggttttgggcccacccttcgcattcctggagcctgagtaag
cggataaggctgtgaaagtgacagattcctgccacctccttccagcgctca
tgcacagggaccgcccctcttcggtgtcctttgctgcacaagtgcatttgca
cattcctgtctcaatctggtttctcccccttaaaagatgggaatgtgacctgct
tggagccctcgcctcgccagggcaccccatccgtcccttcaggggtgg
agatggactgtccctctgcaaggctggatgaactcagaccaaacaggcca
acttgctccccaaatacgcccacccctaccgggctgcaggaattcgcctgt
caccactgctgaagggtgaccttgcagccctgagagcatccccatgactt
gcccaccagatgaagtctggttgtggcaggtcgcgctcagggactcccg
ggtcccacctgggggtgggaggatcctcctttgctcgtggtcgccccagc
cacgccctcctttccaagcgccagtctccagagctccgtgccccggcgga
ggcggtctggctctctctccttgcccctctctccttgcccctagcagcccttc
tcctaaaccctctgagcagcgggcacctcctcccgaggccctgggctaag
tccccacccttcatctcaagccttcctccttgactccctcttcccagagttcct
tgaaataggtggtaagtacacaccgatgacggaaaacaaagactaagag
gttaaagagggctgaggattacggccccggtagggctgcgcgcgaggg
ggtcgagtggccgggcggtcccgttgccgggcagacagaggtgcggtt
ctcccgggcgcctgcgctgccggccccgccggagccctcccagccgg
cgcccagtttactcatcccggagaggtgatcccgggcgcgagggcggg
cgcagggcgtccggagaacccagtaatccgagaatgcagcatcagccct
tcccaccaggcacttccttccttttcccgaacgtccaggaaggggggccg
cgcacttataaactcgggccggacccgccggcctgtcagaggctgcctc
gctggggctgcgcgcggcggccggacacatctggtccgagaccaacgc
gagcgactgtcactggcagctccctgcgcctctcagcccggccgggcc
cctgcgcttggcgtgctgacaccatgcttggggtcctggtccttggcgcgc
tggccctggccggcctggggttccccgcacccgcagagccgcagccgg
gtggcagccagtgcgtcgagcacgactgcttcgcgctctacccgggccc
cgcgaccttcctcaatgccagtcagatctgcgacggactgcggggccac
ctaatgacagtgcgctcctcggtggctgccgatgtcatttccttgctactgaa
cggcgacggcggcgttggccgccggcgcctctggatcggcctgcagct
gccaccggctgcggcgaccccaagcgcctcgggcccctgcgcggctt
ccagtgggttacgggagacaacaacaccagctatagcaggtgggcacg
gctcgacctcaatggggctccctctgcgggcccgttgtgcgtcgctgtctc
cgctgctgaggccactgtgcccagcgagccgatctgggaggagcagca
gtgcgaagtgaaggccgatggcttcctctgcgagttccacttcccagccac
ctgcaggccactggctgtggagcccggcgccgcggctgccgccgtctc
gatcacctacggcacccgttcgcggcccgcggagcggacttccaggc
gctgccggtgggcagctccgccgcggtggctcccctcggcttacagcta
atgtgcaccgcgccgcccgagcggtccaggggcactgggccaggga
ggcgccgggcgcttgggactgcagcgtgggagaacggcggctgcgagc
acgcgtgcaatgcgatccctggggctccccgctgccagtgcccagccgg
cgcgccctgcaggcagacgggcgctcctgcaccgcatccgcgacgca
gtcctgcaacgacctctgcgagcacttctgcgttcccaacccccgaccagc
cgggctcctactcgtgcatgtgcgagaccggctaccggctggcggccga
ccaacaccggtgcgaggacgtggatgactgcatactggagcccagtccg
tgtccgcagcgctgtgtcaacacacagggtggcttcgagtgccactgcta
ccctaactacgacctggtggacggcgagtgtgtggagcccgtgtggacccg
```

TABLE 2-continued

Sequences

| SEQ ID NO: Description | Sequence |
|---|---|
| | tgcttcagagccaactgcgagtaccagtgccagccctgaaccaaactag |
| | ctacctctgcgtctgcgccgagggcttcgcgcccattccccacgagccgc |
| | acaggtgccagatgttttgcaaccagactgcctgtccagccgactgcgac |
| | cccaacacccaggctagctgtgagtgccctgaaggctacatcctggacga |
| | cggtttcatctgcacggacatcgacgagtgcgaaaacggcggcttctgct |
| | ccgggggtgtgccacaacctccccggtaccttcgagtgcatctgcgggccc |
| | gactcggcccttgcccgccacattggcaccgactgtgactccggcaaggt |
| | ggacggtggcgacagcggctctggcgagcccccgcccagcccgacgc |
| | ccggctccaccttgactcctccggccgtggggctcgtgcattcgggcttgc |
| | tcataggcatctccatcgcgagcctgtgcctggtggtggcgcttttggcgct |
| | cctctgccacctgcgcaagaagcagggcgccgccagggccaagatgga |
| | gtacaagtgcgcggccccttccaaggaggtagtgctgcagcacgtgcgg |
| | accgagcggacgccgcagagactcggatccggagagggcagaggaa |
| | gtcttctaacatgcggtgacgtggaggagaatcccggccctatgttgacaa |
| | cattgctgccgatactgctgctgtctggctgggccttttgtagccaagacgc |
| | ctcagatggcctccaaaagacttcatatgctccagatctcctacttccgcgac |
| | ccctatcacgtgtggtaccagggcaacgcgtcgctgggggggacacctaa |
| | cgcacgtgctggaaggcccagacaccaacaccacgatcattcagctgca |
| | gcccttgcaggagcccgagagctgggcgcgcacgcagagtggcctgca |
| | gtcctacctgctccagttccacggcctcgtgcgcctggtgcaccaggagc |
| | ggaccttggcctttcctctgaccatccgctgcttcctgggctgtgagctgcc |
| | tcccgagggctctagagcccatgtcttcttcgaagtggctgtgaatgggag |
| | ctcctttgtgagtttccggccggagagagccttgtggcaggcagacaccc |
| | aggtcacctccggagtggtcaccttcaccctgcagcagctcaatgcctaca |
| | accgcactcggtatgaactgcgggaattcctggaggacacctgtgtgcag |
| | tatgtgcagaaacatatttccgcggaaaacacgaaagggagccaaacaa |
| | gccgctcctacacttcgctggtcctgggcgtcctggtgggcagtttcatcat |
| | tgctggtgtggctgtaggcatcttcctgtgcacaggtggacggcgatgttg |
| | agcgcggccgcttccctttagtgagggttaatgcttcgagcagacatgata |
| | agatacattgatgagtttggacaaaccacaactagaatgcagtgaaaaaaa |
| | tgctttatttgtgaaatttgtgatgctattgctttatttgtaaccattataagctgc |
| | aataaacaagttaacaacaacaattgcattcatttttatgtttcaggttcaggg |
| | gggagatgtgggaggttttttaaagcaagtaaaacctctacaaatgtggtaaa |
| | atccgataaggatcgatgggacagcccccccccaaagcccccagggat |
| | gtaattacgtccctcccccgctagggcagcagcgagccgcccggggctc |
| | cggtccggtccggcgctcccccgcatccccgagccggcagcgtgcggg |
| | gacagcccgggcacggggaaggtggcacgggatcgctttcctctgaac |
| | gcttctcgctgctctttgagcctgcagacacctgggggggatacggggaaa |
| | atctagtgggacagcccccccccaaagcccccagggatgtaattacgtcc |
| | ctcccccgctagggcagcagcgagccgcccggggctccggtccggtcc |
| | ggcgctcccccgcatccccgagccggcagcgtgcggggacagcccgg |
| | gcacggggaaggtggcacgggatcgctttcctctgaacgcttctcgctgct |
| | ctttgagcctgcagacacctggggggatacggggaaaaatcgatgggac |
| | agcccccccccaaagcccccagggatgtaattacgtcctcccccgctag |
| | ggcagcagcgagccgcccggggctccggtccggtccggcgctccccc |
| | gcatccccgagccggcagcgtgcggggacagcccgggcacggggaa |
| | ggtggcacgggatcgctttcctctgaacgcttctcgctgctctttgagcctg |
| | cagacacctgggggggatacggggaaaatctagtgggacagcccccccc |
| | caaagcccccagggatgtaattacgtccctcccccgctagggcagcagc |
| | gagccgcccggggctccggtccggtccggcgctcccccgcatccccga |
| | gccggcagcgtgcggggacagcccgggcacggggaaggtggcacgg |
| | gatcgctttcctctgaacgcttctcgctgctctttgagcctgcagacacctgg |
| | ggggatacggggaaaaatcgatagcgataaggatccactagttattaata |
| | gtaatcaattacggggtcattagttcatagcccatatatggagttccgcgtta |
| | cataacttacggtaaatggcccgcctggctgaccgcccaacgacccccg |
| | cccattgacgtcaataatgacgtatgttcccatagtaacgccaatagggact |
| | ttccattgacgtcaatgggtggagtatttacggtaaactgcccacttggcag |
| | tacatcaagtgtatcatatgccaagtacgccccctattgacgtcaatgacgg |
| | taaatggcccgcctggcattatgcccagtacatgaccttatgggactttcct |
| | acttggcagtacatctacgtattagtcatcgctattaccatgggtcgaggtga |
| | gccccacgttctgcttcactctccccatctcccccccctccccacccccaat |
| | tttgtatttatttattttttaattattttgtgcagcgatgggggcgggggggggg |
| | gggcgcgcgccaggcgggcggggcgggcgaggggcggggcg |
| | gggcgaggcggagaggtgcggcggcagccaatcagagcggcgcgct |
| | ccgaaagtttccttttatggcgaggcggcggcggcggcggccctataaaa |
| | agcgaagcgcgcggcgggcgggagtcgctgcgttgccttcgccccgtg |
| | ccccgctccgcgccgcctcgcgccgcccgcccccggctctgactgaccg |
| | cgttactcccacaggtgagcgggcgggacggcccttctcctccgggctgt |
| | aattagcgcttggtttaatgacggctcgtttcttttcgtgtggctgcgtgaaagc |
| | cttaaagggctccgggagggcccttttgtgcggggggggagcggctcggg |
| | gggtgcgtgcgtgtgtgtgtgcgtggggagcgccgcgtgcggcccgcg |
| | ctgcccggcggctgtgagcgctgcgggcgcggcgcggggctttgtgcg |
| | ctccgcgtgtgcgcgaggggagcgcggccgggggcggtgccccgcg |
| | gtgcggggggctgcgaggggaacaaaggctgcgtgcggggtgtgtg |

TABLE 2-continued

Sequences

| SEQ ID NO: Description | Sequence |
|---|---|
| | cgtggggggtgagcagggggtgtgggcgcggcggtcgggctgtaac<br>ccccccctgcacccccctcccgagttgctgagcacggcccggcttcgg<br>gtgcggggctccgtgcggggcgtggcgcggggctcgccgtgccgggc<br>gggggtggcggcaggtgggggtgccgggcggggcggggccgcctc<br>gggccggggagggctcgggggagggggcgcggcggccccggagcgc<br>cggcggctgtcgaggcgcggcgagccgcagccattgcctttatggtaat<br>cgtgcgagagggcgcagggacttcctttgtcccaaatctggcggagccg<br>aaatctgggaggcgccgccgcacccctctagcgggcgcgggcgaag<br>cggtgcggcgccggcaggaaggaaatgggcggggagggccttcgtgc<br>gtcgccgcgccgccgtccccttctccatctccagcctcggggctgccgca<br>ggggacggctgccttcggggggggacggggcaggcggggttcggct<br>tctggcgtgtgaccggcggctctagagcctctgctaaccatgttcatgcctt<br>cttcttttcctacagctcctgggcaacgtgctggttgttgtgctgtctcatcat<br>tttggcaaagaattccgctgcgactcggcggagtcccggcggcgcgtcct<br>tgttctaacccggcgcgccctcaggatgtggcccctggtagcggcgctgtt<br>gctgggctcggcgtgctgcggatcagctcagctactatttaataaaacaaa<br>atctgtagaattcacgttttgtaatgacactgtcgtcattccatgctttgttacta<br>atatggaggcacaaaacactactgaagtatacgtaaagtggaaatttaaag<br>gaagagatatttacaccctttgatggagctctaaacaagtccactgtccccac<br>tgactttagtagtgcaaaaattgaagtctcacaattactaaaaggagatgcct<br>ctttgaagatggataagagtgatgctgtctcacacacaggaaactacacttg<br>tgaagtaacagaattaaccagagaaggtgaaacgatcatcgagctaaaat<br>atcgtgttgtttcatggtttctccaaatgaaaatattcttattgttattttcccaat<br>ttttgctatactcctgttctggggacagtttggtattaaaacacttaaatataga<br>tccggtggtatggatgagaaaacaattgctttacttgttgctggactagtgat<br>cactgtcattgtcattgttggagccattctttcgtcccaggtgaatattcatta<br>aagaatgctactggccttggtttaattgtgacttctacagggatattaatatta<br>cttcactactatgtgtttagtacagcgattggattaacctccttcgtcattgcca<br>tattggttattcaggtgatagcctatatcctcgctgtggttggactgagtctct<br>gtattgcggcgtgtataccaatgcatggccctcttctgatttcaggtttgagta<br>tcttagctctagcacaattacttggactagtttatatgaaatttgtggcttccaa<br>tcagaagactatacaacctcctaggaaagctgtagaggaacccccttaatgc<br>attcaaagaatcaaaaggaatgatgaatgatgaaggatccggagccacga<br>acttctctctgttaaagcaagcaggagacgtggaagaaaaccccggtcct<br>atggagcgtccgcaacccgacagcatgccccaggatttgtcagaggccc<br>tgaaggaggccaccaaggaggtgcacacccaggcagagaatgctgagt<br>tcatgaggaactttcagaagggccaggtgacccgagacggcttcaagctg<br>gtgatggcctccctgtaccacatctatgtggccctggaggaggagattgag<br>cccaacaaggagagcccagtcttcgccccctgtctacttcccagaagagct<br>gcaccgcaaggctgccctggagcaggacctggccttctggtacgggccc<br>cgctggcaggaggtcatcccctacacaccagccatgcagcgctatgtgaa<br>gcggctccacgaggtggggcgcacagagcccgagctgctggtggccca<br>cgcctacacccgctacctgggtgacctgtctgggggccaggtgctcaaaa<br>agattgcccagaaagccctggacctgcccagctctggcgagggcctggc<br>cttcttcaccttccccaacattgccagtgccaccaagttcaagcagctctac<br>cgctcccgcatgaactccctggagatgactcccgcagtcaggcagaggg<br>tgatagaagaggccaagactgcgttcctgctcaacatccagctctttgagg<br>agttgcaggagctgctgacccatgacaccaaggaccagagcccctcacg<br>ggcaccagggcttcgccagcgggccagcaacaaagtgcaagattctgcc<br>cccgtggagactcccagagggaagcccccactcaacacccgctcccag<br>gctccgcttctccgatgggtccttacactcagctttctggtggcgacagttg<br>ctgtagggctttatgccatgtgagcggcgcgccggcaccggtaccaagct<br>taagagcgctagctggccagacatgataagatacattgatgagtttggaca<br>aaccacaactagaatgcagtgaaaaaaatgctttatttgtgaaatttgtgatg<br>ctattgctttatttgtaaccattataagctgcaataaacaagttaacaacaaca<br>attgcattcattttatgtttcaggttcaggggggaggtgtgggaggtttttttaaa<br>gcaagtaaaacctctacaaatgtggtatggaattggagcccactgtgttca<br>tcttacagatggaaatactgacattcagaggagttagttaacttgcctaggtg<br>attcagctaataagtgcaagaaagatttcaatccaaggtgatttgattctgaa<br>gcctgtgctaatcacattacaccaagctacaacttcatttatataataataagtc<br>agctttcaagggcctttcaggtgtcctgcacttctacaagctgtgccatttag<br>tgaacacaaaatgagccttctgatgaagtagtcttttcattatttcagatattag<br>aacactaaaattcttagctgccagctgattgaaggctgggacaaaattcaa<br>acatgcatctacaacaatatatatctcaatgttagtctccaaattctattgactt<br>caactcaagagaatataaagagctagtctttatacactctttaaggtatgatg<br>ggtcccgatttttccccgtatccccccaggtgtctgcaggctcaaagagca<br>gcgagaagcgttcagaggaaagcgatcccgtgccaccttccccgtgccc<br>gggctgtccccgcacgctgccggctcggggatgcgggggagcgccgg<br>accggaccggagcccgggcggctcgctgctgccctagcggggggagg<br>gacgtaattacatccctgggggctttggggggggggctgtcccactagattt<br>tccccgtatccccccaggtgtctgcaggctcaaagagcagcgagaagcg<br>ttcagaggaaagcgatcccgtgccaccttccccgtgcccgggctgtcccc<br>gcacgctgccggctcggggatgcggggagcgccggaccggaccgg<br>agccccgggcggctcgctgctgccctagcggggagggacgtaattac |

TABLE 2-continued

Sequences

| SEQ ID NO: | Description | Sequence |
|---|---|---|

```
atccctgggggctttggggggggggctgtcccatcggatcttctagtcctgc
aggagtcaatgggaaaaacccattggagccaagtacactgactcaatagg
gactttccattgggtttgcccagtacataaggtcaatagggggtgagtcaa
caggaaagtcccattggagccaagtacattgagtcaatagggactttccaa
tgggttttgcccagtacataaggtcaatgggaggtaagccaatgggtttttc
ccattactgacatgtatacgcgtcgacgtcggcgcgttcagcctaaagcttt
tttccccgtatcccccagatgtctgcaggctcaaagagcagcgagaagc
gttcagaggaaagcgatcccgtgccaccttccccgtgcccgggctgtccc
cgcacgctgccggctcggggatgcggggggagcgcggaccggaccg
gagccccgggcggctcgctgctgccctagcgggggagggacgtaatta
catccctgggggctttggggggggggctgtccctgcggccgcgaattcgta
atcatggtcatagctgtttcctgtgtgaaattgttatccgctcacaattccaca
caacatacgagccggaagcataaagtgtaaagcctggggtgcctaatga
gtgagctaactcacattaattgcgttgcgctcactgcccgctttccagtcgg
gaaacctgtcgtgccaggggtctagccgcggtctaggaagctttctaggg
tacctctagggatccactagttattaatagtaatcaattacggggtcattagtt
catagcccatatatggagttccgcgttacataaacttacggtaaatggcccgc
ctggctgaccgcccaacgacccccgcccattgacgtcaataatgacgtat
gttcccatagtaacgccaatagggactttccattgacgtcaatgggtggagt
atttacggtaaactgcccacttggcagtacatcaagtgtatcatatgccaagt
acgcccctattgacgtcaatgacggtaaatggcccgcctggcattatgcc
cagtacatgaccttatgggactttcctacttggcagtacatctacgtattagtc
atcgctattaccatgggtcgaggtgagccccacgttctgcttcactctcccc
atctcccccccctcccccaccccaattttgtatttatttattttttaattattttgtgt
cagcgatggggggcgggggggggggggggcgcgcgccaggcggggcg
gggcggggcgaggggcggggcggggcgaggcggagaggtgcggc
ggcagccaatcagagcggcgcgctccgaaagtttccttttatggcgaggc
ggcggcggcggcggcccctataaaaagcgaagcgcgcggcgggcggg
agtcgctgcgttgccttcgccccgtgccccgctccgcgccgcctcgcgcc
gcccgcccggctctgactgaccgcgttactcccacaggtgagcgggcg
ggacggcccttctcctccgggctgtaattagcgcttggtttaatgacggctc
gtttcttttctgtggctgcgtgaaagccttaaagggctccgggagggccctt
tgtgcgggggggagcggctcggggggtgcgtgcgtgtgtgtgtgcgtg
gggagcgccgcgtgcggcccgcgctgcccggcggctgtgagcgctgc
gggcgcggcgcgggcgctttgtgcgctccgcgtgtgcgcgagggagc
gcggcgggggcggtgccccgcggtggggggggctgcgagggaa
caaaggctgcgtgcggggtgtgtgcgtgggggggtgagcaggggtgt
gggcgcggcggtcgggctgtaacccccccctgcacccccctccccgagt
tgctgagcacggcccggcttcgggtgcggggctccgtgcggggcgtgg
cgcggggctcgccgtgccgggcggggggtggcggcaggtgggggtg
ccggcggggcggggccgcctcgggcggggagggctcggggggag
gggcgcggcggcccccggagcgccggcggctgtcgaggcgcggcgag
ccgcagccattgcctttttatggtaatcgtgcgagagggcgcagggacttcc
tttgtcccaaatctggcggagccgaaatctgggaggcgccgccgcaccc
cctctagcgggcgcgggcgaagcggtgcggcgccggcaggaaggaaa
tgggcggggagggccttcgtgcgtcgccgcgccgccgtcccttctccat
ctccagcctcggggctgccgcagggggacggctgccttcgggggggac
ggggcagggcggggttcggcttctggcgtgtgaccggcggctctagag
cctctgctaaccatgttcatgccttcttcttttcctacagctcctgggcaacgt
gctggttgttgtgctgtctcatcattttggcaaagaattccgctgcgactcgg
cggagtcccggcggcgcgtccttgttctaacccggcgcgccctcaggat
ggagcctcccggccgccgcgagtgtccctttccttcctggcgctttcctgg
gttgcttctggcggccatggtgttgctgctgtactccttctccgatgcctgtg
aggagccaccaacatttgaagctatggagctcattggtaaaccaaaaccct
actatgagattggtgaacgagtagattataagtgtaaaaaaggatacttctat
atacctcctcttgccacccatactatttgtgatcggaatcatacatggctacct
gtctcagatgacgcctgttatagagaaacatgtccatatatacgggatccttt
aaatggccaagcagtccctgcaaatgggacttacgagtttggttatcagat
gcactttatttgtaatgagggttattacttaattggtgaagaaattctatattgtg
aacttaaaggatcagtagcaatttggagcggtaagcccccaatatgtgaaa
aggttttgtgtacaccacctccaaaaataaaaaatggaaaacacacctttag
tgaagtagaagtatttgagtatcttgatgcagtaacttatagttgtgatcctgc
acctggaccagatccattttcacttattggagagagcacgatttattgtggtg
acaattcagtgtggagtcgtgctgctccagagtgtaaagtggtcaaatgtc
gatttccagtagtcgaaaatggaaaacagatatcaggatttggaaaaaaatt
ttactacaaagcaacagttatgtttgaatgcgataaggggttttttacctcgatg
gcagcgacacaattgtctgtgacagtaacagtacttgggatcccccagttc
caaagtgtcttaaagtgctgcctccatctagtacaaaacctccagctttgagt
cattcagtgtcgacttcttccactacaaaatctccagcgtccagtgcctcag
gtcctaggcctacttacaagcctccagtctcaaattatccaggatatcctaaa
cctgaggaaggaatacttgacagtttggatgtttgggtcattgctgtgattgt
tattgccatagttgttggagttgcagtaatttgtgttgtcccgtacagatatctt
caaaggaggaagaagaaaggcacatacctaactgatgagacccacaga
gaagtaaaatttacttctctcggatccggagccacgaacttctctctctgttaaa
```

TABLE 2-continued

Sequences

SEQ
ID
NO: Description          Sequence

```
gcaagcaggagacgtggaagaaaaccccggtcctatgaccgtcgcgcg
gccgagcgtgcccgcggcgctgcccctcctcggggagctgccccggct
gctgctgctggtgctgttgtgcctgccggccgtgtggggtgactgtggcct
tcccccagatgtacctaatgcccagccagctttggaaggccgtacaagtttt
cccgaggatactgtaataacgtacaaatgtgaagaaagctttgtgaaaattc
ctggcgagaaggactcagtgatctgccttaagggcagtcaatggtcagat
attgaagagttctgcaatcgtagctgcgaggtgccaacaaggctaaattct
gcatccctcaaacagccttatatcactcagaattattttccagtcggtactgtt
gtggaatatgagtgccgtccaggttacagaagagaaccttctctatcacca
aaactaacttgccttcagaatttaaaatggtccacagcagtcgaattttgtaa
aaagaaatcatgccctaatccgggagaaatacgaaatggtcagattgatgt
accaggtggcatattatttggtgcaaccatctccttctcatgtaacacagggt
acaaattatttggctcgacttctagtttttgtcttatttcaggcagctctgtccag
tggagtgacccgttgccagagtgcagagaaatttattgcccagcaccacc
acaaattgacaatggaataattcaaggggaacgtgaccattatggatatag
acagtctgtaacgtatgcatgtaataaaggattcaccatgattggagagcac
tctatttattgtactgtgaataatgatgaaggagagtggagtggcccaccac
ctgaatgcagaggaaaatctctaacttccaaggtcccaccaacagttcaga
aacctaccacagtaaatgttccaactacagaagtctcaccaacttctcagaa
aaccaccacaaaaaccaccacaccaaatgctcaagcaacacggagtaca
cctgtttccaggacaaccaagcattttcatgaaacaaccccaaataaagga
agtggaaccacttcaggtactacccgtcttctatctgggcacacgtgtttca
cgttgacaggtttgcttgggacgctagtaaccatgggcttgctgacttagg
gcgcgccggcaccggtaccaagcttaagagcgctagctggccagacat
gataagatacattgatgagtttggacaaaccacaactagaatgcagtgaaa
aaaatgctttatttgtgaaatttgtgatgctattgctttatttgtaaccattataag
ctgcaataaacaagttaacaacaacaattgcattcattttatgtttcaggttca
gggggaggtgtgggaggtttttaaagcaagtaaaacctctacaaatgtgg
tatggaattggagccccactgtgttcatcttacagatggaaatactgacattc
agaggagttagttaacttgcctaggtgattcagctaataagtgcaagaaag
atttcaatccaaggtgatttgattctgaagcctgtgctaatcacattacaccaa
gctacaacttcatttataaataataagtcagctttcaagggcctttcaggtgtc
ctgcacttctacaagctgtgccatttagtgaacacaaaatgagccttctgatg
aagtagtcttttcattatttcagatattagaacactaaaattcttagctgccagc
tgattgaaggctgggacaaaattcaaacatgcatctacaacaatatatatct
caatgttagtctccaaattctattgacttcaactcaagagaatataaagagct
agtctttatacactctttaaggtatgatatcatctggaaagtaacaaaattgat
gcaaatttgaatgaactttatcatggtgtatttacacaatgtgtttcttctccctg
caatgtatttctttctctaattccttccatttgatctttcatacacaatctggttctg
atgtatgttttttggatgcacttttcaactccaaaagacagagctagttactttc
ttcctggtgctccaagcactgtatttgtatctgtattcaagccctttgcaatatt
gtactggatcattatttcacctctaggatggcttccccaggcaacttgtgttca
cccagagactacattttgtatcttgttgacctttgaacttccaccagtgtctaa
aaataatatgtatgcaaaattacttgctatgagaatgtataattaaacaatata
aaaaggagaagcaaggagagaaacacaggtgtgtatttgtgtttgtgtgct
taaaaggcagtgtggaaaaggaagaaatgccatttatagtgaggagacaa
agttatattacctcttatctggcttttaaggagatttgtgctgagctaaaaatcct
atattcatagaaaagccttacctgagttgccaatacctcaattctaaaataca
gcatagcaaaactttaacctccaaatcaagcctctacttgaatccttttctga
gggatgaataaggcataggcatcaggggctgttgccaatgtgcattagct
gtttgcagcctcaccttctttcatggagtttaagatatagtgtattttcccaagg
tttgaactagctcttcatttctttatgttttaaatgcactgacctcccacattccct
ttttagtaaaatattcagaaataaatttatcatctggaaagtaacaaaattgatg
caaatttgaatgaactttatcatggtgtatttacacaatgtgtttcttctccctgc
aatgtatttctttctctaattccttccatttgatctttcatacacaatctggttctga
tgtatgtttttggatgcacttttcaactccaaaagacagagctagttactttctt
cctggtgctccaagcactgtatttgtatctgtattcaagccctttgcaatattgt
actggatcattatttcacctctaggatggcttccccaggcaacttgtgttcac
ccagagactacattttgtatcttgttgacctttgaacttccaccagtgtctaaa
aataatatgtatgcaaaattacttgctatgagaatgtataattaaacaatataa
aaaggagaagcaaggagagaaacacaggtgtgtatttgtgtttgtgtgctt
aaaaggcagtgtggaaaaggaagaaatgccatttatagtgaggagacaa
agttatattacctcttatctggcttttaaggagatttgtgctgagctaaaaatcct
atattcatagaaaagccttacctgagttgccaatacctcaattctaaaataca
gcatagcaaaactttaacctccaaatcaagcctctacttgaatccttttctga
gggatgaataaggcataggcatcaggggctgttgccaatgtgcattagct
gtttgcagcctcaccttctttcatggagtttaagatatagtgtattttcccaagg
tttgaactagctcttcatttctttatgtttttaaatgcactgacctcccacattccct
ttttagtaaaatattcagaaataaatttatcccggcttgtcgacgacggatcatc
tggaaagtaacaaaattgatgcaaatttgaatgaactttatcatggtgtattta
cacaatgtgtttcttctccctgcaatgtatttctttctctaattccttccatttgatc
tttcatacacaatctggttctgatgtatgtttttggatgcacttttcaactccaa
aagacagagctagttactttcttcctggtgctccaagcactgtatttgtatctg
tattcaagccctttgcaatattgtactggatcattatttcacctctaggatggct
```

TABLE 2-continued

| Sequences | |
|---|---|

| SEQ ID NO: Description | Sequence |
|---|---|
| | tccccaggcaacttgtgttcacccagagactacattttgtatcttgttgaccttt |
| | gaacttccaccagtgtctaaaaataatatgtatgcaaaattacttgctatgag |
| | aatgtataattaaacaatataaaaaggagaagcaaggagagagaaacacag |
| | gtgtgtatttgtgtttgtgtgcttaaaaggcagtgtggaaaaggaagaaatg |
| | ccatttatagtgaggagacaaagttatattacctcttatctggcttttaaggag |
| | attttgctgagctaaaaatcctatattcatagaaaagccttacctgagttgcca |
| | atacctcaattctaaaatacagcatagcaaaactttaacctccaaatcaagc |
| | ctctacttgaatccttttctgagggatgaataaggcataggcatcaggggct |
| | gttgccaatgtgcattagctgtttgcagcctcaccttctttcatggagtttaag |
| | atatagtgtattttcccaaggtttgaactagctcttcatttctttatgtttttaaatg |
| | cactgacctcccacattccctttttagtaaaatattcagaaataatttaaattcg |
| | tggaatcccacccagcagacaagtatggctggatattttatataacgtgttta |
| | cgcataagttaatatatgctgaatgagtgatttagctgtgaaacaacatgaa |
| | atgagaaagaatgattagtaggggtctggagcttattttaacaagcagcctg |
| | aaaacagagagtatgaataaaaaaaattaaatacaagagtgtgctattacc |
| | aattatgtataatagtcttatacatctaacttcaattccaatcactatatgcttat |
| | actaaaaaacgaagtatagagtcaaccttctttgactaacagctcttccctag |
| | tcagggacattagcccaagtatagtctttattttcctggggtaagaaaagaa |
| | ggattgggaagtaggaatgcaaagaaataaaaaataattctgtcattgttca |
| | aataagaatgtcatctgaaaataaactgccttacatgggaatgctcttatttgt |
| | caggtatattaaggaaacaaacatcaaaaatgacccaaatgaactcaaca |
| | atcttatcaagaagaattctgaggtggtaacctggaccccaagacctggag |
| | ccactcttgatctgggtaggatgctaaaggacgcgatcgcattt |
| | |
| 12 B201 vector | atgtctcctatgtctcatctaaatggatgaggtttgagagttcccatcacggc |
| | atggtggaaacgaatccgactaggagccataagttcacggcttcgatccct |
| | ggcctcgctcagggggttaaggatccggtgttgctgtgtgagctgtggtgtag |
| | gtcacagatgcggttcggatctggcgttgctgcggctgtggtgtaggctgg |
| | tggctgtagctccgatttgacccctagcctagggacctccatatgccgtgg |
| | gtatggccctaaaaagccaaataaaataaaataagtaaatggttgaggtttg |
| | acacagaaagtttatttatttatgtatttacttatctttttttttttttttttttttgtcttt |
| | ctgctatttcttgggctgctcccgcggcatatggaggttcccaggctaggg |
| | gtcgaattggagctacagccaccagcctacaccacagccgcagcaatgc |
| | cagatccgagccgcctctgtgacctacaccacagctcatggcaacgctgg |
| | atcgttaacccactgagcaagggctgggaccgaacccgcaacctcatggt |
| | tcctagtcggattcgttaaccactgcgccatgacgggaactcctacttatcta |
| | ttttttaaagcatatggaagttcccaggctaggggggttgaatcggagctgca |
| | actgccggcttacaccacagccagagcaacgccggatctgagcagtgtct |
| | gggacctacaccacagctcacagccacaccggatcctcaatccactgaat |
| | gaggccaggaatcaaacctgtgtcctcatggatactagtcagattcatttcc |
| | gctgagcaatgacaggaactcctgacacagaaattttagattaaaattgaa |
| | gatgagccccttccttttgtacgacctttgtgtgcagattttcgaggataagtc |
| | cttgagcttgaagtttagggtcatggatcctcataacagtttcctggcctgtg |
| | aggcttggatctcagtataaacagaagtgctggcagcagtagacacagca |
| | gcagctgttttcaggaacaaatactgggcacctgccttgtggacctgcctg |
| | actccaccactctcttgggtatccacaaagtggacccagaggttcagagca |
| | gccctgggatccaaattttttttaatttattttttatcttttattttttgtctttttcgaaa |
| | ttttagggctacacccatgagatatggaggttcccaggctaagggtccaat |
| | cggagctacaactgccggcctacaccacagctcatggcaatgctggatcc |
| | ttaacccgctgagcgaggccagggatcaaacccacaacctcatgattcct |
| | agttggattcgttaaccactgagccacgatgggaactccctgggatgcaaa |
| | ttttgtcatctagccctaggatgtagctatcatcctgatttgagaagagaggc |
| | agagtctcaggtggcttctctctcatgaatgcagagctaagggtggccaca |
| | cgtacttgagttcatccgatgcacacagcattgtgctaaaatattgaccattt |
| | ggccctttgctgacttttggtttgagggatatgaccttcatgagcatacaga |
| | ggataatatgtatgcatgtatgcatgtgtgtacacatgtgcgcatgcatgtat |
| | atacctgcataattatgtatttgtttatgtatgcaggtgcatgtgtatgtatatat |
| | ttattatttatttatttgggggccacacccatgacatttggaagttcctgggac |
| | agagattgaatcccagccacagctttgacctacgccatggacacagcaac |
| | actggattcttaacccctgtgccacagcgggaactcctagaagatagtatt |
| | tcatgatgatatttgactaaaaataggggtcaggctttgaagtttaaataaatt |
| | cgaccagatataatggccatccaggaagttatactttgccttgttcaaatttgg |
| | accacggggaaggtggttggcgacatgtaacagaaatctgactccagtgc |
| | aggtttcgctcccgtgacgggaagcccagaggtgggcagccctaaggct |
| | ggggctctgatttcatgatgctcttagcatcttgagtcccttccctcttcttgct |
| | tttatctcagcctcgggctgctgcaccttctgtctttgtggtgagtctacctatt |
| | ccacttagctcggcttcaggggtgtatttccacgacttcgttagagtaaggttg |
| | gggccagctgtgctctgccggcaggaggtgtgcttgcaggggccatgga |
| | tgtggccaggacctaatgtgacggtggggagcaggatggggatgaggat |
| | gtgaccacagagccttgggaaccacgtcatccacgtcatacactgagagc |
| | aggtggttctcatgcaggtgcatcagaatcccgaggacggcttgtccaaa |
| | cccagatggctgggcccaagccctgagctcccgatttgggaggccttgg |
| | ctgggcccgaaatctgccttcctgactagaccgagtgatgaatggtgttc |
| | atagacaagacatacactaacactggtcttgggggctccttgccacaccct |

TABLE 2-continued

Sequences

| SEQ ID NO: | Description | Sequence |
|---|---|---|

```
gaaggggtccgtgaaactgacggggccagagaaggtgctggttcctcca
tggaaggtctcagtgaggccattctgctgcccggctgggtcacgctgggg
gagtgagggtgcatcccctcctgggatctggtcaaaggcagattctgattc
tggaagcacggggtagggccagagatgccaccttctaacaagcccccag
gtgaagatgttgacctgggaccttatggtggggggtggcggagctcaag
gtggcagacacctccctctctctcaacctgtgtcacagcagggccatccta
ctggctctcgctcggccagagatggcgatgccagaacacactggggcag
ggtgtccacattttttgtcacttccactgagccctggggactgactcatttaaat
gacattctcaactctttggaaagaagctgggccagaaatggaaatggcag
caaacacttttttgggaaacaggaagccaatttttttttttcaatcatgattttccc
cagattcagagactgcttaactcccaatgaaatacttttagattacgagctaa
aataccgaaaagctgtcaagctcaagaccacaggaaaacagccgaaga
acaaacaccatgagaaaacagtcacagagtgcctctgcggcggatttcaa
gttccagacttccttgctgtcagctgtgtgtacttgtcccgcctgcagtagga
ccagctggggtttaagtctgtaccatggacactgctgccaggattctcctct
gcatctgctgacttccagctcttcagggccagctggccataggagcataaa
ctgacatccagttccaggaggcagcatctgtccccatggcctgcaggaca
ccagatcagtagaggcccccagggccacctttcctgtgggggcccttgaa
gggacccgggaaggctggatcttgctaaagcttccacaagtcccttccaa
aggagagtaaattctaaacagaagcttttgccagtgcttctctgggatctgg
cttcaggattattcctagtctgaaaagtcttcctggtggtttggacacgggca
aatgcttggtgggtgggctggctctggatgcaggtgagtggggtcggaa
gttctccctccttcccacaaagcttgacggagccaggggcacccgcggg
cctgtggatgggagaggggtttctggtgacggactcaagtcttggcagcc
cctgaccccagagcaggctccctccccacagctgctctccgtgagtccttc
acttgcccaagttcaagatgtacccagttctggagctgccaaaccatcctg
catcctgacgtcagccacccaagttctggggtagctggtctgccacccag
gtggatgaaaagaggccacatacctgcaccagcatctgcgaatctctgaa
gaacatcaataataaaaagacaactaacccgattaaaacacaggtagaga
atctgaacagacattcatcggaagaagaattacgactggccaaaaagctc
ataaaaagatggtcaaagtcattggtcagggaaatgtaaatcaaaccgcat
tgagataccatctcactccctctcggatggctggaatgaaaaaaaacctctt
ctttcctcccttcattgtcttggcacccttgtggaaattaattgactaaaattca
tgaaatacaaaaattttttaggagttcccgtcgtggctcagtggttaacaaatc
tgactaggaaccatgaggtttcaggttcgattcctggcctcactcagtgggt
tagggatctggtgttgccatgagctgtggtgtaggtcgcagacgcagctc
ggatcccgcattgctgtggctctggcgtaggccggcggctacagctctga
ttcaacctctagcctgggaatagcccaagaaatggcaaaaagaccaaaaa
aaaaaaaaaaaaaaaaactcgtttgagcatttttgcatgtgtacattgtccat
ttgtgtgccttccaagatttattttttggagtctcaactctgtcattgatttatgtct
ctccttaggccagaaccacactgttttggtgaccatggctttgtagtaaaattt
gaaatctgaaagtgtgagccctcctgttttgtttctcttctccatgattagtttg
gttattcagagtcccttgaatttccaggtgaatttttaggattagcaggaaaatt
tctgcagagatggcagcagagattttttaataggagttatgttgaatctggag
gttaatttcagttttgctaccttgactgtattaagtcttccagtctataagcataa
gatgtctttttatttacttaggtctttttaaaatttctttgggcactcccattgtggt
gcatcggaaatgaatccgactagtatccacaagaacacaggttcaatccct
ggcattgctcagtgggttaaggatcctgcattgccatgaagaactgtggtg
gaggccagcagctgcagctctgatttgacccctagcctgggaacttccata
tgccttgggtatggccctaaaaaagcaaactaagtaagtaagtaaataaata
aatgaataaataaaatttctttcaaaattgtaattttgtaattttttgtaattttcaga
gtgtacattttgcccttttcaatacattattcctacatattttattcttttttgatactat
tataaatgaaatttataattaattcatttatatgaatttcattttcaatttgcatattg
ctactacaatagaaatgcactttttaattatttttatggccataccatatatatat
gtgtgtgtgtgtatgtgtgtcatttttactgtacagcagaaattgacacaaca
ttgtaaatcaactacacttaaaaaatgaagaaataaccacctgtgattatggc
tactgtgttggacactttaggcatcccccccacccgtccccgccccacacc
cctgagtgctagtgacggatgttcccacccaggggggcctggagcctttatc
accagccatcgggaatcagaaccgtatctcacagtccccatgcctgtagc
acctggaattgtgcccttggactcgtgggtgttctgcttctcagtgggagaa
gcttaggttctaagtcagagcagggacagcccccatgtgctcaggaccca
gtgtgaaggggtctgcctcaggggacctgggggttacaagggtaagaga
aggtgttcatgttggaactagaagttcttttttcaccgctctgaagaaaaaagc
tgcctcccacccttggtacagctcttctgctaacagtgaatcaggcagaac
gtgttcaagaagtgacccagcctggtgggggccagacctgacccttgatg
gtccctcaacccctccgagggtcccgcccttcctttactgctttgttgtctgtc
ctgagaggtttggctaatgtcgaaccaagggtgtggctggtcctgtcccctt
tcctgtctcacgcacccacctctgaagtctctgtagctggttccagccggga
tctggagccactcccccgccccaggcccagtggtacagactcttgcaga
gtcgggggccctgactcagccccaccgccagcgggatgtcaggccag
cacccgccccactcccactgatctgggggggggtgtctttccttcctccttcc
aaaggagcctcagaccttcctgtggggcacggggcagtgggattcagg
aggctctgagtcagcaggccggcattgaggagtataaagggacccagt
tcctcccccttcacttgtggcttatcgccgccccaccctgccccaaggtca
```

TABLE 2-continued

Sequences

| SEQ ID NO: Description | Sequence |
|---|---| ctgcggtcagtacagtcctcagctgccagcaggtgcctgtctttacttgtga
ggccgccacgctctcctgtttctccaggtctgggctctgttggaagtgggg
gcccgaccccagggtaagatgggggatctgcgtgtcctgccctcagagg
cctcctcctcccccgcacccctaaccctttcagcccaacaaggctggagatc
tcccacatctttggcttcgttaagagttcaacagcgccgccaccggcatgt
cgctgagcagaggatggcacagggtgttaaaaaaaaaaaaaggttgcca
cactccgttcggttttgggcccaccctttcgcattcctggagcctgagtaag
cggataaggctgtgaaagtgacagattcctgccacctccttccagcgctca
tgcacagggaccgcccctcttcggtgtcctttgctgcacaagtgcatttgca
cattcctgtctcaatctggtttctcccccttaaaagatgggaatgtgacctgct
tggagcccctcgcctcgccagggcaccccatccgtcccttcaggggtgg
agatggactgtccctctgcaaggctggatgaactcagaccaaacaggcca
acttgctccccaaatacgcccacccctaccgggctgcagaaattcgcatgt
caccactgctgaagggtgaccttgcagccctgagagcatccccatgactt
gcccaccagatgaagtctggttgtggcaggtcgcgctcagggactcccg
ggtcccacctgggggtgggaggatcctcctttgctcgtggtcgcccaga
cacgccctcctttccaagcgccagtctccagagctccgtgcccggcgga
ggcggtctggctctctctccttgcccctctctccttgcccctagcagcccttc
tcctaaacctctgagcagcgggcacctcctcccgaggccctgggctaag
tccccacccttcatctcaagccttcctccttgactccctcttcccagagttcct
tgaaataggtggtaagtacacaccgatgacggaaaacaaagactaagag
gttaaagagggctgaggattacggccccggtagggctgcgcgcgaggg
ggtcgagtggccgggcggtcccgtcgccgggcagacagaggtgcggtt
ctcccgggcgcctgcgctgccggccccgcccggagccctcccagccgg
cgcccagtttactcatcccggagaggtgatcccgggcgcgagggcggg
cgcagggcgtccggagaacccagtaatccgagaatgcagcatcagccct
tcccaccaggcacttccttccttttcccgaacgtccagggagggggggccg
cgcacttataaaactcgggccggacccgccggcctgtcagaggctgcctc
gctggggctgcgcgcggcggccggacacatctggtccgagaccaacgc
gagcgactgtcactggcagctccctgcgcctctcagccccggccgggcc
cctgcgcttggcgtgctgacaccatgcttggggtcctggtccttggcgcgc
tggccctggccggcctggggttccccgcaccgcagagccgcagccgg
gtggcagccagtgcgtcgagcacgactgcttcgcgctctacccgggccc
cgcgaccttcctcaatgccagtcagatctgcgacggactgcggggccac
ctaatgacagtgcgctcctcggtggctgccgatgtcatttccttgctactgaa
cggcgacggcggcgttggccgccggcgcctctggatcggcctgcagct
gccaccggctgcggcgaccccaagcgcctcgggccctgcgcggctt
ccagtgggttacgggagacaacaacaccagctatagcaggtgggcacg
gctcgacctcaatgggctcccctctgcggcccgttgtgcgtcgctgtctc
cgctgctgaggccactgtgcccagcgagccgatctgggaggagcagca
gtgcgaagtgaaggccgatggcttcctctgcgagttccacttcccagccac
ctgcaggccactggctgtggagcccggcgccgcggctgccgccgtctc
gatcacctacggcaccccgttcgcggcccgcggagcggacttccaggc
gctgccggtgggcagctccgccgcggtggctcccctcggcttacagcta
atgtgcaccgcgccgcccggagcggtccaggggcactgggccaggga
ggcgccgggcgcttgggactgcagcgtggagaacggcggctgcgagc
acgcgtgcaatgcgatccctggggctccccgctgccagtgcccagccgg
cgccgccctgcaggcagacgggcgctcctgcaccgcatccgcgacgca
gtcctgcaacgacctctgcgagcacttctgcgttcccaaccccgaccagc
cgggctcctactcgtgcatgtgcgagaccggctaccggctggcggccga
ccaacaccggtgcgaggacgtggatgactgcatactggagcccagtccg
tgtccgcagcgctgtgtcaacacacagggtggcttcgagtgccactgcta
ccctaactacgacctggtggacggcgagtgtgtggagcccgtggacccg
tgcttcagagccaactgcgagtaccagtgccagcccctgaaccaaactag
ctacctctgcgtctgcgccgagggcttcgcgcccattccccacgagccgc
acaggtgccagatgtttttgcaaccagactgcctgtccagccgactgcgac
cccaacacccaggctagctgtgagtgccctgaaggctacatcctggacga
cggtttcatctgcacggacatcgacgagtgcgaaaacggcggcttctgct
ccgggggtgtgccacaacctccccggtaccttcgagtgcatctgcgggccc
gactcggcccttgcccgccacattggcaccgactgtgactccggcaaggt
ggacggtggcgacagcggctctggcgagcccccgcccagcccgacgc
ccggctccaccttgactcctccggccgtggggctcgtgcattcgggcttgc
tcataggcatctccatcgcgagcctgtgcctggtggtggcgctttttggcgct
cctctgccacctgcgcaagaagcagggcgccgccagggccaagatgga
gtacaagtgcgcggcccccttccaaggaggtagtgctgcagcacgtgcgg
accgagcggacgccgcagagactcggatccggagagggcagaggaa
gtcttctaacatgcggtgacgtggaggagaatcccggccctatgttgacaa
cattgctgccgatactgctgctgtctggctgggccttttgtagccaagacgc
ctcagatggcctccaaagacttcatatgctccagatctcctacttccgcgac
ccctatcacgtgtggtaccagggcaacgcgtcgctggggggacacctaa
cgcacgtgctggaaggcccagacaccaacaccacgatcattcagctgca
gcccttgcaggagcccgagagctgggcgcgcacgcagagtggcctgca
gtcctacctgctccagttccacggcctcgtgcgcctggtgcaccaggagc
ggaccttggcctttcctctgaccatccgctgcttcctgggctgtgagctgcc TABLE 2-continued Sequences SEQ
ID
NO: Description                Sequence

```
                              tcccgagggctctagagcccatgtcttcttcgaagtggctgtgaatgggag
                              ctcctttgtgagtttccggccggagagagccttgtggcaggcagacaccc
                              aggtcacctccggagtggtcaccttcaccctgcagcagctcaatgcctaca
                              accgcactcggtatgaactgcgggaattcctggaggacacctgtgtgcag
                              tatgtgcagaaacatatttccgcggaaaacacgaaagggagccaaacaa
                              gccgctcctacacttcgctggtcctgggcgtcctggtgggcagtttcatcat
                              tgctggtgtggctgtaggcatcttcctgtgcacaggtggacggcgatgttg
                              agcgcggccgcttcccttagtgagggttaatgcttcgagcagacatgata
                              agatacattgatgagtttggacaaaccacaactagaatgcagtgaaaaaaa
                              tgctttatttgtgaaatttgtgatgctattgctttatttgtaaccattataagctgc
                              aataaacaagttaacaacaacaattgcattcattttatgtttcaggttcaggg
                              ggagatgtgggaggttttttaaagcaagtaaaacctctacaaatgtggtaaa
                              atccgataaggatcgatgggacagcccccccccaaagcccccagggat
                              gtaattacgtccctcccccgctagggcagcagcgagccgcccggggctc
                              cggtccggtccggcggctcccccgcatccccgagccggcagcgtgcggg
                              gacagcccgggcacggggaaggtggcacgggatcgctttcctctgaac
                              gcttctcgctgctctttgagcctgcagacacctgggggggatacggggaaa
                              atctagtgggacagcccccccccaaagcccccagggatgtaattacgtcc
                              ctcccccgctagggcagcagcgagccgcccggggctccggtccggtcc
                              ggcgctcccccgcatccccgagccggcagcgtgcggggacagcccgg
                              gcacggggaaggtggcacgggatcgctttcctctgaacgcttctcgctgct
                              ctttgagcctgcagacacctggggggatacggggaaaaatcgatgggac
                              agccccccccaaagcccccagggatgtaattacgtccctcccccgctag
                              ggcagcagcgagccgcccggggctccggtccggtccggcgctcccccc
                              gcatccccgagccggcagcgtgcggggacagcccgggcacggggaa
                              ggtggcacgggatcgctttcctctgaacgcttctcgctgctctttgagcctg
                              cagacacctgggggggatacggggaaaatctagtgggacagcccccccc
                              caaagcccccagggatgtaattacgtccctcccccgctagggcagcagc
                              gagccgcccggggctccggtccggtccggcgctcccccgcatccccga
                              gccggcagcgtgcggggacagcccgggcacggggaaggtggcacgg
                              gatcgctttcctctgaacgcttctcgctgctctttgagcctgcagacacctgg
                              ggggatacggggaaaaatcgatagcgataaggatccactagttattaata
                              gtaatcaattacggggtcattagttcatagcccatatatggagttccgcgtta
                              cataacttacggtaaatggcccgcctggctgaccgcccaacgacccccg
                              cccattgacgtcaataatgacgtatgttcccatagtaacgccaatagggact
                              ttccattgacgtcaatgggtggagtatttacggtaaactgcccacttggcag
                              tacatcaagtgtatcatatgccaagtacgccccctattgacgtcaatgacgg
                              taaatggcccgcctggcattatgcccagtacatgaccttatgggactttcct
                              acttggcagtacatctacgtattagtcatcgctattaccatgggtcgaggtga
                              gccccacgttctgcttcactctccccatctcccccccctccccaccccccaat
                              tttgtatttatttatttttttaattattttgtgcagcgatggggcggggggggggg
                              gggcgcgcgccaggcggggcggggcggggcgaggggcggggcg
                              gggcgaggcggagaggtgcggcggcagccaatcagagcggcgcgct
                              ccgaaagtttccttttatggcgaggcggcggcggcggcggcccctataaaa
                              agcgaagcgcgcggcgggcgggagtcgctgcgttgccttcgccccgtg
                              ccccgctccgcgccgcctcgcgccgcccgccccggctctgactgaccg
                              cgttactcccacaggtgagcgggcgggacggcccttctcctccgggctgt
                              aattagcgcttggtttaatgacggctcgtttctttttctgtggctgcgtgaaagc
                              cttaaagggctccgggagggccctttgtgcggggggagcggctcggg
                              gggtgcgtgcgtgtgtgtgtgcgtggggagcgccgcgtgcggcccgcg
                              ctgcccggcggctgtgagcgctgcgggcgcggcgcggggctttgtgcg
                              ctccgcgtgtgcgcgaggggagcgcggccgggggcggtgccccgcg
                              gtgcggggggctgcgaggggaacaaaggctgcgtgcggggtgtgtg
                              cgtggggggtgagcaggggtgtgggcgcggcggtcgggctgtaac
                              ccccccctgcacccccctccccgagttgctgagcacggcccggcttcgg
                              gtgcggggctccgtgcggggcgtggcgcggggctcgccgtgccgggc
                              gggggtggcggcaggtggggtgccgggcggggcgggccgcctc
                              gggccggggagggctcggggagggcgcggcggccccggagcgc
                              cggcggctgtcgaggcgcggcgagccgcagccattgccttttatggtaat
                              cgtgcgagagggcgcagggacttcctttgtcccaaatctggcggagccg
                              aaatctgggaggcgccgccgcaccccctctagcgggcgcgggcgaag
                              cggtgcggcgcggcaggaaggaaatgggcggggagggccttcgtgc
                              gtcgccgcgccgccgtcccccttctccatctccagcctcggggctgccgca
                              gggggacggctgccttcgggggggacggggcagggcggggttcggct
                              tctggcgtgtgaccggcgggctctagagcctctgctaaccatgttcatgcctt
                              cttcttttttcctacagctcctgggcaacgtgctggttgttgtgctgtctcatcat
                              tttggcaaagaattccgctgcgactcggcggagtcccggcggcgcgtcct
                              tgttctaacccggcgcgccctcaggatgtggccctggtagcggcgctgtt
                              gctgggctcggcgtgctgcgggatcagctcagctactatttaataaaacaa
                              atctgtagaattcacgtttttgtaatgacactgtcgtcattccatgctttgttacta
                              atatggaggcacaaaacactactgaagtatacgtaaagtggaaatttaaag
                              gaagagatatttacacctttgatggagctctaaacaagtccactgtccccac
                              tgactttagtagtgcaaaaattgaagtctcacaattactaaaaggagatgcct
                              ctttgaagatggataagagtgatgctgtctcacacacaggaaactacacttg
```

TABLE 2-continued

Sequences

| SEQ ID NO: | Description | Sequence |
|---|---|---| tgaagtaacagaattaaccagagaaggtgaaacgatcatcgagctaaaat
atcgtgttgtttcatggttttctccaaatgaaaatattcttattgttattttcccaat
ttttgctatactcctgttctggggacagtttggtattaaaacacttaaatataga
tccggtggtatggatgagaaaacaattgctttacttgttgctggactagtgat
cactgtcattgtcattgttggagccattcttttcgtcccaggtgaatattcatta
aagaatgctactggccttggtttaattgtgacttctacagggatattaatatta
cttcactactatgtgtttagtacagcgattggattaacctccttcgtcattgcca
tattggttattcaggtgatagcctatatcctcgctgtggttggactgagtctct
gtattgcggcgtgtataccaatgcatggccctcttctgatttcaggtttgagta
tcttagctctagcacaattacttggactagtttatatgaaatttgtggcttccaa
tcagaagactatacaacctcctaggaaagctgtagaggaacccttaatgc
attcaaagaatcaaaaggaatgatgaatgatgaaggatccggagccacga
acttctctctgttaaagcaagcaggagacgtggaagaaaaccccggtcct
atggagcgtccgcaacccgacagcatgccccaggatttgtcagaggccc
tgaaggaggccaccaaggaggtgcacacccaggcagagaatgctgagt
tcatgaggaactttcagaagggccaggtgacccgagacggcttcaagctg
gtgatggcctccctgtaccacatctatgtggccctggaggaggagattgag
cgcaacaaggagagcccagtcttcgcccctgtctacttcccagaagagct
gcaccgcaaggctgccctggagcaggacctggccttctggtacgggccc
cgctggcaggaggtcatcccctacacaccagccatgcagcgctatgtgaa
gcggctccacgaggtggggcgcacagagcccgagctgctggtggccca
cgcctacacccgctacctgggtgacctgtctgggggccaggtgctcaaaa
agattgcccagaaagccctggacctgcccagctctggcgagggcctggc
cttcttcaccttccccaacattgccagtgccaccaagttcaagcagctctac
cgctcccgcatgaactccctggagatgactcccgcagtcaggcagaggg
tgatagaagaggccaagactgcgttcctgctcaacatccagctctttgagg
agttgcaggagctgctgacccatgacaccaaggaccagagcccctcacg
ggcaccagggcttcgccagcgggccagcaacaaagtgcaagattctgcc
cccgtggagactcccagagggaagcccccactcaacacccgctcccag
gctccgcttctccgatgggtccttacactcagctttctggtggcgacagttg
ctgtagggctttatgccatgtgagcggcgcgccggcaccggtaccaagct
taagagcgctagctggccagacatgataagatacattgatgagtttggaca
aaccacaactagaatgcagtgaaaaaaatgctttatttgtgaaatttgtgatg
ctattgctttatttgtaaccattataagctgcaataaacaagttaacaacaaca
attgcattcattttatgtttcaggttcaggggggaggtgtgggaggtttttttaaa
gcaagtaaaacctctacaaatgtggtatggaattggagcccactgtgttca
tcttacagatggaaatactgacattcagaggagttagttaacttgcctaggtg
attcagctaataagtgcaagaaagatttcaatccaaggtgatttgattctgaa
gcctgtgctaatcacattacaccaagctacaacttcatttataaataataagtc
agcttcaagggcctttcaggtgtcctgcacttctacaagctgtgccatttag
tgaacacaaaatgagccttctgatgaagtagtcttttcattatttcagatattag
aacactaaaattcttagctgccagctgattgaaggctgggacaaaattcaa
acatgcatctacaacaatatatatctcaatgttagtctccaaattctattgactt
caactcaagagaatataaagagctagtctttatacactctttaaggtatgatg
ggtcccgatttttccccgtatcccccaggtgtctgcaggctcaaagagca
gcgagaagcgttcagaggaaagcgatcccgtgccaccttccccgtgccc
gggctgtccccgcacgctgccggctcggggatgcgggggagcgccgg
accggaccggagcccgggcggctcgctgctgccctagcgggggagg
gacgtaattacatccctgggggctttggggggggggctgtcccactagattt
tccccgtatcccccaggtgtctgcaggctcaaagagcagcgagaagcg
ttcagaggaaagcgatcccgtgccaccttccccgtgcccgggctgtcccc
gcacgctgccggctcggggatgcgggggagcgccggaccggaccgg
agccccgggcggctcgctgctgccctagcggggggagggacgtaattac
atccctgggggctttgggggggggctgtcccatcggatcttctagtcctgc
aggagtcaatgggaaaaacccattggagccaagtacactgactcaatagg
gactttccattgggttttgcccagtacataaggtcaataggggggtgagtcaa
caggaaagtcccattggagccaagtacattgagtcaataggggactttccaa
tgggttttgcccagtacataaggtcaatgggaggtaagccaatgggtttttc
ccattactgacatgtatacgcgtcgacgtcggcgcgttcagcctaaagcttt
tttcccgtatcccccaggtgtctgcaggctcaaagagcagcgagaagc
gttcagaggaaagcgatcccgtgccaccttccccgtgcccgggctgtccc
cgcacgctgccggctcggggatgcgggggagcgccggaccggaccg
gagccccgggcggctcgctgctgccctagcggggggagggacgtaatta
catccctgggggctttggggggggggctgtccctgcgggccgcgaattcgta
atcatggtcatagctgtttcctgtgtgaaattgttatccgctcacaattccaca
caacatacgagccggaagcataaagtgtaaagcctggggtgcctaatga
gtgagctaactcacattaattgcgttgcgctcactgcccgctttccagtcgg
gaaacctgtcgtgccaggggtctagccgcggtctaggaagctttctaggg
tacctctagggatccactagttattaatagtaatcaattacggggtcattagtt
catagcccatatatggagttccgcgttacataacttacggtaaatggcccgc
ctggctgaccgcccaacgacccccgcccattgacgtcaataatgacgtat
gttcccatagtaacgccaataggga cttt ccattgacgtcaatgggtggagt
atttacggtaaactgcccacttggcagtacatcaagtgtatcatatgccaagt
acgccccctattgacgtcaatgacggtaaatggcccgcctggcattatgcc TABLE 2-continued Sequences

| SEQ ID NO: Description | Sequence |
|---|---|

```
cagtacatgaccttatgggactttcctacttggcagtacatctacgtattagtc
atcgctattaccatgggtcgaggtgagccccacgttctgcttcactctcccc
atctcccccccctccccacccccaattttgtatttatttatttttttaattattttgtg
cagcgatgggggcgggggggggggggggcgcgcgccaggcggggcg
gggcggggcgaggggcggggcggggcgaggcggagaggtgcggc
ggcagccaatcagagcggcgcgctccgaaagtttccttttatggcgaggc
ggcggcggcggcggccctataaaaagcgaagcgcgcggcgggcggg
agtcgctgcgttgccttcgccccgtgccccgctccgcgccgcctcgcgcc
gcccgccccggctctgactgaccgcgttactcccacaggtgagcgggcg
ggacggcccttctcctccgggctgtaattagcgcttggtttaatgacggctc
gtttcttttctgtggctgcgtgaaagccttaaagggctccgggagggccctt
tgtgcggggggggagcggctcgggggggtgcgtgcgtgtgtgtgtgcgtg
gggagcgccgcgtgcggcccgcgctgcccggcggctgtgagcgctgc
gggcgcggcgcgggggctttgtgcgctccgcgtgtgcgcgagggggagc
gcggccggggcgggtgccccgcggtgggggggggctgcgaggggaa
caaaggctgcgtgcggggtgtgtgcgtggggggggtgagcaggggggtgt
gggcgcggcggtcgggctgtaaccccccccctgcaccccccctccccgagt
tgctgagcacggcccggcttcgggtgcggggctccgtgcggggcgtgg
cgcgggggctcgccgtgccgggcgggggtggcggcaggtgggggtg
ccgggcggggcggggccgcctcgggccggggagggctcgggggag
gggcgcggcggccccggagcgccggcggctgtcgaggcgcggcgag
ccgcagccattgccttttatggtaatcgtgcgagagggcgcaggggacttcc
tttgtcccaaatctggcggagccgaaatctgggaggcgccgccgcaccc
cctctagcgggcgcgggcgaagcggtgcggcgccggcaggaaggaaa
tgggcggggagggccttcgtgcgtcgccgcgccgccgtcccccttctccat
ctccagcctcggggctgccgcaggggggacggctgccttcggggggggac
ggggcagggcggggttcggcttctggcgtgtgaccggcggctctagag
cctctgctaaccatgttcatgccttcttctttttcctacagctcctgggcaacgt
gctggttgttgtgctgtctcatcattttggcaaagaattccgctgcgactcgg
cggagtcccggcggcgcgtccttgttctaacccggcgcgccctcaggat
ggagcctcccggccgccgcgagtgtcccttttccttcctggcgcctttcctgg
gttgcttctggcggccatggtgttgctgctgtactccttctccgatgcctgtg
aggagccaccaacatttgaagctatggagctcattggtaaaccaaaaccct
actatgagattggtgaacgagtagattataagtgtaaaaaaggatacttctat
atacctcctcttgccacccatactatttgtgatcggaatcatacatggctacct
gtctcagatgacgcctgttatagagaaacatgtccatatatacgggatccttt
aaatggccaagcagtccctgcaaatgggacttacgagtttggttatcagat
gcactttatttgtaatgagggttattacttaattggtgaagaaattctatattgtg
aacttaaaggatcagtagcaatttggagcggtaagcccccaatatgtgaaa
aggtttttgtgtacaccacctccaaaaataaaaaatggaaaacacacctttag
tgaagtagaagtatttgagtatcttgatgcagtaacttatagttgtgatcctgc
acctggaccagatccattttcacttattggagagagcacgatttattgtggtg
acaattcagtgtggagtcgtgctgctccagagtgtaaagtggtcaaatgtc
gatttccagtagtcgaaaatggaaaacagatatcaggatttggaaaaaatt
ttactacaaagcaacagttatgtttgaatgcgataagggtttttacctcgatg
gcagcgacacaattgtctgtgacagtaacagtacttgggatcccccagttc
caaagtgtcttaaagtgctgcctccatctagtacaaaacctccagctttgagt
cattcagtgtcgacttcttccactacaaaatctccagcgtccagtgcctcag
gtcctaggcctacttacaagcctccagtctcaaattatccaggatatcctaaa
cctgaggaaggaatacttgacagtttggatgtttgggtcattgctgtgattgt
tattgccatagttgttggagttgcagtaatttgtgttgtcccgtacagatatctt
caaaggaggaagaagaaaggcacatacctaactgatgagacccacaga
gaagtaaaatttacttctctcggatccggagccacgaacttctctctgttaaa
gcaagcaggagacgtggaagaaaaccccggtcctatgaccgtcgcgcg
gccgagcgtgcccgcggcgctgcccctcctcggggagctgccccggct
gctgctgctggtgctgttgtgcctgccggccgtgtggggtgactgtggcct
tcccccagatgtacctaatgcccagccagctttggaaggccgtacaagtttt
cccgaggatactgtaataacgtacaaatgtgaagaaagctttgtgaaaattc
ctggcgagaaggactcagtgatctgccttaagggcagtcaatggtcagat
attgaagagttctgcaatcgtagctgcgaggtgccaacaaggctaaattct
gcatccctcaaacagccttatatcactcagaattattttccagtcggtactgtt
gtggaatatgagtgccgtccaggttacagaagagaaccttctctatcacca
aaactaacttgccttcagaatttaaaatggtccacagcagtcgaattttgtaa
aaagaaatcatgccctaatccgggagaaatacgaaatggtcagattgatgt
accaggtggcatattatttggtgcaaccatctccttctcatgtaacacagggt
acaaattatttggctcgacttctagttttttgtcttatttcaggcagctctgtccag
tggagtgacccgttgccagagtgcagagaaatttattgcccagcaccacc
acaaattgacaatggaataattcaaggggaacgtgaccattatggatatag
acagtctgtaacgtatgcatgtaataaaggattcaccatgattggagagcac
tctatttattgtactgtgaataatgatgaaggagagtggagtggcccaccac
ctgaatgcagaggaaaatctctaacttccaaggtcccaccaacagttcaga
aacctaccacagtaaatgttccaactacagaagtctcaccaacttctcagaa
aaccaccacaaaaaccaccacaccaaatgctcaagcaacacggagtaca
cctgtttccaggacaaccaagcattttcatgaaacaaccccaaataaagga
```

TABLE 2-continued

Sequences

```
SEQ
ID
NO: Description          Sequence agtggaaccacttcaggtactacccgtcttctatctgggcacacgtgtttca
                        cgttgacaggtttgcttgggacgctagtaaccatgggcttgctgacttagg
                        gcgcgccggcaccggtaccaagcttaagagcgctagctggccagacat
                        gataagatacattgatgagtttggacaaaccacaactagaatgcagtgaaa
                        aaaatgctttatttgtgaaatttgtgatgctattgctttatttgtaaccattataag
                        ctgcaataaacaagttaacaacaacaattgcattcattttatgtttcaggttca
                        gggggaggtgtgggaggttttttaaagcaagtaaaacctctacaaatgtgg
                        tatggaattggagccccactgtgttcatcttacagatggaaatactgacattc
                        agaggagttagttaacttgcctaggtgattcagctaataagtgcaagaaag
                        atttcaatccaaggtgatttgattctgaagcctgtgctaatcacattacaccaa
                        gctacaacttcatttataaataataagtcagctttcaagggcctttcaggtgtc
                        ctgcacttctacaagctgtgccatttagtgaacacaaaatgagccttctgatg
                        aagtagtcttttcattatttcagatattagaacactaaaattcttagctgccagc
                        tgattgaaggctgggacaaaattcaaacatgcatctacaacaatatatatct
                        caatgttagtctccaaattctattgacttcaactcaagagaatataaagagct
                        agtctttatacactctttaaggtatgatatcatctggaaagtaacaaaattgat
                        gcaaatttgaatgaactttatcatggtgtatttacacaatgtgtttcttctccctg
                        caatgtatttctttctctaattccttccatttgatctttcatacacaatctggttctg
                        atgtatgttttttggatgcacttttcaactccaaaagacagagctagttactttc
                        ttcctggtgctccaagcactgtatttgtatctgtattcaagccctttgcaatatt
                        gtactggatcattatttcacctctaggatggcttccccaggcaacttgtgttca
                        cccagagactacattttgtatcttgttgacctttgaacttccaccagtgtctaa
                        aaataatatgtatgcaaaattacttgctatgagaatgtataattaaacaatata
                        aaaaggagaagcaaggagagaaacacaggtgtgtatttgtgtttgtgtgct
                        taaaaggcagtgtggaaaaggaagaaatgccatttatagtgaggagacaa
                        agttatattacctcttatctggcttttaaggagattttgctgagctaaaaatcct
                        atattcatagaaaagccttacctgagttgccaatacctcaattctaaaataca
                        gcatagcaaaactttaacctccaaatcaagcctctacttgaatccttttctga
                        gggatgaataaggcataggcatcaggggctgttgccaatgtgcattagct
                        gtttgcagcctcaccttctttcatggagtttaagatatagtgtattttcccaagg
                        tttgaactagctcttcatttctttatgttttaaatgcactgacctcccacattccct
                        ttttagtaaaatattcagaaataaatttatcatctggaaagtaacaaaattgatg
                        caaatttgaatgaactttatcatggtgtatttacacaatgtgtttcttctccctgc
                        aatgtatttctttctctaattccttccatttgatctttcatacacaatctggttctga
                        tgtatgttttttggatgcacttttcaactccaaaagacagagctagttactttctt
                        cctggtgctccaagcactgtatttgtatctgtattcaagccctttgcaatattgt
                        actggatcattatttcacctctaggatggcttccccaggcaacttgtgttcac
                        ccagagactacattttgtatcttgttgacctttgaacttccaccagtgtctaaa
                        aataatatgtatgcaaaattacttgctatgagaatgtataattaaacaatataa
                        aaaggagaagcaaggagagaaacacaggtgtgtatttgtgtttgtgtgctt
                        aaaaggcagtgtggaaaaggaagaaatgccatttatagtgaggagacaa
                        agttatattacctcttatctggcttttaaggagattttgctgagctaaaaatcct
                        atattcatagaaaagccttacctgagttgccaatacctcaattctaaaataca
                        gcatagcaaaactttaacctccaaatcaagcctctacttgaatccttttctga
                        gggatgaataaggcataggcatcaggggctgttgccaatgtgcattagct
                        gtttgcagcctcaccttctttcatggagtttaagatatagtgtattttcccaagg
                        tttgaactagctcttcatttctttatgtttaaatgcactgacctcccacattccct
                        ttttagtaaaatattcagaaataaatttatcccggcttgtcgacgacggatcatc
                        tggaaagtaacaaaattgatgcaaatttgaatgaactttatcatggtgtattta
                        cacaatgtgtttcttctccctgcaatgtatttctttctctattccttccatttgatct
                        ttcatacacaatctggttctgatgtatgttttttggatgcacttttcaactccaaa
                        agacagagctagttactttcttcctggtgctccaagcactgtatttgtatctgt
                        attcaagccctttgcaatattgtactggatcattatttcacctctaggatggctt
                        ccccaggcaacttgtgttcacccagagactacattttgtatcttgttgacctttt
                        gaacttccaccagtgtctaaaaataatatgtatgcaaaattacttgctatgag
                        aatgtataattaaacaatataaaaaggagaagcaaggagagaaacacag
                        gtgtgtatttgtgtttgtgtgcttaaaaggcagtgtggaaaaggaagaaatg
                        ccatttatagtgaggagacaaagttatattacctcttatctggcttttaaggag
                        attttgctgagctaaaaatcctatattcatagaaaagccttacctgagttgcca
                        atacctcaattctaaaatacagcatagcaaaactttaacctccaaatcaagc
                        ctctacttgaatccttttctgagggatgaataaggcataggcatcaggggct
                        gttgccaatgtgcattagctgtttgcagcctcaccttctttcatggagtttaag
                        atatagtgtattttcccaaggtttgaactagctcttcatttctttatgtttttaaatg
                        cactgacctcccacattccctttttagtaaaatattcagaaataaatttatcccg
                        gcttgtcgacgcgtccgtcgtcaggatcatccatcaggacatagcgttgg
                        ctaccgtgatattgctgaagagcttggcggcgaatgggctgaccgcttcc
                        tcgtgctttacggtatcgccgctcccgattcgcagcgcatcgccttctatcg
                        ccttcttgacgagttcttctgagggggatcaattctctagagctcgctgatcag
                        cctcgactgtgccttctagttgccagccatctgttgtttgcccctcccccgtg
                        ccttccttgaccctggaaggtgccactcccactgtcctttcctaataaaatga
                        ggaaattgcatcgcattgtctgagtaggtgtcattctattctgggggtggg
                        gtggggcaggacagcaaggggggaggattgggaagacaatagcaggca
                        tgctggggatgcggtgggctctatggcttctgaggcggaaagaaccagct
                        ggggggcgcgcacctcgaccatctccaggatgccttttgatagagctgggtc
```

TABLE 2-continued

<div align="center">Sequences</div>

SEQ
ID
NO: Description                Sequence

```
                              ctctgcgttcctttaaagtgtttgagatcaagtccgagaagaggtggcaagc
                              gatcgcgacatatttaaatcgcgctagtttaaaatacatcattgcaatgaaaa
                              taaatgttttttattaggcagaatccagatgctcaaggcccttcataatatccc
                              ccagtttagtagttggacttagggaacaaaggaacctttaatagaaattgga
                              cagcaagaaagctctagctttagaagaactcatcaagaagtctgtagaag
                              gcaattctctgggagtcaggggctgcaatgccatagagcactaggaacct
                              gtctgcccactctcccctagctcttctgctatgtccctggttgctagggcaa
                              tgtcctggtacctgtcagccactcccagcctgccacagtctatgaagccag
                              agaaccttccattttcaaccatgatgttgggaaggcaggcatccccatgagt
                              caccactaggtcctcaccatctggcatggatgccttgagcctggcaaatag
                              ttcagcaggggccaggccctggtgttcttcatccaagtcatcttggtccacc
                              aggccagcctccatcctggttctggccctctctatcctgtgcttggcctggt
                              ggtcaaaggggcaggtggctgggtcaagggtgtggagtcttctcatggc
                              atcagccatgattgacactttctcagctggagctaggtgagaggaaagga
                              ggtcctgcccaggcacctcacctagtaggagccagtcccttccagcttctg
                              tgaccacatcaaggacagctgcacaggggaccccagttgttgccaacca
                              ggagagtctggcagcctcatcctggagctcattgagagccccactgaggt
                              ctgtctttacaaaaaggactggcctgccttgggctgaaagtctgaaaactg
                              ctgcatcagagcaaccaatggtctgctgtgcccagtcatagccaaacagtc
                              tctcaacccaggcagctggagaacctgcatgtaggccatcttgttcaatcat
                              gatggctcctcctgtcaggagaggaaagagaagaaggttagtacaattgc
                              tatagtgagttgtattatactatgcttatgattaattgtcaaactagggctgcag
                              ggttcatagtgccacttttcctgcactgccccatctcctgcccaccctttccc
                              aggcatagacagtcagtgacttaccaaactcacaggagggagaaggcag
                              aagctttttgcaaaagcctaggctcatgagacaataaccctgataaatgctt
                              caataatattgaaaaaggaagagtaccaggtatgagtattcaacatttccgt
                              gtcgcccttattcccttttttgcggcattttgccttcctgttttttgctcacccaga
                              aacgctggtgaaagtaaaagatgctgaagatcagttgggtgcacgagtgg
                              gttacatcgaactggatctcaacagcggtaagatccttgagagtttttcgccc
                              cgaagaacgttttccaatgatgagcacttttaaagttctgctatgtggcgcg
                              gtattatcccgtattgacgccgggcaagagcaactcggtcgccgcataca
                              ctattctcagaatgacttggttgagtactcaccagtcacagaaaagcatctta
                              cggatggcatgacagtaagagaattatgcagtgctgccataaccatgagt
                              gataacactgcggccaacttacttctgacaacgatcggaggaccgaagga
                              gctaaccgcttttttgcacaacatgggggatcatgtaactcgccttgatcgtt
                              gggaaccggagctgaatgaagccataccaaacgacgagcgtgacacca
                              cgatgcctgtagcaatggcaacaacgttgcgcaaactattaactggcgaa
                              ctacttactctagcttcccggcaacaattaatagactggatggaggcggata
                              aagttgcaggaccacttctgcgctcggcccttccggctggctggtttattgc
                              tgataaatctggagccggtgagcgtgggtctcgcggtatcattgcagcact
                              ggggccagatggtaagccctcccgtatcgtagttatctacacgacgggga
                              gtcaggcaactatggatgaacgaaatagacagatcgctgagataggtgcc
                              tcactgattaagcattggtaactgtcagaccaagtttactcatatatactttag
                              attgatttaaaacttcattttttaatttaaaaggatctaggtgaagatcctttttgat
                              aatctcatgaccaaaatcccttaacgtgagttttcgttccactgagcgtcaga
                              ccccgtagaaaagatcaaaggatcttcttgagatcctttttttctgcgcgtaat
                              ctgctgcttgcaaacaaaaaaaccaccgctaccagcggtggtttgtttgcc
                              ggatcaagagctaccaactctttttccgaaggtaactggcttcagcagagc
                              gcagataccaaatactgttcttctagtgtagccgtagttaggccaccacttca
                              agaactctgtagcaccgcctacatacctcgctctgctaatcctgttaccagt
                              ggctgctgccagtggcgataagtcgtgtcttaccgggttggactcaagac
                              gatagttaccggataaggcgcagcggtcgggctgaacggggggttcgtg
                              cacacagcccagcttgggagcgaacgacctacaccgaactgagataccta
                              cagcgtgagctatgagaaagcgccacgcttcccgaagggagaaaggcg
                              gacaggtatccggtaagcggcagggtcggaacaggagagcgcacgag
                              ggagcttccagggggaaacgcctggtatctttatagtcctgtcgggtttcgc
                              cacctctgacttgagcgtcgatttttgtgatgctcgtcagggggggcggagc
                              ctatggaaaaacgccagcaacgcggcctttttacggttcctggccttttgct
                              ggccttttgctcacatggctcgacagatttaattaacaagaccgacctgtcc
                              ggtgccctgaatgaactgcaggacgaggcagcgcggctatcgtggctgg
                              ccacgacgggcgttccttgcgcagctgtgctcgacgttgtcactgaagcg
                              ggaagggactggctgctattgggcgaagtgccggggcaggatctcctgt
                              catctcaccttgctcctgccgagaaagtatccatcatggctgatgcaatgcg
                              gcggctgcatacgcttgatccggctacctgcccattcgaccaccaagcga
                              aacatcgcatcgagcgagcacgtactcggatggaagccggtcttgtcgat
                              caggatgatctggacgaagagcatcaggggctcgcgccagccgaactgt
                              tcgccaggctcaaggcgcgcatgcccgacggcgaggatctcgtcgtgac
                              ccatggcgatgcctgcttgccgaatatcatggtggaaaatggccgcttttct
                              ggattcatcgactgtggccggctgggtgtggcggatcgctggcctcgatg
                              gccgtgatacggcctgcaggatcatttgccagccatctgttgtttgcccctc
                              ccccgtgccttccttgaccctggaaggtgccactcccactgtcctttcctaat
                              aaaatgaggaaattgcatgccggcagcgtgcggggacagcccgggcac
                              ggggaaggtggcacgggatcgctttcctctgaacgcttctcgctgctctttg
                              agcctgcagacacctggggggatacggggaaaagttagtttaaacgttcg
```

TABLE 2-continued

Sequences

| SEQ ID NO: | Description | Sequence |
|---|---|---|
| | | cgatagtatacggcctgcaggatgactttggcctcgatggccgtgccagg |
| | | gcgtgcccttgggctccccgggcgcggcgattaagacgt |
| 13 | B202 vector | atcatctggaaagtaacaaaattgatgcaaatttgaatgaactttatcatggt |
| | | gtatttacacaatgtgtttcttctccctgcaatgtatttctttctctattccttccat |
| | | ttgatctttcatacacaatctggttctgatgtatgtttttttggatgcactttcaac |
| | | tccaaaagacagagctagttactttcttcctggtgctccaagcactgtatttgt |
| | | atctgtattcaagccctttgcaatattgtactggatcattatttcacctctagga |
| | | tggcttccccaggcaacttgtgttcacccagagactacattttgtatcttgttg |
| | | acctttgaacttccaccagtgtctaaaaataaatatgtatgcaaaattacttgct |
| | | atgagaatgtataattaaacaatataaaaaggagaagcaaggagagaaac |
| | | acaggtgtgtatttgtgtttgtgtgcttaaaaggcagtgtggaaaaggaaga |
| | | aatgccatttatagtgaggagacaaagttatattacctcttatctggcttttaa |
| | | ggagattttgctgagctaaaaatcctatattcatagaaaagccttacctgagt |
| | | tgccaatacctcaattctaaaatacagcatagcaaaactttaacctccaaatc |
| | | aagcctctacttgaatccttttctgagggatgaataaggcataggcatcagg |
| | | ggctgttgccaatgtgcattagctgtttgcagcctcaccttctttcatggagtt |
| | | taagatatagtgtattttcccaaggtttgaactagctcttcatttctttatgtttta |
| | | aatgcactgacctcccacattccctttttagtaaaatattcagaaataatttatc |
| | | ccggcttgtcgacggcgtccgtcgtcaggatcatccatcaggacatagcg |
| | | ttggctacccgtgatattgctgaagagcttggcggcgaatgggctgaccg |
| | | cttcctcgtgctttacggtatcgccgctcccgattcgcagcgcatcgccttct |
| | | atcgccttcttgacgagttcttctgagggatcaattctctagagctcgctga |
| | | tcagcctcgactgtgccttctagttgccagccatctgttgtttgcccctcccc |
| | | cgtgccttccttgaccctggaaggtgccactcccactgtcctttcctaataaa |
| | | atgaggaaattgcatcgcattgtctgagtaggtgtcattctattctggggggt |
| | | ggggtggggcaggacagcaaggggggaggattgggaagacaatagcag |
| | | gcatgctggggatgcggtgggctctatggcttctgaggcggaaagaacc |
| | | agctgggggcgcgcacctcgaccatctccaggatgcctttgatagagctg |
| | | ggtcctctgcgttcctttaaagtgtttgagatcaagtccgagaagaggtggc |
| | | aagcgatcgcgacatatttaaatcgcgctagtttaaaatacatcattgcaatg |
| | | aaaataaatgttttttattaggcagaatccagatgctcaaggcccttcataata |
| | | tcccccagtttagtagttggacttagggaacaaaggaacctttaatagaaat |
| | | tggacagcaagaaagctctagctttagaagaactcatcaagaagtctgtag |
| | | aaggcaattctctgggagtcaggggctgcaatgccatagagcactaggaa |
| | | cctgtctgcccactctcccccctagctcttctgctatgtccctggttgctaggg |
| | | caatgtcctggtacctgtcagccactcccagcctgccacagtctatgaagc |
| | | cagagaaccttccattttcaaccatgatgttgggaaggcaggcatccccat |
| | | gagtcaccactaggtcctcaccatctggcatggatgccttgagcctggcaa |
| | | atagttcagcagggccaggccctggtgttcttcatccaagtcatcttggtc |
| | | caccaggccagcctccatcctggttctggccctctctatcctgtgcttggcc |
| | | tggtggtcaaaggggcaggtggctgggtcaagggtgtggagtcttctcat |
| | | ggcatcagccatgattgacactttctcagctggagctaggtgagaggaaa |
| | | ggaggtcctgcccaggcacctcacctagtaggagccagtcccttccagct |
| | | tctgtgaccacatcaaggacagctgcacaggggaccccagttgttgccaa |
| | | ccaggagagtctggcagcctcatcctggagctcattgagagccccactga |
| | | ggtctgtctttacaaaaaggactggcctgccttgggctgaaagtctgaaaa |
| | | ctgctgcatcagagcaaccaatggtctgctgtgcccagtcatagccaaaca |
| | | gtctctcaacccaggcagctggagaacctgcatgtaggccatcttgttcaat |
| | | catgatggctcctcctgtcaggagaggaaagagaagaaggttagtacaat |
| | | tgctatagtgagttgtattatactatgcttatgattaattgtcaaactagggctg |
| | | cagggttcatagtgccacttttcctgcactgccccatctcctgcccacccttt |
| | | cccaggcatagacagtcagtgacttaccaaactcacaggagggagaagg |
| | | cagaagcttttttgcaaaagcctaggctcatgagacaataaccctgataaat |
| | | gcttcaataatattgaaaaaggaagagtaccaggtatgagtattcaacatttc |
| | | cgtgtcgcccttattcccttttttgcggcattttgccttcctgttttttgctcaccc |
| | | agaaacgctggtgaaagtaaaagatgctgaagatcagttgggtgcacga |
| | | gtgggttacatcgaactggatctcaacagcggtaagatccttgagagtttc |
| | | gcccgaagaacgtttccaatgatgagcacttttaaagttctgctatgtggc |
| | | gcggtattatcccgtattgacgccgggcaagagcaactcggtcgccgcat |
| | | acactattctcagaatgacttggttgagtactcaccagtcacagaaaagcat |
| | | cttacggatggcatgacagtaagagaattatgcagtgctgccataaccatg |
| | | agtgataacactgcggccaacttacttctgacaacgatcggaggaccgaa |
| | | ggagctaaccgcttttttgcacaacatgggggatcatgtaactcgccttgat |
| | | cgttgggaaccggagctgaatgaagccataccaaacgacgagcgtgaca |
| | | ccacgatgcctgtagcaatggcaacaacgttgcgcaaactattaactggc |
| | | gaactacttactctagcttcccggcaacaattaatagactggatggaggcg |
| | | gataaagttgcaggaccacttctgcgctcggcccttccggctggctggttta |
| | | ttgctgataaatctggagccggtgagcgtgggtctcgcggtatcattgcag |
| | | cactggggccagatggtaagccctcccgtatcgtagttatctacacgacgg |
| | | ggagtcaggcaactatggatgaacgaaatagacagatcgctgagataggt |
| | | gcctcactgattaagcattggtaactgtcagaccaagtttactcatatatactt |
| | | tagattgatttaaaacttcatttttaatttaaaaggatctaggtgaagatcctttttt |
| | | gataatctcatgaccaaaatcccttaacgtgagttttcgttccactgagcgtc |

TABLE 2-continued

Sequences

| SEQ ID NO: Description | Sequence |
|---|---|
| | agaccccgtagaaaagatcaaaggatcttcttgagatcctttttttctgcgcg |
| | taatctgctgcttgcaaacaaaaaaaccaccgctaccagcggtggtttgttt |
| | gccggatcaagagctaccaactcttttccgaaggtaactggcttcagcag |
| | agcgcagataccaaatactgttcttctagtgtagccgtagttaggccaccac |
| | ttcaagaactctgtagcaccgcctacatacctcgctctgctaatcctgttacc |
| | agtggctgctgccagtggcgataagtcgtgtcttaccgggttggactcaag |
| | acgatagttaccggataaggcgcagcggtcgggctgaacggggggttcg |
| | tgcacacagcccagcttggagcgaacgacctacaccgaactgagatacc |
| | tacagcgtgagctatgagaaagcgccacgcttcccgaagggagaaagg |
| | cggacaggtatccggtaagcggcagggtcggaacaggagagcgcacg |
| | agggagcttccaggggggaaacgcctggtatctttatagtcctgtcgggtttc |
| | gccacctctgacttgagcgtcgatttttgtgatgctcgtcagggggggcgga |
| | gcctatggaaaaacgccagcaacgcggcctttttacggttcctggccttttg |
| | ctggcctttgctcacatggctcgacagatttaattaacaagaccgacctgtc |
| | cggtgccctgaatgaactgcaggacgaggcagcgcggctatcgtggctg |
| | gccacgacgggcgttccttgcgcagctgtgctcgacgttgtcactgaagc |
| | gggaagggactggctgctattgggcgaagtgccggggcaggatctcctg |
| | tcatctcaccttgctcctgccgagaaagtatccatcatggctgatgcaatgc |
| | ggcggctgcatacgcttgatccggctacctgcccattcgaccaccaagcg |
| | aaacatcgcatcgagcgagcacgtactcggatggaagccggtcttgtcga |
| | tcaggatgatctggacgaagagcatcaggggctcgcgccagccgaactg |
| | ttcgccaggctcaaggcgcgcatgcccgacggcgaggatctcgtcgtga |
| | cccatggcgatgcctgcttgccgaatatcatggtggaaaatggccgcttttc |
| | tggattcatcgactgtggccggctgggtgtggcggatcgctggcctcgat |
| | ggccgtgataccggcctgcaggatcatttgccagccatctgttgtttgcccct |
| | cccccgtgccttccttgaccctggaaggtgccactcccactgtcctttccta |
| | ataaaatgaggaaattgcatgccggcagcgtgcggggacagcccgggc |
| | acggggaaggtggcacgggatcgctttcctctgaacgcttctcgctgctct |
| | ttgagcctgcagacacctgggggggatacggggaaaagttagtttaaacgtt |
| | cgcgatagtatacggcctgcaggatgactttggcctcgatggccgtgcca |
| | gggcgtgcccttgggctccccgggcgcggcgattaagacgtatgtctcct |
| | atgtctcatctaaatggatgaggtttgagagttcccatcacggccatggtgga |
| | aacgaatccgactaggagccataagttcacggcttcgatccctggcctcg |
| | ctcaggggggttaaggatccggtgttgctgtgagctgtggtgtaggtcacag |
| | atgcggttcggatctggcgttgctgcggctgtggtgtaggctggtggctgt |
| | agctccgatttgacccctagctagggacctccatatgccgtgggtatggc |
| | cctaaaaagccaaataaaataaaataagtaaatggttgaggtttgacacag |
| | aaagtttatttatttatgtatttacttatctttttttttttttttttttttgtctttctgctatt |
| | tcttgggctgctcccgcggcatatggaggttcccaggctaggggtcgaatt |
| | ggagctacagccaccagcctacaccacagccgcagcaatgccagatcc |
| | gagccgcctctgtgacctacaccacagctcatggcaacgctggatcgtta |
| | acccactgagcaagggctgggaccgaacccgcaacctcatggttcctagt |
| | cggattcgttaaccactgcgccatgacgggaactcctacttatctatttttttaa |
| | agcatatggaagttcccaggctaggggggttgaatcggagctgcaactgcc |
| | ggcttacaccacagccagagcaacgccggatctgagcagtgtctgggac |
| | ctacaccacagctcacagccacaccggatcctcaatccactgaatgaggc |
| | caggaatcaaacctgtgtcctcatggatactagtcagattcatttccgctga |
| | gcaatgacaggaactcctgacacagaaattttagattaaaattgaagatga |
| | gccccttccttttgtacgacctttgtgtgcagattttcgaggataagtccttga |
| | gcttgaagtttttagggtcatggatcctcataacagtttcctggcctgtgaggc |
| | ttggatctcagtataaacagaagtgctggcagcagtagacacagcagcag |
| | ctgttttcaggaacaaatactgggcacctgccttgtggacctgcctgactcc |
| | accactctcttgggtatccacaaagtggacccagaggttcagagcagccc |
| | tgggatccaaatttttttaatttatttttttatctttttatttttttgtcttttcgaaatttttta |
| | gggctacacccatgagatatggaggttcccaggctaagggtccaatcgga |
| | gctacaactgccggcctacaccacagctcatggcaatgctggatccttaac |
| | ccgctgagcgaggccagggatcaaacccacaacctcatgattcctagttg |
| | gattcgttaaccactgagccacgatgggaactccctgggatgcaaattttgt |
| | catctagccctaggatgtagctatcatcctgatttgagaagagaggcagag |
| | tctcaggtggcttctctctcatgaatgcagagctaagggtggccacacgta |
| | cttgagttcatccgatgcacacagcattgtgctaaaatattgaccatttggcc |
| | cttttgctgacttttggtttgagggatatgaccttcatgagcatacagaggata |
| | atatgtatgcatgtatgcatgtgtgtacacatgtgcgcatgcatgtatatacct |
| | gcataattatgtatttgtttatgtatgcaggtgcatgtgtatgtatatatttattatt |
| | tatttatttgggggccacacccatgacatttggaagttcctgggacagagat |
| | tgaatcccagccacagctttgacctacgccatggacacagcaacactgga |
| | ttcttaaccccctgtgccacagcgggaactcctagaagatagtatttcatgat |
| | gatatttgactaaaaataggggtcaggctttgaagtttaaataaaattcgacca |
| | gataaatggccatccaggaagttatactttgccttgttcaaatttggaccacg |
| | gggaaggtggttggcgacatgtaacagaaatctgactccagtgcaggtttc |
| | gctcccgtgacgggaagcccagaggtgggcagccctaaggctggggct |
| | ctgatttcatgatgctcttagcatcttgagtcccttccctcttcttgcttttatctc |
| | agcctcgggctgctgcaccttctgtctttgtggtgagtctacctattccactta |
| | gctcggcttcagggtgtattccacgacttcgttagagtaaggttggggcca |

TABLE 2-continued

| Sequences | | |
|---|---|---|

| SEQ ID NO: | Description | Sequence |
|---|---|---|
| | | gctgtgctctgccggcaggaggtgtgcttgcaggggccatggatgtggc |
| | | caggacctaatgtgacggtggggagcaggatggggatgaggatgtgac |
| | | cacagagccttgggaaccacgtcatccacgtcatacactgagagcaggtg |
| | | gttctcatgcaggtgcatcagaatcccgaggacggcttgtccaaacccag |
| | | atggctgggcccaagccctgagctcccgatttgggaggccttggctgggc |
| | | cccgaaatctgccttcctgactagaccgagtgatgaatggtgttcatagaca |
| | | agacatacactaacactggtcttgggggctccttgccacaccctgaaggg |
| | | gtccgtgaaactgacggggccagagaaggtgctggttcctccatggaag |
| | | gtctcagtgaggccattctgctgcccggctgggtcacgctgggggagtga |
| | | gggtgcatccctcctgggatctggtcaaaggcagattctgattctggaag |
| | | cacggggtagggccagagatgccaccttctaacaagcccccaggtgaag |
| | | atgttgacctgggaccttatggtgggggggtggcggagctcaaggtggca |
| | | gacacctccctctctctcaacctgtgtcacagcagggccatcctactggctc |
| | | tcgctcggccagagatggcgatgccagaacacactggggcagggtgtcc |
| | | acatttttgtcacttccactgagccctggggactgactcatttaaatgacattc |
| | | tcaactctttggaaagaagctgggccagaaatggaaatggcagcaaacac |
| | | tttttgggaaacaggaagccaatttttttttttcaatcatgattttccccagattca |
| | | gagactgcttaactcccaatgaaatacttttagattacgagctaaaataccg |
| | | aaaagctgtcaagctcaagaccacaggaaaacagccgaagaacaaaca |
| | | ccatgagaaaacagtcacagagtgcctctgcggcgggatttcaagttccag |
| | | acttccttgctgtcagctgtgtgtacttgtcccgcctgcagtaggaccagct |
| | | ggggtttaagtctgtaccatggacactgctgccaggattctcctctgcatct |
| | | gctgacttccagctcttcagggccagctggccataggagcataaactgac |
| | | atccagttccaggaggcagcatctgtccccatggcctgcaggacaccaga |
| | | tcagtagaggcccccagggccacctttcctgtggggggcccttgaaggga |
| | | cccgggaaggctggatcttgctaaagcttccacaagtcccttccaaagga |
| | | gagtaaattctaaacagaagcttttgccagtgcttctctgggatctggcttca |
| | | ggattattcctagtctgaaaagtcttcctggtggtttggacacgggcaaatg |
| | | cttggtgggtgggctggctctggatgcaggtgagtggggtcggaagttct |
| | | ccctccttcccacaaagcttgacggagccaggggcacccgcgggcctgt |
| | | ggatgggagaggggtttctggtgacgggactcaagtcttggcagcccctga |
| | | ccccagagcaggctccctccccacagctgctctccgtgagtccttcacttg |
| | | cccaagttcaagatgtacccagttctggagctgccaaaccatcctgcatcct |
| | | gacgtcagccacccaagttctggggtagctggtctgccacccaggtggat |
| | | gaaaagaggccacatacctgcaccagcatctgcgaatctctgaagaacat |
| | | caataataaaaagacaactaacccgattaaaacacaggtagagaatctga |
| | | acagacattcatcggaagaagaattacgactggccaaaaagctcataaaa |
| | | agatggtcaaagtcattggtcagggaaatgtaaatcaaaccgcattgagat |
| | | accatctcactccctctcggatggctggaatgaaaaaaaacctcttctttcct |
| | | cccttcattgtcttggcacccttgtggaaattaattgactaaaattcatgaaat |
| | | acaaaaattttttaggagttcccgtcgtggctcagttggttaacaaatctgacta |
| | | ggaaccatgaggtttcaggttcgattcctggcctcactcagtgggttaggg |
| | | atctggtgttgccatgagctgtggtgtaggtcgcagacgcagctcggatcc |
| | | cgcattgctgtggctctggcgtaggccggcggctacagctctgattcaacc |
| | | tctagcctgggaatagcccaagaaatggcaaaaagaccaaaaaaaaaaa |
| | | aaaaaaaaaaactcgtttttgagcatttttgcatgtgtacattgtccatttgtgtg |
| | | ccttccaagatttattttttggagtctcaactctgtcattgatttatgtctctcctta |
| | | ggccagaaccacactgtttttggtgaccatggctttgtagtaaaatttgaaatc |
| | | tgaaagtgtgagccctcctgttttgtttctcttctccatgattagtttggttattc |
| | | agagtcccttgaatttccaggtgaatttttaggattagcaggaaaatttctgca |
| | | gagatggcagcagagattttttaatagggattatgttgaatctggaggttaatt |
| | | tcagtttttgctaccttgactgtattaagtcttccagtctataagcataagatgtc |
| | | tttttatttacttaggtcttttaaaatttctttgggcactcccattgtggtgcatcg |
| | | gaaatgaatccgactagtatccacaagaacacaggttcaatccctggcatt |
| | | gctcagtgggttaaggatcctgcattgccatgaagaactgtggtggaggc |
| | | cagcagctgcagctctgatttgacccctagcctgggaacttccatatgcctt |
| | | gggtatggccctaaaaagcaaactaagtaagtaagtaaataaataaatgaa |
| | | taaataaaattctttcaaaattgtaattttgtaatttttgtaattttcagagtgtac |
| | | attttgcccttcaatacattattcctacatattttattcttttttgatactattataaat |
| | | gaaatttataattaattcatttatatgaatttcattttcaatttgcatattgctacta |
| | | caatagaaatgcacttttttaattattttttatggccataccatatatatatgtgtgt |
| | | gtgtgtgtatgtgtgtcattttactgtacagcagaaattgacacaacattgtaa |
| | | atcaactacacttaaaaaatgaagaaataaccacctgtgattatggctactgt |
| | | gttggacactttaggcatccccccacccegtccccgccccacacccctga |
| | | gtgctagtgacggatgttcccacccaggggggcctggagcctttatcacca |
| | | gccatcgggaatcagaaccgtatctcacagtccccatgcctgtagcacctg |
| | | gaattgtgcccttggactcgtgggtgttctgcttctcagtgggagaagctta |
| | | ggttctaagtcagagcagggacagcccccatgtgctcaggacccagtgtg |
| | | aaggggtctgcctcagggggacctgggggttacaagggtaagagaaggt |
| | | gttcatgttggaactagaagttcttttttcaccgctctgaagaaaaaagctgcc |
| | | tcccacccttggtacagctcttctgctaacagtgaatcaggcagaacgtgtt |
| | | caagaagtgacccagcctggtggggggccagacctgacccttgatggtcc |
| | | ctcaacccctccgagggtcccgcccttcctttactgctttgttgtctgtcctga |
| | | gaggtttggctaatgtcgaaccaagggtgtggctggtcctgtcccctttcct |

TABLE 2-continued

<div align="center">Sequences</div>

| SEQ ID NO: Description | Sequence |
|---|---|
| | gtctcacgcacccacctctgaagtctctgtagctggttccagccgggatct |
| | ggagccactcccccgccccaggcccagtggtacagactcttgcagagt |
| | cgggggcccctgactcagccccaccgccagcgggatgtcaggccagca |
| | cccgccccactcccactgatctggggggggtgtctttccttcctccttccaa |
| | aggagcctcagaccttcctgtggggcacggggcagtgggattcaggag |
| | gctctgagtcagcaggccggcattgaggagtataaagggaccccagttcc |
| | tccccctttcacttgtggcttatcgccgccccaccctgccccaaggtcactg |
| | cggtcagtacagtcctcagctgccagcaggtgcctgtctttacttgtgaggc |
| | cgccacgctctcctgtttctccaggtctgggctctgttggaagtgggggcc |
| | cgaccccagggtaagatgggggatctgcgtgtcctgccctcagaggcct |
| | cctcctccccgcacccctaacccttcagcccaacaaggctggagatctcc |
| | cacatctttggcttcgttaagagttcaacagcgccgccacccggcatgtcg |
| | ctgagcagaggatggcacagggtgttaaaaaaaaaaaaaggttgccaca |
| | ctccgttcggttttgggcccacccttcgcattcctggagcctgagtaagcg |
| | gataaggctgtgaaagtgacagattcctgccacctccttccagcgctcatg |
| | cacagggaccgcccctcttcggtgtcctttgctgcacaagtgcatttgcaca |
| | ttcctgtctcaatctggtttctccccccttaaaagatgggaatgtgacctgcttg |
| | gagccctcgcctcgccagggcaccccatccgtcccttcaggggtggag |
| | atggactgtccctctgcaaggctggatgaactcagaccaaacaggccaac |
| | ttgctccccaaatacgcccacccctaccgggctgcagaaattcgcatgtca |
| | ccactgctgaagggtgaccttgcagccctgagagcatccccatgacttgc |
| | ccaccagatgaagtctggttgtggcaggtcgcgctcagggactcccgggt |
| | cccacctgggggtgggaggatcctcctttgctcgtggtcgccccagacac |
| | gccctcctttccaagcgccagtctccagagctccgtgccccggcggagg |
| | cggtctggctctctctccttgcccctctctccttgcccctagcagcccttctcc |
| | taaaccctctgagcagcgggcacctcctcccgagggccctgggctaagtcc |
| | ccaccttcatctcaagccttcctccttgactccctcttcccagagttccttga |
| | aataggtggtaagtacacaccgatgacggaaaacaaagactaagaggtta |
| | aagagggctgaggattacggccccggtagggctgcgcgcgaggggggt |
| | cgagtggccgggcggtcccgtcgccgggcagacagaggtgcggttctc |
| | ccgggcgcctgcgctgccggccccgcccggagccctcccagccggcg |
| | cccagtttactcatcccggagaggtgatcccgggcgcgaggggcgggcg |
| | cagggcgtccggagaacccagtaatccgagaatgcagcatcagcccttc |
| | ccaccaggcacttccttccttttcccgaacgtccagggagggggggccgcg |
| | cacttatataaactcgggccggacccgccggcctgtcagaggctgcctcgct |
| | ggggctgcgcgcggcggccggacacatctggtccgagaccaacgcga |
| | gcgactgtcactggcagctccctgcgcctctcagccccggccgggcccc |
| | tgcgcttggcgtgctgacaccatgcttggggtcctggtccttggcgcgctg |
| | gccctggccggcctggggttccccgcaccgcagagccgcagccgggt |
| | ggcagccagtgcgtcgagcacgactgcttcgcgctctacccgggccccg |
| | cgaccttcctcaatgccagtcagatctgcgacggactgcggggccaccta |
| | atgacagtgcgctcctcggtggctgccgatgtcatttccttgctactgaacg |
| | gcgacggcggcgttggccgccggcgcctctggatcggcctgcagctgc |
| | cacccggctgcggcgaccccaagcgcctcgggccccctgcgcgggcttcc |
| | agtgggttacgggagacaacaacaccagctatagcaggtgggcacggct |
| | cgacctcaatggggctcccctctgcggcccgttgtgcgtcgctgtctccgc |
| | tgctgaggccactgtgcccagcgagccgatctgggaggagcagcagtg |
| | cgaagtgaaggccgatggcttcctctgcgagttccacttcccagccacctg |
| | caggccactggctgtggagcccggcgccgcgggctgccgccgtctcgatc |
| | acctacggcaccccgttcgcgggcccgcgggagcggacttccaggcgctg |
| | ccggtgggcagctccgccgcggtggctcccctcggcttacagctcaatgtg |
| | caccgcgccgcccggagcggtccaggggcactgggccagggaggcg |
| | ccgggcgcttgggactgcagcgtggagaacggcggctgcgagcacgc |
| | gtgcaatgcgatccctggggctccccgctgccagtgcccagccggcgcc |
| | gccctgcaggcagacgggcgctcctgcaccgcatccgcgacgcagtcct |
| | gcaacgacctctgcgagcacttctgcgcgttcccaaccccgaccagccggg |
| | ctcctactcgtgcatgtgcgagaccggctaccggctggcggccgaccaa |
| | caccggtgcgaggacgtggatgactgcatactggagcccagtccgtgtc |
| | cgcagcgctgtgtcaacacacagggtggcttcgagtgccactgctaccct |
| | aactacgacctggtggacggcgagtgtgtggagcccgtggacccgtgctt |
| | cagagccaactgcgagtaccagtgccagcccctgaaccaaactagctac |
| | ctctgcgtctgcgccgagggcttcgcgcccattccccacgagccgcaca |
| | ggtgccagatgttttgcaaccagactgcctgtccagccgactgcgaccccc |
| | aacacccaggctagctgtgagtgccctgaaggctacatcctggacgacg |
| | gtttcatctgcacggacatcgacgagtgcgaaaacggcggcttctgctcc |
| | ggggtgtgccacaacctccccggtaccttcgagtgcatctgcgggcccga |
| | ctcggcccttgcccgccacattggcaccgactgtgactccggcaaggtgg |
| | acggtggcgacagcggctctggcgagcccccgcccagcccgacgccc |
| | ggctccaccttgactcctccggccgtggggctcgtgcattcgggcttgctc |
| | ataggcatctccatcgcgagcctgtgcctggtggtggcgcgcttttggcgctc |
| | ctctgccacctgcgcaagaagcagggcgccgccagggccaagatggag |
| | tacaagtgcgcggcccccttccaaggaggtagtgctgcagcacgtgcgga |
| | ccgagcggacgccgcagagactctgagcggcctccgtccaggagcctg |
| | gctccgtccagtcgacccgggcggccgcttcccttttagtgagggttaatgc |

TABLE 2-continued

Sequences

| SEQ ID NO: Description | Sequence |
|---|---|
| | ttcgagcagacatgataagatacattgatgagtttggacaaaccacaacta |
| | gaatgcagtgaaaaaaatgctttatttgtgaaatttgtgatgctattgctttattt |
| | gtaaccattataagctgcaataaacaagttaacaacaacaattgcattcatttt |
| | atgtttcaggttcagggggagatgtgggaggtttttttaaagcaagtaaaacc |
| | tctacaaatgtggtaaaatccgataaggatcgatgggacagcccccccc |
| | aaagcccccagggatgtaattacgtccctcccccgctagggcagcagcg |
| | agccgcccggggctccggtccggtccggcgctcccccgcatccccgag |
| | ccggcagcgtgcggggacagcccgggcacggggaaggtggcacggg |
| | atcgctttcctctgaacgcttctcgctgctctttgagcctgcagacacctggg |
| | gggatacggggaaaatctagtgggacagcccccccccaaagcccccag |
| | ggatgtaattacgtccctcccccgctagggcagcagcgagccgcccggg |
| | gctccggtccggtccggcgctcccccgcatccccgagccggcagcgtg |
| | cggggacagcccgggcacggggaaggtggcacgggatcgctttcctct |
| | gaacgcttctcgctgctctttgagcctgcagacacctgggggggatacggg |
| | gaaaaatcgatgggacagcccccccccaaagcccccagggatgtaatta |
| | cgtccctcccccgctagggcagcagcgagccgcccggggctccggtcc |
| | ggtccggcgctcccccgcatccccgagccggcagcgtgcggggacag |
| | cccgggcacggggaaggtggcacgggatcgctttcctctgaacgcttctc |
| | gctgctctttgagcctgcagacacctgggggggatacggggaaaatctagt |
| | gggacagcccccccccaaagccccagggatgtaattacgtccctcccc |
| | cgctagggcagcagcgagccgcccggggctccggtccggtccggcgct |
| | cccccgcatccccgagccggcagcgtgcggggacagcccgggcacgg |
| | ggaaggtggcacgggatcgctttcctctgaacgcttctcgctgctctttgag |
| | cctgcagacacctgggggggatacggggaaaaatcgatagcgataaggat |
| | ccactagttattaatagtaatcaattacggggtcattagttcatagcccatata |
| | tggagttccgcgttacataacttacggtaaatggcccgcctggctgaccgc |
| | ccaacgacccccgcccattgacgtcaataatgacgtatgttcccatagtaa |
| | cgccaatagggactttccattgacgtcaatgggtggagtatttacggtaaac |
| | tgcccacttggcagtacatcaagtgtatcatatgccaagtacgcccctatt |
| | gacgtcaatgacggtaaatggcccgcctggcattatgcccagtacatgac |
| | cttatgggactttcctacttggcagtacatctacgtattagtcatcgctattacc |
| | atgggtcgaggtgagccccacgttctgcttcactctccccatctcccccc |
| | ctccccacccccaattttgtatttatttattttttaattattttgtgcagcgatggg |
| | ggcggggggggggggggcgccaggcggggcggggcggggc |
| | gagggcggggcggggcgaggcggagaggtgcggcggcagccaat |
| | cagagcggcgcgctccgaaagtttcctttatggcgaggcggcggcggc |
| | ggcggccctataaaaagcgaagcgcgcggcgggcgggagtcgctgcg |
| | ttgccttcgccccgtgccccgctccgcgccgcctcgcgccgcccgcccc |
| | ggctctgactgaccgcgttactcccacaggtgagcgggcgggacggccc |
| | ttctcctccgggctgtaattagcgcttggtttaatgacggcctgtttcttttctg |
| | tggctgcgtgaaagccttaaagggctccgggagggccctttgtgcgggg |
| | gggagcggctcggggggtgcgtgcgtgtgtgtgtgcgtggggagcgcc |
| | gcgtgcggcccgcgctgcccggcggctgtgagcgctgcgggcgcggc |
| | gcggggctttgtgcgctccgcgtgtgcgcgaggggagcgcggccgggg |
| | ggcggtgccccgcggtggggggggctgcgaggggaacaaaggctg |
| | cgtgcggggtgtgtgcgtgggggggtgagcagggggtgtgggcgcgg |
| | cggtcgggctgtaaccccccctgcacccccctccccgagttgctgagca |
| | cggcccggcttcgggtgcggggctccgtgcggggcgtggcgcgggc |
| | tcgccgtgccgggcggggggtggcggcaggtggggtgccgggcgg |
| | ggcggggccgcctcgggccggggagggctcggggagggcgcgg |
| | cggccccggagcgccggcggctgtcgaggcgcggcgagccgcagcc |
| | attgcctttttatggtaatcgtgcgagagggcgcagggacttcctttgtccca |
| | aatctggcggagccgaaatctgggaggcgccgccgcaccccctctagc |
| | gggcgcgggcgaagcggtgcggcgccggcaggaaggaaatgggcgg |
| | ggagggccttcgtgcgtcgccgcgccgccgtccccttctccatctccagc |
| | ctcggggctgccgcagggggacggctgccttcgggggggacggggca |
| | gggcggggttcggcttctggcgtgtgaccggcggctctagagcctctgct |
| | aaccatgttcatgccttcttcttttttcctacagctcctgggcaacgtgctggtt |
| | gttgtgctgtctcatcattttggcaaagaattccgctgcgactcggcggagt |
| | cccggcggcgcgtccttgttctaacccggcgcgccctcaggatgtggccc |
| | ctggtagcggcgctgttgctgggctcggcgctgcggatcagctcagct |
| | actatttaataaaacaaaatctgtagaattcacgttttgtaatgacactgtcgt |
| | cattccatgctttgttactaatatggaggcacaaaacactactgaagtatacg |
| | taaagtggaaatttaaaggaagagatatttacacctttgatggagctctaaa |
| | caagtccactgtccccactgactttagtagtgcaaaaattgaagtctcacaa |
| | ttactaaaaggagatgcctctttgaagatggataagagtgatgctgtctcac |
| | acacaggaaactacacttgtgaagtaacagaattaaccagagaaggtgaa |
| | acgatcatcgagctaaaatatcgtgttgtttcatggttttctccaaatgaaat |
| | attcttattgttattttcccaattttttgctatactcctgttctggggacagtttggt |
| | attaaaacacttaaatatagatccggtggtatggatgagaaaacaattgcttt |
| | acttgttgctggactagtgatcactgtcattgtcattgttggagccattcttttc |
| | gtcccaggtgaatattcattaaagaatgctactggccttggtttaattgtgact |
| | tctacagggatattaatattacttcactactatgtgtttagtacagcgattggat |
| | taacctccttcgtcattgccatattggttattcaggtgatagcctatatcctcgc |

TABLE 2-continued

Sequences

| SEQ ID NO: Description | Sequence |
| --- | --- |

```
tgtggttggactgagtctctgtattgcggcgtgtataccaatgcatggccct
cttctgatttcaggtttgagtatcttagctctagcacaattacttggactagttta
tatgaaatttgtggcttccaatcagaagactatacaacctcctaggaaagct
gtagaggaacccccttaatgcattcaaagaatcaaaaggaatgatgaatgat
gaaggatccggagccacgaacttctctctgttaaagcaagcaggagacgt
ggaagaaaaccccggtcctatggagcgtccgcaacccgacagcatgcc
ccaggatttgtcagaggccctgaaggaggccaccaaggaggtgcacac
ccaggcagagaatgctgagttcatgaggaactttcagaagggccaggtg
acccgagacggcttcaagctggtgatggcctccctgtaccacatctatgtg
gccctggaggaggagattgagcgcaacaaggagagcccagtcttcgcc
cctgtctacttcccagaagagctgcaccgcaaggctgccctggagcagg
acctggccttctggtacgggccccgctggcaggaggtcatcccctacaca
ccagccatgcagcgctatgtgaagcggctccacgaggtggggcgcaca
gagcccgagctgctggtggcccacgcctacacccgctacctgggtgacc
tgtctggggcaggtgctcaaaaagattgcccagaaagccctggacctg
cccagctctggcgagggcctggccttcttcaccttccccaacattgccagt
gccaccaagttcaagcagctctaccgctcccgcatgaactccctggagat
gactcccgcagtcaggcagagggtgatagaagaggccaagactgcgttc
ctgctcaacatccagctctttgaggagttgcaggagctgctgacccatgac
accaaggaccagagcccctcacgggcaccagggcttcgccagcgggc
cagcaacaaagtgcaagattctgccccgtggagactcccagagggaag
cccccactcaacacccgctcccaggctccgcttctccgatgggtccttaca
ctcagctttctggtggcgacagttgctgtagggctttatgccatgtgagcgg
cgcgccggcaccggtaccaagcttaagagcgctagctggccagacatga
taagatacattgatgagtttggacaaaccacaactagaatgcagtgaaaaa
aatgctttatttgtgaaatttgtgatgctattgctttatttgtaaccattataagct
gcaataaacaagttaacaacaacaattgcattcattttatgtttcaggttcagg
gggaggtgtgggaggtttttaaagcaagtaaaacctctacaaatgtggtat
ggaattggagccccactgtgttcatcttacagatggaaatactgacattcag
aggagttagttaacttgcctaggtgattcagctaataagtgcaagaaagattt
caatccaaggtgatttgattctgaagcctgtgctaatcacattacaccaagct
acaacttcatttataaataataagtcagctttcaagggcctttcaggtgtcctg
cacttctacaagctgtgccatttagtgaacacaaaatgagccttctgatgaa
gtagtcttttcattatttcagatattagaacactaaaattcttagctgccagctg
attgaaggctgggacaaaattcaaacatgcatctacaacaatatatatctca
atgttagtctccaaattctattgacttcaactcaagagaatataaagagctagt
ctttatacactctttaaggtatgatccgtcagggccacacccgctgcatatg
gaggttcccaggctaggggtctaatcagagctgtagctgccaacctatgc
cacagccacagcaacgccagatttgagctgcaactgtgacctacaccata
gcttgtggcagctctggatccttaacccactgagcgaggccagggatcga
acccacaaccttatggttcctagttggattcatttccactgcgccacgacag
gaactcctacaccaaaaattttttatattgtctatttcattcaaagaaaaagccc
tgctaagtatgactggcttaattattttttcattgcccactaatagattgtgacctc
agtttgaaaaatattgtttttaagtaaccaatcctctactgagaattagagtattc
ataattctctcctgttacaaacaatgctgcatgaagctgctttatactcattgtg
tgattatttctgagagcaagatcctagattgtataatcactgtttacttaaaatt
ctgataaaatataggcagcatgctggaaaactgaattctgaccccagatct
gtcaccgccacgaagcataaactttgggcaattctttgcattgctctgagtct
cagtttccccatcaggaacctgctgttctcaacatcctagaatccgctttgag
tgcagatgccccaccccctgactcagagagggcaggacttttactcaggcc
tttctcccccttttccgctccctgttcctcggaagcagcccagggaaaaggg
aaaaagcaggtctgggctggagagcgtgatgcagggcggggcagagg
gagggcaggagggaggccggcccccctagtaggaaatgagacagggta
ggaataacactttataagcccgtcgccctctttctcctcccatgccctggcc
accttccagcctcctccgtccagcctcctcccctcccagacactcctcatttc
ttttccctctaggctgcagtcagccgccagccagagccccccacccggc
cccaccgccggccagagccaggagcccaggtgtggtggagaacttcag
ctacaggatgttgacaacattgctgccgatactgctgctgtctggctgggcc
ttttgtagccaagacgcctcagatggcctccaaagacttcatatgctccaga
tctcctacttccgcgaccccatcacgtgtggtaccagggcaacgcgtcgc
tggggggacacctaacgcacgtgctggaaggcccagacaccaacacca
cgatcattcagctgcagcccttgcaggagcccgagagctgggcgcgcac
gcagagtggcctgcagtcctacctgctccagttccacggcctcgtgcgcct
ggtgcaccaggagcggaccttggcctttcctctgaccatccgctgcttcct
gggctgtgagctgcctcccgagggctctagagcccatgtcttcttcgaagt
ggctgtgaatgggagctcctttgtgagtttccggccggagagagccttgtg
gcaggcagacacccaggtcacctccggagtggtcaccttcaccctgcag
cagctcaatgcctacaaccgcactcggtatgaactgcgggaattcctgga
ggacacctgtgtgcagtatgtgcagaaacatatttccgcgggaaaacacga
aagggagccaaacaagccgctcctacacttcgctggtcctgggcgtcctg
gtgggcagtttcatcattgctggtgtggctgtaggcatcttcctgtgcacag
gtggacggcgatgttgagcgcggccgcttccctttagtgagggttaatgct
tcgagcagacatgataagatacattgatgagtttggacaaaccacaactag
aatgcagtgaaaaaaatgctttatttgtgaaatttgtgatgctattgctttatttg
```

TABLE 2-continued

Sequences

| SEQ ID NO: | Description | Sequence |
|---|---|---| taaccattataagctgcaataaacaagttaacaacaacaattgcattcatttta
tgtttcaggttcagggggagatgtgggaggttttttaaagcaagtaaaacct
ctacaaatgtggtaaaatccgataaggatcgatgggacagcccccccca
aagcccccagggatgtaattacgtccctcccccgctagggcagcagcga
gccgcccggggctccggtccggtccggcgctcccccgcatccccgagc
cggcagcgtgcggggacagcccgggcacggggaaggtggcacggga
tcgctttcctctgaacgcttctcgctgctctttgagcctgcagacacctgggg
ggatacggggaaaatctagtgggacagccccccccaaagcccccagg
gatgtaattacgtccctcccccgctagggcagcagcgagccgcccgggg
ctccggtccggtccggcgctcccccgcatccccgagccggcagcgtgc
ggggacagcccgggcacggggaaggtggcacgggatcgctttcctctg
aacgcttctcgctgctctttgagcctgcagacacctgggggggatacgggg
aaaaatcgatgggacagcccccccccaaagccccagggatgtaattac
gtccctcccccgctagggcagcagcgagccgcccggggctccggtccg
gtccggcgctcccccgcatccccgagccggcagcgtgcggggacagcc
cgggcacggggaaggtggcacgggatcgctttcctctgaacgcttctcgc
tgctctttgagcctgcagacacctgggggggatacggggaaaatctagtgg
gacagcccccccccaaagccccagggatgtaattacgtccctcccccg
ctagggcagcagcgagccgcccggggctccggtccggtccggcgctcc
cccgcatccccgagccggcagcgtgcggggacagcccgggcacggg
gaaggtggcacgggatcgctttcctctgaacgcttctcgctgctctttgagc
ctgcagacacctgggggggatacggggaaaaatcgatagcgataaggatc
cactagttattaatagtaatcaattacgggtcattagttcatagcccatatat
ggagttccgcgttacataacttacggtaaatggcccgcctggctgaccgcc
caacgacccccgcccattgacgtcaataatgacgtatgttcccatagtaac
gccaatagggactttccattgacgtcaatgggtggagtatttacggtaaact
gcccacttggcagtacatcaagtgtatcatatgccaagtacgcccccctattg
acgtcaatgacggtaaatggcccgcctggcattatgcccagtacatgacct
tatgggactttcctacttggcagtacatctacgtattagtcatcgctattaccat
gggtcgaggtgagccccacgttctgcttcactctccccatctcccccccct
ccccacccccaattttgtatttatttattttttaattattttgtgcagcgatgggg
gcggggggggggggggcgcgccaggcggggcggggcggggcg
aggggcggggcgggcgaggcggagaggtgcggcggcagccaatca
gagcggcgcgctccgaaagtttccttttatggcgaggcggcggcggcgg
cggccctataaaaagcgaagcgcgcggcgggcgggagtcgctgcgttg
ccttcgccccgtgccccgctccgcgccgcctcgcgccgcccgcccccgg
ctctgactgaccgcgttactcccacaggtgagcgggcgggacggcccttc
tcctccgggctgtaattagcgcttggtttaatgacggctcgtttcttttctgtg
gctgcgtgaaagccttaaagggctccgggaggcccctttgtgcggggggg
gagcggctcggggggtgcgtgcgtgtgtgtgtgcgtggggagcgccgc
gtgcggcccgcgctgcccggcggctgtgagcgctgcggggcgcggcgc
ggggctttgtgcgctccgcgtgtgcgcgaggggagcgcggccggggg
cggtgccccgcggtgcgggggggggctgcgaggggaacaaaggctgcgt
gcggggtgtgtgcgtggggggggtgagcaggggggtgtgggcgcggcgg
tcgggctgtaacccccccctgcacccccctccccgagttgctgagcacgg
cccggcttcgggtgcggggctccgtgcggggcgtggcgcggggctcgc
cgtgccgggcgggggggtggcggcaggtgggggtgccgggcggggcg
gggccgcctcgggccggggagggctcggggagagggcgcggcggc
cccggagcgccggcggctgtcgaggcgcggcgagccgcagccattgc
cttttatggtaatcgtgcgagagggcgcagggacttcctttgtcccaaatct
ggcggagccgaaatctgggaggcgccgccgcaccccctctagcgggc
gcgggcgaagcggtgcggcgccggcaggaaggaaatgggcggggag
ggccttcgtgcgtcgccgcgccgccgtccccttctccatctccagcctcgg
ggctgccgcaggggacggctgccttcggggggggacggggcagggc
ggggttcggcttctggcgtgtgaccggcgggctctagagcctctgctaacc
atgttcatgccttcttcttttttcctacagctcctgggcaacgtgctggttgttgt
gctgtctcatcattttggcaaagaattccgctgcgactcggcggagtcccg
gcggcgcgtccttgttctaacccggcgcgccctcaggatggagcctcccg
gccgccgcgagtgtccctttccttcctggcgctttcctgggttgcttctggc
ggccatggtgttgctgctgtactccttctccgatgcctgtgaggagccacca
acatttgaagctatggagctcattggtaaaccaaaaccctactatgagattg
gtgaacgagtagattataagtgtaaaaaaggatacttctatataacctcctctt
gccacccatactatttgtgatcggaatcatacatggctacctgtctcagatga
cgcctgttatagagaaacatgtccatatatacgggatcctttaaatggccaa
gcagtccctgcaaatgggacttacgagtttggttatcagatgcactttatttgt
aatgagggttattacttaattggtgaagaaattctatattgtgaacttaaagga
tcagtagcaatttggagcggtaagcccccaatatgtgaaaaggttttgtgta
caccacctccaaaaataaaaaatggaaaacacaccctttagtgaagtagaa
gtatttgagtatcttgatgcagtaacttatagttgtgatcctgcacctggacca
gatccatttttcactttattggagagagcacgatttattgtggtgacaattcagtg
tggagtcgtgctgctccagagtgtaaagtggtcaaatgtcgatttccagtag
tcgaaaatggaaaacagatatcaggatttggaaaaaaattttactacaaagc
aacagttatgtttgaatgcgataagggttttttacctcgatggcagcgacaca
attgtctgtgacagtaacagtacttgggatcccccagttccaaagtgtcttaa TABLE 2-continued Sequences

| SEQ ID NO: | Description | Sequence |
|---|---|---|
| | | agtgctgcctccatctagtacaaaacctccagctttgagtcattcagtgtcga |
| | | cttcttccactacaaaatctccagcgtccagtgcctcaggtcctaggcctac |
| | | ttacaagcctccagtctcaaattatccaggatatcctaaacctgaggaagga |
| | | atacttgacagtttggatgtttgggtcattgctgtgattgttattgccatagttgt |
| | | tggagttgcagtaatttgtgttgtcccgtacagatatcttcaaaggaggaag |
| | | aagaaaggcacatacctaactgatgagacccacagagaagtaaaatttac |
| | | ttctctcggatccggagccacgaacttctctctgttaaagcaagcaggaga |
| | | cgtggaagaaaaccccggtcctatgaccgtcgcgcggccgagcgtgcc |
| | | cgcggcgctgcccctcctcggggagctgcccggctgctgctgctggtg |
| | | ctgttgtgcctgccggccgtgtggggtgactgtggccttcccccagatgta |
| | | cctaatgcccagccagctttggaaggccgtacaagttttcccgaggatact |
| | | gtaataacgtacaaatgtgaagaaagctttgtgaaaattcctggcgagaag |
| | | gactcagtgatctgccttaagggcagtcaatggtcagatattgaagagttct |
| | | gcaatcgtagctgcgaggtgccaacaaggctaaattctgcatccctcaaac |
| | | agccttatatcactcagaattattttccagtcggtactgttgtggaatatgagt |
| | | gccgtccaggttacagaagagaaccttctctatcaccaaaactaacttgcct |
| | | tcagaatttaaaatggtccacagcagtcgaattttgtaaaaagaaatcatgc |
| | | cctaatccgggagaaatacgaaatggtcagattgatgtaccaggtggcata |
| | | ttatttggtgcaaccatctccttctcatgtaacacagggtacaaattatttggct |
| | | cgacttctagtttttgtcttatttcaggcagctctgtccagtggagtgacccgt |
| | | tgccagagtgcagagaaatttattgcccagcaccaccacaaattgacaatg |
| | | gaataattcaaggggaacgtgaccattatggatatagacagtctgtaacgt |
| | | atgcatgtaataaaggattcaccatgattggagagcactctatttattgtactg |
| | | tgaataatgatgaaggagagtggagtggcccaccacctgaatgcagagg |
| | | aaaatctctaacttccaaggtcccaccaacagttcagaaacctaccacagt |
| | | aaatgttccaactacagaagtctcaccaacttctcagaaaaccaccacaaa |
| | | aaccaccacaccaaatgctcaagcaacacggagtacacctgtttccagga |
| | | caaccaagcattttcatgaaacaaccccaaataaaggaagtggaaccactt |
| | | caggtactacccgtcttctatctgggcacacgtgtttcacgttgacaggtttg |
| | | cttgggacgctagtaaccatgggcttgctgacttagggcgcgccggcacc |
| | | ggtaccaagcttaagagcgctagctggccagacatgataagatacattgat |
| | | gagtttggacaaaccacaactagaatgcagtgaaaaaaatgctttatttgtg |
| | | aaatttgtgatgctattgctttatttgtaaccattataagctgcaataaacaagt |
| | | taacaacaacaattgcattcattttatgtttcaggttcaggggggaggtgtggg |
| | | aggttttttaaagcaagtaaaaacctctacaaatgtggtatggaattggagcc |
| | | ccactgtgttcatcttacagatggaaatactgacattcagaggagttagttaa |
| | | cttgcctaggtgattcagctaataagtgcaagaaagatttcaatccaaggtg |
| | | atttgattctgaagcctgtgctaatcacattacaccaagctacaacttcatttat |
| | | aaataataagtcagctttcaagggcctttcaggtgtcctgcacttctacaagc |
| | | tgtgccatttagtgaacacaaaatgagccttctgatgaagtagtcttttcatta |
| | | tttcagatattagaacactaaaattcttagctgccagctgattgaaggctggg |
| | | acaaaattcaaacatgcatctacaacaatatatatctcaatgttagtctccaa |
| | | attctattgacttcaactcaagagaatataaagagctagtctttatacactcttt |
| | | aaggtatgatatcatctggaaagtaacaaaattgatgcaaatttgaatgaact |
| | | ttatcatggtgtatttacacaatgtgtttcttctccctgcaatgtatttctttctcta |
| | | attccttccatttgatctttcatacacaatctggttctgatgtatgtttttttggatg |
| | | cactttttcaactccaaaagacagagctagttactttcttcctggtgctccaag |
| | | cactgtatttgtatctgtattcaagccctttgcaatattgtactggatcattatttc |
| | | acctctaggatggcttccccaggcaacttgtgttcacccagagactacatttt |
| | | gtatcttgttgacctttgaacttccaccagtgtctaaaaataatatgtatgcaa |
| | | aattacttgctatgagaatgtataattaaacaatataaaaaggagaagcaag |
| | | gagagaaacacaggtgtgtatttgtgtttgtgtgcttaaaaggcagtgtgga |
| | | aaaggaagaaatgccatttatagtgaggagacaaagttatattacctcttatc |
| | | tggctttttaaggagattttgctgagctaaaaatcctatattcatagaaaagcct |
| | | tacctgagttgccaatacctcaattctaaaatacagcatagcaaaactttaac |
| | | ctccaaatcaagcctctacttgaatcctttttctgagggatgaataaggcatag |
| | | gcatcaggggctgttgccaatgtgcattagctgtttgcagcctcaccttcttt |
| | | catggagtttaagatatagtgtattttcccaaggtttgaactagctcttcatttct |
| | | ttatgttttaaatgcactgacctcccacattccctttttagtaaaatattcagaa |
| | | ataatttatcccggcttgtcgacgacgg |
| 14 | B209 vector | atcatctggaaagtaacaaaattgatgcaaatttgaatgaactttatcatggt |
| | | gtatttacacaatgtgtttcttctccctgcaatgtatttctttctctaattccttcca |
| | | tttgatctttcatacacaatctggttctgatgtatgtttttttggatgcacttttcaa |
| | | ctccaaaagacagagctagttactttcttcctggtgctccaagcactgtattt |
| | | gtatctgtattcaagccctttgcaatattgtactggatcattatttcacctctag |
| | | gatggcttccccaggcaacttgtgttcacccagagactacattttgtatcttgt |
| | | tgacctttgaacttccaccagtgtctaaaaataatatgtatgcaaaattacttg |
| | | ctatgagaatgtataattaaacaatataaaaaggagaagcaaggagagaa |
| | | acacaggtgtgtatttgtgtttgtgtgcttaaaaggcagtgtggaaaaggaa |
| | | gaaatgccatttatagtgaggagacaaagttatattacctcttatctggctttt |
| | | aaggagattttgctgagctaaaaatcctatattcatagaaaagccttacctga |
| | | gttgccaatacctcaattctaaaatacagcatagcaaaactttaacctccaaa |
| | | tcaagcctctacttgaatcctttttctgagggatgaataaggcataggcatca |

TABLE 2-continued

| | | Sequences |
|---|---|---|

SEQ
ID
NO: Description                Sequence

```
ggggctgttgccaatgtgcattagctgtttgcagcctcaccttctttcatgga
gtttaagatatagtgtattttcccaaggtttgaactagctcttcatttctttatgtt
ttaaatgcactgacctcccacattccctttttagtaaaatattcagaaataattt
aaattcgtggaatcccacccagcagacaagtatggctggatattttatataa
cgtgtttacgcataagttaatatatgctgaatgagtgatttagctgtgaaaca
acatgaaatgagaaagaatgattagtaggggtctggagcttattttaacaag
cagcctgaaaacagagagtatgaataaaaaaaattaaatacaagagtgtg
ctattaccaattatgtataatagtcttatacatctaacttcaattccaatcactat
atgcttatactaaaaaacgaagtatagagtcaaccttctttgactaacagctc
ttccctagtcagggacattagcccaagtatagtctttatttttcctggggtaag
aaaagaaggattgggaagtaggaatgcaaagaaataaaaaaataattctgt
cattgttcaaataagaatgtcatctgaaaataaactgccttacatgggaatgc
tcttatttgtcaggtatattaaggaaacaaacatcaaaaatgacccaaatgaa
ctcaacaatcttatcaagaagaattctgaggtggtaacctggaccccaaga
cctggagccactcttgatctgggtaggatgctaaaggacgcgatcgcattt
aaatacatcattgcaatgaaaataaatgtttttttattaggcagaatccagatgc
tcaaggcccttcataatatcccccagtttagtagttggacttagggaacaaa
ggaacctttaatagaaattggacagcaagaaagctctagctttagaagaac
tcatcaagaagtctgtagaaggcaattctctgggagtcaggggctgcaatg
ccatagagcactaggaacctgtctgcccactctcccccctagctcttctgcta
tgtccctggttgctagggcaatgtcctggtacctgtcagccactcccagcct
gccacagtctatgaagccagagaaccttccattttcaaccatgatgttggga
aggcaggcatccccatgagtcaccactaggtcctcaccatctggcatgga
tgccttgagcctggcaaatagttcagcaggggccaggccctggtgttcttc
atccaagtcatcttggtccaccaggccagcctccatcctggttctggccctc
tctatcctgtgcttggcctggtggtcaaaggggcaggtggctgggtcaag
ggtgtggagtcttctcatggcatcagccatgattgacactttctcagctgga
gctaggtgagaggaaaggaggtcctgcccaggcacctcacctagtagga
gccagtcccttccagcttctgtgaccacatcaaggacagctgcacaggggg
accccagttgttgccaaccaggagagtctggcagcctcatcctggagctc
attgagagccccactgaggtctgtctttacaaaaaggactggcctgccttg
ggctgaaagtctgaaaactgctgcatcagagcaaccaatggtctgctgtgc
ccagtcatagccaaacagtctctcaacccaggcagctggagaacctgcat
gtaggccatcttgttcaatcatgatggctcctcctgtcaggagaggaaaga
gaagaaggttagtacaattgctatagtgagttgtattatactatgcttatgatta
attgttaaactagggctgcagggttcatagtgccactttcctgcactgcccc
atctcctgcccaccctttcccaggcatagacagtcagtgacttaccaaactc
acaggagggagaaggcagaagcttttttgcaaaagcctaggctcatgaga
caataaccctgataaatgcttcaataatattgaaaaaggaagagtatgagta
ttcaacatttccgtgtcgccccttattccctttttttgcggcattttgccttcctgtttt
tgctcacccagaaacgctggtgaaagtaaaagatgctgaagatcagttgg
gtgcacgagtgggttacatcgaactggatctcaacagcggtaagatccttg
agagttttcgccccgaagaacgttttccaatgatgagcacttttaaagttctg
ctatgtggcgcggtattatcccgtattgacgccgggcaagagcaactcggt
cgccgcatacactattctcagaatgacttggttgagtactcaccagtcacag
aaaagcatcttacggatggcatgacagtaagagaattatgcagtgctgcca
taaccatgagtgataacactgcggccaacttacttctgacaacgatcggag
gaccgaaggagctaaccgcttttttgcacaacatgggggatcatgtaactc
gccttgatcgttgggaaccggagctgaatgaagccataccaaacgacga
gcgtgacaccacgatgcctgtagcaatggcaacaacgttgcgcaaactat
taactggcgaactacttactctagcttcccggcaacaattaatagactggat
ggaggcggataaagttgcaggaccacttctgcgctcggcccttccggctg
gctggtttattgctgataaatctggagccggtgagcgtgggtctcgcggtat
cattgcagcactggggccagatggtaagccctcccgtatcgtagttatcta
cacgacggggagtcaggcaactatggatgaacgaaatagacagatcgct
gagataggtgcctcactgattaagcattggtaactgtcagaccaagtttact
catatatactttagattgatttaaaacttcattttaattaaaaggatctaggtg
aagatccttttgataatctcatgaccaaaatcccttaacgtgagttttcgttcc
actgagcgtcagaccccgtagaaaagatcaaaggatcttcttgagatccttt
ttttctgcgcgtaatctgctgcttgcaaacaaaaaaaccaccgctaccagcg
gtggtttgtttgccggatcaagagctaccaactctttttccgaaggtaactgg
cttcagcagagcgcagataccaaatactgttcttctagtgtagccgtagtta
ggccaccacttcaagaactctgtagcaccgcctacatacctcgctctgcta
atcctgttaccagtggctgctgccagtggcgataagtcgtgtcttaccgggt
tggactcaagacgatagttaccggataaggcgcagcggtcgggctgaac
ggggggttcgtgcacacagcccagcttggagcgaacgacctacaccga
actgagatacctacagcgtgagctatgagaaagcgccacgcttcccgaag
ggagaaaggcggacaggtatccggtaagcggcagggtcggaacagga
gagcgcacgagggagcttccaggggggaaacgcctggtatctttatagtcc
tgtcgggtttcgccacctctgacttgagcgtcgatttttgtgatgctcgtcag
ggggggcggagcctatggaaaaacgccagcaacgcggcctttttacggtt
cctggccttttgctggccttttgctcacatggctcgacagatttaattaaacag
tgtgactagggaggcaaaacatacctactaaagggtggtagcataattcag
ttcttatgtgagtatgtgtatgtgtgtgagtatgtgcacatgcacatacatttta
```

TABLE 2-continued

Sequences

| SEQ ID NO: Description | Sequence |
|---|---|
| | aaaggtctgtaatatactaacatgttcatagtggttacacctagcttataggta |
| | acattttttcccctgtatccttgtttgtgtttatcaaattttcataacagtaatggt |
| | agaaggagtacctgacatggtaccatacatgctctgggccctgcctaatttc |
| | tcaatttcctttattgcccataccccccattgcttgacaagcataagtccatact |
| | ggcttgtttttcgttcctcagactcagtacaccatgtagctccatgccctggg |
| | tctttgtatgtgctatttctactgcttagagtgctattgcccctgaccaccacgt |
| | ggtcagcaacttctcttctgtgtctgtgtccatggtctatgattccagatgtcat |
| | cttcactaactacccttctaatatgcccttccatcccacccgtcctcatcctta |
| | ccccagccactctctatttggtggctctgttttattttcttcctagctcatcactc |
| | tttgaaatgaacttatttacttattcattatttgcttctttcactagaatgaatgctc |
| | catgagagcagggacctgctttatcttgctcgccactgtattctcagtgccta |
| | gaactacgtctggcacatagtaggtgctcaataaatatcgatcaaatgaaa |
| | gaatgagcaaacgaacaaatgaacaacacgtgaggtaggcatcatgattc |
| | cattcaacagaggagaaaaacagacttaaagaattgaagtggtggagctg |
| | cattttgatcttgactgactccaacatccatgctcttgaccactgtgcatctcc |
| | agagtgtaatgaacatactttacttttatattccaccaaaataacaaagccat |
| | gcccatgttagtagagagttaatcgacagtgcccttaaaatatgcatgcacc |
| | cagggtacaactatgcatgctgccctgtgtttcagttggatccaaatgaatt |
| | gccgtaaacaaagagggattcaatgtctttgactagtttgggatattttcct |
| | agtaaccaactttgcaaaataaagccactaatgacaaggagctttgttctac |
| | ttctgcatcactcaactgtcaattttatctcttgcaagacttctaatctactaga |
| | acttttgtttttctgtgatttctgaacagagaagactaatccaaaccctgtcatt |
| | ccagaggaatggaaagcccaattcattaaaaccgtcggcgcgttcagcct |
| | aaagctttttctccgtatcccccccaggtgtctgcaggctcaaagagactcat |
| | gtctcctatgtctcatctaaatggatgaggtttgagagttcccatccacggcat |
| | ggtggaaacgaatccgactaggagccataagttcacggcttcgatccctg |
| | gcctcgctcaggggttaaggatccggtgttgctgtgagctgtggtgtagg |
| | tcacagatgcggttcggatctggcgttgctgcggctgtggtgtaggctggt |
| | ggctgtagctccgatttgacccctagcctagggacctccatatgccgtggg |
| | tatggccctaaaaagccaaataaaataaaataagtaaatggttgaggtttga |
| | cacagaaagtttatttatttatgtatttacttatcttttttttttttttttttttttttgtctttct |
| | gctatttcttgggctgctcccgcggcatatggaggttcccaggctaggggt |
| | cgaattggagctacagccaccagcctacaccacagccgcagcaatgcca |
| | gatccgagccgcctctgtgacctacaccacagctcatggcaacgctggat |
| | cgttaacccactgagcaagggctgggaccgaacccgcaacctcatggttc |
| | ctagtcggattcgttaaccactgcgccatgacgggaactcctacttatctatt |
| | tttaaagcatatggaagttcccaggctaggggttgaatcggagctgcaa |
| | ctgccggcttacaccacagccagagcaacgccggatctgagcagtgtct |
| | gggacctacaccacagctcacagccacaccggatcctcaatccactgaat |
| | gaggccaggaatcaaacctgtgtcctcatggatactagtcagattcatttcc |
| | gctgagcaatgacaggaactcctgacacagaaattttagattaaaattgaa |
| | gatgagccccttccttttgtacgacctttgtgtgcagattttcgaggataagtc |
| | cttgagcttgaagttttagggtcatggatcctcataacagtttcctggcctgtg |
| | aggcttggatctcagtataaacagaagtgctggcagcagtagacacagca |
| | gcagctgttttcaggaacaaatactgggcacctgccttgtggacctgcctg |
| | actccaccactctcttgggtatccacaaagtggacccagaggttcagagca |
| | gccctgggatccaaattttttttaatttattttttatcttttattttttgtcttttcgaaa |
| | tttttagggctacacccatgagatatggaggttcccaggctaagggtccaat |
| | cggagctacaactgccggcctacaccacagctcatggcaatgctggatcc |
| | ttaacccgctgagcgaggccagggatcaaacccacaacctcatgattcct |
| | agttggattcgttaaccactgagccacgatgggaactccctgggatgcaaa |
| | ttttgtcatctagccctaggatgtagctatcatcctgatttgagaagagaggc |
| | agagtctcaggtggcttctctctcatgaatgcagagctaagggtggccaca |
| | cgtacttgagttcatccgatgcacacagcattgtgctaaaatattgaccattt |
| | ggcccttttgctgacttttggtttgagggatatgaccttcatgagcatacaga |
| | ggataatatgtatgcatgtatgcatgtgtgtacacatgtgcgcatgcatgtat |
| | atacctgcataattatgtatttgtttatgtatgcaggtgcatgtgtatgtatatat |
| | ttattatttatttatttgggggccacacccatgacatttggaagttcctgggac |
| | agagattgaatcccagccacagctttgacctacgccatggacacagcaac |
| | actggattcttaacccctgtgccacagcgggaactcctagaagatagtatt |
| | tcatgatgatatttgactaaaaataggggtcaggctttgaagtttaaataaatt |
| | cgaccagataaatggccatccaggaagttatactttgccttgttcaaatttgg |
| | accacggggaaggtggttggcgacatgtaacagaaatctgactccagtgc |
| | aggtttcgctcccgtgacgggaagcccagaggtgggcagccctaaggct |
| | ggggctctgatttcatgatgctcttagcatcttgagtcccttccctcttcttgct |
| | tttatctcagcctcgggctgctgcaccttctgtctttgtggtgagtctacctatt |
| | ccacttagctcggcttcagggtgtatttccacgacttcgttagagtaaggttg |
| | gggccagctgtgctctgccggcaggaggtgtgcttgcaggggccatgga |
| | tgtggccaggacctaatgtgacggtggggagcaggatggggatgggaggat |
| | gtgaccacagagccttgggaaccacgtcatccacgtcatacactgagagc |
| | aggtggttctcatgcaggtgcatcagaatcccgaggacggcttgtccaaa |
| | cccagatggctgggcccaagccctgagctcccgatttgggaggccttgg |
| | ctgggcccccgaaatctgccttcctgactagaccgagtgatgaatggtgttc |
| | atagacaagacatacactaacactggtcttggggggctccttgccacaccct |

TABLE 2-continued

Sequences

| SEQ ID NO: | Description | Sequence |
|---|---|---| gaaggggtccgtgaaactgacgggccagagaaggtgctggttcctcca
tggaaggtctcagtgaggccattctgctgcccggctgggtcacgctgggg
gagtgagggtgcatcccctcctgggatctggtcaaaggcagattctgattc
tggaagcacggggtagggccagagatgccaccttctaacaagcccccag
gtgaagatgttgacctgggaccttatggtgggggggtggcggagctcaag
gtggcagacacctccctctctctcaacctgtgtcacagcagggccatccta
ctggctctcgctcggccagagatggcgatgccagaacacactggggcag
ggtgtccacattttttgtcacttccactgagccctggggactgactcatttaaat
gacattctcaactctttggaaagaagctgggccagaaatggaaatggcag
caaacactttttgggaaacaggaagccaatttttttttttcaatcatgattttccc
cagattcagagactgcttaactcccaatgaaatacttttagattacgagctaa
aataccgaaaagctgtcaagctcaagaccacaggaaaacagccgaaga
acaaacaccatgagaaaacagtcacagagtgcctctgcggcggatttcaa
gttccagacttccttgctgtcagctgtgtgtacttgtcccgcctgcagtagga
ccagctggggtttaagtctgtaccatggacactgctgccaggattctcctct
gcatctgctgacttccagctcttcagggccagctggccataggagcataaa
ctgacatccagttccaggaggcagcatctgtccccatggcctgcaggaca
ccagatcagtagaggcccccagggccacctttcctgtgggggcccttgaa
gggacccgggaaggctggatcttgctaaagcttccacaagtcccttccaa
aggagagtaaattctaaacagaagcttttgccagtgcttctctgggatctgg
cttcaggattattcctagtctgaaaagtcttcctggtggtttggacacgggca
aatgcttggtgggtgggctggctctggatgcaggtgagtggggtcggaa
gttctccctccttcccacaaagcttgacggagccaggggcacccgcggg
cctgtggatgggagaggggtttctggtgacggactcaagtcttggcagcc
cctgacccccagagcaggctccctccccacagctgctctccgtgagtccttc
acttgcccaagttcaagatgtacccagttctggagctgccaaaccatcctg
catcctgatgtcagccacccaagttctggggtagctggtctgccacccagg
tggatgaaaagaggccacatacctgcaccagcatctgcgaatctctgaag
aacatcaataataaaaagacaactaacccagttaaaacacaggtagagaa
tctgaacagacattcatcggaagaagaattacgactggccaaaaagctcat
aaaaagatggtcaaagtcattggtcagggaaatgtaaatcaaaccgcattg
agataccatctcactccctctcggatggctggaatgaaaaaaaacctcttct
ttcctccctttcattgtcttggcacccttgtggaaattaattgactaaaattcat
gaaatacaaaaattttttaggagttcccgtcgtggctcagtggttaacaaatct
gactaggaaccatgaggtttcaggttcgattcctggcctcactcagtgggtt
agggatctggtgttgccatgagctgtggtgtaggtcacagacgcagctcg
gatcccgcattgctgtggctctggcgtaggccggcggctacagctctgatt
caacctctagcctgggaatagcccaagaaatggcaaaaagaccaaaaaa
aaaaaaaaaaaaaaaactcgttttgagcatttttgcatgtgtacattgtccatt
tgtgtgccttccaagatttattttttggagtctcaactctgtcattgatttatgtctc
tccttaggccagaaccacactgttttggtgaccatggctttgtagtaaaattt
gaaatctgaaagtgtgagccctcctgtttttgtttctcttctccatgattagtttg
gttattcagagtcccttgaatttccaggtgaattttaggattagcaggaaaatt
tctgcagagatggcagcagagattttaatagggattatgttgaatctggag
gttaatttcagtttttgctaccttgactgtattaagtcttccagtctataagcataa
gatgtctttttatttacttaggtcttttaaaatttctttgggcactcccattgtggt
gcatcggaaatgaatccgactagtatccacaagaacacaggttcaatccct
ggcattgctcagtgggttaaggatcctgcattgccatgaagaactgtggtg
gaggccagcagctgcagctctgatttgacccctagcctgggaacttccata
tgccttgggtatggccctaaaaagcaaactaagtaagtaagtaaataaata
aatgaataaataaaatttctttcaacattgtaattttgtaattttttgtaattttcaga
gcgtacattttgccctttcaatacattattcctacatattttattcttttttgatactat
tataaatgaaatttataattaattcatttatatgaatttcattttcaatttgcatattg
ctactacaatagaaatgcactttttaattattttttatggccatactatatatatatg
tgtgtgtgtgtgtatgtgtgtcattttactgtacagcagaaattgacacaacat
tgtaaatcaactacacttaaaaaatgaagaaataaccacctgtgattatggct
actgtgttggacactttaggcatccccccaccccgtccccgccccacaccc
ctgagtgctagtgacggatgttcccacccaggggggcctggagcctttatca
ccagccatcgggaatcagaaccgtatctcacagtccccatgcctggagca
cctggaattgtgcccttggactcgtgggtgttctgcttctcagtgggagaag
cttaggttctaaagtcagagcaggggacagcccccatgtgctcaggacccag
tgtgaaggggtctgcctcaggggacctgggggttacaagggtaagagaa
ggtgttcatgttggaactagaagttctttttcactgctctgaagaaaaaagct
gcctccacccttggtacagctcttctgctaacagtgaatcaggcagaacg
tgttcaagaagtgacccagcctggtggggccagacctgacccttgatgg
tccctcaacccctccgagggtcccgcccttcctttactgctttgttgtctgtcc
tgagaggtttggctaatgtcgaaccaagggtgtggctggtcctgtccccttt
cctgtctcacgcacccacctctgaagtctctgtagctggttccagccgggat
ctggagccactcccccgccccaggcccagtggtacagactcttgcaga
gtcgggggccctgactcagcccccaccgccagcgggatgtcaggccag
cacccgccccactcccactgatctggggggggggtgtctttccttcctccttcc
aaaggagcctcagaccttcctgtggggcacggggcagtgggattcagg
aggctctgagtcagcaggccggcattgaggagtataaagggacccagt
tcctcccccttttcacttgtggcttatcgccgcccaccctgccccaaggtca TABLE 2-continued Sequences

| SEQ ID NO: Description | Sequence |
|---|---|
| | ctgcggtcagtacagtcctcagctgccagcaggtgcctgtctttacttgtga |
| | ggccgccacgctctcctgtttctccaggtctgggctctgttggaagtgggg |
| | gcccgacccccgggtaagatgggggatctgcgtgtcctgccctcagagg |
| | cctcctcctccccgcacccctaaccctttcagcccaacaaggctggagatc |
| | tcccacatctttggcttcgttaagagttcaacagcgccgccacccggcatgt |
| | cgctgagcagaggatggcacagggtgttaaaaaaaaaaaaaaggttgcca |
| | cactccgttcggttttgggcccaccctttcgcattcctggagcctgagtaag |
| | cggataaggctgtgaaagtgacagattcctgccacctccttccagcgctca |
| | tgcacagggaccgcccctcttcggtgtcctttgctgcacaagtgcatttgca |
| | cattcctgtctcaatctggtttctccccccttaaaagatgggaatgtgacctgct |
| | tggagccctcgcctcgccagggcaccccatccgtcccttcaggggtgg |
| | agatggactgtccctctgcaaggctggatgaactcagaccaaacaggcca |
| | acttgctccccaaatacgcccacccctaccgggctgcaggaattcgcctgt |
| | caccactgctgaagggtgaccttgcagccctgagagcatccccatgactt |
| | gcccaccagatgaagtctggttgtggcaggtcgcgctcagggactcccg |
| | ggtcccacctgggggtgggaggatcctcctttgctcgtggtcgccccagc |
| | cacgccctcctttccaagcgccagtctccagagctccgtgccccggcgga |
| | ggcggtctggctctctctccttgcccctctctccttgccccctagcagcccttc |
| | tcctaaaccctctgagcagcgggcacctcctcccgagggccctgggctaag |
| | tccccacccttcatctcaagccttcctccttgactccctcttcccagagttcct |
| | tgaaataggtggtaagtacacaccgatgacggaaaacaaagactaagag |
| | gttaaagagggctgaggattacggccccggtagggctgcgcgcgaggg |
| | ggtcgagtggccgggcggtcccgttgccgggcagacagaggtgcggtt |
| | ctcccgggcgcctgcgctgccggccccgcccggagccctcccagccgg |
| | cgcccagtttactcatcccggagaggtgatcccgggcgcgagggcggg |
| | cgcagggcgtccggagaacccagtaatccgagaatgcagcatcagccct |
| | tcccaccaggcacttccttccttttcccgaacgtccaggaaggggggccg |
| | cgcacttataaaactcgggccggacccgccggcctgtcagaggctgcctc |
| | gctggggctgcgcgcggcggccggacacatctggtccgagaccaacgc |
| | gagcgactgtcactggcagctccctgcgcctctcagccccggccgggcc |
| | cctgcgcttggcgtgctgacaccatgcttggggtcctggtccttggcgcgc |
| | tggccctggccggcctggggttccccgcacccgcagagccgcagccgg |
| | gtggcagccagtgcgtcgagcacgactgcttcgcgctctacccgggccc |
| | cgcgaccttcctcaatgccagtcagatctgcgacggactgcggggccac |
| | ctaatgacagtgcgctcctcggtggctgccgatgtcatttccttgctactgaa |
| | cggcgacggcggcgttggccgccggcgcctctggatcggcctgcagct |
| | gccacccggctgcggcgaccccaagcgcctcgggccctgcgcggctt |
| | ccagtgggttacgggagacaacaacaccagctatagcaggtgggcacg |
| | gctcgacctcaatggggctcccctctgcgggcccgttgtgcgtcgctgtctc |
| | cgctgctgaggccactgtgcccagcgagccgatctgggaggagcagca |
| | gtgcgaagtgaaggccgatggcttcctctgcgagttccacttcccagccac |
| | ctgcaggccactggctgtggagcccggcgccgcggctgccgccgtctc |
| | gatcacctacggcaccccgttcgcggcccgcggagcggacttccaggc |
| | gctgccggtgggcagctccgccgcgggtggctccccctcggcttacagcta |
| | atgtgcaccgcgccgcccggagcggtccaggggcactgggccaggga |
| | ggcgccgggcgcttgggactgcagcgtggagaacggcggctgcgagc |
| | acgcgtgcaatgcgatccctggggctccccgctgccagtgcccagccgg |
| | cgccgccctgcaggcagacgggcgctcctgcaccgcatccgcgacgca |
| | gtcctgcaacgacctctgcgagcacttctgcgttcccaaccccgaccagc |
| | cgggctcctactcgtgcatgtgcgagaccggctaccggctggcggccga |
| | ccaacaccggtgcgaggacgtggatgactgcatactggagcccagtccg |
| | tgtccgcagcgctgtgtcaacacacagggtggcttcgagtgccactgcta |
| | ccctaactacgacctggtggacggcgagtgtgtggagcccgtgaccccg |
| | tgcttcagagccaactgcgagtaccagtgccagccctgaaccaaactag |
| | ctacctctgcgtctgcgccgagggcttcgcgcccattccccacgagccgc |
| | acaggtgccagatgtttgcaaccagactgcctgtccagccgactgcgac |
| | cccaacacccaggctagctgtgagtgccctgaaggctacatcctggacga |
| | cggtttcatctgcacggacatcgacgagtgcgaaaacggcggcttctgct |
| | ccgggggtgtgccacaacctccccggtaccttcgagtgcatctgcgggccc |
| | gactcggcccttgcccgccacattggcaccgactgtgactccggcaaggt |
| | ggacggtggcgacagcggctctggcgagccccgcccagcccgacgc |
| | ccggctccaccttgactcctccggccgtggggctcgtgcattcgggcttgc |
| | tcataggcatctccatcgcgagcctgtgcctggtggtggcgctttttggcgct |
| | cctctgccacctgcgcaagaagcagggcgccgccagggccaagatgga |
| | gtacaagtgcgcggcccccttccaaggaggtagtgctgcagcacgtgcgg |
| | accgagcggacgccgcagagactcggatccggagagggcagaggaa |
| | gtcttctaacatgcggtgacgtggaggagaatcccggccctatgttgacaa |
| | cattgctgccgatactgctgctgtctggctgggccttttgtagccaagacgc |
| | ctcagatggcctccaaagacttcatatgctccagatctcctacttccgcgac |
| | ccctatcacgtgtggtaccagggcaacgcgtcgctggggggacacctaa |
| | cgcacgtgctggaaggcccagacaccaacaccacgatcattcagctgca |
| | gcccttgcaggagcccgagagctgggcgcgcacgcagagtggcctgca |
| | gtcctacctgctccagttccacggcctcgtgcgcctggtgcaccaggagc |
| | ggaccttggcctttcctctgaccatccgctgcttcctgggctgtgagctgcc |

TABLE 2-continued

Sequences

| SEQ ID NO: | Description | Sequence |
|---|---|---| tcccgagggctctagagcccatgtcttcttcgaagtggctgtgaatgggag
ctcctttgtgagtttccggccggagagagccttgtggcaggcagacaccc
aggtcacctccggagtggtcaccttcaccctgcagcagctcaatgcctaca
accgcactcggtatgaactgcgggaattcctggaggacacctgtgtgcag
tatgtgcagaaacatatttccgcggaaaacacgaaagggagccaaacaa
gccgctcctacacttcgctggtcctgggcgtcctggtgggcagtttcatcat
tgctggtgtggctgtaggcatcttcctgtgcacaggtggacggcgatgttg
agcgcggccgcttccctttagtgagggttaatgcttcgagcagacatgata
agatacattgatgagtttggacaaaccacaactagaatgcagtgaaaaaaa
tgctttatttgtgaaatttgtgatgctattgctttatttgtaaccattataagctgc
aataaacaagttaacaacaacaattgcattcattttatgtttcaggttcaggg
ggagatgtgggaggtttttttaaagcaagtaaaacctctacaaatgtggtaaa
atccgataaggatcgatgggacagcccccccccaaagcccccagggat
gtaattacgtccctcccccgctagggcagcagcgagccgcccggggctc
cggtccggtccggcgctcccccgcatccccgagccggcagcgtgcggg
gacagcccgggcacggggaaggtggcacgggatcgctttcctctgaac
gcttctcgctgctctttgagcctgcagacacctgggggggatacggggaaa
atctagtgggacagcccccccccaaagcccccagggatgtaattacgtcc
ctcccccgctagggcagcagcgagccgcccggggctccggtccggtcc
ggcgctcccccgcatccccgagccggcagcgtgcggggacagcccgg
gcacggggaaggtggcacgggatcgctttcctctgaacgcttctcgctgct
ctttgagcctgcagacacctgggggggatacggggaaaaatcgatgggac
agcccccccccaaagcccccagggatgtaattacgtccctcccccgctag
ggcagcagcgagccgcccggggctccggtccggtccggcgctcccc
gcatccccgagccggcagcgtgcggggacagcccgggcacggggaa
ggtggcacgggatcgctttcctctgaacgcttctcgctgctctttgagcctg
cagacacctgggggggatacggggaaaatctagtgggacagcccccccc
caaagcccccagggatgtaattacgtccctcccccgctagggcagcagc
gagccgcccggggctccggtccggtccggcgctcccccgcatccccga
gccggcagcgtgcggggacagcccgggcacggggaaggtggcacgg
gatcgctttcctctgaacgcttctcgctgctctttgagcctgcagacacctgg
ggggatacggggaaaaatcgatagcgataaggatccactagttattaata
gtaatcaattacggggtcattagttcatagcccatatatggagttccgcgtta
cataacttacggtaaatggcccgcctggctgaccgcccaacgacccccg
cccattgacgtcaataatgacgtatgttcccatagtaacgccaatagggact
ttccattgacgtcaatgggtggagtatttacggtaaactgcccacttggcag
tacatcaagtgtatcatatgccaagtacgccccctattgacgtcaatgacgg
taaatggcccgcctggcattatgcccagtacatgaccttatgggactttcct
acttggcagtacatctacgtattagtcatcgctattaccatgggtcgaggtga
gccccacgttctgcttcactctccccatctccccccctcccccacccccaat
tttgtatttatttattttttaattattttgtgcagcgatggggcggggggggggg
gggcgcgcgccaggcggggcggggcggggcgagggcggggcg
gggcgaggcggagaggtgcggcggcagccaatcagagcggcgcgct
ccgaaagtttccttttatggcgaggcggcggcggcggccctataaaa
agcgaagcgcgcggcgggcgggagtcgctgcgttgccttcgccccgtg
ccccgctccgcgccgcctcgcgccgcccgccccggctctgactgaccg
cgttactcccacaggtgagcggggggacggcccttctcctccgggctgt
aattagcgcttggtttaatgacggctcgtttcttttctgtggctgcgtgaaagc
cttaaagggctccgggagggccctttgtgcggggggggagcggctcggg
gggtgcgtgcgtgtgtgtgtgcgtggggagcgccgcgtgcggcccgcg
ctgcccggcggctgtgagcgctgcgggcgcggcgcggggctttgtgcg
ctccgcgtgtgcgcgagggggagcgcggccggggcggtgcccgcg
gtgcggggggctgcgaggggaacaaaggctgcgtgcggggtgtgtg
cgtgggggggtgagcaggggtgtgggcgcggcggtcgggctgtaac
cccccctgcaccccccctccccgagttgctgagcacggcccggcttcgg
gtgcggggctccgtgcggggcgtggcgcggggctcgccgtgccgggc
gggggtggcggcaggtgggggtgccgggcggggggggccgcctc
gggccggggagggctcggggagggggcgcggcggccccggagcgc
cggcggctgtcgaggcgcggcgagccgcagccattgccttttatggtaat
cgtgcgagagggcgcagggacttcctttgtcccaaatctggcggagccg
aaatctgggaggcgccgccgcaccccctctagcgggcgcgggcgaag
cggtgcggcgccggcaggaaggaaatgggcgggagggccttcgtgc
gtcgccgcgccgccgtccccttctccatctccagcctcggggctgccgca
gggggacggctgccttcggggggggacggggcagggcggggttcggct
tctggcgtgtgaccggcgggctctagagcctctgctaaccatgttcatgcctt
cttctttttcctacagctcctgggcaacgtgctggttgttgtgctgtctcatcat
tttggcaaagaattccgctgcgactcggcggagtcccggcggcgcgtcct
tgttctaacccggcgcgccctcaggatgggaatccaaggagggtctgtcc
tgttcgggctgctgctcgtcctggctgtcttctgccattcaggtcatagcctg
cagtgctacaactgtcctaacccaactgctgactgcaaaacagccgtcaat
tgttcatctgattttgatgcgtgtctcattaccaaagctgggttacaagtgtata
acaagtgttggaagtttgagcattgcaatttcaacgacgtcacaacccgctt
gagggaaaatgagctaacgtactactgctgcaagaaggacctgtgtaactt
taacgaacagcttgaaaatggtgggacatccttatcagagaaaacagttctt TABLE 2-continued Sequences

| SEQ ID NO: Description | Sequence |
|---|---| ctgctggtgactccatttctggcagcagcctggagccttcatcccggatcc
ggagagggcagaggaagtcttctaacatgcggtgacgtggaggagaatc
ccggccctatggagcgtccgcaacccgacagcatgccccaggatttgtca
gaggccctgaaggaggccaccaaggaggtgcacacccaggcagagaa
tgctgagttcatgaggaactttcagaagggccaggtgacccgagacggct
tcaagctggtgatggcctccctgtaccacatctatgtggccctggaggagg
agattgagcgcaacaaggagagcccagtcttcgcccctgtctacttccca
gaagagctgcaccgcaaggctgccctggagcaggacctggccttctggt
acgggccccgctggcaggaggtcatccctacacaccagccatgcagc
gctatgtgaagcggctccacgaggtggggcgcacagagcccgagctgc
tggtggcccacgcctacacccgctacctgggtgacctgtctgggggcca
ggtgctcaaaaagattgcccagaaagccctggacctgcccagctctggc
gagggcctggccttcttcaccttccccaacattgccagtgccaccaagttc
aagcagctctaccgctcccgcatgaactccctggagatgactcccgcagt
caggcagagggtgatagaagaggccaagactgcgttcctgctcaacatc
cagctctttgaggagttgcaggagctgctgacccatgacaccaaggacca
gagcccctcacgggcaccagggcttcgccagcgggccagcaacaaagt
gcaagattctgcccccgtggagactcccagagggaagcccccactcaac
acccgctcccaggctccgcttctccgatgggtccttacactcagctttctgg
tggcgacagttgctgtagggctttatgccatgtgagcggcgcgccggcac
cggtaccaagcttaagagcgctagctggccagacatgataagatacattg
atgagtttggacaaaccacaactagaatgcagtgaaaaaaatgctttatttgt
gaaatttgtgatgctattgctttatttgtaaccattataagctgcaataaacaag
ttaacaacaacaattgcattcatttatgtttcaggttcaggggggaggtgtgg
gaggttttttaaagcaagtaaaacctctacaaatgtggtatggaattggagc
cccactgtgttcatcttacagatggaaatactgacattcagaggagttagtta
acttgcctaggtgattcagctaataagtgcaagaaagatttcaatccaaggt
gatttgattctgaagcctgtgctaatcacattacaccaagctacaacttcattt
ataaataataagtcagctttcaagggcctttcaggtgtcctgcacttctacaa
gctgtgccatttagtgaacacaaaatgagccttctgatgaagtagtcttttcat
tatttcagatattagaacactaaaattcttagctgccagctgattgaaggctg
ggacaaaattcaaacatgcatctacaacaatatatatctcaatgttagtctcc
aaattctattgacttcaactcaagagaatataaagagctagtctttatacactc
tttaaggtatgatgggtcccgattttttccccgtatcccccccaggtgtctgcag
gctcaaagagcagcgagaagcgttcagaggaaagcgatcccgtgccac
cttccccgtgcccgggctgtccccgcacgctgccggctcggggatgcgg
gggagcgccggaccggaccggagcccgggcggctcgctgctgccct
agcgggggagggacgtaattacatccctgggggctttggggggggggct
gtcccactagattttccccgtatcccccaggtgtctgcaggctcaaagag
cagcgagaagcgttcagaggaaagcgatcccgtgccaccttccccgtgc
ccgggctgtccccgcacgctgccggctcggggatgcgggggagcgcc
ggaccggaccggagcccgggcggctcgctgctgccctagcggggga
gggacgtaattacatccctgggggctttggggggggggctgtcccatcgga
tcttctagtcctgcaggagtcaatgggaaaaacccattggagccaagtaca
ctgactcaatagggactttccattgggttttgcccagtacataaggtcaatag
ggggtgagtcaacaggaaagtcccattggagccaagtacattgagtcaat
agggactttccaatgggtttttgcccagtacataaggtcaatgggaggtaag
ccaatgggtttttcccattactgacatgtatacgcgtcgacgtcggcgcgttc
agcctaaagcttttttccccgtatcccccaggtgtctgcaggctcaaagag
cagcgagaagcgttcagaggaaagcgatcccgtgccaccttccccgtgc
ccgggctgtccccgcacgctgccggctcggggatgcgggggagcgcc
ggaccggaccggagcccgggcggctcgctgctgccctagcggggga
gggacgtaattacatccctgggggctttggggggggggctgtccctgcgg
ccgcgaattcgtaatcatggtcatagctgtttcctgtgtgaaattgttatccgc
tcacaattccacacaacatacgagccggaagcataaagtgtaaagcctgg
ggtgcctaatgagtgagctaactcacattaattgcgttgcgctcactgcccg
ctttccagtcgggaaacctgtcgtgccaggggtctagccgcggtctagga
agctttctagggtacctctagggatccactagttattaatagtaatcaattacg
gggtcattagttcatagcccatatatggagttccgcgttacataacttacggt
aaatggcccgcctggctgaccgcccaacgacccccgcccattgacgtca
ataatgacgtatgttcccatagtaacgccaataggactttccattgacgtca
atgggtggagtatttacggtaaactgcccacttggcagtacatcaagtgtat
catatgccaagtacgccccctattgacgtcaatgacggtaaatggcccgcc
tggcattatgcccagtacatgaccttatgggactttcctacttggcagtacat
ctacgtattagtcatcgctattaccatgggtcgaggtgagccccacgttctg
cttcactctccccatctccccccctccccacccccaattttgtatttatttatttt
tttaattattttttgtgcagcgatggggcggggggggggggggcgcgcgc
caggcggggcggggcgggcgaggggcggggcggggcgaggcgg
agaggtgcggcggcagccaatcagagcggcgcgctccgaaagtttcctt
ttatggcgaggcggcggcggcggcggcccctataaaaagcgaagcgcgc
ggcgggcgggagtcgctcgcgttgccttcgcccctgcccccgctccgcgc
cgcctcgcgccgcccgcccccggctctgactgaccgcgttactcccacag
gtgagcgggcgggacgccttctcctccgggctgtaattagcgcttggtt
taatgacggctcgtttctttttctgtggctgcgtgaaagccttaaagggctccg TABLE 2-continued

| Sequences | |
|---|---|

SEQ
ID
NO: Description        Sequence

```
ggagggccctttgtgcggggggggagcggctcggggggtgcgtgcgtgt
gtgtgtgcgtggggagcgccgcgtgcggcccgcgctgcccggcggctg
tgagcgctgcgggcgcggcgcggggctttgtgcgctccgcgtgtgcgc
gaggggagcgcggccggggcggtgccccgcggtgcggggggggctg
cgaggggaacaaaggctgcgtgcggggtgtgtgcgtggggggggtgag
caggggggtgtgggcgcggcggtcgggctgtaacccccccctgcacccc
cctccccgagttgctgagcacggcccggcttcgggtgcggggctccgtg
cggggcgtggcgcggggctcgccgtgccgggcgggggggtggcggca
ggtgggggtgccgggcggggcggggccgcctcgggccggggaggg
ctcggggggagggggcgcggcggcccggagcgccggcggctgtcgag
gcgcggcgagccgcagccattgccttttatggtaatcgtgcgagagggcg
cagggacttcctttgtcccaaatctggcggagccgaaatctgggaggcgc
cgccgcaccccctctagcgggcgcgggcgaagcggtgcggcgccggc
aggaaggaaatgggcggggagggccttcgtgcgtcgccgcgccgccgt
ccc+cttctccatctccagcctcggggctgccgcaggggggacggctgcctt
cggggggggacggggcagggcggggttcggcttctggcgtgtgaccgg
cggctctagagcctctgctaaccatgttcatgccttcttcttttcctacagctc
ctgggcaacgtgctggttgttgtgctgtctcatcattttggcaaagaattccg
ctgcgactcggcggagtcccggcggcgcgtccttgttctaacccggcgc
gccctcaggatggagcctcccggccgccgcgagtgtccctttccttcctg
gcgctttcctgggttgcttctggcggccatggtgttgctgctgtactccttctc
cgatgcctgtgaggagccaccaacatttgaagctatggagctcattggtaa
accaaaaccctactatgagattggtgaacgagtagattataagtgtaaaaa
aggatacttctatataacctcctcttgccacccatactatttgtgatcggaatca
tacatggctacctgtctcagatgacgcctgttatagagaaacatgtccatata
tacgggatcctttaaatggccaagcagtccctgcaaatgggacttacgagt
ttggttatcagatgcactttatttgtaatgagggttattacttaattggtgaaga
aattctatattgtgaacttaaaggatcagtagcaatttggagcggtaagccc
ccaatatgtgaaaaggttttgtgtacaccacctccaaaaataaaaaatggaa
aacacacctttagtgaagtagaagtatttgagtatcttgatgcagtaacttata
gttgtgatcctgcacctggaccagatccattttcacttattggagagagcac
gatttattgtggtgacaattcagtgtggagtcgtgctgctccagagtgtaaa
gtggtcaaatgtcgatttccagtagtcgaaaatggaaaacagatatcagga
tttggaaaaaaattttactacaaagcaacagttatgtttgaatgcgataaggg
tttttacctcgatggcagcgacacaattgtctgtgacagtaacagtacttggg
atcccccagttccaaagtgtcttaaagtgctgcctccatctagtacaaaacct
ccagctttgagtcattcagtgtcgacttcttccactacaaaatctccagcgtc
cagtgcctcaggtcctaggcctacttacaagcctccagtctcaaattatcca
ggatatcctaaacctgaggaaggaatacttgacagtttggatgtttgggtca
ttgctgtgattgttattgccatagttgttggagttgcagtaatttgtgttgtccc
gtacagatatcttcaaaggaggaagaagaaaggcacatacctaactgatg
agacccacagagaagtaaaatttacttctctcggatccggagccacgaact
tctctctgttaaagcaagcaggagacgtggaagaaaacccccggtcctatg
accgtcgcgcggccgagcgtgcccgcggcgctgcccctcctcggggag
ctgcccggctgctgctgctggtgctgttgtgcctgccggccgtgtggggt
gactgtggccttcccccagatgtacctaatgcccagccagctttggaaggc
cgtacaagtttcccgaggatactgtaataacgtacaaatgtgaagaaagct
ttgtgaaaattcctggcgagaaggactcagtgatctgccttaagggcagtc
aatggtcagatattgaagagttctgcaatcgtagctgcgaggtgccaacaa
ggctaaattctgcatccctcaaacagccttatatcactcagaattattttccag
tcggtactgttgtggaatatgagtgccgtccaggttacagaagagaaccttc
tctatcaccaaaactaacttgccttcagaatttaaaatggtccacagcagtcg
aatttgtaaaaagaaatcatgccctaatccgggagaaatacgaaatggtc
agattgatgtaccaggtggcatattatttggtgcaaccatctccttctcatgta
acacagggtacaaattatttggctcgacttctagttttttgtcttatttcaggcag
ctctgtccagtggagtgacccgttgccagagtgcagagaaatttattgccc
agcaccaccacaaattgacaatggaataattcaaggggaacgtgaccatt
atggatatagacagtctgtaacgtatgcatgtaataaaggattcaccatgatt
ggagagcactctatttattgtactgtgaataatgatgaaggagagtggagtg
gcccaccacctgaatgcagaggaaaatctctaacttccaaggtcccacca
acagttcagaaacctaccacagtaaatgttccaactacagaagtctcacca
acttctcagaaaaccaccacaaaaaccaccacaccaaatgctcaagcaac
acggagtacacctgtttccaggacaaccaagcattttcatgaaacaacccc
aaataaaggaagtggaaccacttcaggtactacccgtcttctatctgggca
cacgtgtttcacgttgacaggtttgcttgggacgctagtaaccatgggcttg
ctgacttagggcgcgccggcaccggtaccaagcttaagagcgctagctg
gccagacatgataagatacattgatgagtttggacaaaccacaactagaat
gcagtgaaaaaaatgctttatttgtgaaatttgtgatgctattgctttatttgtaa
ccattataagctgcaataaacaagttaacaacaacaattgcattcattttatgt
ttcaggttcaggggaggtgtgggaggttttttaaagcaagtaaaacctcta
caaatgtggtatgggaattggagccccactgtgttcatcttacagatggaaat
actgacattcagaggagttagttaacttgcctaggtgattcagctaataagtg
caagaaagatttcaatccaaggtgatttgattctgaagcctgtgctaatcaca
ttacaccaagctacaacttcatttataaataataagtcagctttcaagggcctt
```

TABLE 2-continued

Sequences

| SEQ ID NO: | Description | Sequence |
|---|---|---|
| | | tcaggtgtcctgcacttctacaagctgtgccatttagtgaacacaaaatgag |
| | | ccttctgatgaagtagtcttttcattatttcagatattagaacactaaaattctta |
| | | gctgccagctgattgaaggctgggacaaaattcaaacatgcatctacaaca |
| | | atatatatctcaatgttagtctccaaattctattgacttcaactcaagagaatat |
| | | aaaagagctagtctttatacactctttaaggtatgatatcatctggaaagtaac |
| | | aaaattgatgcaaatttgaatgaactttatcatggtgtatttacacaatgtgttt |
| | | cttctccctgcaatgtatttctttctctaattccttccatttgatctttcatacacaa |
| | | tctggttctgatgtatgttttttggatgcacttttcaactccaaaagacagagct |
| | | agttactttcttcctggtgctccaagcactgtatttgtatctgtattcaagccctt |
| | | tgcaatattgtactggatcattatttcacctctaggatggcttccccaggcaa |
| | | cttgtgttcacccagagactacattttgtatcttgttgacctttgaacttccacc |
| | | agtgtctaaaaataatatgtatgcaaaattacttgctatgagaatgtataatta |
| | | aacaatataaaaaggagaagcaaggagagaaacacaggtgtgtatttgtg |
| | | tttgtgtgcttaaaaggcagtgtggaaaaggaagaaatgccatttatagtga |
| | | ggagacaaagttatattacctcttatctggcttttaaggagattttgctgagct |
| | | aaaaatcctatattcatagaaaagccttacctgagttgccaatacctcaattct |
| | | aaaatacagcatagcaaaactttaacctccaaatcaagcctctacttgaatc |
| | | cttttctgagggatgaataaggcataggcatcaggggctgttgccaatgtg |
| | | cattagctgtttgcagcctcaccttctttcatggagtttaagatatagtgtatttt |
| | | cccaaggtttgaactagctcttcatttctttatgttttaaatgcactgacctccc |
| | | acattcccttttagtaaaatattcagaaataatttatcatctggaaagtaacaa |
| | | aattgatgcaaatttgaatgaactttatcatggtgtatttacacaatgtgtttctt |
| | | ctccctgcaatgtatttctttctctaattccttccatttgatctttcatacacaatct |
| | | ggttctgatgtatgttttttggatgcacttttcaactccaaaagacagagctag |
| | | ttactttcttcctggtgctccaagcactgtatttgtatctgtattcaagccctttg |
| | | caatattgtactggatcattatttcacctctaggatggcttccccaggcaactt |
| | | gtgttcacccagagactacattttgtatcttgttgacctttgaacttccaccagt |
| | | gtctaaaaataatatgtatgcaaaattacttgctatgagaatgtataattaaac |
| | | aatataaaaaggagaagcaaggagagaaacacaggtgtgtatttgtgtttg |
| | | tgtgcttaaaaggcagtgtggaaaaggaagaaatgccatttatagtgagga |
| | | gacaaagttatattacctcttatctggcttttaaggagattttgctgagctaaa |
| | | aatcctatattcatagaaaagccttacctgagttgccaatacctcaattctaaa |
| | | atacagcatagcaaaactttaacctccaaatcaagcctctacttgaatccttt |
| | | ctgagggatgaataaggcataggcatcaggggctgttgccaatgtgcatta |
| | | gctgtttgcagcctcaccttctttcatggagtttaagatatagtgtattttccca |
| | | aggtttgaactagctcttcatttctttatgtttaaatgcactgacctcccacatt |
| | | ccttttagtaaaatattcagaaataatttatcccggcttgtcgacgacgg |
| 7 | B212 vector | cggaggaccgaaggagctaaccgcttttttgcacaacatgggggatcatg |
| | | taactcgccttgatcgttgggaaccggagctgaatgaagccataccaaac |
| | | gacgagcgtgacaccacgatgcctgtagcaatggcaacaacgttgcgca |
| | | aactattaactggcgaactacttactctagcttcccggcaacaattaatagac |
| | | tggatggaggcggataaagttgcaggaccacttctgcgctcggcccttcc |
| | | ggctggctggtttattgctgataaatctggagccggtgagcgtgggtctcg |
| | | cggtatcattgcagcactggggccagatggtaagccctcccgtatcgtagt |
| | | tatctacacgacggggagtcaggcaactatggatgaacgaaatagacag |
| | | atcgctgagataggtgcctcactgattaagcattggtaactgtcagaccaa |
| | | gtttactcatatatactttagattgatttaaaacttcatttttaatttaaaaggatct |
| | | aggtgaagatcctttttgataatctcatgaccaaaatcccttaacgtgagtttt |
| | | cgttccactgagcgtcagacccgtagaaaagatcaaaggatcttcttgag |
| | | atcctttttttctgcgcgtaatctgctgcttgcaaacaaaaaaaccaccgcta |
| | | ccagcggtggtttgtttgccggatcaagagctaccaactctttttccgaagg |
| | | taactggcttcagcagagcgcagataccaaatactgttcttctagtgtagcc |
| | | gtagttaggccaccacttcaagaactctgtagcaccgcctacatacctcgct |
| | | ctgctaatcctgttaccagtggctgctgccagtggcgataagtcgtgtctta |
| | | ccgggttggactcaagacgatagttaccggataaggcgcagcggtcggg |
| | | ctgaacggggggttcgtgcacacagcccagcttggagcgaacgacctac |
| | | accgaactgagatacctacagcgtgagctatgagaaagcgccacgcttcc |
| | | cgaagggagaaaggcggacaggtatccggtaagcggcagggtcggaa |
| | | caggagagcgcacgagggagcttccaggggggaaacgcctggtatcttta |
| | | tagtcctgtcgggtttcgccacctctgacttgagcgtcgatttttgtgatgctc |
| | | gtcaggggggcggagcctatggaaaaacgccagcaacgcggccttttta |
| | | cggttcctggccttttgctggccttttgctcacatggctcgacagatttaatta |
| | | acaagaccgacctgtccggtgccctgaatgaactgcaggacgaggcagc |
| | | gcggctatcgtggctggccacgacgggcgttccttgcgcagctgtgctcg |
| | | acgttgtcactgaagcgggaagggactggctgctattgggcgaagtgcc |
| | | ggggcaggatctcctgtcatctcaccttgctcctgccgagaaagtatccatc |
| | | atggctgatgcaatgcggcggctgcatacgcttgatccggctacctgccc |
| | | attcgaccaccaagcgaaacatcgcatcgagcgagcagtactcggatg |
| | | gaagccggtcttgtcgatcaggatgatctggacgaagagcatcaggggct |
| | | cgcgccagccgaactgttcgccaggctcaaggcgcgcatgcccgacgg |
| | | cgaggatctcgtcgtgacccatggcgatgcctgcttgccgaatatcatggt |
| | | ggaaaatggccgcttttctggattcatcgactgtggccggctgggtgtggc |
| | | ggatcgctggcctcgatggccgtgccagggcgtgcccttgggctccccg |

Sequences

SEQ
ID
NO: Description        Sequence

```
ggcgcggcgattaagacgtaagtcttggcagcccctgaccccagagcag
gctccctccccacagctgctctccgtgagtccttcacttgcccaagttcaag
atgtacccagttctggagctgccaaaccatcctgcatcctgatgtcagcca
cccaagttctggggtagctggtctgccacccaggtggatgaaaagaggc
cacatacctgcaccagcatctgcgaatctctgaagaacatcaataataaaa
agacaactaacccagttaaaacacaggtagagaatctgaacagacattcat
cggaagaagaattacgactggccaaaaagctcataaaaagatggtcaaa
gtcattggtcagggaaatgtaaatcaaaccgcattgagataccatctcactc
cctctcggatggctggaatgaaaaaaaacctcttctttcctccctttcattgtc
ttggcacccttgtggaaattaattgactaaaattcatgaaatacaaaaattttt
aggagttcccgtcgtggctcagtggttaacaaatctgactaggaaccatga
ggtttcaggttcgattcctggcctcactcagtgggttagggatctggtgttgc
catgagctgtggtgtaggtcacagacgcagctcggatcccgcattgctgtg
gctctggcgtaggccggcggctacagctctgattcaacctctagcctggg
aatagcccaagaaatggcaaaaagaccaaaaaaaaaaaaaaaaaaaaa
actcgttttgagcatttttgcatgtgtacattgtccatttgtgtgccttccaagat
ttatttttggagtctcaactctgtgtcattgatttatgtctctccttaggccagaa
ccacactgtttggtgaccatggctttgtagtaaaatttgaaatctgaaagtgt
gagccctcctgttttgtttctcttctccatgattagtttggttattcagagtccctt
gaatttccaggtgaattttaggattagcaggaaaatttctgcagagatggca
gcagagattttaatagggattatgttgaatctggaggttaatttcagtttttgct
accttgactgtattaagtcttccagtctataagcataagatgtcttttttatttactt
aggtcttttaaaatttctttgggcactcccattgtggtgcatcggaaatgaatc
cgactagtatccacaagaacacaggttcaatccctggcattgctcagtggg
ttaaggatcctgcattgccatgaagaactgtggtggaggccagcagctgc
agctctgatttgacccctagcctgggaacttccatatgccttgggtatggcc
ctaaaaagcaaactaagtaagtaagtaaataaataaatgaataaataaaatt
tctttcaacattgtaattttgtaattttgtaattttcagagcgtacattttgcccttt
caatacattattcctacatattttattcttttttgatactattataaatgaaatttata
attaattcatttatatgaatttcatttttcaatttgcatattgctactacaatagaaa
tgcactttttaattattttttatggccatactatatatatatgtgtgtgtgtgtatg
tgtgtcattttactgtacagcagaaattgacacaacattgtaaatcaactaca
cttaaaaaatgaagaaataaccacctgtgattatggctactgtgttggacact
ttaggcatcccccacccccgtcccgccccacacccctgagtgctagtga
cggatgttcccacccagggggcctggagcctttatcaccagccatcggga
atcagaaccgtatctcacagtccccatgcctggagcacctggaattgtgcc
cttggactcgtgggtgttctgcttctcagtgggagaagcttaggttctaagtc
agagcagggacagcccccatgtgctcaggaccagtgtgaagggtctg
cctcaggggacctgggggttacaagggtaagagaaggtgttcatgttgga
actagaagttctttttcactgctctgaagaaaaaagctgcctcccacccttgg
tacagctcttctgctaacagtgaatcaggcagaacgtgttcaagaagtgac
ccagcctggtgggggccagacctgacccttgatggtccctcaacccctcc
gagggtcccgcccttcctttactgctttgttgtctgtcctgagagggtttggcta
atgtcgaaccaagggtgtggctggtcctgtccccttttcctgtctcacgcacc
cacctctgaagtctctgtagctggttccagccgggatctggagccactccc
cccgccccagggcccagtggtacagactcttgcagagtcggggggcccctg
actcagcccaccgccagcgggatgtcaggccagcacccgccccactc
ccactgatctggggggggtgtctttccttcctccttccaaaggagcctcaga
ccttcctgtggggcacgggggcagtgggattcaggaggctctgagtcag
caggccggcattgaggagtataaagggacccagttcctcccccttcact
tgtggcttatcgccgccccaccctgccccaaggtcactgcggtcagtaca
gtcctcagctgccagcaggtgcctgtctttacttgtgaggccgccacgctct
cctgtttctccaggtctgggctctgttggaagtgggggcccgacccccgg
gtaagatgggggatctgcgtgtcctgccctcagaggcctcctcctccccg
cacccctaacccttcagcccaacaaggctgggagatctcccacatctttgg
cttcgttaagagttcaacagcgccgccacccggcatgtcgctgagcagag
gatggcacagggtgttaaaaaaaaaaaaaggttgccacactccgttcggtt
ttggggcccacccttttcgcattcctggagcctgagtaagcggataaggctgt
gaaagtgacagattcctgccacctccttccagcgctcatgcacagggacc
gcccctcttcggtgtcctttgctgcacaagtgcatttgcacattcctgtctcaa
tctggtttctcccccttaaaagatgggaatgtgacctgcttggagcccctcg
cctcgccagggcacccatccgtcccttcaggggtggagatggactgtcc
ctctgcaaggctggatgaactcagaccaaacaggccaacttgctccccaa
atacgcccacccctaccgggctgcaggaattcgcctgtcaccactgctga
agggtgaccttgcagccctgagagcatccccatgacttgcccaccagatg
aagtctggttgtggcaggtcgcgctcagggactcccgggtcccacctggg
ggtgggaggatcctcctttgctcgtggtcgcccagccacgccctcctttc
caagcgccagtctccagagctccgtgcccgggcggaggcggtctggctc
tctctccttgcccctctctccttgcccctagcagcccttctctcctaaaccctctg
agcagcgggcacctcctcccgagggccctgggctaagtccccacccttcat
ctcaagccttcctccttgactccctcttcccagagttccttgaaataggtggt
aagtacacaccgatgacggaaaacaaagactaagaggttaaagagggct
gaggattacggcccccggtagggctgcgcgcgaggggggtcgagtggcc
gggcggtcccgtcgccgggcagacagaggtgcggttctcccgggcgcc
```

TABLE 2-continued

| | Sequences |
|---|---|

| SEQ ID NO: Description | Sequence |
|---|---| tgcgctgccggccccgcccggagccctcccagccggcgcccagtttact
catcccggagaggtgatcccgggcgcgagggcgggcgcagggcgtcc
ggagaacccagtaatccgagaatgcagcatcagcccttcccaccaggca
cttccttccttttcccgaacgtccagggagggggccgcgcacttataaac
tcgggccggacccgccggcctgtcagaggctgcctcgctggggctgcg
cgcggcggccggacacatctggtccgagaccaacgcgagcgactgtca
ctggcagctccctgcgcctctcagccccggccgggccctgcgcttggc
gtgctgacaccatgcttggggtcctggtccttggcgcgctggccctggcc
ggcctggggttccccgcacccgcagagccgcagccgggtggcagcca
gtgcgtcgagcacgactgcttcgcgctctacccgggccccgcgaccttcc
tcaatgccagtcagatctgcgacggactgcggggccacctaatgacagtg
cgctcctcggtggctgccgatgtcatttccttgctactgaacggcgacggc
ggcgttggccgccggcgcctctggatcggcctgcagctgccacccggct
gcggcgaccccaagcgcctcgggccctgcgcggcttccagtgggttac
gggagacaacaacaccagctatagcaggtgggcacggctcgacctcaat
ggggctcccctctgcggcccgttgtgcgtcgctgtctccgctgctgaggc
cactgtgcccagcgagccgatctgggaggagcagcagtgcgaagtgaa
ggccgatggcttcctctgcgagttccacttcccagccacctgcaggccact
ggctgtggagcccggcgcgcggctgccgccgtctcgatcacctacggc
accccgttcgcggcccgcggagcggacttccaggcgctgccggtgggc
agctccgccgcggtggctcccctcggcttacagctaatgtgcaccgcgcc
gcccggagcggtccaggggcactgggccagggaggcgccgggcgctt
gggactgcagcgtggagaacggcggctgcgagcacgcgtgcaatgcg
atccctggggctccccgctgccagtgcccagccggcgccgccctgcag
gcagacgggcgctcctgcaccgcatccgcgacgcagtcctgcaacgac
ctctgcgagcacttctgcgttcccaacccccgaccagccgggctcctactcg
tgcatgtgcgagaccggctaccggctggcggccgaccaacaccggtgc
gaggacgtggatgactgcatactggagcccagtccgtgtccgcagcgct
gtgtcaacacacagggtggcttcgagtgccactgctaccctaactacgac
ctggtggacggcgagtgtgtggagcccgtggacccgtgcttcagagcca
actgcgagtaccagtgccagcccctgaaccaaactagctacctctgcgtct
gcgccgagggcttcgcgcccattccccacgagccgcacaggtgccagat
gttttgcaaccagactgcctgtccagccgactgcgacccccaacacccagg
ctagctgtgagtgccctgaaggctacatcctggacgacggtttcatctgca
cggacatcgacgagtgcgaaaacggcggcttctgctccggggtgtgcca
caacctccccggtaccttcgagtgcatctgcgggcccgactcggcccttg
cccgccacattggcaccgactgtgactccggcaaggtggacggtggcga
cagcggctctggcgagcccccgcccagcccgacgcccggctccacctt
gactcctccggccgtggggctcgtgcattcgggcttgctcataggcatctc
catcgcgagcctgtgcctggtggtggcgctttttggcgctcctctgccacct
gcgcaagaagcagggcgccgccagggccaagatggagtacaagtgcg
cggcccccttccaaggaggtagtgctgcagcacgtgcggaccgagcgga
cgccgcagagactcggatccggagagggcagaggaagtcttctaacatg
cggtgacgtggaggagaatcccggccctatgttgacaacattgctgccga
tactgctgctgtctggctgggccttttgtagccaagacgcctcagatggcct
ccaaagacttcatatgctccagatctcctacttccgcgacccctatcacgtgt
ggtaccagggcaacgcgtcgctggggggacacctaacgcacgtgctgg
aaggcccagacaccaacaccacgatcattcagctgcagcccttgcagga
gcccgagagctgggcgcgcacgcagagtggcctgcagtcctacctgctc
cagttccacggcctcgtgcgcctggtgcaccaggagcggaccttggcctt
tcctctgaccatccgctgcttcctgggctgtgagctgcctcccgagggctct
agagcccatgtcttcttcgaagtggctgtgaatgggagctcctttgtgagttt
ccggccggagagagccttgtggcaggcagacacccaggtcacctccgg
agtggtcaccttcaccctgcagcagctcaatgcctacaaccgcactcggta
tgaactgcgggaattcctggaggacacctgtgtgcagtatgtgcagaaac
atatttccgcgcggaaaacacgaaagggagccaaacaagccgctcctacact
tcgctggtcctgggcgtcctggtgggcagtttcatcattgctggtgtggctg
taggcatcttcctgtgcacaggtggacggcgatgttgagcgcggccgctt
cccttttagtgagggttaatgcttcgagcagacatgataagatacattgatga
gtttggacaaaccacaactagaatgcagtgaaaaaaatgctttatttgtgaa
atttgtgatgctattgctttatttgtaaccattataagctgcaataaacaagtta
acaacaacaattgcattcatttttatgtttcaggttcagggggagatgtggga
ggttttttaaagcaagtaaaacctctacaaatgtggtaaaatccgataaggat
cgatgggacagccccccccaaagcccccagggatgtaattacgtccct
cccccgctagggcagcagcgagccgcccgggggctccggtccggtccg
gcgctcccccgcatccccgagccggcagcgtgcggggacagcccggg
cacgggaaggtggcacgggatcgctttcctctgaacgcttctcgctgctc
tttgagcctgcagacacctggggggatacggggaaaatctagtgggaca
gccccccccaaagcccccagggatgtaattacgtccctcccccgctagg
gcagcagcgagccgcccggggctccggtccggtccggcgctcccccg
catccccgagccggcagcgtgcggggacagcccgggcacggggaag
gtggcacgggatcgctttcctctgaacgcttctcgctgctctctttgagcctgc
agacacctggggggatacggggaaaaatcgatgggacagcccccccccc
aaagcccccagggatgtaattacgtccctcccccgctagggcagcagcg TABLE 2-continued Sequences SEQ
ID
NO: Description        Sequence agccgcccggggctccggtccggtccggcgctcccccgcatccccgag
ccggcagcgtgcggggacagcccgggcacggggaaggtggcacggg
atcgctttcctctgaacgcttctcgctgctctttgagcctgcagacacctggg
gggatacggggaaaatctagtgggacagcccccccccaaagcccccag
ggatgtaattacgtccctcccccgctagggcagcagcgagccgcccggg
gctccggtccggtccggcgctcccccgcatccccgagccggcagcgtg
cggggacagcccgggcacggggaaggtggcacgggatcgctttcctct
gaacgcttctcgctgctctttgagcctgcagacacctggggggatacggg
gaaaaatcgatagcgataaggatccactagttattaatagtaatcaattacg
gggtcattagttcatagcccatatatggagttccgcgttacataacttacggt
aaatggcccgcctggctgaccgcccaacgaccccccgcccattgacgtca
ataatgacgtatgttcccatagtaacgccaatagggactttccattgacgtca
atgggtggagtatttacggtaaactgcccacttggcagtacatcaagtgtat
catatgccaagtacgccccctattgacgtcaatgacggtaaatggcccgcc
tggcattatgcccagtacatgaccttatgggactttcctacttggcagtacat
ctacgtattagtcatcgctattaccatgggtcgaggtgagccccacgttctg
cttcactctccccatctccccccccctccccacccccaattttgtatttatttattt
tttaattattttgtgcagcgatggggcggggggggggggggcgcgcgc
caggcggggcggggcggggcgagggcggggcggggcgaggcgg
agaggtgcggcggcagccaatcagagcggcgcgctccgaaagtttcctt
ttatggcgaggcggcggcggcggcggccctataaaaagcgaagcgcgc
ggcgggcgggagtcgctgcgttgccttcgccccgtgccccgctccgcgc
cgcctcgcgccgcccgcccccggctctgactgaccgcgttactcccacag
gtgagcgggcgggacggcccttctcctccgggctgtaattagcgcttggtt
taatgacggctcgtttcttttctgtggctgcgtgaaagccttaaagggctccg
ggagggccctttgtgcggggggggagcggctcggggggtgcgtgcgtgt
gtgtgtgcgtggggagcgccgcgtgcggcccgcgcgctgcccggcggctg
tgagcgctgcgggcgcggcgcggggctttgtgcgctccgcgtgtgcgc
gaggggagcgcggccggggcggtgccccgcggtgcggggggggctg
cgaggggaacaaaggctgcgtgcggggtgtgtgcgtggggggggtgag
caggggtgtgggcgcggcggtcgggctgtaacccccccctgcacccc
cctccccgagttgctgagcacggcccggcttcgggtgcggggctccgtg
cggggcgtggcgcggggctcgccgtgccgggcgggggtggcggca
ggtgggggtgccgggcggggcggggccgcctcgggccggggaggg
ctcgggggaggggcgcggcggcccggagcgccggcggctgtcgag
gcgcggcgagccgcagccattgcctttatggtaatcgtgcgagagggcg
cagggacttcctttgtcccaaatctggcggagccgaaatctgggaggcgc
cgccgcaccccctctagcgggcgcgggcgaagcggtgcggcgccggc
aggaaggaaatgggcggggagggccttcgtgcgtcgccgcgccgccgt
ccccttctccatctccagcctcggggctgccgcaggggacggctgcctt
cgggggggacggggcagggcggggttcggcttctggcgtgtgaccgg
cggctctagagcctctgctaaccatgttcatgccttcttcttttttcctacagctc
ctgggcaacgtgctggttgttgtgctgtctcatcattttggcaaagaattccg
ctgcgactcggcgggagtcccggcggcgcgtccttgttctaacccggcgc
gccctcaggatgggaatccaaggagggtctgtcctgttcgggctgctgct
cgtcctggctgtcttctgccattcaggtcatagcctgcagtgctacaactgtc
ctaacccaactgctgactgcaaaacagccgtcaattgttcatctgattttgat
gcgtgtctcattaccaaagctgggttacaagtgtataacaagtgttggaagt
ttgagcattgcaatttcaacgacgtcacaacccgcttgagggaaaatgagc
taacgtactactgctgcaagaaggacctgtgtaactttaacgaacagcttga
aaatggtgggacatccttatcagagaaaacagttcttctgctggtgactcca
tttctggcagcagcctggagccttcatcccggatccggagagggcagag
gaagtcttctaacatgcggtgacgtggaggagaatcccggccctatggag
cgtccgcaacccgacagcatgccccaggatttgtcagaggccctgaagg
aggccaccaaggaggtgcacaccaggcagagaatgctgagttcatga
ggaactttcagaagggccaggtgacccgagacggcttcaagctggtgat
ggcctccctgtaccacatctatgtggccctggaggaggagattgagcgca
acaaggagagcccagtcttcgcccctgtctacttcccagaagagctgcac
cgcaaggctgccctggagcaggacctggccttctggtacgggcccgct
ggcaggaggtcatcccctacacaccagccatgcagcgctatgtgaagcg
gctccacgaggtggggcgcacagagcccgagctgcggtggcccacgc
ctacacccgctacctgggtgacctgtctggggccaggtgctcaaaaaga
ttgcccagaaagccctggacctgcccagctctggcgagggcctggccttc
ttcaccttccccaacattgccagtgccaccaagttcaagcagctctaccgct
cccgcatgaactccctggagatgactcccgcagtcaggcagagggtgat
agaagaggccaagactgcgttcctgctcaacatccagctctttgaggagtt
gcaggagctgctgacccatgacaccaaggaccagagcccctcacgggc
accagggcttcgccagcgggccagcaacaaagtgcaagattctgccccc
gtggagactcccagagggaagcccccactcaacacccgctcccaggctc
cgcttctccgatggggtccttacactcagctttctggtggcgacagttgctgta
gggctttatgccatgtgagcggcgcgccggcaccggtaccaagcttaag
agcgctagctggccagacatgataagatacattgatgagtttggacaaacc
acaactagaatgcagtgaaaaaaatgctttatttgtgaaatttgtgatgctatt
gctttatttgtaaccattataagctgcaataaacaagttaacaacaacaattg TABLE 2-continued

| | | |
|---|---|---|
| Sequences | | |

| SEQ ID NO: | Description | Sequence |
|---|---|---|
| | | cattcattttatgtttcaggttcaggggggaggtgtgggaggttttttaaagca |
| | | agtaaaacctctacaaatgtggtatggaattggagccccactgtgttcatctt |
| | | acagatggaaatactgacattcagaggagttagttaacttgcctaggtgatt |
| | | cagctaataagtgcaagaaagatttcaatccaaggtgatttgattctgaagc |
| | | ctgtgctaatcacattacaccaagctacaacttcatttataaataataagtcag |
| | | ctttcaagggcctttcaggtgtcctgcacttctacaagctgtgccatttagtg |
| | | aacacaaaatgagccttctgatgaagtagtcttttcattatttcagatattaga |
| | | acactaaaattcttagctgccagctgattgaaggctgggacaaaattcaaa |
| | | catgcatctacaacaatatatatctcaatgttagtctccaaattctattgacttc |
| | | aactcaagagaatataaagagctagtcttttatacactcttaaggtatgatgg |
| | | gtcccgattttcccgtatcccccaggtgtctgcaggctcaaagagcag |
| | | cgagaagcgttcagaggaaagcgatcccgtgccaccttccccgtgcccg |
| | | ggctgtccccgcacgctgccggctcgggggatgcgggggagcgccgga |
| | | ccggaccggagccccgggcggctcgctgctgccctagcggggggaggg |
| | | acgtaattacatccctgggggctttggggggggctgtcccactagattttc |
| | | cccgtatcccccaggtgtctgcaggctcaaagagcagcgagaagcgtt |
| | | cagaggaaagcgatcccgtgccaccttccccgtgcccgggctgtccccg |
| | | cacgctgccggctcggggatgcggggggagcgccggaccggaccgga |
| | | gccccgggcggctcgctgctgccctagcgggggagggacgtaattacat |
| | | ccctgggggctttggggggggggctgtcccatcggatcttctagtcctgca |
| | | ggagtcaatgggaaaaacccattggagccaagtacactgactcaatagg |
| | | gactttccattgggttttgcccagtacataaggtcaataggggggtgagtcaa |
| | | caggaaagtcccattggagccaagtacattgagtcaataggggactttccaa |
| | | tgggttttgcccagtacataaggtcaatgggaggtaagccaatgggttttc |
| | | ccattactgacatgtatacgcgtcgacgtcggcgcgttcagcctaaagcttt |
| | | tttccccgtatcccccaggtgtctgcaggctcaaagagcagcgagaagc |
| | | gttcagaggaaagcgatcccgtgccaccttccccgtgcccgggctgtccc |
| | | cgcacgctgccggctcggggatgcggggggagcgccggaccggaccg |
| | | gagcccggggcggctcgctgctgccctagcggggggaggacgtaatta |
| | | catccctggggggctttgggggggggggctgtccctgcggccgcgaattcgta |
| | | atcatggtcatagctgtttcctgtgtgaaattgttatccgctcacaattccaca |
| | | caacatacgagccggaagcataaagtgtaaagcctggggtgcctaatga |
| | | gtgagctaactcacattaattgcgttgcgctcactgcccgctttccagtcgg |
| | | gaaacctgtcgtgccaggggtctagccgcggtctaggaagctttctaggg |
| | | tacctctagggatccactagttattaatagtaatcaattacggggtcattagtt |
| | | catagcccatatatggagttccgcgttacataacttacggtaaatggcccgc |
| | | ctggctgaccgcccaacgacccccgcccattgacgtcaataatgacgtat |
| | | gttcccatagtaacgccaataggggactttccattgacgtcaatgggtggagt |
| | | atttacggtaaactgcccacttggcagtacatcaagtgtatcatatgccaagt |
| | | acgccccctattgacgtcaatgacggtaaatggcccgcctggcattatgcc |
| | | cagtacatgaccttatgggactttcctacttggcagtacatctacgtattagtc |
| | | atcgctattaccatgggtcgaggtgagccccacgttctgcttcactctcccc |
| | | atctcccccccctccccaccccaattttgtatttatttattttttaattattttgtg |
| | | cagcgatgggggcggggggggggggggcgcgcgccaggcggggcg |
| | | gggcggggcgaggggcggggcggggcgaggcggagaggtgcggc |
| | | ggcagccaatcagagcggcgcgctccgaaagtttccttttatggcgaggc |
| | | ggcggcggcggcggcccctataaaaagcgaagcgcgcggcgggcggg |
| | | agtcgctgcgttgccttcgccccgtgccccgctccgcgccgcctcgcgcc |
| | | gcccgccccggctctgactgaccgcgttactcccacaggtgagcgggcg |
| | | ggacggcccttctcctccgggctgtaattagcgcttggtttaatgacggctc |
| | | gtttcttttctgtggctgcgtgaaagccttaaagggctccgggagggcccctt |
| | | tgtgcggggggggagcggctcggggggtgcgtgcgtgtgtgtgcgtg |
| | | gggagcgccgcgtgcggcccgcgctgcccggcggctgtgagcgctgc |
| | | gggcgcggcgcggggctttgtgcgctccgcgtgtgcgcgaggggagc |
| | | gcggccgggggcggtgccccgcggtggggggggctgcgaggggaa |
| | | caaaggctgcgtgcggggtgtgtgcgtggggggggtgagcaggggggtgt |
| | | gggcgcggcggtcgggctgtaacccccccctgcacccccctccccgagt |
| | | tgctgagcacggcccggcttcgggtgcggggctccgtgcggggcgtgg |
| | | cgcgggggctcgccgtgccgggcggggggtggcggcaggtggggggtg |
| | | ccgggcggggcggggccgcctcgggccggggagggctcggggggag |
| | | gggcgcggcggcccccggagcgccggcggctgtcgaggcgcggcgag |
| | | ccgcagccattgccttttatggtaatcgtgcgagagggcgcagggacttcc |
| | | tttgtcccaaatctggcggagccgaaatctgggaggcgccgccgcaccc |
| | | cctctagcgggcgcgggcgaagcggtgcggcgccggcaggaaggaaa |
| | | tgggcgggggagggccttcgtgcgtcgccgcgccgccgtcccccttctccat |
| | | ctccagcctcggggctgccgcaggggacggctgccttcggggggggac |
| | | ggggcagggcggggttcggcttctggcgtgtgaccggcggctctagag |
| | | cctctgctaaccatgttcatgccttcttctttttcctacagctcctgggcaacgt |
| | | gctggttgttgtgctgtctcatcattttggcaaagaattccgctgcgactcgg |
| | | cggagtcccggcggcgcgcgtccttgttctaacccggcgcgccctcaggat |
| | | ggagcctcccggccgccgcgagtgtccctttccttcctggcgctttcctgg |
| | | gttgcttctggcggccatggtgttgctgctgtactccttctccgatgcctgtg |
| | | aggagccaccaacatttgaagctatggagctcattggtaaaccaaaaccct |
| | | actatgagattggtgaacgagtagattataagtgtaaaaaaggatacttctat |

TABLE 2-continued

Sequences

SEQ
ID
NO: Description          Sequence

```
atacctcctcttgccacccatactatttgtgatcggaatcatacatggctacct
gtctcagatgacgcctgttatagagaaacatgtccatatatacgggatccttt
aaatggccaagcagtccctgcaaatgggacttacgagtttggttatcagat
gcactttatttgtaatgagggttattacttaattggtgaagaaattctatattgtg
aacttaaaggatcagtagcaatttggagcggtaagcccccaatatgtgaaa
aggttttgtgtacaccacctccaaaaataaaaaatggaaaacacacctttag
tgaagtagaagtatttgagtatcttgatgcagtaacttatagttgtgatcctgc
acctggaccagatccattttcacttattggagagagcacgatttattgtggtg
acaattcagtgtggagtcgtgctgctccagagtgtaaagtggtcaaatgtc
gatttccagtagtcgaaaatggaaaacagatatcaggatttggaaaaaaatt
ttactacaaagcaacagttatgtttgaatgcgataagggtttttacctcgatg
gcagcgacacaattgtctgtgacagtaacagtacttgggatcccccagttc
caaagtgtcttaaagtgctgcctccatctagtacaaaacctccagctttgagt
cattcagtgtcgacttcttccactacaaaatctccagcgtccagtgcctcag
gtcctaggcctacttacaagcctccagtctcaaattatccaggatatcctaaa
cctgaggaaggaatacttgacagtttggatgtttgggtcattgctgtgattgt
tattgccatagttgttggagttgcagtaatttgtgttgtcccgtacagatatctt
caaaggaggaagaagaaaggcacatacctaactgatgagacccacaga
gaagtaaaatttacttctctcggatccggagccacgaacttctctctgttaaa
gcaagcaggagacgtggaagaaaaccccggtcctatgtggcccctggta
gcggcgctgttgctgggctcggcgtgctgcggatcagctcagctactattt
aataaaacaaatctgtagaattcacgttttgtaatgacactgtcgtcattcca
tgctttgttactaatatggaggcacaaaacactactgaagtatacgtaaagt
ggaaatttaaaggaagagatatttacacctttgatggagctctaaacaagtc
cactgtccccactgactttagtagtgcaaaaattgaagtctcacaattactaa
aaggagatgcctctttgaagatggataagagtgatgctgtctcacacacag
gaaactacacttgtgaagtaacagaattaaccagagaaggtgaaacgatc
atcgagctaaaatatcgtgttgtttcatggttttctccaaatgaaaatattcttat
tgttattttcccaattttttgctatactcctgttctggggacagtttggtattaaaa
cacttaaatatagatccggtggtatggatgagaaaacaattgctttacttgtt
gctggactagtgatcactgtcattgtcattgttggagccattcttttcgtccca
ggtgaatattcattaaagaatgctactggccttggtttaattgtgacttctaca
gggatattaatattacttcactactatgtgtttagtacagcgattggattaacct
ccttcgtcattgccatattggttattcaggtgatagcctatatcctcgctgtggt
tggactgagtctctgtattgcggcgtgtataccaatgcatggccctcttctga
tttcaggtttgagtatcttagctctagcacaattacttggactagtttatatgaa
atttgtggcttccaatcagaagactatacaacctcctaggaaagctgtagag
gaacccttaatgcattcaaagaatcaaaaggaatgatgaatgatgaataa
ctgaagtgggcgcgccggcaccggtaccaagcttaagagcgctagctgg
ccagacatgataagatacattgatgagtttggacaaaccacaactagaatg
cagtgaaaaaaatgctttatttgtgaaatttgtgatgctattgctttatttgtaac
cattataagctgcaataaacaagttaacaacaacaattgcattcattttatgttt
caggttcaggggggaggtgtgggaggttttttaaagcaagtaaaacctctac
aaatgtggtatggaattggagcccactgtgttcatcttacagatggaaata
ctgacattcagaggagttagttaacttgcctaggtgattcagctaataagtgc
aagaaagatttcaatccaaggtgatttgattctgaagcctgtgctaatcacat
tacaccaagctacaacttcatttataaataataagtcagctttcaagggccttt
caggtgtcctgcacttctacaagctgtgccatttagtgaacacaaaatgagc
cttctgatgaagtagtcttttcattatttcagatattagaacactaaaattcttag
ctgccagctgattgaaggctgggacaaaattcaaacatgcatctacaacaa
tatatatctcaatgttagtctccaaattctattgacttcaactcaagagaatata
aagagctagtctttatacactctttaaggtatgatatcatctggaaagtaaca
aaattgatgcaaatttgaatgaactttatcatggtgtatttacacaatgtgtttct
tctccctgcaatgtatttctttctctaattccttccatttgatctttcatacacaatc
tggttctgatgtatgtttttttggatgcacttttcaactccaaaagacagagcta
gttactttcttcctggtgctccaagcactgtatttgtatctgtattcaagcccttt
gcaatattgtactggatcattatttcacctctaggatggcttccccaggcaac
ttgtgttcacccagagactacattttgtatcttgttgacctttgaacttccacca
gtgtctaaaaataatatgtatgcaaaattacttgctatgagaatgtataattaa
acaatataaaaaggagaagcaaggagagaaacacaggtgtgtatttgtgtt
tgtgtgcttaaaaggcagtgtggaaaaggaagaaatgccatttatagtgag
gagacaaagttatattacctcttatctggcttttaaggagattttgctgagcta
aaaatcctatattcatagaaaagccttacctgagttgccaatacctcaattcta
aaatacagcatagcaaaactttaacctccaaatcaagcctctacttgaatcct
tttctgagggatgaataaggcataggcatcaggggctgttgccaatgtgca
ttagctgtttgcagcctcaccttctttcatggagtttaagatatagtgtattttcc
caaggtttgaactagctcttcatttctttatgttttaaatgcactgacctcccac
attccctttttagtaaaatattcagaaataatttatcatctggaaagtaacaaaa
ttgatgcaaatttgaatgaactttatcatggtgtatttacacaatgtgtttcttct
ccctgcaatgtatttctttctctaattccttccatttgatctttcatacacaatctg
gttctgatgtatgtttttttggatgcacttttcaactccaaaagacagagctagtt
actttcttcctggtgctccaagcactgtatttgtatctgtattcaagccctttgc
aatattgtactggatcattatttcacctctaggatggcttccccaggcaacttg
tgttcacccagagactacattttgtatcttgttgacctttgaacttccaccagtg
```

TABLE 2-continued

Sequences

| SEQ ID NO: | Description | Sequence |
|---|---|---|
| | | tctaaaaataatatgtatgcaaaattacttgctatgagaatgtataattaaaca atataaaaaggagaagcaaggagagaaacacaggtgtgtatttgtgtttgt gtgcttaaaaggcagtgtggaaaaggaagaaatgccatttatagtgagga gacaaagttatattacctcttatctggcttttaaggagattttgctgagctaaa aatcctatattcatagaaaagccttacctgagttgccaatacctcaattctaaa atacagcatagcaaaactttaacctccaaatcaagcctctacttgaatcctttt ctgagggatgaataaggcataggcatcaggggctgttgccaatgtgcatta gctgtttgcagcctcaccttctttcatggagtttaagatatagtgtattttccca aggtttgaactagctcttcatttctttatgtttaaatgcactgacctcccacatt cccttttagtaaaatattcagaaataatttatcccggcttgtcgacgacggat catctggaaagtaacaaaattgatgcaaatttgaatgaactttatcatggtgt atttacacaatgtgtttcttctccctgcaatgtatttctttctctaattccttccattt gatctttcatacacaatctggttctgatgtatgtttttggatgcacttttcaact ccaaaagacagagctagttactttcttcctggtgctccaagcactgtatttgt atctgtattcaagccctttgcaatattgtactggatcattatttcacctctagga tggcttccccaggcaacttgtgttcacccagagactacattttgtatcttgttg accttttgaacttccaccagtgtctaaaaataatatgtatgcaaaattacttgct atgagaatgtataattaaacaatataaaaaggagaagcaaggagagaaac acaggtgtgtatttgtgtttgtgtgcttaaaaggcagtgtggaaaaggaaga aatgccatttatagtgaggagacaaagttatattacctcttatctggcttttaa ggagattttgctgagctaaaaatcctatattcatagaaaagccttacctgagt tgcccaatacctcaattctaaaatacagcatagcaaaactttaacctccaaatc aagcctctacttgaatccttttctgagggatgaataaggcataggcatcagg ggctgttgccaatgtgcattagctgtttgcagcctcaccttctttcatggagtt taagatatagtgtattttcccaaggtttgaactagctcttcatttctttatgtttta aatgcactgacctcccacattcccttttagtaaaatattcagaaataatttatc ccggcttgtcgacgacggcggtctccgtcgtcaggatcatccggccggc catcaggacatagcgttggctacccgtgatattgctgaagagcttggcggc gaatgggctgaccgcttcctcgtgctttacggtatcgccgctcccgattcgc agcgcatcgccttctatcgccttcttgacgagttcttctgaggggatcaattc tctagagctcgctgatcagcctcgactgtgccttctagttgccagccatctgt tgtttgcccctcccccgtgccttccttgaccctggaaggtgccactcccact gtcctttcctaataaaatgaggaaattgcatcgcattgtctgagtaggtgtca ttctattctggggggtggggtggggcaggacagcaagggggaggattgg gaagacaatagcaggcatgctggggatgcggtgggctctatggcttctga ggcggaaagaaccagctggggggcgcgcacctcgaccatctccaggatg cctttgatagagctgggtcctctgcgttcctttaaagtgtttggagatcaagtcc gagaagaggtggcaagacatatttaaatcgcgctagtttaaaatacatcatt gcaatgaaaataaatgtttttttattaggcagaatccagatgctcaaggcccctt cataatatcccccagtttagtagttggacttagggaacaaaggaacctttaat agaaattggacagcaagaaagctctagctttagaagaactcatcaagaagt ctgtagaaggcaattctctgggagtcaggggctgcaatgccatagagcac taggaacctgtctgcccactctcccctagctcttctgctatgtccctggttg ctagggcaatgtcctggtacctgtcagccactcccagcctgccacagtcta tgaagccagagaaccttccatttttcaaccatgatgttgggaaggcaggcat ccccatgagtcaccactaggtcctcaccatctggcatggatgccttgagcc tggcaaatagttcagcaggggccaggccctggtgttcttcatccaagtcat cttggtccaccaggccagcctccatcctggttctggccctctctatcctgtg cttggcctggtggtcaaaggggcaggtggctgggtcaagggtgtggagt cttctcatggcatcagccatgattgacactttctcagctggagctaggtgag aggaaaggaggtcctgcccaggcacctcacctagtaggagccagtccct tccagcttctgtgaccacatcaaggacagctgcacaggggaccccagttg ttgccaaccaggagagtctggcagcctcatcctggagctcattgagagcc ccactgaggtctgtctttacaaaaaggactggcctgccttgggctgaaagt ctgaaaactgctgcatcagagcaaccaatggtctgctgtgcccagtcatag ccaaacagtctctcaacccaggcagctggagaacctgcatgtaggccatc ttgttcaatcatgatggctcctcctgtcaggagaggaaagagaagaaggtt agtacaattgctatagtgagttgtattatactatgcttatgattaattgtcaaact agggctgcagggttcatagtgccactttcctgcactgccccatctcctgcc caccctttcccaggcatagacagtcagtgacttaccaaactcacaggagg gagaaggcagaagcttttgcaaaagcctaggctcatgagacaataaccc tgataaatgcttcaataatattgaaaaaggaagagtaccaggtatgagtatt caacatttccgtgtcgcccttattcccttttttgcggcattttgccttcctgtttttt gctcacccagaaacgctggtgaaagtaaaagatgctgaagatcagttggg tgcacgagtgggttacatcgaactggatctcaacagcggtaagatccttga gagttttcgccccgaagaacgttttccaatgatgagcacttttaaagttctgct atgtggcgcggtattatcccgtattgacgccgggcaagagcaactcggtc gccgcatacactattctcagaatgacttggttgagtactcaccagtcacaga aaagcatcttacggatggcatgacagtaagagaattatgcagtgctgccat aaccatgagtgataacactgcggccaacttacttctgacaacgat |
| 8 | B214 vector | atgtctcctatgtctcatctaaatggatgaggtttgagagttcccatcacggc atggtggaaacgaatccgactaggagccataagttcacggcttcgatccct ggcctcgctcaggggggttaaggatccggtgttgctgtgagctgtggtgtag |

TABLE 2-continued

Sequences

| SEQ ID NO: | Description | Sequence |
|---|---|---| gtcacagatgcggttcggatctggcgttgctgcggctgtggtgtaggctgg
tggctgtagctccgatttgacccctagcctagggacctccatatgccgtgg
gtatggccctaaaaagccaaataaaataaaataagtaaatggttgaggtttg
acacagaaagtttatttatttatgtatttacttatctttttttttttttttttttttttgtctttt
ctgctatttcttgggctgctcccgcggcatatggaggttcccaggctaggg
gtcgaattggagctacagccaccagcctacaccacagccgcagcaatgc
cagatccgagccgcctctgtgacctacaccacagctcatggcaacgctgg
atcgttaacccactgagcaagggctgggaccgaacccgcaacctcatggt
tcctagtcggattcgttaaccactgcgccatgacgggaactcctacttatcta
tttttttaaagcatatggaagttcccaggctaggggggttgaatcggagctgca
actgccggcttacaccacagccagagcaacgccggatctgagcagtgtct
gggacctacaccacagctcacagccacaccggatcctcaatccactgaat
gaggccaggaatcaaacctgtgtcctcatggatactagtcagattcatttcc
gctgagcaatgacaggaactcctgacacagaaatttttagattaaaattgaa
gatgagcccttccttttgtacgacctttgtgtgcagattttcgaggataagtc
cttgagcttgaagttttagggtcatggatcctcataacagtttcctggcctgtg
aggcttggatctcagtataaacagaagtgctggcagcagtagacacagca
gcagctgttttcaggaacaaatactgggcacctgccttgtggacctgcctg
actccaccactctcttgggtatccacaaagtggacccagaggttcagagca
gccctgggatccaaattttttttaatttatttttttatctttttattttttgtcttttcgaaa
tttttagggctacacccatgagatatggaggttcccaggctaagggtccaat
cggagctacaactgccggcctacaccacagctcatggcaatgctggatcc
ttaacccgctgagcgaggccagggatcaaacccacaacctcatgattcct
agttggattcgttaaccactgagccacgatgggaactccctgggatgcaaa
ttttgtcatctagccctaggatgtagctatcatcctgatttgagaagagaggc
agagtctcaggtggcttctctctcatgaatgcagagctaagggtggccaca
cgtacttgagttcatccgatgcacacagcattgtgctaaaatattgaccattt
ggcccttttgctgacttttggtttgagggatatgaccttcatgagcatacaga
ggataatatgtatgcatgtatgcatgtgtgtacacatgtgcgcatgcatgtat
atacctgcataattatgtatttgtttatgtatgcaggtcatgtgtatgtatatat
ttattatttatttatttggggggccacacccatgacatttggaagttcctgggac
agagattgaatcccagccacagctttgacctacgccatggacacagcaac
actggattcttaacccctgtgccacagcgggaactcctagaagatagtatt
tcatgatgatatttgactaaaaataggggtcaggctttgaagtttaaataaatt
cgaccagatataatggccatccaggaagttatactttgccttgttcaaatttgg
accacggggaaggtggttggcgacatgtaacagaaatctgactccagtgc
aggtttcgctcccgtgacgggaagcccagaggtgggcagccctaaggct
ggggctctgatttcatgatgctcttagcatcttgagtcccttccctcttcttgct
tttatctcagcctcgggctgctgcaccttctgtctttgtggtgagtctacctatt
ccacttagctcggcttcagggtgtatttccacgacttcgttagagtaaggttg
gggccagctgtgctctgccggcaggaggtgtgcttgcaggggccatgga
tgtggccaggacctaatgtgacggtggggagcaggatggggatgaggat
gtgaccacagagccttgggaaccacgtcatccacgtcatacactgagagc
aggtggttctcatgcaggtgcatcagaatcccgaggacggcttgtccaaa
cccagatggctgggcccaagccctgagctcccgatttgggaggccttgg
ctgggcccccgaaatctgccttcctgactagaccgagtgatgaatggtgttc
atagacaagacatacactaacactggtcttgggggctccttgccacaccct
gaaggggtccgtgaaactgacggggccagagaaggtgctggttcctcca
tggaaggtctcagtgaggccattctgctgcccggctgggtcacgctgggg
gagtgagggtgcatcccctcctgggatctggtcaaaggcagattctgattc
tggaagcacggggtagggccagagatgccaccttctaacaagcccccag
gtgaagatgttgacctgggaccttatggtgggggggtggcggagctcaag
gtggcagacacctccctctctctcaacctgtgtcacagcagggccatccta
ctggctctcgctcggccagagatggcgatgccagaacacactggggcag
ggtgtccacattttttgtcacttccactgagccctggggactgactcatttaaat
gacattctcaactctttggaaagaagctgggccagaaatggaaatggcag
caaacactttttgggaaacaggaagccaattttttttttcaaatcatgattttccc
cagattcagagactgcttaactcccaatgaaatactttttagattacgagctaa
aataccgaaaagctgtcaagctcaagaccacaggaaaacagccgaaga
acaaacaccatgagaaaacagtcacagagtgcctctgcggcggatttcaa
gttccagacttccttgctgtcagctgtgtgtacttgtcccgcctgcagtagga
ccagctggggtttaagtctgtaccatggacactgctgccaggattctcctct
gcatctgctgacttccagctcttcagggccagctggccataggagcataaa
ctgacatccagttccaggaggcagcatctgtccccatggcctgcaggaca
ccagatcagtagaggcccccagggccacctttcctgtggggggcccttgaa
gggacccgggaaggctggatcttgctaaagcttccacaagtcccttccaa
aggagagtaaattctaaacagaagcttttgccagtgcttctctgggatctgg
cttcaggattattcctagtctgaaaagtcttcctggtggtttggacacgggca
aatgcttggtgggtgggctggctctggatgcaggtgaggtggggtcggaa
gttctccctccttcccacaaagcttgacggagccaggggcacccgcggg
cctgtggatgggagaggggtttctggtgacggactcaagtcttggcagcc
cctgaccccagagcaggctccctccccacagctgctctccgtgagtccttc
acttgcccaagttcaagatgtacccagttctggagctgccaaaccatcctg
catcctgacgtcagccacccaagttctggggtagctggtctgccacccag TABLE 2-continued Sequences SEQ
ID
NO: Description                Sequence gtggatgaaaagaggccacatacctgcaccagcatctgcgaatctctgaa
                              gaacatcaataataaaaagacaactaacccgattaaaacacaggtagaga
                              atctgaacagacattcatcggaagaagaattacgactggccaaaaagctc
                              ataaaaagatggtcaaagtcattggtcagggaaatgtaaatcaaaccgcat
                              tgagataccatctcactccctctcggatggctggaatgaaaaaaaacctctt
                              ctttcctccctttcattgtcttggcacccttgtggaaattaattgactaaaattca
                              tgaaatacaaaaattttaggagttcccgtcgtggctcagtggttaacaaatc
                              tgactaggaaccatgaggtttcaggttcgattcctggcctcactcagtgggt
                              tagggatctggtgttgccatgagctgtggtgtaggtcgcagacgcagctc
                              ggatcccgcattgctgtggctctggcgtaggccggcggctacagctctga
                              ttcaacctctagcctgggaatagcccaagaaatggcaaaaagaccaaaaa
                              aaaaaaaaaaaaaaaactcgttttgagcatttttgcatgtgtacattgtccat
                              ttgtgtgccttccaagatttattttttggagtctcaactctgtcattgatttatgtct
                              ctccttaggccagaaccacactgttttggtgaccatggctttgtagtaaaattt
                              gaaatctgaaagtgtgagccctcctgtttttgtttctcttctccatgattagtttg
                              gttattcagagtcccttgaatttccaggtgaattttaggattagcaggaaaatt
                              tctgcagagatggcagcagagattttttaatagggattatgttgaatctggag
                              gttaatttcagttttgctaccttgactgtattaagtcttccagtctataagcataa
                              gatgtctttttatttacttaggtcttttaaaatttctttgggcactcccattgtggt
                              gcatcggaaatgaatccgactagtatccacaagaacacaggttcaatccct
                              ggcattgctcagtgggttaaggatcctgcattgccatgaagaactgtggtg
                              gaggccagcagctgcagctctgatttgacccctagcctgggaacttccata
                              tgccttgggtatggccctaaaaagcaaactaagtaagtaagtaaataaata
                              aatgaataaataaaatttctttcaaaattgtaattttgtaatttttgtaattttcaga
                              gtgtacattttgccctttcaatacattattcctacatattttattcttttttgatactat
                              tataaatgaaatttataattaattcatttatatgaatttcattttcaatttgcatattg
                              ctactacaatagaaatgcactttttaattattttttatggccataccatatatatat
                              gtgtgtgtgtgtatgtgtgtcattttactgtacagcagaaattgacacaaca
                              ttgtaaatcaactacacttaaaaaatgaagaaataaccacctgtgattatggc
                              tactgtgttggacactttaggcatcccccacccgtcccgccccacacc
                              cctgagtgctagtgacggatgttcccacccaggggggcctggagcctttatc
                              accagccatcgggaatcagaaccgtatctcacagtccccatgcctgtagc
                              acctggaattgtgcccttggactcgtgggtgttctgcttctcagtgggagaa
                              gcttaggttctaagtcagagcagggacagcccccatgtgctcaggaccca
                              gtgtgaaggggtctgcctcaggggacctgggggttacaagggtaagaga
                              aggtgttcatgttggaactagaagttcttttttcaccgctctgaagaaaaaagc
                              tgcctcccacccttggtacagctcttctgctaacagtgaatcaggcagaac
                              gtgttcaagaagtgacccagcctggtgggggccagacctgacccttgatg
                              gtccctcaacccctccgagggtcccgcccttcctttactgctttgttgtctgtc
                              ctgagaggtttggctaatgtcgaaccaagggtgtggctggtcctgtcccctt
                              tcctgtctcacgcacccacctctgaagtctctgtagctggttccagccggga
                              tctggagccactcccccgccccaggcccagtggtacagactcttgcaga
                              gtcgggggccctgactcagccccaccgccagcgggatgtcaggccag
                              cacccgccccactcccactgatctggggggggtgtctttccttcctccttcc
                              aaaggagcctcagaccttcctgtggggcacggggcagtgggattcagg
                              aggctctgagtcagcaggccggcattgaggagtataaagggacccccagt
                              tcctcccccctttcacttgtggcttatcgccgccccaccctgccccaaggtca
                              ctgcggtcagtacagtcctcagctgccagcaggtgcctgtctttacttgtga
                              ggccgccacgctctcctgtttctccaggtctgggctctgttggaagtgggg
                              gcccgaccccagggtaagatgggggatctgcgtgtcctgccctcagagg
                              cctcctcctccccgcacccctaaccctttcagcccaacaaggctggagatc
                              tcccacatctttggcttcgttaagagttcaacagcgccgccacccggcatgt
                              cgctgagcagaggatggcacagggtgttaaaaaaaaaaaaaaggttgcca
                              cactccgttcggttttgggcccaccctttcgcattcctggagcctgagtaag
                              cggataaggctgtgaaagtgacagattcctgccacctccttccagcgctca
                              tgcacagggaccgcccctcttcggtgtcctttgctgcacaagtgcatttgca
                              cattcctgtctcaatctggtttctccccccttaaaagatgggaatgtgacctgct
                              tggagcccctcgcctcgccagggcaccccatccgtcccttcaggggtgg
                              agatggactgtccctctgcaaggctggatgaactcagaccaaacaggcca
                              acttgctccccaaatacgcccaccccctaccgggctgcagaaattcgcatgt
                              caccactgctgaagggtgaccttgcagccctgagagcatccccatgactt
                              gcccaccagatgaagtctggttgtggcaggtcgcgctcagggactcccg
                              ggtcccacctgggggtgggaggatcctcctttgctcgtggtcgccccaga
                              cacgccctcctttccaagcgccagtctccagagctccgtgccccggcgga
                              ggcggtctggctctctctccttgcccctctctccttgcccctagcagcccttc
                              tcctaaaccctctgagcagcgggcacctcctcccgaggccctgggctaag
                              tccccacccttcatctcaagccttcctccttgactccctcttcccagagttcct
                              tgaaataggtggtaagtacacaccgatgacggaaaacaaagactaagag
                              gttaaagagggctgaggattacggccccggtagggctgcgcgcgaggg
                              ggtcgagtggccgggcggtcccgtcgccgggcagacagaggtgcggtt
                              ctcccgggcgcctgcgctgccggccccgcccggagccctcccagccgg
                              cgcccagtttactcatcccggagaggtgatcccgggcgcgagggcggg
                              cgcagggcgtccggagaacccagtaatccgagaatgcagcatcagccct
                              tcccaccaggcacttccttcctttttcccgaacgtccagggagggggccg TABLE 2-continued Sequences

| SEQ ID NO: Description | Sequence |
|---|---| cgcacttataaactcgggccggacccgccggcctgtcagaggctgcctc
gctggggctgcgcgcggcggccggacacatctggtccgagaccaacgc
gagcgactgtcactggcagctccctgcgcctctcagccccggccgggcc
cctgcgcttggcgtgctgacaccatgcttggggtcctggtccttggcgcgc
tggccctggccggcctggggttccccgcacccgcagagccgcagccgg
gtggcagccagtgcgtcgagcacgactgcttcgcgctctacccgggccc
cgcgaccttcctcaatgccagtcagatctgcgacggactgcggggccac
ctaatgacagtgcgctcctcggtggctgccgatgtcatttccttgctactgaa
cggcgacggcggcgttggccgccggcgcctctggatcggcctgcagct
gccacccggctgcggcgaccccaagcgcctcgggcccctgcgcggctt
ccagtgggttacgggagacaacaacaccagctatagcaggtgggcacg
gctcgacctcaatggggctccctctgcggcccgttgtgcgtcgctgtctc
cgctgctgaggccactgtgcccagcgagccgatctgggaggagcagca
gtgcgaagtgaaggccgatggcttcctctgcgagttccacttcccagccac
ctgcaggccactggctgtggagcccggcgccgcggctgccgccgtctc
gatcacctacggcaccccgttcgcggcccgcggagcggacttccaggc
gctgccggtgggcagctccgccgcggtggctcccctcggcttacagcta
atgtgcaccgcgccgcccggagcggtccaggggcactgggccaggga
ggcgccgggcgcttgggactgcagcgtggagaacggcggctgcgagc
acgcgtgcaatgcgatccctggggctccccgctgccagtgcccagccgg
cgccgccctgcaggcagacgggcgctcctgcaccgcatccgcgacgca
gtcctgcaacgacctctgcgagcacttctgcgttcccaaccccgaccagc
cgggctcctactcgtgcatgtgcgagaccggctaccggctggcggccga
ccaacaccggtgcgaggacgtggatgactgcatactggagcccagtccg
tgtccgcagcgctgtgtcaacacacagggtggcttcgagtgccactgcta
ccctaactacgacctggtggacggcgagtgtgtggagcccgtggacccg
tgcttcagagccaactgcgagtaccagtgccagcccctgaaccaaactag
ctacctctgcgtctgcgcgcgagggcttcgcgcccattccccacgagccgc
acaggtgccagatgtttttgcaaccagactgcctgtccagccgactgcgac
cccaacacccaggctagctgtgagtgccctgaaggctacatcctggacga
cggtttcatctgcacggacatcgacgagtgcgaaaacggcggcttctgct
ccggggtgtgccacaacctccccggtaccttcgagtgcatctgcgggcc
gactcggcccttgcccgccacattggcaccgactgtgactccggcaaggt
ggacggtggcgacagcggctctggcgagcccccgcccagcccgacgc
ccggctccaccttgactcctccggccgtggggctcgtgcattcgggcttgc
tcataggcatctccatcgcgagcctgtgcctggtggtggcgcttttggcgct
cctctgccacctgcgcaagaagcagggcgccgccagggccaagatgga
gtacaagtgcgcggcccccttccaaggaggtagtgctgcagcacgtgcgg
accgagcggacgccgcagagactcggatccggagagggcagaggaa
gtcttctaacatgcggtgacgtggaggagaatcccggccctatgttgacaa
cattgctgccgatactgctgctgtctggctgggcctttttgtagccaagacgc
ctcagatggcctccaaagacttcatatgctccagatctcctacttccgcgac
ccctatcacgtgtggtaccagggcaacgcgtcgctggggggacacctaa
cgcacgtgctggaaggcccagacaccaacaccacgatcattcagctgca
gcccttgcaggagcccgagagctgggcgcgcacgcagagtggcctgca
gtcctacctgctccagttccacggcctcgtgcgcctggtgcaccaggagc
ggaccttggcctttcctctgaccatccgctgcttcctgggctgtgagctgcc
tcccgagggctctagagcccatgtcttcttcgaagtggctgtgaatgggag
ctcctttgtgagtttccggccggagagagccttgtggcaggcagacaccc
aggtcacctccggagtggtcaccttcaccctgcagcagctcaatgcctaca
accgcactcggtatgaactgcgggaattcctggaggacacctgtgtgcag
tatgtgcagaaacatatttccgcgcgaaaacacgaaagggagccaaacaa
gccgctcctacacttcgctggtcctgggcgtcctggtgggcagtttcatcat
tgctggtgtggctgtaggcatcttcctgtgcacaggtggacggcgatgttg
agcgcggccgcttccctttagtgagggttaatgcttcgagcagacatgata
agatacattgatgagtttggacaaaccacaactagaatgcagtgaaaaaaa
tgctttatttgtgaaatttgtgatgctattgctttatttgtaaccattataagctgc
aataaacaagttaacaacaacaattgcattcattttatgttttcaggttcaggg
ggagatgtgggaggtttttttaaagcaagtaaaacctctacaaatgtggtaaa
atccgataaggatcgatgggacagcccccccccaaagcccccagggat
gtaattacgtccctcccccgctagggcagcagcgagccgcccggggctc
cggtccggtccggcgctccccgcatccccgagccggcagcgtgcggg
gacagcccgggcacggggaaggtggcacgggatcgctttcctctgaac
gcttctcgctgctctttgagcctgcagacacctggggggatacggggaaa
atctagtgggacagcccccccaaagcccccagggatgtaattacgtcc
ctcccccgctagggcagcagcgagccgcccggggctccggtccggtcc
ggcgctccccgcatccccgagccggcagcgtgcggggacagcccgg
gcacggggaaggtggcacgggatcgctttcctctgaacgcttctcgctgct
ctttgagcctgcagacacctggggggatacggggaaaatcgatgggac
agcccccccaaagccccagggatgtaattacgtccctcccccgctag
ggcagcagcgagccgcccggggctccggtccggtccggcgctccccc
gcatccccgagccggcagcgtgcggggacagcccgggcacggggaa
ggtggcacgggatcgctttcctctgaacgcttctcgctgctctttgagcctg
cagacacctggggggatacggggaaaatctagtgggacagccccccccc TABLE 2-continued Sequences

| SEQ ID NO: Description | Sequence |
|---|---|
| | caaagcccccagggatgtaattacgtccctcccccgctagggcagcagc |
| | gagccgcccgggggctccggtccggtccggcgctcccccgcatccccga |
| | gccggcagcgtgcggggacagcccgggcacggggaaggtggcacgg |
| | gatcgctttcctctgaacgcttctcgctgctctttgagcctgcagacacctgg |
| | ggggatacggggaaaaatcgatagcgataaggatccactagttattaata |
| | gtaatcaattacggggtcattagttcatagcccatatatggagttccgcgtta |
| | cataacttacggtaaatggcccgcctggctgaccgcccaacgaccccg |
| | cccattgacgtcaataatgacgtatgttcccatagtaacgccaatagggact |
| | ttccattgacgtcaatgggtggagtatttacggtaaactgcccacttggcag |
| | tacatcaagtgtatcatatgccaagtacgccccctattgacgtcaatgacgg |
| | taaatggcccgcctggcattatgcccagtacatgaccttatgggactttcct |
| | acttggcagtacatctacgtattagtcatcgctattaccatgggtcgaggtga |
| | gccccacgttctgcttcactctccccatctccccccctccccaccccccaat |
| | tttgtatttatttattttttaattattttgtgcagcgatggggggcggggggggggg |
| | ggggcgcgcgccaggcggggcggggcggggcgaggggcggggcg |
| | gggcgaggcggagaggtgcggcggcagccaatcagagcggcgcgct |
| | ccgaaagtttccttttatggcgaggcggcggcggcggcggccctataaaa |
| | agcgaagcgcgcggcgggcgggagtcgctgcgttgccttcgccccgtg |
| | ccccgctccgcgccgcctcgcgccgcccgccccggctctgactgaccg |
| | cgttactcccacaggtgagcgggcgggacggcccttctcctccgggctgt |
| | aattagcgcttggtttaatgacggctcgtttctttctgtggctgcgtgaaagc |
| | cttaaagggctccgggagggccctttgtgcggggggagcggctcggg |
| | gggtgcgtgcgtgtgtgtgtgcgtggggagcgccgcgtgcggcccgcg |
| | ctgcccggcgggctgtgagcgctgcgggcgcggcgcggggctttgtgcg |
| | ctccgcgtgtgcgcgaggggagcgcggccggggcggtgccccgcg |
| | gtgcgggggggctgcgaggggaacaaaggctgcgtgcggggtgtgtg |
| | cgtggggggtgagcaggggggtgtgggcgcggcggtcgggctgtaac |
| | ccccccctgcacccccctccccgagttgctgagcacggcccggcttcgg |
| | gtgcggggctccgtgcggggcgtggcgcggggctcgccgtgccgggc |
| | gggggtggcggcaggtgggggtgccgggcggggcggggccgcctc |
| | gggccggggagggctcggggagggggcgcggcggcccccggagcgc |
| | cggcggctgtcgaggcgcggcgagccgcagccattgccttttatggtaat |
| | cgtgcgagagggcgcagggacttcctttgtcccaaatctggcggagccg |
| | aaatctgggaggcgccgccgcaccccctctagcgggcgcgggcgaag |
| | cggtgcggcgccggcaggaaggaaatgggcggggagggccttcgtgc |
| | gtcgccgcgccgccgtcccttctccatctccagcctcggggctgccgca |
| | gggggacggctgccttcggggggggacggggcagggcggggttcggct |
| | tctggcgtgtgaccggcggctctagagcctctgctaaccatgttcatgcctt |
| | cttctttttcctacagctcctgggcaacgtgctggttgttgtgctgtctcatcat |
| | tttggcaaagaattccgctgcgactcggcggagtcccggcggcgcgtcct |
| | tgttctaacccggcgcgccctcaggatgggaatccaaggagggtctgtcc |
| | tgttcgggctgctgctcgtcctggctgtcttctgccattcaggtcatagcctg |
| | cagtgctacaactgtcctaacccaactgctgactgcaaaacagccgtcaat |
| | tgttcatctgatttgatgcgtgtctcattaccaaagctgggttacaagtgtata |
| | acaagtgttggaagtttgagcattgcaatttcaacgacgtcacaacccgctt |
| | gagggaaaatgagctaacgtactactgctgcaagaaggacctgtgtaactt |
| | taacgaacagcttgaaaatggtgggacatccttatcagagaaaacagttctt |
| | ctgctggtgactccatttctggcagcagcctggagccttcatcccggatcc |
| | ggagagggcagaggaagtcttctaacatgcggtgacgtggaggagaatc |
| | ccggccctatggagcgtccgcaacccgacagcatgccccaggatttgtca |
| | gaggccctgaaggaggccaccaaggaggtgcacacccaggcagagaa |
| | tgctgagttcatgaggaacttcagaagggccaggtgacccgagacggct |
| | tcaagctggtgatggcctccctgtaccacatctatgtgccctggaggagg |
| | agattgagcgcaacaaggagagcccagtcttcgccctgtctacttccca |
| | gaagagctgcaccgcaaggctgccctggagcaggacctggccttctggt |
| | acgggccccgctggcaggaggtcatcccctacacaccagccatgcagc |
| | gctatgtgaagcggctccacgaggtggggcgcacagagcccgagctgc |
| | tggtggcccacgcctacacccgctacctgggtgacctgtctgggggcca |
| | ggtgctcaaaaagattgcccagaaagccctggacctgcccagctctggc |
| | gagggcctggccttcttcaccttccccaacattgccagtgccaccaagttc |
| | aagcagctctaccgctcccgcatgaactccctggagatgactcccgcagt |
| | caggcagagggtgatagaagaggccaagactgcgttcctgctcaacatc |
| | cagctctttgaggagttgcaggagctgctgacccatgacaccaaggacca |
| | gagccctcacgggcaccagggcttcgccagcgggccagcaacaaagt |
| | gcaagattctgcccccgtggagactcccagagggaagcccccactcaac |
| | acccgctcccaggctccgcttctccgatgggtccttacactcagctttctgg |
| | tggcgacagttgctgtagggctttatgccatgtgagcggcgcgccggcac |
| | cggtaccaagcttaagagcgctagctggccagacatgataagatacattg |
| | atgagtttggacaaaccacaactagaatgcagtgaaaaaaatgctttatttgt |
| | gaaatttgtgatgctattgctttatttgtaaccattataagctgcaataaacaag |
| | ttaacaacaacaattgcattcattttatgtttcaggttcaggggggaggtgtgg |
| | gaggttttttaaagcaagtaaaaacctctacaaatgtggtatggaattggagc |
| | cccactgtgttcatcttacagatggaaatactgacattcagaggagttagtta |
| | acttgcctaggtgattcagctaataagtgcaagaaagatttcaatccaaggt |

TABLE 2-continued

Sequences

| SEQ ID NO: Description | Sequence |
|---|---|
| | gatttgattctgaagcctgtgctaatcacattacaccaagctacaacttcattt |
| | ataaataataagtcagctttcaagggcctttcaggtgtcctgcacttctacaa |
| | gctgtgccatttagtgaacacaaaatgagccttctgatgaagtagtcttttcat |
| | tatttcagatattagaacactaaaattcttagctgccagctgattgaaggctg |
| | ggacaaaattcaaacatgcatctacaacaatatatatctcaatgttagtctcc |
| | aaattctattgacttcaactcaagagaatataaagagctagtctttatacactc |
| | tttaaggtatgatgggtcccgatttttccccgtatcccccccaggtgtctgcag |
| | gctcaaagagcagcgagaagcgttcagaggaaagcgatcccgtgccac |
| | cttccccgtgcccgggctgtccccgcacgctgccggctcggggatgcgg |
| | gggagcgccggaccggaccggagccccgggcggctcgctgctgccct |
| | agcggggagggacgtaattacatccctgggggctttggggggggggct |
| | gtcccactagattttccccgtatcccccaggtgtctgcaggctcaaagag |
| | cagcgagaagcgttcagaggaaagcgatcccgtgccaccttccccgtgc |
| | ccgggctgtccccgcacgctgccggctcggggatgcgggggagcgcc |
| | ggaccggaccggagccccgggcggctcgctgctgccctagcgggga |
| | gggacgtaattacatccctgggggctttggggggggggctgtcccatcgga |
| | tcttctagtcctgcaggagtcaatgggaaaaacccattggagccaagtaca |
| | ctgactcaatagggactttccattgggttttgcccagtacataaggtcaatag |
| | ggggtgagtcaacaggaaagtcccattggagccaagtacattgagtcaat |
| | agggactttccaatgggtttttgcccagtacataaggtcaatgggaggtaag |
| | ccaatgggtttttcccattactgacatgtatacgcgtcgacgtcggcgcgttc |
| | agcctaaagcttttttccccgtatcccccaggtgtctgcaggctcaaagag |
| | cagcgagaagcgttcagaggaaagcgatcccgtgccaccttccccgtgc |
| | ccgggctgtccccgcacgctgccggctcggggatgcgggggagcgcc |
| | ggaccggaccggagccccgggcggctcgctgctgccctagcgggga |
| | gggacgtaattacatccctgggggctttggggggggggctgtccctgcgg |
| | ccgcgaattcgtaatcatggtcatagctgtttcctgtgtgaaattgttatccgc |
| | tcacaattccacacaacatacgagccggaagcataaagtgtaaagcctgg |
| | ggtgcctaatgagtgagctaactcacattaattgcgttgcgctcactgcccg |
| | ctttccagtcgggaaacctgtcgtgccaggggctctagccgcggtctagga |
| | agctttctagggtacctctagggatccactagttattaatagtaatcaattacg |
| | gggtcattagttcatagcccatatatggagttccgcgttacataacttacggt |
| | aaatggcccgcctggctgaccgcccaacgacccccgcccattgacgtca |
| | ataatgacgtatgttcccatagtaacgccaataggactttccattgacgtca |
| | atgggtggagtatttacggtaaaactgcccacttggcagtacatcaagtgtat |
| | catatgccaagtacgcccccctattgacgtcaatgacggtaaatggcccgcc |
| | tggcattatgcccagtacatgaccttatgggactttcctacttggcagtacat |
| | ctacgtattagtcatcgctattaccatgggtcgaggtgagccccacgttctg |
| | cttcactctccccatctcccccccctccccacccccaattttgtatttatttattt |
| | tttaattattttgtgcagcgatggggcggggggggggggggcgcgcgc |
| | caggcggggcggggcggggcgaggggcggggcggggcgaggcgg |
| | agaggtgcggcggcagccaatcagagcggcgcgctccgaaagtttcctt |
| | ttatggcgaggcggcggcggcggcggcgggccctataaaaagcgaagcgcgc |
| | ggcgggcgggagtcgctgcgttgccttcgccccgtgccccgctccgcgc |
| | cgcctcgcgccgcccgcccggctctgactgaccgcgttactcccacag |
| | gtgagcgggcgggacggccttctcctccgggctgtaattagcgcttggtt |
| | taatgacggctcgtttctttttctgtggctgcgtgaaagccttaaagggctccg |
| | ggagggcccttttgtgcggggggggagcggctcgggggggtgcgtgcgtgt |
| | gtgtgtgcgtggggagcgccgcgtgcggcccgcgctgcccggcggctg |
| | tgagcgctgcgggcgcggcgcggggctttgtgcgctccgcgtgtgcgc |
| | gaggggagcgcggccggggcggtgccccgcggtgcgggggggctg |
| | cgaggggaacaaaggctgcgtgcggggtgtgtgcgtggggggggtgag |
| | caggggtgtgggcgcggcggtcgggctgtaaccccccccctgcacccc |
| | cctccccgagttgctgagcacggcccggcttcgggtgcggggctccgtg |
| | cggggcgtggcgcggggctcgccgtgccgggcgggggtggcggca |
| | ggtgggggtgccgggcggggcggggccgcctcgggccggggaggg |
| | ctcgggggagggcgcggcggcggcccccggagcgccggcgggctgtcgag |
| | gcgcggcgagccgcagccattgccttttatggtaatcgtgcgagagggcg |
| | cagggacttcctttgtcccaaatctggcggagccgaaatctgggaggcgc |
| | cgccgcaccccctctagcgggcgcgggcgaagcggtgcggcgccggc |
| | aggaaggaaatgggcggggaggggccttcgtgcgtcgccgcgccgccgt |
| | cccctttctccatctccagcctcggggctgccgcaggggggacggctgcctt |
| | cggggggggacggggcagggcggggttcggcttctggcgtgtgaccgg |
| | cggctctagagcctctgctaaccatgttcatgccttcttcttttttcctacagctc |
| | ctgggcaacgtgctggttgttgtgctgtctcatcattttggcaaagaattccg |
| | ctgcgactcggcggagtcccggcggcgcgtccttgttctaacccggcgc |
| | gccctcaggatggagcctcccggccgccgcgcgagtgtcccttttccttcctg |
| | gcgctttcctggggttgcttctggcggccatggtgttgctgctgtactccttctc |
| | cgatgcctgtgaggagccaccaacatttgaagctatggagctcattggtaa |
| | accaaaaccctactatgagattggtgaacgagtagattataagtgtaaaaa |
| | aggatacttctatataacctcctcttgccacccatactatttgtgatcggaatca |
| | tacatggctacctgtctcagatgacgcctgttatagagaaacatgtccatata |
| | tacgggatcctttaaatggccaagcagtccctgcaaatgggacttacgagt |
| | ttggttatcagatgcactttatttgtaatgaggggttattacttaattggtgaaga |

TABLE 2-continued

Sequences

| SEQ ID NO: | Description | Sequence |
|---|---|---| aattctatattgtgaacttaaaggatcagtagcaatttggagcggtaagccc
ccaatatgtgaaaaggttttgtgtacaccacctccaaaaataaaaaatggaa
aacacacctttagtgaagtagaagtatttgagtatcttgatgcagtaacttata
gttgtgatcctgcacctggaccagatccattttcacttattggagagagcac
gatttattgtggtgacaattcagtgtggagtcgtgctgctccagagtgtaaa
gtggtcaaatgtcgatttccagtagtcgaaatggaaaacagatatcagga
tttggaaaaaaattttactacaaagcaacagttatgtttgaatgcgataaggg
tttttacctcgatggcagcgacacaattgtctgtgacagtaacagtacttggg
atcccccagttccaaagtgtcttaaagtgctgcctccatctagtacaaaacct
ccagctttgagtcattcagtgtcgacttcttccactacaaaatctccagcgtc
cagtgcctcaggtcctaggcctacttacaagcctccagtctcaaattatcca
ggatatcctaaacctgaggaaggaatacttgacagtttggatgtttgggtca
ttgctgtgattgttattgccatagttgttggagttgcagtaatttgtgttgtccc
gtacagatatcttcaaaggaggaagaagaaaggcacatacctaactgatg
agacccacagagaagtaaaatttacttctctcggatccggagccacgaact
tctctctgttaaagcaagcaggagacgtggaagaaaaccccggtcctatg
accgtcgcgcggccgagcgtgcccgcggcgctgccctcctcggggag
ctgccccggctgctgctgctggtgctgttgtgcctgccggccgtgtggggt
gactgtggccttcccccagatgtacctaatgcccagccagctttggaaggc
cgtacaagttttcccgaggatactgtaataacgtacaaatgtgaagaaagct
ttgtgaaaattcctggcgagaaggactcagtgatctgccttaagggcagtc
aatggtcagatattgaagagttctgcaatcgtagctgcgaggtgccaacaa
ggctaaattctgcatccctcaaacagccttatatcactcagaattattttccag
tcggtactgttgtggaatatgagtgccgtccaggttacagaagagaaccttc
tctatcaccaaaactaacttgccttcagaatttaaaatggtccacagcagtcg
aattttgtaaaaagaaatcatgccctaatccgggagaaatacgaaatggtc
agattgatgtaccaggtggcatattatttggtgcaaccatctccttctcatgta
acacagggtacaaattatttggctcgacttctagttttgtcttatttcaggcag
ctctgtccagtggagtgacccgttgccagagtgcagagaaatttattgccc
agcaccaccacaaattgacaatggaataattcaaggggaacgtgaccatt
atggatatagacagtctgtaacgtatgcatgtaataaaggattcaccatgatt
ggagagcactctatttattgtactgtgaataatgatgaaggagagtggagtg
gcccaccacctgaatgcagaggaaaatctctaacttccaaggtcccacca
acagttcagaaacctaccacagtaaatgttccaactacagaagtctcacca
acttctcagaaaaccaccacaaaaaccaccacaccaaatgctcaagcaac
acggagtacacctgtttccaggacaaccaagcattttcatgaaacaacccc
aaataaaggaagtggaaccacttcaggtactacccgtcttctatctgggca
cacgtgtttcacgttgacaggtttgcttgggacgctagtaaccatgggcttg
ctgacttagggcgcgccggcaccggtaccaagcttaagagcgctagctg
gccagacatgataagatacattgatgagtttggacaaaccacaactagaat
gcagtgaaaaaaatgctttatttgtgaaatttgtgatgctattgctttatttgtaa
ccattataagctgcaataaacaagttaacaacaacaattgcattcattttatgt
ttcaggttcaggggggaggtgtggggaggttttttaaagcaagtaaaacctcta
caaatgtggtatggaattggagccccactgtgttcatcttacagatggaaat
actgacattcagaggagttagttaacttgcctaggtgattcagctaataagtg
caagaaagatttcaatccaaggtgatttgattctgaagcctgtgctaatcaca
ttacaccaagctacaacttcatttataaataataagtcagctttcaagggcctt
tcaggtgtcctgcacttctacaagctgtgccatttagtgaacacaaaatgag
ccttctgatgaagtagtcttttcattatttcagatattagaacactaaaattctta
gctgccagctgattgaaggctgggacaaaattcaaacatgcatctacaaca
atatatatctcaatgttagtctccaaattctattgacttcaactcaagagaatat
aaagagctagtctttatacactctttaaggtatgatatcatctggaaagtaac
aaaattgatgcaaatttgaatgaactttatcatggtgtatttacacaatgtgttt
cttctccctgcaatgtatttctttctctaattccttccatttgatctttcatacacaa
tctggttctgatgtatgtttttttggatgcacttttcaactccaaaagacagagct
agttactttcttcctggtgctccaagcactgtatttgtatctgtattcaagcccctt
tgcaatattgtactggatcattatttcacctctaggtggcttccccaggcaa
cttgtgttcacccagagactacattttgtatcttgttgacctttgaacttccacc
agtgtctaaaaataatatgtatgcaaaattacttgctatgagaatgtataatta
aacaatataaaaaggagaagcaaggagagaaacacaggtgtgtatttgtg
tttgtgtgcttaaaaggcagtgtggaaaaggaagaaaatgccatttatagtga
ggagacaaagttatattacctcttatctggcttttaaggagattttgctgagct
aaaaatcctatattcatagaaaagccttacctgagttgccaatacctcaattct
aaaatacagcatagcaaaactttaacctccaaatcaagcctctacttgaatc
cttttctgagggatgaataaggcataggcatcagggggctgttgccaatgtg
cattagctgtttgcagcctcaccttctttcatggagtttaagatatagtgtatttt
cccaaggtttgaactagctcttcatttctttatgttttaaatgcactgacctccc
acattcccttttttagtaaaatattcagaaataatttatcatctggaaagtaacaa
aattgatgcaaatttgaatgaactttatcatggtgtatttacacaatgtgtttctt
ctccctgcaatgtatttctttctctaattccttccatttgatctttcatacacaatct
ggttctgatgtatgtttttttggatgcacttttcaactccaaaagacagagctag
ttactttcttcctggtgctccaagcactgtatttgtatctgtattcaagccctttg
caatattgtactggatcattatttcacctctaggatggcttccccaggcaactt
gtgttcacccagagactacattttgtatcttgttgacctttgaacttccaccagt TABLE 2-continued Sequences SEQ
ID
NO: Description        Sequence

```
gtctaaaaataatatgtatgcaaaattacttgctatgagaatgtataattaaac
aatataaaaaggagaagcaaggagagaaacacaggtgtgtatttgtgtttg
tgtgcttaaaaggcagtgtgtggaaaaggaagaaatgccatttatagtgagga
gacaaagttatattacctcttatctggcttttaaggagattttgctgagctaaa
aatcctatattcatagaaaagccttacctgagttgccaatacctcaattctaaa
atacagcatagcaaaactttaacctccaaatcaagcctctacttgaatcctttt
ctgagggatgaataaggcataggcatcaggggctgttgccaatgtgcatta
gctgtttgcagcctcaccttctttcatggagtttaagatatagtgtattttccca
aggtttgaactagctcttcatttctttatgtttaaatgcactgacctcccacatt
ccctttttagtaaaatattcagaaataatttatcccggcttgtcgacgacggat
catctggaaagtaacaaaattgatgcaaatttgaatgaactttatcatggtgt
atttacacaatgtgtttcttctccctgcaatgtatttctttctct-
attccttccatttgatctttcatacacaatctggttctgatgtatgttttttggatg
cactttttcaactccaaaagacagagctagttactttcttcctggtgctccaag
cactgtatttgtatctgtattcaagccctttgcaatattgtactggatcattatttc
acctctaggatggcttccccaggcaacttgtgttcacccagagactacatttt
gtatcttgttgacctttgaacttccaccagtgtctaaaaataatatgtatgcaa
aattacttgctatgagaatgtataattaaacaatataaaaaggagaagcaag
gagagaaacacaggtgtgtatttgtgtttgtgtgcttaaaaggcagtgtgga
aaaggaagaaatgccatttatagtgaggagacaaagttatattacctcttatc
tggcttttaaggagattttgctgagctaaaaatcctatattcatagaaaagcct
tacctgagttgccaatacctcaattctaaaatacagcatagcaaaactttaac
ctccaaatcaagcctctacttgaatccttttctgagggatgaataaggcatag
gcatcaggggctgttgccaatgtgcattagctgtttgcagcctcaccttcttt
catggagtttaagatatagtgtattttcccaaggtttgaactagctcttcatttct
ttatgtttaaatgcactgacctcccacattcccttttagtaaaatattcagaa
ataatttatcccggcttgtcgacggcgtccgtcgtcaggatcatccatcagg
acatagcgttggctacccgtgatattgctgaagagcttggcggcgaatgg
gctgaccgcttcctcgtgctttacggtatcgccgctcccgattcgcagcgc
atcgccttctatcgccttcttgacgagttcttctgaggggatcaattctctaga
gctcgctgatcagcctcgactgtgccttctagttgccagccatctgttgtttg
cccctcccccgtgccttccttgaccctggaaggtgccactcccactgtcctt
tcctaataaaatgaggaaattgcatcgcattgtctgagtaggtgtcattctatt
ctggggggtggggtggggcaggacagcaaggggggaggattgggaag
acaatagcaggcatgctggggatgcggtgggctctatggcttctgaggcg
gaaagaaccagctgggggcgcgcacctcgaccatctccaggatgcctt
gatagagctgggtcctctgcgttcctttaaagtgtttgagatcaagtccgag
aagaggtggcaagcgatcgcgacatatttaaatcgcgctagtttaaaatac
atcattgcaatgaaaataaatgttttttattaggcagaatccagatgctcaag
gcccttcataatatcccccagtttagtagttggacttagggaacaaaggaac
ctttaatagaaattggacagcaagaaagctctagctttagaagaactcatca
agaagtctgtagaaggcaattctctgggagtcaggggctgcaatgccata
gagcactaggaacctgtctgcccactctcccctagctcttctgctatgtcc
ctggttgctagggcaatgtcctggtacctgtcagccactcccagcctgcca
cagtctatgaagccagagaaccttccattttcaaccatgatgttgggaaggc
aggcatcccatgagtcaccactaggtcctcaccatctggcatggatgcct
tgagcctggcaaatagttcagcaggggccaggccctggtgttcttcatcca
agtcatcttggtccaccaggccagcctccatcctggttctggccctctctatc
ctgtgcttggcctggtggtcaaaggggcaggtggctgggtcaagggtgtg
gagtcttctcatggcatcagccatgattgacactttctcagctggagctaggt
gagaggaaaggaggtcctgcccaggcacctcacctagtaggagccagt
cccttccagcttctgtgaccacatcaaggacagctgcacaggggacccca
gttgttgccaaccaggagagtctggcagcctcatcctggagctcattgaga
gccccactgaggtctgtctttacaaaaaggactggcctgccttgggctgaa
agtctgaaaactgctgcatcagagcaaccaatggtctgctgtgcccagtca
tagccaaacagtctctcaacccaggcagctggagaacctgcatgtaggcc
atcttgttcaatcatgatggctcctcctgtcaggagaggaaagagaagaag
gttagtacaattgctatagtgagttgtattatactatgcttatgattaattgtcaa
actagggctgcagggttcatagtgccacttttcctgcactgccccatctcct
gcccaccctttcccaggcatagacagtcagtgacttaccaaactcacagg
agggagaaggcagaagctttttgcaaaagcctaggctcatgagacaataa
ccctgataaatgcttcaataatattgaaaaaggaagagtaccaggtatgagt
attcaacatttccgtgtcgcccttattccctttttttgcggcattttgccttcctgtt
tttgctcacccagaaacgctggtgaaagtaaaagatgctgaagatcagttg
ggtgcacgagtgggttacatcgaactggatctcaacagcggtaagatcctt
gagagttttcgccccgaagaacgttttccaatgatgagcacttttaaagttct
gctatgtggcgcggtattatcccgtattgacgccgggcaagagcaactcg
gtcgccgcatacactattctcagaatgacttggttgagtactcaccagtcac
agaaaagcatcttacggatggcatgacagtaagagaattatgcagtgctgc
cataaccatgagtgataacactgcggccaacttacttctgacaacgatcgg
aggaccgaaggagctaaccgcttttttgcacaacatgggggatcatgtaac
tcgccttgatcgttgggaaccggagctgaatgaagccataccaaacgacg
agcgtgacaccacgatgcctgtagcaatggcaacaacgttgcgcaaacta
ttaactggcgaactacttactctagcttcccggcaacaattaatagactggat
```

TABLE 2-continued

Sequences

| SEQ ID NO: | Description | Sequence |
|---|---|---|
| | | ggaggcggataaagttgcaggaccacttctgcgctcggcccttccggctg gctggtttattgctgataaatctggagccggtgagcgtgggtctcgcggtat cattgcagcactggggccagatggtaagccctcccgtatcgtagttatcta cacgacggggagtcaggcaactatggatgaacgaaatagacagatcgct gagataggtgcctcactgattaagcattggtaactgtcagaccaagtttact catatatactttagattgatttaaaacttcatttttaatttaaaaggatctaggtg aagatcctttttgataatctcatgaccaaaatcccttaacgtgagttttcgttcc actgagcgtcagacccgtagaaaagatcaaaggatcttcttgagatcctttt ttttctgcgcgtaatctgctgcttgcaaacaaaaaaaccaccgctaccagcg gtggtttgtttgccggatcaagagctaccaactctttttccgaaggtaactgg cttcagcagagcgcagataccaaatactgttcttctagtgtagccgtagtta ggccaccacttcaagaactctgtagcaccgcctacatacctcgctctgcta atcctgttaccagtggctgctgccagtggcgataagtcgtgtcttaccgggt tggactcaagacgatagttaccggataaggcgcagcggtcgggctgaac ggggggttcgtgcacacagcccagcttggagcgaacgacctacaccga actgagatacctacagcgtgagctatgagaaagcgccacgcttcccgaag ggagaaaggcggacaggtatccggtaagcggcagggtcggaacagga gagcgcacgagggagcttccaggggaaacgcctggtatctttatagtcc tgtcgggtttcgccacctctgacttgagcgtcgatttttgtgatgctcgtcag ggggacggagcctatggaaaaacgccagcaacgcggcctttttacggtt cctggccttttgctggccttttgctcacatggctcgacagatttaattaacaag accgacctgtccggtgccctgaatgaactgcaggacgaggcagcgcgg ctatcgtggctggccacgacgggcgttccttgcgcagctgtgctcgacgtt gtcactgaagcgggaagggactggctgctattgggcgaagtgccgggg caggatctcctgtcatctcaccttgctcctgccgagaaagtatccatcatgg ctgatgcaatgcggcggctgcatacgcttgatccggctacctgcccattcg accaccaagcgaaacatcgcatcgagcgagcacgtactcggatggaag ccggtcttgtcgatcaggatgatctggacgaagagcatcaggggctcgcg ccagccgaactgttcgccaggctcaaggcgcgcatgcccgacggcgag gatctcgtcgtgacccatggcgatgcctgcttgccgaatatcatggtggaa aatggccgcttttctggattcatcgactgtggccggctgggtgtggcggat cgctggcctcgatggccgtgccagggcgtgcccttgggctccccgggcgcggcgatta agacgt |
| 9 | B217 vector | caagaccgacctgtccggtgccctgaatgaactgcaggacgaggcagc gcggctatcgtggctggccacgacgggcgttccttgcgcagctgtgctcg acgttgtcactgaagcgggaagggactggctgctattgggcgaagtgcc ggggcaggatctcctgtcatctcaccttgctcctgccgagaaagtatccatc atggctgatgcaatgcggcggctgcatacgcttgatccggctacctgccc attcgaccaccaagcgaaacatcgcatcgagcgagcacgtactcggatg gaagccggtcttgtcgatcaggatgatctggacgaagagcatcaggggct cgcgccagccgaactgttcgccaggctcaaggcgcgcatgcccgacgg cgaggatctcgtcgtgacccatggcgatgcctgcttgccgaatatcatggt ggaaaatggccgcttttctggattcatcgactgtggccggctgggtgtggc ggatcgctggcctcgatggccgtgccagggcgtgcccttgggctccccg ggcgcgttaattaagacgtgggtcccgattttttccccgtatccccccaggtg tctgcaggctcaaagagcagcgagaagcgttcagaggaaagcgatccc gtgccaccttccccgtgcccgggctgtccccgcacgctgccggctcggg gatgcggggagcgccggaccggaccggagccccgggcggctcgct gctgccctagcggggagggacgtaattacatccctgggggctttgggg ggggctgtcccactagattttccccgtatcccccccaggtgtctgcaggct caaagagcagcgagaagcgttcagaggaaagcgatcccgtgccaccttc cccgtgcccgggctgtccccgcacgctgccggctcggggatgcgggg agcgccggaccggaccggagccccgggcggctcgctgctgccctagc gggggagggacgtaattacatccctgggggctttggggggggctgtcc catcggatcttctagtcctgcaggtttaaaccttaagtgtacaaaaaagcag gctttaaaggaaccaattcagtcgactggatccggtaccaaggtcgggca ggaagagggcctatttcccatgattccttcatatttgcatatacgatacaagg ctgttagagagataattagaattaatttgactgtaaacacaaagatattagta caaaatacgtgacgtagaaagtaataatttcttgggtagtttgcagttttaaaa ttatgtttaaaatggactatcatatgcttaccgtaacttgaaagtatttcgattt cttggctttatatatcttgtggaaaggacgaaacaccgtagttcaggtgaac ggcactgttttagagctagaaatagcaagttaaaataaggctagtccgttat caacttgaaaaagtggcaccgagtcggtgctttttttctagacccatgtaca aaaaagcaggctttaaaggaaccaattcagtcgactggatccggtaccaa ggtcgggcaggaagagggcctatttcccatgattccttcatatttgcatatac gatacaaggctgttagagagataattagaattaatttgactgtaaacacaaa gatattagtacaaaatacgtgacgtagaaagtaataatttcttgggtagtttg |

TABLE 2-continued

| Sequences | | |
| --- | --- | --- |

| SEQ ID NO: Description | | Sequence |
| --- | --- | --- |
| | | cagttttaaaattatgtttttaaaatggactatcatatgcttaccgtaacttgaaa |
| | | gtatttcgatttcttggcttttatatatcttgtggaaaggacgaaacaccggac |
| | | ggaccccatctgtccaggttttagagctagaaatagcaagttaaaataagg |
| | | ctagtccgttatcaacttgaaaaagtggcaccgagtcggtgcttttttttctag |
| | | aggtaccgagtttactccctatcagtgatagagaacgtatgaagagtttact |
| | | ccctatcagtgatagagaacgtatgcagactttactccctatcagtgataga |
| | | gaacgtataaggagtttactccctatcagtgatagagaacgtatgaccagtt |
| | | tactccctatcagtgatagagaacgtatctacagtttactccctatcagtgata |
| | | gagaacgtatatccagtttactccctatcagtgatagagaacgtataagcttt |
| | | aggcgtgtacggtgggcgcctataaaagcagagctcgtttagtgaaccgt |
| | | cagatcgcctggagcaattccacaacacttttgtcttataccaactttccgta |
| | | ccacttcctaccctcgtaaaaccggtgccaccatggactataaggaccac |
| | | gacggagactacaaggatcatgatattgattacaaagacgatgacgataa |
| | | gatggcccccaaagaagaagcggaaggtcggtatccacggagtcccagc |
| | | agccgacaagaagtacagcatcggcctggacatcggcaccaactctgtg |
| | | ggctgggccgtgatcaccgacgagtacaaggtgcccagcaagaaattca |
| | | aggtgctgggcaacaccgaccggcacagcatcaagaagaacctgatcg |
| | | gagccctgctgttcgacagcggcgaaacagccgaggccacccggctga |
| | | agagaaccgccagaagaagatacaccagacggaagaaccggatctgct |
| | | atctgcaagagatcttcagcaacgagatggccaaggtggacgacagcttc |
| | | ttccacagactggaagagtccttcctggtggaagaggataagaagcacga |
| | | gcggcacccatcttcggcaacatcgtggacgaggtggcctaccacgag |
| | | aagtaccccaccatctaccacctgagaaagaaactggtgacagcaccg |
| | | acaaggccgacctgcggctgatctatctggccctggcccacatgatcaag |
| | | ttccggggccacttcctgatcgagggcgacctgaaccccgacaacagcg |
| | | acgtggacaagctgttcatccagctggtgcagacctacaaccagctgttcg |
| | | aggaaaacccccatcaacgccagcggcgtggacgccaaggccatcctgt |
| | | ctgccagactgagcaagagcagacggctggaaaatctgatcgcccagct |
| | | gcccggcgagaagaagaatggcctgttcggaaacctgattgccctgagc |
| | | ctgggcctgacccccaacttcaagagcaacttcgacctggccgaggatgc |
| | | caaactgcagctgagcaaggacacctacgacgacgacctggacaacctg |
| | | ctggcccagatcggcgaccagtacgccgacctgtttctggccgccaaga |
| | | acctgtccgacgccatcctgctgagcgacatcctgagagtgaacaccgag |
| | | atcaccaaggcccccctgagcgcctctatgatcaagagatacgacgagc |
| | | accaccaggacctgaccctgctgaaagctctcgtgcggcagcagctgcct |
| | | gagaagtacaaagagattttcttcgaccagagcaagaacggctacgccg |
| | | gctacattgacggcggagccagccaggaagagttctacaagttcatcaag |
| | | cccatcctggaaaagatggacggcaccgaggaactgctcgtgaagctga |
| | | acagagaggacctgctgcggaagcagcggaccttcgacaacggcagca |
| | | tccccaccagatccacctgggagagctgcacgccattctgcggcggca |
| | | ggaagatttttacccattcctgaaggacaaccgggaaaagatcgagaaga |
| | | tcctgaccttccgcatcccctactacgtgggccctctggccaggggaaac |
| | | agcagattcgcctggatgaccagaaagagcgaggaaaccatcacccccct |
| | | ggaacttcgaggaagtggtggacaagggcgcttccgcccagagcttcat |
| | | cgagcggatgaccaacttcgataagaacctgcccaacgagaaggtgctg |
| | | cccaagcacagcctgctgtacgagtacttcaccgtgtataacgagctgacc |
| | | aaagtgaaatacgtgaccgagggaatgagaaagcccgccttcctgagcg |
| | | gcgagcagaaaaaggccatcgtggacctgctgttcaagaccaaccggaa |
| | | agtgaccgtgaagcagctgaaagaggactacttcaagaaaatcgagtgct |
| | | tcgactccgtggaaatctccggcgtggaagatcggttcaacgcctccctg |
| | | ggcacataccacgatctgctgaaaattatcaaggacaaggacttcctggac |
| | | aatgaggaaaacgaggacattctggaagatatcgtgctgaccctgacact |
| | | gtttgaggacagagagatgatcgaggaacggctgaaaacctatgcccac |
| | | ctgttcgacgacaaagtgatgaagcagctgaagcggcggagatacaccg |
| | | gctgggcaggctgagccggaagctgatcaacggcatccgggacaagc |
| | | agtccggcaagacaatcctggatttcctgaagtccgacggcttcgccaac |
| | | agaaacttcatgcagctgatccacgacgacagcctgacctttaaagagga |
| | | catccagaaagcccaggtgtccggccagggcgatagcctgcacgagca |
| | | cattgccaatctggccggcagccccgccattaagaagggcatcctgcaga |
| | | cagtgaaggtggtggacgagctcgtgaaagtgatgggccggcacaagc |
| | | ccgagaacatcgtgatcgaaatggccagagagaaccagaccacccaga |
| | | agggacagaagaacagccgcgagagaatgaagcggatcgaagagggc |
| | | atcaaagagctgggcagccagatcctgaaagaacaccccgtggaaaaca |
| | | cccagctgcagaacgagaagctgtacctgtactacctgcagaatgggcg |
| | | ggatatgtacgtggaccaggaactggacatcaaccggctgtccgactacg |
| | | atgtggaccatatcgtgcctcagagctttctgaaggacgactccatcgaca |
| | | acaaggtgctgaccagaagcgacaagaaccggggcaagagcgacaac |
| | | gtgccctccgaagaggtcgtgaagaagatgaagaactactggcggcagc |
| | | tgctgaacgccaagctgattacccagagaaagttcgacaatctgaccaag |
| | | gccgagagaggcggcctgagcgaactggataaggccggcttcatcaag |
| | | agacagctggtggaaacccggcagatcacaaagcacgtggcacagatc |
| | | ctggactcccggatgaacactaagtacgacgagaatgacaagctgatccg |
| | | ggaagtgaaagtgatcacccctgaagtccaagctggtgtccgatttccgga |
| | | aggatttccagttttacaaagtgcgcgagatcaacaactaccaccacgccc |

TABLE 2-continued

| Sequences |
| --- |

| SEQ ID NO: | Description | Sequence |
| --- | --- | --- |

```
acgacgcctacctgaacgccgtcgtgggaaccgccctgatcaaaaagta
ccctaagctggaaagcgagttcgtgtacggcgactacaaggtgtacgacg
tgcggaagatgatcgccaagagcgagcaggaaatcggcaaggctaccg
ccaagtacttcttctacagcaacatcatgaacttttttcaagaccgagattacc
ctggccaacggcgagatccggaagcggcctctgatcgagacaaacggc
gaaaccggggagatcgtgtgggataagggccgggattttgccaccgtgc
ggaaagtgctgagcatgccccaagtgaatatcgtgaaaaagaccgaggt
gcagacaggcggcttcagcaaagagtctatcctgcccaagaggaacagc
gataagctgatcgccagaaagaaggactgggaccctaagaagtacggc
ggcttcgacagccccaccgtggcctattctgtgctggtggtggccaaagtg
gaaaagggcaagtccaagaaactgaagagtgtgaaagagctgctgggg
atcaccatcatggaaagaagcagcttcgagaagaatcccatcgactttctg
gaagccaagggctacaaagaagtgaaaaaggacctgatcatcaagctgc
ctaagtactccctgttcgagctggaaaacggccggaagagaatgctggcc
tctgccggcgaactgcagaagggaaacgaactggccctgccctccaaat
atgtgaacttcctgtacctggccagccactatgagaagctgaagggctccc
ccgaggataatgagcagaaacagctgtttgtggaacagcacaagcactac
ctggacgagatcatcgagcagatcagcgagttctccaagagagtgatcct
ggccgacgctaatctggacaaagtgctgtccgcctacaacaagcaccgg
gataagcccatcagagagcaggccgagaatatcatccacctgttttaccctg
accaatctgggagcccctgccgccttcaagtactttgacaccaccatcgac
cggaagaggtacaccagcaccaaagaggtgctggacgccaccctgatc
caccagagcatcaccggcctgtacgagacacggatcgacctgtctctcagct
gggaggcgacaaaaggccggcggccacgaaaaaggccggccaggca
aaaaagaaaaagtaagaattcctagagctcgctgatcagcctcgactgtgc
cttctagttgccagccatctgttgtttgcccctcccccgtgccttccttgaccc
tggaaggtgccactcccactgtcctttcctaataaaatgaggaaattgcatc
gcattgtctgagtaggtgtcattctattctgggggggtggggtggggcagga
cagcaagggggaggattgggaagagaatagcaggcatgctgggggagc
ggccgcttccctttagtgagggttaatgcttcgagcagacatgataagatac
attgatgagtttggacaaaccacaactagaatgcagtgaaaaaaatgcttta
tttgtgaaatttgtgatgctattgctttatttgtaaccattataagctgcaataaa
caagttaacaacaacaattgcattcattttatgtttcaggttcaggggggagat
gtgggaggttttttaaagcaagtaaaacctctacaaatgtggtaaaatccga
taaggatcgatgggacagcccccccccaaagcccccagggatgtaatta
cgtccctcccccgctagggcagcagcgagccgcccggggctccggtcc
ggtccggcgctcccccgcatccccgagccggcagcgtgcggggacag
cccgggcacggggaaggtggcacgggatcgctttcctctgaacgcttctc
gctgctctttgagcctgcagacacctgggggggatacggggaaaatctagt
gggacagccccccccaaagcccccagggatgtaattacgtccctcccc
cgctagggcagcagcgagccgcccggggctccggtccggtccggcgct
cccccgcatccccgagccggcagcgtgcggggacagcccgggcacgg
ggaaggtggcacgggatcgctttcctctgaacgcttctcgctgctctttgag
cctgcagacacctgggggggatacggggaaaatcgatgggacagcccc
ccccaaagcccccagggatgtaattacgtccctcccccgctagggcag
cagcgagccgcccggggctccggtccggtccggcgctcccccgcatcc
ccgagccggcagcgtgcggggacagcccgggcacggggaaggtggc
acgggatcgctttcctctgaacgcttctcgctgctctttgagcctgcagaca
cctggggggatacggggaaaatctagtgggacagccccccccccaaagc
ccccagggatgtaattacgtccctcccccgctagggcagcagcgagccg
cccggggctccggtccggtccggcgctcccccgcatccccgagccggc
agcgtgcggggacagcccgggcacggggaaggtggcacgggatcgct
ttcctctgaacgcttctcgctgctctttgagcctgcagacacctgggggat
acggggaaaatcgatagcgataaggatccactagttattaatagtaatca
attacggggtcattagttcatagcccatatatggagttccgcgttacataactt
acggtaaatggcccgcctggctgaccgcccaacgacccccgcccattga
cgtcaataatgacgtatgttcccatagtaacgccaatagggactttccattga
cgtcaatgggtggagtatttacggtaaactgcccacttggcagtacatcaa
gtgtatcatatgccaagtacgccccctattgacgtcaatgacggtaaatggc
ccgcctggcattatgcccagtacatgaccttatgggactttcctacttggca
gtacatctacgtattagtcatcgctattaccatggtcgaggtgagccccacg
ttctgcttcactctccccatctccccccctccccaccccccaattttgtatttat
ttattttttaattattttgtgcagcgatggggcggggggggggggggggggg
gggccagcggggcggggcggggcgaggggcggggcgggcgag
gcggagaggtgcggcggcagccaatcagagcggcgcgctccgaaagtt
tccttttatggcgaggcggcggcggcggcggccctataaaaagcgaagc
gcgcggcggggggagtcgctgcgttgccttcgccccgtgccccgctcc
gcgccgcctcgcgccgcccgcccggctctgactgaccgcgttactccc
acaggtgagcgggcgggacggcccttctcctccggggctgtaattagcgct
tggtttaatgacggcgtttcttttctgtggctgcgtgaaagccttaaaggg
ctccgggagggcccttgtgcggggggggagcggctcggggggtgcgtg
cgtgtgtgtgtgcgtggggagcgccgcgtgcggctccgcgctgcccggc
ggctgtgagcgctgcggggcgcggcgcggggctttgtgcgctccgcagt
gtgcgcgaggggagcgcggccgggggcggtgccccgcggtgcgggg
```

TABLE 2-continued

Sequences

| SEQ ID NO: Description | Sequence |
|---|---|
| | ggggctgcgaggggaacaaaggctgcgtgcggggtgtgtgcgtgggg |
| | gggtgagcaggggtgtgggcgcgtcggtcgggctgcaacccccctg |
| | cacccccctccccgagttgctgagcacggcccggcttcgggtgcggggc |
| | tccgtacggggcgtggcgcggggctcgccgtgccgggcggggggtgg |
| | cggcaggtgggggtgccgggcggggcggggccgcctcgggccgggg |
| | agggctcgggggagggggcgcggcggcccccggagcgccggcggctg |
| | tcgaggcgcggcgagccgcagccattgccttttatggtaatcgtgcgaga |
| | gggcgcagggacttcctttgtcccaaatctgtgcggagccgaaatctggg |
| | aggcgccgccgcaccccctctagcgggcgcggggcgaagcggtgcgg |
| | cgccggcaggaaggaaatgggcggggagggccttcgtgcgtcgccgc |
| | gccgccgtccccttctccctctccagcctcggggctgtccgcgggggggac |
| | ggctgccttcggggggggacggggcagggcggggttcggcttctggcgt |
| | gtgaccggcggctctagagcctctgctaaccatgttcatgccttcttctttttc |
| | ctacagctcctgggcaacgtgctggttattgtgctgtctcatcattttggcaa |
| | agaattccgctgcgactcggcggagtcccggcggcgcgtccttgttctaa |
| | cccggcgcgccgccaccatgtctagattagataaaagtaaagtgattaaca |
| | gcgcattagagctgcttaatgaggtcggaatcgaaggtttaacaacccgta |
| | aactcgcccagaagctaggtgtagagcagcctacattgtattggcatgtaa |
| | aaaataagcgggctttgctcgacgccttagccattgagatgttagataggc |
| | accatactcacttttgccctttagaaggggaaagctggcaagatttttttacgt |
| | aataacgctaaaagttttagatgtgctttactaagtcatcgcgatggagcaa |
| | aagtacatttaggtacacggcctacagaaaaacagtatgaaactctcgaaa |
| | atcaattagcctttttatgccaacaaggttttcactagagaatgcattatatgc |
| | actcagcgctgtggggcattttactttaggttgcgtattggaagatcaagag |
| | catcaagtcgctaaagaagaaagggaaacacctactactgatagtatgcc |
| | gccattattacgacaagctatcgaattatttgatcaccaaggtgcagagcca |
| | gccttcttattcggccttgaattgatcatatgcggattagaaaaacaacttaa |
| | atgtgaaagtgggtccgcgtacagccgcgcgcgtacgaaaaacaattac |
| | gggtctaccatcgagggcctgctcgatctcccggacgacgacgcccccg |
| | aagaggcggggctggcggctccgcgcctgtcctttctccccgcgggaca |
| | cacgcgcagactgtcgacggcccccccgaccgatgtcagcctggggga |
| | cgagctccacttagacggcgaggacgtggcgatggcgcatgccgacgc |
| | gctagacgatttcgatctggacatgttgggggacggggattccccgggtc |
| | cgggatttaccccccacgactccgccccctacggcgcgctctggatatggcc |
| | gacttcgagtttgagcagatgtttaccgatgcccttggaattgacgagtacg |
| | gtgggtagtagggcgcgccggcaccggtaccaagcttaagagcgctag |
| | ctggccagacatgataagatacattgatgagtttggacaaaccacaactag |
| | aatgcagtgaaaaaaatgctttatttgtgaaatttgtgatgctattgctttatttg |
| | taaccattataagctgcaataaacaagttaacaacaacaattgcattcatttta |
| | tgtttcaggttcagggggaggtgtgggaggttttttaaagcaagtaaaacct |
| | ctacaaatgtggtatggaattggagcccactgtgttcatcttacagatgga |
| | aatactgacattcagaggagttagttaacttgcctaggtgattcagctaataa |
| | gtgcaagaaagatttcaatccaaggtgatttgattctgaagcctgtgctaatc |
| | acattacaccaagctacaacttcatttataaataataagtcagctttcaaggg |
| | cctttcaggtgtcctgcacttctacaagctgtgccatttagtgaacacaaaat |
| | gagccttctgatgaagtagtcttttcattatttcagatattagaacactaaaatt |
| | cttagctgccagctgattgaaggctgggacaaaattcaaacatgcatctac |
| | aacaatatatatctcaatgttagtctccaaattctattgacttcaactcaagag |
| | aatataaagagctagtctttatacactctttaaggtatgatatcatctggaaag |
| | taacaaaattgatgcaaatttgaatgaactttatcatggtgtatttacacaatgt |
| | gtttcttctccctgcaatgtatttctttctctaattccttccatttgatctttcataca |
| | caatctggttctgatgtatgttttttggatgcacttttcaactccaaaagacag |
| | agctagttactttcttcctggtgctccaagcactgtatttgtatctgtattcaag |
| | ccctttgcaatattgtactggatcattatttcacctctaggatggcttccccag |
| | gcaacttgtgttcacccagagactacattttgtatcttgttgacctttgaacttc |
| | caccagtgtctaaaaataatatgtatgcaaaattacttgctatgagaatgtata |
| | attaaacaatataaaaaggagaagcaaggagagaaacacaggtgtgtatt |
| | tgtgtttgtgtgcttaaaaggcagtgtggaaaaggaagaaatgccatttata |
| | gtgaggagacaaagttatattacctcttatctggcttttaaggagattttgctg |
| | agctaaaaatcctatattcatagaaaagccttacctgagttgccaatacctca |
| | attctaaaatacagcatagcaaaactttaacctccaaatcaagcctctacttg |
| | aatccttttctgagggatgaataaggcataggcatcaggggctgttgccaat |
| | gtgcattagctgtttgcagcctcaccttctttcatggagtttaagatatagtgta |
| | ttttcccaaggtttgaactagctcttcatttctttatgttttaaatgcactgacctc |
| | ccacattcccttttttagtaaaatattcagaaataatttggggtcccgatttttccc |
| | cgtatcccccccaggtgtctgcaggctcaaagagcagcgagaagcgttca |
| | gaggaaagcgatcccgtgccaccttccccgtgcccgggctgtccccgca |
| | cgctgccggctcggggatgcggggggagcgccggaccggaccggagc |
| | cccggcgggctcgctgctgccctagcggggagggggacgtaattacatcc |
| | ctggggggctttgggggggggggctgtcccactagattttccccgtatccccccc |
| | aggtgtctgcaggctcaaagagcagcgagaagcgttcagaggaaagcg |
| | atcccgtgccaccttccccgtgcccgggctgtccccgcacgctgccggct |
| | cggggatgcgggggagcgccggaccggaccggagccccgggcggct |
| | cgctgctgccctagcggggagggacgtaattacatccctggggggctttg |

TABLE 2-continued

Sequences

SEQ
ID
NO: Description        Sequence gggggggggctgtcccatcggatcttctagtcctgcaggagtcaatgggaa
                       aaacccattggagccaagtacactgactcaatagggactttccattgggttt
                       tgcccagtacataaggtcaatagggggtgagtcaacaggaaagtcccatt
                       ggagccaagtacattgagtcaatagggactttccaatgggttttgcccagta
                       cataaggtcaatgggaggtaagccaatgggttttttcccattactgacatgtat
                       acgcgtcgacgtcggcgcgttcagcctaaagcttttttcccgtatccccc
                       aggtgtctgcaggctcaaagagcagcgagaagcgttcagaggaaagcg
                       atcccgtgccaccttccccgtgcccgggctgtccccgcacgctgccggct
                       cggggatgcgggggagcgccggaccggaccggagccccgggcggct
                       cgctgctgccctagcggggggagggacgtaattacatccctgggggctttg
                       ggggggggctgtccctgcggccgcgaattcgtaatcatggtcatagctgtt
                       tcctgtgtgaaattgttatccgctcacaattccacacaacatacgagccgga
                       agcataaagtgtaaagcctggggtgcctaatgagtgagctaactcacatta
                       attgcgttgcgctcactgcccgctttccagtcgggaaacctgtcgtgccag
                       gggtctagccgcggtctaggaagctttctagggtacctctagggatccact
                       agttattaatagtaatcaattacggggtcattagttcatagcccatatatggag
                       ttccgcgttacataacttacggtaaatggcccgcctggctgaccgcccaac
                       gacccccgcccattgacgtcaataatgacgtatgttcccatagtaacgcca
                       atagggactttccattgacgtcaatgggtggagtatttacggtaaactgccc
                       acttggcagtacatcaagtgtatcatatgccaagtacgcccccctattgacgt
                       caatgacggtaaatggcccgcctggcattatgcccagtacatgaccttatg
                       ggactttcctacttggcagtacatctacgtattagtcatcgctattaccatggg
                       tcgaggtgagccccacgttctgcttcactctccccatctcccccccctcccc
                       accccaattttgtatttatttattttttaattatttttgtgcagcgatggggcgg
                       gggggggggggcgcgcgccaggcggggcggggcggggcgaggg
                       gcggggcggggcgaggcggagaggtgcggcggcagccaatcagagc
                       ggcgcgctccgaaagtttccttttatggcgaggcggcggcggcggcggc
                       cctataaaaagcgaagcgcgcggcgggcgggagtcgctgcgttgccttc
                       gccccgtgccccgctccgcgccgcctcgcgccgcccgcccccggctctg
                       actgaccgcgttactcccacaggtgagcgggggacggcccttctcctc
                       cgggctgtaattagcgcttggtttaatgacggctcgtttcttttctgtggctgc
                       gtgaaagccttaaagggctccgggagggcccttttgtgcggggggagc
                       ggctcggggggtgcgtgcgtgtgtgtgtgcgtggggagcgccgcgtgc
                       ggcccgcgctgcccggcggctgtgagcgctgcgggcgcggcgcggg
                       gctttgtgcgctccgcgtgtgcgcgaggggagcgcggccgggggcggt
                       gccccgcggtgggggggggctgcgaggggaacaaaggctgcgtgcg
                       gggtgtgtgcgtggggggggtgagcaggggggtgtgggcgcggcggtcg
                       ggctgtaacccccccctgcaccccccctccccgagttgctgagcacggcc
                       cggcttcgggtgcggggctccgtgcggggcgtggcgcggggctcgcc
                       gtgccgggcgggggggtggcggcaggtggggggtgccgggcggggcgg
                       ggccgcctcgggccggggaggggctcggggggaggggcgcggcggcc
                       ccggagcgccggcggctgtcgaggcgcggcgagccgcagccattgcct
                       tttatggtaatcgtgcgagagggcgcagggacttcctttgtcccaaatctgg
                       cggagccgaaatctgggaggcgccgccgcacccccctctagcgggcgc
                       gggcgaagcggtgcggcgccggcaggaaggaaatgggcggggagg
                       gccttcgtgcgtcgccgcgccgcgtccccttctccatctccagcctcggg
                       gctgccgcagggggacggctgccttcggggggggacggggcagggcg
                       gggttcggcttctggcgtgtgaccggcggctctagagcctctgctaaccat
                       gttcatgccttcttcttttttcctacagctcctgggcaacgtgctggttgttgtgc
                       tgtctcatcattttggcaaagaattccgctgcgactcggcggagtcccggc
                       ggcgcgtccttgttctaacccggcgcgccctcaggatggagcctcccggc
                       cgccgcgagtgtcccctttccttcctggcgctttcctgggttgcttctggcgg
                       ccatggtgttgctgctgtacctcttctccgatgcctgtgaggagccaccaac
                       atttgaagctatggagctcattggtaaaccaaaaccctactatgagattggt
                       gaacgagtagattataagtgtaaaaaaggatacttctatataacctcctcttgc
                       cacccatactatttgtgatcggaatcatacatggctacctgtctcagatgacg
                       cctgttatagagaaacatgtccatatatacgggatcctttaaatggccaagc
                       agtccctgcaaatgggacttacgagtttggttatcagatgcactttatttgtaa
                       tgagggttattacttaattggtgaagaaattctatattgtgaacttaaaggatc
                       agtagcaatttggagcggtaagcccccaatatgtgaaaaggttttgtgtaca
                       ccacctccaaaaataaaaaatggaaaacacacctttagtgaagtagaagta
                       tttgagtatcttgatgcagtaacttatagttgtgatcctgcacctggaccagat
                       ccattttcacttattggagagagcacgatttattgtggtgacaattcagtgtgg
                       agtcgtgctgctccagagtgtaaagtggtcaaatgtcgatttccagtagtcg
                       aaaatggaaaacagatatcaggatttggaaaaaaattttactacaaagcaa
                       cagttatgtttgaatgcgataaagggttttttacctcgatggcagcgacacaatt
                       gtctgtgacagtaacagtacttgggatcccccagttccaaagtgtcttaaag
                       tgctgcctccatctagtacaaaacctccagctttgagtcattcagtgtcgact
                       tcttccactacaaaatctccagcgtccagtgcctcaggtcctaggcctactt
                       acaagcctccagtctcaaattatccaggatatcctaaacctgaggaaggaa
                       tacttgacagtttggatgtttgggtcattgctgtgattgttattgccatagttgtt
                       ggagttgcagtaatttgtgttgtcccgtacagatatcttcaaaggaggaaga
                       agaaaggcacatacctaactgatgagacccacagagaagtaaaatttactt
                       ctctcggatccggagccacgaacttctctctgttaaagcaagcaggagac TABLE 2-continued Sequences SEQ
ID
NO: Description                     Sequence

```
gtggaagaaaacccccggtcctatgaccgtcgcgcggccgagcgtgccc
gcggcgctgcccctcctcggggagctgccccggctgctgctgctggtgct
gttgtgcctgccggccgtgtggggtgactgtggccttcccccagatgtacc
taatgcccagccagctttggaaggccgtacaagtttttcccgaggatactgt
aataacgtacaaatgtgaagaaagctttgtgaaaattcctggcgagaagga
ctcagtgatctgccttaagggcagtcaatggtcagatattgaagagttctgc
aatcgtagctgcgaggtgccaacaaggctaaattctgcatccctcaaacag
ccttatatcactcagaattattttccagtcggtactgttgtggaatatgagtgc
cgtccaggttacagaagagaaccttctctatcaccaaaactaacttgccttc
agaatttaaaatggtccacagcagtcgaattttgtaaaaagaaatcatgccc
taatccgggagaaatacgaaatggtcagattgatgtaccaggtggcatatt
atttggtgcaaccatctccttctcatgtaacacagggtacaaattatttggctc
gacttctagtttttgtcttatttcaggcagctctgtccagtggagtgacccgtt
gccagagtgcagagaaatttattgcccagcaccaccacaaattgacaatg
gaataattcaagggaacgtgaccattatggatatagacagtctgtaacgt
atgcatgtaataaaggattcaccatgattggagagcactctatttattgtactg
tgaataatgatgaaggagagtggagtggcccaccacctgaatgcagagg
aaaatctctaacttccaaggtcccaccaacagttcagaaacctaccacagt
aaatgttccaactacagaagtctcaccaacttctcagaaaaccaccacaaa
aaccaccacaccaaatgctcaagcaacacggagtacacctgtttccagga
caaccaagcattttcatgaaacaaccccaaataaaggaagtggaaccactt
caggtactacccgtcttctatctgggcacacgtgtttcacgttgacaggtttg
cttgggacgctagtaaccatgggcttgctgacttagggcgcgccggcacc
ggtaccaagcttaagagcgctagctggccagacatgataagatacattgat
gagtttggacaaaccacaactagaatgcagtgaaaaaaatgctttatttgtg
aaatttgtgatgctattgctttatttgtaaccattataagctgcaataaacaagt
taacaacaacaattgcattcatttttatgtttcaggttcagggggaggtgtggg
aggttttttaaagcaagtaaaacctctacaaatgtggtatggaattggagcc
ccactgtgttcatcttacagatggaaatactgacattcagaggagttagttaa
cttgcctaggtgattcagctaataagtgcaagaaagatttcaatccaaggtg
atttgattctgaagcctgtgctaatcacattacaccaagctacaacttcatttat
aaataataagtcagctttcaagggcctttcaggtgtcctgcacttctacaagc
tgtgccatttagtgaacacaaaatgagccttctgatgaagtagtcttttcatta
tttcagatattagaacactaaaattcttagctgccagctgattgaaggctggg
acaaaattcaaacatgcatctacaacaatatatatctcaatgttagtctccaa
attctattgacttcaactcaagagaatataaagagctagtctttatacactcttt
aaggtatgatatcatctggaaagtaacaaaattgatgcaaatttgaatgaact
ttatcatggtgtatttacacaatgtgtttcttctccctgcaatgtatttctttctcta
attccttccatttgatctttcatacacaatctggttctgatgtatgttttttggatg
cacttttcaactccaaaagacagagctagttactttcttcctggtgctccaag
cactgtatttgtatctgtattcaagccctttgcaatattgtactggatcattatttc
acctctaggatggcttcccaggcaacttgtgttcacccagagactacatttt
gtatcttgttgacctttgaacttccaccagtgtctaaaaataatatgtatgcaa
aattacttgctatgagaatgtataattaaacaatataaaaaggagaagcaag
gagagaaacacaggtgtgtatttgtgtttgtgtgcttaaaaggcagtgtgga
aaaggaagaaatgccatttatagtgaggagacaaagttatattacctcttatc
tggcttttaaggagattttgctgagctaaaaatcctatattcatagaaaagcct
tacctgagttgccaatacctcaattctaaaatacagcatagcaaaactttaac
ctccaaatcaagcctctacttgaatcctttctgagggatgaataaggcatag
gcatcaggggctgttgccaatgtgcattagctgtttgcagcctcaccttcttt
catggagtttaagatatagtgtattttcccaaggtttgaactagctcttcatttct
ttatgtttttaaatgcactgacctcccacattccctttttagtaaaatattcagaa
ataatttatcatctggaaagtaacaaaattgatgcaaatttgaatgaactttat
catggtgtatttacacaatgtgtttcttctccctgcaatgtatttctttctctaatt
ccttccatttgatctttcatacacaatctggttctgatgtatgttttttggatgca
ctttcaactccaaaagacagagctagttactttcttcctggtgctccaagca
ctgtatttgtatctgtattcaagccctttgcaatattgtactggatcattatttcac
ctctaggatggcttcccaggcaacttgtgttcacccagagactacattttgt
atcttgttgacctttgaacttccaccagtgtctaaaaataatatgtatgcaaaa
ttacttgctatgagaatgtataattaaacaatataaaaaggagaagcaagga
gagaaacacaggtgtgtatttgtgtttgtgtgcttaaaaggcagtgtggaaa
aggaagaaatgccatttatagtgaggagacaaagttatattacctcttatctg
gctttttaaggagattttgctgagctaaaaatcctatattcatagaaaagcctta
cctgagttgccaatacctcaattctaaaatacagcatagcaaaactttaacct
ccaaatcaagcctctacttgaatcctttctgagggatgaataaggcatagg
catcaggggctgttgccaatgtgcattagctgtttgcagcctcaccttctttc
atggagtttaagatatagtgtattttcccaaggtttgaactagctcttcatttctt
tatgtttttaaatgcactgacctcccacattcccttttttagtaaaatattcagaaa
taatttatcccggcttgtcgacgacggaaatccggcttgtcgacgacggcg
gtctccgtcgtcaggatcatccggccggccatcaggacatagcgttggct
acccgtgatattgctgaagagcttggcggcgaatgggctgaccgcttcctc
gtgctttacggtatcgccgctcccgattcgcagcgcatcgccttctatcgcc
ttcttgacgagttcttctgagggatcaattctctagagctcgctgatcagcc
tcgactgtgccttctagttgccagccatctgttgtttgccccctcccccgtgcct
```

TABLE 2-continued

Sequences

| SEQ ID NO: | Description | Sequence |
|---|---|---|
| | | tccttgaccctggaaggtgccactcccactgtcctttcctaataaaatgagg |
| | | aaattgcatcgcattgtctgagtaggtgtcattctattctgggggtggggt |
| | | ggggcaggacagcaaggggggaggattgggaagacaatagcaggcatg |
| | | ctggggatgcggtgggctctatggcttctgaggcggaaagaaccagctg |
| | | ggggcgcgcacctcgaccatctccaggatgcctttgatagagctgggtcc |
| | | tctgcgttcctttaaagtgtttgagatcaagtccgagaagaggtggcaagac |
| | | atgcgatcgcgctagtttaaaatacatcattgcaatgaaaataaatgttttttat |
| | | taggcagaatccagatgctcaaggcccttcataatatcccccagtttagtag |
| | | ttggacttagggaacaaaggaacctttaatagaaattggacagcaagaaa |
| | | gctctagctttagaagaactcatcaagaagtctgtagaaggcaattctctgg |
| | | gagtcaggggctgcaatgccatagagcactaggaacctgtctgcccactc |
| | | tccccctagctcttctgctatgtccctggttgctagggcaatgtcctggtacc |
| | | tgtcagccactcccagcctgccacagtctatgaagccagagaaccttccat |
| | | tttcaaccatgatgttgggaaggcaggcatccccatgagtcaccactaggt |
| | | cctcaccatctggcatggatgccttgagcctggcaaatagttcagcaggg |
| | | gccaggccctggtgttcttcatccaagtcatcttggtccaccaggccagcct |
| | | ccatcctggttctggccctctctatcctgtgcttggcctggtggtcaaaggg |
| | | gcaggtggctgggtcaagggtgtggagtcttctcatggcatcagccatgat |
| | | tgacactttctcagctggagctaggtgagaggaaaggaggtcctgcccag |
| | | gcacctcacctagtaggagccagtcccttccagcttctgtgaccacatcaa |
| | | ggacagctgcacaggggaccccagttgttgccaaccaggagagtctggc |
| | | agcctcatcctggagctcattgagagcccactgaggtctgtcttttacaaaa |
| | | aggactggcctgccttgggctgaaagtctgaaaactgctgcatcagagca |
| | | accaatggtctgctgtgcccagtcatagccaaacagtctctcaacccaggc |
| | | agctggagaacctgcatgtaggccatcttgttcaatcatgatggctcctcct |
| | | gtcaggagaggaaagagaagaaggttagtacaattgctatagtgagttgta |
| | | ttatactatgcttatgattaattgttaaactagggctgcagggttcatagtgcc |
| | | acttttcctgcactgccccatctcctgcccaccctttcccaggcatagacagt |
| | | cagtgacttaccaaactcacaggaggagaaggcagaagctttttgcaaa |
| | | agcctaggctcatgagacaataaccctgataaatgcttcaataatattgaaa |
| | | aaggaagagtaccaggtatgagtattcaacatttccgtgtcgcccttattcc |
| | | ctttttttgcggcattttgccttcctgtttttgctcacccagaaacgctggtgaaa |
| | | gtaaaagatgctgaagatcagttgggtgcacgagtgggttacatcgaactg |
| | | gatctcaacagcggtaagatccttgagagttttcgccccgaagaacgttttc |
| | | caatgatgagcacttttaaagttctgctatgtggcgcggtattatcccgtattg |
| | | acgccgggcaagagcaactcggtcgccgcatacactattctcagaatgac |
| | | ttggttgagtactcaccagtcacagaaaagcatcttacggatggcatgaca |
| | | gtaagagaattatgcagtgctgccataaccatgagtgataacactgcggcc |
| | | aacttacttctgacaacgatcggaggaccgaaggagctaaccgcttttttgc |
| | | acaacatggggatcatgtaactcgccttgatcgttgggaaccggagctg |
| | | aatgaagccataccaaacgacgagcgtgacaccacgatgcctgtagcaa |
| | | tggcaacaacgttgcgcaaactattaactggcgaactacttactctagcttc |
| | | ccggcaacaattaatagactggatggaggcggataaagttgcaggacca |
| | | cttctgcgctcggcccttccggctggctggtttattgctgataaatctggagc |
| | | cggtgagcgtgggtctcgcggtatcattgcagcactggggccagatggta |
| | | agccctcccgtatcgtagttatctacacgacggggagtcaggcaactatgg |
| | | atgaacgaaatagacagatcgctgagataggtgcctcactgattaagcatt |
| | | ggtaatcgcgactgtcagaccaagtttactcatatatactttagattgatttaa |
| | | aacttcatttttaatttaaaaggatctaggtgaagatcctttttgataatctcatg |
| | | accaaaatcccttaacgtgagttttcgttccactgagcgtcagaccacgtgc |
| | | ccgtagaaaagatcaaaggatcttcttgagatcctttttttctgcgcgtaatct |
| | | gctgcttgcaaacaaaaaaaccaccgctaccagcggtggtttgtttgccgg |
| | | atcaagagctaccaactctttttccgaaggtaactggcttcagcagagcgc |
| | | agataccaaatactgttcttctagtgtagccgtagttaggccaccacttcaag |
| | | aactctgtagcaccgcctacatacctcgctctgctaatcctgttaccagtgg |
| | | ctgctgccagtggcgataagtcgtgtcttaccgggttggactcaagacgat |
| | | agttaccggataaggcgcagcggtcgggctgaacggggggttcgtgcac |
| | | acagcccagcttggagcgaacgacctacaccgaactgagatacctacag |
| | | cgtgagctatgagaaagcgccacgcttcccgaagggagaaaggcggac |
| | | aggtatccggtaagcggcagggtcggaacaggagagcgcacgaggga |
| | | gcttccaggggaaacgcctggtatctttatagtcctgtcgggtttcgccac |
| | | ctctgacttgagcgtcgatttttgtgatgctcgtcaggggggcggagcctat |
| | | ggaaaaacgccagcaacgcggcctttttacggttcctggccttttgctggc |
| | | cttttgctcacatggctcgacagatttaatcgggaggatccggagagggca |
| | | gttaatcgctcgagtgtaca |

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

What is claimed is:

1. A transgenic porcine animal comprising genetic modifications that result in:
   (i) the lack of expression of functional alpha 1,3 galactosyltransferase;
   (ii) a knockout of a gene selected from the group consisting of CMAH, B4GalNT2, growth hormone receptor (GHR), and a combination thereof; and
   (iii) incorporation and expression at a single genomic locus of at least six transgenes encoded by a polycistronic vector, wherein the polycistronic vector comprises SEQ ID NO: 12.

2. The transgenic porcine animal of claim 1, wherein the single genomic locus is GGTA1 and an additional genetic modification comprises the knockout of β4GalNT2, CMAH, and GHR.

3. Cells derived from the transgenic porcine animal of claim 1.

4. An organ derived from the transgenic porcine animal of claim 1.

5. The organ of claim 4, wherein the organ is selected from the group consisting of heart, lung, liver, pancreas, and kidney.

6. A tissue derived from the transgenic porcine animal of claim 1.

7. The tissue of claim 6, wherein the tissue is selected from the group consisting of vascular tissue, heart valve, retinal tissue, neural tissue, and corneal tissue.

8. The tissue of claim 7, wherein the vascular tissue is a vascular graft.

9. A method for xenotransplantation comprising administering, to a subject in need thereof, organs, tissues or cells derived from the transgenic porcine animal of claim 1.

10. A method of making a transgenic pig comprising at least six transgenes comprising the step of:
   (i) transfecting a porcine cell with a single polycistronic vector comprising SEQ ID NO: 12;
   (ii) producing a multitransgenic porcine cell comprising at least six transgenes by incorporating and expressing the polycistronic vector at a single genomic locus;
   (iii) generating a multitransgenic porcine zygote by injecting the nucleus of the multitransgenic porcine cell into a reconstructed somatic cell nuclear transfer (SCNT); and
   (iv) permitting the multitransgenic porcine zygote to mature into a multitransgenic pig;
   wherein the porcine cell and the multitransgenic pig lack expression of alpha 1,3 galactosyltransferase (GTKO); and
   wherein the transgenic porcine animal comprises a deletion of a gene selected from the group consisting of CMAH, B4GalNT2, GGTA1, GHR, and a combination thereof.

11. A transgenic porcine animal comprising genetic modifications that result in:
   (i) the lack of expression of functional alpha 1,3 galactosyltransferase; and
   (ii)
   incorporation and expression at a single genomic locus of a polycistronic vector comprising SEQ ID NO: 12.

12. Cells derived from the transgenic porcine animal of claim 11.

13. An organ derived from the transgenic porcine animal of claim 11.

14. The organ of claim 13, wherein the organ is selected from the group consisting of heart, lung, liver, pancreas, and kidney.

15. A tissue derived from the transgenic porcine animal of claim 11.

16. The tissue of claim 15, wherein the tissue is selected from the group consisting of vascular tissue, heart valve, retinal tissue, neural tissue, and corneal tissue.

17. The tissue of claim 16, wherein the vascular tissue is a vascular graft.

18. A method for xenotransplantation comprising administering, to a subject in need thereof, organs, tissues or cells derived from the transgenic porcine animal of claim 11.

\*   \*   \*   \*   \*

SEQUENCE LISTING

```
Sequence total quantity: 14
SEQ ID NO: 1              moltype = DNA  length = 20
FEATURE                   Location/Qualifiers
source                    1..20
                          mol_type = other DNA
                          organism = synthetic construct
SEQUENCE: 1
ccctccttcc cacaaagctt                                          20

SEQ ID NO: 2              moltype = DNA  length = 20
FEATURE                   Location/Qualifiers
source                    1..20
                          mol_type = other DNA
                          organism = synthetic construct
SEQUENCE: 2
actggcattg aggaaggtcg                                          20

SEQ ID NO: 3              moltype =   length =
SEQUENCE: 3
000

SEQ ID NO: 4              moltype =   length =
SEQUENCE: 4
000

SEQ ID NO: 5              moltype = DNA  length = 20
FEATURE                   Location/Qualifiers
source                    1..20
                          mol_type = other DNA
                          organism = synthetic construct
SEQUENCE: 5
cccacacaca accagagaca                                          20

SEQ ID NO: 6              moltype = DNA  length = 20
FEATURE                   Location/Qualifiers
source                    1..20
                          mol_type = other DNA
                          organism = synthetic construct
SEQUENCE: 6
gtgcaggtat gtggcctctt                                          20

SEQ ID NO: 7              moltype = DNA  length = 24315
FEATURE                   Location/Qualifiers
source                    1..24315
                          mol_type = other DNA
                          organism = synthetic construct
SEQUENCE: 7
cggaggaccg aaggagctaa ccgctttttt gcacaacatg ggggatcatg taactcgcct  60
tgatcgttgg gaaccggagc tgaatgaagc cataccaaac gacgagcgtg acaccacgat  120
gcctgtagca atggcaacaa cgttgcgcaa actattaact ggcgaactac ttactctagc  180
ttcccggcaa caattaatag actggatgga ggcggataaa gttgcaggac cacttctgcg  240
ctcggccctt ccggctggct ggtttattgc tgataaatct ggagccggtg agcgtgggtc  300
tcgcggtatc attgcagcac tggggccaga tggtaagccc tcccgtatcg tagttatcta  360
cacgacgggg agtcaggcaa ctatggatga acgaaataga cagatcgctg agataggtgc  420
ctcactgatt aagcattggt aactgtcaga ccaagtttac tcatatatac tttagattga  480
```

-continued

```
tttaaaacttt catttttaat ttaaaaggat ctaggtgaag atcctttttg ataatctcat   540
gaccaaaatc ccttaacgtg agttttcgtt ccactgagcg tcagaccccg tagaaaagat   600
caaaggatct tcttgagatc cttttttttct gcgcgtaatc tgctgcttgc aaacaaaaaa   660
accaccgcta ccagcggtgg tttgtttgcc ggatcaagag ctaccaactc tttttccgaa   720
ggtaactggc ttcagcagag cgcagatacc aaatactgtt cttctagtgt agccgtagtt   780
aggccaccac ttcaagaact ctgtagcacc gcctacatac ctcgctctgc taatcctgtt   840
accagtggct gctgccagtg gcgataagtc gtgtcttacc gggttggact caagacgata   900
gttaccggat aaggcgcagc ggtcgggctg aacggggggt tcgtgcacac agcccagctt   960
ggagcgaacg acctacaccg aactgagata cctacagcgt gagctatgag aaagcgccaa  1020
gcttcccgaa gggagaaagg cggacaggta tccggtaagc ggcagggtcg gaacaggaga  1080
gcgcacgagg gagcttccag ggggaaacgc ctggtatctt tatagtcctg tcgggtttcg  1140
ccacctctga cttgagcgtc gatttttgtg atgctcgtca gggggggcgga gcctatggaa  1200
aaacgccagc aacgcggcct ttttacggtt cctggccttt tgctggcctt ttgctcacat  1260
ggctcgacag atttaattaa caagaccgac ctgtccggtg ccctgaatga actgcaggac  1320
gaggcagcgc ggctatcgtg gctggccacg acgggcgttc cttgcgcagc tgtgctcgac  1380
gttgtcactg aagcgggaag ggactggctg ctattgggcg aagtgccggg gcaggatctc  1440
ctgtcatctc accttgctcc tgccgagaaa gtatccatca tggctgatgc aatgcggcgg  1500
ctgcatacgc ttgatccggc tacctgccca ttcgaccacc aagcgaaaca tcgcatcgag  1560
cgagcacgta ctcggatgga agccggtctt gtcgatcagg atgatctgga cgaagagcat  1620
caggggctcg cgccagccga actgttcgcc aggctcaagg cgcgcatgcc cgacggcgag  1680
gatctcgtcg tgacccatgg cgatgcctgc ttgccgaata tcatggtgga aaatggccgc  1740
ttttctggat tcatcgactg tggccggctg ggtgtggcgg atcgctacgt tcgatggcgc  1800
tgccagggcg tgcccttggg ctccccgggc gcggcgatta agacgtaagt cttggcagcc  1860
cctgacccca gagcaggctc cctccccaca gctgctctcc gtgagtcctt cacttgccca  1920
agttcaagat gtacccagtt ctggagctgc caaaccatcc tgcatcctga tgtcagccac  1980
ccaagttctg gggtagctgg tctgccaccc aggtggatga aaagaggcca catacctgca  2040
ccagcatctg cgaatctctg aagaacatca ataataaaaa gacaactaac ccagttaaaa  2100
cacaggtaga gaatctgaac agacattcat cggaagaaga attacgactg gccaaaaagc  2160
tcataaaaag atggtcaaag tcattggtca gggaaatgta aatcaaaccg cattgagata  2220
ccatctcact ccctctcgga tggctggaat gaaaaaaaac ctcttctttc ctccctttca  2280
ttgtcttggc acccttgtgg aaattaattg actaaaattc atgaaataca aaaattttta  2340
ggagttcccg tcgtggctca gtggttaaca aatctgacta ggaaccatga ggtttcaggt  2400
tcgattcctg gcctcactca gtgggttagg gatctggtgt tgccatgagc tgtggtgtag  2460
gtcacagacg cagctcggat cccgcattgc tgtggctctg gcgtaggccg gcggctacag  2520
ctctgattca acctctagcc tgggaatagc ccaagaaatg gcaaaaagac caaaaaaaaa  2580
aaaaaaaaaa aaactcgttt tgagcatttt tgcatgtgta cattgtccat ttgtgtgcct  2640
tccaagattt attttggag tctcaactct gtgtcattga tttatgtctc tccttaggcc  2700
agaaccacac tgtttttggtg accatggctt tgtagtaaaa tttgaaatct gaaagtgtga  2760
gccctcctgt tttgtttctc ttctccatga ttagtttggt tattcagagt cccttgaatt  2820
tccaggtgaa ttttaggatt agcaggaaaa tttctgcaga gatggcagca gagattttta  2880
atagggatta tgttgaatct ggaggttaat ttcagttttg ctaccttgac tgtattaagt  2940
cttccagtct ataagcataa gatgtctttt tatttactta ggtcttttaa aatttctttg  3000
ggcactccca ttgtggtgca tcggaaatga atccgactag tatccacaag aacacaggtt  3060
caatccctgg cattgctcag tgggttaagg atcctgcatt gccatgaaga actgtggtgg  3120
aggccagcag ctgcagctct gatttgaccc ctagcctggg aacttccata tgccttgggt  3180
atggccctaa aaagcaaact aagtaagtaa gtaaataaat aaatgaataa ataaaatttc  3240
tttcaacatt gtaattttgt aattttgta attttcagag cgtacatttt gccctttcaa  3300
tacattattc ctacatattt tattcttttt gatactatta taaatgaaat ttataattaa  3360
ttcatttata tgaatttcat tttcaatttg catattgcta ctacaataga aatgcacttt  3420
ttaattattt ttatggccat actatatata tatgtgtgtg tgtgtgtatg tgtgtcattt  3480
tactgtacag cagaaattga cacaacattg taaatcaact acacttaaaa aatgaagaaa  3540
taaccacctg tgattatggc tactgtgttg gacactttag gcatccccc accccgtccc  3600
cgccccacac ccctgagtgc tagtgacgga tgttcccacc caggggggcct ggagccttta  3660
tcaccagcca tcgggaatca gaaccgtatc tcacagtccc catgcctgga gcacctggaa  3720
ttgtgcccct ggactcgtgg gtgttctgct tctcagtggg agaagcttag gttctaagtc  3780
agagcaggga cagcccccat gtgctcagga cccagtgtga aggggtctgc ctcaggggac  3840
ctgggggtta caagggtaag agaaggtgtt catgttggaa ctagaagttc tttttcactg  3900
ctctgaagaa aaaagctgcc tcccacccct ggtacagctc ttctgctaac agtgaatcag  3960
gcagaacgtg ttcaagaagt gacccagcct ggtgggggc agacctgacc cttgatggtc  4020
cctcaacccc tccgagggtc ccgcccttcc tttactgctt tgttgtctgt cctgagaggt  4080
ttggctaatg tcgaaccaag ggtgtggctg gtcctgtccc ctttcctgtc tcacgcaccc  4140
acctctgaag tctctgtagc tggttccagc cgggatctgg agccactccc cccgccccag  4200
gcccagtggt acagactctt gcagagtcgg gggcccctga ctcagcccca ccgccagcgg  4260
gatgtcaggc cagcacccgc cccactccca ctgatctcgg ggggtgtct ttccttcctg  4320
cttccaaagg agcctcagac cttcctgtgg ggcacggggg cagtgggatt caggaggctc  4380
tgagtcagca ggccggcatt gaggagtata aagggacccc agttcctccc cctttcactt  4440
gtggcttatc gccgccccac cctgcccaa ggtcactgcg gtcagtacag tcctcagctg  4500
ccagcaggtg cctgtcttta cttgtgaggc cgccacgctc tcctgtttct ccaggtctgg  4560
gctctgttgg aagtgggggc ccgaccccg ggtaagatgg gggatctgcg tgtcctgccc  4620
tcagaggcct cctcctcccc gcacccctaa ccctttcagc ccaacaaggc tggagatctc  4680
ccacatcttt ggcttcgtta agagttcaac agcgccgcca cccggcatgt cgctgagcag  4740
aggatggcac agggtgttaa aaaaaaaaaa aggttgccac actccgttcg gttttgggcc  4800
cacccttttcg cattcctgga gcctgagtaa gcggataagg ctgtgaaagt gacagattcc  4860
tgccacctcc ttccagcgct catgcacagg gaccgcccct cttcggtgtc ctttgctgca  4920
caagtgcatt tgcacattcc tgtctcaatc tggtttctcc cccttaaaag atgggaatgt  4980
gacctgcttg gagcccctcg cctcgccagg gcacccatc cgtcccttca ggggtggaga  5040
tggactgtcc ctctgcaagg ctggatgaac tcagaccaaa caggccaact tgctccccaa  5100
atacgcccac ccctaccggg ctgcaggaat tcgcctgtca ccactgctga agggtgacct  5160
tgcagccctg agagcatccc catgacttgc ccaccagatg aagtctggtt gtggcaggtc  5220
```

-continued

```
gcgctcaggg actcccgggt cccacctggg ggtgggagga tcctcctttg ctcgtggtcg   5280
ccccagccac gccctccttt ccaagcgcca gtctccagag ctccgtgccc cggcggaggc   5340
ggtctggctc tctctccttg cccctctctc cttgccccta gcagcccttc tcctaaaccc   5400
tctgagcagc gggcacctcc tcccgaggcc ctgggctaag tccccaccct tcatctcaag   5460
ccttcctcct tgactccctc ttcccagagt tccttgaaat aggtggtaag tacacaccga   5520
tgacggaaaa caaagactaa gaggttaaag agggctgagg attacggccc cggtagggct   5580
gcgcgcgagg gggtcgagtg gccgggcggt cccgtcgccg ggcagacaga ggtgcggttc   5640
tcccgggcgc ctgcgctgcc ggccccgccc ggagccctcc cagccggcgc ccagtttact   5700
catcccggag aggtgatccc gggcgcgagg gcgggcgcag ggcgtccgga gaacccagta   5760
atccgagaat gcagcatcag cccttcccac caggcacttc cttccttttc ccgaacgtcc   5820
agggagggg gccgcgcact tataaactcg ggccggaccc gccggcctgt cagaggctgc   5880
ctcgctgggg ctgcgcgcgg cggccggaca catctggtcc gagaccaacg cgagcgactg   5940
tcactggcag ctccctgcgc ctctcagccc cggccgggcc cctgcgcttg gcgtgctgac   6000
accatgcttg gggtcctggt ccttggccgcg ctggccctgg ccggcctggg gttccccgca   6060
cccgcagagc cgcagccggg tggcagccag tgcgtcgagc acgactgctt cgcgctctac   6120
ccgggccccg cgaccttcct caatgccagt cagatctgcg acggactgcg gggccaccta   6180
atgacagtgc gctcctcggt ggctgccgat gtcatttcct tgctactgaa cggcgacggc   6240
ggcgttggcc gccggcgcct ctggatcggc ctgcagctga cacccggctg cggcgacccc   6300
aagcgcctcg ggcccctgcg cggcttccag tgggttacgg gagacaacaa caccagctat   6360
agcaggtggg cacggctcga cctcaatggg gctcccctct gcggcccgtt gtgcgtcgct   6420
gtctccgctg ctgaggccac tgtgcccagc gagccgatct gggaggagca gcagtgcgaa   6480
gtgaagccgg atggcttcct ctgcgagttc cacttcccag ccacctgcag gccactggct   6540
gtggagcccg gcgccgcggc tgccgccgtc tcgatcacct acggcacccc gttcgcggcc   6600
cgcggagcgg acttccaggc gctgccggtg ggcagctccg ccgcggtggc tccccctcggc   6660
ttacagctaa tgtgcaccgc gccgcccgga gcggtccagg ggcactgggc cagggaggcg   6720
ccgggcgctt gggactgcag cgtggagaac ggcggctgcg agcacgcgtg caatgcgatc   6780
cctggggctc cccgctgcca gtgcccagcc ggcgccgccc tgcaggcaga cgggcgctcc   6840
tgcaccgcat ccgcgacgca gtcctgcaac gacctctgcg agcacttctg cgttcccaac   6900
cccgaccagc cgggctccta ctcgtgcatg tgcgagaccg gctaccggct ggcggccgac   6960
caacaccggt gcgaggacgt ggatgactgc atactggagc ccagtccgtg tccgcagcgc   7020
tgtgtcaaca cacagggtgg cttcgagtgc cactgctacc ctaactacga cctggtggac   7080
ggcgagtgtg tggagcccgt ggacccgtgc ttcagagcca actgcgagta ccagtgccag   7140
cccctgaacc aaaactagcta cctctgcgtc tgcgccgagg gcttcgcgcc cattccccac   7200
gagccgcaca ggtgccagat gttttgcaac cagactgcct gtccagccga ctgcgacccc   7260
aacaccagg ctagctgtga gtgccctgaa ggctacatcc tggacgacgg tttcatctgc   7320
acggacatcg acgagtgcga aaacggcggc ttctgctccg gggtgtgcca caacctcccc   7380
ggtaccttcg agtgcatctg cgggcccgac tcggcccttg cccgccacat tggcaccgac   7440
tgtgactccg gcaaggtgga cggtggcgac agcggctctg gcgagccccc gcccagcccg   7500
acgcccggct ccaccttgac tcctccggcc gtggggctcg tgcattcggg cttgctcata   7560
ggcatctcca tcgcgagcct gtgcctggtg gtggcgcttt tggcgctcct ctgccacctg   7620
cgcaagaagc agggcgccgc cagggccaag atggagtaca agtgcgcggc cccttccaag   7680
gaggtagtgc tgcagcacgt gcggaccgag cggacgccgc agagactcgg atccggagag   7740
ggcagagaa gtcttctaac atgcgggtac gtggagagaa atcccggccc tatgttgaca   7800
acattgctgc cgatactgct gctgtctggc tgggcctttt gtagccaaga cgcctcagat   7860
ggcctccaaa gacttcatat gctccagatc tcctacttcc gcgacccta tcacgtgtgg   7920
taccagggca acgcgtcgct gggggggacac ctaacgcacg tgctggaagg cccagacacc   7980
aacaccacga tcattcagct gcagcccttg caggagcccg agagctgggc gcgcacgcag   8040
agtggcctgc agtcctacct gctccagttc cacggcctcg tgcgcctggt gcaccaggag   8100
cggaccttgg cctttcctct gaccatccgc tgcttcctgg gctgtgagct gcctcccgag   8160
ggctctagag cccatgtctt cttcgaagtg gctgtgaatg ggagctcctt tgtgagtttc   8220
cggccggaga gagccttgtg gcaggcagac acccaggtca cctccggagt ggtcaccttc   8280
accctgcagc agctcaatgc ctacaacacgc actcggtatg aactgcggga attcctggag   8340
gacacctgtg tgcagtatgt gcagaaacat atttccgcgg aaaacacgaa agggagccaa   8400
acaagccgct cctacacttc gctggtcctg ggcgtcctgg tgggcagttt catcattgct   8460
ggtgtggctg taggcatctt cctgtgcaca ggtggacggc gatgttgagc gcggccgcatt   8520
cccttagtg agggttaatg cttcgagcag acatgataag atacattgat gagtttggac   8580
aaaccacaac tagaatgcag tgaaaaaaat gctttatttg tgaaatttgt gatgctattg   8640
ctttatttgt aaccattata agctgcaata aacaagttaa caacaacaat tgcattcatt   8700
ttatgtttca ggttcagggg gagatgtggg aggtttttta aagcaagtaa aacctctaca   8760
aatgtggtaa aatccgataa ggatcgatgg gacagcccc ccccaaagcc cccagggatg   8820
taattacgtc cctcccccgc tagggcagca gcgagccgcc cggggctccg gtccggtccg   8880
gcgctccccc gcatccccga gccggcagcg tgcgggggaca gcccgggcac ggggaaggtg   8940
gcacgggatc gctttcctct gaacgcttct cgctgctctt tgagcctgca gacacctggg   9000
gggatacggg gaaaatctag tgggacagcc cccccccaaa gcccccaggg atgtaattac   9060
gtccctcccc cgctagggca gcagcgagcc gcccgggggct ccggtccggt ccggcgctcg   9120
cccgcatccc cgagccggca gcgtgcgggg acagcccggg cacggggaag gtggcacggg   9180
atcgctttct tctgaacgct tctcgctgct ctttgagcct gcagacacct ggggggatac   9240
ggggaaaaat cgatgggaca gcccccccc aaagccccca gggatgtaat tacgtccctc   9300
ccccgctagg gcagcagcga gccgcccggg gctccgggt ccggtccggt ccggcgcgcat   9360
ccccgagccg gcagcgtgcg gggacagccc gggcacgggg aaggtggcac gggatcgctt   9420
tcctctgaac gcttctcgct gctctttgag cctgcagaca cctggggggga tacggggaaa   9480
atctagtggg acagccccc cccaaagccc ccagggatgt aattacgtcc ctcccccgct   9540
agggcagcag cgagccgccc ggggctccgg tccggtccgg cgctccccg catccccgag   9600
ccggcagcgt gcggggacag cccgggcacg gggaaggtgg cacgggatcg cttcctctg   9660
aacgcttctc gctgctcttt gagcctgcag acacctgggg ggatacgggg aaaaatcgat   9720
agcgataagg atccactagt tattaatagt aatcaattac ggggtcatta gttcatagcc   9780
catatatgga gttccgcgtt acataactta cggtaaatgg cccgcctggc tgaccgccca   9840
acgaccccc cccattgacg tcaataatga cgtatgttcc catagtaacg ccaatagggga   9900
ctttccattg acgtcaatgg gtggagtatt tacggtaaac tgcccacttg gcagtacatc   9960
```

-continued

```
aagtgtatca tatgccaagt acgcccccta ttgacgtcaa tgacggtaaa tggcccgcct   10020
ggcattatgc ccagtacatg accttatggg actttcctac ttggcagtac atctacgtat   10080
tagtcatcgc tattaccatg ggtcgaggtg agccccacgt tctgcttcac tctccccatc   10140
tccccccct ccccacccc aattttgtat ttatttattt tttaattatt ttgtgcagcg    10200
atggggcgg ggggggggg ggcgcgcgcc aggcggggcg aggggcgggg               10260
cggggcgagg cggagaggtg cggcggcagc caatcagagc ggcgcgctcc gaaagtttcc   10320
ttttatggcg aggcggcggc ggcggcggcc ctataaaaag cgaagcgcgc ggcgggcggg   10380
agtcgctgcg ttgccttcgc cccgtgcccc gctccgcgcc gcctcgcgcc gcccgccccg   10440
gctctgactg accgcgttac tcccacaggt gagcgggcgg gacggccctt ctcctccggg   10500
ctgtaattag cgcttggttt aatgacggct cgtttctttt ctgtggctgc gtgaaagcct   10560
taaagggctc cggagggcc ctttgtgcgg ggggagcgg ctcggggggt gcgtgcgtgt     10620
gtgtgtgcgt ggggagcgcc gcgtgcgcc cgcgctgccc ggcggctgtg agcgctgcgg    10680
gcgcggcgcg gggctttgtg cgctccgcgt gtgcgcgagg ggagcgcggc cggggcggt    10740
gcccgcggt gcgggggggc tgcgagggga acaaaggctg cgtgcgggt gtgtgcgtgg     10800
gggggtgagc aggggtgtg ggcgcggcgg tcgggctgta accccccct gcacccccct     10860
ccccgagttg ctgagcacgg cccggcttcg ggtgcgggc tccgtgcggg gcgtggcgcg    10920
gggctcgccg tgccgggcgg ggggtggcgg caggtggggg tgccgggcgg ggcggggccg   10980
cctcggggcg gggagggctc gggggagggg cgcggcggcg ccggagcgcc ggcggctgtc   11040
gaggcgcggc gagccgcagc cattgccttt tatggtaatc gtgcgagagg gcgcagggac   11100
ttcctttgtc ccaaatctgg cggagccgaa atctgggagg cgccgccgca ccccctctag   11160
cgggcgcggg cgaagcggtg cggcgccggc aggaaggaaa tgggcgggga gggccttcgt   11220
gcgtcgccgc gccgccgtcc ccttctccat ctccagcctc gggcgctgccg caggggacg    11280
gctgccttcg gggggggacgg ggcagggcgg ggttcggctt ctggcgtgtg accggcggct  11340
ctagagcctc tgctaaccat gttcatgcct tcttcttttt cctacagctc ctgggcaacg   11400
tgctggttgt tgtgctgtct catcattttg gcaaagaatt ccgctgcgac tcggcggagt   11460
cccggcggcg cgtccttgtt ctaacccggc gcgccctcag gatgggaatc caaggagggt   11520
ctgtcctgtt cgggctgctg ctcgtcctgg ctgtcttctg ccattcaggt catagcctgc   11580
agtgctacaa ctgtcctaac ccaactgctg actgcaaaac agccgtcaat tgttcatctg   11640
attttgatgc gtgtctcatt accaaagctg ggttacaagt gtataacaag tgttggaagt   11700
ttgagcattg caatttcaac gacgtcacaa cccgcttgag ggaaaatgag ctaacgtact   11760
actgctgcaa gaaggacctg tgtaacttta acgaacagct tgaaaatggt gggacatcct   11820
tatcagagaa aacagttctt ctgctggtga ctccatttct ggcagcagcc tggagccttc   11880
atcccggatc cggagagggc agaggaagtc ttctaacatg cggtgacgtg gaggagaatc   11940
ccggccctat ggagcgtccg caacccgaca gcatgcccca ggatttgtca gaggccctga   12000
aggaggccac caaggaggtg cacacccagg cagagaatgc tgagttcatg aggaactttc   12060
agaagggcca ggtgacccga gacggcttca agctggtgat ggcctccctg taccacatct   12120
atgtggccct ggaggaggag attgagcgca acaaggagag cccagtcttc gcccctgtct   12180
acttcccaga agagctgcac cgcaaggctg ccctggagca ggacctggcc ttctggtacg   12240
ggccccgctg gcaggaggtc atccctaca caccagccat gcagcgctat gtgaagcggc   12300
tccacgaggt ggggcgcaca gagcccgagc tgctggtggc ccacgcctac accgctacc    12360
tgggtgacct gtctgggggc caggtgctca aaaagattgc ccagaaagcc ctggacctgc   12420
ccagctctgg cgagggcctg gccttcttca cctttccca cattgccagt gccaccaagt   12480
tcaagcagct ctaccgctcc cgcatgaact ccctggagat gactcccgca gtcaggcaga   12540
gggtgatga agaggccaag actgcgttcc tgctcaacat ccagctcttt gaggagttgc    12600
aggagctgct gacccatgac accaaggacc agagcccctc acgggcacca gggcttcgcc   12660
agcgggccag caacaaagtg caagattctg cccccgtgga gactcccaga gggaagcccc   12720
cactcaacac ccgctcccag gctccgcttc tccgatgggt ccttacactc agctttctgg   12780
tggcgacagt tgctgtaggg ctttatgcca tgtgagcggc gcgccggcac cggtaccaag   12840
cttaagagcg ctagctggcc agacatgata agatacattg atgagtttgg acaaaccaca   12900
actagaatgc agtgaaaaaa atgctttatt tgtgaaattt gtgatgctat tgctttattt   12960
gtaaccatta taagctgcaa taaacaagtt aacaacaaca attgcattca ttttatgttt   13020
caggttcagg gggaggtgtg ggaggttttt taaagcaagt aaaacctcta caaatgtggt   13080
atggaattgg agccccactg tgttcatctt acagatggaa atactgacat tcagaggagt   13140
tagttaactt gcctaggtga ttcagctaat aagtgcaaga aagatttcaa tccaaggtga   13200
tttgattctg aagcctgtgc taatcacatt acaccaagct acaacttcat ttataaataa   13260
taagtcagct ttcaagggcc tttcaggtgt cctgcacttc tacaagctgt gccatttagt   13320
gaacacaaaa tgagccttct gatgaagtag tcttttcatt atttcagata ttagaacact   13380
aaaattctta gctgccagct gattgaaggc tgggacaaaa ttcaaacatg catctacaac   13440
aatatatatc tcaatgttag tctccaaatt cttattgactt caactcaaga gaatataaag   13500
agctagtctt tatacactct ttaaggtatg atgggtcccg attttcccc gtatccccc     13560
aggtgtctgc aggctcaaag agcagcgaga agcgttcaga ggaaagcgat cccgtgccac   13620
cttcccgtg cccgggctgt ccccgcacgc tgccggctcg gggatgcggg ggagcgccgg    13680
accggaccgg agcccgggc ggctcgctgc tgccctagcg ggggagggac gtaattacat    13740
ccctgggggc tttggggggg ggctgtccca ctagattttc cccgtatccc ccaggtgtc    13800
tgcaggctca aagagcagcg agaagcgttc agaggaaagc gatcccgtgc caccttcccc   13860
gtgcccgggc tgtccccgca cgctgccggc tcggggatgc gggggagcgc cggaccggac   13920
cggagccccg ggcggctcgc tgctgcccta gcggggggagg gacgtaatta catccctggg   13980
ggctttgggg ggggggctgtc ccatcggatc ttctagtcct gcaggagtca atgggaaaaa   14040
cccattggag ccaagtacac tgactcaata gggactttcc attggtgttt gcccagtaca   14100
taaggtcaat aggggtgag tcaacaggaa agtcccattg gagccaagta cattgagtca    14160
ataggggactt tccaatgggt tttgcccagt acataaggtc aatgggaggt aagccaatgg   14220
gttttttccca ttactgacat gtatacgcgt cgacgtcggc gcgttcagcc taaagctttt   14280
ttccccgtat cccccaggt gtctgcaggc tcaaagagca gcgagaagcg ttcagaggaa    14340
agcgatcccg tgccaccttc cccgtgcccg ggctgtccca cgacgctgcg gctcgggga    14400
tgcgggggag cgccgaccg gaccggagcc ccggcggcgg cgctgctgcc ctagcggggg    14460
agggacgtaa ttacatccct ggggggcttt gggggggggc gtccctgcgg ccgcgaattc   14520
gtaatcatgg tcatagctgt ttcctgtgtg aaattgttat ccgctcacaa ttccacacaa   14580
catacgagcc ggaagcataa agtgtaaagc ctggggtgcc taatgagtga gctaactcac   14640
attaattgcg ttgcgctcac tgcccgcttt ccagtcggga aacctgtcgt gccagggggtc  14700
```

-continued

```
tagccgcggt ctaggaagct ttctagggta cctctaggga tccactagtt attaatagta   14760
atcaattacg gggtcattag ttcatagccc atatatggag ttccgcgtta cataacttac   14820
ggtaaatggc ccgcctggct gaccgcccaa cgacccccgc ccattgacgt caataatgac   14880
gtatgttccc atagtaacgc caatagggac tttccattga cgtcaatggg tggagtattt   14940
acggtaaact gcccacttgg cagtacatca agtgtatcat atgccaagta cgccccctat   15000
tgacgtcaat gacggtaaat ggcccgcctg gcattatgcc cagtacatga ccttatggga   15060
ctttcctact tggcagtaca tctacgtatt agtcatcgct attaccatgg tcgaggtga   15120
gccccacgtt ctgcttcact ctccccatct cccccccctc cccacccca attttgtatt   15180
tatttatttt ttaattatt tgtgcagcga tggggggcggg ggggggggggg gcgcgcgcca   15240
ggcggggcgg ggcggggcga ggggcgggggc ggggcgaggc ggagaggtgc ggcggcagcc   15300
aatcagagcg gcgcgctccg aaagtttcct tttatggcga ggcggcggcg gcggcggccc   15360
tataaaaagc gaagcgcgcg gcgggcggga gtcgctgcgt tgccttcgcc ccgtgccccg   15420
ctccgcgccg cctcgcgccg cccgcccggg ctctgactga ccgcgttact cccacaggtg   15480
agcgggcggg acggcccttc tcctccgggc tgtaattagc gcttggttta atgacggctc   15540
gtttcttttc tgtggctgcg tgaaagcctt aaagggctcc gggagggccc tttgtgcggg   15600
ggggagcggc tcgggggggtg cgtgcgtgtg tgtgtgcgtg gggagcgccg cgtgcggccc   15660
gcgctgcccg gcggctgtga gcgctgcggg cgcggcgcgg ggctttgtgc gctccgcgtg   15720
tgcgcgaggg gagcgcggcc ggggcgggtg ccccgcggtg cgggggggct gcgaggggaa   15780
caaaggctgc gtgcggggtg tgtgcgtggg ggggtgagca ggggggtgtgg gcgcggcggt   15840
cgggctgtaa cccccccctg cacccccctc cccgagttgc tgagcacggc ccggcttcgg   15900
gtgcgggggct ccgtgcgggg cgtggcgcgg ggctcgccgt gccgggcggg gggtggcggc   15960
aggtggggggt gccgggcggg gcggggccgc ctcgggccgg ggggaggggct cg ggggaggggc   16020
gcggcggccc cggagcgccg gcggctgtcg aggcgcggcg agccgcagcc attgcctttt   16080
atggtaatcg tgcgagaggg cgcagggact tcctttgtcc caaatctggc ggagccgaaa   16140
tctgggaggc gccgccgcac ccctctagc gggcgcgggc gaagcggtgc ggcgccggca   16200
ggaaggaaat gggcggggag ggccttcgtg cgtcgccgcg ccgccgtccc cttctccatc   16260
tccagcctcg gggctgccgc aggggggacgg ctgccttcgg gggggacggg gcagggcggg   16320
gttcggcttc tggcgtgtga ccggcggctc tagagcctct gctaaccatg ttcatgcctt   16380
cttcttttc ctacagctcc tgggcaacgt gctggttgtt gtgctgtctc atcattttgg   16440
caaagaattc cgctcgcgact cggcggagtc ccggcggcgc gtccttgttc taacccggcg   16500
cgccctcagg atggagcctc ccggccgccg cgagtgtccc tttccttcct ggcgctttcc   16560
tgggttgctt ctggcggcca tggtgttgct gctgtactcc ttctccgatg cctgtgagga   16620
gccaccaaca tttgaagcta tggagctcat tggtaaacca aaaccctact atgagattgg   16680
tgaacgagta gattataagt gtaaaaaagg atacttctat ataccctcctc ttgccacca   16740
tactatttgt gatcggaatc atacatggct acctgtctca gatgacgcct gttatagaga   16800
aacatgtcca tatatacggg atcctttaaa tggccaagca gtccctgcaa atgggactta   16860
cgagtttggt tatcagatgc actttatttg taatgagggt tattacttaa ttggtgaaga   16920
aattctatat tgtgaactta aaggatcagt agcaatttgg agcggtaagc ccccaatatg   16980
tgaaaaggtt ttgtgtacac cacctccaaa aataaaaaat ggaaaacaca cctttagtga   17040
agtagaagta tttgagtatc ttgatgcagt aacttatagt tgtgatcctg cacctggacc   17100
agatccattt tcacttattg gagagagcac gatttattgt ggtgacaatt cagtgtggag   17160
tcgtgctgct ccagagtgta aagtggtcaa atgtcgattt ccagtagtcg aaaatggaaa   17220
acagatatca ggatttggaa aaaaatttta ctacaaagca cagttatgt ttgaatgcaa   17280
taagggtttt tacctcgatg gcagcgacac aattgtctgt gacagtaaca gtacttggga   17340
tccccccagtt ccaaagtgtc ttaaagtgct gcctccatct agtacaaaac ctccagcttt   17400
gagtcattca gtgtcgactt cttccactac aaaatctcca gcgtccagtg cctcaggtcc   17460
taggctact tacaagcctc cagtctcaaa ttatccagca tatccagaag ctgaggaagg   17520
aatacttgac agtttggatg tttgggtcat tgctgtgatt gttattgcca tagttgttgg   17580
agttgcagta atttgtgttg tcccgtacag atatcttcaa aggaggaaga agaaaggcac   17640
atacctaact gatgagaccc acagagaagt aaaaatttact tctctcggat ccggagccac   17700
gaacttctct ctgttaaagc aagcaggaga cgtggaagaa aaccccggtc ctatgtgtcc   17760
cctggtagcg gcgctgttgc tgggctcggc gtgctgcgga tcagctcagc tactatttaa   17820
taaaacaaaa tctgtagaat tcacgttttg taatgacact gtcgtcattc catgctttgt   17880
tactaatatg gaggcacaaa acactactga agtatacgta aagtggaaat ttaaaggaag   17940
agatatttac accttttgatg gagctctaaa caagtccact gtccccactg actttagtag   18000
tgcaaaaatt gaagtctcac aattactaaa aggagatgcc tctttgaaga tggataagaa   18060
tgatgctgtc tcacacacag gaaactcac ttgtgaagta acagaattaa ccagagaagg   18120
tgaaacgatc atcgagctaa aatatcgtgt tgtttcatgg ttttctccaa atgaaaatat   18180
tcttattgtt attttcccaa tttttgctat actcctgttc tggggacagt ttggtattaa   18240
aacacttaaa tatagatccg gtggtatgga tgagaaaaca attgctttac ttgttgctga   18300
actagtgatc actgtcattg tcattgttgg agccattctt ttcgtccag gtgaatattc   18360
attaaagaat gctactggcc ttggttaat tgtgacttct acaggatat taatattact   18420
tcactactat gtgtttagta cagcgattgg attaacctcc ttcgtcattg ccatattggt   18480
tattcaggtg atagcctata tcctcgctgt ggttggactg agtctctgta ttgctcgtat   18540
tataccaatg catggccctc ttctgatttc aggtttgagt atcttagctc tagcacaatt   18600
acttggacta gtttatatga aatttgtggc ttccaatcag aagactatac aacctcctag   18660
gaaagctgta gaggaacccc ttaatgcatt caaagaatca aaaggaatga tgaatgatga   18720
ataactgaag tgggcgcgcc ggcaccggta ccaagcttaa gagcgctagc tggccagaca   18780
tgataagata cattgatgag tttggacaaa ccacaactag aatgcagtga aaaaaatgct   18840
ttatttgtga aatttgtgat gctattgctt tatttgtaac cattataagc tgcaataaac   18900
aagttaacaa caacaattgc attcatttta tgtttcaggt tcaggggggag gtgtgggagg   18960
ttttttaaag caagtaaaac ctctacaaat gtggtatgga attggagccc cactgtgttc   19020
atcttacaga tggaaatact gacattcaga ggagttagt aacttgccta ggtgattcag   19080
ctaataagtg caagaaagat ttcaatccaa ggtgattttga ttctgaagcc tgtgctaatc   19140
acattacacc aagctacaac ttcatttata aataataagt cagctttcaa gggcctttca   19200
ggtgtcctgc acttctacaa gctgtgccat ttagtgaaca caaaatgagc cttctgatga   19260
agtagtcttt tcattatttc agatattaga acactaaaat tcttagctgc cagctgattg   19320
aaggctggga caaaattcaa acatgcatct acaacaatat atatctcaat gttagtctcc   19380
aaattctatt gacttcaact caagagaata taaagagcta gtctttatac actctttaag   19440
```

-continued

```
gtatgatatc atctggaaag taacaaaatt gatgcaaatt tgaatgaact ttatcatggt   19500
gtatttacac aatgtgtttc ttctccctgc aatgtatttc tttctctaat tccttccatt   19560
tgatctttca tacacaatct ggttctgatg tatgtttttt ggatgcactt ttcaactcca   19620
aaagacagag ctagttactt tcttcctggt gctccaagca ctgtatttgt atctgtattc   19680
aagccctttg caatattgta ctggatcatt atttcacctc taggatggct tccccaggca   19740
acttgtgttc acccagagac tacattttgt atcttgttga cctttgaact tccaccagtg   19800
tctaaaaata atatgtatgc aaaattactt gctatgagaa tgtataatta aacaatataa   19860
aaaggagaag caaggagaga aacacaggtg tgtatttgtg tttgtgtgct taaaaggcag   19920
tgtggaaaag gaagaaatgc catttatagt gaggagacaa agttatatta cctcttatct   19980
ggcttttaag gagattttgc tgagctaaaa atcctatatt catagaaaag ccttacctga   20040
gttgccaata cctcaattct aaaatacagc atagcaaaac tttaacctcc aaatcaagcc   20100
tctacttgaa tcctttttctg agggatgaat aaggcatagg catcagggga tgttgccaat   20160
gtgcattagc tgtttgcagc ctcaccttct ttcatggagt ttaagatata gtgtattttc   20220
ccaaggtttg aactagctct tcatttcttt atgttttaaa tgcactgacc tcccacattc   20280
ccttttttagt aaaatattca gaaataattt atcatctgga aagtaacaaa attgatgcaa   20340
atttgaatga acttatcat ggtgtatta cacaatgtgt ttcttctccc tgcaatgtat   20400
ttctttctct aattccttcc atttgatctt tcatacacaa tctggttctg atgtatgttt   20460
tttggatgca cttttcaact ccaaaagaca gagctagtta cttttcttcct ggtgctccaa   20520
gcactgtatt tgtatctgta ttcaagccct ttgcaatatt gtactggatc attatttcac   20580
ctctaggatg gcttccccag gcaacttgtt caccagga gactacattt tgtatcttgt   20640
tgacctttga acttccacca gtgtctaaaa ataaatatgta tgcaaaatta cttgctatga   20700
gaatgtataa ttaaacaata taaaaaggag aagcaaggag agaaacacag gtgtgtattt   20760
gtgtttgtgt gcttaaaagg cagtgtggaa aaggaagaaa tgccatttat agtgaggaga   20820
caaagttata ttacctctta tctggctttt aaggagattt tgctgagcta aaaatcctat   20880
attcatagaa aagccttacc tgagttgcca atacctcaat tctaaaatac agcatagcaa   20940
aactttaacc tccaaatcaa gcctctactt gaatccttttt ctgagggatg aataaggcat   21000
aggcatcagg ggctgttgcc aatgtgcatt agctgtttgc agcctcacct tctttcatgg   21060
agtttaagat atagtgtatt ttcccaaggt ttgaactagc tcttcatttc tttatgtttt   21120
aaatgcactg acctcccaca ttcccttttt agtaaaatat tcagaaataa tttatcccgg   21180
cttgtcgacg acggatcatc tggaaagtaa caaaattgat gcaaatttga atgaacttta   21240
tcatggtgta tttacacaat gtgtttcttc tccctgcaat gtatttcttt ctctaattcc   21300
ttccatttga tctttcatac acaatctggt tctgatgtat gttttttgga tgcactttttc   21360
aactccaaaa gacagagcta gttacttttct tcctggtgct ccaagcactg tatttgtatc   21420
tgtattcaag cccttttgcaa tattgtactg gatcattatt tcacctctag gatggcttcc   21480
ccaggcaact tgtgttcacc cagagactac attttgtatc ttgttgacct ttgaacttcc   21540
accagtgtct aaaaataata tgtatgcaaa attacttgct atgagaatgt ataattaaac   21600
aatataaaaa ggagaagcaa ggagagaaac acaggtgtgt atttgtgttt gtgtgcttaa   21660
aaggcagtgt ggaaaaggaa gaaatgccat ttatagtgag gagacaaagt tatattacct   21720
cttatctggc ttttaaggag attttgctga gctaaaaatc ctatattcat agaaaagcct   21780
tacctgagtt gccaatacct caattctaaa atacagcata gcaaaacttt aacctccaaa   21840
tcaagcctct acttgaatcc ttttctgagg gatgaataag gcataggcat caggggctgt   21900
tgccaatgtg cattagctgt ttgcagcctc accttcttttc atggagttta agatatagtg   21960
tattttccca aggtttgaac tagctcttca tttctttatt ttttaaatgc actgacctcc   22020
cacattccct ttttagtaaa atattcagaa ataattttatc ccggcttgtc gacgacggcg   22080
gtctccgtcg tcaggatcat ccggccggcc atcaggacat agcgttggct acccgtgata   22140
ttgctgaaga gcttggcggc gaatgggctg accgcttcct cgtgctttac ggtatcgccg   22200
ctcccgattc gcagcgcatc gccttctatc gccttcttga cgagttcttc tgaggggatc   22260
aattctctag agctcgctga tcagcctcga ctgtgccttc tagttgccag ccatctgttg   22320
tttgcccctc ccccgtgcct tccttgaccc tggaaggtgc cactcccact gtcctttcct   22380
aataaaatga ggaaattgca tcgcattgtc tgagtaggtg tcattctatt ctggggggtg   22440
gggtggggca ggacagcaag gggggaggatt gggaagacaa tagcaggcat gctggggatg   22500
cggtgggctc tatggcttct gaggcggaaa gaaccagctg ggggcgcgca cctcgaccat   22560
ctccaggatg cctttgatag agctgggtcc tctgcgttcc tttaaagtgt ttgagatcaa   22620
gtccgagaag aggtggcaag acatatttaa atcgcgctag tttaaaatac atcattgcaa   22680
tgaaaataaa tgtttttttat taggcagaat ccagatgctc aaggcccttc ataatatccc   22740
ccagtttagt agttggactt agggaacaaa ggaacctttta atagaaattg gacagcaaga   22800
aagctctagc tttagaagaa ctcatcaaga agtctgtaga aggcaattct ctgggagtca   22860
ggggctgcaa tgccatagag cactaggaac ctgtctgccc actctccccc tagctcttct   22920
gctatgtccc tggttgctag ggcaatgtcc tggtacctgt cagccactcc cagcctgcca   22980
cagtctatga agccagagaa ccttccattt tcaaccatga tgttgggaag gcaggcatcc   23040
ccatgagtca ccactaggtc ctcaccatct ggcatggatg ccttgagcct ggcaaatagt   23100
tcagcagggg ccaggccctg gtgttcttca tccaagtcat cttggtccac caggccagcc   23160
tccatcctgg ttctggccct ctctatcctg tgcttggcct ggtggtcaaa ggggcaggtg   23220
gctgggtcaa gggtgtggag tcttctcatg gcatcagcca tgattgacac tttctcagct   23280
ggagctaggt gagaggaaag gaggtcctgc ccaggcacct cacctagtag gagccagtcc   23340
cttccagctt ctgtgaccac atcaaggaca gctgcacagg ggaccccagt tgttgccaac   23400
caggagagtc tggcagcctc atcctggagc tcattgagag ccccactgag gtctgtcttc   23460
acaaaaagga ctggcctgcc ttgggctgaa agtctgaaaa ctgctgcatc agagcaacca   23520
atggtctgct gtgcccagtc atagccaaac agtctctcaa cccagcagc tggagaacct   23580
gcatgtaggc catcttgttc aatcatgatg gctcctcctg tcaggagagg aaagagaaga   23640
aggttagtac aattgctata gtgagttgta ttatactatg cttatgatta attgtcaaac   23700
tagggctgca gggttcatag tgccactttt cctgcactgc cccatctcct gcccacccctt   23760
tcccaggcat agacagtcag tgacttacca aactcacagg agggagaagg cagaagcttt   23820
ttgcaaaagc ctaggctcat gagacaataa ccctgataaa tgcttcaata atattgaaaa   23880
aggaagagta ccaggtatga gtattcaaca tttccgtgtc gccctttattc ccttttttgc   23940
ggcattttgc cttcctgttt ttgctcaccc agaaacgctg gtgaaagtaa aagatgctga   24000
agatcagttg ggtgcacgag tgggttacat cgaactggat ctcaacagcg gtaagatcct   24060
tgagagtttt cgccccgaag aacgttttcc aatgatgagc acttttaaag ttctgctatg   24120
tggcgcggta ttatcccgta ttgacgccgg gcaagagcaa ctcggtcgcc gcatacacta   24180
```

```
ttctcagaat gacttggttg agtactcacc agtcacagaa aagcatctta cggatggcat   24240
gacagtaaga gaattatgca gtgctgccat aaccatgagt gataacactg cggccaactt   24300
acttctgaca acgat                                                     24315

SEQ ID NO: 8              moltype = DNA   length = 28565
FEATURE                   Location/Qualifiers
source                    1..28565
                          mol_type = other DNA
                          organism = synthetic construct
SEQUENCE: 8
atgtctccta tgtctcatct aaatggatga ggtttgagag ttcccatcac ggcatggtgg   60
aaacgaatcc gactaggagc cataagttca cggcttcgat ccctggcctc gctcaggggg   120
ttaaggatcc ggtgttgctg tgagctgtgg tgtaggtcac agatgcggtt cggatctggc   180
gttgctgcgg ctgtggtgta ggctggtggc tgtagctccg atttgacccc tagcctaggg   240
acctccatat gccgtgggta tggccctaaa aagccaaata aaataaaata agtaaatggt   300
tgaggtttga cacagaaagt ttatttattt atgtatttac ttatcttttt ttttttttt   360
tttttgtct ttctgctatt tcttgggctg ctcccgcggc atatggaggt tcccaggcta   420
ggggtcgaat tggagctaca gccaccagcc tacaccacg ccgcagcaat gccagatccg   480
agccgcctct gtgacctaca ccacagctca tggcaacgct ggatcgttaa cccactgagc   540
aagggctggg accgaacccg caacctcatg gttcctagtc ggattcgtta accactgcgc   600
catgacggga actcctactt atctatttt taaagcatat ggaagttccc aggctagggg   660
gttgaatcgg agctgcaact gccggcttac accacagcca gagcaacgcc ggatctgagc   720
agtgtctggg acctacacca cagctcacg ccacaccgga tcctcaatcc actgaatgag   780
gccaggaatc aaacctgtgt cctcatggat actagtcaga ttcatttccg ctgagcaatg   840
acaggaactc ctgacacaga aattttagat taaaattgaa gatgagcccc ttccttttgt   900
acgacctttg tgtgcagatt ttcgaggata agtccttgag cttgaagttt tagggtcatg   960
gatcctcata acagtttcct ggcctgtgag gcttggatct cagtataaac agaagtgctg   1020
gcagcagtag acacagcagc agctgttttc aggaacaaat actgggcacc tgccttgtgg   1080
acctgcctga ctccaccact ctcttgggta tccacaaagt ggaccagag gttcagagca   1140
gccctgggat ccaaattttt ttaatttatt tttttatctt tattttttgt cttttcgaaa   1200
tttttagggc tacacccatg agatatggag gttcccaggc taagggtcca atcggagcta   1260
caactgccgg cctacaccac agctcatggc aatgctggat ccttaacccg ctgagcgagg   1320
ccagggatca aacccacaac ctcatgattc ctagttggat tcgttaacca ctgagccacg   1380
atgggaactc cctgggatgc aaattttgtc atctagccct aggatgtagc tatcatcctg   1440
atttgagaag agaggcagag tctcaggtgg cttctctctc atgaatgcag agctaagggt   1500
ggccacacgt acttgagttc atccgatgca cacagcattg tgctaaaata ttgaccattt   1560
ggcccttttg ctgacttttg gtttgaggga tatgaccttc atgagcatac agaggataat   1620
atgtatgcat gtatgcatgt gtgtacacat gtgcgcatgc atgtatatac ctgcataatt   1680
atgtatttgt ttatgtatgc aggtgcatgt gtatgtatat atttattatt tatttattg   1740
ggggccacac ccatgacatt tggaagttcc tgggacagag attgaatccc agccacagct   1800
ttgacctacg ccatggacac agcaacactg gattcttaac cccctgtgcc acagcgggaa   1860
ctcctagaag atagtatttc atgatgatat ttgactaaaa ataggggtca ggctttgaag   1920
tttaaataaa ttcgaccaga taaatgccca tccaggaagt tatactttgc cttgttcaaa   1980
tttggaccac ggggaaggtg gttggcgaca tgtaacagaa atctgactcc agtgcaggtt   2040
tcgctcccgt gacgggaagc ccagaggtgg gcagccctaa ggctggggct ctgatttcat   2100
gatgctctta gcatcttgag tcccttccct cttcttgctt ttatctcagc ctcgggctgc   2160
tgcaccttct gtctttgtgg tgagtctacc tattccactt agctcggctt cagggtgtat   2220
ttccacgact tcgttagagt aaggttgggg ccagctgtgc tctgccggca ggaggtgtgc   2280
ttgcagggc catggatgtg gccaggacct aatgtgacgg tggggagcag gatgggatg   2340
aggatgtgac cacagagcct tgggaaccac gtcatccacg tcatacactg agagcaggtg   2400
gttctcatgc aggtgcatca gaatcccgag gacggcttgt ccaaacccag atggctgggc   2460
ccaagccctg agctcccgat ttgggaggcc ttggctgggc cccgaaatct gccttcctga   2520
ctagaccgag tgatgaatgg tgttcataga caagacatac actaacactg gtcttcgggg   2580
ctccttgcca caccctgaag gggtccgtga aactgacggg gccagagaag gtgctggttc   2640
ctccatggaa ggtctcagtg aggccattct gctgcccggc tgggtcacgc tggggagttg   2700
agggtgcatc ccctcctggg atctggtcaa aggcagattc tgattctgga agcacggggt   2760
agggccagag atgccacctt ctaacaagcc cccaggtgaa gatgttgacc tgggacctta   2820
tggtgggggg tggcggagct caaggtggca gacacctccc tctctctcaa cctgtgtcac   2880
agcagggcca tcctactggc tctcgctcgg ccagagatgg cgatgccaga acacactggg   2940
gcagggtgtc cacatttttg tcacttccac tgagccctgg ggactgactc atttaaatga   3000
cattctcaac tctttggaaa gaagctgggc cagaaatgga aatggcagca aacactttt   3060
gggaaacagg aagccaattt tttttttcaa tcatgatttt ccccagattc agagactgct   3120
taactcccaa tgaaatactt ttagattacg agctaaaata ccgaaaagct gtcaagctca   3180
agaccacagg aaaacagccg aagaacaaac accatgagaa aacagtcaca gagtgcctct   3240
gcggcggatt tcaagttcca gacttccttg ctgtcagctg tgtgtacttg tcccgcctgc   3300
agtaggacca gctggggttt aagtctgtac catggacact gctgccagga ttctcctctg   3360
catctgctga cttccagctc ttcagggcca gctggccata ggagcataaa ctgacatcca   3420
gttccaggag gcagcatctg tccccatggc ctgcaggaca ccagatcagt agaggccccc   3480
agggccacct ttcctgtggg ggcccttgaa gggaccccgg aaggctggat cttgctaaag   3540
cttccacaag tcccttccaa aggagagtaa attctaaaca gaagcttttg ccagtgcttc   3600
tctgggatct ggcttcagga ttattcctag tctgaaaagt cttcctggtg gtttggacac   3660
gggcaaatgc ttggtggtg ggctggctct ggatgcaggt gagtggggtc ggaagttctc   3720
cctccttccc acaaagcttg acggagccag gggcaccccgc gggcctgtgg atgggagagg   3780
ggtttctggt gacggactca agtcttggca gcccctgacc ccagagcagg ctccctcccc   3840
acagctgctc tccgtgagtc cttcacttgc ccaagttcaa gatgtaccca gttctggagc   3900
tgccaaacca tcctgcatcc tgacgtcagc caccccaagtt ctggggtagc tggtctgcca   3960
cccaggtgga tgaaaagagg ccacatacct gcaccagcat ctgcgaatct ctgaagaaca   4020
tcaataataa aaagacaact aacccgatta aaacacaggt agagaatctg aacagacatt   4080
catcggaaga agaattacga ctggccaaaa agctcataaa aagatggtca aagtcattgg   4140
```

-continued

```
tcagggaaat gtaaatcaaa ccgcattgag ataccatctc actccctctc ggatggctgg   4200
aatgaaaaaa aacctcttct ttcctccctt tcattgtctt ggcacccttg tggaaattaa   4260
ttgactaaaa ttcatgaaat acaaaaattt ttaggagttc ccgtcgtggc tcagtggtta   4320
acaaatctga ctaggaacca tgaggtttca ggttcgattc ctggcctcac tcagtgggtt   4380
agggatctgg tgttgccatg agctgtggtg taggtcgcag agcagctcg gatcccgcat    4440
tgctgtggct ctggcgtagg ccggcggcta cagctctgat tcaacctcta gcctgggaat   4500
agcccaagaa atggcaaaaa gaccaaaaaa aaaaaaaaaa aaaaaactcg ttttgagcat   4560
ttttgcatgt gtacattgtc catttgtgtg ccttccaaga tttattttg gagtctcaac   4620
tctgtcattg atttatgtct ctccttaggc cagaaccaca ctgttttggt gaccatggct   4680
ttgtagtaaa atttgaaatc tgaaagtgtg agccctcctg ttttgtttct cttctccatg   4740
attagtttgg ttattcagag tcccttgaat ttccaggtga attttaggat tagcaggaaa   4800
atttctgcag agatggcagc agagattttt aatagggatt atgttgaatc tggaggttaa   4860
ttttcagtttt gctaccttga ctgtattaag tcttccagtc tataagcata agatgtcttt   4920
ttatttactt aggtcttta aaatttcttt gggcactccc attgtggtgc atcggaaatg   4980
aatccgacta gtatccacaa gaacacaggt tcaatccctg gcattgctca gtgggttaag   5040
gatcctgcat tgccatgaag aactgtggtg gaggccagca gctgcagctc tgatttgacc   5100
cctagcctgg gaacttccat atgccttggg tatggcccta aaaagcaaac taagtaagta   5160
agtaaataaa taaatgaata aataaaattt ctttcaaaat tgtaattttg taatttttgt   5220
aattttcaga gtgtacattt tgcccttca atacattatt cctacatatt ttattctttt   5280
tgatactatt ataaatgaaa tttataatta attcattat atgaatttca ttttcaattt    5340
gcatattgct actacaatag aaatgcactt tttaattatt tttatggcca taccatatat   5400
atatgtgtgt gtgtgtgtat gtgtgtcatt ttactgtaca gcagaaattg acacaacatt   5460
gtaaatcaac tacacttaaa aaatgaagaa ataaccacct gtgattatgg ctactgtgtt   5520
ggacacttta ggcatccccc cacccgtcc ccgccccaca ccctgagtg ctagtgacgg      5580
atgttcccac ccaggggcc tggagccttt atcaccagcc atcgggaatc agaaccgtat     5640
ctcacagtcc ccatgcctgt agcacctgga attgtgcctt tggactcgtg ggtgttctgc   5700
ttctcagtgg gagaagctta ggttctaagt cagagcaggg acagcccca tgtgctcagg     5760
acccagtgtg aaggggtctg cctcagggga cctgggggtt acaagggtaa gagaaggtgt   5820
tcatgttgga actagaagtt cttttcacc gctctgaaga aaaaagctgc ctcccaccct     5880
tggtacagct cttctgctaa cagtgaatca ggcagaacgt gttcaagaag tgacccagcc   5940
tggtggggc cagacctgac ccttgatggt ccctcaaccc ctccgagggt cccgcccttc     6000
ctttactgct ttgttgtctg tcctgagagg tttggctaat gtcgaaccaa gggtgtggct   6060
ggtcctgtcc cctttcctgt ctcacgcacc cacctctgaa gtctctgtag ctggttccag   6120
ccgggatctg gagccactcc ccccgcccca ggcccagtgg tacagactct tgcagagtcg   6180
ggggcccctg actcagcccc accgccagcg ggatgtcagg ccagcacccg ccccactccc   6240
actgatctgg ggggggtgtc tttccttcct ccttccaaag gagcctcaga ccttcctgtg   6300
gggcacgggg gcagtgggat tcaggaggct ctgagtcagc aggccggcat tgaggagtat   6360
aaagggaccc cagttcctcc ccctttcact tgtggcttat cgccgcccca ccctgcccca   6420
aggtcactgc ggtcagtaca gtcctcagct gccagcaggt gcctgtcttt acttgtgagg   6480
ccgccacgct ctcctgtttc tccaggtctg ggctctgttg gaagtggggg cccgacccca   6540
gggtaagatg ggggatctgc gtgtcctgcc ctcagaggcc tcctcctccc cgcacccta    6600
acccttcag cccaacaagg ctggagatct cccacatctt tggcttcgtt aagagttcaa    6660
cagcgccgcc accggccatg tcgctgagca gaggatggca cagggtgtta aaaaaaaaaa   6720
aaggttgcca cactccgttc ggttttgggc ccaccctttc gcattcctgg agcctgagta   6780
agcggataag gctgtgaaag tgacagattc ctgccacctc cttccagcgc tcatgcacag   6840
ggaccgcccc tcttcggtgt cctttgctgc acaagtgcat ttgcacattc ctgtctcaat   6900
ctggtttctc cccttaaaa gatgggaatg tgacctgctt ggagcccctc gcctcgccag    6960
ggcaccccat ccgtcccttc aggggtggag atggactgtc cctctgcaag gctggatgaa   7020
ctcagaccaa acaggccaac ttgctcccca aatacgccca cccctaccgg gctgcagaaa   7080
ttcgcatgtc accactgctg aagggtgacc ttgcagccct gagagcatcc ccatgacttg   7140
cccaccagat gaagtctggt tgtggcaggt cgcgctcagg gactcccggg tcccacctgg   7200
gggtgggagg atcctccttt gctcgtggtc gccccagaca cgccctcctt tccaagcgcc   7260
agtctccaga gctccgtgcc ccggcggagg cggtctggct ctctctcctt gcccctctct   7320
ccttgcccct agcagcccctt ctcctaaacc ctctgagcag cgggcacctc ctcccgaggc   7380
cctggcctaa gtccccaccc ttcatctcaa gccttcctcc ttgactccct cttcccagag   7440
ttccttgaaa taggtggtaa gtacacaccg atgacggaaa acaaagacta agaggttaaa   7500
gagggctgag gattacggcc ccggtagggc tgcgcgcgag ggggtcgagt ggccgggcgg   7560
tcccgtcgcc gggcagacag aggtgcggtt ctcccgggcg cctgcgctgc cggccccgcc   7620
cggagccctc ccagccggcg cccagtttac tcatcccgga gaggtgatcc cgggcgcgag   7680
ggcggggcgca gggcgtccga agaacccagt aatccgacca tgcagcatca gcccttccca   7740
ccaggcactt cttcttttt cccgaacgtc cagggagggg ggccgcgcac ttataaactc    7800
gggccggacc cgccggcctg tcagaggctg cctcgctggg gctgcgcgcg gcggccggac   7860
acatctggtc cgagaccaac gcgagcgact gtcactggca gctccctgcg cctctcagcc   7920
ccggccgggc ccctgcgctt ggcgtgctga caccatgctt ggggtcctgg tccttggcgg   7980
gctggccctg gccggcctgg ggttcccgc acccgcagag ccgcagcgg gtggcagcca     8040
gtgcgtcgag cacgactgct tcgcgctcta cccgggcccc gcgaccttcc tcaatgccag   8100
tcagatctgc gacggactgc ggggccacct aatgacagtg cgctcctcgg tggctgccga   8160
tgtcatttcc ttgctactga acggcgacgg cggcgttggc cgcggcgcc tctggatcgg   8220
cctgcagctg ccacccggct gcggcgaccc caagcgcctg ggcccctgc gcggcttcca    8280
gtgggttacg ggagacaaca acaccagcta tagcaggtgg gcacggctcg acctcaatgg   8340
ggctcccctc tgcggccgt tgtgcgtcgc tgtctccgct gctgaggcca ctgtgcccag    8400
cgagccgatc tgggaggagc agcagtgcga agtgaaggcc gatggcttcc tctgcgagtt   8460
ccacttccca gccacctgca ggccactggc tgtgagcccc ggcgccgcgg ctgccgccgt   8520
ctcgatcacc tacggcacc cgttcgcggc ccgcgggagg gacttccagg cgctgcccgt    8580
gggcagctcc gccgcggtgg ctccctcgg cttacagcta atgtgcaccg cgccgcccgg   8640
agcggtccag gggcactggg ccagggaggc gccgggcgct tgggactgca gcgtggagaa   8700
cggcggctgc gagcacgcgt gcaatgcgat ccctgggggct ccccgctgcc agtgcccagc   8760
cggcgccgcc ctgcaggcag acgggcgctc ctgcaccgca tccgcgacgc agtcctgcaa   8820
cgacctctgc gagcacttct gcgttcccaa ccccgaccag ccgggctcct actcgtgcat   8880
```

-continued

```
gtgcgagacc ggctaccggc tggcggccga ccaacaccgg tgcgaggacg tggatgactg   8940
catactggag cccagtccgt gtccgcagcg ctgtgtcaac acacaggggtg gcttcgagtg   9000
ccactgctac cctaactacg acctggtgga cggcgagtgt gtggagcccg tggacccgtg   9060
cttcagagcc aactgcgagt accagtgcca gcccctgaac caaactagct acctctgcgt   9120
ctgcgccgag ggcttcgcgc ccattcccca cgagccgcac aggtgccaga tgttttgcaa   9180
ccagactgcc tgtccagccg actgcgaccc caacacccag gctagctgtg agtgccctga   9240
aggctacatc ctggacgacg gtttcatctg cacggacatc gacgagtgcg aaaacggcgg   9300
cttctgctcc ggggtgtgcc acaacctccc cggtaccttc gagtgcatct gcgggcccga   9360
ctcggccctt gcccgccaca ttggcaccga ctgtgactcc ggcaaggtgg acggtggcga   9420
cagcggctct ggcgagcccc cgcccagccc gacgcccggc tccaccttga ctcctccggc   9480
cgtgggggctc gtgcattcgg gcttgctcat aggcatctcc atcgcgagcc tgtgcctggt   9540
ggtggcgctt ttggcgctcc tctgccacct gcgcaagaag cagggcgccg ccagggccaa   9600
gatggagtac aagtgcgcgg ccccttccaa ggaggtagtg ctgcagcacg tgcggaccga   9660
gcggacgccg cagagactcg gatccggaga gggcagagga agtcttctaa catgcggtga   9720
cgtgggaggag aatcccggcc ctatgttgac aacattgctg ccgatactgc tgctgtctga   9780
ctgggccttt tgtagccaag acgcctcaga tggcctccaa agacttcata tgctccagat   9840
ctcctacttc cgcgaccccct atcacgtgtg gtaccagggc aacgcgtcgc tggggggaca   9900
cctaacgcac gtgctggaag gcccagacac caacaccacg atcattcagc tgcagcccct   9960
gcaggagccc gagagctggg cgcgcacgca gagtggcctg cagtcctacc tgctccagtt   10020
ccacggcctc gtgcgcctgg tgcaccagga gcggaccttg gcctttcctc tgaccatccg   10080
ctgcttcctg ggctgtgagc tgcctcccga gggctctaga gcccatgtct tcttcgaagt   10140
ggctgtgaat gggagctcct ttgtgagttt ccggccggaa agagccttgt ggcaggcaga   10200
cacccaggtc acctccggag tggtcacctt caccctgcag cagctcaatg cctacaaccg   10260
cactcggtat gaactgcggg aattcctgga ggacacctgt gtgcagtatg tgcagaaaca   10320
tatttccgcg gaaaacacga aagggagcca aacaagccgc tcctacactt cgctggtcct   10380
gggcgtcctg gtgggcagtt tcatcattgc tggtgtgtact gtaggcatct tcctgtgcac   10440
aggtggacgg cgatgttgag gcgggccgct tcccttagt gagggttaat gcttcgagca   10500
gacatgataa gatacattga tgagtttgga caaaccacaa ctagaatgca gtgaaaaaaa   10560
tgctttattt gtgaaatttg tgatgctatt gctttatttg taaccattat aagctgcaat   10620
aaacaagtta acaacaacaa ttgcattcat tttatgtttc aggttcaggg ggagatgtgg   10680
gaggtttttt aaagcaagta aaacctctac aaatgtggta aaatccgata aggatccgatg   10740
ggacagcccc cccccaaagc ccccagggat gtaattacgt ccctccccg ctagggcagc   10800
agcgagccgc ccgggggctcc ggtccggtcc ggcgctcccc cgcatccccg agccggcagc   10860
gtgcggggac agcccgggca cggggaaggt ggcacgggat cgctttcctc tgaacgcttc   10920
tcgctgctct ttgagcctgc agacacctgg ggggatacgg ggaaaatcta gtgggacagc   10980
cccccccaa agccccagg gatgtaatta cgtccctccc ccgctagggc agcagcgagc   11040
cgcccggggc tccggtccgg tccggcgctc ccccgcatcc ccgagccggc agcgtgcggg   11100
gacagcccgg gcacggggaa ggtggcacgg gatcgctttc ctctgaacgc ttctcgctgc   11160
tctttgagcc tgcagacacc tggggggata cggggaaaaa tcgatgggac agccccccc   11220
caaagcccc agggatgtaa ttacgtccct ccccgctag ggcagcagcg agccgcccg   11280
ggctccggtc cggtccggcg ctccccccgca tccccgagcc ggcagcgtgc ggggacagcc   11340
cgggcacggg gaaggtggca cgggatcgct ttcctctgaa cgcttctcgc tgctctttga   11400
gcctgcagac acctggggggg atacggggaa aatctagtgg gacagccccc ccccaaagcc   11460
cccagggatg taattacgtc cctccccgc tagggcagca gcgagccgcc cggggctccg   11520
gtccggtccg gcgctccccc gcatccccga gccggcagc tgcggggaca gcccgggcac   11580
gggggaaggtg gcacgggatc gctttcctct gaacgcttct cgctgctctt tgagcctgca   11640
gacacctggg gggatacggg gaaaaatcga tagcgataag gatccactag ttattaatag   11700
taatcaatta cggggtcatt agttcatagc ccatatatgg agttccgcgt tacataactt   11760
acggtaaatg gcccgcctgg ctgaccgccc aacgacccc gcccattgac gtcaataatg   11820
acgtatgttc ccatagtaac gccaataggg actttccatt gacgtcaatg ggtggagtat   11880
ttacggtaaa ctgcccactt ggcagtacat caagtgtatc atatgccaag tacgcccct   11940
attgacgtca atgacggtaa atggcccgcc tggcattatg cccagtacat gaccttatgg   12000
gactttccta cttggcagta catctacgta ttagtcatcg ctattaccat gggtcgaggt   12060
gagcccacg ttctgcttca ctctccccat ctcccccccc tccccacccc caattttgta   12120
tttatttatt ttttaattat tttgtgcagc gatggggggcg ggggggggggg gggcgcgcgc   12180
caggcgggggc ggggcggggc gaggggcggg gcggggcgagggt gcggcggcag   12240
ccaatcagag cggcgcgctc cgaaagtttc cttttatggc gaggcggcgg cggcggcggc   12300
cctataaaaa gcgaagcgcg cggcgggcgg gagtcgctgc gttgccttcg ccccgtgccc   12360
cgctccgcgc cgcctcgcgc cgcccgcccc ggctctgact gaccgcgtta ctcccacagg   12420
tgagcggggc ggacggccct tctcctccgg gctgtaatta gcgcttggtt taatgacggc   12480
tcgtttcttt tctgtggctg cgtgaaagcc ttaaagggct ccgggaggggc cctttgtgcg   12540
gggggggagcg gctcgggggg tgcgtgcgtg tgtgtgtgcg tggggagcgc cgcgtgcggc   12600
ccgcgctgcc cggcggctgt gagcgctgcg ggcgcggcgc ggggcttgt gcgctccgcg   12660
tgtgcgcgag gggagcgcgg ccgggggcgg tgccccgcgg tgcgggggcg ctgcgaggggg   12720
aacaaaggct gcgtgcgggg tgtgtgcgtg ggggggtgag caggggggtgt gggcgcggcg   12780
gtcgggctgt aaccccccc tgcaccccc tccccgagtt gctgagcacg gcccggcttc   12840
gggtgcgggg ctccgtgcgg ggcgtggcgc ggggctcgcc gtgccgggcg gggggttggcg   12900
gcaggtgggg gtgccgggcg gggcggggcc gcctcgggcg ggggagggct cgggggaggg   12960
gcgcggcggc cccggagcgc ggcggctgt cgaggcgcgg cgagccgcag ccattgcctt   13020
ttatggtaat cgtgcgagag ggcgcaggga cttcctttgt cccaaatctg gcggagccga   13080
aatctgggag gcgccgccgc accccctcta gcgggcgcgg gcgaagcggt gcggcgccgg   13140
caggaaggaa atgggcgggg agggccttcg tgcgtcgccg cgccgccgtc cccttctcca   13200
tctccagcct cggggctgcc gcagggggac ggctgccttc gggggggacg gggcaggggcg   13260
gggttcgtgc tctggcgtgt gaccggcggc tctagagctg ctaacca tgttcatgcc   13320
ttcttctttt tcctacagct cctgggcaac gtgctggtt ttgtgctgtc tcatcatttt   13380
ggcaaagaat tccgctgcga ctcggcggag tcccggcggc gcgtccttgt tctaacccgg   13440
cgcgccctca ggatgggaat ccaaggaggg tctgtcctgt tcgggctgct gctcgtcctg   13500
gctgtcttct gccattcagg tcatagcctg cagtgctaca actgtcctaa cccaactgct   13560
gactgcaaaa cagccgtcaa ttgttcatct gattttgatg cgtgtctcat taccaaagct   13620
```

-continued

```
gggttacaag tgtataacaa gtgttggaag tttgagcatt gcaatttcaa cgacgtcaca   13680
acccgcttga gggaaaatga gctaacgtac tactgctgca agaaggacct gtgtaacttt   13740
aacgaacagc ttgaaaatgg tgggacatcc ttatcagaga aaacagttct tctgctggtg   13800
actccatttc tggcagcagc ctggagcctt catcccggat ccggagaggg cagaggaagt   13860
cttctaacat gcggtgacgt ggaggagaat cccggcccta tggagcgtcc gcaacccgac   13920
agcatgcccc aggatttgtc agaggccctg aaggaggcca ccaaggaggt gcacacccag   13980
gcagagaatg ctgagttcat gaggaacttt cagaagggcc aggtgacccg agacggcttc   14040
aagctggtga tggcctccct gtaccacatc tatgtggccc tggaggagga gattgagcgc   14100
aacaaggaga gcccagtctt cgcccctgtc tacttcccag aagagctgca ccgcaaggct   14160
gccctggagc aggacctggc cttctggtac gggccccgct ggcaggaggt catcccctac   14220
acaccagcca tgcagcgcta tgtgaagcgg ctccacgagg tggggcgcac agagcccgag   14280
ctgctggtgg cccacgccta cacccgctac ctgggtgacc tgtctggggg ccaggtgctc   14340
aaaaagattg cccagaaagc cctggacctg cccagctctg gcgagggcct ggccttcttc   14400
accttcccca acattgccag tgccaccaag ttcaagcagc tctaccgctc ccgcatgaac   14460
tccctggaga tgactcccgc agtcaggcag agggtgatag aagaggccaa gactgcgttc   14520
ctgctcaaca tccagctctt tgaggagttg caggagctgc tgacccatga caccaaggac   14580
cagagcccct cacgggcacc agggcttcgc cagcgggcca gcaacaaagt gcaagattct   14640
gcccccgtgg agactcccag agggaagccc ccactcaaca cccgctccca ggctccgctt   14700
ctccgatggg tccttacact cagctttctg gtgtcgacag ttgctgtagg gctttatgcc   14760
atgtgagcgg cgcgccggca ccggtaccaa gcttaagagc gctagctggc cagacatgat   14820
aagatacatt gatgagtttg gacaaaccac aactagaatg cagtgaaaaa aatgctttat   14880
ttgtgaaatt tgtgatgcta ttgctttatt tgtaaccatt ataagctgca ataaacaagt   14940
taacaacaac aattgcattc attttatgtt tcaggttcag ggggaggtgt gggaggtttt   15000
ttaaagcaag taaaacctct acaaatgtgg tatggaattg gagccccact gtgttcatct   15060
tacagatgga aatactgaca ttcagaggag ttagttaact tgcctaggtg attcagctaa   15120
taagtgcaag aaagatttca atccaaggtg atttgattct gaagcctgtg ctaatcacat   15180
tacaccaagc tacaacttca tttataaata ataagtcagc tttcaagggc ctttcaggtg   15240
tcctgcactt ctacaagctg tgccatttag tgaacacaaa atgagccttc tgatgaagta   15300
gtcttttcat tatttcagat attagaacac taaaattctt agctgccagc tgattgaagg   15360
ctgggacaaa attcaaacat gcatctacaa caatatatat ctcaatgtta gtctccaaat   15420
tctattgact tcaactcaag agaatataaa gagctagtct ttatacactc tttaaggtat   15480
gatgggtccc gattttttccc cgtatccccc caggtgtctg caggctcaaa gagcagcgag   15540
aagcgttcag aggaaagcga tcccgtgcca ccttccccgt gcccgggctg tccccgcacg   15600
ctgccggctc ggggatgcgg gggagcgccg gaccggaccg gagccccggg cggctcgctg   15660
ctgccctagc gggggaggga cgtaattaca tccctggggg ctttgggggg gggctgtccc   15720
actagatttt ccccgtatcc ccccaggtgt ctgcaggctc aaaagagcagc gagaagcgtt   15780
cagaggaaag cgatcccgtg ccaccttccc cgtgcccggg ctgtccccgc acgctgccgg   15840
ctcggggatg cggggggagcg ccggaccgga ccggagcccc gggcggctcg ctgctgccct   15900
agcggggggag ggacgtaatt acatccctgg gggctttggg ggggggctgt cccatcggat   15960
cttctagtcc tgcaggagtc aatgggaaaa acccattgga gccaagtaca ctgactcaat   16020
agggactttc cattgggttt tgcccagtac ataaggtcaa taggggggtga gtcaacagga   16080
aagtcccatt ggagccaagt acattgagtc aatagggact ttccaatggg ttttgcccag   16140
tacataaggt caatgggagg taagccaatg ggtttttccc attactgaca tgtatacgcg   16200
tcgacgtcgg cgcgttcagc ctaaagcttt tttccccgta tcccccccagg tgtctgcagg   16260
ctcaaagagc agcgagaagc gttcagagga aagcgatccc gtgccacctt ccccgtgccc   16320
gggctgtccc cgcacgctgc cggctcgggg atgcggggga gcgccggacc ggaccggagc   16380
cccgggcggc tcgctgctgc cctagcgggg gagggacgta attacatccc tgggggcttt   16440
ggggggggggc tgtccctgcg gccgcgaatt cgtaatcatg gtcatagctg tttcctgtgt   16500
gaaattgtta tccgctcaca attccacaca acatacgagc cggaagcata aagtgtaaag   16560
cctggggtgc ctaatgagtg agctaactca cattaattgc gttgcgctca ctgcccgctt   16620
tccagtcggg aaacctgtcg tgccagcggt ctagccgacc tctaggaagc tttctagggt   16680
acctctaggg atccactagt tattaatagt aatcaattac ggggtcatta gttcatagcc   16740
catatatgga gttccgcgtt acataactta cggtaaatgg cccgcctggc tgaccgccca   16800
acgacccccg cccattgacg tcaataatga cgtatgttcc catagtaacg ccaataggga   16860
ctttccattg acgtcaatgg gtggagtatt tacggtaaac tgcccacttg gcagtacatc   16920
aagtgtatca tatgccaagt acgcccccta ttgacgtcaa tgacggtaaa tggcccgcct   16980
ggcattatgc ccagtacatg accttatggg actttcctac ttggcagtac atctacgtat   17040
tagtcatcgc tattaccatg gtcgaggtg agccccacgt tctgcttcac tctccccatc   17100
tcccccccct ccccaccccc aattttgtat ttatttattt tttaattatt ttgtgcagcg   17160
atgggggcgg ggggggggggg ggcgcgcgcc aggcggggcg gggcggggcg agggggcgggg   17220
cggggcgagg cggagaggtg cggcggcagc caatcagagc ggcgcgctcc gaaagtttcc   17280
ttttatggcg aggcggcggc ggcggcggcc ctataaaaag cgaagcgcgc ggcgggcggg   17340
agtcgctgcg ttgccttcgc cccgtgcccc gctccgcgcc gcctcgcgcc gcccgccccg   17400
gctctgactg accgcgttac tcccacaggt gagcggggcg gggcggcctt ctcctccggg   17460
ctgtaattag cgcttggttt aatgacggct cgtttctttt ctgtggctgc gtgaaagcct   17520
taaagggctc cgggagggcc ctttgtgcgg gggggagcgg ctcggggggt gcgtgcgtgt   17580
gtgtgtgcgt ggggagcgcc gcgtgcggcc cgcgctgccc ggcggctgtg agcgctgcg   17640
gcgcggcgcg gggctttgtg cgctccgcgt gtgcgcgagg ggagcgcggc cgggggcggt   17700
gccccggcgg tgcggggggc tgcgagggga acaaaggctg cgtgcgggtg tgtgcgtgg   17760
gggggtgagc aggggggtgtg ggcgcggcgg tcgggctgta accccccccct gcacccccct   17820
ccccgagttg ctgagcacgg cccggcttcg ggtgcggggc tccgtacggg gcgtggcgcg   17880
gggctcgccg tgccgggcgg ggggtggcgg caggtggggg tgccgggcgg ggcggggccg   17940
cctcgggccg ggggagggct cgggggagggg cgcggcggcc ccggagcgcc ggcggctgtc   18000
gaggcgcgggc gagccgcagc cattgccttt tatggtaatc gtgcgagagg gcgcagggac   18060
ttcctttgtc ccaaatctgg cggagccgaa atctggcagg cgcgccgcca ccccctctag   18120
cgggcgcggg cgaagcggtg cggcgccggc aggaaggaaa tgggcgggga gggccttcgt   18180
gcgtcgccgc gccgccgtcc ccttctccat ctccagcctc ggggctgccg cagggggacg   18240
gctgccttcg ggggggacgg ggcagggcgg ggttcggctt ctggcgtgtg accggcggct   18300
ctagagcctc tgctaaccat gttcatgcct tcttcttttt cctacagctc ctgggcaacg   18360
```

-continued

```
tgctggttgt tgtgctgtct catcattttg gcaaagaatt ccgctgcgac tcggcggagt  18420
cccggcggcg cgtccttgtt ctaacccggc gcgccctcag gatggagcct cccggccgcc  18480
gcgagtgtcc ctttccttcc tggcgctttc ctgggttgct tctggcggcc atggtgttgc  18540
tgctgtactc cttctccgat gcctgtgagg agccaccaac atttgaagct atggagctca  18600
ttggtaaacc aaaaccctac tatgagattg gtgaacgagt agattataag tgtaaaaaag  18660
gatacttcta tatacctcct cttgccaccc atactatttg tgatcggaat catcatggc   18720
tacctgtctc agatgacgcc tgttatagag aaacatgtcc atatatacgg gatcctttaa  18780
atggccaagc agtccctgca aatgggactt acgagtttgg ttatcagatg cactttattt  18840
gtaatgaggg ttattactta attggtgaag aaattctata ttgtgaactt aaaggatcag  18900
tagcaatttg gagcggtaag cccccaatat gtgaaaaggt tttgtgtaca ccacctccaa  18960
aaataaaaaa tggaaaacac accctttagtg aagtagaagt atttgagtat cttgatgcag  19020
taacttatag ttgtgatcct gcacctggac cagatccatt ttcacttatt ggagagagca  19080
cgatttattg tggtgacaat tcagtgtgga gtcgtgctgc tccagagtgt aaagtggtca  19140
aatgtcgatt tccagtagtc gaaaatggaa aacagatatc aggatttgga aaaaaatttt  19200
actacaaagc aacagttatg tttgaatgcg ataagggttt ttacctcgat ggcagcgaca  19260
caattgtctg tgacagtaac agtacttggg atcccccagt tccaaagtgt cttaaagtgc  19320
tgcctccatc tagtacaaaa cctccagctt tgagtcattc agtgtcgact tcttccacta  19380
caaaatctcc agcgtccagt gcctcaggtc ctaggcctac ttacaagcct ccagtctcaa  19440
attatccagg atatcctaaa cctgaggaag gaatacttga cagtttggat gtttgggtca  19500
ttgctgtgat tgttattgcc atagttgttg gagttgcagt aatttgtgtt gtcccgtaca  19560
gatatcttca aaggaggaag aagaaaggca catacctaac tgatgagacc cacagagaag  19620
taaaatttac ttctctcgga tccggagcca cgaacttctc tcgttaaag caagcaggag  19680
acgtggaaga aaaccccggt cctatgaccg tcgcgcggcc gagcgtgccc gcggcgctgc  19740
ccctcctcgg ggagctgccc cggctgctgc tgctggtgct gttgtgcctg ccggccgtgt  19800
ggggtgactg tggccttccc ccagatgtac ctaatgccca gccagctttg gaaggccgta  19860
caagtttccc cgaggatact gtaataacgt acaaatgtga agaaagcttt gtgaaaattc  19920
ctggcgagaa ggactcagtg atctgcctta agggcagtca atggtcagat attgaagagt  19980
tctgcaatcg tagctgcgag gtgccaacaa ggctaaattc tgcatccctc aaacagcctt  20040
atatcactca gaattatttt ccagtcggta ctgttgtgga atatgagtgc cgtccaggtt  20100
acagaagaga accttctcta tcaccaaaac taacttgcct tcagaattta aaatggtcca  20160
cagcagtcga attttgtaaa aagaaatcat gccctaatcc gggagaaata cgaaatggtc  20220
agattgatgt accaggtggc atattatttg gtgcaaccat ctccttctca tgtaacacag  20280
ggtacaaatt atttggctcg acttctagtt tttgtcttat ttcaggcagc tctgtccagt  20340
ggagtgaccc gttgccagag tgcagagaaa tttattgccc agcaccacca caaattgaca  20400
atggaataat tcaagggaa cgtgaccatt atggatatag acagtctgta acgtatgcat  20460
gtaataaagg attcaccatg attggagagc actctattta ttgtactgtg aataatgatg  20520
aaggagagtg gagtggccca ccacctgaat gcagaggaaa atctctaact tccaaggtcc  20580
caccaacagt tcagaaacct accacagtaa atgttccaac tacagaagtc tcaccaactt  20640
ctcagaaaac caccacaaaa accaccacac caaatgctca agcaacacgg agtacacctg  20700
tttccaggac aaccaagcat tttcatgaaa caaccccaaa taaaggaagt ggaaccactc  20760
caggtactac ccgtcttcta tctgggcaca cgtgtttcac gttgacaggt ttgcttggga  20820
cgctagtaac catgggcttg ctgacttagg gcgcgccggc accggtacca gcttaagag   20880
cgctagctgg ccagacatga taagatacat tgatgagttt ggacaaacca caactagaat  20940
gcagtgaaaa aaatgcttta tttgtgaaat ttgtgatgct attgctttat ttgtaaccat  21000
tataagctgc aataaacaag ttaacaacaa caattgcatt cattttatgt ttcaggttca  21060
gggggaggtg tgggaggttt tttaaagcaa gtaaaacctc tacaaatgtg gtatggaatt  21120
ggagccccac tgtgttcatc ttacagatgg aaatactgac attcagagga gttagttaac  21180
ttgcctaggt gattcagcta ataagtgcaa gaaagatttc aatccaaggt gatttgattc  21240
tgaagcctgt gctaatcaca ttacaccaag ctacaacttc atttataaat aataagtcag  21300
ctttcaaggg cctttcaggt gtcctgcact tctacaagct gtgccattta gtgaacacaa  21360
aatgagcctt ctgatgaagt agtcttttca ttatttcaga tattagaaca ctaaaattct  21420
tagctgccag ctgattgaag gctgggacaa aattcaaaca tgcatctaca acaatatata  21480
tctcaatgtt agtctccaaa ttctattgac ttcaactcaa gagaatataa agagctagtc  21540
tttatacact cttttaaggta tgatatcatc tggaaagtaa caaaattgat gcaaatttga  21600
atgaacttta tcatggtgta tttacacaat gtgtttcttc tccctgcaat gtatttcttt  21660
ctctaattcc ttccatttga tcttttcatac acaatctggt tctgatgtat gtttttttgga  21720
tgcacttttc aactccaaaa gacagagcta gttactttct tcctggtgct ccaagcactg  21780
tatttgtatc tgtattcaag ccctttgcaa tattgtactg gatcattatt tcacctctag  21840
gatggcttcc ccaggcaact tgtgttcacc cagagactac attttgtatc ttgttgacct  21900
ttgaacttcc accagtgtct aaaaataata tgtatgcaaa attacttgct atggaaatgt  21960
ataattaaac aatataaaaa ggagaagcaa ggagagaaac acaggtgtgt atttgtgttt  22020
gtgtgcttaa aaggcagtgt ggaaaaggaa gaaatgccat ttatagtgag gagacaaagt  22080
tatattacct cttatctggc tttttaggag attttgctga gctaaaaatc ctatattcat  22140
agaaaagcct tacctgagtt gccaatacct caattctaaa atacagcata gcaaaacttt  22200
aacctccaaa tcaagcctct acttgaatcc ttttctgagg gatgaataag gcataggcat  22260
caggggctgt tgccaatgtg cattagctgt ttgcagcctc accttctttc atggagttta  22320
agatatagtg tattttccca aggtttgaac tagctcttca tttcttatg ttttaaatgc   22380
actgacctcc cacattccct ttttagtaaa atattcagaa ataatttaaa atctggaaag  22440
taacaaaatt gatgcaaatt tgaatgaact ttatcatggt gtatttacac aatgtgtttc  22500
ttctccctgc aatgtatttc tttctctaat tccttccatt tgatctttca tacacaatct  22560
ggttctgatg tatgtttttt ggatgcactt tcaactccca aagacagag ctagttactt   22620
tcttcctggt gctccaagca ctgtatttgt atctgtattc aagccctttg caatattgta  22680
ctggatcatt atttcacctc taggatggct ccccaggca acttgtgttc acccagagac   22740
tacatttttg atcttgttga cctttgaact tccaccagtg tctaaaaata atatgtatgc  22800
aaaattactt gctatgagaa tgtataatta aacaatataa aaggagaag caaggagaga   22860
aacacaggtg tgtatttgtg tttgtgtgct taaaaggcag tgtggaaaag gaagaaatgc  22920
catttatagt gaggagacaa agttatatta cctcttatct ggcttttaag gagattttgc  22980
tgagctaaaa atcctatatt catagaaaag ccttacctga gttgccaata cctcaattct  23040
aaaatacagc atagcaaaac tttaacctcc aaatcaagcc tctacttgaa tccttttctg  23100
```

```
agggatgaat aaggcatagg catcagggc tgttgccaat gtgcattagc tgtttgcagc  23160
ctcaccttct ttcatggagt ttaagatata gtgtattttc ccaaggtttg aactagctct  23220
tcatttcttt atgtttttaaa tgcactgacc tcccacattc cctttttagt aaaatattca  23280
gaaataattt atcccggctt gtcgacgacg gatcatctgg aaagtaacaa aattgatgca  23340
aatttgaatg aactttatca tggtgtattt acacaatgtg tttcttctcc ctgcaatgta  23400
tttctttctc tattccttcc atttgatctt tcatacacaa tctggttctg atgtatgttt  23460
tttggatgca cttttcaact ccaaaagaca gagctagtta ctttcttcct ggtgctccaa  23520
gcactgtatt tgtatctgta ttcaagccct ttgcaatatt gtactggatc attatttcac  23580
ctctaggatg gcttccccag gcaacttgtg ttcacccaga gactacattt tgtatcttgt  23640
tgacctttga acttccacca gtgtctaaaa ataatatgta tgcaaaatta cttgctatga  23700
gaatgtataa ttaaacaata taaaaaggag aagcaaggag agaaacacag gtgtgtattt  23760
gtgtttgtgt gcttaaaagg cagtgtggaa aaggaagaaa tgccatttat agtgaggaga  23820
caaagttata ttacctctta tctggctttt aaggagattt tgctgagcta aaaatcctat  23880
attcatagaa aagccttacc tgagttgcca atacctcaat tctaaaatac agcatagcaa  23940
aactttaacc tccaaatcaa gcctctactt gaatcctttt ctgagggatg aataaggcat  24000
aggcatcagg ggctgttgcc aatgtgcatt agctgtttgc agcctcacct tctttcatgg  24060
agtttaagat atagtgtatt ttcccaaggt ttgaactagc tcttcatttc tttatgtttt  24120
aaatgcactg acctcccaca ttcccttttt agtaaaaatat tcagaaataa tttatcccgg  24180
cttgtcgacg gcgtccgtcg tcaggatcat ccatcaggac atagcgttgg ctacccgtga  24240
tattgctgaa gagcttggcg gcgaatgggc tgaccgcttc ctcgtgcttt acggtatcgc  24300
cgctcccgat tcgcagcgca tcgccttcta tcgccttctt gacgagttct tctgagggga  24360
tcaattctct agagctcgct gatcagcctc gactgtgcct tctagttgcc agccatctgt  24420
tgtttgcccc tcccccgtgc cttccttgac cctggaaggt gccactccca ctgtcctttc  24480
ctaataaaat gaggaaattg catcgcattg tctgagtagg tgtcattcta ttctgggggg  24540
tggggtgggg caggacagca aggggagga ttgggaagac aatagcaggc atgctgggga  24600
tgcggtgggc tctatggctt ctgaggcgga aagaaccagc tggggcgcgg cacctcgacc  24660
atctccagga tgcctttgat agagctgggc cctctgcgtt cctttaaagt gtttgagatc  24720
aagtccgaga agaggtggca agcgatcgcg acatatttaa atcgcgctag tttaaaatac  24780
atcattgcaa tgaaaataaa tgtttttttat taggcagaat ccagatgctc aaggcccttc  24840
ataatatccc ccagtttagt agttggactt agggaacaaa ggaacctta atagaaattg  24900
gacagcaaga aagctctagc tttagaagaa ctcatcaaga agtctgtaga aggcaattct  24960
ctgggagtca ggggctgcaa tgccatagag cactaggaac ctgtctgccc actctccccc  25020
tagctcttct gctatgtccc tggttgctag ggcaatgtcc tggtacctgt cagccactcc  25080
cagcctgcca cagtctatga agccagagaa ccttccattt tcaaccatga tgttgggaag  25140
gcaggcatcc ccatgagtca ccactaggtc ctcaccatct ggcatggatg ccttgagcct  25200
ggcaaatagt tcagcagggg ccaggccctg gtgttcttca tccaagtcat cttggtccac  25260
caggccagcc tccatcctgg ttctggccct ctctatcctg tgcttggcct ggtggtcaaa  25320
ggggcaggtg gctgggtcaa gggtgtggag tcttctcatg gcatcagcca tgattgacac  25380
tttctcagct ggagctaggt gagaggaaag gaggtcctgc ccaggcacct cacctagtag  25440
gagccagtcc cttccagctt ctgtgaccac atcaaggaca gctgcacagg ggaccccagt  25500
tgttgccaac caggagagtc tggcagcctc atcctggagc tcattgagag ccccactgag  25560
gtctgtcttt acaaaaagga ctggcctgcc ttgggctgaa agtctgaaaa ctgctgcatc  25620
agagcaacca atggtctgct gtgcccagtc atagccaaac agtctctcaa cccaggcagc  25680
tggagaacct gcatgtaggc catcttgttc aatcatgatg gctcctcctg tcaggagagg  25740
aaagagaaga aggttagtac aattgctata gtgagttgta ttatactatg cttatgatta  25800
attgtcaaac tagggctgca gggttcatag tgccactttt cctgcactgc cccatctcct  25860
gcccaccctt tcccaggcat agacagtcag tgacttacca aactcacagg agggagaagg  25920
cagaagcttt ttgcaaaagc ctaggctcat gagacaataa ccctgataaa tgcttcaata  25980
atattgaaaa aggaagagta ccaggtatga gtattcaaca tttccgtgtc gcccttattc  26040
ccttttttgc ggcattttgc cttcctgttt ttgctcaccc agaaacgctg gtgaaagtaa  26100
aagatgctga agatcagttg ggtgcacgag tgggttacat cgaactggat ctcaacagcg  26160
gtaagatcct tgagagtttt cgccccgaag aacgttttcc aatgatgagc acttttaaag  26220
ttctgctatg tggcgcggta ttatcccgta ttgacgccgg gcaagagcaa ctcggtcgcc  26280
gcatacacta ttctcagaat gacttggttg agtactcacc agtcacagaa aagcatctta  26340
cggatggcat gacagtaaga gaattatgca gtgctgccat aaccatgagt gataacactg  26400
cggccaactt acttctgaca acgatcggag gaccgaagga gctaaccgct tttttgcaca  26460
acatggggga tcatgtaact cgccttgatc gttgggaacc ggagctgaat gaagccatac  26520
caaacgacga gcgtgacacc acgatgcctg tagcaatggc aacaacgttg cgcaaactat  26580
taactggcga actacttact ctagcttccc ggcaacaatt aatagactgg atggaggcgg  26640
ataaagttgc aggaccactt ctgcgctcgg cccttccggc tggctggttt attgctgata  26700
aatctggagc cggtgagcgt gggtctcgcg gtatcattgc agcactgggg ccagatggta  26760
agccctcccg tatcgtagtt atctacacga cggggagtca ggcaactatg gatgaacgaa  26820
atagacagat cgctgagata ggtgcctcac tgattaagca ttggtaactg tcagaccaag  26880
tttactcata tatactttag attgatttaa aacttcattt ttaatttaaa aggatctagg  26940
tgaagatcct ttttgataat ctcatgacca aaatccctta acgtgagttt tcgttccact  27000
gagcgtcaga ccccgtagaa aagatcaaag gatcttcttg agatcctttt tttctgcgcg  27060
taatctgctg cttgcaaaca aaaaaaccac cgctaccagc ggtggtttgt ttgccggatc  27120
aagagctacc aactctttt ccgaaggtaa ctggcttcag cagagcgcag ataccaaata  27180
ctgttcttct agtgtagccg tagttaggcc accacttcaa gaactctgta gcaccgccta  27240
catacctcgc tctgctaatc ctgttaccag tggctgctgc cagtggcgat aagtcgtgtc  27300
ttaccgggtt ggactcaaga cgatagttac cggataaggc gcagcggtcg gctgaacgg  27360
ggggttcgtg cacacagccc agcttggagc gaacgaccta caccgaactg agatacctac  27420
agcgtgagct atgagaaagc gccacgcttc ccgaaggag aaaggcggac aggtatccgg  27480
taagcggcag ggtcggaaca ggagagcgca cgagggagct tccaggggga aacgcctggt  27540
atctttatag tcctgtcggg tttcgccacc tctgacttga gcgtcgattt ttgtgatgct  27600
cgtcaggggg gcggagccta tggaaaaacg ccagcaacgc ggcctttta cggttcctgg  27660
ccttttgctg gccttttgct cacatggctc gacagattta attaacaaga ccgacctgtc  27720
cggtgccctg aatgaactgc aggacgaggc agcgcggcta tcgtggctgg ccacgacggg  27780
cgttccttgc gcagctgtgc tcgacgttgt cactgaagcg ggaagggact ggctgctatt  27840
```

```
gggcgaagtg ccggggcagg atctcctgtc atctcacctt gctcctgccg agaaagtatc  27900
catcatggct gatgcaatgc ggcggctgca tacgcttgat ccggctacct gcccattcga  27960
ccaccaagcg aaacatcgca tcgagcgagc acgtactcgg atggaagccg gtcttgtcga  28020
tcaggatgat ctgacgaag agcatcaggg gctcgcgcca gccgaactgt tcgccaggct  28080
caaggcgcgc atgcccgacg gcgaggatct cgtcgtgacc catggcgatg cctgcttgcc  28140
gaatatcatg gtgaaaatg gccgcttttc tggattcatc gactgtggcc ggctgggtgt  28200
ggcggatcgc tggcctcgat ggccgtgata cggcctgcag gatcatttgc cagccatctg  28260
ttgtttgccc ctccccgtg ccttccttga ccctggaagg tgccactccc actgtccttt  28320
cctaataaaa tgaggaaatt gcatgccggc agcgtgcggg gacagcccgg gcacggggga  28380
ggtggcacgg gatcgctttc ctctgaacgc ttctcgctgc tctttgagcc tgcagacacc  28440
tgggggggata cggggaaaag ttagtttaaa cgttcgcgat agtatacggc ctgcaggatg  28500
actttggcct cgatggccgt gccagggcgt gcccttgggc tccccgggcg cggcgattaa  28560
gacgt                                                               28565

SEQ ID NO: 9              moltype = DNA   length = 23836
FEATURE                  Location/Qualifiers
source                   1..23836
                         mol_type = other DNA
                         organism = synthetic construct
SEQUENCE: 9
caagaccgac ctgtccggtg ccctgaatga actgcaggac gaggcagcgc ggctatcgtg  60
gctggccacg acgggcgttc cttgcgcagc tgtgctcgac gttgtcactg aagcgggaag  120
ggactggctg ctattgggcg aagtgccggg gcaggatctc ctgtcatctc accttgctcc  180
tgccgagaaa gtatccatca tggctgatgc aatgcggcgg ctgcatacgc ttgatccggc  240
tacctgccca ttcgaccacc aagcgaaaca tcgcatcgag cgagcacgta ctcggatgga  300
agccggtctt gtcgatcagg atgatctgga cgaagacagg caggggctcg cgccagccga  360
actgttcgcc aggctcaagg cgcgcatgcc cgacgcgcag gatctcgtcg tgacccatgg  420
cgatgcctgc ttgccgaata tcatggtgga aaatggccgc ttttctggat tcatcgactg  480
tggccggctg ggtgtggcgg atcgctggcc tcgatgccg tgccagggcg tgcccttggg  540
ctccccggg gcgttaatta agacgtgggt cccgattttt ccccgtatcc cccaggtgt  600
ctgcaggctc aaagagcagc gagaagcgtt cagaggaaag cgatcccgtg ccaccttccc  660
cgtgcccggg ctgtccccgc acgctgccgg ctcggggatg cggggggagcg ccggaccgga  720
ccggagcccc gggcggctcg ctgctgccct agcgggggag ggacgtaatt acatccctgg  780
gggctttggg gggggggctgt cccactagat tttcccgta tcccccagg tgtctgcagg  840
ctcaaagagc agcgagaagc gttcagagga aagcgatccc gtgccaccct ccccgtgccc  900
gggctgtccc cgcacgctgc cggctcgggg atgcggggga gcgccggacc ggaccggagc  960
cccgggcggc tcgctgctgc cctagcgggg gaggacgta attacatccc tggggggcttt  1020
gggggggggc tgtcccatcg gatcttctag tcctgcaggt ttaaaccta agtgtacaaa  1080
aaagcaggct ttaaaggaac caattcagtc gactggatcc ggtaccaagg tcgggcagga  1140
agagggccta tttcccatga ttccttcata tttgcatata cgatacaagg ctgttagaga  1200
gataattaga attaatttga ctgtaaacac aaagatatta gtacaaaata cgtgacgtag  1260
aaagtaataa tttcttgggt agtttgcagt tttaaaatta tgttttaaaa tggactatca  1320
tatgcttacc gtaacttgaa agtatttcga tttcttgggt ttatatatct tgtggaaagg  1380
acgaaacacc gtagttcagg tgaacggcac tgtttttagag ctagaaatag caagttaaaa  1440
taaggctagt ccgttatcaa cttgaaaaag tggcaccgag tcggtgcttt ttttctagac  1500
ccatgtacaa aaaagcaggc tttaaaggaa ccaattcagt cgactggatc cggtaccaag  1560
gtcgggcagg aagagggcct atttcccatg attccttcat atttgcatat acgatacaag  1620
gctgttagag agataattag aattaatttg actgtaaaca caaagatatt agtacaaaat  1680
acgtgacgta gaaagtaata atttcttggg tagtttgcag ttttaaaatt atgttttaaa  1740
atggactatc atatgcttac cgtaacttga agtatttcg atttcttggc tttatatatc  1800
ttgtggaaag gacgaaacac cggacggacc ccatctgtcc aggttttaga gctagaaata  1860
gcaagttaaa ataaggctag tccgttatca acttgaaaaa gtggcaccga gtcggtgctt  1920
tttttctaga ggtaccgagt ttactcccta tcagtgatag agaacgtatg aagagtttac  1980
tccctatcag tgatagagaa cgtatgcaga ctttactccc tatcagtgat agagaacgta  2040
taaggagttt actccctatc agtgatagag aacgtatgac cagtttactc cctatcagtg  2100
atagagaacg tatctacagt ttactcccta tcagtgatag agaacgtata tccagtttac  2160
tccctatcag tgatagagaa cgtataagct ttaggcgtgt acggtgggcg cctataaaag  2220
cagagctcgt ttagtgaacc gtcagatcgc ctggagcaat tccacaacac ttttgtctta  2280
taccaacttt ccgtaccact tcctaccctc gtaaaaccgg tgccaccatg gactataagg  2340
accacgacgg agactacaag gatcatgata ttgattacaa agacgatgac gataagatgg  2400
ccccaaagaa gaagcggaag gtcggtatcc acggagtccc agcagccgac aagaagtaca  2460
gcatcggcct ggacatcggc accaactctg tgggctgggc cgtgatcacc gacgagtaca  2520
aggtgcccag caagaaattc aaggtgctgg gcaacaccga ccggcacagc atcaagaaga  2580
acctgatcgg agccctgctg ttcgacagcg gcgaaacacc ggcggccagga  2640
gaaccgccag aagaagatac accagacgga agaaccggat ctgctatctg caagagatct  2700
tcagcaacga gatggccaag gtggacgaca gcttcttcca cagactggaa gagtccttcc  2760
tggtggaaga ggataagaag cacgagcggc accccatctt cggcaacatc gtggacgagg  2820
tggcctacca cgagaagtac cccaccatct accacctgag aaagaaactg gtggacagca  2880
ccgacaaggc cgacctgcgg ctgatctatc tggccctggc ccacatgatc aagttccggg  2940
gccacttcct gatcgagggc gacctgaacc ccgacaacag cgacgtggac aagctgttca  3000
tccagctggt gcagacctac aaccagctgt tcgaggaaaa ccccatcaac gccagcggcg  3060
tggacgccaa ggccatcctg tctgccgac tgagcaagag cagacggctg gaaaatctga  3120
tcgcccagct gcccggcgag aagaagaatg gcctgttcgg aaacctgatt gccctgagcc  3180
tgggcctgac ccccaacttc aagagcaact tcgacctggc cgaggatgcc aaactgcagc  3240
tgagcaagga cacctacgac gacgacctgg acaacctgct ggcccagatc ggcgaccagt  3300
acgccgacct gtttctggcc gccaagaacc tgtccgacgc catcctgctg agcgacatcc  3360
tgagagtgaa caccgagatc accaaggccc cctgagcgc ctctatgatc aagagatacg  3420
acgagcacca ccaggacctg accctgctga aagctctcgt cggcagcag ctgcctgaga  3480
agtacaaaga gatttttcttc gaccagagca agaacggcta cgccggctac attgacggcg  3540
```

```
gagccagcca ggaagagttc tacaagttca tcaagcccat cctggaaaag atggacggca 3600
ccgaggaact gctcgtgaag ctgaacagag aggacctgct gcggaagcag cggaccttcg 3660
acaacggcag catcccccac cagatccacc tgggagagct gcacgccatt ctgcggcggc 3720
aggaagattt ttacccattc ctgaaggaca accgggaaaa gatcgagaag atcctgacct 3780
tccgcatccc ctactacgtg ggccctctgg ccagggaaca cagcagattc gcctggatga 3840
ccagaaagag cgaggaaacc atcaccccct ggaacttcga ggaagtggtg gacaagggcg 3900
cttccgccca gagcttcatc gagcggatga ccaacttcga taagaacctg cccaacgaga 3960
aggtgctgcc caagcacagc ctgctgtacg agtacttcac cgtgtataac gagctgacca 4020
aagtgaaata cgtgaccgag ggaatgagaa agcccgcctt cctgagcggc gagcagaaaa 4080
aggccatcgt ggacctgctg ttcaagacca accggaaagt gaccgtgaag cagctgaaag 4140
aggactactt caagaaaatc gagtgcttcg actccgtgga aatctccggc gtggaagatc 4200
ggttcaacgc ctccctgggc acataccacg atctgctgaa aattatcaag gacaaggact 4260
tcctggacaa tgaggaaaac gaggacattc tggaagatat cgtgctgacc ctgacactgt 4320
ttgaggacag agagatgatc gaggaacggc tgaaaaccta tgcccacctg ttcgacgaca 4380
aagtgatgaa gcagctgaag cggcggagat acaccggctg gggcaggctg agccggaagc 4440
tgatcaacgc catccgggac aagcagtccg gcaaagacaa cctggatttc ctgaagtccg 4500
acggcttcgc caacagaaac ttcatgcagc tgatccacga cgacagcctg acctttaaag 4560
aggacatcca gaaagcccag gtgtccggcc agggcgatag cctgcacgag cacattgcca 4620
atctggccgg cagccccgcc attaagaagg gcatcctgca gacagtgaag gtggtggacg 4680
agctcgtgaa agtgatgggc cggcacaagc ccgagaacat cgtgatcgaa atggccagag 4740
agaaccagac cacccagaag ggacagaaga acagccgcga gaatgaag cggatcgaag 4800
agggcatcaa agagctgggc agccagatcc tgaaagaaca ccccgtggaa aacacccagc 4860
tgcagaacga gaagctgtac ctgtactacc tgcagaatgg gcgggatatg tacgtggacc 4920
aggaactgga catcaaccgg ctgtccgact acgatgtgga ccatatcgtg cctcagagct 4980
ttctgaagga cgactccatc gacaacaagg tgctgaccag aagcgacaag aaccggggca 5040
agagcgacaa cgtgccctcc gaagaggtcg tgaagaagat gaagaactac tggcggcagc 5100
tgctgaacgc caagctgatt acccagaaa agttcgacaa tctgaccaag gccgagagcg 5160
gcggcctgag cgaactggat aaggccggct tcatcaagag acagctggtg gaaacccggc 5220
agatcacaaa gcacgtggca cagatcctgg actcccggat gaacactaag tacgacgaga 5280
atgacaagct gatccgggaa gtgaaagtga tcaccctgaa gtccaagctg gtgtccgatt 5340
tccggaagga tttccagttt tacaaagtgc gcgagatcaa caactaccac cacgcccacg 5400
acgcctacct gaacgccgtc gtgggaaccg ccctgatcaa aaagtaccct aagctggaaa 5460
gcgagttcgt gtacggcgac tacaaggtgt acgacgtgcg gaagatgatc gccaagagcg 5520
agcaggaaat cggcaaggct accgccaagt acttcttcta cagcaacatc atgaactttt 5580
tcaagaccga gattaccctg gccaacggcg agatccggaa gcggcctctg atcgagacaa 5640
acggcgaaac cggggagatc gtgtgggata agggccggga ttttgccacc gtgcggaaag 5700
tgctgagcat gccccaagtg aatatcgtga aaaagaccga ggtgcagaca ggcggcttca 5760
gcaaagagtc tatcctgccc aagaggaaca gcgataagct gatcgccaga aagaaggact 5820
gggaccctaa gaagtacggc ggcttcgaca gccccaccgt tgcctattct gtgctggtga 5880
tggccaaagt ggaaaagggc aagtccaaga aactgaagag tgtgaaagag ctgctgggga 5940
tcaccatcat ggaaagaagc agcttcgaga agaatcccat cgactttctg gaagccaagg 6000
gctacaaaga agtgaaaaag gacctgatca tcaagctgcc taagtactcc ctgttcgagc 6060
tggaaacgg ccggaagaga atgctggcct ctgccggcga actgcagaag ggaaacgaac 6120
tggccctgcc ctccaaatat gtgaacttcc tgtacctggc cagccactat gagaagctga 6180
agggctcccc cgaggataat gagcagaaac agctgtttgt ggaacagcac aagcactacc 6240
tggacgagat catcgagcag atcagcgagt ctccaagag agtgatcctg ccgacgcta 6300
atctggacaa agtgctgtcc gcctacaaca agcaccggga taagcccatc agagacgcag 6360
gccagagaatat catccacctg tttaccctga ccaatctggg agcccctgcc gccttcaagt 6420
actttgacac caccatcgac cggaagaggt acaccagcac caaagaggtg ctggacgcca 6480
ccctgatcca ccagagcatc accggcctgt acgagacacg gatcgacctg tctcagctgg 6540
gaggcgacaa aaggccggcg gccacgaaaa aggccggcca ggcaaaaaag aaaaagtaag 6600
aattcctaga gctcgctgat cagcctcgac tgtgccttct agttgccagc catctgttgt 6660
ttgcccctcc cccgtgcctt ccttgaccct ggaaggtgcc actcccactg tcctttccta 6720
ataaaatgag gaaattgcat cgcattgtct gagtaggtgt cattctattc tggggggtgg 6780
ggtggggcag gacagcaagg gggaggattg ggaagagaat agcaggcatg ctggggagcg 6840
gccgcttccc tttagtgagg gttaatgctt cgagcagaca tgataagata cattgatgag 6900
tttggacaaa ccacaactag aatgcagtga aaaaaatgct ttatttgtga aatttgtgat 6960
gctattgctt tatttgtaac cattataagc tgcaataaac aagttaacaa caacaattgc 7020
attcatttta tgtttcaggt tcagggggag atgtgggagg tttttaaag caagtaaaac 7080
ctctacaaat gtggtaaaat ccgataagga tcgatgggac agcccccccc caaagccccc 7140
agggatgtaa ttacgtccct cccccgctag ggcagcagcg agccgccgg ggctccggtc 7200
cggtccggc ctcccccgca tccccgagcc ggcagcgtgc ggggacagcc cgggcacggg 7260
gaaggtggca cgggatcgct ttcctctgaa cgcttctcgc tgctctttga gcctgcagac 7320
acctcccgggaa atacgggaa aatctagtgg gacagccctc cccaaagcc cccagggatg 7380
taattacgtc cctcccccgc tagggcagca gcgagccgcc cggggctccg gtccggtccg 7440
gcgctcccc gcatccccga gccggcagcg tgcggggaca gcccgggcac ggggaaggtg 7500
gcacgggatc gctttcctct gaacgcttct cgctgctctt tgagcctgca gacacctggg 7560
gggatacggg gaaaaatcga tgggacagcc cccccaaa gccccccagg atgtaattac 7620
gtccctcccc cgctagggca gcagcgagcc gcccggggct ccggtccggt ccggcgctcc 7680
cccgcatccc cgagccggca gcgtgcgggg acagcccggg cacgggggaag gtggcacggg 7740
atcgctttcc tctgaacgct tctcgctgct cttttgagcct gcagacacct ggggggatac 7800
ggggaaaatc tagtgggaca gcccccccc aaagccccca gggatgtaat tacgtccctc 7860
ccccgctagg gcagcagcga gccgcccggg gctccggtcg gtccggcgc tccccgcat 7920
ccccgaggcg gcagcgtgcg gggacagccc gggcacgggg aaggtggcac gggatcgctt 7980
tcctctgaac gcttctcgct gctctttgag cctgcagaca cctgggggga tacgggaaa 8040
aatcgatagc gataaggatc cactagttat taatagtaat caattacggg gtcattagtt 8100
catagcccat atatggagtt ccgcgttaca taacttacgg taaatggccc gcctggctga 8160
ccgcccaacg accccgccc attgacgtca ataatgacgt atgttcccat agtaacgcca 8220
atagggactt tccattgacg tcaatgggtg gagtatttac ggtaaactgc ccacttggca 8280
```

-continued

```
gtacatcaag tgtatcatat gccaagtacg ccccctattg acgtcaatga cggtaaatgg  8340
cccgcctggc attatgccca gtacatgacc ttatgggact ttcctacttg gcagtacatc  8400
tacgtattag tcatcgctat taccatggtc gaggtgagcc ccacgttctg cttcactctc  8460
cccatctccc cccctcccc  accccaatt ttgtatttat ttatttttta attattttgt  8520
gcagcgatgg gggcgggggg ggggggggg  ggggccaggc ggggcggggc ggggcgaggg  8580
gcggggcggg gcgaggcgga gaggtgcggc ggcagccaat cagagcggcg cgctccgaaa  8640
gtttcctttt atggcgaggc ggcggcggcg gcggccctat aaaaagcgaa gcgcgcggcg  8700
ggcgggagtc gctgcgttgc cttcgccccg tgccccgctc cgcgccgcct cgcgccgccc  8760
gccccggctc tgactgaccg cgttactccc acaggtgagc gggcgggacg gcccttctcc  8820
tccgggctgt aattagcgct tggtttaatg acggctcgtt tcttttctgt ggctgcgtga  8880
aagccttaaa gggctccggg agggcccttt gtgcgggggg gagcggctcg gggggtgcgt  8940
gcgtgtgtgt gtgcgtgggg agcgccgcgt gcggctccgc gctgcccggc ggctgtgagc  9000
gctgcgggcg cggcgcgggg ctttgtgcgc tccgcagtgt gcgcgagggg agcgcggccg  9060
ggggcggtgc cccgcggtgc ggggggggct gcgagggga  caaaggctgc gtgcggggtg  9120
tgtgcgtggg ggggtgagca gggggtgtgg gcgcgtcggt cgggctgcaa ccccccctgc  9180
accccctcc  ccgagttgct gagcacggcc cggcttcggg tgcggggctc cgtacgggc  9240
gtggcgcggg gctcgccgtg ccgggcgggg ggtggcggca ggtgggggtg ccgggcgggg  9300
cggggccgcc tcgggccggg gagggctcgg gggagggacg cggcggcccc cggagcgccg  9360
gcggctgtcg aggcgcggcg agccgcagcc attgcctttt atggtaatcg tgcgagaggg  9420
cgcagggact tcctttgtcc caaatctgtg cggagccgaa atctgggagg cgccgccgca  9480
ccccctctag cgggcgcggg gcgaagcggt gcggcgccgg caggaaggaa atgggcgggg  9540
agggccttcg tgcgtcgccg cgccgccgtc ccctcctccc tctccagcct cggggctgtc  9600
cgcggggggga cggctgcctt cggggggggac ggggcagggc ggggttcggc ttctggcgtg  9660
tgaccggcgg ctctagagcc tctgctaacc atgttcatgc cttcttcttt ttcctacagc  9720
tcctgggcaa cgtgctggtt attgtgctgt ctcatcattt tggcaaagaa ttccgctgcg  9780
actcggcgga gtcccggccg cgcgtccttg ttctaaccg gcgcgccgcc accatgtcta  9840
gattagataa aagtaaagtg attaacagcg cattagagct gcttaatgag gtcggaatcg  9900
aaggtttaac aacccgtaaa ctcgcccaga agctaggtgt agagcagcct acattgtatt  9960
ggcatgtaaa aaataagcgg gctttgctcg acgccttagc cattgagatg ttagataggc 10020
accatactca cttttgccct ttagaagggg aaagctggca agatttttta cgtaataacg 10080
ctaaaagttt tagatgtgct ttactaagtc atcgcgatgg agcaaaagta catttaggta 10140
cacggcctac agaaaaacag tatgaaactc tcgaaaatca attagccttt ttatgccaac 10200
aaggttttc  actagagaat gcattatatg cactcagcgc tgtggggcat tttactttag 10260
gttgcgtatt ggaagatcaa gagcatcaag tcgctaaaga agaaagggaa acacctacta 10320
ctgatagtat gccgccatta ttacgacaag ctatcgaatt atttgatcac caaggtgcag 10380
agccagcctt cttattcggc cttgaattga tcatatgcgg attagaaaaa caacttaaat 10440
gtgaaagtgg gtccgcgtac agccgcgcgc gtacgaaaaa caattacggg tctaccatcg 10500
agggcctgct cgatctcccg gacgacgacg ccccgaaga  ggcggggctg gcggctccgc 10560
gcctgtcctt tctccccgcg ggacacacgc gcagactgtc gacggcccc  ccgaccgatg 10620
tcagcctggg ggacgagctc cacttagacg gcgaggacgt ggcgatggcg catgccgacg 10680
cgctagacga tttcgatctg gacatgttgg gggacgggga ttccccgggt ccgggattta 10740
cccccacga  ctccgccccc tacggcgctc tggatatggc cgacttcgag tttgagcaga 10800
tgtttaccga tgcccttgga attgacgagt acggtgggac gtagggcgcg ccggcaccgg 10860
taccaagctt aagagcgcta gctggccaga catgataaga tacattgatg agtttggaca 10920
aaccacaact agaatgcagt gaaaaaaatg ctttatttgt gaaatttgtg atgctattgc 10980
tttatttgta accattataa gctgcaataa acaagttaac aacaacaatt gcattcattt 11040
tatgtttcag gttcagggggg aggtgtggga ggttttttaa agcaagtaaa acctctacaa 11100
atgtggtatg gaattggagc cccactgtgt tcatcttaca gatggaaata ctgacattca 11160
gaggagttag ttaacttgcc taggtgattc agctaataag tgcaagaaag atttcaatcc 11220
aaggtgattt gattctgaag cctgtgctaa tcacattaca ccaagctaca acttcattta 11280
taaataataa gtcagctttc aagggccttt caggtgtcct gcacttctac aagctgtgcc 11340
atttagtgaa cacaaaatga gccttctgat gaagtagtct tttcattatt tcagatatta 11400
gaacactaaa attcttagct gccagctgat tgaaggctgg gacaaaattc aaacatgcat 11460
ctacaacaat atatatctca atgttagtct ccaaattcta ttgacttcaa ctcaagagaa 11520
tataaagagc tagtctttat acactctttta aggtatgata tcatctggaa agtaacaaaa 11580
ttgatgcaaa tttgaatgaa ctttatcatg gtgtatttac acaatgtgtt tcttctccct 11640
gcaatgtatt tctttctcta attccttcca tttgatcttt catacacaat ctggttctga 11700
tgtatgtttt ttggatgcac ttttcaactc caaaagacag agctagttac tttcttcctg 11760
gtgctccaag cactgtattt gtatctgtat tcaagccctt tgcaatattg tactggatca 11820
ttatttcacc tctaggatgg cttccccagg caacttgtgt tcacccagag actacatttt 11880
gtatcttgtt gacctttgaa cttccaccag tgtctaaaaa taatatgtat gcaaaattac 11940
ttgctatgag aatgtataat aaacaatat  aaaaaggaga agcaaggaga gaaacacagg 12000
tgtgtatttg tgtttgtgtg cttaaaaggc agtgtggaaa aggaagaaat gccatttata 12060
gtgaggagac aaagttatat tacctcttat ctggctttaa aggagatttt gctgagctaa 12120
aaatcctata ttcatagaaa agccttacct gagttgccaa tacctcaatt ctaaaataca 12180
gcatagcaaa actttaacct ccaaatcaag cctctacttg aatccttttc tgagggatga 12240
ataaggcata ggcatcaggg gctgttgcca atgtgcatta gctgtttgca gcctcacctt 12300
ctttcatgga gtttaagata tagtgtattt tcccaaggtt tgaactagct cttcatttct 12360
ttatgtttta aatgcactga cctcccacat tccctttttta gtaaaatatt cagaaataat 12420
ttgggtcccg attttttcccc gtatcccccc aggtgtctgc aggctcaaag agcagcgaga 12480
agcgttcaga ggaaagcgat cccgtgccac cttccccgtg cccgggctgt ccccgcacgc 12540
tgccggctcg gggatgcggg ggagcgccgg accggaccgg agcccgggc  ggctcgctgc 12600
tgccctagcg gggagggac  gtaattacat ccctgggggc tttgggggggg ggctgtccca 12660
ctagattttc cccgtatccc cccaggtgtc tgcaggctca aagagcagcg agaagaagcgttc 12720
agaggaaagc gatcccgtgc caccttcccc gtgcccgggc tgtccccgca cgctgccgtga 12780
tcggggatgc gggggagcgc cggaccggac cggagcccg  ggcggctcgc tgctgcccta 12840
gcggggggag gacgtaatta catccctggg ggctttgggg ggggctgtc  ccatcggatc 12900
ttctagtcct gcaggagtca atgggaaaaa cccattggag ccaagtacac tgactcaata 12960
gggactttcc attgggtttt gcccagtaca taaggtcaat aggggggtgag tcaacaggaa 13020
```

```
agtcccattg gagccaagta cattgagtca atagggactt tccaatgggt tttgcccagt   13080
acataaggtc aatgggaggt aagccaatgg gtttttccca ttactgacat gtatacgcgt   13140
cgacgtcggc gcgttcagcc taaagctttt ttccccgtat cccccaggt gtctgcaggc     13200
tcaaagagca gcgagaagcg ttcagaggaa agcgatcccg tgccaccttc cccgtgcccg   13260
ggctgtcccc gcacgctgcc ggctcggga tgcgggggag cgccggaccg gaccggagcc     13320
ccgggcggct cgctgctgcc ctagcggggg agggacgtaa ttacatccct gggggctttg   13380
ggggggggct gtccctgcgg ccgcgaattc gtaatcatgg tcatagctgt ttcctgtgtg   13440
aaattgttat ccgctcacaa ttccacacaa catacgagcc ggaagcataa agtgtaaagc   13500
ctggggtgcc taatgagtga gctaactcac attaattgcg ttgcgctcac tgcccgcttt   13560
ccagtcggga aacctgtcgt gccagggtc tagccgcggt ctaggaagct ttctaggta     13620
cctctaggga tccactagtt attaatagta atcaattacg gggtcattag ttcatagccc   13680
atatatggag ttccgcgtta cataacttac ggtaaatggc ccgcctggct gaccgcccaa   13740
cgaccccgc ccattgacgt caataatgac gtatgttccc atagtaacgc caatagggac     13800
tttccattga cgtcaatggg tggagtattt acggtaaact gcccacttgg cagtacatca   13860
agtgtatcat atgccaagta cgccccctat tgacgtcaat gacggtaaat ggcccgcctg   13920
gcattatgcc cagtacatga ccttatggga ctttcctact tggcagtaca tctacgtatt   13980
agtcatcgct attaccatgg tcgaggtga gccccacgtt ctgcttcact ctccccatct     14040
cccccccctc cccaccccca attttgtatt tatttatttt ttaattattt tgtgcagcga   14100
tggggcgggg gggggggggg gcgcgcgcca ggcggggcgg ggcggggcga ggggcgggc     14160
ggggcgaggc ggagaggtgc ggcggcagcc aatcagagcg gcgcgctccg aaagtttcct   14220
tttatggcga ggcggcggcg gcggcggccc tataaaaagc gaagcgcgcg gcgggcggga   14280
gtcgctgcgt tgccttcgcc ccgtgccccg ctccgcgccg cctcgcgccg cccgccccgg   14340
ctctgactga ccgcgttact cccacaggtg agcgggcggg acggcccttc tcctccgggc   14400
tgtaattagc gcttggttta atgacggctc gtttcttttc tgtggctgcg tgaaagcctt   14460
aaaagggctcc gggagggccc tttgtgcggg ggggagcggc tcgggggggtg cgtgcgtgtg   14520
tgtgtgcgtg gggagccgcg cgtgcggccc gcgctgcccg gcggctgtga gcgctgcggg   14580
cgcggcgcgg ggctttgtgc gctccgcgtg tgcgcgaggg gagcgcggcc ggggcggtg     14640
ccccgcggtg cggggggggct gcgagggga caaaggctgc gtgcggggtg tgtgcgtggg   14700
ggggtgagca ggggggtgtgg gcgcggcggt cgggctgtaa cccccccctg cacccccctc   14760
cccgagttgc tgagcacggc ccggcttcgg gtgcggggct cgtgcgggg cgtggcgcgg     14820
ggctcgccgt gccgggcggg gggtggcggc aggtggggt gccggcgggg gcggggccgc     14880
ctcgggccgg ggagggctcg ggggaggggc gcggcggccc cggagcgccg gcggctgtcg   14940
aggcgcggcg agccgcagcc attgcctttt atggtaatcg tgcgagaggg cgcagggact   15000
tcctttgtcc caaatctggc ggagccgaaa tctgggaggc gccgccgcac ccctctagc     15060
gggcgggggc gaagcggtgc ggcgccggca ggaaggaaat gggcggggag ggccttcgtg   15120
cgtcgccgcg ccgccgtccc cttctccatc tccagcctcg gggctgccgc aggggacgg     15180
ctgccttcgg gggggacggg gcagggcggg gttcggcttc tggcgtgtga ccggcggctc   15240
tagagcctct gctaaccatg ttcatgcctt cttctttttc ctacagctcc tgggcaacgt   15300
gctggttgtt gtgctgtctc atcattttgg caaagaattc cgttgcgact cggcggagtc   15360
ccggcggcgc gtccttgttc taacccggcg cgccctcagg atggagcctc ccggccgccg   15420
cgagtgtccc tttccttcct ggcgctttcc tgggttgctt ctggcggcca tggtgttgct   15480
gctgtactcc ttctccgatg cctgtgagga gccaccaaca tttgaagcta tggagctcat   15540
tggtaaacca aaaccctact atgagattgg tgaacgagta gattataagt gtaaaaaagg   15600
atacttctat atacctcctc ttgccacccca tactatttgt gatcggaatc atacatggct   15660
acctgtctca gatgacgcct gttatagaga aacatgtcca tatatacggg atcctttaaa   15720
tggccaagca gtccctgcaa atgggactta cgagtttggt tatcagatgc actttatttg   15780
taatgagggt tattacttaa ttggtgaaga aattctatat tgtgaactta aaggatcagt   15840
agcaatttgg agcggtaagc ccccaatatg tgaaaaggtt ttgtgtacac cacctccaaa   15900
aataaaaaat ggaaaacaca cctttagtga agtagaagta tttgagtatc ttgatgcagt   15960
aacttatagt tgtgatcctg cacctggacc agatccattt tcacttattg gagagagcac   16020
gatttattgt ggtgacaatt cagtgtggag tcgtgctgct ccagagtgta aagtggtcaa   16080
atgtcgattt ccagtagtcg aaaatgggaaa acagatatca ggatttggaa aaaaatttta   16140
ctacaaagca acagttatgt ttgaatgcga taagggtttt tacctcgatg gcagcgacac   16200
aattgtctgt gacagtaaca gtacttggga tcccccagtt ccaaagtgtc ttaaagtgct   16260
gcctccatct agtacaaaac ctccagcttt gagtcattca gtgtcgactt cttccactac   16320
aaaatctcca gcgtccagtg cctcaggtcc taggcctact tacaagcctc cagtctcaaa   16380
ttatccagga tatcctaaac ctgaggaagg aatacttgac agtttggatg tttgggtcat   16440
tgctgtgatt gttattgcca tagttgttgg agttgcagta atttgtgttg tcccgtacag   16500
atatcttcaa aggaggaaga agaaaggcac atacctaact gatgagaccc acagagaagt   16560
aaaatttact tctctcggat ccggagccac gaacttctct ctgttaaagc aagcaggaga   16620
cgtggaagaa aaccccggtc ctatgaccgt cgcgcggccg agcgtgcccg cggcgctgcc   16680
cctcctcggg gagctgcccc ggctgctgct gctggtgctg ttgtgcctgc cggccgtgtg   16740
gggtgactgt ggccttcccc cagatgtacc taatgcccag ccagctttgg aaggccgtac   16800
aagttttccc caggatactg taataacgta caaatgtgaa gaaagctttg tgaaaattcc   16860
tggcgagaag gactcagtga tctgcctaa gggcagtcaa tggtcagata ttgaagagtt   16920
ctgcaatcgt agctgcgagg tgccaacaag gctaaattct gcatccctca aacagcctta   16980
tatcactcag aattattttc cagtcggtac tgttgtggaa tatgagtgcc gtccaggtta   17040
cagaagagaa ccttctctat caccaaaact aacttgcctt cagaatttaa aatggtccac   17100
agcagtcgaa ttttgtaaaa agaaatcatg ccctaatccg ggagaaatac gaaatggtca   17160
gattgatgta ccaggtggca tattatttgg tgcaaccatc tccttctcat gtaacacagg   17220
gtacaaatta tttggctcga cttctagttt ttgtcttatt tcaggcagct ctgtccagtg   17280
gagtgacccg ttgccagagt gcagagaaat ttattgccca gcaccaccac aaattgacaa   17340
tggaataatt caaggggaac gtgaccatta tggatataga cagtctgtaa cgtatgcatg   17400
taataaagga ttcaccatga ttggagagca ctctatttat gtactgtgaa taatgatga   17460
aggagagtgg agtggcccac cacctgaatg cagaggaaaa tctctaactt ccaaggtccc   17520
accaacagtt cagaaaccta ccacagtaaa tgttccaact acagaagtct caccaacttc   17580
tcagaaaacc accacaaaaa ccaccacacc aaatgctcaa gcaacacgga gtacacctgt   17640
ttccaggaca accaagcatt ttcatgaaac aaccccaaat aaaggaagtg gaaccacttc   17700
aggtactacc cgtcttctat ctgggcacac gtgtttcacg ttgacaggtt tgcttgggac   17760
```

-continued

```
gctagtaacc atgggcttgc tgacttaggg cgcgccggca ccggtaccaa gcttaagagc  17820
gctagctggc cagacatgat aagatacatt gatgagtttg gacaaaccac aactagaatg  17880
cagtgaaaaa aatgctttat ttgtgaaatt tgtgatgcta ttgctttatt tgtaaccatt  17940
ataagctgca ataaacaagt taacaacaac aattgcattc attttatgtt tcaggttcag  18000
ggggaggtgt gggaggtttt ttaaagcaag taaaacctct acaaatgtgg tatggaattg  18060
gagccccact gtgttcatct tacagatgga aatactgaca ttcagaggag ttagttaact  18120
tgcctaggtg attcagctaa taagtgcaag aaagatttca atccaaggtg atttgattct  18180
gaagcctgtg ctaatcacat tacaccaagc tacaacttca tttataaata ataagtcagc  18240
tttcaagggc ctttcaggtg tcctgcactt ctacaagctg tgccatttag tgaacacaaa  18300
atgagccttc tgatgaagta gtcttttcat tatttcagat attagaacac taaaattctt  18360
agctgccagc tgattgaagg ctgggacaaa attcaaacat gcatctacaa caatatatat  18420
ctcaatgtta gtctccaaat tctattgact tcaactcaag agaatataaa gagctagtct  18480
ttatacactc tttaaggtat gatatcatct ggaaagtaac aaaattgatg caaatttgaa  18540
tgaactttat catggtgtat ttacacaatg tgtttcttct ccctgcaatg tatttctttc  18600
tctaattcct tccatttgat ctttcataca caatctggtt ctgatgtatg tttttttggat  18660
gcacttttca actccaaaag acagagctag ttacttctt cctggtgctc caagcactgt  18720
atttgtatct gtattcaagc cctttgcaat attgtactgg atcattattt cacctctagg  18780
atggcttccc caggcaactt gtgttcaccc agagactaca ttttgtatct tgttgacctt  18840
tgaacttcca ccagtgtcta aaaataatat gtatgcaaaa ttacttgcta tgagaatgta  18900
taattaaaca atataaaaag gagaagcaag gagagaaaca caggtgtgta tttgtgtttg  18960
tgtgcttaaa aggcagtgtg gaaaggaag aaatgccatt tatagtgagg agacaaagtt  19020
atattacctc ttatctggct tttaaggaga ttttgctgag ctaaaaatcc tatattccata  19080
gaaaagcctt acctgagttg ccaatacctc aattctaaaa tacagcatag caaaacttta  19140
acctccaaat caagcctcta cttgaatcct tttctgaggg atgaataagg cataggcatc  19200
aggggctgtt gccaatgtgc attagctgtt tgcagcctca ccttctttca tggagtttaa  19260
gatatagtgt attttcccaa ggtttgaact agctcttcat ttctttatgt tttaaatgca  19320
ctgacctccc acattcctt tttagtaaaa tattcagaaa taatttatca tctggaaagt  19380
aacaaaattg atgcaaattt gaatgaactt tatcatggtg tatttacaca atgtgtttct  19440
tctccctgca atgtatttct ttctctaatt ccttccattt gatctttcat acacaatctg  19500
gttctgatgt atgttttttg gatgcacttt tcaactccaa aagacagagc tagttactttt  19560
cttcctggtg ctccaagcac tgtatttgta tctgtattca agccctttgc aatattgtac  19620
tggatcatta tttcacctct aggatggctt ccccaggcaa cttgtgttca cccagagact  19680
acattttgta tcttgttgac ctttgaactt ccaccagtgt ctaaaaataa tatgtatgca  19740
aaattaccttg ctatgagaat gtataattaa acaatataaa aaggagaagc aaggagagaaa  19800
acacaggtgt gtatttgtgt ttgtgtgctt aaaaggcagt gtggaaaagg aagaaatgcc  19860
atttatagtg aggagacaaa gttatattac ctcttatctg gcttttaagg attttgct  19920
gagctaaaaa tcctatattc atagaaaagc cttacctgag ttgccaatac ctcaattcta  19980
aaatacagca tagcaaaaact ttaacctcca aatcaagcct ctacttgaat cctttttctga  20040
gggatgaata ggcataggct atcaggggct gttgccaatg tgcattagct gtttgcagcc  20100
tcaccttctt tcatggagtt taagatatag tgtatttttcc caaggtttga actagctctt  20160
catttcttta tgtttaaat gcactgacct cccacattcc ctttttagta aaatattcag  20220
aaataattta tcccggcttg tcgacgacgg aaatccggct tgtcgacgac ggcggtctcc  20280
gtcgtcagga tcatccggcc ggccatcagg acatagcgtt ggctacccgt gatattgctg  20340
aagagcttgg cggcgaatgg gctgaccgct tcctcgtgct ttacggtatc gccgctcccg  20400
attcgcagcg catcgccttc tatcgccttc ttgacgagtt cttctgaggg gatcaattct  20460
ctagagctcg ctgatcagcc tcgactgtgc cttctagttg ccagccatct gttgtttgcc  20520
cctccccgt gccttccttg accctggaag gtgccactcc cactgtcctt tcctaataaa  20580
atgaggaaat tgcatcgcat tgtctgagta ggtgtcattc tattctgggg ggtggggtgg  20640
ggcaggacag caaggggag gattgggaag acaatagcag gcatgctggg gatgcggtgg  20700
gctctatggc ttctgaggcg gaaagaacca gctgggggcg cgcacctcga ccatctccag  20760
gatgcctttg atagacgtgg gtcctctgcg ttcctttaaa gtgtttgaga tcaagtccga  20820
gaagaggtgg caagacatgc gatcgcgcta gtttaaaata catcattgca atgaaaataa  20880
atgtttttta ttaggcagaa tccagatgct caaggccctt cataatatcc cccagtttag  20940
tagttggact tagggaacaa aggaacctttt aatagaaatt ggacagcaag aaagctctag  21000
ctttagaaga actcatcaag aagtctgtag aaggcaattc tctgggagtc aggggctgca  21060
atgccataga gcactaggaa cctgtctgcc cactctcccc ctagctcttc tgctatgtcc  21120
ctggttgcta gggcaatgtc ctggtacctg tcagccactc ccagcctgcc acagtctatg  21180
aagccagaga accttccatt ttcaaccatg atgttgggaa ggcaggcatc cccatgagtc  21240
accactaggt cctcaccatc tggcatggat gccttgagcc tggcaaatag ttcagcaggg  21300
gccaggccct ggtgttcttc atccaagtca tcttggtcca ccaggccagc ctccatcctg  21360
gttctggccc tctctatcct gtgcttggcc tggtggtcaa aggggcaggt ggctgggtca  21420
agggtgtgga gtcttctcat ggcatcagcc atgattgaca cttttctcagc tggagctagg  21480
tgagaggaaa ggaggtcctg cccaggcacc tcacctagta ggagccagtc ccttccagct  21540
tctgtgacca catcaaggac agctgcacag gggaccccag ttgttgccaa ccaggagagt  21600
ctggcagcct catcctggag ctcattgaga gccccactga ggtctgtctt tacaaaaagg  21660
actggctgc cttgggctga aagtctgaaa actgctgcat cagagcaacc aatggtctgc  21720
tgtgcccagt catagccaaa cagtctctca acccaggcag ctggagaacc tgcatgtagg  21780
ccatcttgtt caatcatgat ggctcctcct gtcaggagag gaaagagaag aaggttagta  21840
caattgctat agtgagttgt attatactat gcttatgatt aattgttaaa ctagggctga  21900
agggttcata gtgccacttt tcctgcactg ccccatctcc tgcccaccct ttcccaggca  21960
tagacagtca gtgacttacc aaactcacag gagggagaag gcagaagctt tttgcaaaag  22020
cctaggctca tgagacaata accctgataa atgcttcaat aatattgaaa aaggaagagt  22080
accaggtatg agtattcaac atttccgtgt cgcccttatt cccttttttg cggcattttg  22140
ccttcctgtt tttgctcacc cagaaacgct ggtgaaagta aaagatgctg aagatcagtt  22200
gggtgcacga gtgggttaca tcgaactgga tctcaacagc ggtaagatcc ttgagagttt  22260
tcgccccgaa gaacgttttc caatgatgag cacttttaaa gttctgctat gtggcgcggt  22320
attatcccgt attgacgccg ggcaagagca actcggtcgc cgcatacact attctcagaa  22380
tgacttggtt gagtactcac cagtcacaga aaagcatctt acggatggca tgacagtaag  22440
agaattatgc agtgctgcca taaccatgag tgataacact gcggccaact tacttctgac  22500
```

-continued

```
aacgatcgga ggaccgaagg agctaaccgc ttttttgcac aacatggggg atcatgtaac    22560
tcgccttgat cgttgggaac cggagctgaa tgaagccata ccaaacgacg agcgtgacac    22620
cacgatgcct gtagcaatgg caacaacgtt gcgcaaacta ttaactggcg aactacttac    22680
tctagcttcc cggcaacaat taatagactg gatggaggcg gataaagttg caggaccact    22740
tctgcgctcg gcccttccgg ctggctggtt tattgctgat aaatctggag ccggtgagcg    22800
tgggtctcgc ggtatcattg cagcactggg gccagatggt aagccctccc gtatcgtagt    22860
tatctacacg acggggagtc aggcaactat ggatgaacga aatagacaga tcgctgagat    22920
aggtgcctca ctgattaagc attggtaatc gcgactgtca gaccaagttt actcatatat    22980
actttagatt gatttaaaac ttcatttta atttaaaagg atctaggtga agatcctttt    23040
tgataatctc atgaccaaaa tcccttaacg tgagttttcg ttccactgag cgtcagacca    23100
cgtgcccgta gaaaagatca aaggatcttc ttgagatcct ttttttctgc gcgtaatctg    23160
ctgcttgcaa acaaaaaaac caccgctacc agcggtggtt tgtttgccgg atcaagagct    23220
accaactctt tttccgaagg taactggctt cagcagagcg cagataccaa atactgttct    23280
tctagtgtag ccgtagttag gccaccactt caagaactct gtagcaccgc ctacatacct    23340
cgctctgcta atcctgttac cagtggctgc tgccagtggc gataagtcgt gtcttaccgg    23400
gttggactca agacgatagt taccggataa ggcgcagcgg tcgggctgaa cggggggttc    23460
gtgcacacag cccagcttgg agcgaacgac ctacaccgaa ctgagatacc tacagcgtga    23520
gctatgagaa agcgccacgc ttcccgaagg gagaaaggcg gacaggtatc cggtaagcgg    23580
cagggtcgga acaggagagc gcacgaggga gcttccaggg ggaaacgcct ggtatcttta    23640
tagtcctgtc gggtttcgcc acctctgact tgagcgtcga tttttgtgat gctcgtcagg    23700
ggggcggagc ctatggaaaa acgccagcaa cgcggccttt ttacggttcc tggccttttg    23760
ctggcctttt gctcacatgg ctcgacagat ttaatcggga ggatccggag agggcagtta    23820
atcgctcgag tgtaca                                                    23836

SEQ ID NO: 10          moltype =   length =
SEQUENCE: 10
000

SEQ ID NO: 11          moltype = DNA   length = 29705
FEATURE                Location/Qualifiers
source                 1..29705
                       mol_type = other DNA
                       organism = synthetic construct
SEQUENCE: 11
aaatacatca ttgcaatgaa aataaatgtt ttttattagg cagaatccag atgctcaagg    60
cccttcataa tatcccccag tttagtagtt ggacttaggg aacaaaggaa cctttaatag    120
aaattggaca gcaagaaagc tctagcttta gaagaactca tcaagaagtc tgtagaaggc    180
aattctctgg gagtcagggg ctgcaatgcc atagagcact aggaacctgt ctgcccactc    240
tcccctagc tcttctgcta tgtccctggt tgctagggca atgtcctgct acctgtcagc    300
cactcccagc ctgccacagt ctatgaagcc agagaacctt ccattttcaa ccatgatgtt    360
gggaaggcag gcatccccat gagtcaccac taggtcctca ccatctggca tggatgcctt    420
gagcctggca aatagttcag caggggccag gccctggtgt tcttcatcca agtcatcttg    480
gtccaccagg ccagcctcca tcctggttct ggccctctct atcctgtgct tggcctggtg    540
gtcaaagggg caggtggctg ggtcaagggt gtggagtctt ctcatggcat cagccatgat    600
tgacactttc tcagctggag ctaggtgaga ggaaaggagg tcctgcccag gcacctcacc    660
tagtaggagc cagtcccttc cagcttctgt gaccacatca aggacagctg cacaggggac    720
cccagttgtt gccaaccagg agagtctggc agcctcatcc tggagctcat tgagagcccc    780
actgaggtct gtctttacaa aaaggactgg cctgcctgg gctgaaagtc tgaaaactgc    840
tgcatcagag caaccaatgg tctgctgtgc ccagtcatag ccaaacagtc tctcaaccca    900
ggcagctgga gaacctgcat gtaggccatc ttgttcaatc atgatggctc ctcctgtcag    960
gagaggaaag agaagaaggt tagtacaatt gctatagtga gttgtattat actatgtta    1020
tgattaattg ttaaactagg gctgcagggt tcatagtgcc actttcctg cactgcccca    1080
tctcctgccc accctttccc aggcatagac agtcagtgac ttaccaaact cacaggaggg    1140
agaaggcaga agcttttttgc aaaagcctag gctcatgaga caataaccct gataaatgct    1200
tcaataatat tgaaaaagga agagtatgag tattcaacat ttccgtgtcg cccttattcc    1260
cttttttgcg gcattttgcc ttcctgtttt tgctcaccca gaaacgctgg tgaaagtaaa    1320
agatgctgaa gatcagttgg gtgcacgagt gggttacatc gaactggatc tcaacagcgg    1380
taagatcctt gagagttttc gccccgaaga acgttttcca atgatgagca cttttaaagt    1440
tctgctatgt ggcgcggtat tatcccgtat tgacgccggg caagagcaac tcggtcgccg    1500
catacactat tctcagaatg acttggttga gtactcacca gtcacagaaa agcatcttac    1560
ggatggcatg acagtaagag aattatgcag tgctgccata accatgagtg ataacactgc    1620
ggccaactta cttctgacaa cgatcggagg accgaaggag ctaaccgctt ttttgcacaa    1680
catggggat catgtaactc gccttgatcg ttgggaaccg gagctgaatg aagccatacc    1740
aaacgacgag cgtgacacca cgatgcctgt agcaatggca acaacgttgc gcaaactatt    1800
aactggcgaa ctacttactc tagcttcccg gcaacaatta atagactgga tggaggcgga    1860
taaagttgca ggaccacttc tgcgctcggc ccttccggct ggctggttta ttgctgataa    1920
atctggagcc ggtgagcgtg ggtctcgcgg tatcattgca gcactggggc cagatggtaa    1980
gccctcccgt atcgtagtta tctacacgac ggggagtcag gcaactatgg atgaacgaaa    2040
tagacagatc gctgagatag gtgcctcact gattaagcat tggtaactgt cagaccaagt    2100
ttactcatat atactttaga ttgatttaaa acttcatttt taatttaaaa ggatctaggt    2160
gaagatcctt tttgataatc tcatgaccaa aatcccttaa cgtgagtttt cgttccactg    2220
agcgtcgac cccgtagaaa agatcaaagg atcttcttga tcctttttt ttctgcgcgt    2280
aatctgctgc ttgcaaacaa aaaaaccacc gctaccagcg gtggtttgtt tgccggatca    2340
agagctacca actctttttc cgaaggtaac tggcttcagc agagcgcaga taccaaatac    2400
tgttcttcta gtgtagccgt agttaggcca ccacttcaag aactctgtag caccgcctac    2460
atacctcgct ctgctaatcc tgttaccagt ggctgctgcc agtggcgata agtcgtgtct    2520
taccgggttg gactcaagac gatagttacc ggataaggcg cagcggtcgg ctgaacggg    2580
gggttcgtga cacagcccca gcttggagcg aacgacctac accgaactga gatacctaca    2640
gcgtgagcta tgagaaagcg ccacgcttcc cgaagggaga aaggcggaca ggtatccggt    2700
```

-continued

```
aagcggcagg gtcggaacag gagagcgcac gagggagctt ccagggggaa acgcctggta   2760
tctttatagt cctgtcgggt ttcgccacct ctgacttgag cgtcgatttt tgtgatgctc   2820
gtcaggggg cggagcctat ggaaaaacgc cagcaacgcg gccttttac ggttcctggc   2880
cttttgctgc cctttgctc acatggctcg acagatttaa ttaaacagtg tgactaggga   2940
ggcaaaacat acctactaaa gggtggtagc ataattcagt tcttatgtga gtatgtgtat   3000
gtgtgtgagt atgtgcacat gcacatacat tttaaaaggt ctgtaatata ctaacatgtt   3060
catagtggtt acacctagct tataggtaac atttttttccc ctgtatcctt gtttgtgttt   3120
atcaaatttt cataacagta atggtagaag gagtacctga catggtacca tacatgctct   3180
gggccctgcc taatttctca atttcctta ttgcccatac ccccattgct tgacaagcat   3240
aagtccatac tggcttgttt ttcgttcctc agactcagta caccatgtag ctccatgccc   3300
tgggtctttg tatgtgctat ttctactgct tagagtgcta ttgcccctga ccaccacgtg   3360
gtcagcaact tctcttctgt gtctgtgtcc atggtctatg attccagatg tcatcttcac   3420
taactaccct tctaatatgc ccttccatcc cacccgtcct catccttacc ccagccactc   3480
tctatttggt ggctctgttt tattttcttc ctagctcatc actctttgaa atgaacttat   3540
ttacttattc attatttgct tctttcacta gaatgaatgc tccatgagag cagggacctg   3600
ctttatcttg ctcgccactg tattctcagt gcctagaact acgtctggca catagtaggt   3660
gctcaataaa tatcgatcaa atgaaagaat gagcaaacga acaaatgaac aacacgtgag   3720
gtaggcatca tgattccatt caacagagga gaaaaacaga cttaaagaat tgaagtggtg   3780
gagctgcatt ttgatcttga ctgactccaa catccatgct cttgaccact gtgcatctcc   3840
agagtgtaat gaacatactt tacttttata ttccaccaaa ataacaaagc catgcccatg   3900
ttagtagaga gttaatcgac agtgcccta aaatatgcat gcacccaggg tacaactatg   3960
catgctgccc tgtgttttca gttggatcca aatgaattgc cgtaaacaaa gaggggattc   4020
aatgtctttg actagtttgg gatattttcc tagtaaccaa ctttgcaaaa taaagccact   4080
aatgacaagg agctttgttc tacttctgca tcactcaact gtcaattttt atctcttgca   4140
agacttctaa tctactagaa cttttgtttt tctgtgattt ctgaacagag aagactaatc   4200
caaaccctgt cattccagag gaatggaaag cccaattcat taaaaccgtc ggcgcgttca   4260
gcctaaagct tttttctccg tatccccca ggtgtctgca ggctcaaaga gactcatgtc   4320
tcctatgtct catctaaatg gatgaggttt gagagttccc atcacggcat ggtgggaaacg   4380
aatccgacta ggagccataa gttcacggct tcgatccctg gcctcgctca gggggttaag   4440
gatccggtgt tgctgtgagc tgtggtgtag gtcacagatg cggttcggat ctggcgttgc   4500
tgcggctgtg gtgtaggctg gtggctgtag ctccgatttg accctagcc tagggacctc   4560
catatgccgt gggtatggcc ctaaaaagcc aaataaaata aaataagtaa atggttgagg   4620
tttgacacag aaagtttatt tatttatgta tttacttatc ttttttttttt tttttttttt   4680
tgtcttttctg ctatttcttg ggctgctccc gcggcatatg gaggttccca ggctaggggt   4740
cgaattggag ctacagccac cagcctacac cacagccgca gcaatgccag atccgagccg   4800
cctctgtgac ctacaccaca gctcatggca acgctggatc gttaacccac tgagcaaggg   4860
ctgggaccga acccgcaacc tcatggttcc tagtcggatt cgttaaccac tgcgccatga   4920
cgggaactcc tacttatcta ttttttaaag catatggaag ttcccaggct aggggttga   4980
atcggagctg caactgccgg cttacaccac agccagagca acgccggatc tgagcagtgt   5040
ctgggaccta caccacagct cacagccaca ccggatcctc aatccactga atgaggccag   5100
gaatcaaacc tgtgtcctca tggatactag tcagattcat ttccgctgag caatgacagg   5160
aactcctgac acagaaattt tagattaaaa ttgaagatga gcccttcct tttgtacgac   5220
ctttgtgtgc agattttcga ggataagtcc ttgagcttga agtttaggg tcatggatcc   5280
tcataacagt ttcctggcct gtgaggcttg gatctcagta taaacagaag tgctggcagc   5340
agtagacaca gcagcagctg ttttcaggaa caaatactgg gcacctgcct tgtggacctg   5400
cctgactcca ccactctctt gggtatccac aaagtggacc cagaggttca gagcagccct   5460
gggatccaaa ttttttttaat ttatttttta tcttttattt tttgtctttt cgaaatttt   5520
agggctacac ccatgagata tggaggttcc caggctaagg gtccaatcgg agctacaact   5580
gccggcctac accacagctc atggcaatgc tggatcctta acccgctgag cgaggccagg   5640
gatcaaaccc acaacctcat gattcctagt tggattcgtt aaccactgag ccacgatggg   5700
aactccctgg gatgcaaatt ttgtcatcta gccctaggat gtagctatca tcctgatttg   5760
agaagagagg cagagtctca ggtggcttct ctctcatgaa tgcagagcta agggtggcca   5820
cacgtacttg agttcatccg atgcacacag cattgtgcta aaatattgac catttggccc   5880
ttttgctgac ttttggtttg agggatatga ccttcatgag catacagagg ataatatgta   5940
tgcatgtatg catgtgtgta cacatgtgcg catgcatgta tatacctgca taattatgta   6000
tttgtttatg tatgcaggtg catgtgtatg tatatatttta ttatttattt atttgggggc   6060
cacacccatg acatttggaa gttcctggga cagagattga atcccagcca cagctttgac   6120
ctacgccatg gacacagcaa cactggattc ttaacccct gtgccacagc gggaactcct   6180
agaagatagt atttcatgat gatatttgac taaaaataagg ggtcaggctt tgaagtttaa   6240
ataaattcga ccagataaat ggccatccag gaagttatac tttgccttgt tcaaatttgg   6300
accacgggga aggtggttgg cgacatgtaa cagaaatctg actccagtgc aggtttcgct   6360
cccgtgacgg gaagcccaga ggtgggcagc cctaaggctg gggctctgat ttcatgatgc   6420
tcttagcatc ttgagtccct tccctcttct tgctttttatc tcagcctcgg gctgctgcac   6480
cttctgtctt tgtggtgagt ctacctattc cacttagctc catttcaggg tgtatttcca   6540
cgacttcgtt agagtaaggt tggggccagc tgtgctctgc cggcaggagg tgtgcttgca   6600
ggggccatgg atgtggccag gacctaatgt gacggtgggg agcaggatgg ggatgaggat   6660
gtgaccacag agccttggga accacgtcat ccacgtcata cactgagagc aggtggttct   6720
catgcaggtg catcagaatc ccgaggacgg cttgtccaaa cccagatggc tgggcccaag   6780
ccctgagctc ccgatttggg aggccttggc tgggcccga aatctgcctt cctgactaga   6840
ccgagtgatg aatggtgttc atagacaaga catacactaa cactggtctt ggggggctcct   6900
tgccacaccc tgaaggggtc cgtgaaactg acggggccag agaaggtgct ggttcctcca   6960
tggaaggtct cagtgaggcc attctgctgc ccggctgggt cacgctgggg gagtgagggt   7020
gcatcccctc ctgggatctg gtcaaaggca gattctgatt ctggaagcac ggggtagggc   7080
cagagatgcc accttctaac aagcccccag gtgaagatgt tgacctggga ccttatggtg   7140
gggggtggcg gagctcaagg tggcagacac ctccctctct ctcaacctgt gtcacagcag   7200
ggccatccta ctggctctcg ctcggccaga gatggcgatg ccagaacaca ctggggcagg   7260
gtgtccacat ttttgtcact tccactgagc cctgggact gactcattta aatgacattc   7320
tcaactcttt ggaaagaagc tgggccagaa atggaaatgg cagcaaacac tttttgggaa   7380
acaggaagcc aatttttttt ttcaatcatg attttcccca gattcagaga ctgcttaact   7440
```

-continued

```
cccaatgaaa tactttttaga ttacgagcta aaataccgaa aagctgtcaa gctcaagacc  7500
acaggaaaac agccgaagaa caaacaccat gagaaaacag tcacagagtg cctctgcggc  7560
ggatttcaag ttccagactt ccttgctgtc agctgtgtgt acttgtcccg cctgcagtag  7620
gaccagctgg ggtttaagtc tgtaccatgg acactgctgc caggattctc ctctgcatct  7680
gctgacttcc agctcttcag ggccagctgg ccataggagc ataaactgac atccagttcc  7740
aggaggcagc atctgtcccc atggcctgca ggacaccaga tcagtagagg ccccagggc   7800
cacctttcct gtgggggccc ttgaagggac ccgggaaggc tggatcttgc taaagcttcc  7860
acaagtccct tccaaaggag agtaaaattct aaacagaagc ttttgccagt gcttctctgg  7920
gatctggctt caggattatt cctagtctga aaagtcttcc tggtggtttg gacacgggca  7980
aatgcttggt gggtgggctg gctctggatg caggtgagtg gggtcggaag ttctccctcc  8040
ttcccacaaa gcttgacgga gccagggggca cccgcgggcc tgtggatggg agaggggttt  8100
ctggtgacgg actcaagtct tggcagcccc tgacccccaga gcaggctccc tccccacagc  8160
tgctctccgt gagtccttca cttgcccaag ttcaagatgt acccagttct ggagctgcca  8220
aaccatcctg catcctgatg tcagccaccc aagttctggg gtagctggtc tgccacccag  8280
gtggatgaaa agaggccaca tacctgcacc agcatctgcg aatctctgaa gaacatcaat  8340
aataaaaaga caactaaccc agttaaaaca caggtagaga atctgaacag acattcatcg  8400
gaagaagaat tacgactggc caaaaagctc ataaaaagat ggtcaaagtc attggtcagg  8460
gaaatgtaaa tcaaaccgca ttgagatacc atctcactcc ctctcggatg gctggaatga  8520
aaaaaaacct cttcttttcct cccttttcatt gtcttggcac ccttgtggaa attaattgac  8580
taaaattcat gaaatacaaa aatttttagg agttcccgtc gtggctcagt ggttaacaaa  8640
tctgactagg aaccatgagg tttcaggttc gattcctggc ctcactcagt gggttaggga  8700
tctggtgttg ccatgagctg tggtgtaggt cacagacgca gctcggatcc cgcattgctg  8760
tggctctggc gtaggccggc ggctacagct ctgattcaac ctctagcctg ggaatagccc  8820
aagaaatggc aaaaagacca aaaaaaaaaa aaaaaaaaaa actcgttttg agcatttttg  8880
catgtgtaca ttgtccattt gtgtgccttc caagatttat ttttggagtc tcaactctgt  8940
cattgattta tgtctctcct taggccagaa ccacactgtt ttggtgacca tggctttgta  9000
gtaaaatttg aaatctgaaa gtgtgagccc tcctgttttg tttctcttct ccatgattag  9060
tttggttatt cagagtccct tgaatttcca ggtgaatttt aggattagca ggaaaatttc  9120
tgcagagatg gcagcagaga tttttaatag ggattatgtt gaatctggag gttaatttca  9180
gttttgctac cttgactgta ttaagtcttc cagtctataa gcataagatg tcttttttatt  9240
tacttaggtc tttttaaaatt tctttgggca ctcccattgt ggtgcatcgg aaatgaatcc  9300
gactagtatc cacaagaaca caggttcaat ccctggcatt gctcagtggg ttaaggatcc  9360
tgcattgcca tgaagaactg tggtggaggc cagcagctgc agctctgatt tgaccccctag  9420
cctgggaact tccatatgcc ttgggtatgg ccctaaaaag caaactaagt aagtaagtaa  9480
ataaataaat gaataaataa aatttctttc aacattgtaa ttttgtaatt tttgtaattt  9540
tcagagcgta cattttgccc tttcaataca ttattcctac atatttttatt cttttttgata  9600
ctattataaa tgaaatttat aattaattca tttatatgaa tttcattttc aatttgcata  9660
ttgctactac aatagaaatg cactttttaa ttatttttat ggccatacta tatatatatg  9720
tgtgtgtgtg tgtatgtgtg tcattttact gtacagcaga aattgacaca acattgtaaa  9780
tcaactacac ttaaaaaatg aagaaataac cacctgtgat tatggctact gtgttggaca  9840
ctttaggcat cccccccaccc cgtccccgcc ccacacccct gagtgctagt gacggatgtt  9900
cccacccagg gggcctggag cctttatcac cagccatcgg gaatcagaac cgtatctcac  9960
agtccccatg cctggagcac ctggaattgt gcccttgaac tcgtgggtgt tctgcttctc  10020
agtgggagaa gcttaggttc taagtcagag cagggacagc ccccatgtgc tcaggaccca  10080
gtgtgaaggg gtctgcctca ggggacctgg gggttacaag ggtaagagaa ggtgttcatg  10140
ttggaactag aagttctttt tcactgctct gaagaaaaaa gctgcctccc acccttggta  10200
cagctcttct gctaacagtg aatcaggcag aacgtgttca agaagtgacc cagcctggtg  10260
ggggccagac ctgacccttg atggtccctc aaccccctccg agggtcccgc ccttcctttta  10320
ctgctttgtt gtctgtcctg agaggtttgg ctaatgtcga accaagggtg tggctggtcc  10380
tgtcccctttt cctgtctcac gcacccacct ctgaagtctc tgtagctggt tccagccggg  10440
atctggagcc actcccccg ccccaggccc agtggtacag actcttgcag agtcggggcc  10500
ccctgactca gccccaccgc cagcgggatg tcaggccagc acccgcccca ctcccactga  10560
tctgggggggg gtgtctttcc ttcctccttc caaaggagcc tcagaccttc ctgtggggca  10620
cggggggcagt gggattcagg aggctctgag tcagcaggcc ggcattgagg agtataaagg  10680
gaccccagtt cctcccccctt tcacttgtgg cttatcgccg cccacccctg ccccaaggtc  10740
actgcggtca gtacagtcct cagctgccag caggtgcctg tctttacttg tgaggccgcc  10800
acgctctcct gtttctccag gtctgggctc tgttggaagt gggggcccga cccccgggta  10860
agatggggga tctgcgtgtc ctgccctcag aggcctcctc ctccccgcac ccctaaccct  10920
ttcagcccaa caaggctgga gatctcccac atctttggct tcgttaagag ttcaacagcg  10980
ccgccacccg gcatgtcgct gagcagagga tggcacaggt gttaaaaaa aaaaaaaggt  11040
tgccacactc cgttcggttt tgggcccacc cttttcgcatt cctggagcct gagtaagcgg  11100
ataaggctgt gaaagtgaca gattcctgcc acctccttcc agcgctcatg cacagggacc  11160
gcccctcttc ggtgtcctttt gctgcacaag tgcatttgca cattcctgtc tcaatctggt  11220
ttctccccct taaaagatgg gaatgtgacc tgcttggagc cccctgcctc gccagggcac  11280
cccatccgtc ccttcagggg tggagatgga ctgtccctct gcaaggctgg atgaactcag  11340
accaaacagg ccaacttgct ccccaaatac gcccacccct accgggctgc aggaattcgc  11400
ctgtcaccac tgctgaaggg tgaccttgca gccctgagag catccccatg acttgcccac  11460
cagatgaagt ctggttgtgg caggtcgcgc tcagggactc ccgggtccca cctgggggtg  11520
ggaggatcct cctttgctcg tggtcgcccc agccacgccc tggctctctc tccttgcccc  11580
ccagagctcc gtgccccggc ggaggcggtc tggctctctc tccttgcccc tctctccttg  11640
ccctagcag cccttctcct aaaccctctg agcagcgggc acctcctccc gaggccctgg  11700
gctaagtccc caccctttcat ctcaagccctt cctccttgac tccctcttcc cagagttcct  11760
tgaaataggt ggtaagtaca caccgatgac ggaaaacaaa gactaagagg ttaaagaggg  11820
ctgaggatta cggcccggt aggggctgcgc gcgagggggt cgagtggccg ggcggtcccg  11880
ttgccgggca gacagaggtg cggttctccc gggcgcctgc gctgccggcc cgcccggag  11940
ccctcccagc cggcgccag tttactcatc ccggagaggt gatcccgggc gcgagggcgg  12000
gcgcaggggc tccggagaac ccagtaatcc gagaatgcag catcagccct tcccaccagg  12060
cacttccttc ctttttcccga acgtccagga aggggggccg cgcacttata aactcgggcc  12120
ggacccgccg gcctgtcaga ggctgcctcg ctggggctgc gcgcgcggc cggacacatc  12180
```

-continued

```
tggtccgaga ccaacgcgag cgactgtcac tggcagctcc ctgcgcctct cagccccggc  12240
cgggcccctg cgcttggcgt gctgacacca tgcttggggt cctggtcctt ggcgcgctgg  12300
ccctggccgg cctgggggttc cccgcacccg cagagccgca gccgggtggc agccagtgcg  12360
tcgagcacga ctgcttcgcg ctctacccgg gccccgcgac cttcctcaat gccagtcaga  12420
tctgcgacgg actgcggggc cacctaatga cagtgcgctc ctcggtggct gccgatgtca  12480
tttccttgct actgaacggc gacggcggcg ttggccgccg gcgcctctgg atcggcctgc  12540
agctgccacc cggctgcggc gaccccaagc gcctcgggcc cctgcgcggc ttccagtggg  12600
ttacgggaga caacaacacc agctatagca ggtgggcacg gctcgacctc aatgggggctc  12660
ccctctgcgg cccgttgtgc gtcgctgtct ccgctgctga ggccactgtg cccagcgagc  12720
cgatctggga ggagcagcag tgcgaagtga aggccgatgg cttcctctgc gagttccact  12780
tcccagccac ctgcaggcca ctggctgtgg agcccggcgc cgcggctgcc gccgtctcga  12840
tcacctacgg caccccgttc gcggcccgcg gagcggactt ccaggcgctg ccggtgggca  12900
gctccgccgc ggtggctccc ctcggcttac agctaatgtg caccgcgccg cccggagcgg  12960
tccaggggca ctgggccagg gaggcgccgg gcgcttggga ctgcagcgtg gagaacggcg  13020
gctgcgagca cgccgtgcaat gcgatccctg gggctccccg ctgccagtgc ccagccggcg  13080
ccgccctgca ggcagacggg cgctcctgca ccgcatccgc gacgcagtcc tgcaacgacc  13140
tctgcgagca cttctgcgtt cccaaccccg accagccggg ctcctactcg tgcatgtgcg  13200
agaccggcta ccggctggcg gcgaccaac accggtgcga ggtggacggt ggcgtggat gactgcatac  13260
tggagcccag tccgtgtccg cagcgctgtg tcaacacaca gggtggcttc gagtgccact  13320
gctaccctaa ctacgacctg gtggacggcg agtgtgtgga gcccgtggac ccgtgcttca  13380
gagccaactg cgagtaccag tgccagcccc tgaaccaaac tagctacctc tgcgtctgcg  13440
ccgaggggctt cgcgcccatt ccccacgagc cgcacaggtg ccagatgttt tgcaaccaga  13500
ctgcctgtcc agccgactgc gacccccaaca cccaggctag ctgtgagtgc cctgaaggct  13560
acatcctgga cgacggtttc atctgcacgg acatcgacga gtgcgaaaac ggcggcttct  13620
gctccggggt gtgccacaac ctccccggta ccttcgagtg catctgcggg cccgactcgg  13680
cccttgcccg ccacattggc accgactgtg actccggcaa ggtggacggt ggcgaacggg  13740
gctctggcga gcccccgccc agcccgacgc ccggctccac cttgactcct ccggccgtgg  13800
ggctcgtgca ttcgggcttg ctcataggca tctccatcgc gagcctgtgc ctggtggtgg  13860
cgcttttggc gctcctctgc cacctgcgca agaagcaggg cgccgccagg gccaagatgg  13920
agtacaagtg cgcggcccct tccaaggagg tagtgctgca gcacgtgcgg accgagcgga  13980
cgccgcagag actcggatcc ggagagggca gaggaagtct tctaacatgc ggtgacgtgg  14040
aggagaatcc cggccctatg ttgacaacat tgctgccgat actgctgctg tctggctggg  14100
cctttttgtag ccaagacgcc tcagatggcc tccaaagact tcatatgctc cagatctcct  14160
acttccgcga cccctatcac gtgtggtacc agggcaacgc gtcgctgggg ggacacctaa  14220
cgcacgtgct ggaaggccca gacaccaaca ccacgatcat tcagctgcag cccttgcagg  14280
agcccgagag ctgggcgcgc acgcagagtg gcctgcagtc ctacctgctc cagttccacg  14340
gcctcgtgcg cctggtgcac caggagcgga ccttggcctt tcctctgacc atccgctgct  14400
tcctgggctg tgagctgcct cccgagggct ctagagccca tgtcttcttc gaagtggctg  14460
tgaatggggag ctcctttgtg agtttccggc cggagagagc cttgtggcag gcagacaccc  14520
aggtcacctc cggagtggtc acctttcaccc tgcagcagct caatgcctac aaccgcactc  14580
ggtatgaact gcggggaattc ctggaggaca cctgtgtgca gtatgtgcag aaacatattt  14640
ccgcggaaaa cacgaaaggg agccaaacaa gccgctccta cacttcgctg gtcctgggcg  14700
tcctgtggg cagtttcatc attgctggtg tggctgtaag catcttcctg tgcacaggtg  14760
gacggcgatg ttgagcgcgg ccgcttccct ttagtgaggg ttaatgcttc gagcagacat  14820
gataagatac attgatgagt ttggacaaac cacaactaga atgcagtgaa aaaaatgctt  14880
tatttgtgaa atttgtgatg ctattgcttt atttgtaacc attataagct gcaataaaca  14940
agttaacaac aacaattgca ttcattttat gtttcaggtt caggggggaga tgtgggaggt  15000
tttttaaagc aagtaaaacc tctacaaatg tggtaaaatc cgataaggat cgatgggaca  15060
gcccccccc aaagcccca gggatgtaat tacgtccctc ccccgctagg gcagcagcga  15120
gccgcccggg gctccggtcc ggtccggcgc tcccccgcat ccccgagccg gcagcgtgcg  15180
gggacagccc gggcacgggg aaggtggcac gggatcgctt tcctctgaac gcttctcgct  15240
gctctttgag cctgcagaca cctgggggga tacggggaaa atctagtggg acagcccccc  15300
cccaaagccc ccaggatgt aattacgtcc ctccccgct anggcagcag cgagccgccc  15360
ggggctccgg tccggtccgg cgctcccccg catccccgag ccggcagcgt gcggggacag  15420
cccgggcacg gggaaggtgg cacgggatcg ctttcctctg aacgcttctc gctgctcttt  15480
gagcctgcag acacctgggg ggatacgggg aaaaatcgat gggacagccc cccccaaag  15540
cccccaggga tgtaattacg tccctccccc gctagggcag cagcgagccg cccggggctc  15600
cggtccggtc cggcgctccc ccgcatcccc gagccggcag cgtgcgggga cagcccgggc  15660
acggggaagg tggcacggga tcgctttcct ctgaacgctt ctcgctgctc tttgagcgtc  15720
cagacacctg gggggatacg gggaaaatct agtgggacag cccccccca aagccccag  15780
ggatgtaatt acgtccctcc cccgctaggg cagcagcgag ccgcccgggg ctccggtccg  15840
gtccggcgct cccccgcatc cccgagccgg cagcgtgcgg ggacagcccg gcacggggga  15900
aggtggcacg ggatcgcttt cctctgaacg cttctcgctg ctctttgagc ctgcagacac  15960
ctgggggat acggggaaaa atcgatagcg ataaggatcc actagttatt aatagtaatc  16020
aattacgggg tcattagttc atagcccata tatggagttc cgcgttacat aacttacggt  16080
aaatggcccg cctggctgac cgcccaacga cccccgccca ttgacgtcaa taatgacgta  16140
tgttcccata gtaacgccaa tagggacttt ccattgacgt caatgggtgg agtatttacg  16200
gtaaactgcc cacttggcag tacatcaagt gtatcatatg ccaagtacgc ccctattga  16260
cgtcaatgac ggtaaatggc ccgcctggca ttatgcccag tacatgacct tatgggactt  16320
tcctacttgg cagtacatct acgtattagt catcgctatt accatgggtc gaggtgagcc  16380
ccacgttctg cttcactctc cccatctccc ccccctcccc accccaatt ttgtatttat  16440
ttattttta attattttgt gcagcgatgg gggcggggg gggggggcg cgcgccaggc  16500
ggggcgggc ggggcgaggg gcggggcggg gcgaggcgga gaggtgcggc ggcagccaat  16560
cagagcggcg cgctccgaaa gtttcctttt atggcgaggc ggcggcggcg gcggccctat  16620
aaaaagcgaa gcgcgcggcg ggcgggagtc gctgcgttgc cttcgccccg tgccccgctc  16680
cgcgccgcct cgcgccgccc gccccggctc tgactgaccg cgttactccc acaggtgagc  16740
gggcgggacg gcccttctcc tccgggctgt aattagcgct tggtttaatg acggctcgtt  16800
tctttttctgt ggctgcgtga aagccttaaa gggctccggg agggcccttt gtgcgggggg  16860
gagcggctcg ggggtgcgt gcgtgtgtgt gtgcgtgggg agcgccgcgt gcggcccgcg  16920
```

-continued

```
ctgcccggcg gctgtgagcg ctgcgggcgc ggcgcggggc tttgtgcgct ccgcgtgtgc  16980
gcgaggggag cgcggccggg ggcggtgccc cgcggtgcgg gggggctgcg agggggaacaa  17040
aggctgcgtg cggggtgtgt gcgtgggggg gtgagcaggg ggtgtgggcg cggcggtcgg  17100
gctgtaaccc cccctgcac cccctcccc gagttgctga gcacggcccg gcttcgggtg  17160
cggggctccg tgcggggcgt ggcgcgggc tcgccgtgcc gggggcggga tggcggcagg  17220
tgggggtgcc gggcggggcg gggccgcctc gggccgggga gggctcgggg gaggggcgcg  17280
gcggccccgg agcgccggcg gctgtcgagg cgcggcgagc cgcagccatt gccttttatg  17340
gtaatcgtgc gagagggcgc agggacttcc tttgtcccaa atctggcgga gccgaaatct  17400
gggaggcgcc gccgcacccc ctctagcggg cgcgggcgaa gcggtgcggc gccggcagga  17460
aggaaatggg cggggagggc cttcgtgcgt cgccgcgccg ccgtcccctt ctccatctcc  17520
agcctcgggg ctgccgcagg gggacggctg ccttcggggg ggacggggca gggcggggtt  17580
cggcttctgg cgtgtgaccg gcggctctag agcctctgct aaccatgttc atgccttctt  17640
cttttttccta cagctcctgg gcaacgtgct ggttgttgtg ctgtctcatc attttggcaa  17700
agaattccgc tgcgactcgg cggagtcccg gcggcgcgtc cttgttctaa cccggcgcgc  17760
cctcaggatg tggcccctgg tagcggcgct gttgctgggc tcggcgtgct gcggatcagc  17820
tcagctacta tttaataaaa caaaatctgt agaattcacg ttttgtaatg acactgtcgt  17880
cattccatgc tttgttacta atatggaggc acaaaacact actgaagtat acgtaaagtg  17940
gaaatttaaa ggaagagata tttacacctt tgatggagct ctaaacaagt ccactgtccc  18000
cactgacttt agtagtgcaa aaattgaagt ctcacaatta ctaaaaggag atgcctcttt  18060
gaagatggat aagagtgatg ctgtctcaca cacaggaaac tacacttgtg aagtaacaga  18120
attaaccaga gaaggtgaaa cgatcatcga gctaaaatat cgtgttgttt catggttttc  18180
tccaaatgaa aatattctta ttgttatttt cccaattttt gctatactcc tgttctgggg  18240
acagtttggt attaaaacac ttaaatatag atccggtggt atggatgaga aaacaattgc  18300
tttacttgtt gctggactag tgatcactgt cattgtcatt gttggagcca ttcttttcgt  18360
cccaggtgaa tattcattaa agaatgctac tggccttggt ttaattgtga cttctacagg  18420
gatattaata ttacttcact actatgtgtt tagtacagcg attggattaa cctccttcgt  18480
cattgccata ttggttattc aggtgatagc ctatatcctc gctgtggttg gactgagtct  18540
ctgtattgcg gcgtgtatac caatgcatgg ccctcttctg atttcaggtt tgagtatctt  18600
agctctagca caattacttg gactagttta tatgaaattt gtggcttcca atcagaagac  18660
tatacaacct cctaggaaag ctgtagagga accccttaat gcattcaaag aatcaaaagg  18720
aatgatgaat gatgaaggat ccggagccac gaacttctct ctgttaaagc aagcaggaga  18780
cgtggaagaa aaccccggtc ctatggagcg tccgcaaccc gacagcatgc cccaggattt  18840
gtcagaggcc ctgaaggagg ccaccaagga ggtgcacacc caggcagaga atgctgagtt  18900
catgaggaac tttcagaagg gccaggtgac ccgagacggc ttcaagctgg tgatggcctc  18960
cctgtaccac atctatgtgg ccctggagga ggagattgac cgcaacaagg agagcccagt  19020
cttcgcccct gtctacttcc cagaagagct gcaccgcaag gctgccctgg agcaggacct  19080
ggccttctgg tacgggcccc gctggcagga ggtcatcccc tacacaccag ccatgcagcg  19140
ctatgtgaag cggctccacg aggtggggcg cacagagccc gagctgctgg tggcccacgc  19200
ctacaccgac tacctgggtg acctgtctgg gggccaggtg ctcaaaaaga ttgcccagaa  19260
agccctggac ctgcccagct ctggcgaggg cctggccttc ttcaccttcc ccaacattgc  19320
cagtgccacc aagttcaagc agctctaccg ctcccgcatg aactccctgg agatgactcc  19380
cgcagtcagg cagagggtga tagaagaggc caagactgcg ttcctgctca acatccagct  19440
ctttgaggag ttgcaggagc tgctgaccca tgacaccaag gaccagagcc cctcacgggc  19500
accagggctt cgccagcggg ccagcaacaa agtgcaagat tctgcccccg tggagactcc  19560
cagagggaag cccccactca acacccgctc ccaggctccg cttctccgat gggtccttac  19620
actcagcttt ctggtggcga cagttgctgt agggctttat gccatgtgag cggcgcgccg  19680
gcaccggtac caagcttaag agcgctagct ggccagacat gataagatac attgatgagt  19740
ttggacaaac cacaactaga atgcagtgaa aaaaatgctt tatttgtgaa atttgtgatg  19800
ctattgcttt atttgtaacc attataagct gcaataaaca agttaacaac aacaattgca  19860
ttcattttat gtttcaggtt cagggggagg tgtgggaggt tttttaaagc aagtaaaacc  19920
tctacaaatg tggtatggaa ttggagcccc actgtgttca tcttacagat ggaaatactg  19980
acattcagag gagttagtta acttgcctag gtgattcagc taataagtgc aagaaagatt  20040
tcaatccaag gtgatttgat tctgaagcct gtgctaatca cattcaccca agctacaact  20100
tcatttataa ataataagtc agctttcaag ggcctttcag gtgtcctgca cttctacaag  20160
ctgtgccatt tagtgaacac aaaatgagcc ttctgatgaa gtagtcttt cattatttca  20220
gatattagaa cactaaaatt cttagctgcc agctgattga aggctgggac aaaattcaaa  20280
catgcatcta caacaatata tatctcaatg ttagtctcca aattctattg acttcaactc  20340
aagagaatat aaagagctag tctttataca ctctttaagg tatgatgggt cccgattttt  20400
ccccgtatcc cccaggtgt ctgcaggctc aaagagcagc gagaagcgtt cagaggaaag  20460
cgatcccgtg ccaccttccc cgtgcccggg ctgtccccgc acgctgccgg ctcggggatg  20520
cggggggagcg ccggaccgga ccggagcccc gggcggctcg ctgctgccct agcgggggag  20580
ggacgtaatt acatccctgg gggctttggg ggggggctgt cccactagat tttccccgta  20640
tccccccagg tgtctgcagg ctcaaagagc agcgagaagc gttcagagga aagcgatccc  20700
gtgccacctt ccccgtgccc gggctgtccc cgcacgctgc cggctcgggg atgcgggggag  20760
gcgccggacc ggaccggagc cccggccggc tcgctgctgc cctagcgggg gagggacgta  20820
attacatccc tgggggcttt ggggggggc tgtcccatcg gatcttctag tcctgcagga  20880
gtcaatggga aaacccatt ggagccaagt acactgactc aatagggact ttccattggg  20940
ttttgcccag tacataaggt caataggggg tgagtcaaca ggaaagtccc attggagcca  21000
agtacattga gtcaatagggg actttccaat gggtttttgc cagtacataca ggcaatggg  21060
aggtaagcca atgggttttt cccattactg acatgtatac gcgtcgacgt cggcgcgttc  21120
agcctaaagc ttttttcccc gtatccccc aggtgtctgc aggctcaaag agcagcgaga  21180
agcgttcaga ggaaagcgat cccgtgccac cttccccgtg cccgggctgt ccccgcacgc  21240
tgccggctcg gggatgcggg ggagcgccgg accgaccgg agcccgggc ggctcgctgc  21300
tgccctagg ggggagggac gtaattacat ccctgggggc tttggggggg gctgtccc  21360
gcggccgcga attcgtaatc atggtcatag ctgtttcctg tgtgaaattg ttatccgctc  21420
acaattccac acaacatacg agccggaagc ataaagtgta aagcctgggg tgcctaatga  21480
gtgagctaac tcacattaat tgcgttgcgc tcactgcccg ctttccagtc gggaaacctg  21540
tcgtgccagg ggtctagccg cggtctagga agctttctag ggtacctcta gggatccact  21600
agttattaat agtaatcaat tacggggtca ttagttcata gcccatatat ggagttccgc  21660
```

-continued

```
gttacataac ttacggtaaa tggcccgcct ggctgaccgc ccaacgaccc ccgcccattg 21720
acgtcaataa tgacgtatgt tcccatagta acgccaatag ggactttcca ttgacgtcaa 21780
tgggtggagt atttacggta aactgcccac ttggcagtac atcaagtgta tcatatgcca 21840
agtacgcccc ctattgacgt caatgacggt aaatggcccg cctggcatta tgcccagtac 21900
atgaccttat gggactttcc tacttggcag tacatctacg tattagtcat cgctattacc 21960
atggtcgag gtgagcccca cgttctgctt cactctcccc atctcccccc cctccccacc 22020
cccaattttg tatttattta tttttaatt attttgtgca gcgatggggg cgggggggg 22080
gggggcgcgc gccaggcggg gcggggcggg gcgaggggcg gggcggggcg aggcggagag 22140
gtgcggcggc agccaatcag agcggcgcgc tccgaaagtt tccttttatg gcgaggcggc 22200
ggcggcggcg gccctataaa aagcgaagcg cgcggcgggc gggagtcgct gcgttgcctt 22260
cgcccccgtgc cccgctccgc gccgcctcgc gccgcccgcc ccggctctga ctgaccgcgt 22320
tactcccaca ggtgagcggg cgggacggcc cttctcctcc gggctgtaat tagcgcttgg 22380
tttaatgacg gctcgtttct tttctgtggc tgcgtgaaag ccttaaaggg ctccgggagg 22440
gcccttgtg cggggggag cggctcgggg ggtgcgtgcg tgtgtgtgtg cgtggggagc 22500
gccgcgtgcg gcccgcgctg cccggcggct gtgagcgctg cgggcgcggc gcggggcttt 22560
gtgcgctccg cgtgtgcgcg aggggagcgc ggccgggggc ggtgccccgc ggtgcggggg 22620
ggctgcgagg ggaacaaagg ctgcgtgcgg ggtgtgtgcg tgggggggtg agcagggggt 22680
gtgggcgcgg cggtcgggct gtaaccccc cctgcacccc cctccccgag ttgctgagca 22740
cggcccggct tcgggtgcgg ggctccgtgc ggggcgtgcc gcggggctcg ccgtgccggg 22800
cgggggtgg cggcaggtgg gggtgccggg cggggcgggg ccgcctcggg ccggggaggg 22860
ctcgggggag gggcgcggcg gccccggagc gccggcggct gtcgaggcgc ggcgagccgc 22920
agccattgcc ttttatggta atcgtgcgag agggcgcaag gacttccttt gtcccaaatc 22980
tggcggagcc gaaatctggg aggcgccgcc gcacccctc tagcgggcgc gggcgaagcg 23040
gtgcggcgcc ggcaggaagg aaatgggcgg ggagggcctt cgtgcgtcgc cgcgccgccg 23100
tccccttctc catctccagc ctcggggctg ccgcaggggg acggctgcct tcggggggga 23160
cggggcaggg cggggttcgg cttctggcgt gtgaccggcg gctctagagc ctctgctaac 23220
catgttcatg ccttcttctt tttcctacag ctcctgggca acgtgctggt tgttgtgctg 23280
tctcatcatt ttggcaaaga attccgctgc gactcggcgg agtcccggcg gcgcgtcctt 23340
gttctaaccc ggcgcgccct caggatggag cctcccggcc gccgcgagtg tcccttcct 23400
tcctggcgct ttcctgggtt gcttctggcg gccatggtgt tgctgctgta ctccttctcc 23460
gatgcctgtg aggagccacc aacatttgaa gctatggagc tcattggtaa accaaaaccc 23520
tactatgaga ttggtgaacg agtagattat aagtgtaaaa aaggatactt ctatatacct 23580
cctcttgcca cccatactat ttgtgatcgg aatcatacat ggctacctgt ctcagatgac 23640
gcctgttata gagaaacatg tccatatata cgggatcctt taaatggcca agcagtccct 23700
gcaaatggga cttacgagtt tggttatcag atgcactta tttgtaatga gggttattac 23760
ttaattggtg aagaaattct atattgtgaa cttaaaggat cagtagcaat ttggagcggt 23820
aagcccccaa tatgtgaaaa ggttttgtgt acaccacctc caaaaataaa aaatggaaaa 23880
cacacccttta gtgaagtaga agtatttgag tatcttgatg cagtaactta tagttgtgat 23940
cctgcacctg gaccagatcc attttcactt attggagaga gcacgattta ttgtggtgac 24000
aattcagtgt ggagtcgtgc tgctccagag tgtaaagtgg tcaaatgtcg atttccagta 24060
gtcgaaaatg gaaaacagat atcaggattt ggaaaaaaat tttactacaa agcaacagtt 24120
atgtttgaat gcgataaggg tttttacctc gatggcagcg acacaattgt ctgtgacagt 24180
aacagtactt gggatccccc agttccaaag tgtcttaaag tgctgcctcc atctagtaca 24240
aaacctccag ctttgagtca ttcagtgtcg acttcttcca ctacaaaatc tccagcgtcc 24300
agtgcctcag gtcctaggcc tacttacaag cctccagtct caaattatcc aggatatcct 24360
aaacctgagg aaggaatact tgacagtttg gatgtttggg tcattgctgt gattgttatt 24420
gccatagttg ttggagttgc agtaaatttgt gttgtcccgt acagatatct tcaaaggagg 24480
aagaagaaag gcacatacct aactgatgag acccacagag aagtaaaatt tacttctctc 24540
ggatccggag ccacgaactt ctctctgtta aagcaagcag gagacgtgga agaaaacccc 24600
ggtcctatga ccgtcgcgcg gccgagcgtg cccgcggcgc tgcccctcct cggggagctg 24660
ccccggctgc tgctgctggt gctgttgtgc ctgccgggtg tggggtga ctgtggcctt 24720
cccccagatg tacctaatgc ccagccagct ttggaaggcc gtacaagttt tcccgaggat 24780
actgtaataa cgtacaaatg tgaagaaagc tttgtgaaaa ttcctggcga gaaggactca 24840
gtgatctgcc ttaagggcag tcaatggtca gatattgaag agttctgcaa tcgtagctgc 24900
gaggtgccaa caaggctaaa ttctgcatcc ctcaaacagc cttatatcac tcagaattat 24960
tttccagtcg gtactgttgt ggaatatgag tgccgtccag gttacagaag agaaccttct 25020
ctatcaccaa aactaacttg ccttcagaat ttaaaatggt ccacagcagt cgaatttgt 25080
aaaaagaaat catgccctaa tccgggagaa atacgaaatg gtcagattga tgtaccaggt 25140
ggcatattat ttggtgcaac catctccttc tcatgtaaca cagggtacaa attatttggc 25200
tcgacttcta gttttttgtct tatttcaggc agctctgtcc agtggagtga cccgttgcca 25260
gagtgcagag aaatttattg cccagcacca ccacaaattg acaatggaat aattcaaggg 25320
gaacgtgacc attatggata tagacagtct gtaacgtatg catgtaataa aggattcacc 25380
atgattggag agcactctat ttattgtact gtgaataatg atgaaggaga gtggagtggc 25440
ccaccacctg aatgcagagg aaaatctcta acttccaagg tcccaccaac agttcagaaa 25500
cctaccacag taaatgttcc aactacagaa gtctccaccaa cttctcagaa aaccaccaca 25560
aaaaccacca caccaaatgc tcaagcaaca cggagtacac ctgtttccag gacaaccaag 25620
cattttcatg aaacaaccccc aaataaagga agtggaacca cttcaggtac tacccgtctt 25680
ctatctgggc acacgtgttt cacgttgaca ggtttgcttg gacgctagt aaccatgggc 25740
ttgctgactt agggcgcgcc ggcaccggta ccaagctaag gtggcag catgcagctc 25800
tgataagata cattgatgag tttggacaaa ccacaactag aatgcagtga aaaaaatgct 25860
ttatttgtga aatttgtgat gctattgctt tatttgtaac cattataagc tgcaataaac 25920
aagttaacaa caacaattgc attcatttta tgtttcaggt tcagggggag gtgtgggagg 25980
tttttttaaag caagtaaaac ctctacaaat gtggtatgga attggagccc cactgtgttc 26040
atcttacaga tggaaatact gacattcaga ggagttagtt aacttgccta ggtgattcag 26100
ctaataagtg caagaaagat ttcaatccaa ggtgatttga ttctgaagcc tgtgctaatc 26160
acattacacc aagctacaac ttcatttata aataataagt cagctttcaa gggcctttca 26220
ggtgtcctgc acttctacaa gctgtgccat ttagtgaaca caaaatgagc cttctgatga 26280
agtagtcttt tcattatttc agatattaga acactaaaat tcttagctgc cagctgattg 26340
aaggctggga caaaattcaa acatgcatct acaacaatat atatctcaat gttagtctcc 26400
```

```
aaattctatt gacttcaact caagagaata taaagagcta gtctttatac actctttaag  26460
gtatgatatc atctggaaag taacaaaatt gatgcaaatt tgaatgaact ttatcatggt  26520
gtatttacac aatgtgtttc ttctccctgc aatgtatttc tttctctaat tccttccatt  26580
tgatctttca tacacaatct ggttctgatg tatgtttttt ggatgcactt ttcaactcca  26640
aaagacagag ctagttactt tcttcctggt gctccaagca ctgtatttgt atctgtattc  26700
aagccctttg caatattgta ctggatcatt atttcacctc taggatggct tccccaggca  26760
acttgtgttc acccagagac tacattttgt atcttgttga cctttgaact tccaccagtg  26820
tctaaaaata atatgtatgc aaaattactt gctatgagaa tgtataatta aacaatataa  26880
aaaggagaag caaggagaga aacacaggtg tgtatttgtg tttgtgtgct taaaaggcag  26940
tgtggaaaag gaagaaatgc catttatagt gaggagacaa agttatatta cctcttatct  27000
ggcttttaag gagattttgc tgagctaaaa atcctatatt catagaaaag ccttacctga  27060
gttgccaata cctcaattct aaaatacagc atagcaaaac tttaacctcc aaatcaagcc  27120
tctacttgaa tccttttctg agggatgaat aaggcatagg catcagggc tgttgccaat  27180
gtgcattagc tgtttgcagc ctcaccttct ttcatggagt ttaagatata gtgtattttc  27240
ccaaggtttg aactagctct tcatttcttt atgtttttaaa tgcactgacc tcccacattc  27300
cctttttagt aaaatattca gaaataattt atcatctgga aagtaacaaa attgatgcaa  27360
atttgaatga acttatcat ggtgtattta cacaatgtgt ttcttctccc tgcaatgtat  27420
ttctttctct aattccttcc atttgatctt tcatacacaa tctggttctg atgtatgttt  27480
tttggatgca cttttcaact ccaaaagaca gagctagtta ctttcttcct ggtgctccaa  27540
gcactgtatt tgtatctgta ttcaagccct ttgcaatatt gtactggatc attatttcac  27600
ctctaggatg gcttccccag gcaacttgtg ttcacccaga gactacattt tgtatcttgt  27660
tgacctttga acttccacca gtgtctaaaa ataatatgta tgcaaaatta cttgctatga  27720
gaatgtataa ttaaacaata taaaaaggag aagcaaggag agaaacacag gtgtgtattt  27780
gtgtttgtgt gcttaaaagg cagtgtggaa aaggaagaaa tgccatttat agtgaggaga  27840
caaagttata ttacctctta tctggctttt aaggagattt gctgagcta aaaatcctat  27900
attcatagaa aagccttacc tgagttgcca atacctcaat ctaaaatac agcatagcaa  27960
aactttaacc tccaaatcaa gcctctactt gaatcctttt ctgagggatg aataaggcat  28020
aggcatcagg ggctgttgcc aatgtgcatt agctgtttgc agcctcacct tctttcatgg  28080
agtttaagat atagtgtatt ttcccaaggt ttgaactagc tcttcatttc tttatgtttt  28140
aaatgcactg acctcccaca ttcccttttt agtaaaatat tcagaaataa tttatatccg  28200
cttgtcgacg acggatcatc tggaaagtaa caaaattgat gcaaatttga atgaacttta  28260
tcatggtgta tttacacaat gtgtttcttc tccctgcaat gtatttcttt ctctaattcc  28320
ttccatttga tctttcatac acaatctggt tctgatgtat gttttttgga tgcactttc  28380
aactccaaaa gacagagcta gttactttct tcctggtgct ccaagcactg tatttgtatc  28440
tgtattcaag ccctttgcaa tattgtactg gatcattatt tcacctctag gatggcttcc  28500
ccaggcaact tgtgttcacc cagagactac attttgtatc ttgttgacct ttgaacttcc  28560
accagtgtct aaaaataata tgtatgcaaa attacttgct atgagaatgt ataattaaac  28620
aatataaaaa ggagaagcaa ggagagaaac acaggtgtgt atttgtgttt gtgtgcttaa  28680
aaggcagtgt ggaaaaggaa gaaatgccat ttatagtgag gagacaaagt tatattacct  28740
cttatctggc ttttaaggag attttgctga gctaaaaatc ctatattcat agaaaagcct  28800
tacctgagtt gccaatacct caattctaaa atacagcata gcaaaacttt aacctccaaa  28860
tcaagcctct acttgaatcc ttttctgagg atgaataag gcataggcat caggggctgt  28920
tgccaatgtg cattagctgt ttgcagcctc accttctttc atggagttta agatatagt  28980
tattttccca aggtttgaac tagctcttca tttctttatg ttttaaatgc actgacctcc  29040
cacattccct ttttagtaaa atattcagaa ataatttaaa ttcgtggaat cccacccagc  29100
agacaagtat ggctggatat tttatataac gtgtttacgc ataagttaat atatgctgaa  29160
tgagtgattt agctgtgaaa caacatgaaa tgagaaagaa tgattagtag gggtcttggag  29220
cttattttaa caagcagcct gaaaacagag agtatgaata aaaaaaatta aatacaagag  29280
tgtgctatta ccaattatgt ataatagtct tatacatcta acttcaattc caatcactat  29340
atgcttatac taaaaaacga agtatagagt caaccttctt tgactaacag ctcttcccta  29400
gtcagggaca ttagcccaag tatagtcttt attttttcctg gggtaagaaa agaaggattg  29460
ggaagtagga atgcaaagaa ataaaaaata attctgtcat tgttcaaata agaatgtcat  29520
ctgaaaataa actgccttac atgggaatgc tcttatttgt caggtatatt aaggaaacaa  29580
acatcaaaaa tgacccaaat gaactcaaca atcttatcaa gaagaattct gaggtggtaa  29640
cctggacccc aagacctgga gccactcttg atctgggtag gatgctaaag gacgcgatcg  29700
cattt                                                              29705

SEQ ID NO: 12          moltype = DNA  length = 29153
FEATURE                Location/Qualifiers
source                 1..29153
                       mol_type = other DNA
                       organism = synthetic construct
SEQUENCE: 12
atgtctccta tgtctcatct aaatggatga ggtttgagag ttcccatcac ggcatggtgg  60
aaacgaatcc gactaggagc cataagttca cggcttcgat ccctggcctc gctcaggggg  120
ttaaggatcc ggtgttgctg tgagctgtgg tgtaggtcac agatgcggtt cggatctggc  180
gttgctgcgg ctgtggtgta ggctggtggc tgtagctccg atttgacccc tagcctaggg  240
acctccatat gccgtgggta tggccctaaa aagccaaata aaataaaata agtaaatggt  300
tgaggtttga cacagaaagt ttatttattt atgtatttac ttatcttttt ttttttttt  360
tttttttgtct ttctgctatt tcttgggctg ctcccgcgcg atatggaggt tcccaggcta  420
ggggtcgaat tggagctaca gccaccagcc tacaccacag ccgcagcaat gccagatccg  480
agccgcctct gtgacctaca ccacagctca tggcaacgct ggatcgttaa cccactgagc  540
aagggctggg accgaacccg caaccttcatg gttcctagtc ggattcgtta accactgcgc  600
catgacggga actcctactt atctattttt taaagcatat ggaagttccc aggctagggg  660
gttgaatcgg agctgcaact gccggcttac accacagcca gagcaacgcc ggatcgtagc  720
agtgtctggg acctacacca cagctcacag ccacaccgga tcctcaatcc actgaatgag  780
gccaggaatc aaacctgtgt cctcatggat actagtcaga ttcatttccg ctgagcaatg  840
acaggaactc ctgacacaga aatttagat taaaattgaa gatgagcccc ttccttttgt  900
acgacctttg tgtgcagatt ttcgaggata agtccttgag cttgaagttt tagggtcatg  960
```

```
gatcctcata acagtttcct ggcctgtgag gcttggatct cagtataaac agaagtgctg   1020
gcagcagtag acacagcagc agctgttttc aggaacaaat actgggcacc tgccttgtgg   1080
acctgcctga ctccaccact ctcttgggta tccacaaagt ggacccagag gttcagagca   1140
gccctgggat ccaaattttt ttaatttatt ttttatcttt tattttttgt cttttcgaaa   1200
tttttagggc tacacccatg agatatggag gttcccaggc taagggtcca atcggagcta   1260
caactgccgg cctacaccac agctcatggc aatgctggat ccttaacccg ctgagcgagg   1320
ccagggatca aacccacaac ctcatgattc ctagttggat tcgttaacca ctgagccacg   1380
atgggaactc cctgggatgc aaattttgtc atctagccct aggatgtagc tatcatcctg   1440
atttgagaag agaggcagag tctcaggtgg cttctctctc atgaatgcag agctaagggt   1500
ggccacacgt acttgagttc atccgatgca cacagcattg tgctaaaata ttgaccattt   1560
ggcccttttg ctgacttttg gtttgaggga tatgaccttc atgagcatac agaggataat   1620
atgtatgcat gtatgcatgt gtgtacacat gtgcgcatgc atgtatatac ctgcataatt   1680
atgtatttgt ttatgtatgc aggtgcatgt gtatgtatat atttattatt tatttatttg   1740
ggggccacac ccatgacatt tggaagttcc tgggacagag attgaatccc agccacagct   1800
ttgacctacg ccatggacac agcaacactg gattcttaac cccctgtgcc acagcgggaa   1860
ctcctagaag atagtatttc atgatgatat ttgactaaaa ataggggtca ggctttgaag   1920
tttaaataaa ttcgaccaga taaatggcca tccaggaagt tatacttttgc cttgttcaaa   1980
tttggaccac ggggaaggtg gttggcgaca tgtaacagaa atctgactcc agtgcaggtt   2040
tcgctcccgt gacgggaagc ccagaggtgg gcagccctaa ggctggggct ctgatttcat   2100
gatgctctta gcatcttgag tcccttccct cttcttgctt ttatctcagc ctcgggctgc   2160
tgcaccttct gtctttgtgg tgagtctacc tattccactt agctcggctt cagggtgtat   2220
ttccacgact tcgttagagt aaggttgggg ccagctgctg tctgccggca ggaggtgtgc   2280
ttgcaggggc catggatgtg gccaggacct aatgtgacgg tggggagcag gatggggatg   2340
aggatgtgac cacagagcct tgggaaccac gtcatccacg tcatacactg agagcaggtg   2400
gttctcatgc aggtgcatca gaatcccgag gacggcttgt ccaaacccag atggctgggc   2460
ccaagccctg agctcccgat ttgggaggcc ttggctgggc cccgaaatct gccttcctga   2520
ctagaccgag tgatgaatgg tgttcataga caagacatac actaacactg gtcttggggg   2580
ctccttgcca caccctgaag gggtccgtga aactgacggg gccagagaag gtgctggttc   2640
ctccatggaa ggtctcagtg aggccattct gctgcccggc tgggtcacgc tggggggagtg   2700
agggtgcatc ccctcctggg atctggtcaa aggcagattc tgattctgga agcacggggt   2760
agggccagag atgccacctt ctaacaagcc cccaggtgaa gatgttgacc tgggacctta   2820
tggtgggggg tggcggagct caaggtggca gacacctccc tctctctcaa cctgtgtcac   2880
agcagggcca tcctactggc tctcgctcgg ccagagatgg cgatgccaga acacactggg   2940
gcagggtgtc cacatttttg tcacttccac tgagcctgg ggactgactc atttaaatga    3000
cattctcaac tctttggaaa gaagctgggc cagaaatgga aatggcagca aacactttt    3060
gggaaacagg aagccaattt ttttttttcaa tcatgatttt ccccagattc agagactgct   3120
taactcccaa tgaaatactt ttagattacg agctaaaata ccgaaaagct gtcaagctca   3180
agaccacagg aaaacagccg aagaacaaac accatgagaa aacagtcaca gagtgcctct   3240
gcggcggatt tcaagttcca gacttccttg ctgtcagctg tgtgtacttg tcccgcctgc   3300
agtaggacca gctggggttt aagtctgtac catggacact gctgccagga ttctcctctg   3360
catctgctga cttccagctc ttcagggcca gctggccata ggagcataaa ctgacatcca   3420
gttccaggag gcagcatctg tccccatggc ctgcaggaca ccagatcagt agaggccccc   3480
agggccacct ttcctgtggg ggcccttgaa gggacccggg aaggctggat cttgctaaag   3540
cttccacaag tcccttccaa aggagagtaa attctaaaca gaagcttttg ccagtgcttc   3600
tctgggatct ggcttcagga ttattcctag tctgaaaagt cttcctggtg gtttggacac   3660
gggcaaatgc ttggtgggtg ggctggctct ggatgcaggt gagtggggtc ggaagttctc   3720
cctccttccc acaaagcttg acggagccag gggcacccgc gggcctgtgg atgggagagg   3780
ggtttctggt gacggactca agtcttggca gcccctgacc ccagagcagg ctccctcccc   3840
acagctgctc tccgtgagtc cttcacttgc ccaagttcaa gatgtaccca gttctggagc   3900
tgccaaacca tcctgcatcc tgacgtcagc cacccaagtt ctggggtagc tggtctgcca   3960
cccaggtgga tgaaaagagg ccacatacct gcaccagcat ctgcgaatct ctgaagaaca   4020
tcaataataa aaagacaact aacccgatta aaacacaggt agagaatctg aacagacatt   4080
catcggaaga agaattacga ctggccaaaa agctcataaa aagatggtca aagtcattgg   4140
tcagggaaat gtaaatcaaa ccgcattgag ataccatctc actccctctc ggatggctgg   4200
aatgaaaaaa aacctcttct ttcctccctt tcattgtctt ggcacccttg tggaaattaa   4260
ttgactaaaa ttcatgaaat acaaaaattt ttaggagttc ccgtcgtggc tcagtggtta   4320
acaaatctga ctaggaacca tgaggtttca ggttcgattc ctggcctcac tcagtgggtt   4380
agggatctgc tgttgccatg agctgtggtg taggtcgcag acgcagctcg gatcccgcat   4440
tgctgtggct ctggcgtagg ccggcggcta cagctctgat tcaacctcta gcctgggaat   4500
agcccaagaa atggcaaaaa gaccaaaaaa aaaaaaaaaa aaaaaactg tttgagcat    4560
ttttgcatgt gtacattgtc catttgtgtg ccttccaaga tttatttttg gagtctcaac   4620
tctgtcattg atttatgtct ctccttaggc cagaaccaca ctgtttggt gaccatggct    4680
ttgtagtaaa atttgaaatc tgaaagtgtg agccctcctg ttttgtttct cttctccatg   4740
attagtttgg ttattcagag tccctgaat ttccaggtga attttaggat tagcaggaaa    4800
atttctgcag agatggcagc agagattttt aatagggatt atgttgaatc tggaggttaa   4860
tttcagtttt gctaccttga ctgtattaag tcttccagtc tataagcata agatgtcttt   4920
ttatttactt aggtctttta aaatttcttt gggcactccc attgtggtgc atcggaaatg   4980
aatccgacta gtatccacaa gaacacaggt tcaatccctg gcattgctca gtgggttaag   5040
gatcctgcat tgccatgaag aactgtggtg gaggccagca gctgcagctc tgatttgacc   5100
cctagcctgg gaacttccat atgccttggg tatggcccta aaaagcaaac taagtaagta   5160
agtaaataaa taaatgaata aataaaattt ctttcaaaat tgtaattttg taattttgt    5220
aattttcaga gtgtacattt tgcccttcta atacattatt cctacatatt ttattctttt   5280
tgatactatt ataaatgaaa tttataatta attcatttat atgaattcca ttttcaattt   5340
gcatattgct actacaatag aaatgcactt tttaattatt tttatggcca taccatatat   5400
atatgtgtgt gtgtgtgtat gtgtgtcatt ttactgtaca gcagaaattg acacaacatt   5460
gtaaatcaac tacacttaaa aaatgaagaa ataaccacct gtgattatgg ctactgtgtt   5520
ggacacttta ggcatccccc cacccgtcc ccgcccaca cccctgagtg ctagtgacgg     5580
atgttccac ccaggggcc tggagccttt atcaccagcc atcgggaatc agaaccgtat     5640
ctcacagtcc ccatgcctgt agcacctgga attgtgccct tggactcgtg ggtgttctgc   5700
```

-continued

```
ttctcagtgg gagaagctta ggttctaagt cagagcaggg acagcccca tgtgctcagg    5760
acccagtgtg aaggggtctg cctcagggga cctgggggtt acaagggtaa gagaaggtgt    5820
tcatgttgga actagaagtt ctttttcacc gctctgaaga aaaaagctgc ctcccaccct    5880
tggtacagct cttctgctaa cagtgaatca ggcagaacgt gttcaagaag tgacccagcc    5940
tggtgggggc cagacctgac ccttgatggt ccctcaaccc ctccgaggg cccgcccttc    6000
ctttactgct ttgttgtctg tcctgagagg tttggctaat gtcgaaccaa gggtgtggct    6060
ggtcctgtcc cctttcctgt ctcacgcacc cacctctgaa gtctctgtag ctggttccag    6120
ccgggatctg gagccactcc ccccgcccca ggcccagtgg tacagactct tgcagagtcg    6180
ggggccctg actcagcccc accgccagcg ggatgtcagg ccagcacccg ccccactcc    6240
actgatctgg gggggtgtc tttccttcct ccttccaaag gagcctcaga ccttcctgtg    6300
gggcacgggg gcagtgggat tcaggaggct ctgagtcagc aggccggcat tgaggagtat    6360
aaagggaccc cagttcctcc ccctttcact tgtggcttat cgccgcccca ccctgcccca    6420
aggtcactgc ggtcagtaca gtcctcagct gccagcaggt gcctgtcttt acttgtgagg    6480
ccgccacgct ctcctgtttc tccaggtctg ggctctgttg gaagtggggg cccgacccca    6540
gggtaagatg ggggatctgc gtgtcctgcc ctcagaggcc tcctcctccc cgcaccccta    6600
acccttcag cccaacaagg ctggagatct cccacatctt tggcttcgtt aagagttcaa    6660
cagcgccgcc acccggcatg tcgctgagca gaggatggca cagggtgtta aaaaaaaaa    6720
aaggttgcca cactccgttc ggttttgggc ccacccttc gcattcctgg agcctgagta    6780
agcggataag gctgtgaaag tgacagattc ctgccacctc cttccagcgc tcatgcacag    6840
ggaccgcccc tcttcggtgt cctttgctgc acaagtgcat ttgcacattc ctgtctcaat    6900
ctggtttctc ccccttaaaa gatgggaatg tgacctgctt ggagcccctc gcctcgccag    6960
ggcaccccat ccgtcccttc aggggtggag atggactgtc cctctgcaag gctggatgaa    7020
ctcagaccaa acaggccaac ttgctcccca aatacgccca cccctaccgg gctgcagaaa    7080
ttcgcatgtc accactgctg aagggtgacc ttgcagccct gagagcatcc ccatgacttg    7140
cccaccagat gaagtctggt tgtggcaggt cgcgctcagg gactcccggg tcccacctgg    7200
gggtgggagg atcctccttt gctcgtcgtc gccccagaca cgccctcctt tccaagcgcc    7260
agtctccaga gctccgtgcc ccggcggagg cggtctggct ctctctcctt gcccctctct    7320
ccttgcccct agcagccctt ctcctaaacc ctctgagcag cgggcacctc ctcccgaggc    7380
cctgggctaa gtccccaccc ttcatctcaa gccttcctcc ttgactccct cttcccagag    7440
ttccttgaaa taggtggtaa gtacacaccg atgacggaaa acaaagacta agaggttaaa    7500
gagggctgag gattacggcc ccggtagggc tgcgcgcgag ggggtcgagt ggccgggcgg    7560
tcccgtcgcc gggcagacag aggtgcggtt ctcccgggcg cctgcgctgc cggccccgcc    7620
cggagccctc ccagccggcg cccagtttac tcatcccgga gaggtgatcc cgggcgcgag    7680
ggcgggcgca gggcgtccgg agaacccagt aatccgagaa tgcagcatca gcccttccca    7740
ccaggcactt ccttccttt cccgaacgtc cagggagggg ggccgcgcac ttataaactc    7800
gggccggacc cgccggcctg tcagaggctg cctcgctggg gctgcgcgcg gcggccggac    7860
acatctggtc cgagaccaac gcgagcgact gtcactggca gctccctgcg cctctcagcc    7920
ccggccgggc ccctgcgctt ggcgtgctga caccatgctt ggggtcctgg tccttggcgc    7980
gctggccctg gccggccctgg ggttccccgc accgcagg ccgcagccgg gtggcagcca    8040
gtgcgtcgag cacgactgct tcgcgctcta cccgggcccc gcgaccttcc tcaatgccag    8100
tcagatctgc gacggactgc ggggccacct aatgacagtg cgctcctcgg tggctgccga    8160
tgtcatttcc ttgctactga acggcgacgg cggcgttggc cgccggcgcc tctggatcgg    8220
cctgcagctg ccacccggct gcgggcgacc caagcgcctc gcggccccctgc gcggcttcca    8280
gtggggttacg ggagacaaca acaccagcta tagcaggtgg gcacggctcg acctcaatgg    8340
ggctcccctc tgcggcccgt tgtgcgtcgc tgtctccgct gctgaggcca ctgtgcccag    8400
cgagccgatc tgggaggagc agcagtgcga agtgaaggcc gatggcttcc tctgcgagtt    8460
ccacttccca gccacctgca ggccactggc tgtggagccc gcggccgcgg ctgccgccgt    8520
ctcgatcacc tacggcaccc cgttcgcggc ccgcggagcg gacttccagg cgctgccggt    8580
gggcagctcc gccgcggtgg ctccccctcgg cttacagcta atgtgcaccg cgccgcccgg    8640
agcggtccag gggcactggg ccagggaggc gccgggcgct tgggactgca gcgtgggaga    8700
cggcggctgc gagcacgcgt gcaatgcgat cctggggcgt ccccgcttgc agtgcccagc    8760
cggcgccgcc ctgcaggcag acgggcgctc ctgcaccgca tccgcgacgc agtcctgcaa    8820
cgacctctgc gagcacttct gcgttccaa ccccgaccag ccgggctcct actcgtgcat    8880
gtgcgagacc ggctaccggc tggcggccga ccaacaccgg tgcgaggacg tggatgactg    8940
catactggag cccagtccgt gtccgcagcg ctgtgtcaac acacagggtg gcttcgagtg    9000
ccactgctac cctaactacg acctggtgga cggcgagtgt gtggacccg tggacccgtg    9060
cttcagagcc aactgcgagt accagtgcca gccctgaac caaactagct acctctgcgt    9120
ctgcgccgag ggcttcgcgc ccattcccca cgagccgcac aggtgccaga tgtttttgcaa    9180
ccagactgcc tgtccagccg actgcgaccc caacacccag gctagctgtg agtgccctga    9240
aggctacatc ctggacgacg gtttcatctg cacggacatc gacgagtgcg aaaacggccg    9300
cttctgctcc ggggtgtgcc acaacctccc cggtacctcc gagtgcatct gcgggcccga    9360
ctcggccctt gcccgccaca ttggcaccga ctgtgactcc ggcaaggtgg acggtggcga    9420
cagcggctct ggcgagcccc cgcccagccc gacgcccggc tccaccttga ctcctccggc    9480
cgtggggctc gtgcattcgg gcttgctcat aggcatctcc atcgcgagcc tgtgcctggt    9540
ggtggcgctt ttggcgctcc tctgccacct gcgcaagaag caggcgcgcc ccagggccaa    9600
gatggagtac aagtgcgcgg ccccttccaa ggaggtagtg ctgcagcacg tgcggaccga    9660
gcggacgccg cagagactcg gatccggaga gggcagagga agtcttctaa catgcggtga    9720
cgtggaggag aatcccggcc ctatgttgac aacattgctg ccgatactgc tgctgtctga    9780
ctgggccttt gtgtagccaag acgcctcaga tggcctccaa agacttcata tgctccagat    9840
ctcctacttc cgcgacccct atcacgtgtg gtaccagggc aacgcgtcgc tggggggaca    9900
cctaacgcac gtgctggaag gcccagacac caacaccacg atcattcagc tgcagccctt    9960
gcaggagccc gagagctggg cgcgcacgca gagtggcctg cagtcctacc tgctccagtt    10020
ccacggcctc gtgcgcctgg tgcaccagga gcggaccttg gcctttcctc tgaccatccg    10080
ctgctttcctg ggctgtggagc tgcctcccga gggctctaga tgccatgtct tcttcgaagt    10140
ggctgtgaat gggagctcct ttgtgagttt ccggccggag agagccttgt ggcaggcaga    10200
cacccaggtc acctccggag tggtcacctt caccctgcag cagctcaatg cctacaaccg    10260
cactcggtat gaactgcggg aattcctgga ggacacctgt gtgcagtatg tgcagaaaca    10320
tatttccgcg gaaaacacga aagggagcca aacaagccgc tcctcacctt cgctggtcct    10380
gggcgtcctg gtgggcagtt tcatcattgc tggtgtggct gtaggcatct tcctgtgcac    10440
```

-continued

```
aggtggacgg cgatgttgag cgcggccgct tcccttagt gagggttaat gcttcgagca   10500
gacatgataa gatacattga tgagtttgga caaaccacaa ctagaatgca gtgaaaaaaa   10560
tgctttattt gtgaaatttg tgatgctatt gctttatttg taaccattat aagctgcaat   10620
aaacaagtta acaacaacaa ttgcattcat tttatgtttc aggttcaggg ggagatgtgg   10680
gaggttttt aaagcaagta aaacctctac aaatgtggta aaatccgata aggatcgatg   10740
ggacagcccc ccccaaagc ccccaggat gtaattacgt ccctcccccg ctagggcagc   10800
agcgagccgc ccgggctcc ggtccggtcc ggcgctcccc cgcatccccg agccggcagc   10860
gtgcggggac agcccgggca cggggaaggt ggcacgggat cgctttcctc tgaacgcttc   10920
tcgctgctct ttgagcctgc agacacctgg ggggatacgg ggaaaatcta gtgggacagc   10980
cccccccaa agcccccagg gatgtaatta cgtccctccc ccgctagggc agcagcgagc   11040
cgcccggggc tccggtccgg tccggcgctc ccccgcatcc ccgagccggc agcgtgcggg   11100
gacagcccgg gcacggggaa ggtggcacgg gatcgctttc ctctgaacgc ttctcgctgc   11160
tctttgagcc tgcagacacc tggggggata cggggaaaaa tcgatgggac agcccccccc   11220
caaagccccc agggatgtaa ttacgtccct ccccgctag ggcagcagcg agcgccccgg   11280
ggctccggtc cggtccggcg ctcccccgca tccccgagcc ggcagcgtgc ggggacagcc   11340
cgggcacggg gaaggtggca cgggatcgct ttcctctgaa cgcttctcgc tgctctttga   11400
gcctgcagac acctgggggg atacggggaa aatctagtgg gacagccccc ccaaaagcc   11460
cccaggatg taattacgtc cctcccccgc tagggcagcg agcgccgcc cggggctccg   11520
gtccggtccg gcgctccccc gcatccccga gccggcagcg tgcggggaca gcccgggcac   11580
ggggaaggtg gcacgggatc gctttcctct gaacgcttct cgctgctctt tgagcctgca   11640
gacacctggg gggatacggg gaaaaatcga tagcgataag gatccactag ttattaatag   11700
taatcaatta cggggtcatt agttcatagc ccatatatgg agttccgcgt tacataactt   11760
acggtaaatg cccgcctggg ctgaccgccc aacgacccc gcccattgac gtcaataatg   11820
acgtatgttc ccatagtaac gccaataggg actttccatt gacgtcaatg ggtggagtat   11880
ttacggtaaa ctgcccactt ggcagtacat caagtgtatc atatgccaag tacgcccct   11940
attgacgtca atgacggtaa atggcccgcc tggcattatg cccagtacat gaccttatgg   12000
gactttccta cttggcagta catctacgta ttagtcatcg ctattaccat ggtcgaggt   12060
gagccccacg ttctgcttca ctctccccat ctcccccccc tccccacccc caattttgta   12120
tttatttatt ttttaattat tttgtgcagc gatgggggcg ggggggggggg gggcgcgcgc   12180
caggcggggc ggggcggggc gaggggcggg gcggggcag gcggagaggt gcggcggcag   12240
ccaatcagag cggcgcgctc cgaaagtttc cttttatggc gaggcggcgg cggcggcggc   12300
cctataaaaa gcgaagcgcg cggcgggcgg gagtcgctgc gttgccttcg ccccgtgccc   12360
cgctccgcgc cgcctcgcgc cgcccgcccc ggctctgact gaccgcgtta ctcccacagg   12420
tgagcgggcg ggacggcct tctcctccgg gctgtaatta gcgcttggtt taatgacggc   12480
tcgtttcttt tctgtggctg cgtgaaagcc ttaaagggct ccgggagggc cctttgtgcg   12540
gggggagcg gctcgggggg tgcgtgcgtg tgtgtgtgcg tgggagcgc cgcgtgcggc   12600
ccgcgctgcc cggcggctgt gagcgctgcg ggcgcgcgc ggggctttgt gcgctccgcg   12660
tgtgcgcgag gggagcgcgg ccggggcgg tgccccgcgg tgcggggggg ctgcgagggg   12720
aacaaaggct gcgtgcgggg tgtgtgcgtg cagggggtgt gggcgcggcg   12780
gtcgggctgt aacccccccc tgcaccccc tccccgagtt gctgagcacg gcccggcttc   12840
gggtgcgggg ctccgtgcgg ggcgtggcgc ggggctcgcc gtgccgggcg gggggtggcg   12900
gcaggtgggg gtgccgggcg gggcggggcc gcctcgggcc ggggagggct cggggagggg   12960
gcgcggcggc cccggagcgc cggcggctgt cgaggcgcgg cgagccgcag ccattgcctt   13020
ttatggtaat cgtgcgagag ggcgcaggga cttcctttgt cccaaatctg gcggagccga   13080
aatctgggag gcgccgccgc accccctcta gcgggcgcgg gcgaagcggt gcggcgccgg   13140
caggaaggaa atgggcgggg agggccttcg tgcgtcgccg cgccgccgtc cccttctcca   13200
tctccagcct cggggctgcc gcaggggac ggctgccttc ggggggacg gggcagggcg   13260
gggttcggct tctggcgtgt gaccggcggc tctagagcct ctgctaacca tgttcatgcc   13320
ttcttctttt tcctacagct cctgggcaac gtgctggttg ttgtgctgtc tcatcatttt   13380
ggcaaagaat tccgctgcga ctcggcggag tcccggcggc gcgtccttgt tctaacccgg   13440
cgcgccctca ggatgtggcc cctggtagcg gcgctgttgc tgggctcggc gtgctgcgga   13500
tcagctcagc tactatttaa taaaacaaaa tctgtagaat tcacgttttg taatgacact   13560
gtcgtcattc catgctttgt tactaatatg gaggcacaaa acactactga agtatacgta   13620
aagtggaaat ttaaaggaag agatatttac acctttgatg gagctctaaa caagtccact   13680
gtccccactg actttagtag tgcaaaaatt gaagtctcac aattactaaa aggagatgcc   13740
tctttgaaga tggataagag tgatgctgtc tcacacacag gaaactacac ttgtgaagta   13800
acagaattaa ccagagaagg tgaaacgatc atcgagctaa aatatcgtgt tgtttcatgg   13860
ttttctccaa atgaaaatat tcttattgtt attttcccaa tttttgctat actcctgttc   13920
tgggacagt ttggtattaa aacacttaaa tatagatccg gtggtatgga tgagaaaaca   13980
attgctttac ttgttgctgg actagtgatc actgtcattg tcattgttgg agccattctt   14040
ttcgtcccag gtgaatattc attaaagaat gctactggcc ttggtttaat tgtgacttct   14100
acagggatat taatattact tcactactat gtgtttagta cagcgattgg attaacctcc   14160
ttcgtcattg ccatattggt tattcaggtg atagcctata tcctcgctgt ggttggactg   14220
agtctctgta ttgcggcgtg tataccaatg catggcctc tctgatttc aggtttgagt   14280
atcttagctc tagcacaatt acttggacta gtttatatga aatttgtggc ttccaatcag   14340
aagactatac aacctcctag gaaagctgta gaggaacccc ttaatgcatt caaagaatca   14400
aaaggaatga tgaatgatga aggatccgga gccacgaact tctctctgtt aaagcaagca   14460
ggagacgtgg aagaaaaccc cggtcctatg gagcgtccgc aacccgacag catgccccag   14520
gatttgtcag aggccctgaa ggaggccacc aaggaggtgc acaccaggcc agagaatgct   14580
gagttcatga ggaactttca gaagggccag gtgaccgag acggcttcaa gctggtgatg   14640
gcctccctgt accacatcta tgtggccctg gaggaggaga ttgagcgcaa caggagagc   14700
ccagtcttcg cccctgtcta cttcccagaa gagctgcacc gcaaggctgc cctggagcag   14760
gacctggcct tctggtacgg gccccgctgg caggaggtca tccctacac accagccatg   14820
cagcgctatg tgaagcggct ccacgaggtg gggcgacaag agcgcgagct gctggtggcc   14880
cacgcctaca cccgctacct gggtgacctg tctgggggcc aggtgctcaa aaagattgcc   14940
cagaaagccc tggacctgcc cagctctggc gagggcctgg ccttcttcac cttccccaac   15000
attgccagtc ccaccaagtt caagcagctc taccgctccc gcatgaactc cctggagatg   15060
actcccgcag tcaggcagag ggtgatagaa gaggccaaga ctgcgttcct gctcaacatc   15120
cagctctttg aggagttgca ggagctgctg acccatgaca ccaaggacca gagcccctca   15180
```

-continued

```
cgggcaccag ggcttcgcca gcgggccagc aacaaagtgc aagattctgc ccccgtggag  15240
actcccagag ggaagccccc actcaacacc cgctcccagg ctccgcttct ccgatgggtc  15300
cttacactca gctttctggt ggcgacagtt gctgtagggc tttatgccat gtgagcggcg  15360
cgccggcacc ggtaccaagc ttaagagcgc tagctggcca gacatgataa gatacattga  15420
tgagtttgga caaaccacaa ctagaatgca gtgaaaaaaa tgctttattt gtgaaatttg  15480
tgatgctatt gctttatttg taaccattat aagctgcaat aaacaagtta acaacaacaa  15540
ttgcattcat tttatgtttc aggttcaggg ggaggtgtgg gaggtttttt aaagcaagta  15600
aaacctctac aaatgtggta tggaattgga gccccactgt gttcatctta cagatggaaa  15660
tactgacatt cagaggagtt agttaacttg cctaggtgat tcagctaata agtgcaagaa  15720
agatttcaat ccaaggtgat ttgattctga agcctgtgct aatcacatta caccaagcta  15780
caacttcatt tataaataat aagtcagctt tcaagggcct ttcaggtgtc ctgcacttct  15840
acaagctgtg ccatttagtg aacacaaaat gagccttctg atgaagtagt cttttcatta  15900
tttcagatat tagaacacta aaattcttag ctgccagctg attgaaggct gggacaaaat  15960
tcaaacatgc atctacaaca atatatatct caatgttagt ctccaaattc tattgacttc  16020
aactcaagag aatataaaga gctagtcttt atacactctt taaggtatga tgggtcccga  16080
tttttcccg tatcccccca ggtgtctgca ggctcaaaga gcagcgagaa gcgttcagag  16140
gaaagcgatc ccgtgccacc ttccccgtgc ccgggctgtc cccgcacgct gccggctcgg  16200
ggatgcgggg gagcgccgga ccggaccgga gccccgggcg gctcgctgct gccctagcgg  16260
gggagggacg taattacatc cctgggggct ttggggggggg gctgtcccac tagatttttcc  16320
ccgtatcccc ccaggtgtct gcaggctcaa agagcagcga gaagcgttca gaggaaagcg  16380
atcccgtgcc accttccccg tgcccgggct gtccccgcac gctgccggct cggggatgcg  16440
ggggagcgcc ggaccggacc ggagccccgg gcggctcgct gctgccctag cgggggagcg  16500
acgtaattac atccctgggg gctttggggg ggggctgtcc catcggatct tctagtcctg  16560
caggagtcaa tgggaaaaac ccattggagc caagtacact gactcaatag ggactttcca  16620
ttgggttttg cccagtacat aaggtcaata gggggtgagt caacaggaaa gtcccattgg  16680
agccaagtac attgagtcaa tagggacttt ccaatgggtt ttgcccagta cataaggtca  16740
atggggaggta agccaatggg ttttttccat tactgacatg tatacgcgtc gacgtcggcg  16800
cgttcagcct aaagctttt tccccgtatc ccccaggtg tctgcaggct caaagagcag  16860
cgagaagcgt tcagaggaaa gcgatcccgt gccaccttcc ccgtgccggg gctgtccccg  16920
cacgctgccg gctcggggat gcggggggagc gccgaccggg accggagccg cggggcggctc  16980
gctgctgccc tagcgggggga gggacgtaat tacatccctg ggggctttgg ggggggggctg  17040
tccctgcggc cgcgaattcg taatcatggt catagctgtt tcctgtgtga aattgttatc  17100
cgctcacaat tccacacaac atacgagccg gaagcataaa gtgtaaagcc tggggtgcct  17160
aatgagtgag ctaactcaca ttaattgcgt tgcgctcact gcccgctttc cagtcgggaa  17220
acctgtcgtg ccagggggtct agccgcggtc taggaagctt tctagggtac ctctagggat  17280
ccactagtta ttaatagtaa tcaattacgg ggtcattagt tcatagccca tatatggagt  17340
tccgcgttac ataacttacg gtaaatggcc cgcctggctg accgcccaac gacccccgcc  17400
cattgacgtc aataatgacg tatgttccca tagtaacgcc aatagggact ttccattgac  17460
gtcaatgggt ggagtattta cggtaaactg cccacttggc agtacatcaa gtgtatcata  17520
tgccaagtac gccccctatt gacgtcaatg acggtaaatg gcccgcctgg cattatgccc  17580
agtacatgac cttatgggac tttcctactt ggcagtacat ctacgtatta gtcatcgcta  17640
ttaccatggg tcgaggtgag ccccacgttc tgcttcactc tccccatctc cccccctcc  17700
ccacccccaa ttttgtattt atttatttt taattatttt gtgcagcgat gggggcgggg  17760
gggggggggg cgcgcgccag gcggggcggg gcggggcgag gggcggggcg gggcgaggcg  17820
gagaggtgcg gcggcagcca atcagagcgg cgcgctccga aagtttcctt ttatggcgag  17880
gcggcggcgg cggcggccct ataaaaagcg aagcgcgcgg cgggcgggag tcgctgcgtt  17940
gccttcgccc cgtgccccgc tccgccgccg ctccgcccgc cccggcccgc tctgactgac  18000
cgcgttactc ccacaggtga gcgggcggga cggcccttct cctccgggct gtaattagcg  18060
cttggtttaa tgacggctcg tttcttttct gtggctgcgt gaaagcctta aagggctccg  18120
ggagggccct ttgtgcgggg gggagcggct cggggggtgc gtgcgtgtgt gtgtgcgtgg  18180
ggagcgccgc gtgcggcccg cgctgccccgg cggctgtgag cgctgcgggc gcggcgcggg  18240
gctttgtgcg ctccgcgtgt gcgcgagggg agcgcggccg ggggcggtgc ccgcgcggtgc  18300
ggggggggctg cgaggggaac aaaggctgcg tgcggggtgt gtgcgtgggg gggtgagcag  18360
ggggtgtggg cgcggcggtc gggctgtaac ccccccctgc accccctcc ccgagttgct  18420
gagcacggcc cggcttcggg tgcggggctc cgtgcggggc gtggcgcggg gctcgccgtg  18480
ccgggcgggg ggtggcggca ggtgggggtg ccgggcgggc cggggccgcc tcgggcgggg  18540
gagggctcgg gggagggggcg cggcggcccc ggagcgccgg cggctgtcga ggcgcggcga  18600
gccgcagcca ttgcctttta tggtaatcgt gcgagagggc gcaggggactt cctttgtccc  18660
aaatctggcg gagccgaaat ctgggaggcg ccgccgcacc ccctctagcg ggcgcggggcg  18720
aagcggtgcg gcgccggcag gaaggaaatg ggcggggagg gccttcgtgc gtcgccgcgc  18780
cgccgtcccc ttctccatct ccagcctcgg ggctgccgca gggggacggc tgccttcggg  18840
ggggacgggg cagggcgggg ttcggcttct ggcgtgtgac cggcggctct agagcctctg  18900
ctaaccatgt tcatgccttc ttctttttcc tacagctcct gggcaacgtg ctggttgttg  18960
tgctgtctca tcattttggc aaagaattcc gctgcgactc gctgcgactc gctgcgactc  19020
tccttgttct aacccggcgc gccctcagga tggagcctcc cggccgccgc gagtgtccc  19080
ttccttcctg gcgctttcct gggttgcttc tggcggccat ggtgttgctg ctgtactcct  19140
tctccgatgc ctgtgaggag ccaccaacat ttgaagctat ggagctcatt ggtaaaccaa  19200
aaccctacta tgagattggt gaacagtag attataagtg taaaaaagga tacttctata  19260
tacctcctct tgccacccat actatttgtg atcggaatca tacatgctca cctgtctcag  19320
atgacgcctg ttatagagaa acatgtccat atatacggga tccttaaat ggccaagcag  19380
tccctgcaaa tgggacttac gagtttggtt atcagatgca ctttatttgt aatgagggtt  19440
attacttaat tggtgaagaa attctatatt gtgaacttaa aggatcagta gcaatttgga  19500
gcggtaagcc cccaatatgt gaaaaggttt tgtgtacacc acctccaaaa ataaaaaatg  19560
gaaaacacac ctttagtgaa gtagaagtat ttgagtatct tgatgcagta acttatagtt  19620
gtgatcctgc acctggacca gatccatttt cacttattgg agagagcacg atttattgtg  19680
gtgacaattc agtgtggagt cgtgctgctc cagagtgtaa agtggtcaaa tgtcgatttc  19740
cagtagtcga aaatggaaaa cagatatcag gatttggaaa aaaattttac tacaaagcaa  19800
cagttatgtt tgaatgcgat aagggttttt acctcgatgg cagcgacaca attgtctgtg  19860
acagtaacag tacttgggat cccccagttc caaagtgtct taaagtgctg cctccatcta  19920
```

-continued

```
gtacaaaacc tccagctttg agtcattcag tgtcgacttc ttccactaca aaatctccag  19980
cgtccagtgc ctcaggtcct aggcctactt acaagcctcc agtctcaaat tatccaggat  20040
atcctaaacc tgaggaagga atacttgaca gtttggatgt ttgggtcatt gctgtgattg  20100
ttattgccat agttgttgga gttgcagtaa tttgtgttgt cccgtacaga tatcttcaaa  20160
ggaggaagaa gaaaggcaca tacctaactg atgagaccca cagagaagta aaatttactt  20220
ctctcggatc cggagccacg aacttctctc tgttaaagca agcaggagac gtggaagaaa  20280
accccggtcc tatgaccgtc gcgcggccga gcgtgcccgc ggcgctgccc ctcctcgggg  20340
agctgccccg gctgctgctg ctggtgctgt tgtgcctgcc ggccgtgtgg ggtgactgtg  20400
gccttccccc agatgtacct aatgcccagc cagctttgga aggccgtaca agtttcccg  20460
aggatactgt aataacgtac aaatgtgaag aaagctttgt gaaaattcct ggcgagaagg  20520
actcagtgat ctgccttaag ggcagtcaat ggtcagatat tgaagagttc tgcaatcgta  20580
gctgcgaggc gccaacaagg ctaaattctg catccctcaa acagccttat atcactcaga  20640
attattttcc agtcggtact gttgtggaat atgagtgccg tccaggttac agaagagaac  20700
cttctctatc accaaaacta acttgccttc agaatttaaa atggtccaca gcagtcgaat  20760
tttgtaaaaa gaaatcatgc cctaatccgg gagaaatacg aaatggtcag attgatgtac  20820
caggtggcat attatttggt gcaaccatct ccttctcatg taacacaggg tacaaattat  20880
ttggctcgac ttctagtttt tgtcttattt caggcagctc tgtccagtgg agtgacccgt  20940
tgccagagtg cagagaaatt tattgcccag caccaccaca aattgacaat ggaataattc  21000
aaggggaacg tgaccattat ggatatagac agtctgtaac gtatgcatgt aataaaggat  21060
tcaccatgat tggagagcac tctatttatt gtactgtgaa taatgatgaa ggagagtgga  21120
gtgggcccacc acctgaatgc agaggaaaat ctctaacttc caaggtccca ccaacagttc  21180
agaaacctac cacagtaaat gttccaacta cagaagtcct ccaacttct cagaaaacca  21240
ccacaaaaac caccacacca aatgctcaag caacacggag tacacctgtt tccaggacaa  21300
ccaagcattt tcatgaaaca accccaaata aaggaagtgg aaccacttca ggtactaccc  21360
gtcttctatc tgggcacacg tgtttcacgt tgacaggttt gcttgggacg ctagtaacca  21420
tgggcttgct gacttagggc gcgccggcac cggtaccaag cttaagagcg ctagctggcc  21480
agacatgata agatacattg atgagtttgg acaaaccaca actagaatgc agtgaaaaaa  21540
atgctttatt tgtgaaattt gtgatgctat tgctttattt gtaaccatta taagctgcaa  21600
taaacaagtt aacaacaaca attgcattca ttttatgttt caggttcagg gggaggtgtg  21660
ggaggttttt taaagcaagt aaaacctcta caaatgtggt atggaattgg agccccactg  21720
tgttcatctt acagatggaa atactgacat tcagaggaat tagttaactt gcctaggtga  21780
ttcagctaat aagtgcaaga aagatttcaa tccaaggtga tttgattctg aagcctgtgc  21840
taatcacatt acaccaagct acaacttcat ttataaataa taagtcagct ttcaagggcc  21900
tttcaggtgt cctgcacttc tacaagctgt gccatttagt gaacacaaaa tgagccttat  21960
gatgaagtag tcttttcatt atttcagata ttagaacact aaaattctta gctgccagct  22020
gattgaaggc tgggacaaaa ttcaaacatg catctacaac aatatatatc tcaatgttag  22080
tctccaaatt ctattgactt caactcaaga gaatataaag agctagtctt tatacactct  22140
ttaaggtatg atatcatctg gaaagtaaca aaattgatgc aaatttgaat gaactttatc  22200
atggtgtatt tacacaatgt gtttcttctc cctgcaatgt atttcttttct ctaattcctt  22260
ccatttgatc tttcatacac aatctggttc tgatgtatgt tttttggatg cactttttcaa  22320
ctccaaaaga cagagctagt tactttcttc ctggtgctcc aagcactgta tttgtatctg  22380
tattcaagcc ctttgcaata ttgtactgga tcattatttc acctctagga tggcttcccc  22440
aggcaacttg tgttcaccca gagactacat tttgtatctt gttgacctttgaacttccac  22500
cagtgtctaa aaataatatg tatgcaaaat tacttgctat gagaatgtat aattaaacaa  22560
tataaaaagg agaagcaagg agagaaacac aggtgtgtat ttgtgtttgt gtgcttaaaa  22620
ggcagtgtgg aaaaggaaga aatgccattt atagtgagga gacaaagtta tattacctct  22680
tatctggctt ttaaggagat tttgctgagc taaaaatcct atattcatag aaaagcctta  22740
cctgagttgc caatacctca attctaaaat acagcatagc aaaactttaa cctccaaatc  22800
aagcctctac ttgaatcctt ttctgaggga tgaataaggc ataggcatca ggggctgttg  22860
ccaatgtgca ttagctgttt gcagcctcac cttctttcat ggagtttaag atatagtgta  22920
ttttcccaag gtttgaacta gctcttcatt tctttatgtt ttaaatgcac tgacctccca  22980
cattcccttt ttagtaaaat attcagaaat aatttatcat ctggaaagta acaaaattga  23040
tgcaaatttg aatgaacttt atcatggtgt atttacacaa tgtgtttctt ctccctgcaa  23100
tgtatttctt tctctaattc cttccatttg atctttcata cacaatctgg ttctgatgta  23160
tgttttttgg atgcactttt caactccaaa agacagagct agttactttc ttcctggtgc  23220
tccaagcact gtatttgtat ctgtattcaa gcccttttgca atattgtact ggatcattat  23280
ttcacctcta ggatggcttc cccaggcaac ttgtgttcac ccagagacta cattttgtat  23340
cttgttgacc tttgaacttc caccagtgtc taaaaataat atgtatgcaa aattacttgc  23400
tatgagaatg tataattaaa caatataaaa aggagaagca aggagagaaga aggagagagaaa cacaggtgtg  23460
tatttgtgtt tgtgtgctta aaaggcagtg tggaaaagga agaaatgcca tttatagtga  23520
ggagacaaag ttatattacc tcttatctgg cttttaagga gatttgctg agctaaaaat  23580
cctatattca tagaaaagcc ttacctgagt tgccaatacc tcaattctaa aatacagcat  23640
agcaaaactt taacctccaa atcaagcctc tacttgaatc ctttttctgag ggatgaataa  23700
ggcataggca tcaggggctg ttgccaatgt gcattagctg cagcct caccttcttat  23760
catggagttt aagatatagt gtattttccc aaggtttgaa ctagctcttc atttctttat  23820
gttttaaatg cactgacctc ccacattccc ttttagtaa aatattcaga aataatttat  23880
cccggcttgt cgacgacgga tcatctggaa agtaacaaa ttgatgcaaa tttgaatgaa  23940
ctttatcatg gtgtatttac acaatgtgtt tcttctccct gcaatgtatt tcttttctcta  24000
ttccttccat ttgatctttc atacacaatc tggttctgat gtatgttttt tggatgcact  24060
tttcaactcc aaaagacaga gctagttact ttcttcctgg tgctccaagc actgtatttg  24120
tatctgtatt caagcccttt gcaatattgt actggatcat tatttcacct ctaggatggc  24180
ttccccaggc aacttgtgtt cacccagaga ctacattttg tatcttgttg accttttgaac  24240
ttccaccagt gtctaaaaat aatatgtatg caaaattact tgctatgaga atgtataatt  24300
aaacaatata aaaaggagaa gcaaggagag aaacacaggt gtgtatttgt gtttgtgtga  24360
ttaaaaggca gtgtggaaaa ggaagaaatg ccatttatg tgaggagaca aagttatatt  24420
acctcttatc tggctttaa ggagattttg ctgagctaaa aatcctatat tcatagaaaa  24480
gccttacctg agttgccaat acctcaattc taaaatacag catagcaaaa ctttaacctc  24540
caaatcaagc ctctacttga atcctttttct gagggatgaa taaggcatag gcatcagggg  24600
ctgttgccaa tgtgcattag ctgtttgcag cctcaccttc tttcatggag tttaagatat  24660
```

```
agtgtatttt cccaaggttt gaactagctc ttcatttctt tatgttttaa atgcactgac  24720
ctcccacatt cccttttag taaaatattc agaaataatt tatcccggct tgtcgacggc   24780
gtccgtcgtc aggatcatcc atcaggacat agcgttggct acccgtgata ttgctgaaga   24840
gcttggcggc gaatgggctg accgcttcct cgtgctttac ggtatcgccg ctcccgattc   24900
gcagcgcatc gccttctatc gccttcttga cgagttcttc tgaggggatc aattctctag   24960
agctcgctga tcagcctcga ctgtgccttc tagttgccag ccatctgttg tttgcccctc   25020
ccccgtgcct tccttgaccc tggaaggtgc cactcccact gtcctttcct aataaaatga   25080
ggaaattgca tcgcattgtc tgagtaggtg tcattctatt ctgggggggtg gggtggggca   25140
ggacagcaag ggggaggatt gggaagacaa tagcaggcat gctggggatg cggtgggctc   25200
tatggcttct gaggcggaaa gaaccagctg ggggcgcgca cctcgaccat ctccaggatg   25260
cctttgatag agctgggtcc tctgcgttcc tttaaagtgt ttgagatcaa gtccgagaag   25320
aggtggcaag cgatcgcgac atatttaaat cgcgctagtt taaaatacat cattgcaatg   25380
aaaataaatg ttttttatta ggcagaatcc agatgctcaa ggcccttcat aatatccccc   25440
agtttagtag ttggacttag ggaacaaagg aacctttaat agaaattgga cagcaagaaa   25500
gctctagctt tagaagaact catcaagaag tctgtagaag gcaattctct gggagtcagg   25560
ggctgcaatg ccatagagca ctaggaacct gtctgcccac tctcccccta gctcttctgc   25620
tatgtccctg gttgctaggg caatgtcctg gtacctgtca gccactccca gcctgccaca   25680
gtctatgaag ccagagaacc ttccattttc aaccatgatg ttgggaaggc aggcatcccc   25740
atgagtcacc actaggtcct caccatctgg catggatgcc ttgagcctgg caaatagttc   25800
agcaggggcc aggccctggt gttcttcatc caagtcatct tggtccacca ggccagcctc   25860
catcctggtt ctggccctct ctatcctgtg cttggcctgg tggtcaaagg ggcaggtggc   25920
tgggtcaagg gtgtggagtc ttctcatggc atcagccatg attgacactt tctcagctgg   25980
agctaggtga gaggaaagga ggtcctgccc aggcacctca cctagtagga gccagtccct   26040
tccagcttct gtgaccacat caaggacagc tgcacagggg accccagttg ttgccaacca   26100
ggagagtctg gcagcctcat cctggagctc attgagagcc ccactgaggt ctgtctttac   26160
aaaaaggact ggcctgcctt gggctgaaag tctgaaaact gctgcatcag agcaaccaat   26220
ggtctgctgt gcccagtcat agccaaacag tctctcaacc caggcagctg gagaacctgc   26280
atgtaggcca tcttgttcaa tcatgatggc tcctcctgtc aggagaggaa agagaagaag   26340
gttagtacaa ttgctatagt gagttgtatt atactatgct tatgattaat tgtcaaacta   26400
gggctgcagg gttcatagtg ccactttttcc tgcactgccc catctcctgc ccaccctttc   26460
ccaggcatag acagtcagtg acttaccaaa ctcacaggag ggagaaggca gaagcttttt   26520
gcaaaagcct aggctcatga gacaataacc ctgataaatg cttcaataat attgaaaaag   26580
gaagagtacc aggtatgagt attcaacatt tccgtgtcgc ccttattccc tttttttgcgg   26640
cattttgcct tcctgttttt gctcacccag aaacgctggt gaaagtaaaa gatgctgaag   26700
atcagttggg tgcacgagtg ggttacatcg aactggatct caacagcggt aagatccttg   26760
agagtttttcg ccccgaagaa cgttttccaa tgatgagcac ttttaaagtt ctgctatgtg   26820
gcgcggtatt atcccgtatt gacgccgggc aagagcaact cggtcgcgc atacactatt   26880
ctcagaatga cttggttgag tactcaccag tcacagaaaa gcatcttacg gatggcatga   26940
cagtaagaga attatgcagt gctgccataa ccatgagtga taacactgc gccaacttac   27000
ttctgacaac gatcggagga ccgaaggagc taaccgcttt tttgcacaac atgggggatc   27060
atgtaactcg ccttgatcgt tgggaaccgg agctgaatga agccatacca aacgacgagc   27120
gtgacaccac gatgcctgta gcaatggcaa caacgttgcg caaactatta actggcgaac   27180
tacttactct agcttcccgg caacaattaa tagactggat ggaggcggat aaagttgcag   27240
gaccacttct gcgctcggcc cttccggctg gctggtttat tgctgataaa tctggagccg   27300
gtgagcgtgg gtctcgcggt atcattgcag cactggggcc agatggtaag ccctcccgta   27360
tcgtagttat ctacacgacg gggagtcagg caactatgga tgaacgaaat agacagatcg   27420
ctgagatagg tgcctcactg attaagcatt ggtaactgtc agaccaagtt tactcatata   27480
tactttagat tgatttaaaa cttcatttttt aatttaaaag gatctaggtg aagatccttt   27540
ttgataatct catgaccaaa atcccttaac gtgagttttc gttccactga gcgtcagacc   27600
ccgtagaaaa gatcaaagga tcttcttgag atccttttttt tctgcgcgta atctgctgct   27660
tgcaaacaaa aaaaccaccg ctaccagcgg tggtttgttt gccggatcaa gagctaccaa   27720
ctctttttcc gaaggtaact ggcttcagca gagcgcagat accaaatact gttcttctag   27780
tgtagccgta gttaggccac cacttcaaga actctgtagc accgcctaca tacctcgctc   27840
tgctaatcct gttaccagtg gctgctgcca gtggcgataa gtcgtgtctt accgggttgg   27900
actcaagacg atagttaccg gataaggcgc agcggtcggg ctgaacgggg ggttcgtgca   27960
cacagcccag cttggagcga acgacctaca ccgaactgag atacctacag cgtgagctat   28020
gagaaagcgc cacgcttccc gaagggagaa aggcggacag gtatccggta agcggcaggg   28080
tcggaacagg agagcgcacg agggagcttc caggggggaaa cgcctggtat ctttatagtc   28140
ctgtcgggtt tcgccacctc tgacttgagc gtcgatttttt gtgatgctcg tcaggggggc   28200
ggagcctatg gaaaaacgcc agcaacgcgg cctttttacg gttcctggcc ttttgctggc   28260
cttttgctca catggctcga cagatttaat taacaagacc gacctgtccg gtgccctgaa   28320
tgaactgcag gacgaggcag cgcggctatc gtggctggcc acgacgggcg ttccttgcgc   28380
agctgtgctc gacgttgtca ctgaagcggg aagggactgg ctgctattgg gcgaagtgcc   28440
ggggcaggat ctcctgtcat ctcaccttgc tcctgccgag aaagtatcca tcatggctga   28500
tgcaatgcgg cggctgcata cgcttgatcc ggctacctgc ccattcgacc accaagcgaa   28560
acatcgcatc gagcgagcac gtactcggat ggaagccggt cttgtcgatc aggatgatct   28620
ggacgaagag catcaggggc tcgcgccagc cgaactgttc gccaggctca aggcgcgcat   28680
gcccgacggc gaggatctcg tcgtgaccca tggcgatgcc tgcttgccga atatcatggt   28740
ggaaaatggc cgcttttctg gattcatcga ctgtggccgg ctgggtgtgg cggatcgctg   28800
gcctcgatgg ccgtgatacg cctgcagga tcatttgcca gccatctgtt gtttgcccct   28860
ccccgtgcc ttccttgacc ctggaaggtg ccactcccac tgtcctttcc taataaaatg   28920
aggaaattgc atgccggcag cgtgcgggga cagcccgggc acgggaagg tggcacggga   28980
tcgctttcct ctgaacgctt ctcgctgctc tttgagcctg cagacacctg gggggatacg   29040
gggaaaagtt agtttaaacg ttcgcgatag tatacggcct gcaggatgac tttggcctcg   29100
atggccgtgc caggcgtgc ccttgggctc cccgggcgcg gcgattaaga cgt          29153
```

```
SEQ ID NO: 13        moltype = DNA  length = 29351
FEATURE              Location/Qualifiers
source               1..29351
```

-continued

```
                    mol_type = other DNA
                    organism = synthetic construct
SEQUENCE: 13
atcatctgga aagtaacaaa attgatgcaa atttgaatga actttatcat ggtgtattta   60
cacaatgtgt ttcttctccc tgcaatgtat ttctttctct attccttcca tttgatcttt  120
catacacaat ctggttctga tgtatgtttt ttggatgcac tttttcaactc caaaagacag  180
agctagttac tttcttcctg gtgctccaag cactgtattt gtatctgtat tcaagccctt  240
tgcaatattg tactggatca ttatttcacc tctaggatgg cttccccagg caacttgtgt  300
tcacccagag actacatttt gtatcttgtt gacctttgaa cttccaccag tgtctaaaaa  360
taatatgtat gcaaaattac ttgctatgag aatgtataat taaacaatat aaaaaggaga  420
agcaaggaga gaaacacagg tgtgtatttg tgtttgtgtg cttaaaaggc agtgtggaaa  480
aggaagaaat gccatttata gtgaggagac aaagttatat tacctcttat ctggctttta  540
aggagatttt gctgagctaa aaatcctata ttcatagaaa agccttacct gagttgccaa  600
tacctcaatt ctaaaataca gcatagcaaa actttaacct ccaaatcaag cctctacttg  660
aatcctttc tgagggatga ataaggcata ggcatcaggg gctgttgcca atgtgcatta  720
gctgtttgca gcctcacctt ctttcatgga gtttaagata tagtgtattt tcccaaggtt  780
tgaactagct cttcatttct ttatgtttta aatgcactga cctcccacat tcccttttta  840
gtaaaatatt cagaaataat ttatcccggc ttgtcgacgg cgtccgtcgt caggatcatc  900
catcaggaca tagcgttggc tacccgtgat attgctgaag agcttggcgg cgaatgggct  960
gaccgcttcc tcgtgcttta cggtatcgcc gctcccgatt cgcagcgcat cgccttctat 1020
cgccttcttg acgagttctt ctgaggggat caattctcta gagctcgctg atcagcctcg 1080
actgtgcctt ctagttgcca gccatctgtt gtttgcccct cccccgtgcc ttccttgacc 1140
ctggaaggtg ccactcccac tgtcctttcc taataaaatg aggaaattgc atcgcattgt 1200
ctgagtaggt gtcattctat tctgggggggt ggggtggggc aggacagcaa gggggaggat 1260
tgggaagaca atagcaggca tgctggggat gcggtgggct ctatggcttc tgaggcggaa 1320
agaaccagct gggggcgcgc acctcgacca tctccaggat gcctttgata gagctgggtc 1380
ctctgcgttc ctttaaagtg tttgagatca agtccgagaa gaggtggcaa gcgatccgca 1440
catatttaaa tcgcgctagt ttaaaataca tcattgcaat gaaaataaat gttttttatt 1500
aggcagaatc cagatgctca aggcccttca taatatcccc cagtttagta gttggactta 1560
gggaacaaag gaacctttaa tagaaattgg acagcaagaa agctctagct ttagaagaac 1620
tcatcaagaa gtctgtagaa ggcaattctc tgggagtcag gggctgcaat gccatagagc 1680
actaggaacc tgtctgccca ctctccccct agctcttctg ctatgtccct ggttgctagg 1740
gcaatgtcct ggtacctgtc agccactccc agcctgccac agtctatgaa gccagagaac 1800
cttccatttt caaccatgat gttgggaagg caggcatccc catgagtcac cactaggtcc 1860
tcaccatctg gcatggatgc cttgagcctg gcaaatagtt cagcagggggc caggccctgg 1920
tgttcttcat ccaagtcatc ttggtccacc aggccagcct ccatcctggt tctggccctc 1980
tctatcctgt gcttggcctg gtggtcaaag gggcaggtgg ctgggtcaag ggtgtggagt 2040
cttctcatgg catcagccat gattgacact ttctcagctg gagctaggtg agaggaaagg 2100
aggtcctgcc caggcacctc acctagtagg agccagtccc ttccagcttc tgtgaccaca 2160
tcaaggacag ctgcacaggg gaccccagtt gttgccaacc aggagagtct ggcagcctca 2220
tcctggagct cattgagagc cccactgagg tctgtcttta caaaaaggac tggcctgcct 2280
tgggctgaaa gtctgaaaac tgctgcatca gagcaaccaa tggtctgctg tgcccagtca 2340
tagccaaaca gtctctcaac ccaggcagct ggagaacctg catgtaggcc atcttgttca 2400
atcatgatgg ctcctcctgt caggagagga aagagaagaa ggttagtaca attgctatag 2460
tgagttgtat tatactatgc ttatgattaa ttgtcaaact agggctgcag ggttcatagt 2520
gccacttttc ctgcactgcc ccatctcctg cccacccttt cccaggcata gacagtcagt 2580
gacttaccaa actcacagga gggagaaggc agaagctttt tgcaaaagcc taggctcatg 2640
agacaataac cctgataaat gcttcaataa tattgaaaaa ggaagagtac caggtatgag 2700
tattcaacat ttccgtgtcg cccttattcc ctttttttgcg gcattttgcc ttcctgtttt 2760
tgctcaccca gaaacgctgg tgaaagtaaa agatgctgaa gatcagttgg gtgcacgagt 2820
gggttacatc gaactggatc tcaacagcgg taagatcctt gagagttttc gccccgaaga 2880
acgttttcca atgatgagca cttttaaagt tctgctatgt ggcgcggtat tatcccgtat 2940
tgacgccggg caagagcaac tcggtcgccg catacactat tctcagaatg acttggttga 3000
gtactcacca gtcacagaaa agcatcttac ggatggcatg acagtaagag aattatgcag 3060
tgctgccata accatgagtg ataacactgc ggccaactta cttctgacaa cgatcggagg 3120
accgaaggag ctaaccgctt ttttgcacaa catgggggat catgtaactc gccttgatcg 3180
ttgggaaccg gagctgaatg aagccatacc aaacgacgag cgtgacacca cgatgcctgt 3240
agcaatggca acaacgttgc gcaaactatt aactggcgaa ctacttactc tagcttcccg 3300
gcaacaatta atagactgga tggaggcgga taaagttgca ggaccacttc tgcgctcggc 3360
ccttccggct ggctggttta ttgctgataa atctggagcc ggtgagcgtg ggtctcgcgg 3420
tatcattgca gcactggggc cagatggtaa gccctcccgt atcgtagtta tctacacgac 3480
ggggagtcag gcaactatgg atgaacgaaa tagacagatc gctgagatag gtgcctcact 3540
gattaagcat tggtaactgt cagaccaagt ttactcatat atactttaga ttgatttaaa 3600
acttcatttt taatttaaaa ggatctaggt gaagatcctt tttgataatc tcatgaccaa 3660
aatcccttaa cgtgagtttt cgttccactg agcgtcagac cccgtagaaa agatcaaagg 3720
atcttcttga tccttttttt ttctgcgcgt aatctgctgc ttgcaaacaa aaaaaccacc 3780
gctaccagcg gtggtttgtt tgccggatca agagctacca actctttttc cgaaggtaac 3840
tggcttcagc agagcgcaga taccaaatac tgttcttcta gtgtagccgt agttaggcca 3900
ccacttcaag aactctgtag caccgcctac atacctcgct ctgctaatcc tgttaccagt 3960
ggctgctgcc agtggcgata agtcgtgtct taccgggttg gactcaagac gatagttacc 4020
ggataaggcg cagcggtcgg gctgaacggg gggttcgtgc acacagccca gcttggagcg 4080
aacgacctac accgaactga gatacctaca gcgtgagcta tgagaaagcg ccacgcttcc 4140
cgaagggaga aaggcggaca ggtatccggt aagcggcagg gtcggaacag gagagcgcac 4200
gagggagctt ccagggggaa acgcctggta tctttatagt cctgtcgggt ttcgccacct 4260
ctgacttgag cgtcgatttt tgtgatgctc gtcagggggg cggagcctat ggaaaaacgc 4320
cagcaacgcg gcctttttac ggttcctggc cttttgctgg ccttttgctc acatggctcg 4380
acagatttaa ttaacaagac cgacctgtcc ggtgccctga atgaactgca ggacgaggca 4440
gcgcggctat cgtggctggc cacgacgggc gttccttgcg cagctgtgct cgacgttgtc 4500
actgaagcgg gaagggactg gctgctattg ggcgaagtgc cggggcagga tctcctgtca 4560
```

-continued

```
tctcaccttg ctcctgccga gaaagtatcc atcatggctg atgcaatgcg gcggctgcat  4620
acgcttgatc cggctacctg cccattcgac caccaagcga aacatcgcat cgagcgagca  4680
cgtactcgga tggaagccgg tcttgtcgat caggatgatc tggacgaaga gcatcagggg  4740
ctcgcgccag ccgaactgtt cgccaggctc aaggcgcgca tgcccgacgg cgaggatctc  4800
gtcgtgaccc atggcgatgc ctgcttgccg aatatcatgg tggaaaatgg ccgcttttct  4860
ggattcatcg actgtggccg gctgggtgtg gcggatcgct ggcctcgatg gccgtgatac  4920
ggcctgcagg atcatttgcc agccatctgt tgtttgcccc tccccgtgc cttccttgac    4980
cctggaaggt gccactccca ctgtcctttc ctaataaaat gaggaaattg catgccggca  5040
gcgtgcgggg acagcccggg cacggggaag gtggcacggg atcgctttcc tctgaacgct  5100
tctcgctgct ctttgagcct gcagacacct gggggatac ggggaaaagt tagtttaaac    5160
gttcgcgata gtatacggcc tgcaggatga cttttggcctc gatggccgtg ccagggcgtg  5220
cccttgggct ccccgggcgc ggcgattaag acgtatgtct cctatgtctc atctaaatgg  5280
atgaggtttg agagttccca tcacggcatg gtggaaacga atccgactag gagccataag  5340
ttcacggctt cgatccctgg cctcgctcag ggggttaagg atccggtgtt gctgtgagct  5400
gtggtgtagg tcacagatgc ggttcggatc tggcgttgct gcggctgtgg tgtaggctgg  5460
tggctgtagc tccgatttga cccctagcct agggaccttc atatgccgtg ggtatggccc  5520
taaaaagcca aataaaataa aataagtaaa tggttgaggt ttgacacaga aagtttattt  5580
atttatgtat ttacttatct tttttttttt tttttttttt gtctttctgc tatttcttgg  5640
gctgctcccg cggcatatgg aggttcccag gctaggggtc gaattggagc tacagccacc  5700
agcctacacc acagccgcag caatgccaga tccgagccgc ctctgtgacc tacaccacag  5760
ctcatggcaa cgctggatcg ttaacccact gagcaagggc tgggaccgaa cccgcaacct  5820
catggttcct agtcggattc gttaaccact gcgccatgac gggaactcct acttatctat  5880
tttttaaagc atatggaagt tcccaggcta gggggttgaa tcggagctgc aactgccggc  5940
ttacaccaca gccagagcaa cgccggatct gagcagtgtc tgggacctac accacagctc  6000
acagccacac cggatcctca atccactgaa tgaggccagg aatcaaacct gtgtcctcat    6060
ggatactagt cagattcatt tccgctgagc aatgacagga actcctgaca cagaaatttt  6120
agattaaaat tgaagatgag ccccttcctt ttgtacgacc tttgtgtgca gattttcgag  6180
gataagtcct tgagcttgaa gttttagggt catggatcct cataacagtt tcctggcctg  6240
tgaggcttgg atctcagtat aaacagaagt gctggcagca gtagacacag cagcagctgt  6300
tttcaggaac aaatactggg cacctgcctt gtggacctgc ctgactccac cactctcttg  6360
ggtatccaca aagtggaccc agaggttcag agcagccctg ggatccaaat tttttttaatt  6420
tatttttat cttttatttt ttgtctttttc gaaattttta gggctacacc catgagatat  6480
ggaggttccc aggctaaggg tccaatcgga gctacaactg ccggcctaca ccacagctca  6540
tggcaatgct ggatccttaa cccgctgagc gaggccaggg atcaaaccca caacctcatg  6600
attcctagtt ggattcgtta accactgagc cacgatgggga actcctgggg atgcaaattt  6660
tgtcatctag ccctaggatg tagctatcat cctgatttga gaagagaggc agagtctcag  6720
gtggcttctc tctcatgaat gcagagctaa gggtggccac acgtacttga gttcatccga  6780
tgcacacagc attgtgctaa aatattgacc atttggccct tttgctgact tttggtttga  6840
gggatatgac cttcatgagc atacagagga taatatgtat gcatgtatgc atgtgtgtac  6900
acatgtgcgc atgcatgtat atacctgcat aattatgtat ttgtttatgt atgcaggtgc  6960
atgtgtatgt atatatttat tatttatttta tttggggggcc acacccatga catttggaag  7020
ttcctgggac agagattgaa tcccagccac agctttgacc tacgccatgg acacagcaac  7080
actggattct taacccctg tgccacagcg ggaactccta gaagatagta tttcatgatg  7140
atatttgact aaaaataggg gtcaggcttt gaagtttaaa taaattcgac cagataaatg  7200
gccatccagg aagttatact ttgccttgtt caaatttgga ccacggggaa ggtggttggc  7260
gacatgtaac agaaatctga ctccagtgca ggtttcgctc ccgtgacggg aagcccagg    7320
gtgggcagcc ctaaggctgg ggctctgatt tcatgatgct cttagcatct tgagtccctt  7380
ccctcttctt gctttttatct cagcctcggg ctgctgcacc ttctgtcttt gtggtgagtc  7440
tacctattcc acttagctcg gcttcagggt gtatttccac gacttcgtta gagtaaggtt  7500
ggggccagct gtgctctgcc ggcaggaggt gtgcttgcag gggccatgga tgtggccagg  7560
acctaatgtg acggtgggga gcaggatggg gatgaggatg tgaccacaga gccttggcca  7620
ccacgtcatc cacgtcatac actgagagca ggtggttctc atgcaggtgc atcagaatcc  7680
cgaggacggc ttgtccaaac ccagatggct gggcccaagc cctgagctcc cgatttggga  7740
ggccttggct gggccccgaa atctgccttc ctgactagac cgagtgatga atggtgttca  7800
tagacaagac atacactaac actggtcttg ggggctcctt gccacaccct gaaggggtcc  7860
gtgaaactga cggggccaga gaaggtgctg gttcctccat ggaaggtctc agtgaggcca  7920
ttctgctgcc cggctgggtc acgctggggg agtgagggtg catcccctcc tgggatctgg  7980
tcaaaggcag attctgattc tggaagcacg gggtagggcc agagatgcca ccttctaaca  8040
agcccccagg tgaagatgtt gacctgggac cttatggtgg ggggtggcgg agctcaaggt  8100
ggcagacacc tccctctctc tcaacctgtg tcacagcagg gccatcctac tggctctcgc  8160
tcggccagag atggcgatgc cagaacacac tggggcaggg tgtccacatt tttgtcactt  8220
ccactgagcc ctggggactg actcatttaa atgacattct caactctttg gaaagaagct  8280
gggccagaaa tggaaatggc agcaaacact ttttgggaaa caggaagcca attttttttt  8340
tcaatcatga ttttccccag attcagagac tgcttaactc ccaatgaaat actttttagat  8400
tacgagctaa aataccgaaa agctgtcaag ctcaagacca caggaaaaca gccgaagaac  8460
aaacaccatg agaaaacagt cacagagtgc ctctgcggcg gatttcaagt tccagacttc  8520
cttgctgtca gctgtgtgta cttgtcccgc ctgcagtagg accagctggg gtttaagtct  8580
gtaccatgga cactgctgcc aggattctcc tctgcatctg ctgacttcca gctcttcagg  8640
gccagctggc cataggagca taaactgaca tccagttcca ggaggcagca tctgtcccca  8700
tggcctgcag gacaccagat cagtagaggc ccccagggcc acctttcctg tgggggcccct  8760
tgaagggacc cgggaaggct ggatcttgct aaagcttcca caagtccctt ccaaaggaga  8820
gtaaattcta aacagaagct tttgccagtg cttctctggg atctggcttc aggattattc  8880
ctagtctgaa aagtcttcct ggtggtttgg acacgggcaa atgcttggtg ggtgggctgg  8940
ctctggatgc aggtgagtgg ggtcggaagt tctccctcct tcccacaaag cttgacggag  9000
ccaggggcac ccgcgggcct gtggatggga gaggggtttc tggtgacgga ctcaagtctt  9060
ggcagcccct gaccccagag caggctccct ccccacagct gctctccgtg agtccttcac  9120
ttgcccaagt tcaagatgta cccagttctg gagctgccaa accatcctgc atcctgacgt  9180
cagccaccca agttctgggg tagctggtct gccacccagg tggatgaaaa gaggccacat  9240
acctgcacca gcatctgcga atctctgaag aacatcaata ataaaaagac aactaacccg  9300
```

-continued

```
attaaaacac aggtagagaa tctgaacaga cattcatcgg aagaagaatt acgactggcc  9360
aaaaaagctca taaaaagatg gtcaaagtca ttggtcaggg aaatgtaaat caaaccgcat  9420
tgagatacca tctcactccc tctcggatgg ctggaatgaa aaaaaacctc ttctttcctc  9480
cctttcattg tcttggcacc cttgtggaaa ttaattgact aaaattcatg aaatacaaaa  9540
attttagga gttcccgtcg tggctcagtg gttaacaaat ctgactagga accatgaggt  9600
ttcaggttcg attcctggcc tcactcagtg ggttagggat ctggtgttgc catgagctgt  9660
ggtgtaggtc gcagacgcag ctcggatccc gcattgctgt ggctctggcg taggccggcg  9720
gctacagctc tgattcaacc tctagcctgg gaatagccca agaaatggca aaaagaccaa  9780
aaaaaaaaa aaaaaaaaaa ctcgttttga gcatttttgc atgtgtacat tgtccatttg  9840
tgtgccttcc aagatttatt ttttgagtct caactctgtc attgatttat gtctctcctt  9900
aggccagaac cacactgttt tggtgaccat ggctttgtag taaaatttga aatctgaaag  9960
tgtgagccct cctgttttgt ttctcttctc catgattagt ttggttattc agagtccctt  10020
gaatttccag gtgaatttta ggattagcag gaaaaatttct gcagagatgg cagcagagat  10080
ttttaatagg gattatgttg aatctggagg ttaatttcag ttttgctacc ttgactgtat  10140
taagtcttcc agtctataag cataagatgt cttttttattt acttaggtct tttaaaattt  10200
ctttgggcac tcccattgtg gtgcatcgga aatgaatccg actagtatcc acaagaacac  10260
aggttcaatc cctggcattg ctcagtgggt taaggatcct gcattgccat gaagaactgt  10320
ggtggaggcc agcagctgca gctctgattt gaccccctagc ctgggaactt ccatatgcct  10380
tgggtatggc cctaaaaagc aaactaagta agtaagtaaa taaatanaatg aataaataaa  10440
atttctttca aaattgtaat tttgtaattt ttgtaatttt cagagtgtac attttgccct  10500
ttcaatacat tattcctaca tattttattc tttttgatac tattataaat gaaatttata  10560
attaattcat ttatatgaat ttcatttttca atttgcatat tgctactaca atagaaatgc  10620
actttttaat tattttttatg gccataccat atatatatgt gtgtgtgtgt gtatgtgtgt  10680
cattttactg tacagcagaa attgacacaa cattgtaaat caactacact taaaaaatga  10740
agaaataacc acctgtgatt atggctactg tgttggacac tttaggcatc ccccccacccc  10800
gtccccgccc cacacccctg agtgctagtg acggatgttc ccacccaggg ggcctggagc  10860
ctttatcacc agccatcggg aatcagaacc gtatctcaca gtccccatgc ctgtagcacc  10920
tggaattgtg cccttggact cgtgggtgtt ctgcttctca gtgggagaag cttaggttct  10980
aagtcagagc agggacagcc cccatgtgct caggacccag tgtgaagggg tctgcctcag  11040
gggacctggg ggttacaagg gtaagagaag gtgttcatgt tggaactaga agttcttttt  11100
caccgctctg aagaaaaaag ctgcctccca cccttggtac agctcttctg ctaacagtga  11160
atcaggcaga acgtgttcaa gaagtgaccc agcctggtgg gggccagacc tgaccttga  11220
tggtccctca acccctccga gggtcccgcc cttcctttac tgctttgttg tctgtcctga  11280
gaggtttggc taatgtcgaa ccaagggtgt ggctggtcct gtcccctttc ctgtctcacg  11340
cacccacctc tgaagtctct gtagctggtt ccagccggga tctggagcca ctccccccgc  11400
cccaggccca gtggtacaga ctcttgcaga gtcggggggcc cctgactcag ccccaccgcc  11460
agcgggatgt caggccagca cccgccccac tcccactgat ctggggggggg tgtctttcct  11520
tcctccttcc aaaggagcct cagaccttcc tgtgtggggcac ggggggcagtg ggattcagga  11580
ggctctgagt cagcaggccg gcattgagga gtataaaggg accccagttc ctcccccttt  11640
cacttgtggc ttatcgccgc cccaccctgc cccaaggtca ctgcggtcag tacagtcctc  11700
agctgccagc aggtgcctgt ctttacttgt gaggccgcca cgctctcctg tttctccagg  11760
tctgggctct gttggaagtg ggggcccgac cccagggtaa gatgggggat ctgcgtgtcc  11820
tgccctcaga ggcctcctcc tccccgcacc cctaaccctt tcagcccaac aaggctggag  11880
atctcccaca tctttggctt cgttaagagt tcaacagcgc cgccacccgg catgtcgctg  11940
agcagaggat ggcacagggt gttaaaaaaa aaaaaaggtt gccacactcc gttcggtttt  12000
gggcccaccc tttcgcattc ctggagcctg agtaagcgga taaggctgtg aaagtgacag  12060
attcctgcca cctccttcca gcgctcatgc acagggaccg ccctcttcg gtgtcctttg  12120
ctgcacaagt gcatttgcac attcctgtct caatctggtt tctcccccctt aaaagatggg  12180
aatgtgacct gcttggagcc cctcgcctcg ccagggcacc ccatccgtcc cttcagggggt  12240
ggagatggac tgtccctctg caaggctgga tgaactcaga ccaaacaggc caacttgctc  12300
cccaaatacg cccaccccta ccggggctgca gaaattcgca tgtcaccact gctgaagggt  12360
gaccttgcag ccctgagagc atccccatga cttgcccacc agatgaagtc tggttgtggc  12420
aggtcgcgct cagggactcc cgggtcccac ctgggggtgg gaggatcctc ctttgctcgt  12480
ggtcgcccca gacacgccct cctttccaag cgccagtctc cagagctccg tgccccggcg  12540
gaggcggtct ggctctctct ccttgcccct ctctccttgc ccctagcagc ccttctccta  12600
aaccctctga gcagcgggca cctcctcccg aggccctggg ctaagtcccc acccttcatc  12660
tcaagccttc ctccttgact ccctcttccc agagttcctt gaaataggtg gtaagtacac  12720
accgatgacg gaaaacaaag actaagaggt taaagagggc tgaggattac ggccccggta  12780
gggctgcgcg cgagggggtc gagtggccgg gcggtcccgc cgccgggcag acagaggtcg  12840
ggttctcccg ggcgcctgcg ctgccggccc gccccagcc ggcgcccagt  12900
ttactcatcc cggagaggtg atccccggcg cgagggcggg cgcagggcgt ccggagaacc  12960
cagtaatccg agaatgcagc atcagcccctt cccaccaggc acttccttcc tttttcccgaa  13020
cgtccaggga ggggggccgc gcacttataa actcgggccg gacccgccgg cctgtcagag  13080
gctgcctcgc tggggctgcg cgcggcggcc ggacacatct ggtccgagac caacgcgagc  13140
gactgtcact ggcagctccc tgcgcctctc agccccggcc gggcccctgc gcttggcgtg  13200
ctgacaccat gcttgggggtc ctggtccttg gcgcgctggc cctggccggc ctggggttcc  13260
ccgcacccgc agagccgcag ccgggtggca gccagtgcgt cgagcacgac tgcttcgcgc  13320
tctacccggg cccgcgcgacc ttcctcaatg ccagtcagat ctgcgacgga ctgcgggggcc  13380
acctaatgac agtgcgctcc tcggtggctg ccgatgtcat ttccttgcta ctgaacgggg  13440
acggcggcgt tggccgccgg cgcctctgga tcggcctgca gctgccaccc ggctgcggcg  13500
accccaagcg cctcgggccc ctgcgcggct tccagtgggt tacggggac aacaacacca  13560
gctatagcag gtgggcacgg ctcgacctca atgggggctcc cctctgcggc ccgttgtgcg  13620
tcgctgtctc cgctgctgag gccactgtgc ccagcgagc gatctgggag gagcagcagt  13680
gcgaagtgaa ggccgactgg ttcctctgcg agttccactt tgcaggccagc caggaggccc  13740
tggctgtgga gcccggcgcc gcggctgccg ccgtctcgat cacctacgac accccgttcg  13800
cggcccgcgg agcggacttc caggcgctgc cggtggggcag ctccgccgcg gtggctcccc  13860
tcggcttaca gctaatgtgc accgcgccgc ccggagcggt ccaggggcac tgggccaggg  13920
aggcgccggg cgcttgggac tgcagcgtgg agaacgggcg ctgcgagcac gcgtgcaatg  13980
cgatccctgg ggctccccgc tgccagtgcc cagccgggcg cgccctgcag gcagacgggc  14040
```

```
gctcctgcac cgcatccgcg acgcagtcct gcaacgacct ctgcgagcac ttctgcgttc  14100
ccaaccccga ccagccgggc tcctactcgt gcatgtgcga gaccggctac cggctggcgg  14160
ccgaccaaca ccggtgcgag gacgtggatg actgcatact ggagcccagt ccgtgtccgc  14220
agcgctgtgt caacacacag ggtggcttcg agtgccactg ctaccctaac tacgacctgg  14280
tggacggcga gtgtgtggag cccgtggacc cgtgcttcag agccaactgc gagtaccagt  14340
gccagcccct gaaccaaact agctacctct gcgtctgcgc cgagggcttc gcgcccattc  14400
cccacgagcc gcacaggtgc cagatgtttt gcaaccagac tgcctgtcca gccgactgcg  14460
accccaacac ccaggctagc tgtgagtgcc ctgaaggcta catcctggac gacggtttca  14520
tctgcacgga catcgacgag tgcgaaaacg gcggcttctg ctccggggtg tgccacaacc  14580
tccccggtac cttcgagtgc atctgcgggc ccgactcggc ccttgcccgc cacattggca  14640
ccgactgtga ctccggcaag gtggacggtg gcgacagcgg ctctggcgag cccccgccca  14700
gcccgacgcc cggctccacc ttgactcctc cggccgtggg gctcgtgcat tcggggcttgc  14760
tcataggcat ctccatcgcg agcctgtgcc tggtggtggc gcttttggcg ctcctctgcc  14820
acctgcgcaa gaagcagggc gccgccaggg ccaagatgga gtacaagtgc gcggcccctt  14880
ccaaggaggt agtgctgcag cacgtgcgga ccgagcggac gccgcagaga ctctgagcgg  14940
cctccgtcca ggagcctggc tccgtccagt cgacccgggc ggccgcttcc ctttagtgag  15000
ggttaatgct tcgagcagac atgataagat acattgatga gtttggacaa accacaacta  15060
gaatgcagtg aaaaaaatgc tttatttgtg aaatttgtga tgctattgct ttatttgtaa  15120
ccattataag ctgcaataaa caagttaaca acaacaattg cattcatttt atgtttcagg  15180
ttcaggggga gatgtgggag gttttttaaa gcaagtaaaa cctctacaaa tgtggtaaaa  15240
tccgataagg atcgatggga cagccccccc ccaaagcccc cagggatgta attacgtccc  15300
tcccccgcta gggcagcagc gagccgcccg gggctccggt ccggtccggc gctcccccgc  15360
atccccgagc cggcagcgtg cggggacagc ccgggcacgg ggaaggtggc acgggatcgc  15420
tttcctctga acgcttctcg ctgctctttg agcctgcaga cacctggggg gatacgggga  15480
aaatctagtg ggacagcccc cccccaaagc ccccagggat gtaattacgt ccctcccccg  15540
ctagggcagc agcgagccgc ccggggctcc ggtccggtcc ggcgctcccc cgcatccccg  15600
agccggcagc gtgcggggac agcccgggca cggggaaggt ggcacgggat cgctttcctc  15660
tgaacgcttc tcgctgctct ttgagcctgc agacacctgg gggatacggg ggaaaaatcg  15720
atgggacagc ccccccccaa agccccagg gatgtaatta cgtccctccc ccgctagggc  15780
agcagcgagc cgcccggggc tccggtccgg tccggcgctc cccgcatcc ccgagccggc  15840
agcgtgcggg gacagcccgg gcacggggaa ggtggcacgg gatcgctttc ctctgaacgc  15900
ttctcgctgc tctttgagcc tgcagacacc tggggggata cggggaaaat ctagtgggac  15960
agcccccccc caaagccccc agggatgtaa ttacgtccct cccccgctag ggcagcagcg  16020
agccgcccaa ggctccggtc cggtccggcg ctcccccgca tccccgagcc ggcagcgtgc  16080
ggggacagcc cgggcacggg gaaggtggca cgggatcgct ttcctctgaa cgcttctcgc  16140
tgctctttga gcctgcagac acctgggggg atacgggga aaatcgatag cgataaggat  16200
ccactagtta ttaatagtaa tcaattacgg ggtcattagt tcatagccca tatatggagt  16260
tccgcgttac ataacttacg gtaaatggcc cgcctggctg accgcccaac gacccccgcc  16320
cattgacgtc aataatgacg tatgttccca gtagtaacgcc aataggactt tccattgac  16380
gtcaatgggt ggagtattta cggtaaactg cccacttggc agtacatcaa gtgtatcata  16440
tgccaagtac gccccctatt gacgtcaatg acggtaaatg gcccgcctgg cattatgccc  16500
agtacatgac cttatgggac tttcctactt ggcagtacat ctacgtatta gtcatcgcta  16560
ttaccatggg tcgaggtgag ccccacgttc tgcttcactc tccccatctc ccccccctcc  16620
ccacccccaa ttttgtattt atttattttt taattatttt gtgcagcgat ggggggcgggg  16680
gggggggggg cgcgcgccag gcggggcggg gcggggcgag gggcggggcg gggcgaggcg  16740
gagaggtgcg gcggcagcca atcagagcgg cgcgctccga aagtttcctt ttatggcgag  16800
gcggcggcgg cggcggccct ataaaaagcg aagcgcgcgg cgggcgggag tcgctgcgtt  16860
gccttcgccc cgtgccccgc tccgcgccgc ctcgcgccgc ccgcccggc tctgactgac  16920
cgcgttactc ccacaggtga gcgggcggga cggcccttct cctccgggct gtaattagcg  16980
cttggtttaa tgacggctcg tttcttttct gtggctgcgt gaaagcctta aagggctccg  17040
ggagggccct ttgtgcgggg gggagcggct cggggggtgc gtgcgtgtgt gtgtgcgtga  17100
ggagcgccgc gtgcggcccg cgctgccccgg cggctgtgag cgctgcgggc gcggcgcggg  17160
gctttgtgcg ctccgcgtgt gcgcgagggg agcgcggccg ggggcggtgc cccgcggtgc  17220
gggggggctg cgagggggaac aaaggctgcg tgcggggtgt gtgcgtgggg gggtgagcag  17280
ggggtgtggg gcggcggtc gggctgtaac ccccccctgc accccctcc ccgagttgct  17340
gagcacggcc cggcttcggg tgcggggctc cgtgcgggac gtggcgcggg gctcgccgtg  17400
ccgggcgggg ggtggcggca ggtgggggtg ccgggcgggg cggggccgcc tcgggccggg  17460
gagggctcgg gggaggggcg cggcggcccc ggagcgccgg cggctgtcga ggcgcggcga  17520
gccgcagcca ttgcctttta tggtaatcgt gcgagagggc gcagggactt cctttgtccc  17580
aaatctggcg gagccgaaat ctgggaggcg ccgccgcacc ccctctagcg ggcgcggggcg  17640
aagcggtgcg gcgccggcag gaaggaaatg ggcggggagg gccttcgtgc gtcgccgcgc  17700
cgccgtcccc ttctccatct ccagcctcgg ggctgccgca gggggacggc tgccttcggg  17760
ggggacgggg cagggcgggg ttcggcttct ggcgtgtgac cggcggctct agagcctctg  17820
ctaaccatgt tcatgccttc ttctttttcc tacagctcgt cctcgtcccc ccccccccc  17880
tgctgtctca tcattttggc aaagaattcc gctgcgactc ggcggagtcc cggcggcgcg  17940
tccttgttct aacccggcgc gccctcagga tgtggcccct ggtagcggcg ctgttgctgg  18000
gctcggcgtg ctgcggatca gctcagctac tatttaataa aacaaaatct gtagaattca  18060
cgttttgtaa tgacactgtc gtcattccat gctttgttac taatatggag gcacaaaaca  18120
ctactgaagt atacgtaaag tggaaattta aaggaagaga tatttacacc tttgatgaag  18180
ctctaaacaa gtccactgtc cccactgact ttagtagtgc aaaaattgaa gtctcacaat  18240
tactaaaagg agatgcctct ttgaagatgg ataagagtga tgctgtctca cacacaggaa  18300
actacacttg tgaagtaaca gaattaacca gagaaggtga aacgatcatc gagctaaaat  18360
atcgtgttgt ttcatggttt tctccaaatg aaaaatattct tattgttatt ttcccaattt  18420
ttgctatact cctgttctgg gacagtttg gtattaaaac acttaaaat agatccggtg  18480
gtatggatga gaaaacaatt gctttacttg ttgctggaca agtgatcact gtcattgtca  18540
ttgttggagc cattctttc gtcccaggtg aatattcatt aaagaatgct actggccttg  18600
gtttaattgt gacttctaca gggatattaa tattacttca ctactatgtg tttagtacag  18660
cgattggatt aacctccttc gtcattgcca tattggttat tcaggtgata gcctatatcc  18720
tcgctgtggt tggactgagt ctctgtattg cggcgtgtat accaatgcat ggccctcttc  18780
```

```
tgatttcagg tttgagtatc ttagctctag cacaattact tggactagtt tatatgaaat 18840
ttgtggcttc caatcagaag actatacaac ctcctaggaa agctgtagag gaacccctta 18900
atgcattcaa agaatcaaaa ggaatgatga atgatgaagg atccggagcc acgaacttct 18960
ctctgttaaa gcaagcagga gacgtggaag aaaaccccgg tcctatggag cgtccgcaac 19020
ccgacagcat gccccaggat ttgtcagagg ccctgaagga ggccaccaag gaggtgcaca 19080
cccaggcaga gaatgctgag ttcatgagga actttcagaa gggccaggtg acccgagacg 19140
gcttcaagct ggtgatggcc tccctgtacc acatctatgt ggccctggag gaggagattg 19200
agcgcaacaa ggagagccca gtcttcgccc ctgtctactt cccagaagag ctgcaccgca 19260
aggctgccct ggagcaggac ctggccttct ggtacgggcc ccgctggcag gaggtcatcc 19320
cctacacacc agccatgcag cgctatgtga agcggctcca cgaggtgggg cgcacagagc 19380
ccgagctgct ggtggcccac gcctacaccc gctacctggg tgacctgtct gggggccagg 19440
tgctcaaaaa gattgcccag aaagccctgg acctgcccag ctctggcgag ggcctggcct 19500
tcttcacctt ccccaacatt gccagtgcca ccaagttcaa gcagctctac cgctcccgca 19560
tgaactccct ggagatgact cccgcagtca ggcagagggt gatagaagag gccaagactg 19620
cgttcctgct caacatccag ctctttgagg agttgcagga gctgctgacc catgacacca 19680
aggaccagag cccctcacgg gcaccagggc ttcgccagcg ggccagcaac aaagtgcaag 19740
attctgcccc cgtggagact cccagaggga agcccccact caacacccgc tcccaggctc 19800
cgcttctccg atgggtcctt acactcagct ttctggtggc gacagttgct gtagggcttt 19860
atgccatgtg agcggcgcgc cggcaccggt accaagctta agagcgctag ctggccagac 19920
atgataagat acattgatga gtttggacaa accacaacta gaatgcagtg aaaaaaatgc 19980
tttatttgtg aaatttgtga tgctattgct ttatttgtaa ccattataag ctgcaataaa 20040
caagttaaca acaacaattg cattcatttt atgtttcagg ttcaggggga ggtgtgggag 20100
gttttttaaa gcaagtaaaa cctctacaaa tgtggtatgg aattggagcc ccactgtgtt 20160
catcttacag atggaaatac tgacattcag aggagttagt taacttgcct aggtgattca 20220
gctaataagt gcaagaaaga tttcaatcca aggtgatttg attctgaagc ctgtgctaat 20280
cacattacac caagctacaa cttcatttat aaataataag tcagctttca agggcctttc 20340
aggtgtcctg cacttctaca agctgtgcca tttagtgaac acaaatgag ccttctgatg 20400
aagtagtctt ttcattattt cagatattag aacactaaaa ttcttagctg ccagctgatt 20460
gaaggctggg acaaaattca aacatgcatc tacaacaata tatatctcaa tgttagtctc 20520
caaattctat tgacttcaac tcaagagaat ataaagagct agtctttata cactctttaa 20580
ggtatgatcc gtcagggcca cacccgctgc atatggaggt tcccaggcta ggggtctaat 20640
cagagctgta gctgccaacc tatgccacag ccacagcaac gccagatttg agctgcaact 20700
gtgacctaca ccatagcttg tggcagctct ggatccttaa cccactgagc gaggccaggg 20760
atcgaaccca caaccttatg gttcctagtt ggattcattt ccactgcgcc acgacaggaa 20820
ctcctacacc aaaaattttt atattgtcta tttcattcaa agaaaaagcc ctgctaagta 20880
tgactggctt aattattttc attgcccact aatagattgt gacctcagtt tgaaaaatat 20940
tgtttttaagt aaccaatcct ctactgagaa ttagagtatt cataattctc tcctgttaca 21000
aacaatgctg catgaagctg ctttatactc attgtgtgat tatttctgag agcaagatcc 21060
tagattgtat aatcactgtt tacttaaaat tctgataaaa tataggcagc atgctggaaa 21120
actgaattct gaccccagat ctgtcaccgc cacgaagcat aaactttggg caattctttg 21180
cattgctctg agtctcagtt tccccatcag gaacctgctg ttctcaacat cctagaatcc 21240
gctttgagtg cagatgcccc accccctgac tcagagaggg caggacttta ctcaggcctt 21300
tctcccccctt ttccgctccc tgttcctcgg aagcagcccc gggaaaaggg aaaaagcagg 21360
tctgggctgg agagcgtgat gcagggcggg gcagagggag ggcaggaggg aggccggccc 21420
cctagtagga aatgagacag ggtaggaata acactttata agcccgtcgc cctctttctc 21480
ctcccatgcc ctggccacct tccagcctcc tccgtccagc ctcctcccct cccagacact 21540
cctcatttct tttccctcta ggctgcagtc agccgccagc cagagccccc ccacccggcc 21600
ccaccgccgg ccagagccag gagcccaggt gtggtggaca acttcagcta caggatgttg 21660
acaacattgc tgccgatact gctgctgtct ggctgggcct tttgtagcca agacgcctca 21720
gatggcctcc aaagacttca tatgctccag atctcctact tccgcgaccc ctatcacgtg 21780
tggtaccagg gcaacgcgtc gctggggggga cacctaacgc acgtgctgga aggcccagac 21840
accaacacca cgatcattca gctgcagccc ttgcaggagc ccgagagctg ggcgcgcacg 21900
cagagtggcc tgcagtccta cctgctcag ttccacgggc tcgtgcgcct ggtgcaccag 21960
gagcggacct tggcctttcc tctgaccatc cgctgcttcc tgggctgtga gctgcctccc 22020
gagggctcta gagcccatgt cttcttcgaa gtggctgtga atgggagctc ctttgtgagt 22080
ttccggccgg agagagcctt gtggcaggca gacacccagg tcacctccgg agtggtcacc 22140
ttcaccctgc agcagctcaa tgcctacaac cgcactcggt atgaactgcg ggaattcctg 22200
gaggacacct gtgtgcagta tgtgcagaaa catatttccg cggaaaacac gaaagggagc 22260
caaacaagcc gctcctacac ttcgctggtc ctgggcgtcc tggtgggcag tttcatcatt 22320
gctggtgtgg ctgtaggcat cttcctgtgc acaggtggac ggcgatgttg agcgcggccg 22380
cttccctta gtgagggtta atgcttcgag cagacatga aagatacatt gatgagtttg 22440
gacaaaccac aactagaatg cagtgaaaaa aatgctttat ttgtgaaatt tgtgatgcta 22500
ttgctttatt tgtaaccatt ataagctgca ataaacaagt taacaacaac aattgcattc 22560
attttatgtt tcaggttcag ggggagatgt gggaggtttt ttaaagcaag taaacctct 22620
acaaatgtgg taaatccga taaggatcga tgggacagcc ccccccaaa gcccccaggg 22680
atgtaattac gtccctcccc cgctagggca gcagcgagcc gcccggggct ccggtccggt 22740
ccggcgctcc cccgcatccc cgagccgca gcgtgcgggg acagcccggg cacggggaag 22800
gtggcacggg atcgctttcc tctgaacgct tctcgctgct ctttgagcct gcagacacct 22860
ggggggatac ggggaaaatc tagtgggaca gccccccccc aaagcccca gggatgtaat 22920
tacgtccctc cccgctagg gcagcagcga gccgcccggg gctccggtcc ggtccggcgc 22980
tccccgcat ccccgagccg gcagcgtgcg gggacagccc gggcacgggg aaggtggcac 23040
gggatcgctt tcctctgaac gcttctcgct gctctttgag cctgcagaca cctgggggga 23100
tacgggggaaa aatcgatggg acagcccccc cccaaagccc ccaggatgt aattacgtcc 23160
ctcccccgca agggcagcag cgagcgccc gggggctcccg tccggtccg gtccggcgc 23220
catccccgag ccggcagcgt gcggggacag cccgggcacg gggaaggtgg cacgggatcg 23280
ctttcctctg aacgcttctc gctgctcttt gagcctgcag acacctgggg ggatacgggg 23340
aaaatcgagt gggacagccc ccccccaaag ccccaggga tgtaattacg tccctcccc 23400
gctagggcag cagcgagccg cccggggctc cggtccggtc cggcgctccc ccgcatcccc 23460
gagccggcag cgtgcgggga cagcccgggc acggggaagg tggcacggga tcgctttcct 23520
```

-continued

```
ctgaacgctt ctcgctgctc tttgagcctg cagacacctg gggggatacg gggaaaaatc 23580
gatagcgata aggatccact agttattaat agtaatcaat tacggggtca ttagttcata 23640
gcccatatat ggagttccgc gttacataac ttacggtaaa tggcccgcct ggctgaccgc 23700
ccaacgaccc ccgcccattg acgtcaataa tgacgtatgt tcccatagta acgccaatag 23760
ggactttcca ttgacgtcaa tgggtggagt atttacggta aactgcccac ttggcagtac 23820
atcaagtgta tcatatgcca agtacgcccc ctattgacgt caatgacggt aaatggcccg 23880
cctggcatta tgcccagtac atgaccttat gggactttcc tacttggcag tacatctacg 23940
tattagtcat cgctattacc atgggtcgag gtgagcccca cgttctgctt cactctcccc 24000
atctccccc cctccccacc cccaattttg tatttattta tttttaatt attttgtgca 24060
gcgatggggg cggggggggg ggggcgcgc gccaggcggg gcggggcggg gcgaggggcg 24120
gggcggggcg aggcggagag gtgcggcggc agccaatcag agcggcgcgc tccgaaagtt 24180
tccttttatg gcgaggcggc ggcggcgcg gccctataaa aagcgaagcg cgcggcgggc 24240
gggagtcgct gcgttgcctt cgccccgtgc cccgctccgc gccgcctcgc gccgcccgcc 24300
ccggctctga ctgaccgcgt tactcccaca ggtgagcggg cgggacggccc cttctcctcc 24360
gggctgtaat tagcgcttgg tttaatgacg gctcgtttct tttctgtggc tgcgtgaaag 24420
ccttaaaggg ctccgggagg gccctttgtg cgggggggag cggctcgggg ggtgcgtgcg 24480
tgtgtgtgtg cgtggggagc gccgcgtgcg gcccgcgctg cccggcggct gtgagcgctg 24540
cgggcggcgg gcgggggcttt gtgcgctccg cgtgtgcgcg aggggagcgc ggccggggcg 24600
ggtgccccgc ggtgcggggg ggctgcgagg ggaacaaagg ctgcgtgcgg ggtgtgtgcg 24660
tggggggggtg agcaggggt gtgggcgcgg cggtcgggct gtaacccccc cctgcacccc 24720
cctccccgag ttgctgagca cggcccggct tcgggtgcgg ggctccgtgc ggggcgtggc 24780
gcggggctcg ccgtgccggg cgggggggtcg cggcaggtgg ggcggggtgg gccgggggcg 24840
ccgcctcggg ccggggaggg ctcggggagg gggcgcggcg gccccggagc gccggcggct 24900
gtcgaggcgc ggcgagccgc agccattgcc ttttatggta atcgtgcgag agggcgcagg 24960
gacttccttt gtcccaaatc tggcggagcc gaaatctggg aggcgccgcc gcacccctc 25020
tagcgggcgc gggcgaaacg gtgcggcgcc ggcaggaagc aaatgggcgg ggagggcctc 25080
cgtgcgtcgc cgcgccgccg tccccttctc catctccagc ctcggggctg ccgcaggggg 25140
acggctgcct tcgggggggga cggggcaggc cggggttcgg cttctggcgt gtgaccggcg 25200
gctctagagc ctctgctaac catgttcatg ccttcttctt tttcctacag ctcctgggca 25260
acgtgctggt tgttgtgctg tctcatcatt ttggcaaaga attccgctgc gactcggcgg 25320
agtcccggcg gcgcgtcctt gttctaaccc ggcgcgccct caggatggag cctccccggcc 25380
gccgcgagtg tccctttcct tcctggcgct ttcctgggtt gcttctggcg gccatggtgt 25440
tgctgctgta ctccttctcc gatgcctgtg aggagccacc aacatttgaa gctatggagc 25500
tcattggtaa accaaaaccc tactatgaga ttggtaacg agtagattat aagtgtaaaa 25560
aaggatactt ctatatacct cctcttgcca cccatactat ttgtgatcgg aatcatacat 25620
ggctacctgt ctcagatgac gcctgttata gagaaacatg tccatatata cgggatcctt 25680
taaatggcca agcagtccct gcaaatggga cttacgagtt tggttatcag atgcactta 25740
tttgtaatga gggttattac ttaattggta agaaattct atattgtgaa cttaaaggat 25800
cagtagcaat ttggagcggt aagcccccaa tatgtgaaaa ggtttgtat acaccacctc 25860
caaaaataaa aaatggaaaa cacacctta gtgaagtaga agtatttgag tatcttgatg 25920
cagtaactta tagttgtgat cctgcacctg gaccagatcc attttcactt attggagaga 25980
gcacgattta ttgtggtgac aattcagtgt ggagtcgtgc tgctccagag tgtaaagtgg 26040
tcaaatgtcg atttccagta gtcgaaaatg gaaaacagat atcaggattt gggaaaaaat 26100
tttactacaa agcaacagtt atgtttgaat gcgataaggg ttttttacctc gatggcagcg 26160
acacaattgt ctgtgacagt aacagtactt gggatccccc agtccaaag tgtcttaaag 26220
tgctgcctcc atctagtaca aaacctccag ctttgagtca ttcagtgtcg acttcttcca 26280
ctacaaaatc tccagcgtcc agtgccctag gtcctaggcc tacttacaag cctccagtct 26340
caaattatcc aggatatcct aaacctgagg aaggaatact tgacagtttg gatgtttggg 26400
tcattgctgt gattgttatt gccatagttg ttggagttgc agtaatttgt gttgtccccgt 26460
acagatatct tcaaaggagg aagaagaaag gcacatacct aactgatgag acccacagag 26520
aagtaaaatt tacttctctc ggatccggag ccacgaactt ctctctgtta aagcaagcag 26580
gagacgtgga agaaaacccc ggtcctatga ccgtcgcgcg gccgagcgtg cccgcggcgc 26640
tgccctcct cggggagctg ccccggctgc tgctgctggt gctgttgtgc ctgccggccg 26700
tgtggggtga ctgtggcctt ccccagatg tacctaatgc ccagccagct ttggaaggcc 26760
gtacagttt tcccgaggat actgtaataa cgtacaaatg tgaagaagct tttgtgtaaaa 26820
ttcctggcga gaaggactca gtgatctgcc ttaagggcag tcaatggtca gatattgaag 26880
agttctgcaa tcgtagctgc gaggtgccaa caaggctaaa ttctgcatcc ctcaaacagc 26940
cttatatcac tcagaattat tttccagtcg gtactgttgt ggaatatgag tgccgtccag 27000
gttacagaag agaaccttct ctatcaccaa aactaacttg ccttcagaat ttaaaatggt 27060
ccacagcagt cgaattttgt aaaaagaaat catgccctaa tccgggagaa atacgaaatg 27120
gtcagattga tgtaccaggt ggcatattat ttggtgcaac catctccttc tcatgtaaca 27180
cagggtacaa attatttggc tcgacttcta gttttgtct tatttcaggc agctctgtcc 27240
agtggagtga cccgttgcca gagtgcagag aaatttattg cccagcacca ccacaaattg 27300
acaatggaat aattcaaggg aacgtgacc attatggata tagacagtct gtaacgtatg 27360
catgtaataa aggattcacc atgattggag agcactctat ttattgtact gtgaataatg 27420
atgaaggaga gtggagtggc ccaccacctg aatgcagagg aaaatctcta acttccaagg 27480
tcccaccaac agttcagaaa cctaccacag taaatgttcc aactacagaa gtctcaccaa 27540
cttctcagaa aaccaccaca aaaaccacca caccaaatgc tcaagcaaca cggagtacac 27600
ctgtttccag gacaaccaag cattttcatg aaacaacccc aaataaagga agtggaacca 27660
cttcaggtac tacccgtctt ctatctgggc acacgtgttt cacgttgaca ggtttgcttg 27720
ggacgctagt aaccatgggc ttgctgactt agggcgcgcc ggcaccggta ccaagcttaa 27780
gagcgctagc tggccagaca tgataagata cattgatgag tttggacaaa ccacaactag 27840
aatgcagtga aaaaaatgct ttatttgtga aatttgtgat gctattgctt tatttgtaac 27900
cattataagc tgcaataaac aagttaacaa caacaattgc attcatttta tgtttcaggt 27960
tcagggggag gtgtgggagg ttttttaaag caagtaaaac ctctacaaat gtggtatgga 28020
attggagccc cactgtgttc atcttacaga tggaaatact gacattcaga ggagttagtt 28080
aacttgccta ggtgattcag ctaataagtg caagaaagat ttcaatccaa ggtgatttga 28140
ttctgaagcc tgtgctaatc acattacacc aagctacaac ttcatttata aataataagt 28200
cagctttcaa gggcctttca ggtgtcctgc acttctacaa gctgtgccat ttagtgaaca 28260
```

-continued

```
caaaatgagc cttctgatga agtagtcttt tcattatttc agatattaga acactaaaat  28320
tcttagctgc cagctgattg aaggctggga caaaattcaa acatgcatct acaacaatat  28380
atatctcaat gttagtctcc aaattctatt gacttcaact caagagaata taaagagcta  28440
gtctttatac actctttaag gtatgatatc atctggaaag taacaaaatt gatgcaaatt  28500
tgaatgaact ttatcatggt gtatttacac aatgtgtttc ttctccctgc aatgtatttc  28560
tttctctaat tccttccatt tgatctttca tacacaatct ggttctgatg tatgtttttt  28620
ggatgcactt ttcaactcca aaagacagag ctagttactt tcttcctggt gctccaagca  28680
ctgtatttgt atctgtattc aagccctttg caatattgta ctggatcatt atttcacctc  28740
taggatgact tccccaggca acttgtgttc acccagagac tacattttgt atcttgttga  28800
cctttgaact tccaccagtg tctaaaaata atatgtatgc aaaattactt gctatgagaa  28860
tgtataatta aacaatataa aaaggagaag caaggagaga aacacaggtg tgtatttgtg  28920
tttgtgtgct taaaaggcag tgtggaaaag gaagaaatgc catttatagt gaggagacaa  28980
agttatatta cctcttatct ggcttttaag gagatttttgc tgagctaaaa atcctatatt  29040
catagaaaag ccttacctga gttgccaata cctcaattct aaaatacagc atagcaaaac  29100
tttaacctcc aaatcaagcc tctacttgaa tccttttctg agggatgaat aaggcatagg  29160
catcaggggc tgttgccaat gtgcattagc tgtttgcagc ctcaccttct ttcatggagt  29220
ttaagatata gtgtattttc ccaaggtttg aactagctct tcatttcttt atgttttaaa  29280
tgcactgacc tcccacattc ccttttttagt aaaatattca gaaataattt atcccggctt  29340
gtcgacgacg g                                                        29351
```

```
SEQ ID NO: 14           moltype = DNA  length = 29117
FEATURE                 Location/Qualifiers
source                  1..29117
                        mol_type = other DNA
                        organism = synthetic construct
SEQUENCE: 14
atcatctgga aagtaacaaa attgatgcaa atttgaatga actttatcat ggtgtattta  60
cacaatgtgt ttcttctccc tgcaatgtat ttctttctct aattccttcc atttgatctt  120
tcatacacaa tctggttctg atgtatgttt tttggatgca cttttcaact ccaaaagaca  180
gagctagtta ctttcttcct ggtgctccaa gcactgtatt tgtatctgta ttcaagccct  240
ttgcaatatt gtactggatc attatttcac ctctaggatg gcttccccag gcaacttgtg  300
ttcacccaga gactacattt tgtatcttgt tgacctttga acttccacca gtgtctaaaa  360
ataatatgta tgcaaaatta cttgctatga gaatgtataa ttaaacaata taaaaaggag  420
aagcaaggag agaaacacag gtgtgtattt gtgtttgtgt gcttaaaagg cagtgtggaa  480
aaggaagaaa tgccatttat agtgaggaga caaagtttta ttacctctta tctggctttt  540
aaggagattt tgctgagcta aaaatcctat attcatagaa aagccttacc tgagttgcca  600
ataccctcaat tctaaaatac agcatagcaa aactttaacc tccaaatcaa gcctctactt  660
gaatccttttt ctgagggatg aataaggcat aggcatcagg ggctgttgcc aatgtgcatt  720
agctgtttgc agcctcacct tctttcatgg agtttaagat atagtgtatt ttcccaaggt  780
ttgaactagc tcttcatttc tttatgtttt aaatgcactg acctcccaca ttcccttttt  840
agtaaaatat tcagaaataa tttaaattcg tggaatccca cccagcagac aagtatggct  900
ggatatttta tataacgtgt ttacgcataa gttaatatat gctgaatgag tgatttagct  960
gtgaaacaac atgaaatgag aaagaatgat tagtaggggt ctggagctta ttttaacaag  1020
cagcctgaaa acagagagta tgaataaaaa aaattaaata caagagtgtg ctattaccaa  1080
ttatgtataa tagtcttata catctaactt caattccaat cactatatgc ttatactaaa  1140
aaacgaagta tagagtcaac cttcttttgac taacagctct tccctagtca gggacattag  1200
cccaagtata gtctttattt ttcctggggt aagaaaagaa ggattgggaa gtaggaatgc  1260
aaagaaataa aaaataattc tgtcattgtt caaataagaa tgtcatctga aaataaaactg  1320
ccttacatgg gaatgctctt atttgtcagg tatattaagg aaacaaacat caaaaatgac  1380
ccaaatgaac tcaacaatct tatcaagaag aattctgagg tggtaacctg accccaaga  1440
cctggagcca ctcttgatct gggtaggatg ctaaaggacg cgatcgcatt taaatacatc  1500
attgcaatga aaataaatgt tttttattag gcagaatcca gatgctcaag gcccttcata  1560
atatccccca gtttagtagt tggacttagg gaacaaagga acctttaata gaaattggac  1620
agcaagaaag ctctagcttt agaagaactc atcaagaagt ctgtagaagg caattctctg  1680
ggagtcaggg gctgcaatgc catagagcac taggaacctg tctgcccact ctcccctag  1740
ctcttctgct atgtccctgg ttgctagggc aatgtcctgg tacctgtcag ccactcccag  1800
cctgccacag tctatgaagc cagagaacct tccattttca accatgatgt tgggaaggca  1860
ggcatcccca tgagtcacca ctaggtcctc accatctggc atggatgcct tgagcctggc  1920
aaatagttca gcaggggcca ggccctggtg ttcttcatcc aagtcatctt ggtccaccag  1980
gccagcctcc atcctggttc tggccctctc tatcctgtgc ttggcctggt ggtcaaaggg  2040
gcaggtggct gggtcaaggg tgtggagtct tctcatggca tcagccatga ttgcactttt  2100
ctcagctgga gctaggtgag aggaaaggag gtcctgccca ggcacctcac ctagtaggag  2160
ccagtccctt ccagcttctg tgaccacatc aaggacagct gcacagggga ccccagttgt  2220
tgccaaccag gagagtctgg cagcctcatc ctggagctca ttgagagccc cactgaggtc  2280
tgtctttaca aaaaggactg gcctgccttg ggctgaaagt ctgaaaactg ctgcatcaga  2340
gcaaccaatg gtctgctgtg cccagtcata gccaaacagt ctctcaaccc aggcagctgg  2400
agaacctgca tgtaggccat cttgttcaat catgatggct cctcctgtca ggagaggaaa  2460
gagaagaagg ttagtacaat tgctatagtg agttgtatta tactatgctt atgattaatt  2520
gttaaactag ggctgcaggg ttcatagtgc cactttttcct gcactgcccc atctcctgcc  2580
cacccttttcc caggcataga cagtcagtga cttaccaaac tcacaggagg gagaaggcag  2640
aagctttttg caaaagccta ggctcatgag acaataaccc tgataaatgc ttcaataata  2700
ttgaaaaagg aagagtatga gtattcaaca ttttccgtgtc gcccttattc cctttttttgc  2760
ggcatttttgc cttcctgttt ttgctcaccc agaaacgctg gtgaaagtaa aagatgctga  2820
agatcagttg ggtgcacgag tgggttacat cgaactggat ctcaacagcg gtaagatcct  2880
tgagagtttt cgccccgaag aacgtttttcc aatgatgagc acttttaaag ttctgctatg  2940
tggcgcggta ttatcccgta ttgacgccgg gcaagagcaa ctcggtcgcc gcatacacta  3000
ttctcagaat gacttggttg agtactcacc agtcacagaa aagcatctta cggatggcat  3060
gacagtaaga gaattatgca gtgctgccat aaccatgagt gataacactg cggccaactt  3120
acttctgaca acgatcggag gaccgaagga gctaaccgct ttttttgcaca acatggggga  3180
```

-continued

```
tcatgtaact cgccttgatc gttgggaacc ggagctgaat gaagccatac caaacgacga 3240
gcgtgacacc acgatgcctg tagcaatggc aacaacgttg cgcaaactat taactggcga 3300
actacttact ctagcttccc ggcaacaatt aatagactgg atggaggcgg ataaagttgc 3360
aggaccactt ctgcgctcgg cccttccggc tggctggttt attgctgata aatctggagc 3420
cggtgagcgt gggtctcgcg gtatcattgc agcactgggt ccagatggta agccctcccg 3480
tatcgtagtt atctacacga cggggagtca ggcaactatg gatgaacgaa atagacagat 3540
cgctgagata ggtgcctcac tgattaagca ttggtaactg tcagaccaag tttactcata 3600
tatactttag attgatttaa aacttcattt ttaatttaaa aggatctagg tgaagatcct 3660
ttttgataat ctcatgacca aaatccctta acgtgagttt tcgttccact gagcgtcaga 3720
ccccgtagaa aagatcaaag gatcttcttg agatcctttt tttctgcgcg taatctgctg 3780
cttgcaaaca aaaaaaccac cgctaccagc ggtggtttgt ttgccggatc aagagctacc 3840
aactcttttt ccgaaggtaa ctggcttcag cagagcgcag ataccaaata ctgttcttct 3900
agtgtagccg tagttaggcc accacttcaa gaactctgta gcaccgccta catacctcgc 3960
tctgctaatc ctgttaccag tggctgctgc cagtggcgat aagtcgtgtc ttaccgggtt 4020
ggactcaaga cgatagttac cggataaggc gcagcggtcg ggctgaacgg ggggttcgtg 4080
cacacagccc agcttggagc gaacgaccta caccgaactg agatacctac agcgtgagct 4140
atgagaaagc gccacgcttc ccgaagggag aaaggcggac aggtatccgg taagcggcag 4200
ggtcggaaca ggagagcgca cagggagctt tccagggga aacgcctggt atctttatag 4260
tcctgtcggg tttcgccacc tctgacttga gcgtcgattt ttgtgatgct cgtcaggggg 4320
gcggagccta tggaaaaacg ccagcaacgc ggcctttta cggttcctgg ccttttgctg 4380
gccttttgct cacatggctc gacagattta attaaacagt gtgactaggg aggcaaaaca 4440
tacctactaa aggggtag cataattcag ttcttatgtg agtatgtgta tgtgtgtgaa 4500
tatgtgcaca tgcacataca ttttaaaagg tctgtaatat actaacatgt tcatagtggt 4560
tacacctagc ttataggtaa cattttttcc cctgtatcct tgtttgtgtt tatcaaattt 4620
tcataacagt aatggtagaa ggagtacctg acatggtacc atacatgctc tgggccctgc 4680
ctaatttctc aatttccttt attgcccata ccccattgc ttgacaagca taagtccata 4740
ctggcttgtt tttcgttcct cagactcagt acaccatga gctccatgcc ctgggtcttt 4800
gtatgtgcta tttctactgc ttagagtgct attgcccctg accaccacgt ggtcagcaac 4860
ttctcttctg tgtctgtgtc catggtctat gattccagat gtcatcttca ctaactaccc 4920
ttctaatatg cccttccatc ccacccgtcc tcatccttac cccagccact ctctatttgg 4980
tggctctgtt ttattttctt cctagctcat cactctttga aatgaactta tttacttatt 5040
cattatttgc ttctttcact agaatgaatg ctccatgaga gcagggacct gctttatctt 5100
gctcgccact gtattctcag tgcctagaac tacgtctggc acatagtagg tgctcaataa 5160
atatcgatca aatgaaagaa tgagcaaacg aacaaatgaa caacacgtga ggtaggcatc 5220
atgattccat tcaacagagg agaaaaacag acttaaagaa ttgaagtgat ggagctgcat 5280
tttgatcttg actgactcca acatccatgc tcttgaccac tgtgcatctc cagagtgtaa 5340
tgaacatact ttactttat attccaccaa aataacaaag ccatgcccat gttagtagag 5400
agttaatcga cagtgcccct aaaatatgca tgcacccagg gtacaactat gcatgctgcc 5460
ctgtgtttc agttggatcc aaatgaattg ccgtaaacaa agagggagtt caatgtcttt 5520
gactagtttg ggatatttc ctagtaacca actttgcaaa ataaagccac taatgacaag 5580
gagctttgtt ctacttctgc atcactcaac tgtcaatttt tatctcttgc aagacttcta 5640
atctactaga acttttgttt ttctgtgatt tctgaacaga gaagactaat ccaaaccctg 5700
tcattccaga ggaatggaaa gcccaattca ttaaaaccgt cggcgcgttc agcctaaagc 5760
tttttttctcc gtatccccc aggtgtctgc aggctcaaag agactcatgt ctcctatgtc 5820
tcatctaaat ggatgaggtt tgagagttcc catcacggca tggtggaaac gaatccgact 5880
aggagccata agttcacggc ttcgatccct ggcctcgctc aggggggttaa ggatccggtg 5940
ttgctgtgag ctgtggtgta ggtcacagat gcggttcgga tcgcgttg ctgcggctgt 6000
ggtgtaggct ggtggctgta gctccgattt gaccccctagc ctaggacct ccatatgccg 6060
tgggtatggc cctaaaaagc caaataaaat aaaataagta aatggttgag gtttgacaca 6120
gaaagtttat ttatttatgt atttacttat cttttttttt ttttttttt ttgtcttttct 6180
gctatttctt gggctgctcc cgcggcatat ggaggttccc aggctagggg tcgaattgga 6240
gctacagcca ccagcctaca ccacagccgc agcaatgcca gatccgagcc gcctctgtga 6300
cctacaccac agctcatggc aacgctggat cgttaaccca ctgagcaagg gctgggaccg 6360
aacccgcaac ctcatggttc ctagtcggat tcgttaacca ctgcgccatg acgggaactc 6420
ctacttatct attttttaaa gcatatggaa gttcccaggc taggggggttg aatcggagct 6480
gcaactgccg gcttacacca cagccagagc aacgccggat ctgagcagtg tctgggacct 6540
acaccacagc tcacagccac accggatcct caatccactg aatgaggcca ggaatcaaac 6600
ctgtgtcctc atggatacta gtcagattca tttccgctga gcaatgacag gaactcctga 6660
cacagaaatt ttagattaaa attgaagatg agccccttcc ttttgtacga cctttgtgtg 6720
cagattttcg aggataagtc cttgagcttg aagtttag gtcatggatc ctcataacag 6780
tttcctggcc tgtgaggctt ggatctcagt ataaacagaa gtgctggcag cagtagacac 6840
agcagcagct gttttcagga acaaatactg ggcacctgcc ttgtggacct gcctgactcc 6900
accactctct tgggtatcca caaagtggac ccagaggttc agagcagccc tgggatccaa 6960
attttttaa tttatttttt atcttttatt ttttgtctttt tcgaaatttt tagggctaca 7020
cccatgagat atggaggttc ccaggctaag ggtccaatcg gagctacaac tgccggccta 7080
caccacagct catggcaatg ctggatcctt aacccgctga gcgaggccag ggatcaaacc 7140
cacaacctca tgattcctag ttggattcgt taaccactga gccacgatgg gaactccctg 7200
ggatgcaaat tttgtcatct agccctagga tgtagctatc atcctgattt gagaagagag 7260
gcagagtctc aggtggcttc tctctcatga atgcagagct aagggtggcc acacgtactt 7320
gagttcatcc gatgcacaca gcattgtgct aaaatattga ccatttggcc cttttgctga 7380
cttttggtttt gagggatatg accttcatga gcatacagag gataatatgt atgcatgtat 7440
gcatgtgtgt acacatgtgc gcatgcatgt atatacctgc ataattatgt atttgtttat 7500
gtatgcaggt gcatgtgtat gtatatattt attatttatt tatttggggg ccacacccat 7560
gacatttgga agttcctggg acagagattg aatcccagcc acagctttga cctacgccat 7620
ggacacagca acactggatt cttaaccccc tgtgccacag cgggaactcc tagaagatag 7680
tatttcatga tgatatttga ctaaaaatag gggtcaggct ttgaagttta aataaattcg 7740
accagataaa tggccatcca ggaagttata ctttgccttg ttcaaatttg gaccacgggg 7800
aaggtggttg cgacatgta acagaaatct gactccagtc caggtttcgc tcccgtgacg 7860
ggaagcccag aggtgggcag ccctaaggct ggggctctga tttcatgatg ctcttagcat 7920
```

-continued

```
cttgagtccc ttccctcttc ttgctttat ctcagcctcg ggctgctgca ccttctgtct   7980
ttgtggtgag tctacctatt ccacttagct cggcttcagg gtgtatttcc acgacttcgt   8040
tagagtaagg ttggggccag ctgtgctctg ccggcaggag gtgtgcttgc aggggccatg   8100
gatgtggcca ggacctaatg tgacggtggg gagcaggatg gggatgagga tgtgaccaca   8160
gagccttggg aaccacgtca tccacgtcat acactgaggca caggtggttc tcatgcaggt   8220
gcatcagaat cccgaggacg gcttgtccaa acccagatgg ctgggcccaa gccctgagct   8280
cccgatttgg gaggccttgg ctgggccccg aaatctgcct tcctgactag accgagtgat   8340
gaatggtgtt catagacaag acatacacta acactggtct tggggggctcc ttgccacacc   8400
ctgaaggggg ccgtgaaact gacggggcca gagaaggtgc tggttcctcc atggaaggtc   8460
tcagtgaggc cattctgctg cccggctggg tcacgctggg ggagtgaggg tgcatcccct   8520
cctgggatct ggtcaaaggc agattctgat tctggaagca cggggtaggg ccagagatgc   8580
caccttctaa caagcccccca ggtgaagatg ttgacctggg accttatggt ggggggtggc   8640
ggagctcaag gtggcagaca cctccctctc tctcaacctg tgtcacagca gggccatcct   8700
actggctctc gctcggccag agatggcgat gccagaacac actggggcag ggtgtccaca   8760
tttttgtcac ttccactgag ccctggggac tgactcattt aaatgacatt ctcaactctt   8820
tggaaagaag ctgggccaga aatgggaaatg gcagcaaaca cttttggga aacaggaagc   8880
caatttttt tttcaatcat gattttcccc agattcagag actgcttaac tcccaatgaa   8940
atactttag attacgagct aaaataccga aaagctgtca agctcaagac cacaggaaaa   9000
cagccgaaga acaaacacca tgagaaaaca gtcacagagt gcctctgcgg cggatttcaa   9060
gttccagact tccttgctgt cagctgtgtg tacttgtccc gcctgcagta ggaccagctg   9120
gggtttaagt ctgtaccatg gacactgctg ccaggattct cctctgcatc tgctgacttc   9180
cagctcttca gggccagctg gccataggag cataaactga catccagttc caggaggcag   9240
catctgtccc catggcctgc aggacaccag atcagtagag gccccagg ccacctttcc   9300
tgtgggggcc cttgaaggga cccgggaagg ctggatcttg ctaaagcttc cacaagtccc   9360
ttccaaagga gagtaaattc taaacagaag cttttgccag tgcttctctg ggatctggct   9420
tcaggattat tcctagtctg aaaagtcttc ctggtggttt ggacacgggc aaatgcttgg   9480
tgggtgggct ggctctggat gcaggtgagt ggggtcggaa gttctccctc cttcccacaa   9540
agcttgacgg agccagggc acccgcgggc ctgtggatgg gagaggggtt tctggtgacg   9600
gactcaagtc ttggcagccc ctgaccccag agcaggctcc ctccccacag ctgctctccg   9660
tgagtccttc acttgcccaa gttcaagatg tacccagttc tggagctgcc aaaccatcct   9720
gcatcctgat gtcagccacc caagttctgg ggtagctggt ctgccaccca ggtggatgaa   9780
aagaggccac atacctgcac cagcatctgc gaatctctga agaacatcaa taataaaaag   9840
acaactaacc cagttaaaac acaggtagag aatctgaaca gacattcatc ggaagaagaa   9900
ttacgactgg ccaaaaagct cataaaaaga tggtcaaagt cattggtcag ggaaatgtaa   9960
atcaaaccgc attgagatac catctcactc cctctcggat ggctggaatg aaaaaaaacc   10020
tcttctttcc tcccttttcat tgtcttggca cccttgtgga aattaattga ctaaaattca   10080
tgaaatacaa aaatttttag gagttcccgt cgtggctcag tggttaacaa atctgactag   10140
gaaccatgag gtttcaggtt cgattcctgg cctcactcag tgggttaggg atctggtgtt   10200
gccatgagct gtggtgtagg tcacagacgc agctcggatc ccgcattgct gtggctctgg   10260
cgtaggccgg cggctacagc tctgattcaa cctctagcct gggaatagcc caagaaatgg   10320
caaaaagacc aaaaaaaaaa aaaaaaaaa aactcgtttt gagcatttt gcatgtgtac   10380
attgtccatt tgtgtgcctt ccaagattta ttttggagt ctcaactctg tcattgattt   10440
atgtctctcc ttaggccaga accacactgt tttggtgacc atggctttgt agtaaaattt   10500
gaaatctgaa agtgtgagcc ctcctgtttt gtttctcttc tccatgatta gtttggttat   10560
tcagagtccc ttgaatttcc aggtgaattt taggattagc aggaaaattt ctgcagagat   10620
ggcagcagag atttttaata gggattatgt tgaatctgga ggttaaattc agttttgcta   10680
ccttgactgt attaagtctt ccagtctata agcataagat gtctttttat ttacttaggt   10740
cttttaaaat ttctttgggc actcccattg tggtgcatcg gaaatgaatc cgactagtat   10800
ccacaagaac acaggttcaa tccctggcat tgctcagtgg gttaaggatc ctgcattgcc   10860
atgaagaact gtggtggagg ccagcagctg cagctctgat ttgaccccta gcctgggaac   10920
ttccatatgc cttgggtatg gccctaaaaa gcaaactaag taagtaagta aataaataaa   10980
tgaataaata aaatttcttt caacattgta attttgtaat ttttgtaatt ttcagagcgt   11040
acattttgcc ctttcaatac attattccta catattttat tcttttttgat actattataa   11100
atgaaattta taattaattc atttatatga atttcatttt caatttgcat attgctacta   11160
caatagaaat gcactttta attattttta tggccatact atatatatat gtgtgtgtgt   11220
gtgtatgtgt gtcattttac tgtacagcag aaattgacac aacattgtaa atcaactaca   11280
cttaaaaaat gaagaaataa ccacctgtga ttatggctac tgtgttggac actttaggca   11340
tcccccccacc ccgtccccgc cccacaccc tgagtgctag tgacggatgt tcccacccag   11400
ggggcctgga gcctttatca ccagccatcg ggaatcagaa ccgtatctca cagtccccat   11460
gcctggagca cctggaattg tgcccttgga ctcgtgggtg ttctgcttct cagtgggaga   11520
agcttaggtt ctaagtcaga gcagggacag ccccatgtg ctcaggaccc agtgtgaagg   11580
ggtctgcctc aggggacctg ggggttacaa gggtaagaga aggtgttcat gttggaacta   11640
gaagttcttt ttcactgctc tgaagaaaaa agctgcctcc cacccttggt acagctcttc   11700
tgctaacagt gaatcaggca gaacgtgttc aagaagtgac cacgcctggt gggggccaga   11760
cctgacccctt gatggtccct caacccctcc gagggtcccg cccttccttt actgctttgt   11820
tgtctgtcct gagaggtttg gctaatgtcg aaccaagggt gtggctggtc ctgtcccctt   11880
tcctgtctca cgcacccacc tctgaagtct ctgtagctgg ttccagccgg gatctggagc   11940
cactcccccc gccccaggcc cagtggtaca gactcttgca gagtcggggg ccctgactc   12000
agccccaccg ccagcgggat gtcaggccag caccgcccc actcccactg atctgggggg   12060
ggtgtctttc cttcctcctt ccaaaggagc ctcagacctt cctgtggggc acgggggcag   12120
tgggattcag gaggctctga gtcagcaggc cggcattgag gagtataaag ggaccccagt   12180
tcctcccccct ttcacttgtg gcttatcgcc gccccaccct gccccaaggt cactgcggtc   12240
agtacagtcc tcagctgcca gcaggtgcct gtctttactt gtgaggccgc cacgctctcc   12300
tgtttctcca ggtctgggct ctgttggaag tgggggcccg accccgggt aagatggggg   12360
atctgcgtgt cctgccctca gaggcctcct cctccccgca ccctaaccc tttcagccca   12420
acaaggctgg agatctccca catcttggc ttcgttaaga gttcaacagc gccgccaccc   12480
ggcatgtcgc tgagcagagg atggcacagg gtgttaaaaa aaaaaaagg ttgccacact   12540
ccgttcggtt ttgggcccac cctttcgcat tcctggagcc tgagtaagcg gataaggctg   12600
tgaaagtgac agattcctgc cacctccttc cagcgctcat gcacagggac cgcccctctt   12660
```

-continued

```
cggtgtcctt tgctgcacaa gtgcatttgc acattcctgt ctcaatctgg tttctccccc  12720
ttaaaagatg ggaatgtgac ctgcttggag cccctcgcct cgccagggca ccccatccgt  12780
cccttcaggg gtggagatgg actgtccctc tgcaaggctg gatgaactca gaccaaacag  12840
gccaacttgc tccccaaata cgcccacccc taccgggctg caggaattcg cctgtcacca  12900
ctgctgaagg gtgaccttgc agccctgaga gcatccccat gacttgccca ccagatgaag  12960
tctggttgtg gcaggtcgcg ctcagggact cccgggtccc acctgggggt gggaggatcc  13020
tcctttgctc gtggtcgccc cagccacgcc ctcctttcca agcgccagtc tccagagctc  13080
cgtgccccgg cggaggcggt ctggctctct ctccttgccc ctctctcctt gcccctagca  13140
gcccttctcc taaaccctct gagcagcggg cacctcctcc cgaggccctg ggctaagtcc  13200
ccacccttca tctcaagcct tcctccttga ctccctcttc ccagagttcc ttgaaatagg  13260
tggtaagtac acaccgatga cggaaaacaa agactaagag gttaaagagg gctgaggatt  13320
acggccccgg tagggctgcg cgcgaggggg tcgagtggcc gggcggtccc gttgccgggc  13380
agacagaggt gcggttctcc cgggcgcctg cgctgccggc cccgcccgga gccctcccag  13440
ccggcgccca gtttactcat cccggagagg tgatcccggg cgcgaggcgg ggcgcagggc  13500
gtccggagaa cccagtaatc cgagaatgca gcatcagccc ttcccaccag gcacttcctt  13560
ccttttcccg aacgtccagg aagggggggcc gcgcacttat aaactcgggc cggacccgcc  13620
ggcctgtcag aggctgcctc gctggggctg cgcgcgcgcgg ccggacacat ctggtccgag  13680
accaacgcga gcgactgtca ctggcagctc cctgcgcctc tcagccccgg ccgggcccct  13740
gcgcttggcg tgctgacacc atgcttgggg tcctggtcct tggcgcgctg gccctggccg  13800
gcctgggggtt ccccgcaccc gcagagccgc agccgggtgg cagccagtgc gtcgagcacg  13860
actgcttcgc gctctacccg ggccccgcga ccttcctcaa tgccagtcag atctgcgacg  13920
gactgcgggg ccacctaatg acagtgcgct cctcggtggc tccggatgtc atttccttgc  13980
tactgaacgg cgacggcggc gttggccgcc ggcgcctctg gatcggcctg cagctgccac  14040
ccggctgcgg cgaccccaag cgcctcgggc ccctgcgcgg cttccagtgg gttacgggag  14100
acaacaacac cagctatagc aggtgggcac ggctcgacct caatgggct cccctctgcg  14160
gcccgttgtg cgtcgctgtc tccgctgctg aggccactgt gcccagcgag ccgatctggg  14220
aggagcagca gtgcgaagtg aaggccgatg gcttcctctg cgagttccac ttcccagcca  14280
cctgcaggcc actggctgtg gagcccggcg ccgcggctgc cgccgtctcg atcacctacg  14340
gcaccccgtt cgcggcccgc ggagcggact tccaggcgct gccggtgggc agctccgccg  14400
cggtggctcc cctcggctta cagctaatgt gcaccgcgcg ggcccggagcg gtccaggggc  14460
actgggccag ggaggcgccg ggcgcttggg actgcagcgt ggagaacgcg ggctgcgagc  14520
acgcgtgcaa tgcgatccct ggggctcccc gctgccagtg cccagccggc gccgccctgc  14580
aggcagacgg gcgctcctgc accgcatccg cgacgcagtc ctgcaacgac ctctgcgagc  14640
acttctgcgt tcccaacccc gaccagccgg gctcctactc gtgcatgtgc gagaccggct  14700
accggctggc ggccgaccaa caccggtgcg aggacgtgga tgactgcata ctggagccca  14760
gtccgtgtcc gcagcgctgt gtcaacacac agggtggctt cgagtgccac tgctacccta  14820
actacgacct ggtggacggc gagtgtgtgg agcccgtgga cccgtgcttc agagccaact  14880
gcgagtacca gtgccagccc ctgaaccaaa ctagctacct ctgcgtctgc gccgagggct  14940
tcgcgcccat tccccacgag ccgcacaggt gccagatgtt ttgcaaccag actgcctgtc  15000
cagccgactg cgaccccaac acccaggcta gctgtgagtg ccctgaaggc tacatcctgg  15060
acgacggttt catctgcacg gacatcgacg agtgcgaaaa cggcggcttc tgctccgggg  15120
tgtgccacaa cctccccggt accttcgagt gcatctgcgg gcccgactcg gcccttgccc  15180
gccacattgg caccgactgt gactccggca aggtggacgg tggcgacagc ggctctgccg  15240
agcccccgcc cagcccgacg cccggctcca ccttgactcc tccggccgtg gggctcgtgc  15300
attcgggctt gctcataggc atctccatcg cgagcctgtg cctggtggtg gcgctttttgg  15360
cgctcctctg ccacctgcgc aagaagcagg gcgccgccag ggccaagatg gagtacaagt  15420
gcgcgccccc ttccaaggag gtagtgctgc agcacgtgcg gaccgacgcg acgcccgcaga  15480
gactcggatc cggagagggc agaggaagtc ttctaacatg cggtgacgtg gaggagaatc  15540
ccggccctat gttgacaaca ttgctgccga tactgctgct gtctggctgg gccttttgta  15600
gccaagacgc ctcagatggc ctccaaagac ttcatatgct ccagatctcc tacttccgcg  15660
acccctatca cgtgtggtac cagggcaacg cgtcgctggg gggacaccta acgcacgtgc  15720
tggaaggccc agacaccaac accacgatca ttcagctgca gcccttgcag gagcccgaga  15780
gctgggcgcg cacgcagagt ggcctgcagt cctacctgct ccagttccac ggcctcgtgc  15840
gcctggtgca ccaggagcgg accttggcct ttcctctgac catccgctgc ttcctgggct  15900
gtgagctgcc tcccgagggc tctagagccc atgtcttctt cgaagtgcgt gtgaatggga  15960
gctcctttgt gagtttccgg ccggagagag ccttgtggca ggcagacacc caggtcacct  16020
ccggagtggt caccttcacc ctgcagcagc tcaatgccta caaccgcact cggtatgaac  16080
tgcgggaatt cctggaggac acctgtgtgc agtatgtgca gaaacatatt tccgcggaaa  16140
acacgaaagg gagccaaaca agccgctcct acacttcgct ggtcctgggc gtcctggtgg  16200
gcagtttcat cattgctggt gtggctgtag gcatcttcct gtgcacaggt gacggcgat  16260
gttgagcgcg gccgcttccc tttagtgagg gttaatgctt cgagcagaca tgataagata  16320
cattgatgag tttggacaaa ccacaactag aatgcagtga aaaaaatgct ttatttgtga  16380
aatttgtgat gctattgctt tatttgtaac cattataagc tgcaataaac aagttaacaa  16440
caacaattgc attcatttta tgtttcaggt tcagggggag atgtgggagg tttttttaaag  16500
caagtaaaac ctctacaaat gtggtaaaat ccgataagga tcgatgggac agccccccc  16560
caaagccccc agggatgtaa ttacgtccct ccccgctag ggcagcagcg agccgcccgg  16620
ggctccggtc cggtccggcg ctccccgca tccccgagcc ggcagcgtgc ggggacagcc  16680
cgggcacggg gaaggtggca cgggatcgct ttcctctgaa cgcttctcgc tgctctttga  16740
gcctgcagac acctgggggg atacggggaa aatctagtgg gacagccccc cccc aaagccccca gggatgtaat  16800
```

-continued

```
gggatcgctt tcctctgaac gcttctcgct gctctttgag cctgcagaca cctgggggga  17460
tacggggaaa aatcgatagc gataaggatc cactagttat taatagtaat caattacggg  17520
gtcattagtt catagcccat atatggagtt ccgcgttaca taacttacgg taaatggccc  17580
gcctggctga ccgcccaacg accccgccc attgacgtca ataatgacgt atgttcccat  17640
agtaacgcca atagggactt tccattgacg tcaatgggtg gagtatttac ggtaaactgc  17700
ccacttggca gtacatcaag tgtatcatat gccaagtacg cccctattg acgtcaatga  17760
cggtaaatgg cccgcctggc attatgccca gtacatgacc ttatgggact ttcctacttg  17820
gcagtacatc tacgtattag tcatcgctat taccatgggt cgaggtgagc cccacgttct  17880
gcttcactct ccccatctcc cccccctccc caccccaat tttgtattta tttatttttt  17940
aattattttg tgcagcgatg gggcggggg gggggggggc gcgcgccagg cggggcgggg  18000
cggggcgagg ggcggggcgg ggcgaggcgg agaggtgcgg cggcagccaa tcagagcggc  18060
gcgctccgaa agtttccttt tatggcgagg cggcggcggc ggcggcccta taaaaagcga  18120
agcgcgcggc gggcgggagt cgctgcgttg ccttcgcccc gtgccccgct ccgcgccgcc  18180
tcgcgccgcc cgccccggct ctgactgacc gcgttactcc cacaggtgag cgggcgggac  18240
ggcccttctc ctccgggctg taattagcgc ttggtttaat gacggctcgt ttcttttctg  18300
tggctgcgtg aaagccttaa agggctccgg gagggccctt tgtgcggggg ggagcggctc  18360
ggggggtgcg tgcgtgtgtg tgtgcgtggg gagcgccgcg tgcggcccgc gctgcccggc  18420
ggctgtgagc gctgcgggcg cggcgcggga ctttgtcgtc tccgcgtgtg cgcgaggggga  18480
gcgcggccgg gggcggtgcc ccgcggtgcg gggggggctgc gaggggaaca aaggctgcgt  18540
gcggggtgtg tgcgtggggg ggtgagcagg gggtgtgggc gcggcggtcg ggctgtaacc  18600
cccccctgca ccccctccc cgagttgctg agcacggccc ggcttcgggt gcggggctcc  18660
gtgcggggcg tggcgcgggg ctcgccgtgc cgggcggggg gtggcggcag gtgggggtgc  18720
cgggcggggc ggggccgcct cgggccgggg agggctcggg ggaggggcgc ggcggccccg  18780
gagcgccggc ggctgtcgag gcgcggcgag ccgcagccat tgccttttat ggtaatcgtg  18840
cgagagggcg cagggacttc ctttgtccca aatctggcgg agccgaaatc tgggaggcgc  18900
cgccgcaccc cctctagcgg gcgcggggcga agcggtcggg cgccggcagg aaggaaatgg  18960
gcggggaggg ccttcgtgcg tcgccgcgcc gccgtccct tctccatctc cagcctcggg  19020
gctgccgcag ggggacggct gccttcgggg gggacggggc agggcggggt tcggcttctg  19080
gcgtgtgacc ggcggctcta gagcctctgc taaccatgtt catgccttct tcttttttcct  19140
acagctcctg ggcaacgtgc tggttgttgt gctgtctcat cattttggca aagaattccg  19200
ctgcgactcg gcggagtccc tggcggcgcgt ccttgttcta acccggcgcg ccctcaggat  19260
gggaatccaa ggagggtctg tcctgttcgg gctgctgctc gtcctggctg tcttctgcca  19320
ttcaggtcat agcctgcagt gctacaactg tcctaaccca actgctgact gcaaaacagc  19380
cgtcaattgt tcatctgatt ttgatgcgtg tctcattacc aaagctgggt tacaagtgta  19440
taacaagtgt tggaagtttg agcattgcaa tttcaacgac gtcacaaccc gcttgaggga  19500
aaatgagcta acgtactact gctgcaagaa ggacctgtgt aactttaacg aacagccttga  19560
aaatggtggg acatccttat cagagaaaac agttcttctg ctggtgactc catttctggc  19620
agcagcctgg agccttcatc ccggatccgg agagggcaga ggaagtcttc taacatgcgg  19680
tgacgtggag gagaatcccg gccctatgga gcgtccgcaa cccgacagca tgccccagga  19740
tttgtcagag gccctgaagg aggccaccaa ggaggtgcac acccaggcag agaatgctga  19800
gttcatgagg aactttcaga agggccaggt gacccgagac ggcttcaagc tggtgatggc  19860
ctccctgtac cacatctatg tggccctgga ggaggagatt gagcgcaaca aggagagccc  19920
agtcttcgcc cctgtctact tcccagaaga gctgcaccgc aaggctgccc ttgagcagga  19980
cctggccttc tggtacgggc cccgctggca ggaggtcatc ccctacacac cagccatgca  20040
gcgctatgtg aagcggctcc acgaggtggg gcgcacagag cccgagctgc tggtggccca  20100
cgcctacacc cgctacctgg gtgacctgtc tgggggccaa gtgctcaaaa agattgccca  20160
gaaagccctg gacctgccca gctctggcga gggcctggcc ttcttcacct tccccaacat  20220
tgccagtgcc accaagttca agcagctcta ccgctcccgc atgaactccc tggagatgac  20280
tcccgcagtc aggcagaggg tgatagaaga ggccaagact gcgttcctgc tcaacatcca  20340
gctctttgag gagttgcagg agctgctgac ccatgacacc aaggaccaga gcccctcacg  20400
ggcaccaggc cttcgccagc gggccagcaa caaagtgcaa gattctgccc ccgtggagac  20460
tcccagaggg aagcccccac tcaacacccg ctcccaggct ccgcttctcc gatgggtcct  20520
tacactcagc tttctggtgg cgacagttgc tgtagggctt tatgccatgt gagcggcgcg  20580
ccggcaccgg taccaagctt aagagcgcta gctggccaga catgataaga tacattgatg  20640
agtttggaca aaccacaact agaatgcagt gaaaaaaatg ctttatttgt gaaatttgtg  20700
atgctattgc tttatttgta accattataa gctgcaataa acaagttaac aacaacaatt  20760
gcattcattt tatgtttcag gttcaggggg aggtgtggga ggttttttaa agcaagtaaa  20820
acctctacaa atgtggtatg gaattggagc cccactgtgt tcatcttaca gatggaaata  20880
ctgacattca gaggagttag ttaacttgcc taggtgattc agctaataag tgcaagaaag  20940
atttcaatcc aaggtgattt gattctgaag cctgtgctaa tcacattaca ccaagctaca  21000
acttcattta taaataataa gtcagctttc aagggccttt caggtgtcct gcacttctac  21060
aagctgtgcc atttagtgaa cacaaaatga gccttctgat gaagtagtct tttcattatt  21120
tcagatatta gaacactaaa attcttagct gccagctgat tgaaggctgg gacaaaattc  21180
aaacatgcat ctacaacaat atatatctca atgttagtct ccaaattcta ttgacttcaa  21240
ctcaagagaa tataaagagc tagtcttat acactcttta aggtatgatg ggtcccgatt  21300
tttccccgta tcccccccagg tgtctgcagg ctcaaagagc agcgagaagc gttcagagga  21360
aagcgatccc gtgccacctt cccccgtgcc gggctgtccc cgcacgctgc cggctcgggg  21420
atgcggggga gcgccggacc ggaccggagc cccgggcggc tcgctgctgc cctagcgggg  21480
gagggacgta attacatccc tgggggcttt ggggggggga gcgggcggga tgtcccacta  21540
gattttcccc gtatccccc aggtgtctgc aggctcaaag agcagcgaga agcgttcaga  21600
cccgtgccac cttccccgtg cccgggcgt ccccgcacgc tgccggctcg gggatgcggg  21660
ggagcgccgg accggaccgg agcccgggc ggctcgctgc tgcctagcg gggagggac  21720
gtaattacat ccctgggggc tttggggggg ggctgtccca tcggatcttc tagtcctgca  21780
ggagtcaatg ggaaaaaccc attggagcca agtacactga ctcaataggg actttcatt  21840
gggtttttgc cagtacataa ggtcaatagg gggtgagtca acaggaaagt cccattggag  21900
ccaagtacat tgagtcaata gggactttcc aatgggtttt gcccagtaca taaggtcaat  21960
gggaggtaag ccaatgggtt tttcccatta ctgacatgta tacgcgtcga cgtcggcgcg  22020
ttcagcctaa agctttttttc cccgtatccc cccaggtgtc tgcaggctca aagagcagcg  22080
agaagcgttc agaggaaagc gatcccgtgc caccttcccc gtgcccgggc tgtccccgca  22140
```

```
cgctgccggc tcggggatgc gggggagcgc cggaccggac cggagccccg ggcggctcgc 22200
tgctgcccta gcgggggagg gacgtaatta catccctggg ggctttgggg gggggctgtc 22260
cctgcggccg cgaattcgta atcatggtca tagctgtttc ctgtgtgaaa ttgttatccg 22320
ctcacaattc cacacaacat acgagccgga agcataaagt gtaaagcctg gggtgcctaa 22380
tgagtgagct aactcacatt aattgcgttg cgctcactgc ccgctttcca gtcgggaaac 22440
ctgtcgtgcc aggggtctag ccgcggtcta ggaagctttc tagggtacct ctagggatcc 22500
actagttatt aatagtaatc aattacgggg tcattagttc atagcccata tatggagttc 22560
cgcgttacat aacttacggt aaatggcccg cctggctgac cgcccaacga cccccgccca 22620
ttgacgtcaa taatgacgta tgttcccata gtaacgccaa tagggacttt ccattgacgt 22680
caatgggtgg agtatttacg gtaaactgcc cacttggcag tacatcaagt gtatcatatg 22740
ccaagtacgc cccctattga cgtcaatgac ggtaaatggc ccgcctggca ttatgcccag 22800
tacatgacct tatgggactt tcctacttgg cagtacatct acgtattagt catcgctatt 22860
accatgggtc gaggtgagcc ccacgttctg cttcactctc cccatctccc ccccctcccc 22920
acccccaatt ttgtatttat ttattttta attattttgt gcagcgatgg gggcgggggg 22980
gggggggggcg cgcgccaggc ggggcggggc ggggcgaggg gcgggcgggg gcgaggcgga 23040
gaggtgcggc ggcagccaat cagagcggcg cgctccgaaa gtttcctttt atggcgaggc 23100
ggcggcggcg gcggccctat aaaaagcgaa gcgcgcggcg ggcgggagtc gctgcgttgc 23160
cttcgccccg tgccccgctc cgcgccgcct cgcgccgccc gccccggctc tgactgaccg 23220
cgttactccc acaggtgagc gggcgggacg gcccttctcc tccgggctgt aattagcgct 23280
tggtttaatg acggctcgtt tcttttctgt ggctgcgtga aagccttaaa gggctccggg 23340
agggcccttt gtgcgggggg gagcggctcg ggggtgcgt gcgtgtgtgt gtgcgtgggg 23400
agcgccgcgt gcggcccgcg ctgcccggcg gctgtgagcg ctggggcggc ggcgcggggc 23460
tttgtgcgct ccgcgtgtgc gcgaggggag cgcggccggg ggcggtgccc cgcggtgcgg 23520
gggggctgcg aggggaacaa aggctgcgtg cggggtgtgt gcgtggggggg gtgagcaggg 23580
ggtgtgggcg cggcggtcgg gctgtaaccc cccctgcac cccctccc gagttgctga 23640
gcacggcccg gcttcgggtg cggggctccg tgcgggggcgt ggcgcggggc tcgccgtgcc 23700
gggcggggggg tggcggcagg tggggggtgcc gggcggggcg gggccgcctc gggccgggga 23760
gggctcgggg gaggggcgcg gcggccccgg agcgccggcg gctgtcgagg cgcggcgagc 23820
cgcagccatt gccttttatg gtaatcgtgc gagagggcgc agggacttcc tttgtcccaa 23880
atctggcgga gccgaaatct gggaggcgcc gccgcaccc ctctagcggg cgcgggcgaa 23940
gcggtcggc gccggcagga aggaaatggg cggggagggc cttcgtgcgt cgccgcgccg 24000
ccgtcccctt ctccatctcc agcctcgggg ctgccgcagg gggacggctg ccttcggggg 24060
ggacggggca gggcgggggtt cggcttctgg cgtgtgaccg gcggctctag agcctctgct 24120
aaccatgttc atgccttctt cttttttcct a cagctcctgg gcaacgtgct ggttgttgtg 24180
ctgtctcatc attttggcaa agaattccgc tgcgactcgg cggagtcccg gcggcgcgttc 24240
cttgttctaa cccggcgcgc cctcaggatg gagcctcccg gccgccgcga gtgtccctt 24300
ccttcctggc gctttcctgg gttgcttctg gcggccatgg tgttgctgct gtactccttc 24360
tccgatgcct gtgaggagcc accaacattt gaagctatgg agctcattgg taaaccaaaa 24420
ccctactatg agattggtga acgagtagat tataagtgta aaaaggata cttctatata 24480
cctcctcttg ccacccatac tatttgtgat cggaatcata catggctacc tgtctcagat 24540
gacgcctgtt atagagaaac atgtccatat atacgggatc ctttaaatgg ccaagcagtc 24600
cctgcaaatg ggacttacga gtttggttat cagatgcact ttatttgtaa tgagggttat 24660
tacttaattg gtgaagaaat tctatattgt gaacttaaag gatcagtagc aatttggacc 24720
ggtaagcccc caatatgtga aaaggttttg tgtacaccac ctccaaaaat aaaaaatgga 24780
aaacacacct ttagtgaagt agaagtattt gagtatcttg atgcagtaac ttatagttgt 24840
gatcctgcac ctggaccaga tccatttttca cttattggag agagcacgat ttattgtggt 24900
gacaattcag tgtggagtcg tgctgctcca gagtgtaaag tggtcaaatg tcgatttcca 24960
gtagtcgaaa atgaaaaca gatatcagga tttggaaaaa aatttactta caaagcaaca 25020
gttatgtttg aatgcgataa gggttttttac ctcgatggca gcgacacaat tgtctgtgac 25080
agtaacagta cttgggatcc cccagttcca aagtgtctta aagtgctgcc tccatctagt 25140
acaaaacctc cagctttttgag tcattcagtg tcgacttctt ccactacaaa atctccaggg 25200
tccagtgcct caggtcctag gcctacttac aagcctccag tctcaaatta tccaggatat 25260
cctaaacctg aggaaggaat acttgacagt ttggatgttt gggtcattgc tgtgattgtt 25320
attgccatag ttgttggagt tgcagtaatt tgtgttgtcc cgtacagata tcttcaaagg 25380
aggaagaaga aaggcacata cctaactgat gagacccaca gagaagtaaa atttacttct 25440
ctcggatccg gagccacgaa cttctctctg ttaaagcaag caggagacgt ggaagaaaac 25500
cccggtccta tgaccgtcgc gcggccgagc gtgcccgcgg cgctgcccct cctcggggag 25560
ctgcccggc tgctgctgct ggtgctgttg tgcctgccgg ccgtgtgggg tgactgtggc 25620
cttccccagg atgtacctaa tgcccagcca gctttggaag gccgtacaag ttttcccgag 25680
gatactgtaa taacgtacaa atgtgaagaa agctttgtga aaattcctgg cgagaaggac 25740
tcagtgatct gccttaaggg cagtcaatgg tcagatattg aagagttctg caatcgtagc 25800
tgcgaggtgc caacaaggct aaattctgca tccctcaaac agccttatat cactcagaat 25860
tattttccag tcggtactgt tgtggaatat gagtgccgtc caggttacag aagagaacct 25920
tctctatcac caaaactaac ttgccttcag aatttaaaat ggagcacaga agtcgaattt 25980
tgtaaaaaga aatcatgccc taatccggga gaaatacgaa atggtcagat tgatgtacca 26040
ggtggcatat tatttggtgc aaccatctcc ttctcatgta acacagggta caaattattt 26100
ggctcgactt ctagttttttg tcttatttca ggcagctctg tccagtggag tgacccgttg 26160
ccagagtgca gagaaattta ttgcccagca ccaccacaa ttgacaatgg aataattcaa 26220
ggggaacgtc accattatgg atatagacag tctgtaacgt atgcatgtaa taaaggattc 26280
accatgattg gagagcactc tatttattgt actgtgaata atgatgaagg agagtggagt 26340
ggcccaccac ctgaatgcag aggaaaatct ctaacttcca aggtcccacc aacagttcag 26400
aaacctacca cagtaaatgt tccaactaca gaagtctcac caacttctca gaaaaccacc 26460
acaaaaccca ccacaccaaa tgctcaagca acacggagta cacctgtttc caggacaacc 26520
aagcatttttc atgaaacaac cccaataaaa ggaagtggaa ccacttcagg tactacccgt 26580
cttctatctg gcacacgtgt tttcacgttg acaggtttgc ttgggacgct agtaaccatg 26640
ggcttgctga cttagggcgc gccggcaccg gtaccaagct taagagcgct agctggccag 26700
acatgataag atacattgat gagtttggac aaaccacaac tagaatgcag tgaaaaaaat 26760
gctttatttg tgaaatttgt gatgctattg ctttatttgt aaccattata agctgcaata 26820
aacaagttaa caacaacaat tgcattcatt ttatgtttca ggttcagggg gaggtgtggg 26880
```

-continued

```
aggtttttta aagcaagtaa aacctctaca aatgtggtat ggaattggag ccccactgtg  26940
ttcatcttac agatggaaat actgacattc agaggagtta gttaacttgc ctaggtgatt  27000
cagctaataa gtgcaagaaa gatttcaatc caaggtgatt tgattctgaa gcctgtgcta  27060
atcacattac accaagctac aacttcattt ataaataata agtcagcttt caagggcctt  27120
tcaggtgtcc tgcacttcta caagctgtgc catttagtga acacaaaatg agccttctga  27180
tgaagtagtc ttttcattat ttcagatatt agaacactaa aattcttagc tgccagctga  27240
ttgaaggctg ggacaaaatt caaacatgca tctacaacaa tatatatctc aatgttagtc  27300
tccaaattct attgacttca actcaagaga atataaagag ctagtcttta tacactcttt  27360
aaggtatgat atcatctgga aagtaacaaa attgatgcaa atttgaatga actttatcat  27420
ggtgtattta cacaatgtgt ttcttctccc tgcaatgtat ttctttctct aattccttcc  27480
atttgatctt tcatacacaa tctggttctg atgtatgttt tttggatgca cttttcaact  27540
ccaaaagaca gagctagtta ctttcttcct ggtgctccaa gcactgtatt tgtatctgta  27600
ttcaagccct ttgcaatatt gtactggatc attatttcac ctctaggatg gcttccccag  27660
gcaacttgtg ttcacccaga gactacattt tgtatcttgt tgacctttga acttccacca  27720
gtgtctaaaa ataatatgta tgcaaaatta cttgctatga gaatgtataa ttaaacaata  27780
taaaaaggag aagcaaggag agaaacacag gtgtgtattt gtgtttgtgt gcttaaaagg  27840
cagtgtggaa aaggaagaaa tgccatttat agtgaggaga caaagttata ttacctctta  27900
tctggctttt aaggagattt tgctgagcta aaaatcctat attcatagaa aagccttacc  27960
tgagttgcca atacctcaat tctaaaatac agcatagcaa aactttaacc tccaaatcaa  28020
gcctctactt gaatcctttt ctgagggatg aataaggcat aggcatcagg ggctgttgcc  28080
aatgtgcatt agctgtttgc agcctcacct tctttcatgg agtttaagat atagtgtatt  28140
ttcccaaggt ttgaactagc tcttcatttc tttatgtttt aaatgcactg acctcccaca  28200
ttcccttttt agtaaaatat tcagaaataa tttatcatct ggaaagtaac aaaattgatg  28260
caaatttgaa tgaactttat catggtgtat ttacacaatg tgtttcttct ccctgcaatg  28320
tatttctttc tctaattcct tccatttgat cttcataca caatctggtt ctgatgtatg  28380
tttttggat gcactttca actccaaaag acagagctag ttactttctt cctggtgctc  28440
caagcactgt atttgtatct gtattcaagc cctttgcaat attgtactgg atcattattt  28500
cacctctagg atggcttccc caggcaactt gtgttcaccc agagactaca ttttgtatct  28560
tgttgacctt tgaacttcca ccagtgtcta aaaataatat gtatgcaaaa ttacttgcta  28620
tgagaatgta taattaaaca atataaaaag gagaagcaag gagagaaaca caggtgtgta  28680
tttgtgtttg tgtgcttaaa aggcagtgtg gaaaaggaag aaatgccatt tatagtgagg  28740
agacaaagtt atattacctc ttatctggct tttaaggaga ttttgctgag ctaaaaatcc  28800
tatattcata gaaaagcctt acctgagttg ccaataccct aattctaaaa tacagcatag  28860
caaaacttta acctccaaat caagcctcta cttgaatcct tttctgaggg atgaataagg  28920
cataggcatc aggggctgtt gccaatgtgc attagctgtt tgcagcctca ccttctttca  28980
tggagtttaa gatatagtgt atttttccaa ggtttgaact agctcttcat ttctttatgt  29040
tttaaatgca ctgacctccc acattccctt tttagtaaaa tattcagaaa taatttatcc  29100
cggcttgtcg acgacgg                                                  29117
```